US012264175B2

(12) United States Patent
Cheng et al.

(10) Patent No.: US 12,264,175 B2
(45) Date of Patent: Apr. 1, 2025

(54) COMPOSITIONS AND METHODS FOR CAPPING RNAS

(71) Applicant: Verve Therapeutics, Inc., Boston, MA (US)

(72) Inventors: Christopher Cheng, North Reading, MA (US); Kallanthottathil Rajeev, Wayland, MA (US); Caroline Reiss, Somerville, MA (US)

(73) Assignee: Verve Therapeutics, Inc., Boston, MA (US)

( * ) Notice: Subject to any disclaimer, the term of this patent is extended or adjusted under 35 U.S.C. 154(b) by 0 days.

(21) Appl. No.: 18/176,609

(22) Filed: Mar. 1, 2023

(65) Prior Publication Data

US 2023/0331763 A1 Oct. 19, 2023

Related U.S. Application Data

(63) Continuation of application No. PCT/US2021/049158, filed on Sep. 3, 2021.

(60) Provisional application No. 63/074,993, filed on Sep. 4, 2020.

(51) Int. Cl.

*C07H 21/02* (2006.01)
*C12N 9/12* (2006.01)
*C12P 19/34* (2006.01)
*A61K 31/7115* (2006.01)
(Continued)

(52) U.S. Cl.

CPC ........... *C07H 21/02* (2013.01); *C12N 9/1247* (2013.01); *C12P 19/34* (2013.01); *C12Y 207/07006* (2013.01); *A61K 31/7115* (2013.01); *A61K 31/712* (2013.01); *A61K 31/7125* (2013.01)

(58) Field of Classification Search

None
See application file for complete search history.

(56) References Cited

U.S. PATENT DOCUMENTS

| | | |
|---|---|---|
| 3,687,808 A | 8/1972 | Merigan, Jr. et al. |
| 4,587,044 A | 5/1986 | Miller et al. |
| 4,605,735 A | 8/1986 | Miyoshi et al. |

(Continued)

FOREIGN PATENT DOCUMENTS

| | | |
|---|---|---|
| EP | 0816368 A1 | 1/1998 |
| EP | 3352584 B1 | 5/2021 |

(Continued)

OTHER PUBLICATIONS

Agamemnon. et al., Cycling of Ribonucleic Acid Polymerase to Produce Oligonucleotides During Initiation in Vitro at the Lac Uv5 Promoter. Biochemistry 19: 3245-3253 (1980).

(Continued)

*Primary Examiner* — Eric Olson
(74) *Attorney, Agent, or Firm* — Wilson Sonsini Goodrich & Rosati

(57) ABSTRACT

Provided herein are compositions and methods for preparation of 5' end region-modified mRNAs. In particular, the instant disclosure relates to novel mRNA 5' end region motifs and sequence initiators therefore together with assays that are capable of measuring the aspects of the functionality of those motifs and sequence initiators. Further provided herein are compositions and methods of treating conditions related to coronary disease.

6 Claims, 9 Drawing Sheets

Specification includes a Sequence Listing.

5' end initiator: 1007a

(51) Int. Cl.

*A61K 31/712* (2006.01)
*A61K 31/7125* (2006.01)

(56) References Cited

U.S. PATENT DOCUMENTS 4,667,025 A 5/1987 Miyoshi et al.
4,762,779 A 8/1988 Snitman
4,789,737 A 12/1988 Miyoshi et al.
4,824,941 A 4/1989 Gordon et al.
4,828,979 A 5/1989 Klevan et al.
4,835,263 A 5/1989 Nguyen et al.
4,876,335 A 10/1989 Yamane et al.
4,904,582 A 2/1990 Tullis
4,948,882 A 8/1990 Ruth
4,958,013 A 9/1990 Letsinger
5,082,830 A 1/1992 Brakel et al.
5,109,124 A 4/1992 Ramachandran et al.
5,112,963 A 5/1992 Pieles et al.
5,118,802 A 6/1992 Smith et al.
5,138,045 A 8/1992 Cook et al.
5,149,782 A 9/1992 Chang et al.
5,214,136 A 5/1993 Lin et al.
5,218,105 A 6/1993 Cook et al.
5,245,022 A 9/1993 Weis et al.
5,254,469 A 10/1993 Warren, III et al.
5,258,506 A 11/1993 Urdea et al.
5,262,536 A 11/1993 Hobbs, Jr.
5,272,250 A 12/1993 Spielvogel et al.
5,292,873 A 3/1994 Rokita et al.
5,317,098 A 5/1994 Shizuya et al.
5,371,241 A 12/1994 Brush
5,391,723 A 2/1995 Priest
5,414,077 A 5/1995 Lin et al.
5,416,203 A 5/1995 Letsinger
5,451,463 A 9/1995 Nelson et al.
5,486,603 A 1/1996 Buhr
5,510,475 A 4/1996 Agrawal et al.
5,512,439 A 4/1996 Hornes et al.
5,512,667 A 4/1996 Reed et al.
5,514,785 A 5/1996 Van Ness et al.
5,525,465 A 6/1996 Haralambidis et al.
5,541,313 A 7/1996 Ruth
5,545,730 A 8/1996 Urdea et al.
5,552,538 A 9/1996 Urdea et al.
5,565,552 A 10/1996 Magda et al.
5,567,810 A 10/1996 Weis et al.
5,574,142 A 11/1996 Meyer, Jr. et al.
5,578,717 A 11/1996 Urdea et al.
5,578,718 A 11/1996 Cook et al.
5,580,731 A 12/1996 Chang et al.
5,585,481 A 12/1996 Arnold, Jr. et al.
5,587,371 A 12/1996 Sessler et al.
5,591,584 A 1/1997 Chang et al.
5,595,726 A 1/1997 Magda et al.
5,597,696 A 1/1997 Linn et al.
5,599,923 A 2/1997 Sessler et al.
5,599,928 A 2/1997 Hemmi et al.
5,608,046 A 3/1997 Cook et al.
5,672,662 A 9/1997 Harris et al.
5,688,941 A 11/1997 Cook et al.
5,714,166 A 2/1998 Tomalia et al.
6,153,737 A 11/2000 Manoharan et al.
6,172,208 B1 1/2001 Cook
6,214,345 B1 4/2001 Firestone et al.
6,300,319 B1 10/2001 Manoharan
6,335,434 B1 1/2002 Guzaev et al.
6,335,437 B1 1/2002 Manoharan
6,395,437 B1 5/2002 Wollesen
6,444,806 B1 9/2002 Veerapanani et al.
6,486,308 B2 11/2002 Kutyavin et al.
6,525,031 B2 2/2003 Manoharan
6,528,631 B1 3/2003 Cook et al.
6,559,279 B1 5/2003 Manoharan et al.
6,762,298 B2 7/2004 Beaucage et al.
7,074,596 B2 7/2006 Darzynkiewicz et al.
8,153,773 B2 4/2012 Jemielity et al.
8,519,110 B2 8/2013 Kowalska et al.
8,877,901 B2 11/2014 Govindan
8,969,545 B2 3/2015 Kore et al.
9,295,717 B2 3/2016 Sahin et al.
9,428,535 B2 8/2016 De Fougerolles et al.
10,428,106 B2 10/2019 Butora et al.
10,487,105 B2 11/2019 Chivukula et al.
10,494,399 B2 12/2019 Hogrefe et al.
10,519,189 B2 12/2019 Hogrefe et al.
10,563,195 B2 2/2020 Butora et al.
10,570,388 B2 2/2020 Butora et al.
10,837,039 B2 11/2020 Wochner et al.
10,913,768 B2 2/2021 Hogrefe et al.
11,066,436 B2 7/2021 Jemielity et al.
11,207,416 B2 12/2021 Rajeev et al.
11,414,453 B2 8/2022 Hogrefe et al.
2007/0281308 A1 12/2007 Zon et al.
2012/0245335 A1 9/2012 Clark
2013/0123481 A1 5/2013 De Fougerolles et al.
2018/0105551 A1 4/2018 Chivukula et al.
2018/0273576 A1 9/2018 Hogrefe et al.
2019/0211368 A1 7/2019 Butora et al.
2019/0225644 A1* 7/2019 Butora .................. C07H 21/02
2019/0300563 A1 10/2019 Jemielity et al.
2020/0040026 A1 2/2020 Chivukula et al.
2021/0108252 A1 4/2021 Beverly
2021/0261597 A1 8/2021 Hogrefe et al.
2021/0363172 A1 11/2021 Kuhn et al.
2022/0023442 A1 1/2022 Perez-Garcia et al.
2022/0195424 A1 6/2022 Correa, Jr. et al.
2022/0204978 A1 6/2022 Yeo et al.
2022/0220473 A1 7/2022 Yeo et al.
2022/0289786 A1 9/2022 Hogrefe et al.

FOREIGN PATENT DOCUMENTS

EP 3274454 B1 8/2021
EP 3906789 A1 11/2021
EP 3954224 A1 2/2022
EP 3954225 A1 2/2022
EP 3362461 B1 3/2022
EP 4086269 A1 11/2022
EP 4103577 A1 12/2022
EP 4103578 A1 12/2022
EP 4104687 A1 12/2022
WO WO-9819705 A1 5/1998
WO WO-2009120878 A2 10/2009
WO WO-2010093395 A1 8/2010
WO WO-2013176844 A1 11/2013
WO WO-2017053297 A1 3/2017
WO WO-2017066781 A1 4/2017
WO WO-2017066797 A1 4/2017
WO WO-2018075827 A1 4/2018
WO WO-2019175356 A1 9/2019
WO WO-2021021677 A1 2/2021
WO WO-2021162566 A1 * 8/2021 ............. C07H 21/02
WO WO-2021162567 A1 8/2021
WO WO-2022051677 A1 3/2022
WO WO-2022212710 A1 10/2022
WO WO-2023147352 A1 8/2023

OTHER PUBLICATIONS

Ansel. et al., Pharmaceutical Dosage Forms and Drug Delivery Systems. Lippincott-Williams & Wilkins (1999).

Ausubel. et al., Current Protocols in Molecular Biology. Molecular Biology 1(78):1-12 (1994).

Baker. et al., Nonsense-mediated mRNA decay: terminating erroneous gene expression. Current Opinion in Cell Biology 16(3):293-299 (2004).

Behm-Ansmant. et al., Quality Control of Gene Expression: a Stepwise Assembly Pathway for the Surveillance Complex That Triggers Nonsense-mediated Mrna Decay. Genes & Development 20(4):391-398 (2006).

Betz. et al., Klentaq Polymerase Replicates Unnatural Base Pairs by Inducing a Watson-crick Geometry. Nat Chem Biol 8:612-614 (2012).

(56) References Cited

OTHER PUBLICATIONS

Cai, Haini, et al., Variations in Template Protection by the RNA Polymerase Ii Transcription Complex During the Initiation Process. Molecular and Cellular Biology 7: 3371-3379 (1987).
Carpousis, et al., Interaction of RNA polymerase with lacUV5 promoter DNA during mRNA initiation and elongation: Footprinting, methylation, and rifampicin-sensitivity changes accompanying transcription initiation. 183: 165-177 (1985).
Chamberlain, Michael., Characterization of T7-specific ribonucleic acid polymerase. The Journal of Biological Chemistry 248: 2235-2244 (1973).
Chang. et al., The Nonsense-mediated Decay Rna Surveillance Pathway. Annual Review of Biochemistry 76:51-74 (2007).
Clement. et al., Crispresso2 Provides Accurate and Rapid Genome Editing Sequence Analysis. Nat. Biotechnol. 37(3):224-226 (2019).
Crey-Desbiolles, et al., Hybridization Properties and Enzymatic Replication of Oligonucleotides Containing the Photocleavable 7-nitroindole Base Analog. Nucleic Acids Research 33 (5): 1532-1543 (2005).
Damha. et al., Protocols for Oligonucleotides and Analogs. Methods in Molecular Biology 20:81-114 (1993).
Dellinger. et al., Streamlined Process for the Chemical Synthesis of Rna Using 2'-o-thionocarbamate-protected Nucleoside Phosphoramidites in the Solid Phase. Journal of American Society 113: 11540-11556 (2011).
Diebold. et al., Recognition of Viral Single-stranded RNA by Toll-like Receptors. Advanced Drug Delivery Reviews 60(7):813-823 (2008).
Englisch. et al., Chemically Modified Oligonucleotides as Probes and Inhibitors Agnew Chem. Int. Ed. Engl. 30:613-629 (1991).
Flajolet. et al., Woodchuck Hepatitis Virus Enhancer I and Enhancer II are Both Involved in N-myc2 Activation in Woodchuck Liver Tumors. J. Virol. 72(7):6175-80 (1998).
Gennaro, et al. Remington: The Science and Practice of Pharmacy. Nineteenth Edition, Mack Publishing Company, 1995.
Grudzien, et al., Differential Inhibition of mRNA Degradation Pathways by Novel Cap Analogs. Structure, Metabolism, and Catalysis 281: 1857-1867 (2006).
Harlow. et al., Antibodies: a Laboratory Manual (1st Edition). Cold Spring Harbor Laboratory, NY (1988).
Henikoff. et al., Amino Acid Substitution Matrices From Protein Blocks. PNAS USA 89(22):10915-10919 (1992).
Hill, et al., Polymerase Recognition of Synthetic Oligodeoxyribonucleotides Incorporating Degenerate Pyrimidine and Purine Bases. PNAS 95: 4258-4263 (1998).
Hoover, Gennard. Remington's Pharmaceutical Sciences. Mack Publishing Co., Seventeenth Edition, 1985.
Hu, et al., Evolved Cas9 variants with broad PAM compatibility and high DNA specificity. Nature 556(7699):57-63 (2018).
Ikeda, et al., Interactions of the RNA Polymerase of Bacteriophage T7 With its Promoter During Binding and Initiation of Transcription. PNAS 83: 3614-3618 (1986).
Kananov. et al., A New Class of Antivirals: Antisense Oligonucleotides Combined With a Hydrophobic Substituent Effectively Inhibit Influenza Virus Reproduction and Synthesis of Virus-specific Proteins in Mdck Cells. FEBS Letters 259(2):327-330 (1990).
Kennedy, et al., Mechanism for De Novo RNA Synthesis and Initiating Nucleotide Specificity by T7 RNA Polymerase. Journal of Molecular Biology 370: 256-268 (2007).
Kincaid, et al., Exploration of Factors Driving Incorporation of Unnatural Dntps Into DNA by Klenow Fragment (Dna Polymerase I) and Dna Polymerase α. Nucleic Acids Research 33: 2620-2628 (2005).
Koukhareva, et al., 3'-Protected 2'-Deoxynucleoside 5'-Triphosphates as a Tool for Heat-triggered Activation of Polymerase Chain Reaction. Analytical Chemistry 81: 4955-4962 (2009).
Kroschwitz. et al., The Concise Encyclopedia of Polymer Science and Engineering, , J.I., Ed., John Wiley & Sons pp. 858-859 (1990).
Kumar. et al., Template-directed Oligonucleotide Strand Ligation, Covalent Intramolecular Dna Circularization and Catenation Using Click Chemistry. J. Am. Chem. Soc. 129(21):6859-6864 (2007).
Kuzmine. et al., Binding of the Priming Nucleotide in the Initiation of Transcription by T7 RNA Polymerase. J. Biol. Chem. 278(5): 2819-2823 (2003).
Lebedev. et al., Hot Start Pcr With Heat-activatable Primers: a Novel Approach for Improved Pcr Performance NAR (2008) 36(20):E131-1.
Lescure, et al., Efficient and Selective Initiation by Yeast Rna Polymerase B in a Dinucleotide-primed Reaction. Nucleic Acids Research 9:31-45 (1981).
Letsinger. et al., Cholesteryl-conjugated Oligonucleotides: Synthesis, Properties, and Activity as Inhibitors of Replication of Human Immunodeficiency Virus in Cell Culture. PNAS 86(17):6553-6556 (1989).
Liberman. et al., Pharmaceutical Dosage Forms, Marcel Decker, New York, N.Y., 1980.
Loakes. Survey and summary: The applications of universal DNA base analogues. Nucleic Acids Research 29:2437-2447 (2001).
Manoharan. et al., Chemical Modifications to Improve Uptake and Bioavailability of Antisense Oligonucleotides. Ann. N.Y. Acad. Scie 660:306-309 (1992).
Manoharan. et al., Cholic acid-oligonucleotide conjugates for antisense applications. Bioorganic & Medicinal Chemistry Letters 4(8):1053-1060 (1994).
Manoharan. et al., Introduction of a Lipophilic Thioether in the Minor Groove of Nucleic Acids for Antisense Applications. Bioorg. Med. Chem. Let 3:2765-2770 (1993).
Manoharan. et al., Lipidic nucleic acids. Tetrahedron Letters 36(21):3651-3654 (1995).
Manoharan. et al., Oligonucleotide Conjugates: Alteration of the Pharmacokinetic Properties of Antisense Agents. Nucleosides & Nucleotides 14:969-973 (1995).
Manoharan. et al., Oligonucleotide Conjugates: Alteration of the Pharmacokinetic Properties of Antisense Agents. Nucleosides and Nucleotides 14:3-5 (1995).
March. Advanced Organic Chemistry: Reactions, Mechanisms, and Structure. 4th Edition John Wiley & Sons, ISBN: 0-471-60180-2 (1992).
Martin. et al., Processivity in Early Stages of Transcription by T7 RNA Polymerase. Biochemistry 27: 3966-3974 (1988).
Matsuda. et al., siRNA Conjugates Carrying Sequentially Assembled Trivalent N-Aceytlgalactosamine Linked Through Nucleosides Elicit Robust Gene Silencing In Vivo in Hepatocytes, ACS Chem Biol., 2015, vol. 10, No. 5, 7 pages.
Milligan. et al., Oligoribonucleotide Synthesis Using T7 Rna Polymerase and Synthetic DNA Templates. Nucleic Acids Research 15: 8783-8798 (1987).
Mishra. et al., Improved Leishmanicidal Effect of Phosphorotioate Antisense Oligonucleotides by Ldl-mediated Delivery. Biochimica Et Biophysica Acta (BBA)—Gene Structure and Expression 1264(2, 7):229-237 (1995).
Nair. et al., Multivalent N-acetylgalactosamine-conjugated siRNA localizes in hepatocytes and elicits robust RNAi-mediated gene silencing. J Am Chem Soc. 136(49):16958-16961 (2014).
Needleman. et al., A General Method Applicable to the Search for Similarities in the Amino Acid Sequence of Two Proteins. Jouranl of Molecular Biology 48(3):443-453 (1970).
Oberhauser. et al., Effective Incorporation of 2'-o-methyl-oligoribonuclectides Into Liposomes and Enhanced Cell Association Through Modification With Thiocholesterol. Nucleic Acids Research 20(3):533-538 (1992).
Ohkubo. et al., Chemical Synthesis of U1 Snrna Derivatives. Organic Letters 15: 4386-4389 (2013).
Pareds, E. et al.: Manufacturing of Oligonucleotides. Comprehensive Medicinal Chemistry III 2017, pp. 233-279. https://doi.org/10.1016/B978-0-12-409547-2.12423-0.
Pasquinelli. et al., Reverse 5' caps in RNAs made in vitro by phage RNA polymerases, RNA, 1:957-967, 1995.
PCT/US2021/049158 International Preliminary Report on Patentability with Article 34 Amendment dated Jul. 1, 2022 (Pub. No. WO2022051677).

(56) References Cited

OTHER PUBLICATIONS

PCT/US2021/049158 International Search Report and Written Opinion dated Feb. 15, 2022 (Pub. No. WO2022051677).
Pitulle. et al., Initiator Oligonucleotides for the Combination of Chemical and Enzymatic RNA Synthesis. Gene 112: 101-105 (1992).
Preparata. et al., DNA Sequencing by Hybridization Using Semi-degenerate Bases. Journal of Computational Biology 11(4): 753-765 (2004).
Ramzy. et al., Clinical Cytopathology and Aspiration Biopsy: Fundamental principles and practice. McGraw Hill Professional, 2001.
Rosa. et al., Four T7 Rna Polymerase Promoters Contain an Identical 23 Bp Sequence. Cell 16: 815-825 (1979).
Saison-Behmoaras. et al., Short Modified Antisense Oligonucleotides Directed Against Ha-ras Point Mutation Induce Selective Cleavage of the Mrna and Inhibit T24 Cells Proliferation. EMBO J. 10:1111-1118 (1991).
Sambrook. et al., Molecular Cloning: A Laboratory Manual. 4th Edition, 2012.
Sambrook. et al., Molecular Cloning: A Laboratory Manual. Chapter 18:18.1-18.88 (1989).
Sambrook. et al., Molecular cloning: A laboratory manual (Third Edition). Cold Spring Harbor Laboratory Press. Volume 1-3 (2001).
Sanghvi. Chapter 15: Heterocyclic Base Modifications in Nucleic Acids and Their Applications in Antisense Oligonucleotides. Antisense Research and Applications, Crookeand Lebleu Eds., CRC Press (pp. 273-288) (1993).
Sanghvi, Y.S., in Crooke, S.T. and Lebleu, B., eds., Antisense Research and Applications, CRC Press, Boca Raton, 1993, p. 276-278.
Senthilvelan, A. et al.: Highly regioselective methylation of inosine nucleotide: an efficient synthesis of 7-methylinosine nucleotide. Nucleosides, Nucleotides & Nucleic Acids 39(7):1011-1019 (2020) (Abstract).
Shea. et al., Synthesis, Hybridization Properties and Antiviral Activity of Lipid-oligodeoxynucleotide Conjugates. Nucleic Acids Research 18(13):3777-3783 (1990).
Sikorski et al.: The identity and methylation status of the first transcribed nucleotide in eukaryotic mRNA 5' cap modulates protein expression in living cells. Nucleic Acids Research 48(4): 1607-1626 (2020), https://doi.org/10.1093/nar/gkaa032.
Singleton. et al., Dictionary of Microbiology and Molecular Biology. 3rd Edition Wiley & Sons New York, N.Y. (2001).
Stepinski. et al., Synthesis and Properties of Mrnas Containing the Novel ‘anti-reverse’ Cap Analogs 7-methyl(3'0-methyl)gpppg and 7-methyl(E'-deoxy)gpppg. RNA 7:1486-1495 (2001).
Strenkowska. et al., Cap Analogs Modified With 1,2-dithiodiphosphate Moiety Protect Mrna From Decapping and Enhance its Translational Potential. Nucleic Acids Research 44: 9578-9590 (2016).
Svinarchuk. et al., Inhibition of HIV Proliferation in Mt-4 Cells by Antisense Oligonucleotide Conjugated to Lipophilic Groups. Biochimie 75(1-2):49-54 (1993).
Vaghefi. et al., Chemical Synthesis of Nucleoside 5'-triphosphates, In: Nucleoside Triphosphates and their Analogs, pp. 1-22, Taylor & Francis, 2005.
Vladimir. et al., Transcription From Bacteriophage T7 and Sp6 Rna Polymerase Promoters in the Presence of 3'-deoxyribonucleoside 5'-triphosphate Chain Terminators. Biochemistry 24:5716-5723 (1985).
Zufferey. et al., Woodchuck Hepatitis Virus Posttranscriptional Regulatory Element Enhances Expression of Transgenes Delivered by Retroviral Vectors. Journal of Virology 73(4):2886-2892 (1999).
European Communication to applicant regarding observations by third parties dated issued in European Patent Application No. 21865230.3 dated Jul. 23, 2024.
PCT/US2023/014183 International Search Report and Written Opinion dated Aug. 10, 2023.
PCT/US2023/014183 Third Party Observation dated Jun. 28, 2024.
Unknown: New Cap analogues of the 5' end of mRNA, the RNA molecules containing them, their applications and the method of synthesis of the RNA molecule and peptide. P.432884, Aug. 16, 2021, cited in Communication to applicant regarding observations by third parties dated issued in European Patent Application No. 21865230.3 dated Jul. 23, 2024.
Warminski, Marcin et al.: Structural Insights into the Interaction of Clinically Relevant Phosphorothioate mRNA Cap Analogs with Translation Initiation Factor 4E Reveal Stabilization via Electrostatic Thio-Effect. ACS Chem. Biol. 16:334-343 (2021).
Wojcik; Radoslaw et al.: Novel N7-Arylmethyl Substituted Dinucleotide mRNA 50 cap Analogs: Synthesis and Evaluation as Modulators of Translation. Pharmaceutics 13(11): 1941 (2021); https://doi.org/10.3390/pharmaceutics13111941.
U.S. Appl. No. 18/819,275 Application filed Aug. 29, 2024.

* cited by examiner

5′ end initiator: 1007a

5' end initiator: 1107a

COMPOSITIONS AND METHODS FOR CAPPING RNAS

CROSS-REFERENCE

This application is a continuation of International Application No. PCT/US2021/049158, filed Sep. 3, 2021 which claims the benefit of U.S. Provisional Application No. 63/074,993, filed Sep. 4, 2020, which is herein incorporated by reference in its entirety.

SEQUENCE LISTING

The instant application contains a Sequence Listing which has been submitted electronically in XML format and is hereby incorporated by reference in its entirety. Said XML copy, created on Feb. 24, 2023, is named 53989-712.301_SL.xml and is 317,957 bytes in size.

FIELD OF THE DISCLOSURE

The instant disclosure relates to RNA and in particular the 5' end-region of an mRNA molecule, including for example, novel mRNA 5' end region motifs (or mRNA Caps) and initiators thereof.

BACKGROUND

The 5' end region of an mRNA can be an important structural and/or functional feature of eukaryotic mRNA molecules as it is capable of providing stability to the mRNA (e.g., by providing protection against 5' exonucleases) and being involved in RNA splicing, mRNA transport, and other activities that support protein translation. A structural element of a conventional mRNA Cap frequently comprises an inverted 7-methylguanosine ($m^7G$) linked at the 5' end to a triphosphate (ppp) bridge, which phosphate bridge is in turn linked to the first nucleotide ($N_1$) of the mRNA transcript. The 5' end region mRNA motifs and sequence initiators thereof described here differ from the conventional mRNA Caps in several respects, including, for example, that they comprise a chemically modified inverted 7-methylguanosine (m7G) nucleoside structure and/or modified triphosphate (ppp) linkage. Conventional Caps are often one of the most expensive components in the manufacture of mRNA molecules. Accordingly, alternatives to conventional Caps while maintaining or improving capping efficiencies and/or mRNA yields are each independently important aspects to the field.

SUMMARY

Novel mRNA 5' end region motifs and initiators therefore are described herein.

In one aspect, described herein is an in vitro-transcribed (IVT) mRNA sequence initiator comprising a compound of Formula (I) or a salt or solvate thereof:

Formula (I)

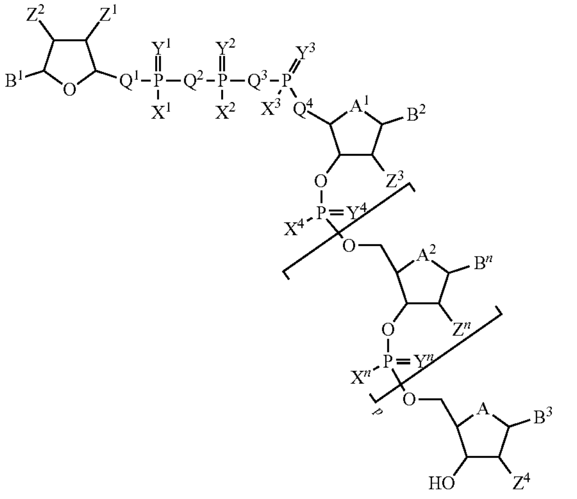

wherein
B1 is

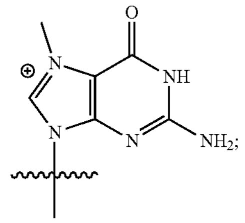 [SMILES: *n1c[n+](C)c2c(=O)[nH]c(N)nc21]

each B2, B3, and Bn is independently a natural, a modified, or an unnatural nucleobase;

each Z1 and Z2 is independently hydrogen, fluorine, —OH, —SH, —CH3, —CH2CH3, —OCH3, —OCH2CH3, —SCH3, —NH2, NHCH3, or NHC(═O)CH3;

each Z3, Z4, and Zn is independently hydrogen, fluorine, —OH, —SH, —CH3, —CH2CH3, —OCH3, —NH2, —NHCH3, —NH(C(═O)CH3), —OCH2CH3, —OCH2OCH3, —OCH2CH2CH3, —OCH(CH3)2, —SCH3, or —OCH2CH2OCH3;

each Q1 and Q4 is independently —CH2-, —CH═CH—, —CH2O—, —CH2S—, —CH2CH2-, —CH2CF2-, —CH2NH2-, —CH2NH(CH3)-, or —CH2N(C(═O)CH3)-;

each Q2 and Q3 is independently —O—, —S—, —CH2-, —CF2-, —NH—, —N(CH3)-, or —N(C(═O)CH3)-;

each X1, X2, X3, X4, and Xn is independently —OH, —SH, —O—, —S—, —NH2, —NHCH3, —NH(C(═O)CH3), —CH3, —CH2CH3, —CH2CH2CH3, —CH(CH3)2, —OCH3, or —OCH2CH3;

each Y1, Y2, Y3, Y4, and Yn is independently ═O, ═S, ═NH, or ═NCH3;

each A, A1, and A2 is independently —O—, —S—, —CH2-, —NH—, —N(CH3)- or —N(C(═O)CH3)-; and p=0, 1, 2, 3, 4, 5 or 6, In another aspect, described herein the compound of Formula (I) satisfies one or more of the following proviso (i) to (iii): (i) at least one of X1, X2, X3, X4, and Xn is —SH or —S—; (ii) at least one of Y1, Y2, Y3, Y4, and Yn is ═S; and (iii) at least one of A, A1, and A2 is —S—.

In another aspect, the IVT mRNA sequence initiator satisfies at least one of X1, X2, X3, X4, and Xn is —SH or —S—; at least one of Y1, Y2, Y3, Y4, and Yn is ═S; or at least one of A, A1, and A2 is —S—.

In one aspect, described herein is an in vitro-transcribed (IVT) mRNA sequence initiator comprising a compound of Formula (II) or a salt or solvate thereof:

Formula (II)

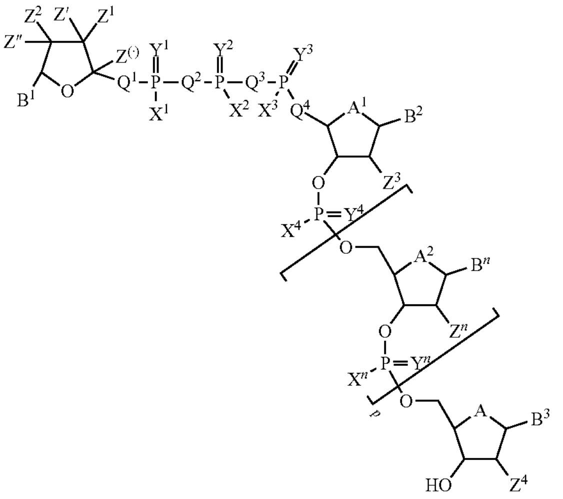

wherein

B1 is

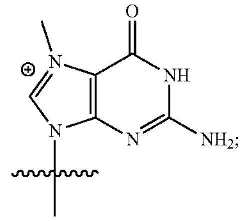 [SMILES: *n1c[n+](C)c2c(=O)[nH]c(N)nc21]

each B2, B3, and Bn is independently a natural, a modified, or an unnatural nucleobase;

each Z1 and Z' is independently is hydrogen, fluorine, —OH, —SH, —CH3, —CH2CH3, —OCH3, —NH(CH3), —NH2, —NH(C(═O)CH3), or —SCH3;

each Z2 and Z" is independently fluorine, —OH, —SH, —CH3, —CH2CH3, —OCH3, —SCH3, —OCH2CH3, —NH2, NHCH3, or NHC(═O)CH3;

Z'" is hydrogen, fluorine, —CH3, —CH2CH3, —OCH3, or —OCH2CH3;

each Z3, Z4, and Zn is independently hydrogen, fluorine, —OH, —CH3, —CH2CH3, —OCH3, —NH2, —NHCH3, —NH(C(═O)CH3), —OCH2CH3, —OCH2OCH3, —OCH2CH2CH3, —OCH(CH3)2, —SCH3, or —OCH2CH2OCH3;

each Q1 and Q4 is independently —CH═CH—, —CH2-, —CH2O—, —CH2S—, —CH2CH2-, —CH2CF2-, —CH2NH2-, —CH2NH(CH3)-, or —CH2N(C(═O)CH3)-;

each Q2 and Q3 is independently —O—, —S—, —CH2-, —CF2-, —NH—, —N(CH3)-, or —N(C(═O)CH3)-;

each X1, X2, X3, X4, and Xn is independently —OH, —SH, —O—, —S—, —NH2, —NHCH3, —NH(C(═O)CH3), —CH3, —CH2CH3, —CH2CH2CH3, —CH(CH3)2, —OCH3 or —OCH2CH3;

each Y1, Y2, Y3, Y4, and Yn is independently ═O, S, ═NH, or ═NCH3;

each A, A1, and A2 is independently —O—, —S—, —CH2-, —NH—, —N(CH3)- or —N(C(═O)CH3)-; and p=0, 1, 2, 3, 4, 5 or 6.

In one aspect, described herein is an in vitro-transcribed (IVT) mRNA sequence initiator comprising a compound of Formula (II) or a salt or solvate thereof:

Formula (II)

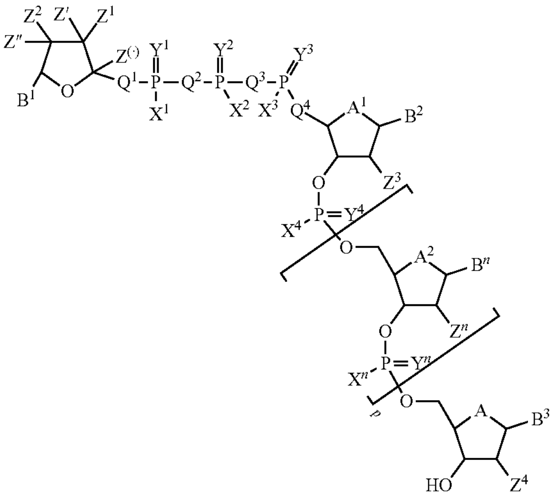

wherein

B1 is

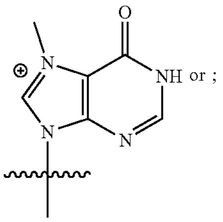 [SMILES: *n1c[n+](C)c2c(=O)[nH]cnc21]

each B2, B3, and Bn is independently a natural, a modified, or an unnatural nucleobase;

each Z' and Z" is independently is hydrogen, fluorine, —OH, —SH, —CH3, —CH2CH3, —OCH3, —NH(CH3), —NH2, —NH(C(═O)CH3), or —SCH3;

Z'" is hydrogen, fluorine, —CH3, —CH2CH3, —OCH3, or —OCH2CH3;

each Z1 and Z2 is independently hydrogen, fluorine, —OH, —SH, —CH3, —CH2CH3, —OCH3, —SCH3, —OCH2CH3, —NH2, NHCH3, or NHC(═O)CH3;

each Z3, Z4, and Zn is independently hydrogen, fluorine, —OH, —CH3, —CH2CH3, —OCH3, —NH2, —NHCH3, —NH(C(═O)CH3), —OCH2CH3, —OCH2OCH3, —OCH2CH2CH3, —OCH(CH3)2, —SCH3, or —OCH2CH2OCH3;

each Q1 and Q4 is independently —CH=CH—, —CH2-, —CH2O—, —CH2S—, —CH2CH2-, —CH2CF2-, —CH2NH2-, —CH2NH(CH3)-, or —CH2N(C(=O)CH3)-;

each Q2 and Q3 is independently —O—, —S—, —CH2-, —CF2-, —NH—, —N(CH3)-, or —N(C(=O)CH3)-;

each X1, X2, X3, X4, and Xn is independently —OH, —SH, —O—, —S—, —NH2, —NHCH3, —NH(C(=O)CH3), —CH3, —CH2CH3, —CH2CH2CH3, —CH(CH3)2, —OCH3 or —OCH2CH3;

each Y1, Y2, Y3, Y4, and Yn is independently =O, =S, —NH, or =NCH3;

each A, A1, and A2 is independently —O—, —S—, —CH2-, —NH—, —N(CH3)- or —N(C(=O)CH3)-; and p=0, 1, 2, 3, 4, 5 or 6.

In another aspect, Z3 is hydrogen, fluorine, —OH, —OCH3, - or —OCH2CH3. In another aspect, wherein Z3 is —OCH3. In another aspect, Z4 and Zn are independently —OH or —OCH3. In another aspect, each Z3, Z4, and Zn are independently —OH or —OCH3. In another aspect, Y2, Y4, and Yn are independently =O or =S. In another aspect, X2 and X3 are independently —O— or —S—.

In one aspect, described herein is an mRNA sequence having a 5'-end region motif (I'):

Motif (I')

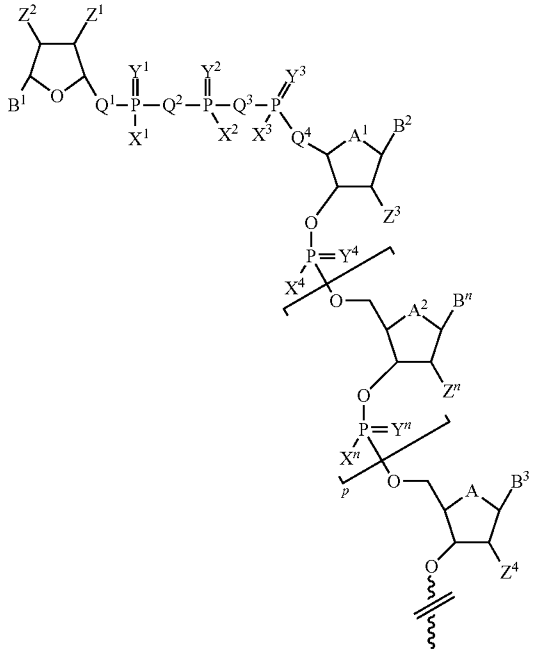

wherein

B1 is

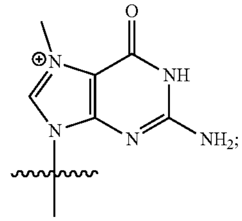 [SMILES: *n1c[n+](C)c2c(=O)[nH]c(N)nc21]

each B2, B3, and Bn is independently a natural, a modified, or an unnatural nucleobase;

each Z1 and Z2 is independently hydrogen, fluorine, —OH, —SH, —CH3, —CH2CH3, —OCH3, —OCH2CH3, —SCH3, —NH2, NHCH3, or NHC(=O)CH3;

each Z3, Z4, and Zn is independently hydrogen, fluorine, —OH, —SH, —CH3, —CH2CH3, —OCH3, —NH2, —NHCH3, —NH(C(=O)CH3), —OCH2CH3, —OCH2OCH3, —OCH2CH2CH3, —OCH(CH3)2, —SCH3, or —OCH2CH2OCH3;

each Q1 and Q4 is independently —CH2-, —CH=CH—, —CH2O—, —CH2S—, —CH2CH2-, —CH2CF2-, —CH2NH2-, —CH2NH(CH3)-, or —CH2N(C(=O)CH3)-;

each Q2 and Q3 is independently —O—, —S—, —CH2-, —CF2-, —NH—, —N(CH3)-, or —N(C(=O)CH3)-;

each X1, X2, X3, X4, and Xn is independently —OH, —SH, —O—, —S—, —NH2, —NHCH3, —NH(C(=O)CH3), —CH3, —CH2CH3, —CH2CH2CH3, —CH(CH3)2, —OCH3, or —OCH2CH3;

each Y1, Y2, Y3, Y4, and Yn is independently =O, =S, =NH, or =NCH3;

each A, A1, and A2 is independently —O—, —S—, —CH2-, —NH—, —N(CH3)- or —N(C(=O)CH3)-; and p=0, 1, 2, 3, 4, 5 or 6, In another aspect, Formula (I) satisfies one or more of the following proviso (i) to (iii): (i) at least one of X1, X2, X3, X4, and Xn is —SH or —S—; (ii) at least one of Y1, Y2, Y3, Y4, and Yn is =S; and (iii) at least one of A, A1, and A2 is —S—. In another aspect, at least one of X1, X2, X3, X4, and Xn is —SH or —S—; at least one of Y1, Y2, Y3, Y4, and Yn is =S; or at least one of A, A1, and A2 is —S—.

In one aspect, described herein, an mRNA sequence having a 5'end region motif (II'):

Motif (II')

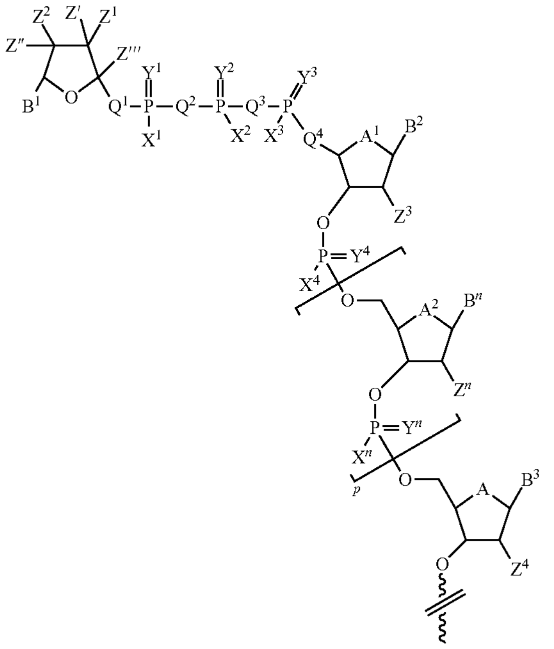

wherein

B1 is

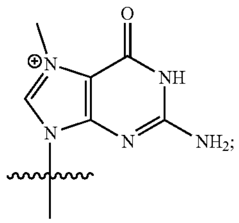 [SMILES: *n1c[n+](C)c2c(=O)[nH]c(N)nc21]

each B2, B3, and Bn is independently a natural, a modified, or an unnatural nucleobase;

each Z1 and Z' is independently is hydrogen, fluorine, —OH, —SH, —CH3, —CH2CH3, —OCH3, —NH(CH3), —NH2, —NH(C(═O)CH3), or —SCH3;

each Z2 and Z" is independently fluorine, —OH, —SH, —CH3, —CH2CH3, —OCH3, —SCH3, —OCH2CH3, —NH2, NHCH3, or NHC(═O)CH3;

Z'" is hydrogen, fluorine, —CH3; —CH2CH3, —OCH3, or —OCH2CH3;

each Z3, Z4, and Zn is independently hydrogen, fluorine, —OH, —CH3, —CH2CH3, —OCH3, —NH2, —NHCH3, —NH(C(═O)CH3), —OCH2CH3, —OCH2OCH3, —OCH2CH2CH3, —OCH(CH3)2, —SCH3, or —OCH2CH2OCH3;

each Q1 and Q4 is independently —CH═CH—, —CH2-, —CH2O—, —CH2S—, —CH2CH2-, —CH2CF2-, —CH2NH2-, —CH2NH(CH3)-, or —CH2N(C(═O)CH3)-;

each Q2 and Q3 is independently —O—, —S—, —CH2-, —CF2-, —NH—, —N(CH3)-, or —N(C(═O)CH3)-;

each X1, X2, X3, X4, and Xn is independently —OH, —SH, —O—, —S—, —NH2, —NHCH3, —NH(C(═O)CH3), —CH3, —CH2CH3, —CH2CH2CH3, —CH(CH3)2, —OCH3 or —OCH2CH3;

each Y1, Y2, Y3, Y4, and Yn is independently ═O, ═S, ═NH, or ═NCH3;

each A, A1, and A2 is independently —O—, —S—, —CH2-, —NH—, —N(CH3)- or —N(C(═O)CH3)-; and p=0, 1, 2, 3, 4, 5 or 6.

In one aspect, described herein, an mRNA sequence having a 5'-end region motif (II"):

Motif (II")

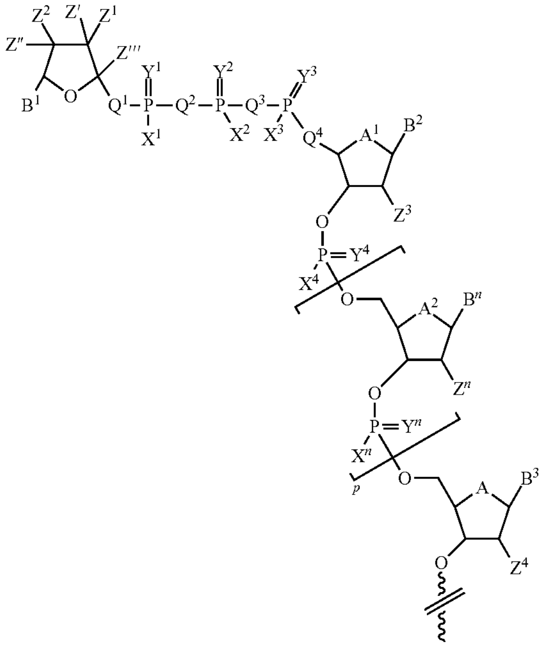

wherein

B1 is

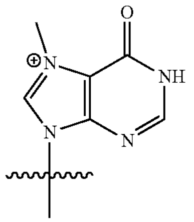

or

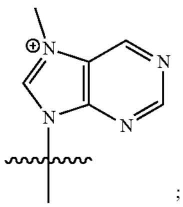

;

each B2, B3, and Bn is independently a natural, a modified, or an unnatural nucleobase;

each Z' and Z" is independently is hydrogen, fluorine, —OH, —SH, —CH3, —CH2CH3, —OCH3, —NH(CH3), —NH2, —NH(C(═O)CH3), or —SCH3;

Z'" is hydrogen, fluorine, —CH3, —CH2CH3, —OCH3, or —OCH2CH3;

each Z1 and Z2 is independently hydrogen, fluorine, —OH, —SH, —CH3, —CH2CH3, —OCH3, —SCH3, —OCH2CH3, —NH2, NHCH3, or NHC(═O)CH3;

each Z3, Z4, and Zn is independently hydrogen, fluorine, —OH, —CH3, —CH2CH3, —OCH3, —NH2, —NHCH3, —NH(C(═O)CH3), —OCH2CH3, —OCH2OCH3, —OCH2CH2CH3, —OCH(CH3)2, —SCH3, or —OCH2CH2OCH3;

each Q1 and Q4 is independently —CH═CH—, —CH2-, —CH2O—, —CH2S—, —CH2CH2-, —CH2CF2-, —CH2NH2-, —CH2NH(CH3)-, or —CH2N(C(═O)CH3)-;

each Q2 and Q3 is independently —O—, —S—, —CH2-, —CF2-, —NH—, —N(CH3)-, or —N(C(═O)CH3)-;

each X1, X2, X3, X4, and Xn is independently —OH, —SH, —O—, —S—, —NH2, —NHCH3, —NH(C(═O)CH3), —CH3, —CH2CH3, —CH2CH2CH3, —CH(CH3)2, —OCH3 or —OCH2CH3;

each Y1, Y2, Y3, Y4, and Yn is independently ═O, ═S, ═NH, or ═NCH3;

each A, A1, and A2 is independently —O—, —S—, —CH2-, —NH—, —N(CH3)- or —N(C(═O)CH3)-; and p=0, 1, 2, 3, 4, 5 or 6.

In one aspect, described herein is a mRNA sequence having a 5'-end region motif, wherein the 5'-end region motif is a compound from Table 1, or a salt or solvate thereof.

In another aspect, described herein is a mRNA sequence having a 5'-end region motif, wherein the 5'-end region motif is a compound from Table 2, or a salt or solvate thereof.

In another aspect, described herein is a mRNA sequence having a 5'-end region motif, wherein the 5'-end region motif is a compound from Table 3, or a salt or solvate thereof.

In another aspect of the mRNA sequence having a 5'-end region motif, $Z^3$ is hydrogen, fluorine, —OH, —$OCH_3$, — or —$OCH_2CH_3$.

In another aspect of the mRNA sequence having a 5'-end region, $Z^3$ is —$OCH_3$.

In another aspect of the mRNA sequence having a 5'-end region motif, each $Z^4$ and $Z''$ is independently —OH or —$OCH_3$.

In another aspect of the mRNA sequence having a 5'-end region motif, each $Z^3$, $Z^4$, and $Z''$ is independently —OH or —$OCH_3$.

In another aspect of the mRNA sequence having a 5'-end region motif, $B^1$ is

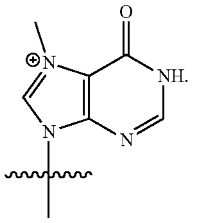 [SMILES: *n1c[n+](C)c2c(=O)[nH]cnc21]

In another aspect of the mRNA sequence having a 5'-end region motif, $B^1$ is

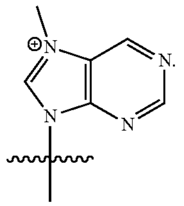 [SMILES: *n1c[n+](C)c2cncnc21]

In another aspect of the mRNA sequence having a 5'-end region motif, $B^1$ is

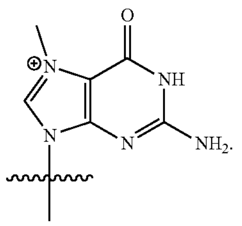 [SMILES: *n1c[n+](C)c2c(=O)[nH]c(N)nc21]

In another aspect of the mRNA sequence having a 5'-end region motif, $Z^1$ is fluorine, —OH, or —OCH3.

In another aspect of the mRNA sequence having a 5'-end region motif, $Z^1$ is fluorine.

In another aspect of the mRNA sequence having a 5'-end region motif, $Z^1$ is —OH.

In another aspect of the mRNA sequence having a 5'-end region motif, $Z^1$ is —$OCH_3$.

In another aspect of the mRNA sequence having a 5'-end region motif, $Z^2$ is fluorine, —OH, or —$OCH_3$.

In another aspect of the mRNA sequence having a 5'-end region motif, $Z^2$ is fluorine.

In another aspect of the mRNA sequence having a 5'-end region motif, $Z^2$ is —OH.

In another aspect of the mRNA sequence having a 5'-end region motif, $Z^2$ is —$OCH_3$.

In another aspect of the mRNA sequence having a 5'-end region motif, $Q^1$ and $Q^4$ is —$CH_2O$—.

In another aspect of the mRNA sequence having a 5'-end region motif, each $Q^2$ and $Q^3$ is —O—

In another aspect of the mRNA sequence having a 5'-end region motif, each $Y^1$ and $Y^3$ is ═O.

In another aspect of the mRNA sequence having a 5'-end region motif, each $Y^2$, $Y^4$, and Yn is independently ═O or ═S.

In another aspect of the mRNA sequence having a 5'-end region motif, one or more of $Y^1$, $Y^2$, $Y^3$, $Y^4$, and $Y''$ is ═S.

In another aspect of the mRNA sequence having a 5'-end region motif, $Y^2$ is ═S.

In another aspect of the mRNA sequence having a 5'-end region motif, $Y^4$ is ═S.

In another aspect of the mRNA sequence having a 5'-end region motif, each $Y^1$, $Y^2$, $Y^3$, $Y^4$, and $Y''$ is ═O.

In another aspect of the mRNA sequence having a 5'-end region motif, each $X^1$, $X^4$, and $X''$ is —$O^-$.

In another aspect of the mRNA sequence having a 5'-end region motif, each $X^2$ and $X^3$ is independently —O or —S—.

In another aspect of the mRNA sequence having a 5'-end region motif, $X^3$ is —O.

In another aspect of the mRNA sequence having a 5'-end region motif, one or more of $X^1$, $X^2$, $X^3$, $X^4$, and $X''$ is —S.

In another aspect of the mRNA sequence having a 5'-end region motif, $X^2$ is —S—.

In another aspect of the mRNA sequence having a 5'-end region motif, $X^4$ is —S—.

In another aspect of the mRNA sequence having a 5'-end region motif, each $X^1$, $X^2$, $X^3$, $X^4$, and $X''$ is —O.

In another aspect of the mRNA sequence having a 5'-end region motif, each A, $A^1$, and $A^2$ is —O—.

In another aspect of the mRNA sequence having a 5'-end region motif, one or more of A, $A^1$, and $A^2$ is —S—.

In another aspect of the mRNA sequence having a 5'-end region motif, A is —S— and $A^1$ and $A^2$ is —O—.

In another aspect of the mRNA sequence having a 5'-end region motif, A2 is —S— and A and $A^1$ is —O—.

In another aspect of the mRNA sequence having a 5'-end region motif, A, $A^1$, and $A^2$ is —O—.

In another aspect of the mRNA sequence having a 5'-end region motif, p is 0.

In another aspect of the mRNA sequence having a 5'-end region motif, p is 1.

In another aspect of the mRNA sequence having a 5'-end region motif, p is 2.

In another aspect of the e mRNA sequence having a 5'-end region motif, wherein each B2, $B^3$, and $B''$ is independently adenine, cytosine, guanine, uracil, thymine, hypoxanthine, or purine.

In another aspect of the mRNA sequence having a 5'-end region motif, $B^2$ is adenine and $B^3$ is guanine.

In another aspect of the mRNA sequence having a 5'-end region motif, $B^2$ is guanine and $B^3$ is adenine.

In another aspect of the mRNA sequence having a 5'-end region motif, protein expression is increased.

In another aspect of the mRNA sequence having a 5'-end region motif, $Q^1$ and $Q^4$ are —$CH_2O$—; $Q^2$ and $Q^3$ are —O—; each $X''$ is independently —OH, —SH, O, or S; each $Y''$ is independently =O or =S; and $B^1$ is

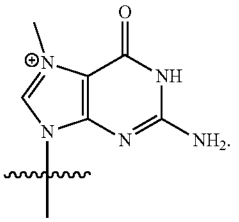 [SMILES: *n1c[n+](C)c2c(=O)[nH]c(N)nc21]

In another aspect of the mRNA sequence having a 5'-end region motif, $Q^1$ and $Q^4$ are —$CH_2O$—; $Q^2$ and $Q^3$ are —O—; each $X''$ is independently —OH, —SH, $O''$, or S; each $Y''$ is independently =O or =S; and $B^1$ is

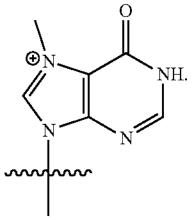 [SMILES: *n1c[n+](C)c2c(=O)[nH]cnc21]

In another aspect of the mRNA sequence having a 5'-end region motif, $Q^1$ and $Q^4$ are —$CH_2O$—; $Q^2$ and $Q^3$ are —O—; each $X''$ is independently —OH, —SH, $O^-$, or $S^-$; each $Y''$ is independently =O or =S; and $B^1$ is

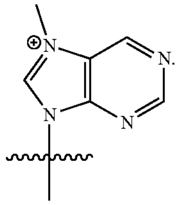 [SMILES: *n1c[n+](C)c2cncnc21]

In another aspect, described herein is a complex comprising an mRNA sequence having a 5'end region motif and a DNA template, wherein the mRNA sequence having a 5'-end region motif comprises a compound described herein, wherein the DNA template comprises a promoter region comprising a transcriptional start site having a first nucleotide at nucleotide position +1, a second nucleotide at nucleotide position +2, and a third nucleotide at nucleotide position +3; and wherein the mRNA sequence having a 5'-end region motif is hybridized to the DNA template at least at nucleotide positions +1, +2, and +3.

In another aspect, described herein is a complex comprising an mRNA sequence having a 5'-end region motif and a DNA template, wherein the mRNA sequence having a 5'end region motif comprises a compound described herein, wherein the DNA template comprises a promoter region comprising a transcriptional start site having a first nucleotide at nucleotide position +1 and a second nucleotide at nucleotide position +2; and wherein the mRNA sequence having a 5'-end region motif is hybridized to the DNA template at least at nucleotide positions +1 and +2.

In another aspect, described herein is a RNA molecule comprising the mRNA sequence having a 5'-end region motif. In another aspect, the RNA comprises a guide RNA or a nuclease mRNA. In another aspect, the RNA comprises an mRNA.

In another aspect, described herein is a method of expressing an mRNA comprising introducing the mRNA described herein into a cell lysate to express the mRNA. In another aspect, the method further comprises measuring the expression level of the mRNA. In another aspect, described herein in the method, the expression level of the mRNA is at least 2-fold, 3-fold, 4-fold, 6-fold, 8-fold, or 20-fold greater compared to a corresponding mRNA without the mRNA sequence having a 5'-end region motif. In another aspect, described herein, the method involves a HeLa cell.

In another aspect, described herein is a method of detecting cellular immune stimulation resulting from mRNA comprising (a) contacting a formulation comprising capped mRNA according the compounds described herein with a cell reporter line and (b) measuring RIG-I activation in said cell reporter line. In another aspect, the reporter line is HEK-Lucia RIG-I model. In another aspect, described herein the cellular immune stimulation is reduced compared to an uncapped mRNA by at least 20%, 50%, 70%, 100%, and 150%.

In another aspect, described herein is a method of producing an mRNA sequence having a 5'-end region motif described herein using an IVT reaction comprising (a) mixing a DNA template, polymerase enzyme, mRNA sequence motif comprising a phosphorothioate group (PS), and nucleoside triphosphates (NTPs) at a specified molar ratio of said mRNA sequence motif to said NTP to generate a mixture (b) incubating said mixture at a specified temperature and duration and (c) harvesting and purifying said mRNA sequence having a 5'-end region motif from said mixture. In another aspect, the molar ratio is 1:5, and the method is capable of producing a yield of at least 80% with a capping efficiency of at least 80%. In another aspect, the molar ratio is 1:2.5, and the method is capable of producing a yield of at least 80% with a capping efficiency of at least 85%. In another aspect, the molar ratio is 1:1.67, and the method is capable of producing a yield of at least 80% with a capping efficiency of at least 90%. In another aspect, the molar ratio is 1:1.25, and the method is capable of producing a yield of at least 80% with a capping efficiency of at least 90%. In another aspect, the molar ratio is 1.0:1.0, and the method is capable of producing a yield of at least 80% with a capping efficiency of at least 80%. In another aspect, the molar ratio is 1:5, and the method is capable of producing a yield of at least 3 mg of mRNA per milliliter (mL) of IVT reaction with a capping efficiency of at least 80%. In another aspect, the molar ratio is 1:2.5, and the method is capable of producing a yield of at least 3 mg of mRNA per milliliter (mL) of IVT reaction with a capping efficiency of at least 85%. In another aspect, the molar ratio is 1:1.67, and the method is capable of producing a yield of at least 3 mg of mRNA per milliliter (mL) of IVT reaction with a capping efficiency of at least 90%. In another aspect, the molar ratio is 1:1.25, and the method is capable of producing a yield of at least 3 mg of mRNA per milliliter (mL) of IVT reaction with a capping efficiency of at least 90%. In another aspect, the molar ratio is 1.0:1.0, and the method is capable of producing a yield of at least 3 mg of mRNA per milliliter (mL) of IVT reaction with a capping efficiency of at least 80%. In another aspect, the NTP is GTP, ATP, CTP, UTP, a modified NTP, or a combination thereof. In another aspect, the modified NTP is N1-methyl pseudoridine.

In another aspect, described herein is cell containing an RNA molecule comprising the mRNA sequence having a 5'end region motif described herein.

In another aspect, described herein is a cell containing a polypeptide translated from an RNA molecule comprising the mRNA sequence having a 5'end region motif described herein.

In another aspect, described herein is a pharmaceutical composition comprising an RNA molecule comprising the mRNA sequence having a 5'end region motif described herein and one or more of pharmaceutically acceptable excipients. In another aspect, the pharmaceutical comprises lipid nanoparticles. In another aspect, the pharmaceutical composition is encapsulated in a-lipid nanoparticle. In another aspect, the pharmaceutical composition further comprises one or more single guide RNAs designed to target one or more specific locations of one or more genes of interest to elicit pharmacological effect upon administration into a mammal.

In another aspect, described herein is a method for synthesizing an RNA molecule comprising: introducing the mRNA sequence having a 5'end region motif described herein into a mixture comprising an RNA polymerase, and incubating the mixture for a time sufficient to allow for transcription of the RNA molecule. In another aspect, the mixture further comprises a DNA template and nucleoside triophosphates.

In another aspect, described herein is a method of gene editing comprising introducing into a cell an RNA molecule, or pharmaceutical composition, wherein the RNA molecule comprises guide RNA or a nuclease mRNA, wherein the RNA molecule is translated in the cell.

In another aspect, described herein is a method for reducing the risk of coronary disease in a subject in need thereof, comprising administering to the subject an effective amount of a pharmaceutical composition described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Novel features of the invention are set forth with particularity in the appended claims and embodied in the mRNA 5' end-region structures described herein. A better understanding of the features and advantages of the present invention will be obtained by reference to the detailed description that sets forth illustrative embodiments of the 5' end-region structures or compounds (sometimes referred herein as motifs) in which the principles of the inventions are utilized, and the accompany drawings of which:

FIG. 1A shows phosophorothioate-modified 5' end initiators and the corresponding in vitro transcribed mRNAs with 5' end region motifs identified in the specification as 1007a.

FIG. 1B shows phosophorothioate-modified 5' end initiators and the corresponding in vitro transcribed mRNAs with 5' end region motifs identified in the specification as 1107a.

DETAILED DESCRIPTION

Figure 1A:
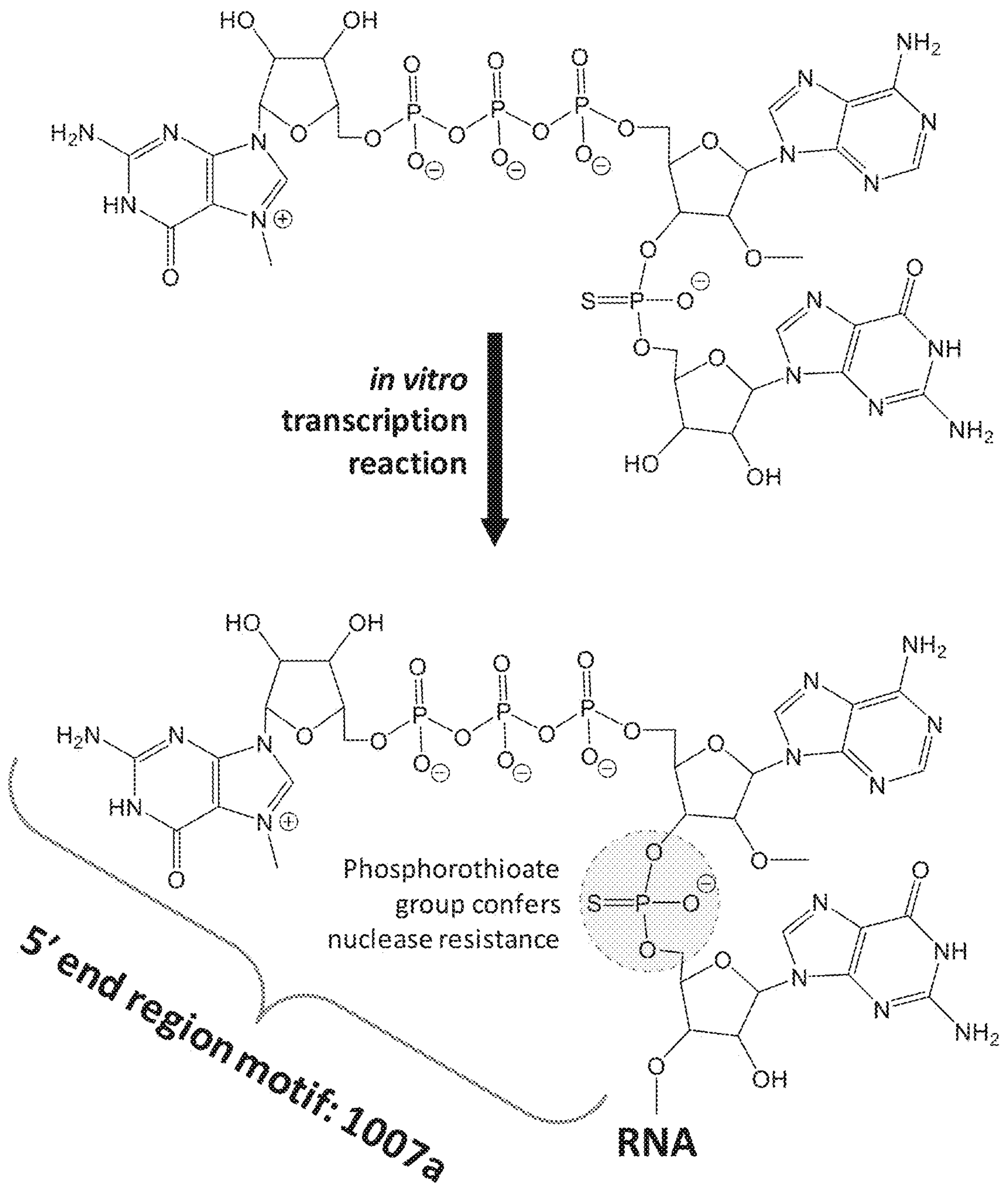

Certain specific details of this description are set forth in order to provide a thorough understanding of various embodiments. However, one skilled in the art will understand that the present disclosure may be practiced without these details. In other instances, well-known structures and/or methods have not been shown or described in detail to avoid unnecessarily obscuring descriptions of the embodiments. Unless the context requires otherwise, throughout the specification and claims which follow, the word “comprise” and variations thereof, such as, “comprises” and “comprising” are to be construed in an open, inclusive sense, that is, as “including, but not limited to.” Further, headings provided herein are for convenience only and do not interpret the scope or meaning of the claimed disclosure. The section headings used herein are for organizational purposes only and are not to be construed as limiting the subject matter described.

Messenger RNA (mRNA), encoding physiologically important proteins for therapeutic applications, has shown significant advantages over DNA-based plasmid and viral vectors for delivering genetic material. Such important advantages include: (i) potentially improved levels of safety when compared to the potential genome damage that can result from viral or plasmid integration, (ii) more immediate protein expression upon mRNA delivery (unlike delayed responses that generally occur with plasmids), (iii) robust dose-dependent control over expression of proteins, and (iv) is capable of facilitating simplification of large scale synthesis of mRNAs as compared to manufacturing of plasmid and viral vectors.

Messenger RNAs can be encoded for virtually any known protein and can be delivered to specific cells, tissues and organs by a variety of methods known to those skilled in the art. Once delivered, such mRNAs are capable of direct ribosomal protein expression within targeted cell or tissue resulting in the production of potentially many hundreds copies of the encoded proteins from a single mRNA molecule.

Several structural elements, present in active mRNA molecule, are utilized to translate the encoded proteins efficiently. One of these elements is the 5'-end region of mRNAs. In naturally occurring mRNA, the 5' end-region comprises a Cap structure, which is an important feature of eukaryotic mRNA molecules (and some viruses). Such Cap structures are known to be involved in protein translation, 5' exonuclease protection, splicing, and mRNA transport. A consistent structural element of a naturally occurring 5' Cap is an inverted 7-methylguanosine ($m^7G$) linked at the 5' end of the mRNA through a triphosphate (ppp) bridge, and this phosphate bridge is linked to the first nucleotide ($N_1$) of the mRNA transcript. This 5' Cap moiety generally represented by $m^7G(ppp)N_1$ is called cap-0. Methylation of the 2'-hydroxyl on N1 ribose ring (i.e., cap-1) is known to be capable of providing an identifier of self-RNA, which thereby serves to shield the mRNA from the innate immune system, which in turn is capable of improving protein expression. This $m^7G(ppp)N_1m$ cap-1 structure is a known conventional cap moiety used in in vitro transcription (IVT) of mRNAs.

Here we present novel mRNA 5' end region motifs and initiators. These novel designs include modification of the purine base of the $m^7G$ moiety; phosphorothioate (PS) substitution in the triphosphate bridge and chemical modifications of phosphodiester linkages, substitution of the 5' end region nucleotides with non-canonical bases, extension of the 5' end region nucleotide oligomer, as well as chemical modification of the ribose rings. Specifically, these mRNA 5' end region structures serve as the terminal 5' end region of an mRNA and provide stability to the mRNA. The chemical structures of the motifs are capable of facilitating and/or modulating mRNA activity and rates of translation initiation and elongation; protecting mRNA by creating a barrier that prevents or interferes with mRNA decapping by 5' exonuclease activity; impacting capping efficiency and reducing the formation of immune-stimulatory by-products, which can improve mRNA safety; and facilitating the mRNA manufacturability by modulating the binding affinity for DNA template during an IVT reaction.

Definitions

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All references cited herein are incorporated by reference in their entirety as though fully set forth. Singleton et al., Dictionary of Microbiology and Molecular Biology 3rd ed., J. Wiley & Sons (New York, NY 2001); March, Advanced Organic Chemistry Reactions, Mechanisms and Structure 5th ed., J. Wiley & Sons (New York, NY 2001); and Sambrook and Russel, Molecular Cloning: A Laboratory Manual 3rd ed., Cold Spring Harbor Laboratory Press (Cold Spring Harbor, NY 2001), provide one skilled in the art with a general guide to many of the terms used in the present application.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

When indicating the number of substituents, the term "one or more" refers to the range from one substituent to the highest possible number of substitution, e.g. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "nucleic acid" as used herein generally refers to one or more nucleobases, nucleosides, or nucleotides, and the term includes polynucleobases, polynucleosides, and polynucleotides. A nucleic acid can include polynucleotides, mononucleotides, and oligonucleoitdes. A nucleic acid can include DNA, RNA, or a mixture thereof, and can be single stranded, double stranded, or partially single or double stranded, and can form secondary structures. In some embodiments, a nucleic acid has multiple double-stranded segments and single stranded segments. For example, a nucleic acid may comprise a polynucleotide, e.g. a mRNA, with multiple double stranded segments within it.

The terms "mRNA sequence initiator", "IVT mRNA sequence initiator" and "initiator" are used interchangeably herein to generally refer to a ribo- or deoxyribo- or chimeric ribo/deoxyribo-oligonucleotide, single stranded, may be naturally occurring or synthetic, and usually include a sequence of between about 2 to about 10 nucleotides, about 3 to about 8 nucleotides or about 3 to about 5 nucleotides. mRNA sequence initiators may contain one or more modification groups. mRNA sequence initiators may be primers, e.g. oligonucleotide primers. mRNA sequence initiators, for example, oligonucleotide primers, may include RNA, DNA, and/or other modified nucleosides. The skilled artisan is capable of designing and preparing mRNA sequence initiators that are appropriate for transcription of DNA template sequence.

mRNA sequence initiators may be capped primers or capped oligonucleotide analogs. For example, a capped mRNA sequence initiator may contain initiating capped oligonucleotide analogs or initiating capped oligonucleotides with Cap 0, Cap 1, Cap 2 or TMG-Cap structure on 5'-end. In some instances, a capped initiator, e.g., a capped primer or capped oligonucleotide analog has an unmodified or open 3'-OH group and it may be extended by RNA polymerase through the incorporation of an NTP onto the 3'-end. In some instances, an initiator as described herein can initiate in vitro transcription under the control of a promoter in a transcription system containing necessary components: DNA template (e.g. DNA plasmid), RNA polymerase, nucleoside 5'-triphosphates and appropriate buffer. An initiator may be a oligonucleotide carrying a terminal 3'-OH group that is a valid substrate for RNA polymerase. In certain embodiments, an initiator is a substrate for RNA polymerase and may be elongated by incorporation of NTP onto the 3'-end. In some embodiments, an initiator is complementary to the DNA template at the initiation site.

The term “unsubstituted” or “unmodified” in the context of mRNA sequence initiators and nucleoside triphosphates (NTPs) as used herein generally refers to an initiating capped initiator and NTPs that have not been modified.

The term “modified initiating capped initiator” as used herein generally refers to an initiating capped mRNA sequence initiator that contains one or more additional modification group(s) or moiety/moieties within the sequence initiator.

The term “modification group(s) or moiety/moeities” as used herein generally refers to any chemical moiety that may be attached or substituted to the mRNA sequence initiator, e.g., an initiating primer at locations, which include, but are not limited to, the sugar, nucleoside base, triphosphate bridge, and/or internucleotide phosphate (e.g., U.S. patent application No. 20070281308). The modification group of a capped initiator may be a group of any nature that is compatible with the process of transcription.

The term “internucleotide linkage” as used herein generally refers to the bond or bonds that connect two nucleosides of an initiator, e.g. an oligonucleotide primer or a nucleic acid and may be a natural phosphodiester linkage or a chemically modified nucleic acid backbone linkage.

The term “polynucleotide”, as used herein generally refers to a molecule comprising two or more linked nucleic acid subunits, e.g., nucleotides, and can be used interchangeably with “oligonucleotide”. For example, a polynucleotide may include one or more nucleotides selected from corresponding nucleosides carrying the nucleobase-adenine (A), cytosine (C), guanine (G), thymine (T) and uracil (U), or variants and combinations thereof. A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups. Ribonucleotides include nucleotides in which the sugar is ribose. Deoxyribonucleotides include nucleotides in which the sugar is deoxyribose. A nucleotide can be a nucleoside monophosphate, nucleoside diphosphate, nucleoside triphosphate or a nucleoside polyphosphate. For example, a nucleotide can be a deoxyribonucleoside polyphosphate, such as a deoxyribonucleoside triphosphate (dNTP), Exemplary dNTPs include deoxyadenosine triphosphate (dATP), deoxycytidine triphosphate (dCTP), deoxyguanosine triphosphate (dGTP), uridine triphosphate (dUTP) and deoxythymidine triphosphate (dTTP). dNTPs can also include detectable tags, such as luminescent tags or markers (e.g., fluorophores). For example, a nucleotide can be a purine (e.g., A or G, or variant thereof) or a pyrimidine (e.g., C, T or U, or variant thereof). In some examples, a polynucleotide is deoxyribonucleic acid (DNA), ribonucleic acid (RNA), or derivatives or variants thereof. Exemplary polynucleotides include, but are not limited to, short interfering RNA (siRNA), a microRNA (miRNA), a plasmid DNA (pDNA), a short hairpin RNA (shRNA), small nuclear RNA (snRNA), messenger RNA (mRNA), precursor mRNA (pre-mRNA), antisense RNA (asRNA), and heteronuclear RNA (hnRNA), and encompasses both the nucleotide sequence and any structural embodiments thereof, such as single-stranded, double-stranded, triple-stranded, helical, hairpin, stem loop, bulge, etc. In some cases, a polynucleotide is circular. A polynucleotide can have various lengths. For example, a polynucleotide can have a length of at least about 7 bases, 8 bases, 9 bases, 10 bases, 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. A polynucleotide can be isolated from a cell or a tissue. For example, polynucleotide sequences may comprise isolated and purified DNA/RNA molecules, synthetic DNA/RNA molecules, and/or synthetic DNA/RNA analogs.

Polynucleotides can include one or more nucleotide variants, including nonstandard nucleotide(s), non-natural nucleotide(s), nucleotide analog(s) and/or modified nucleotides including acrylic and carbocyclic nucleotides. Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 5-methyl-2-thiouracil, 3-(3-amino-3-N-2-carboxypropyl) uracil, (acp3)w, 2,6 diaminopurine and the like. In some cases, nucleotides may include modifications in their phosphate moieties, including modifications to a triphosphate moiety. Non-limiting examples of such modifications include phosphate chains of greater length (e.g., a phosphate chain having, 4, 5, 6, 7, 8, 9, 10 or more phosphate moieties) and modifications with thiol moieties (e.g., alpha-thiotriphosphate and beta-thiotriphosphates). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as amino ally 1-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A. Nat. Chem. Biol. 2012, 8 (7): 612-4, which is herein incorporated by reference for all purposes.

As used herein, the terms “polypeptide”, “protein” and “peptide” are used interchangeably and refer to a polymer of amino acid residues linked via peptide bonds and which may be composed of two or more polypeptide chains. The terms "polypeptide", "protein" and "peptide" refer to a polymer of at least two amino acid monomers joined together through amide bonds. An amino acid may be the L-optical isomer or the D-optical isomer. More specifically, the terms "polypeptide", "protein" and "peptide" refer to a molecule composed of two or more amino acids in a specific order; for example, the order as determined by the base sequence of nucleotides in the gene or RNA coding for the protein. Proteins are essential for the structure, function, and regulation of the body's cells, tissues, and organs, and each protein has unique functions. Examples are hormones, enzymes, antibodies, and any fragments thereof. In some cases, a protein can be a portion of the protein, for example, a domain, a subdomain, or a motif of the protein. In some cases, a protein can be a variant (or mutation) of the protein, wherein one or more amino acid residues are inserted into, deleted from, and/or substituted into the naturally occurring (or at least a known) amino acid sequence of the protein. A protein or a variant thereof can be naturally occurring or recombinant.

As used herein, "hybridize" refers to a process where initiating a capped mRNA sequence initiator anneals to a DNA template in accordance with Watson-Crick base pairing rules under appropriately stringent conditions during a transcription reaction. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to determine the appropriate stringency of hybridization/washing conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J, all of which are incorporated herein by reference in their entireties. In certain embodiments, hybridizations may occur between nucleic acid molecules of 20-100 nucleotides in length. In some embodiments, hybridization may occur between at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 consecutive nucleotides. In some embodiments, the hybridizing nucleic acid molecules may contain up to 1, 2, 3, 4, 5, 6, 7, 8, 9, 10, 11, 12, 13, 14, 15, 16, 17, 18, 19, or 20 mismatches that are tolerated.

As used herein, "complement," "complementary," or "complementarity" in the context of a complex of, for example, an initiating capped oligonucleotide primer and a DNA template refers to standard Watson/Crick base pairing rules. For example, the sequence "5'-A-G-T-C-3'" is complementary to the sequence "3'-T-C-A-G-5'." Certain non-natural or synthetic nucleotides may be included in the nucleic acids described herein; these include but not limited to, base and sugar modified nucleosides, nucleotides, and nucleic acids, such as inosine, 7-deazaguanosine, 2'-O-methylguanosine, 2'-fluoro-2'-deoxycytidine, pseudouridine, Locked Nucleic Acids (LNA), and Peptide Nucleic Acids (PNA). Complementarity does not need to be perfect; duplexes may contain mismatched base pairs, degenerative, or unmatched nucleotides. Those skilled in the art can determine duplex stability empirically considering a number of variables including, for example, the length of the oligonucleotide, base composition and sequence of the oligonucleotide, incidence of mismatched base pairs, ionic strength, components of the hybridization buffer and reaction conditions.

Complementarity may be "complete" or "total" where all of the nucleotide bases of two nucleic acid strands are matched according to recognized base pairing rules, it may be "partial" in which only some of the nucleotide bases of an capped mRNA sequence initiator and a DNA target are matched according to recognized base pairing rules or it may be "absent" where none of the nucleotide bases of two nucleic acid strands are matched according to recognized base pairing rules. The degree of complementarity between a capped mRNA sequence initiator, e.g. a capped primer, and a DNA template may have a significant effect on the strength of hybridization between the initiating capped oligonucleotide and the DNA template and correspondingly the efficiency of the reaction. The term complementarity may also be used in reference to individual nucleotides. For example, a particular nucleotide within an oligonucleotide may be noted for its complementarity, or lack thereof, to a nucleotide within another strand, in contrast or comparison to the complementarity between the rest of an capped mRNA sequence initiator and a DNA strand.

As used herein the term "complete", "total" or "perfectly" complementary means that each of the nucleotide bases of a capped mRNA sequence initiator and a DNA target are matched exactly according to recognized base pairing rules.

As used herein, the term "substantially complementary" refers to two sequences that hybridize under stringent hybridization conditions. Those skilled in the art will understand that substantially complementary sequences need not hybridize along their entire length. In particular, substantially complementary sequences may comprise a contiguous sequence of bases that do not hybridize to a target sequence and may be positioned 3' or 5' to a contiguous sequence of bases that hybridize under stringent hybridization conditions to the target sequence.

As used herein, the term "nucleoside" includes all naturally occurring nucleosides, including all forms of nucleoside bases and furanosides found in nature. Base rings most commonly found in naturally occurring nucleosides are purine and pyrimidine rings. Naturally occurring purine rings include, for example, adenine, guanine, and N6-methyladenine. Naturally occurring pyrimidine rings include, for example, cytosine, thymine, 5-methylcytosine, pseudouracyl. Naturally occurring nucleosides for example include, but are not limited to, ribo, 2'-O-methyl or 2'-deoxyribo derivatives of adenosine, guanosine, cytidine, thymidine, uridine, inosine, 7-methylguanosine or pseudouridine.

As used herein, the terms "nucleoside analogs," "modified nucleosides," or "nucleoside derivatives" include synthetic nucleosides as described herein. Nucleoside derivatives also include nucleosides having modified base or/and sugar moieties, with or without protecting groups and include, for example, 2'-deoxy-2'-fluorouridine, 5-fluorouridine and the like. The compounds and methods provided herein include such base rings and synthetic analogs thereof, as well as unnatural heterocycle-substituted base sugars, and acyclic substituted base sugars. Other nucleoside derivatives that may be utilized with the present disclosure include, for example, LNA nucleosides, halogen-substituted purines (e.g., 6-fluoropurine), halogen-substituted pyrimidines, $N^6$-cthyladenine, $N^4$-(alkyl)-cytosines, 5-ethylcytosine, and the like (U.S. Pat. No. 6,762,298).

As used herein, the terms "universal base," "degenerate base," "universal base analog" and "degenerate base analog" include, for example, a nucleoside analog with an artificial base which is, in certain embodiments, recognizable by RNA polymerase as a substitute for one of the natural NTPs (e.g., ATP, UTP, CTP and GTP) or other specific NTP. Universal bases or degenerate bases are disclosed in Loakes, D., *Nucleic Acids Res.,* 29:2437-2447 (2001); Crey-Desbiolles, C., et. al., *Nucleic Acids Res.,* 33:1532-1543 (2005); Kincaid, K., et. al., Nucleic Acids Res., 33:2620-2628 (2005); Preparata, F P, Oliver, J S, *J. Comput. Biol.* 753-765 (2004); and Hill, F., et. al., *Proc Natl Acad. Sci. USA,* 95:4258-4263 (1998)).

As used herein, the term "modified NTP" refers to a nucleoside 5'-triphosphate having a chemical moiety group bound at any position, including the sugar, base, triphosphate chain, or any combination of these three locations. Examples of such NTPs can be found, for example in "Nucleoside Triphosphates and Their Analogs: Chemistry, Biotechnology and Biological Applications," Vaghefi, M., ed., Taylor and Francis, Boca Raton (2005).

As used herein, the term "specific" when used in reference to a 5' capped mRNA sequence initiator sequence and its ability to hybridize to a DNA template is a sequence that has at least 50% sequence identity with a portion of the DNA template when the capped mRNA sequence initiator and DNA strand are aligned. Higher levels of sequence identity that may be preferred include at least 75%, at least 80%, at least 85%, at least 90%, at least 95%, at least 99%, and most preferable 100% sequence identity.

In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. The unmodified or natural nucleobases can be modified or replaced to provide oligonucleotides having improved properties. For example, nuclease resistant oligonucleotides can be prepared with these bases or with synthetic and natural nucleobases (e.g., inosine, xanthine, hypoxanthine, nubularine, isoguanisine, or tubercidine) and any one of the oligomer modifications described herein. Alternatively, substituted or modified analogs of any of the above bases and "universal bases" can be employed. When a natural base is replaced by a non-natural and/or universal base, the nucleotide is said to comprise a modified nucleobase and/or a nucleobase modification herein. Modified nucleobase and/or nucleobase modifications also include natural, non-natural and universal bases, which comprise conjugated moieties, e.g. a ligand described herein. Preferred conjugate moieties for conjugation with nucleobases include cationic amino groups which can be conjugated to the nucleobase via an appropriate alkyl, alkenyl or a linker with an amide linkage.

As used herein, "unmodified" or "natural" nucleobases include the purine bases adenine (A) and guanine (G), and the pyrimidine bases thymine (T), cytosine (C) and uracil (U). Exemplary modified nucleobases include, but are not limited to, other synthetic and natural nucleobases such as inosine, xanthine, hypoxanthine, nubularine, isoguanisine, tubercidine, 2-(halo)adenine, 2-(alkyl)adenine, 2-(propyl) adenine, 2-(amino)adenine, 2-(aminoalkyll)adenine, 2-(aminopropyl)adenine, 2-(methylthio)-N6-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino)adenine, 8-(halo)adenine, 8-(hydroxyl)adenine, 8-(thioalkyl)adenine, 8-(thiol)adenine, N6-(isopentyl)adenine, N6-(methyl)adenine, N6, N6-(dimethyl)adenine, 2-(alkyl)guanine,2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, N4-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl) uracil, 5-(guanidiniumalkyl)uracil, 5-(1,3-diazole-1-alkyl) uracil, 5-(cyanoalkyl)uracil, 5-(dialkylaminoalkyl)uracil, 5-(dimethylaminoalkyl)uracil, 5-(halo)uracil, 5-(methoxy) uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, dihydrouracil, N-(methyl)uracil, 5-uracil (i.e., pseudouracil), 2-(thio)pseudouracil,4-(thio)pseudouracil,2,4-(dithio)pseudouracil,5-(alkyl)pseudouracil, 5-(methyl) pseudouracil, 5-(alkyl)-2-(thio)pseudouracil, 5-(methyl)-2-(thio)pseudouracil, 5-(alkyl)-4-(thio)pseudouracil, 5-(methyl)-4-(thio)pseudouracil, 5-(alkyl)-2,4-(dithio) pseudouracil, 5-(methyl)-2,4-(dithio)pseudouracil, 1-methylpseudouracil (N1-methylpseudouracil), 1-substituted pseudouracil, 1-substituted 2 (thio)-pseudouracil, 1-substituted 4-(thio)pseudouracil, 1-substituted 2,4-(dithio) pseudouracil, 1-(aminocarbonylethylenyl)-pseudouracil, 1-(aminocarbonylethylenyl)-2 (thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylaminocarbonylethylenyl)-2 (thio)-pseudouracil, 1-(aminoalkylaminocarbonylethylenyl)-4-(thio)pseudouracil, 1-(aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted-1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl) isocarbostyrilyl, 5-(methyl) isocarbostyrilyl, 3-(methyl)-7-(propynyl) isocarbostyrilyl, 7-(aza) indolyl, 6-(methyl)-7-(aza) indolyl, imidizopyridinyl, 9-(methyl)-imidizopyridinyl, pyrrolopyrizinyl, isocarbostyrilyl, 7-(propynyl) isocarbostyrilyl, propynyl-7-(aza) indolyl, 2,4,5-(trimethyl)phenyl, 4-(methyl) indolyl, 4,6-(dimethyl) indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5-nitroindole, 3-nitropyrrole, 6-(aza)pyrimidine, 2-(amino) purine, 2,6-(diamino) purine, 5-substituted pyrimidines, N2-substituted purines, N6-substituted purines, 06-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ori/zo-substituted-6-phenyl-pyrrolo-pyrimidin-2-on-3-yl, bis-ori/zo-substituted-6-phenyl-pyrrolo-pyrimidin-2-on-3-yl, para-(aminoalkylhydroxy)-6-phenyl-pyrrolo-pyrimidin-2-on-3-yl, ori/zo-(aminoalkylhydroxy)-6-phenyl-pyrrolo-pyrimidin-2-on-3-yl, bis-ori/zo-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof. Alternatively, substituted or modified analogs of any of the above bases and “universal bases” can be employed. A universal nucleobase is any nucleobase that can base pair with all of the four naturally occurring nucleobases without substantially affecting the melting behavior, recognition by intracellular enzymes or activity of the oligonucleotide duplex. Some exemplary universal nucleobases include, but are not limited to, 2,4-difluorotoluene, nitropyrrolyl, nitroindolyl, 8-aza-7-deazaadenine, 4-fluoro-6-methylbenzimidazle, 4-methylbenzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylinolyl, 4,6-dimethylindolyl, phenyl, napthalenyl, anthracenyl, phenanthracenyl, pyrenyl, stilbenyl, tetracenyl, pentacenyl, and structural derivatives thereof (see for example, Loakes, 2001, Nucleic Acids Research, 29, 2437-2447, incorporated herein by reference in its entirety). Further nucleobases include those disclosed in U.S. Pat. No. 3,687,808; those disclosed in International Application No. PCT U.S. Ser. No. 09/038,425, filed Mar. 26, 2009; those disclosed in the Concise Encyclopedia Of Polymer Science And Engineering, pages 858-859, Kroschwitz, J. I, ed. John Wiley & Sons, 1990; those disclosed by English et al, Angewandte Chemie, International Edition, 1991, 30, 613; those disclosed in Modified Nucleosides in Biochemistry, Biotechnology and Medicine, Herdewijin, P. Ed. Wiley-VCH, 2008; and those disclosed by Sanghvi, Y. S., Chapter 15, dsRNA Research and Applications, pages 289-302, Crooke, S. T. and Lebleu, B., Eds., CRC Press, 1993. Contents of all of the above are herein incorporated by reference.

As used herein, the term “biological sample” means any biological material from which polynucleotides, polypeptides, biomarkers, and/or metabolites can be prepared or can be extracted out and examined. Non-limiting examples encompasses whole blood, plasma, saliva, check swab, fecal specimen, urine specimen, cell mass, or any other bodily fluid or tissue.

The terms “administer,” “administering”, “administration,” and the like, as used herein, refer to the methods that may be used to enable delivery of compounds or compositions to the desired site of biological action. These methods include, but are not limited to oral routes (p.o.), intraduodenal routes (i.d.), parenteral injection (including intravenous (i.v.), subcutaneous (s.c.), intraperitoneal (i.p.), intramuscular (i.m.), intravascular or infusion (inf.)), topical (top.) and rectal (p.r.) administration. Those of skill in the art are familiar with administration techniques that can be employed with the compounds and methods described herein. In some embodiments, the compounds and compositions described herein are administered orally.

The terms “co-administration” or the like, as used herein, are meant to encompass administration of the selected therapeutic agents to a single patient, and are intended to include treatment regimens in which the agents are administered by the same or different route of administration or at the same or different time.

The terms “effective amount” or “therapeutically effective amount,” as used herein, refer to a sufficient amount of an agent or a compound being administered which will relieve to some extent one or more of the symptoms of the disease or condition being treated; for example a reduction and/or alleviation of one or more signs, symptoms, or causes of a disease, or any other desired alteration of a biological system. For example, an “effective amount” for therapeutic uses can be an amount of an agent that provides a clinically significant decrease in one or more disease symptoms. An appropriate “effective” amount may be determined using techniques, such as a dose escalation study, in individual cases.

The terms “enhance” or “enhancing,” as used herein, means to increase or prolong either in amount, potency or duration a desired effect.

As used herein, “carbohydrate” refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include C5 and above (preferably C5-C8) sugars; di- and trisaccharides include sugars having two or three monosaccharide units (preferably C5-C8).

The term “monosaccharide” embraces radicals of allose, altrose, arabinose, cladinose, erythrose, erythrulose, fructose, D-fucitol, L-fucitol, fucosamine, fucose, fuculose, galactosamine, D-galactosaminitol, N-acetyl-galctosamine, galactose, glucosamine, N-acetyl-glucosamine, glucosaminitol, glucose, glucose-6-phosphate gulose glyceraldehyde, L-glycero-D-mannos-heprose, glycerol, glycerone, gulose idose, lyxose, mannosamine, mannose, mannose-6-phosphate, psicose, quinovose, quinovosamine, rhamnitol, rhamnosamine, rhamnose, ribose, ribulose, sedoheptulose, sorbose, tagatose, talose, tararic acid, throse, xylose and xylulose. The monosaccharide can be in D- or L-configuration. The monosaccharide may further be a deoxy sugar (alcoholic hydroxy group replaced by hydrogen), amino sugar (alcoholic hydroxy group replaced by amino group), a thio sugar (alcoholic hydroxy group replaced by thiol, or C—O replaced by C—S, or a ring oxygen of cyclic form replaced by sulfur), a seleno sugar, a telluro sugar, an aza sugar (ring carbon replaced by nitrogen), a imino sugar (ring oxygen replaced by nitrogen), a phosphano sugar (ring oxygen replaced with phosphorus), a phospha sugar (ring carbon replaced with phosphorus), a C-substituted monosaccharide (hydrogen at a non-terminal carbon atom replaced with carbon), an unsaturated monosaccharide, an alditol (carbonyl group replaced with CHOH group), aldonic acid (aldehydic group replaced by carboxy group), a ketoaldonic acid, a uronic acid, an aldaric acid, and so forth. Amino sugars include amino monosaccharides, preferably galactosamine, glusamine, mannosamine, fucosmine, quinavosamine, neuraminic acid, muramic acid, lactosediamine, acosamine, bacillosamine, daunosamine, desosamine, forosamine, garosamine, kanosamine, kanosamine, mycaminose, myosamine, persosamine, pneumosamine, purpurosamine, rhodosmine. It is understood that the monosaccharide and the like can be further substituted.

The terms "disaccharide", "trisaccharide" and "polysaccharide" embrace radicals of abequose, acrabose, amicetose, amylopectin, amylose, apiose, arcanose, ascarylose, ascorbic acid, boivinose, cellobiose, cellotriose, cellulose, chacotriose, chalcose, chitin, colitose, cyclodextrin, cymarose, dextrin, 2-deoxyribose, 2-deoxyglucose diginose, digitalose, digitoxose, evalose, evemitrose, fructooligosachharide, galto-oligosaccharide, gentianose, genitiobiose, glucan, gluicogen, glylcogen, hamamelose, heparin, inulin, isolevoglucosenone, isomaltose, isomaltotriose, isopanose, kojibiose, lactose, lactosamine, lactosediamine, laminarabiose, levoglucosan, levoglucosenone, β-maltose, maltriose, mannan-oligosaccharдie, amnninotriose, melezitose, melibiose, muramic acid, mycarose, mycinose, neuaminic acid, migerose, nojirimycon, noviose, oleandrose, panose, paratose, planteose, primeverose, raffinose, rhodone, rutinose, oleandrose, panose, paratose, plantcose, primeverose, raffinose, rhodinose, rutinose, sarmentose, sedoheptulose, sedoheptulosan, solatriose, sophorose, stachyose, streptose, sucrose, α,α-trehalose, trahalosamine, turanose, tyvelose, xylobiose, umbelliferose and the like. Further, it is understood that the "disaccharide", "trisaccharide" and "polysaccharide" and the like can further substituted. Disaccharide also includes amino sugars and their derivatives, particularly, a mycaminose derivatized a the C-4' position or a 4 deoxy-3-amino-glucose derivatized at the C-6' position.

The term "subject" or "patient" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human. The term "animal" as used herein comprises human beings and non-human animals. In one embodiment, a "non-human animal" is a mammal, for example a rodent such as rat or a mouse. In one embodiment, a non-human animal is a mouse.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically. The term "treating" further encompasses the concept of "prevent," "preventing," and "prevention," as stated below. It is appreciated that, although not precluded, treating a disorder or condition does not require that the disorder, condition, or symptoms associated therewith be completely eliminated.

The term "preventing" or "prevention" of a disease state denotes causing the clinical symptoms of the disease state not to develop in a subject that can be exposed to or predisposed to the disease state, but does not yet experience or display symptoms of the disease state.

The terms "pharmaceutical composition" and "pharmaceutical formulation" (or "formulation") are used interchangeably and denote a mixture or a solution comprising a therapeutically effective amount of an active pharmaceutical ingredient together with one or more pharmaceutically acceptable excipients to be administered to a subject, e.g., a human in need thereof.

The term "pharmaceutical combination" as used herein, means a product that results from mixing or combining more than one pharmaceutically active ingredient and includes both fixed and non-fixed combinations of the active ingredients. The term "fixed combination" means that the active ingredients, e.g., a compound described herein and a co agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., administration of three or more active ingredients.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use. "Pharmaceutically acceptable" can refer a material, such as a carrier or diluent, which does not abrogate the biological activity or properties of the compound, and is relatively nontoxic, e.g., the material may be administered to an individual without causing undesirable biological effects or interacting in a deleterious manner with any of the components of the composition in which it is contained.

The terms "pharmaceutically acceptable excipient", "pharmaceutically acceptable carrier", "pharmaceutically acceptable vehicle" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents, excipients, preservatives or lubricants used in formulating pharmaceutical products The term "base editing" and "base correction" are used interchangeably to indicate a base change or mutation at a target sequence within the target gene leading to base modification. In certain embodiments, base editing occurs at a single base of the target sequence. In preferred embodiments, base editing does not involve double strand breaks of the target sequence.

As used herein, the term "siRNA" refers to an agent that mediates the targeted cleavage of an RNA transcript. These agents associate with a cytoplasmic multi-protein complex known as RNAi-induced silencing complex (RISC). Agents that are effective in inducing RNA interference are also referred to as siRNA, RNAi agent, or iRNA agent, herein. As used herein, the term siRNA includes microRNAs and pre-microRNAs. As used herein, the terms "siRNA activity" and "RNAi activity" refer to gene silencing by an siRNA.

The term "2'-O-methoxyethyl" (also 2'-MOE, 2'-O($CH_2$)$_2$—$OCH_3$ and 2'-O-(2-methoxyethyl)) refers to an O-methoxy-ethyl modification of the 2' position of a furosyl ring. A 2'-O-methoxyethyl modified sugar is a modified sugar.

The term "2'-O-methoxyethyl nucleotide" means a nucleotide comprising a 2'-O-methoxyethyl modified sugar moiety.

The term "5-methylcytosine" means a cytosine modified with a methyl group attached to the 5' position. A 5-methylcytosine is a modified nucleobase.

The term "oxo" refers to the =O substituent.

The term "alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_8$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. In some embodiments, the alkyl is —$CH(CH_3)_2$ or —$C(CH_3)_3$. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —$CH_2$—, —$CH_2CH_2$—, or —$CH_2CH_2CH_2$—. In some embodiments, the alkylene is —$CH_2$—. In some embodiments, the alkylene is —$CH_2CH_2$—. In some embodiments, the alkylene is —$CH_2CH_2CH_2$—.

The term "alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

The term "alkylamino" refers to a radical of the formula —NHR or —NRR where each R is, independently, an alkyl radical as defined above. Unless stated otherwise specifically in the specification, an alkylamino group may be optionally substituted as described below.

The term "alkenyl" refers to a type of alkyl group in which at least one carbon-carbon double bond is present. In one embodiment, an alkenyl group has the formula —C(R)=$CR_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=$CH_2$, —$C(CH_3)$=$CH_2$, —CH=$CHCH_3$, —$C(CH_3)$—$CHCH_3$, and —$CH_2CH$=$CH_2$. Depending on the structure, an alkenyl group can be monovalent or divalent (i.e., an alkenylene group).

The term "alkynyl" refers to a type of alkyl group in which at least one carbon-carbon triple bond is present. Accordingly, "alkynylene" can refer to a divalent alkynyl group. In one embodiment, an alkenyl group has the formula —C=C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡$CCH_3$—C≡$CCH_2CH_3$, —$CH_2$C≡CH.

The term "aryl" refers to an aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be monovalent or divalent (i.e., an "arylene" group). Unless stated otherwise specifically in the specification, the term "aryl" or the prefix "ar-" (such as in "aralkyl") is meant to include aryl radicals that are optionally substituted. In some embodiments, an aryl group is partially reduced to form a cycloalkyl group defined herein. In some embodiments, an aryl group is fully reduced to form a cycloalkyl group defined herein. In some embodiments, an aryl group is a $C_6$-$C_{14}$ aryl. In some embodiments, an aryl group is a $C_6$-$C_{10}$ aryl.

The term "cycloalkyl" refers to a monocyclic or polycyclic non-aromatic radical, wherein each of the atoms forming the ring (i.e. skeletal atoms) is a carbon atom. In some embodiments, cycloalkyls are saturated or partially unsaturated. In some embodiments, cycloalkyls are spirocyclic or bridged compounds. In some embodiments, cycloalkyls are fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. In some embodiments, the monocyclic cycloalkyl is cyclopropyl, cyclobutyl, cyclopentyl or cyclohexyl. In some embodiments, the monocyclic cycloalkyl is cyclopentenyl or cyclohexenyl. In some embodiments, the monocyclic cycloalkyl is cyclopentenyl. Polycyclic radicals include, for example, adamantyl, 1,2-dihydronaphthalenyl, 1,4-dihydronaphthalenyl, tetrainyl, decalinyl, 3,4-dihydronaphthalenyl-1(2H)-one, spiro[2.2]pentyl, norbornyl and bicycle[1.1.1]pentyl. Unless otherwise stated specifically in the specification, a cycloalkyl group may be optionally substituted. Depending on the structure, a cycloalkyl group can be monovalent or divalent (i.e., a cycloalkylene group).

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms.

The term "heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkylene groups include, but are not limited to —$OCH_2CH_2O$—, —$OCH_2CH_2OCH_2CH_2O$—, or —$OCH_2CH_2OCH_2CH_2OCH_2CH_2O$—.

The term "heterocycloalkyl" refers to a cycloalkyl group that includes at least one heteroatom selected from nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of heterocycloalkyl radicals include, but are not limited to, dioxolanyl, thienyl[1,3]dithianyl, tetrahydroquinolyl, tetrahydroisoquinolyl, decahydroquinolyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 12 carbons in the ring. In some embodiments, heterocycloalkyls have from 2 to 10 carbons in the ring. In some embodiments, heterocycloalkyls have from 2 to 10 carbons in the ring and 1 or 2 N atoms. In some embodiments, heterocycloalkyls have from 2 to 10 carbons in the ring and 3 or 4 N atoms. In some embodiments, heterocycloalkyls have from 2 to 12 carbons, 0-2 N atoms, 0-2 O atoms, 0-2 P atoms, and 0-1 S atoms in the ring. In some embodiments, heterocycloalkyls have from 2 to 12 carbons, 1-3 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted. As used herein, the term "heterocycloalkylene" can refer to a divalent heterocycloalkyl group.

The term "heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-6 N atoms in the ring. In some embodiments, a heteroaryl contains 1-4 N atoms in the ring. In some embodiments, a heteroaryl contains 4-6 N atoms in the ring. In some embodiments, a heteroaryl contains 0-4 N atoms, 0-1 O atoms, 0-1 P atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$ heteroaryl. In some embodiments, monocyclic heteroaryl is a $C_1$-$C_5$ heteroaryl. In some embodiments, monocyclic heteroaryl is a 5-membered or 6-membered heteroaryl. In some embodiments, a bicyclic heteroaryl is a $C_6$-$C_9$ heteroaryl. In some embodiments, a heteroaryl group is partially reduced to form a heterocycloalkyl group defined herein. In some embodiments, a heteroaryl group is fully reduced to form a heterocycloalkyl group defined herein. Depending on the structure, a heteroaryl group can be monovalent or divalent (i.e., a "heteroarylene" group).

The term "substituted," "substituent" or the like, unless otherwise indicated, can refer to the replacement of one or more hydrogen radicals in a given structure individually and independently with the radical of a specified substituent including, but not limited to: D, halogen, —CN, —NH2, —NH(alkyl), —N(alkyl)$_2$, —OH, —$CO_2H$, —$CO_2$alkyl, —C(═O)NH2, —C(═O)NH(alkyl), —C(═O)N(alkyl)$_2$, —S(═O)$_2$NH$_2$, —S(═O)$_2$NH(alkyl), —S(═O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —$NH_2$, —NH($CH_3$), —N($CH_3$)$_2$, —OH, —$CO_2H$, —$CO_2$($C_1$-$C_4$ alkyl), —C(═O)$NH_2$, —C(═O)NH($C_1$-$C_4$ alkyl), —C(═O)N($C_1$-$C_4$ alkyl)$_2$, —S(═O)$_2$NH$_2$, —S(═O)$_2$NH($C_1$-$C_4$ alkyl), —S(═O)$_2$N($C_1$-$C_4$ alkyl)$_2$, $C_1$-$C_4$ alkyl, $C_3$-$C_6$ cycloalkyl, $C_1$-$C_4$ fluoroalkyl, $C_1$-$C_4$ heteroalkyl, $C_1$-$C_4$ alkoxy, $C_1$-$C_4$ fluoroalkoxy, —S$C_1$—$C_4$ alkyl, —S(═O)$C_1$-$C_4$ alkyl, and —S(═O)$_2$($C_1$-$C_4$ alkyl). In some embodiments, optional substituents are independently selected from D, halogen, —CN, —$NH_2$, —OH, —NH($CH_3$), —N($CH_3$)$_2$, —NH(cyclopropyl), —$CH_3$, —$CH_2CH_3$, —CF3, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (═O).

The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

"About" means within +10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can also be stated as the mass of pharmaceutical drug product or drug substance per mass of subject tissue (e.g., mg/kg or g/kg).

"Modified internucleoside linkage" refers to a substitution or any change from a naturally occurring internucleoside bond. For example, a phosphorothioate linkage is a modified internucleoside linkage.

"Modified nucleobase" refers to any nucleobase other than adenine, cytosine, guanine, thymidine, or uracil. For example, 5-methylcytosine is a modified nucleobase. An "unmodified nucleobase" means the purine bases adenine (A) and guanine (G), and the pyrimidine bases thymine (T), cytosine (C), and uracil (U).

"Modified nucleoside" means a nucleoside having at least one modified sugar moiety, and/or modified nucleobase.

"Modified nucleotide" means a nucleotide having at least one modified sugar moiety, modified internucleoside linkage and/or modified nucleobase.

"Modified oligonucleotide" means an oligonucleotide comprising at least one modified nucleotide.

"Modified sugar" refers to a substitution or change from a natural sugar. For example, a 2'-O-methoxyethyl modified sugar is a modified sugar.

"Motif" means the pattern of chemically distinct regions in an antisense compound.

"Statin" means an agent that inhibits the activity of HMG-COA reductase.

"Symptom of cardiovascular disease or disorder" means a phenomenon that arises from and accompanies the cardiovascular disease or disorder and serves as an indication of it. For example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever are symptoms of cardiovascular disease or disorder.

"Target nucleic acid," and "target sequence" refer to a nucleic acid capable of being targeted by a genome editing composition. For example, a target DNA sequence within or adjacent to the ANGPTL3 gene may be targeted by a guide nucleotide associated with a Cas9 nuclease.

Methods for detection and/or measurement of polypeptides in biological material are well known in the art and include, but are not limited to, Western-blotting, flow cytometry, ELISAs, RIAS, and various proteomics techniques. An exemplary method to measure or detect a polypeptide is an immunoassay, such as an ELISA. This type of protein quantitation can be based on an antibody capable of capturing a specific antigen, and a second antibody capable of detecting the captured antigen. Exemplary assays for detection and/or measurement of polypeptides are described in Harlow, E. and Lane, D. Antibodies: A Laboratory Manual, (1988), Cold Spring Harbor Laboratory Press.

Methods for detection and/or measurement of RNA in biological material are well known in the art and include, but are not limited to, Northern-blotting, RNA protection assay, RT PCR. Suitable methods are described in Molecular Cloning: A Laboratory Manual (Fourth Edition) By Michael R. Green, Joseph Sambrook, Peter MacCallum 2012, 2,028 pp, ISBN 978-1-936113-42-2.

A ribonucleoprotein (RNP) refers to a nucleoprotein that contains RNA. A RNP can be a complex of a ribonucleic acid and an RNA-binding protein. Such a combination can also be referred to as a protein-RNA complex. These complexes can function in a number of biological functions that include, but are not limited to, DNA replication, DNA modification, gene expression, metabolism and modification of RNA, and pre-mRNA splicing.

As used herein, the term "biomarker" or "marker" are used interchangeably to refer to any biochemical marker, serological marker, genetic marker, or other clinical or echographic characteristic that can be used to classify a sample from a patient as being associated with an pathological condition, such as a cardiovascular disease or disorder.

As used herein, the term "antibody" includes but is not limited to a population of immunoglobulin molecules, which can be polyclonal or monoclonal and of any class and isotype, or a fragment of an immunoglobulin molecule. There are five major classes of immunoglobulins: IgA, IgD, IgE, IgG, and IgM, and several of these may be further divided into subclasses (isotypes), e.g., IgG1, IgG2, IgG3, IgG4, IgA1 (human), IgA2 (human), IgAa (canine), IgAb (canine), IgAc (canine), and IgAd (canine). Such fragment generally comprises the portion of the antibody molecule that specifically binds an antigen. For example, a fragment of an immunoglobulin molecule known in the art as Fab, Fab' or F(ab')2 is included within the meaning of the term antibody.

The term "label," as used herein, refers to a detectable compound, composition, or solid support, which can be conjugated directly or indirectly (e.g., via covalent or non-covalent means, alone or encapsulated) to a monoclonal antibody or a protein. The label may be detectable by itself (e.g., radioisotope labels, chemiluminescent dye, electrochemical labels, metal chelates, latex particles, or fluorescent labels) or, in the case of an enzymatic label, may catalyze chemical alteration of a substrate compound or composition which is detectable (e.g., enzymes such as horseradish peroxidase, alkaline phosphatase, and the like). The label employed in the current disclosure could be, but is not limited to alkaline phosphatase; glucose-6-phosphate dehydrogenase ("G6PDH"); horseradish peroxidase (HRP); chemiluminescers such as isoluminol, fluorescers such as fluorescein and rhodamine compounds; ribozymes; and dyes. The label may also be a specific binding molecule which itself may be detectable (e.g., biotin, avidin, streptavidin, digioxigenin, maltose, oligohistidine, e.g., hex-histidine, 2, 4-dinitrobenzene, phenylarsenate, ssDNA, dsDNA, and the like). The utilization of a label produces a signal that may be detected by means such as detection of electromagnetic radiation or direct visualization, and that can optionally be measured.

"Substantial binding" or "substantially binding" refer to an amount of specific binding or recognizing between molecules in an assay mixture under particular assay conditions. In its broadest aspect, substantial binding relates to the difference between a first molecule's incapability of binding or recognizing a second molecule, and the first molecules capability of binding or recognizing a third molecule, such that the difference is sufficient to allow a meaningful assay to be conducted to distinguish specific binding under a particular set of assay conditions, which includes the relative concentrations of the molecules, and the time and temperature of an incubation. In another aspect, one molecule is substantially incapable of binding or recognizing another molecule in a cross-reactivity sense where the first molecule exhibits a reactivity for a second molecule that is less than 25%, e.g. less than 10%, e.g., less than 5% of the reactivity exhibited toward a third molecule under a particular set of assay conditions, which includes the relative concentration and incubation of the molecules. Specific binding can be tested using a number of widely known methods, e.g, an immunohistochemical assay, an enzyme-linked immunosorbent assay (ELISA), a radioimmunoassay (RIA), or a western blot assay.

As used herein, the term "substantially the same amino acid sequence" includes an amino acid sequence that is similar, but not identical to, the naturally-occurring amino acid sequence. For example, an amino acid sequence, e.g., polypeptide, that has substantially the same amino acid sequence as a flagellin protein can have one or more modifications such as amino acid additions, deletions, or substitutions relative to the amino acid sequence of the naturally-occurring flagellin protein, provided that the modified polypeptide retains substantially at least one biological activity of flagellin such as immunoreactivity. The "percentage similarity" between two sequences is a function of the number of positions that contain matching residues or conservative residues shared by the two sequences divided by the number of compared positions times 100. In this regard, conservative residues in a sequence is a residue that is physically or functionally similar to the corresponding reference residue, e.g., that has a similar size, shape, electric charge, chemical properties, including the ability to form covalent or hydrogen bonds, or the like.

The term "targeting moiety" refers to any molecule that provides an enhanced affinity for a selected target, e.g., a cell, cell type, tissue, organ, region of the body, or a compartment, e.g., a cellular, tissue or organ compartment. Some exemplary targeting moieties include, but are not limited to, antibodies, antigens, carbohydrate base moieties, folates, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands.

The term "heterologous" refers to any two or more nucleic acid or polypeptide sequences that are not normally found in the same relationship to each other in nature. For instance, a heterologous nucleic acid is typically recombinantly produced, having two or more sequences, e.g., from unrelated genes arranged to make a new functional nucleic acid, e.g., a promoter from one source and a coding region from another source. Similarly, a heterologous polypeptide will often refer to two or more subsequences that are not found in the same relationship to each other in nature (e.g., a fusion protein).

As used herein, the term "fragment" includes a peptide, polypeptide or protein segment of amino acids of the full-length protein, provided that the fragment retains reactivity with at least one antibody in sera of disease patients.

An "epitope" is the antigenic determinant on a polypeptide that is recognized for binding by a paratope on antibodies specific to the polypeptide, for example, an IBD-associated antibody.

The term "clinical factor" includes a symptom in a patient that is associated with a disease. Examples of clinical factors for cardiovascular disease include, without limitation, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever. In some embodiments, a diagnosis of a cardiovascular disease is based upon a combination of analyzing the presence or level of one or more markers in a patient using statistical algorithms and determining whether the patient has one or more clinical factors.

The term "prognosis" includes a prediction of the probable course and outcome of a pathological condition, for example a cardiovascular disease, or the likelihood of recovery from the disease. In some embodiments, the use of statistical algorithms provides a prognosis of cardiovascular disease in a patient. For example, the prognosis can be surgery, development of one or more clinical factors, development of intestinal cancer, or recovery from the disease.

The term "CRISPR-Cas system" referred herein includes a CRISPR-associated protein translated from an mRNA encoding the said protein and a single guide RNA. In some embodiments, the CRISPR-associated protein may have inherent endonucleolyitc activity. In some embodiments, the CRISPR-Cas system facilitate guide RNA mediated gene alteration. protein or proteins produced from protein-encoded mRNA can facilitate base or nucleobase and/or gene editing within a targeted segment of a gene of interest.

Provided herein are methods and compositions for targeted delivery of therapeutic agents such as nucleic acid agents. The therapeutic agents as used herein may be connected to or associated with a targeting moiety to assist targeted delivery. For example, the therapeutic agent and the targeting moiety may form a conjugate. The therapeutic agent may comprise a nucleic acid guided programmable nuclease system complexed with nucleic acids, such as guide RNAs. In some embodiments, the guide RNAs may be chemically modified. In some embodiments, the modified guide RNAs can be used for the preparation of a medicament for the treatment of any disease, disorder or condition relating to a gene where the gene may be altered, manipulated, edited, and modified by insertion or deletion of DNA. According to a further aspect of the disclosure, the modified guide RNA may be used for altering genes by deleting, substituting, repairing or inserting on or more nucleotide or a segment of DNA. This can be done in microorganisms, or animals, in particular mammals and more particularly in humans. Human cells or tissue may be genetically altered or amended using the guide RNAs of the present disclosure and the CRISPR/Cas system known in the art in vitro and then inserted back into the patient in need thereof. In another aspect of the disclosure there is provided a pharmaceutical composition comprising a modified guide RNA according to the disclosure and a CRISPR-Cas system and a pharmaceutically acceptable carrier or excipient. The pharmaceutical composition may include a vector or a cell with the modified guide RNA of the disclosure.

Compounds

In one aspect, described herein is an IVT mRNA sequence initiator of Formula (I) or a salt or solvate thereof:

Formula (I)

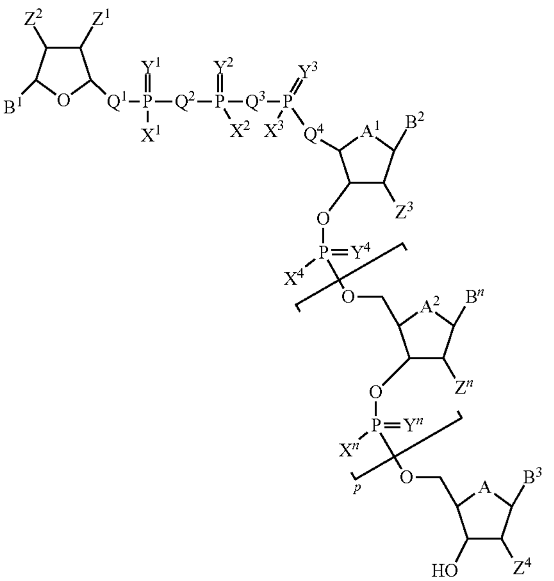

wherein $B^1$ is

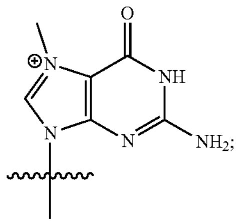 [SMILES: *n1c[n+](C)c2c(=O)[nH]c(N)nc21]

each $B^2$, $B^3$, and $B''$ is independently a natural, a modified, or an unnatural nucleobase;

each $Z^1$ and $Z^2$ is independently hydrogen, fluorine, —OH, —SH, —$CH_3$, —$CH_2CH_3$, —$OCH_3$, —$OCH_2CH_3$, —$SCH_3$, —$NH_2$, $NHCH_3$, or $NHC(=O)CH_3$;

each $Z^3$, $Z^4$, and $Z''$ is independently hydrogen, fluorine, —OH, —SH, —$CH_3$, —$CH_2CH_3$, —$OCH_3$, —$NH_2$, —$NHCH_3$, —$NH(C(=O)CH_3)$, —$OCH_2CH_3$, —$OCH_2OCH_3$, —$OCH_2CH_2CH_3$, —$OCH(CH_3)_2$, —$SCH_3$, or —$OCH_2CH_2OCH_3$;

each $Q^1$ and $Q^4$ is independently —$CH_2$—, —CH═CH—, —$CH_2O$—, —$CH_2S$—, —$CH_2CH_2$—, —$CH_2CF_2$—, —$CH_2NH_2$—, —$CH_2NH(CH_3)$—, or —$CH_2N(C(=O)CH_3)$—;

each $Q^2$ and $Q^3$ is independently —O—, —S—, —$CH_2$—, —$CF_2$—, —NH—, —$N(CH_3)$—, or —$N(C(=O)CH_3)$—;

each $X^1$, $X^2$, $X^3$, $X^4$, and $X''$ is independently —OH, —SH, —O, —S, —$NH_2$, —$NHCH_3$, —$NH(C(=O)CH_3)$, —$CH_3$, —$CH_2CH_3$, —$CH_2CH_2CH_3$, —$CH(CH_3)_2$, —$OCH_3$, or —$OCH_2CH_3$;

each $Y^1$, $Y^2$, $Y^3$, $Y^4$, and $Y''$ is independently ═O, ═S, ═NH, or ═$NCH_3$;

each A, A1, and A2 is independently —O—, —S—, —$CH_2$—, —NH—, —$N(CH_3)$— or —$N(C(=O)CH_3)$—; and p=0, 1, 2, 3, 4, 5 or 6, provided that (i) $Z^1$, $Z^2$, and $Z^3$ are hydrogen; (ii) $Q^1$ and $Q^4$ are —$CH_2O$—; (iii) $Q^2$ and $Q^3$ are oxygen; (iv) at least one of $X^1$, $X^2$, $X^3$, $X^4$, and $X''$ is —SH or —S—; (v) at least one of $Y^1$, $Y^2$, $Y^3$, $Y^4$, and $Y''$ is ═S; or (vi) at least one of A, $A^1$, and $A^2$ is —S—.

In some embodiments, the IVT mRNA sequence initiator has a structure of Formula (I-a):

Formula (I-a)

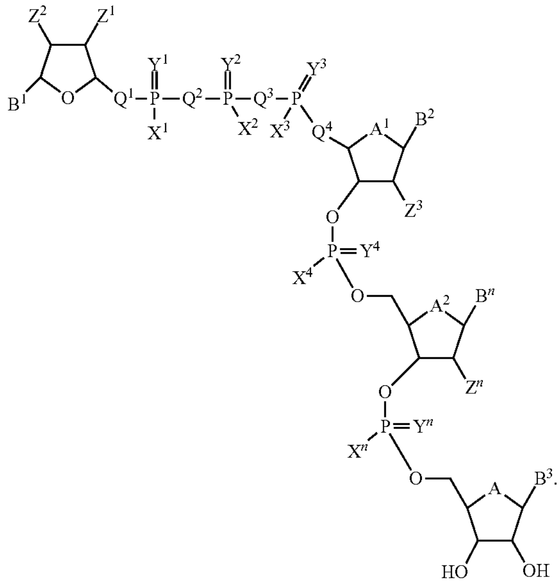

In some embodiments, the IVT mRNA sequence initiator has a structure of Formula (I-b):

Formula (I-b)

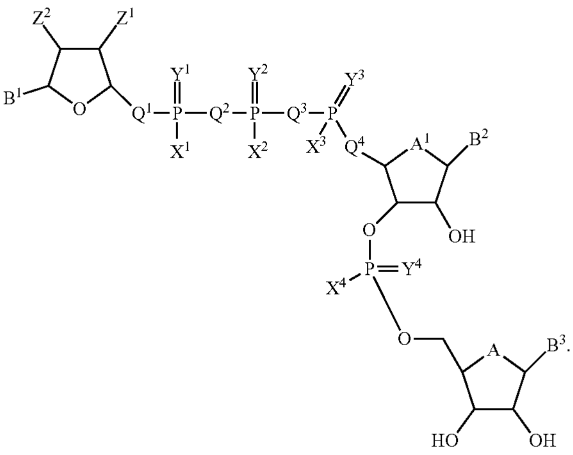

In some embodiments, the IVT mRNA sequence initiator has a structure of Formula (I-c):

Formula (I-c)

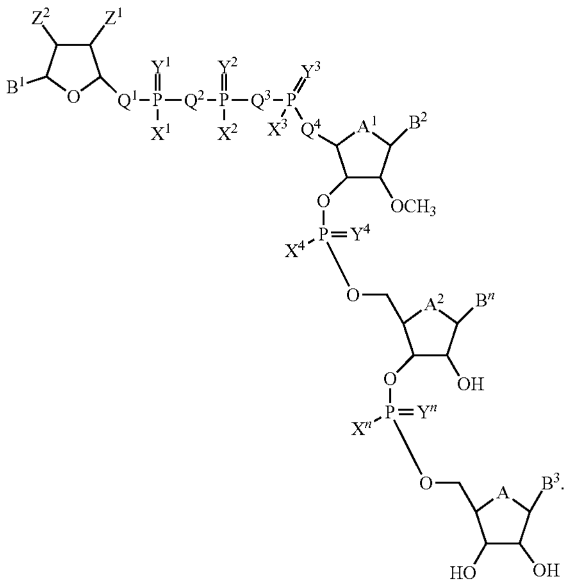

In some embodiments, the IVT mRNA sequence initiator has a structure of Formula (I-d):

Formula (I-d)

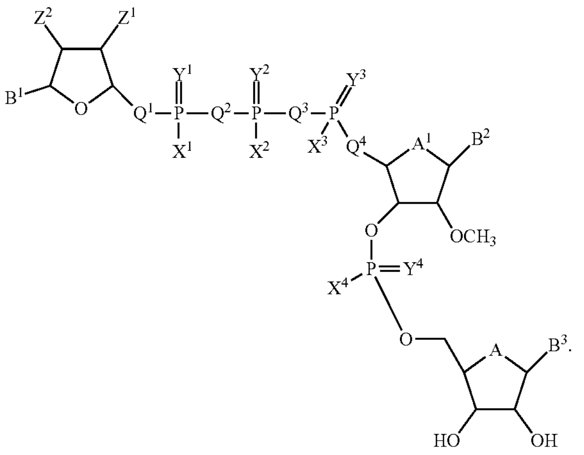

In some embodiments, the IVT mRNA sequence initiator has a structure of Formula (I-e):

Formula (I-e)

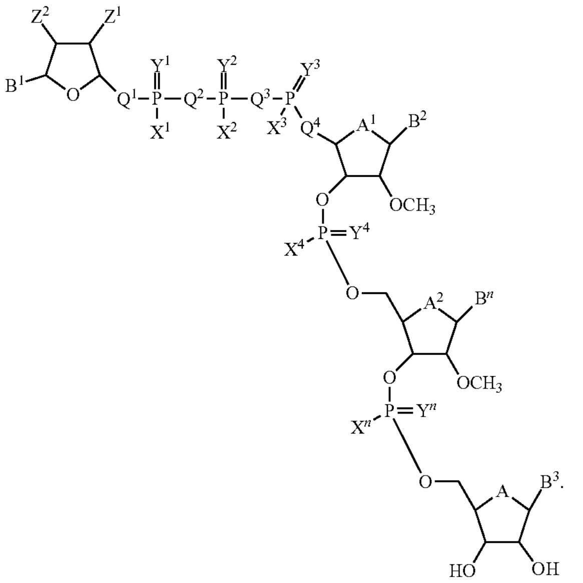

In some embodiments, the IVT mRNA sequence initiator has a structure of Formula (I-f):

Formula (I-f)

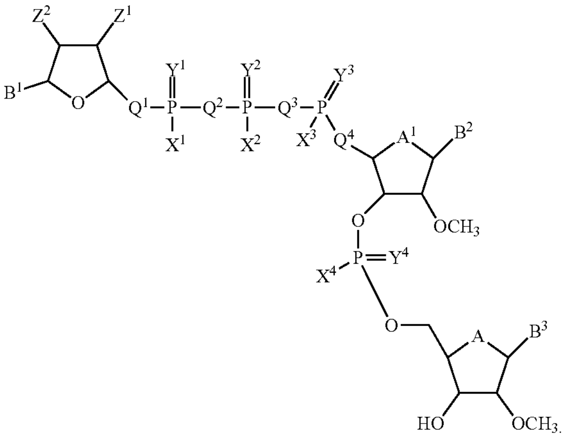

In some embodiments, the IVT mRNA sequence initiator has a structure of Formula (I-g):

Formula (I-g)

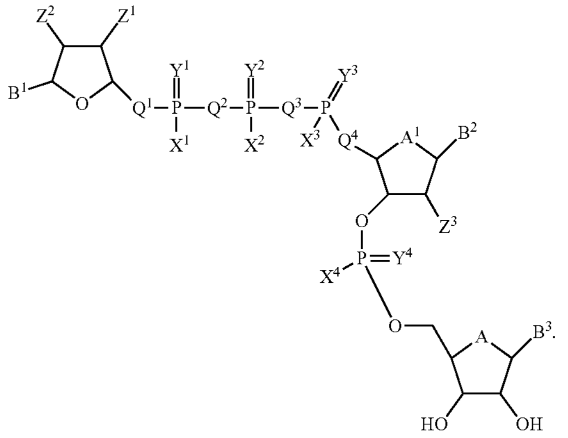

In some embodiments, the IVT mRNA sequence initiator has a structure of Formula (I-h):

Formula (I-h)

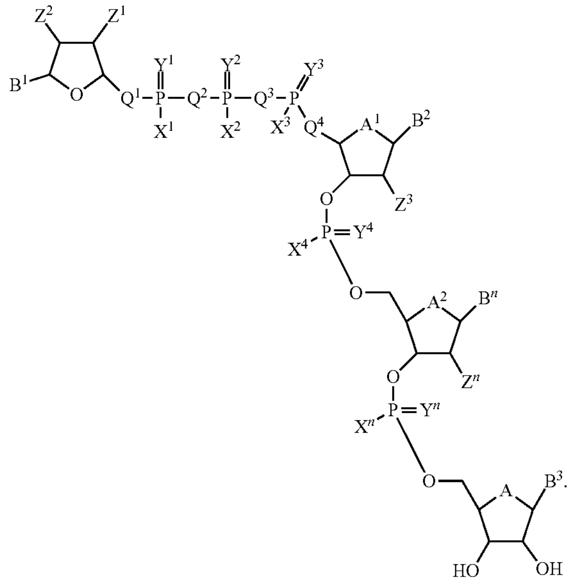

In some embodiments of a compound of Formula (I), (I-a), (I-b), (I-c), (I-d), (I-e), (I-f), (I-g) or (I-h), $Z^1$ is hydrogen, fluorine, —OH, —SH, —$CH_3$, —$CH_2CH_3$, —$OCH_3$, —$OCH_2CH_3$, —$SCH_3$, —$NH_2$, $NHCH_3$, or NHC(=O)$CH_3$. In some embodiments, $Z^1$ is hydrogen. In some embodiments, $Z^1$ is F. In some embodiments, $Z^1$ is —OH. In some embodiments, $Z^1$ is —SH. In some embodiments, $Z^1$ is —$CH_3$. In some embodiments, $Z^1$ is —$CH_2CH_3$. In some embodiments, $Z^1$ is —$OCH_3$. In some embodiments, $Z^1$ is —$OCH_2CH_3$. In some embodiments, $Z^1$ is —$SCH_3$. In some embodiments, $Z^1$ is —$NH_2$. In some embodiments, $Z^1$ is $NHCH_3$. In some embodiments, $Z^1$ is NHC(=O)$CH_3$.

In some embodiments of a compound of Formula (I), (I-a), (I-b), (I-a), (I-d), (I-e), (I-f), (I-g) or (I-h), $Z^2$ is hydrogen, fluorine, —OH, —SH, —$CH_3$, —$CH_2CH_3$, —$OCH_3$, —$OCH_2CH_3$, —$SCH_3$, —$NH_2$, $NHCH_3$, or NHC(=O)$CH_3$. In some embodiments, $Z^2$ is hydrogen. In some embodiments, $Z^2$ is F. In some embodiments, $Z^2$ is —OH. In some embodiments, $Z^2$ is —SH. In some embodiments, $Z^2$ is —$CH_3$. In some embodiments, $Z^2$ is —$CH_2CH_3$. In some embodiments, $Z^2$ is —$OCH_3$. In some embodiments, $Z^2$ is —$OCH_2CH_3$. In some embodiments, $Z^2$ is —$SCH_3$. In some embodiments, $Z^2$ is —$NH_2$. In some embodiments, $Z^2$ is $NHCH_3$. In some embodiments, $Z^2$ is NHC(=O)$CH_3$.

In some embodiments of a compound of Formula (I), (I-a), (I-b), (I-c), (I-d), (I-e), (I-f), (I-g) or (I-h), $Z^3$ is hydrogen, fluorine, —OH, —SH, —$CH_3$, —$CH_2CH_3$, —$OCH_3$, —$NH_2$, —$NHCH_3$, —NH(C(=O)$CH_3$), —$OCH_2CH_3$, —$OCH_2OCH_3$, —$OCH_2CH_2CH_3$, —OCH$(CH_3)_2$, —$SCH_3$, or —$OCH_2CH_2OCH_3$. In some embodiments, $Z^3$ is hydrogen. In some embodiments, $Z^3$ is fluorine. In some embodiments, $Z^3$ is —OH. In some embodiments, $Z^3$ is —SH. In some embodiments, $Z^3$ is —$CH_3$. In some embodiments, $Z^3$ is —$CH_2CH_3$. In some embodiments, $Z^3$ is —$OCH_2OCH_3$. In some embodiments, $Z^3$ is —$OCH_2CH_2CH_3$. In some embodiments, $Z^3$ is —OCH$(CH_3)_2$. In some embodiments, $Z^3$ is —$SCH_3$. In some embodiments, $Z^3$ is —$OCH_2CH_2OCH_3$.

In some embodiments of a compound of Formula (I), (I-a), (I-b), (I-c), (I-d), (I-e), (I-f), (I-g) or (I-h), $Z^4$ is hydrogen, fluorine, —OH, —SH, —$CH_3$, —$CH_2CH_3$, —$OCH_3$, —$NH_2$, —$NHCH_3$, —NH(C(=O)$CH_3$), —$OCH_2CH_3$, —$OCH_2OCH_3$, —$OCH_2CH_2CH_3$, —OCH$(CH_3)_2$, —$SCH_3$, or —$OCH_2CH_2OCH_3$. In some embodiments, $Z^4$ is hydrogen. In some embodiments, $Z^4$ is fluorine. In some embodiments, $Z^4$ is —OH. In some embodiments, $Z^4$ is —SH. In some embodiments, $Z^4$ is —$CH_3$. In some embodiments, $Z^4$ is —$CH_2CH_3$. In some embodiments, $Z^4$ is —$OCH_2OCH_3$. In some embodiments, $Z^4$ is —$OCH_2CH_2CH_3$. In some embodiments, $Z^4$ is —OCH$(CH_3)_2$. In some embodiments, $Z^4$ is —$SCH_3$. In some embodiments, $Z^4$ is —$OCH_2CH_2OCH_3$.

In some embodiments of a compound of Formula (I), (I-a), (I-b), (I-c), (I-d), (I-e), (I-f), (I-g) or (I-h), $Z^n$ is hydrogen, fluorine, —OH, —SH, —$CH_3$, —$CH_2CH_3$, —$OCH_3$, —$NH_2$, —$NHCH_3$, —NH(C(=O)$CH_3$), —$OCH_2CH_3$, —$OCH_2OCH_3$, —$OCH_2CH_2CH_3$, —OCH$(CH_3)_2$, —$SCH_3$, or —$OCH_2CH_2OCH_3$. In some embodiments, $Z^n$ is hydrogen. In some embodiments, $Z^n$ is fluorine. In some embodiments, $Z^n$ is —OH. In some embodiments, $Z^n$ is —SH. In some embodiments, $Z^n$ is —$CH_3$. In some embodiments, $Z^n$ is —$CH_2CH_3$. In some embodiments, $Z^n$ is —$OCH_2OCH_3$. In some embodiments, $Z^n$ is —$OCH_2CH_2CH_3$. In some embodiments, $Z^n$ is —OCH$(CH_3)_2$. In some embodiments, $Z^n$ is —$SCH_3$. In some embodiments, $Z^n$ is —$OCH_2CH_2OCH_3$.

In some embodiments of a compound of Formula (I), (I-a), (I-b), (I-c), (I-d), (I-e), (I-f), (I-g) or (I-h), $B^2$ is independently a natural, a modified, or an unnatural nucleobase. In some embodiments $B^2$ is guanine. In some embodiments $B^2$ is adenine. In some embodiments, $B^2$ is cytosine. In some embodiments, $B^2$ is uracil, In some embodiments, $B^2$ is thymine, In some embodiments, $B^2$ is hypoxanthine. In some embodiments, $B^2$ is purine.

In some embodiments of a compound of Formula (I), (I-a), (I-b), (I-c), (I-d), (I-e), (I-f), (I-g) or (I-h), $B^3$ is independently a natural, a modified, or an unnatural nucleobase. In some embodiments, $B^3$ is guanine. In some embodiments, $B^3$ is adenine. In some embodiments, $B^3$ is cytosine. In some embodiments, $B^3$ is uracil, In some embodiments, $B^3$ is thymine, In some embodiments, $B^3$ is hypoxanthine. In some embodiments, $B^3$ is purine.

In some embodiments of a compound of Formula (I), (I-a), (I-b), (I-c), (I-d), (I-e), (I-f), (I-g) or (I-h), B″ is independently a natural, a modified, or an unnatural nucleobase. In some embodiments, B″ is guanine. In some embodiments, B″ is adenine. In some embodiments, B″ is cytosine. In some embodiments, B″ is uracil, In some embodiments, B″ is thymine, In some embodiments, B″ is hypoxanthine. In some embodiments, B″ is purine.

In some embodiments of a compound of Formula (I), (I-a), (I-b), (I-c), (I-d), (I-c), (I-f), (I-g) or (I-h), at least one of $B^2$, $B^3$, and B″ is adenine. In some embodiments, at least one of $B^2$, $B^3$, and B″ is guanine. In some embodiments $B^2$ is adenine. In some embodiments, $B^3$ is adenine In some embodiments of a compound of Formula (I), (I-a), (I-b), (I-c), (I-d), (I-e), (I-f), (I-g) or (I-h), $Q^1$ is $—CH_2—$, —CH═CH—, $—CH_2O—$, $—CH_2S—$, $—CH_2CH_2—$, $—CH_2CF_2—$, $—CH_2NH_2—$, $—CH_2NH(CH_3)—$, or $—CH_2N(C(═O)CH_3)—$. In some embodiments, $Q^1$ is $—CH_2—$. In some embodiments, $Q^1$ is —CH═CH—. In some embodiments, $Q^1$ is $—CH_2O—$. In some embodiments, $Q^1$ is $—CH_2S—$. In some embodiments, $Q^1$ is $—CH_2CH_2—$. In some embodiments, $Q^1$ is $—CH_2CF_2—$. In some embodiments, $Q^1$ is $—CH_2NH_2—$. In some embodiments, $Q^1$ is $—CH_2NH(CH_3)—$. In some embodiments, $Q^1$ is $—CH_2N(C(═O)CH_3)—$.

In some embodiments of a compound of Formula (I), (I-a), (I-b), (I-c), (I-d), (I-e), (I-f), (I-g) or (I-h), $Q^4$ is $—CH_2—$, $—CH_2CH—$, $—CH_2O—$, $—CH_2S—$, $—CH_2CH_2—$, $—CH_2CF_2—$, $—CH_2NH_2—$, $—CH_2NH(CH_3)—$, or $—CH_2N(C(═O)CH_3)—$. In some embodiments, $Q^4$ is $—CH_2—$. In some embodiments, $Q^4$ is —CH═CH—. In some embodiments, $Q^4$ is $—CH_2O—$. In some embodiments, $Q^4$ is $—CH_2S—$. In some embodiments, $Q^4$ is $—CH_2CH_2—$. In some embodiments, $Q^4$ is $—CH_2CF_2—$. In some embodiments, $Q^4$ is $—CH_2NH_2—$. In some embodiments, $Q^4$ is $—CH_2NH(CH_3)—$. In some embodiments, $Q^4$ is $—CH_2N(C(═O)CH_3)—$.

In some embodiments of a compound of Formula (I), (I-a), (I-b), (I-c), (I-d), (I-e), (I-f), (I-g) or (I-h), $Q^2$ is —O—, —S—, $—CH_2—$, $—CF_2—$, —NH—, $—N(CH_3)—$, or $—N(C(═O)CH_3)—$. In some embodiments, $Q^2$ is —O—. In some embodiments, $Q^2$ is —S—. In some embodiments, $Q^2$ is $—CH_2—$. In some embodiments, $Q^2$ is $—CF_2—$. In some embodiments, $Q^2$ is —NH—. In some embodiments, $Q^2$ is $—N(CH_3)—$. In some embodiments, $Q^2$ is $—N(C(═O)CH_3)$.

In some embodiments of a compound of Formula (I), (I-a), (I-b), (I-c), (I-d), (I-e), (I-f), (I-g) or (I-h), $Q^3$ is —O—, —S—, $—CH_2—$, $—CF_2—$, —NH—, $—N(CH_3)—$, or $—N(C(═O)CH_3)—$. In some embodiments, $Q^3$ is —O—. In some embodiments, $Q^3$ is —S—. In some embodiments, $Q^3$ is $—CH_2—$. In some embodiments, $Q^3$ is $—CF_2—$. In some embodiments, $Q^3$ is —NH—. In some embodiments, $Q^3$ is $—N(CH_3)—$. In some embodiments, $Q^3$ is $—N(C(═O)CH_3)$.

In some embodiments of a compound of Formula (I), (I-a), (I-b), (I-c), (I-d), (I-e), (I-f), (I-g) or (I-h), $X^1$ is —OH, —SH, —O, —S, $—NH_2$, $—NHCH_3$, $—NH(C(═O)CH_3)$, $—CH_3$, $—CH_2CH_3$, $—CH_2CH_2CH_3$, $—CH(CH_3)_2$, $—OCH_3$, or $—OCH_2CH_3$. In some embodiments, $X^1$ is —OH. In some embodiments, $X^1$ is —SH. In some embodiments, $X^1$ is —O. In some embodiments, $X^1$ is —S—. In some embodiments, $X^1$ is $—NH_2$. In some embodiments, $X^1$ is $—NHCH_3$. In some embodiments, $X^1$ is $—NH(C(═O)CH_3)$. In some embodiments, $X^1$ is $—CH_3$. In some embodiments, $X^1$ is $—CH_2CH_3$. In some embodiments, $X^1$ is $—CH_2CH_2CH_3$. In some embodiments, $X^1$ is $—CH(CH_3)_2$. In some embodiments, $X^1$ is $—OCH_3$. In some embodiments, $X^1$ is $—OCH_2CH_3$.

In some embodiments of a compound of Formula (I), (I-a), (I-b), (I-c), (I-d), (I-e), (I-f), (I-g) or (I-h), $X^2$ is —OH, —SH, —O, —S, $—NH_2$, $—NHCH_3$, $—NH(C(═O)CH_3)$, $—CH_3$, $—CH_2CH_3$, $—CH_2CH_2CH_3$, $—CH(CH_3)_2$, $—OCH_3$, or $—OCH_2CH_3$. In some embodiments, $X^2$ is —OH. In some embodiments, $X^2$ is —SH. In some embodiments, $X^2$ is —O. In some embodiments, $X^2$ is —S—. In some embodiments, $X^2$ is $—NH_2$. In some embodiments, $X^2$ is $—NHCH_3$. In some embodiments, $X^2$ is $—NH(C(═O)CH_3)$. In some embodiments, $X^2$ is $—CH_3$. In some embodiments, $X^2$ is $—CH_2CH_3$. In some embodiments, $X^2$ is $—CH_2CH_2CH_3$. In some embodiments, $X^2$ is $—CH(CH_3)_2$. In some embodiments, $X^2$ is $—OCH_3$. In some embodiments, $X^2$ is $—OCH_2CH_3$.

In some embodiments of a compound of Formula (I), (I-a), (I-b), (I-c), (I-d), (I-e), (I-f), (I-g) or (I-h), $X^3$ is —OH, —SH, —O, —S, $—NH_2$, $—NHCH_3$, $—NH(C(═O)CH_3)$, $—CH_3$, $—CH_2CH_3$, $—CH_2CH_2CH_3$, $—CH(CH_3)_2$, $—OCH_3$, or $—OCH_2CH_3$. In some embodiments, $X^3$ is —OH. In some embodiments, $X^3$ is —SH. In some embodiments, $X^3$ is $—O^-$. In some embodiments, $X^3$ is —S—. In some embodiments, $X^3$ is $—NH_2$. In some embodiments, $X^3$ is $—NHCH_3$. In some embodiments, $X^3$ is $—NH(C(═O)CH_3)$. In some embodiments, $X^3$ is $—CH_3$. In some embodiments, $X^3$ is $—CH_2CH_3$. In some embodiments, $X^3$ is $—CH_2CH_2CH_3$. In some embodiments, $X^3$ is $—CH(CH_3)_2$. In some embodiments, $X^3$ is $—OCH_3$. In some embodiments, $X^3$ is $—OCH_2CH_3$.

In some embodiments of a compound of Formula (I), (I-a), (I-b), (I-c), (I-d), (I-e), (I-f), (I-g) or (I-h), $X^4$ is —OH, —SH, —O—, —S, $—NH_2$, $—NHCH_3$, $—NH(C(═O)CH_3)$, $—CH_3$, $—CH_2CH_3$, $—CH_2CH_2CH_3$, $—CH(CH_3)_2$, $—OCH_3$, or $—OCH_2CH_3$. In some embodiments, $X^4$ is —OH. In some embodiments, $X^4$ is —SH. In some embodiments, $X^4$ is —O'. In some embodiments, $X^4$ is —S—. In some embodiments, $X^4$ is $—NH_2$. In some embodiments, $X^4$ is $—NHCH_3$. In some embodiments, $X^4$ is $—NH(C(═O)CH_3)$. In some embodiments, $X^4$ is $—CH_3$. In some embodiments, $X^4$ is $—CH_2CH_3$. In some embodiments, $X^4$ is $—CH_2CH_2CH_3$. In some embodiments, $X^4$ is $—CH(CH_3)_2$. In some embodiments, $X^4$ is $—OCH_3$. In some embodiments, $X^4$ is $—OCH_2CH_3$.

In some embodiments of a compound of Formula (I), (I-a), (I-b), (I-c), (I-d), (I-e), (I-f), (I-g) or (I-h), X″ is —OH, —SH, —O, —S, $—NH_2$, $—NHCH_3$, $—NH(C(═O)CH_3)$, $—CH_3$, $—CH_2CH_3$, $—CH_2CH_2CH_3$, $—CH(CH_3)_2$, $—OCH_3$, or $—OCH_2CH_3$. In some embodiments, X″ is —OH. In some embodiments, X″ is —SH. In some embodiments, X″ is $—O^-$. In some embodiments, X″ is —S. In some embodiments, X″ is $—NH_2$. In some embodiments, X″ is $—NHCH_3$. In some embodiments, X″ is $—NH(C(═O)CH_3)$. In some embodiments, X″ is $—CH_3$. In some embodiments, X″ is $—CH_2CH_3$. In some embodiments, X″ is $—CH_2CH_2CH_3$. In some embodiments, X″ is $—CH(CH_3)_2$. In some embodiments, X″ is $—OCH_3$. In some embodiments, X″ is $—OCH_2CH_3$.

In some embodiments of a compound of Formula (I), (I-a), (I-b), (I-c), (I-d), (I-e), (I-f), (I-g) or (I-h), $Y^1$ is ═O, ═S, ═NH, or $═NCH_3$. In some embodiments, $Y^1$ is ═O. In some embodiments, $Y^1$ is ═S. In some embodiments, $Y^1$ is ═NH. In some embodiments, $Y^1$ is $═NHCH_3$.

In some embodiments of a compound of Formula (I), (I-a), (I-b), (I-c), (I-d), (I-e), (I-f), (I-g) or (I-h), $Y^2$ is ═O, ═S, ═NH, or $═NCH_3$. In some embodiments, $Y^2$ is ═O.

In some embodiments, $Y^2$ is =S. In some embodiments, $Y^2$ is =NH. In some embodiments, $Y^2$ is =$NHCH_3$.

In some embodiments of a compound of Formula (I), (I-a), (I-b), (I-c), (I-d), (I-e), (I-f), (I-g) or (I-h), $Y^3$ is =O, =S, =NH, or =$NCH_3$. In some embodiments, $Y^3$ is =O. In some embodiments, $Y^3$ is =S. In some embodiments, $Y^3$ is =NH. In some embodiments, $Y^3$ is —$NHCH_3$.

In some embodiments of a compound of Formula (I), (I-a), (I-b), (I-c), (I-d), (I-e), (I-f), (I-g) or (I-h), $Y^4$ is —O, =S, =NH, or =$NCH_3$. In some embodiments, $Y^4$ is =O. In some embodiments, $Y^4$ is =S. In some embodiments, $Y^4$ is =NH. In some embodiments, $Y^4$ is =$NHCH_3$.

In some embodiments of a compound of Formula (I), (I-a), (I-b), (I-c), (I-d), (I-e), (I-f), (I-g) or (I-h), $Y''$ is =O, =S, =NH, or =$NCH_3$. In some embodiments, $Y''$ is =O. In some embodiments, $Y''$ is =S. In some embodiments, $Y''$ is =NH. In some embodiments, $Y''$ is =$NHCH_3$.

In some embodiments of a compound of Formula (I), (I-a), (I-b), (I-c), (I-d), (I-e), (I-f), (I-g) or (I-h), A is —O—, —S—, —$CH_2$—, —NH—, —N($CH_3$)— or —N(C(=O)$CH_3$)—. In some embodiments, A is —O—. In some embodiments, A is —S—. In some embodiments, A is —$CH_2$—. In some embodiments, A is —NH—. In some embodiments, A is —N($CH_3$)—. In some embodiments, A is —N(C(=O)$CH_3$)—.

In some embodiments of a compound of Formula (I), (I-a), (I-b), (I-c), (I-d), (I-e), (I-f), (I-g) or (I-h), $A^1$ is —O—, —S—, —$CH_2$—, —NH—, —N($CH_3$)— or —N(C(=O)$CH_3$)—. In some embodiments, $A^1$ is —O—. In some embodiments, $A^1$ is —S—. In some embodiments, $A^1$ is —$CH_2$—. In some embodiments, $A^1$ is —NH—. In some embodiments, $A^1$ is —N($CH_3$)—. In some embodiments, $A^1$ is —N(C(=O)$CH_3$)—.

In some embodiments of a compound of Formula (I), (I-a), (I-b), (I-c), (I-d), (I-e), (I-f), (I-g) or (I-h), $A^2$ is —O—, —S—, —$CH_2$—, —NH—, —N($CH_3$)— or —N(C(=O)$CH_3$)—. In some embodiments, $A^2$ is —O—. In some embodiments, $A^2$ is —S—. In some embodiments, $A^2$ is —$CH_2$—. In some embodiments, $A^2$ is —NH—. In some embodiments, $A^2$ is —N($CH_3$)—. In some embodiments, $A^2$ is —N(C(=O)$CH_3$)—.

In some embodiments of a compound of Formula (I), (I-a), (I-b), (I-c), (I-d), (I-e), (I-f), (I-g) or (I-h), p is 0, 1, 2, 3, 4, 5 or 6. In some embodiments, p is 0. In some embodiments, p is 1. In some embodiments, p is 2. In some embodiments, p is 3. In some embodiments, p is 4. In some embodiments, p is 5. In some embodiments, p is 6.

In some embodiments of a compound of Formula (I), at least one of $X^1$, $X^2$, $X^3$, $X^4$, and $X''$ is —SH.

In some embodiments of a compound of Formula (I), at least one of $X^1$, $X^2$, $X^3$, $X^4$, and $X''$ is —S—.

In some embodiments of a compound of Formula (I), at least one of $Y^1$, $Y^2$, $Y^3$, $Y^4$, and $Y''$ is =S.

In some embodiments of a compound of Formula (I), at least one of A, $A^1$, and $A^2$ is —S—.

In some embodiments of a compound of Formula (I), at least one of $Z^1$, $Z^2$, $Z^3$, $Z^4$, and $Z''$ is —$OCH_3$. In some embodiments, $Z^3$ is —$OCH_3$. In some embodiments, $Z^3$ and $Z^1$ are —$OCH_3$. In some embodiments of a compound of Formula (I), at least one of $Z^1$, $Z^2$, $Z^3$, $Z^4$, and $Z''$ is —OH. In some embodiments, $Z^1$, $Z^2$, and $Z^4$ are —OH. In some embodiments, $Z^2$ and $Z^4$ are —OH.

In some embodiments of a compound of Formula (I), at least one of $Q^1$, $Q^2$, $Q^3$, and $Q^4$ is —$OCH_3$. In some embodiments of a compound of Formula (I), at least one of $Q^1$, $Q^2$, $Q^3$, and $Q^4$ is —O—. In some embodiments, $Q^1$ and $Q^4$ are —$OCH_3$. In some embodiments, $Q^2$ and $Q^3$ are —O—.

In some embodiments of a compound o Formula (I), at least one of $Y^1$, $Y^2$, $Y^3$, $Y^4$, and $Y''$ is =O. In some embodiments, $Y^1$, $Y^2$, $Y^3$, and $Y^4$ is are =O. In some embodiments, $Y^1$, $Y^2$, $Y^3$, $Y^4$, and $Y''$ is =S. In some embodiments, $Y^2$ is =S. In some embodiments, $Y^4$ is =S.

In some embodiments of a compound of Formula (I), at least one of $X^1$, $X^2$, $X^3$, $X^4$, and $X''$ is —$O^-$. In Some embodiments, $X^1$, $X^2$, $X^3$, and $X^4$ are —O. In some embodiments, $X^1$ is —S. In some embodiments, $X^2$ is —S—. In some embodiments, $X^3$ is —S—. In some embodiments, $X^4$ is —S.

In some embodiments of a compound of Formula (I), In some embodiments of a compound of Formula (I), at least one of A, $A^1$, and $A^2$ is —O—. In some embodiments, A, $A^1$, and $A^2$ are —O—.

In one aspect, described herein is a mRNA sequence having a 5'-end region motif of Motif (I'):

Motif (I')

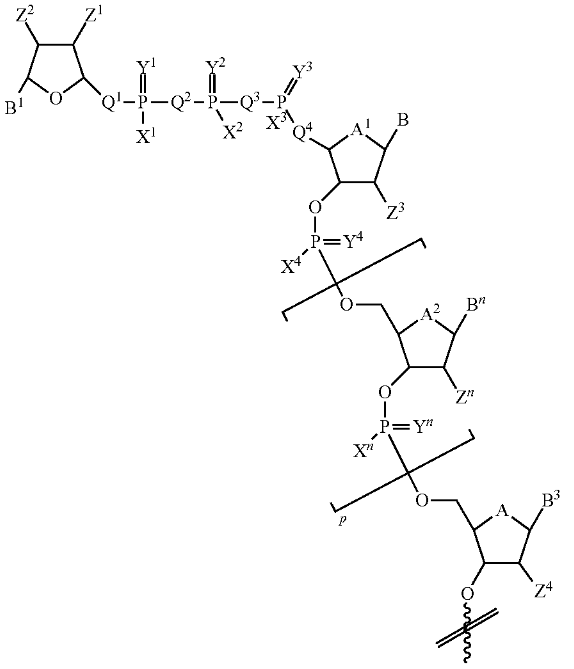

wherein $B^1$ is

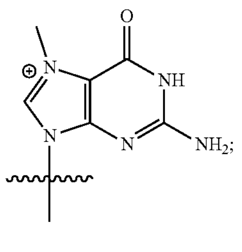 [SMILES: *n1c[n+](C)c2c(=O)[nH]c(N)nc21]

each $B^2$, $B^3$, and $B''$ is independently a natural, a modified, or an unnatural nucleobase;

each $Z^1$ and $Z^2$ is independently hydrogen, fluorine, —OH, —SH, —$CH_3$, —$CH_2CH_3$, —$OCH_3$, —$OCH_2CH_3$, —$SCH_3$, —$NH_2$, $NHCH_3$, or $NHC(=O)CH_3$;

each $Z^3$, $Z^4$, and $Z''$ is independently hydrogen, fluorine, —OH, —SH, —$CH_3$, —$CH_2CH_3$, —$OCH_3$, —$NH_2$, —$NHCH_3$, —$NH(C(=O)CH_3)$, —$OCH_2CH_3$, —$OCH_2OCH_3$, —$OCH_2CH_2CH_3$, —$OCH(CH_3)_2$, —$SCH_3$, or —$OCH_2CH_2OCH_3$;

each $Q^1$ and $Q^4$ is independently —$CH_2$—, —CH═CH—, —$CH_2O$—, —$CH_2S$—, —$CH_2CH_2$—, —$CH_2CF_2$—, —$CH_2NH_2$—, —$CH_2NH(CH_3)$—, or —$CH_2N(C(=O)CH_3)$—;

each $Q^2$ and $Q^3$ is independently —O—, —S—, —$CH_2$—, —$CF_2$—, —NH—, —$N(CH_3)$—, or —$N(C(=O)CH_3)$—;

each $X^1$, $X^2$, $X^3$, $X^4$, and $X''$ is independently —OH, —SH, —$O^-$, —$S^-$, —$NH_2$, —$NHCH_3$, —$NH(C(=O)CH_3)$, —$CH_3$, —$CH_2CH_3$, —$CH_2CH_2CH_3$, —$CH(CH_3)_2$, —$OCH_3$, or —$OCH_2CH_3$;

each $Y^1$, $Y^2$, $Y^3$, $Y^4$, and $Y''$ is independently ═O, —S, ═NH, or ═$NCH_3$;

each A, $A^1$, and $A^2$ is independently —O—, —S—, —$CH_2$—, —NH—, —$N(CH_3)$— or —$N(C(=O)CH_3)$—; and p=0, 1, 2, 3, 4, 5 or 6, provided that (i) $Z^1$, $Z^2$, and $Z^3$ are hydrogen; (ii) $Q^1$ and $Q^4$ are —$CH_2O$—; (iii) $Q^2$ and $Q^3$ are oxygen; (iv) at least one of $X^1$, $X^2$, $X^3$, $X^4$, and $X''$ is —SH or —S; (v) at least one of $Y^1$, $Y^2$, $Y^3$, $Y^4$, and $Y''$ is —S; or (vi) at least one of A, $A^1$, and $A^2$ is —S—.

In some embodiments, the mRNA sequence having a 5'-end region motif has a structure of Motif (I'-a):

Motif (I'-a)

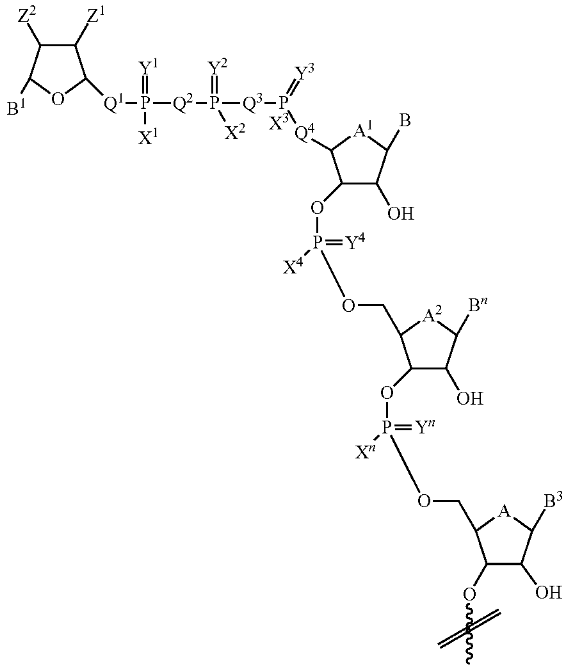

In some embodiments, the mRNA sequence having a 5'-end region motif has a structure of Motif (I'-b):

Motif (I'-b)

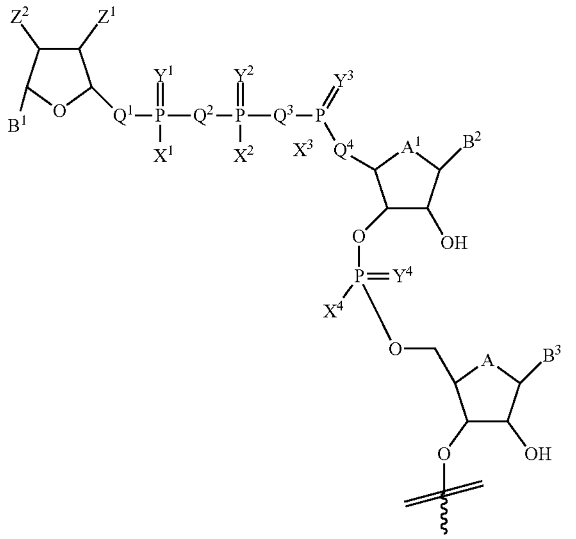

In some embodiments, the mRNA sequence having a 5'-end region motif has a structure of Motif (I'-c):

Motif (I'-c)

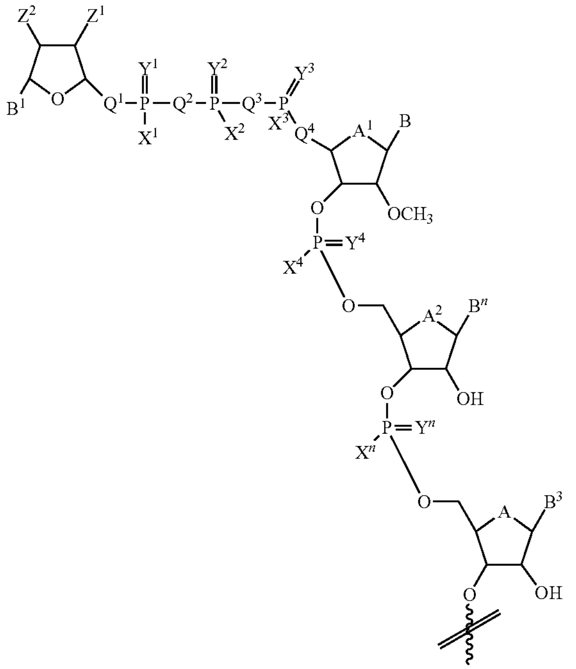

In some embodiments, the mRNA sequence having a 5'-end region motif has a structure of Motif (I'-d):

Motif (I'-d)

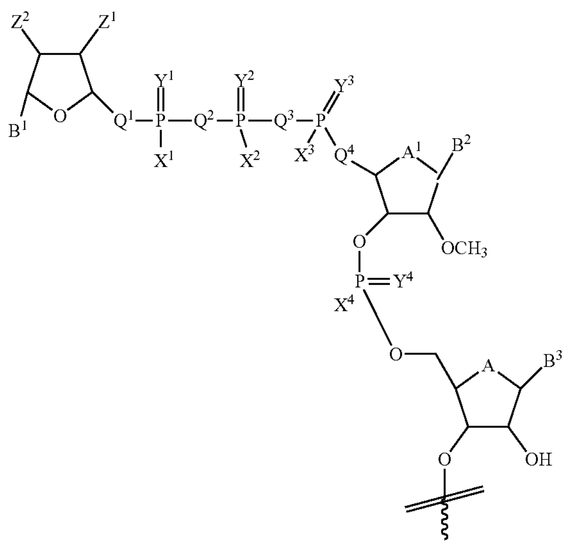

In some embodiments, the mRNA sequence having a 5'-end region motif has a structure of Motif (I'-e):

Motif (I'-e)

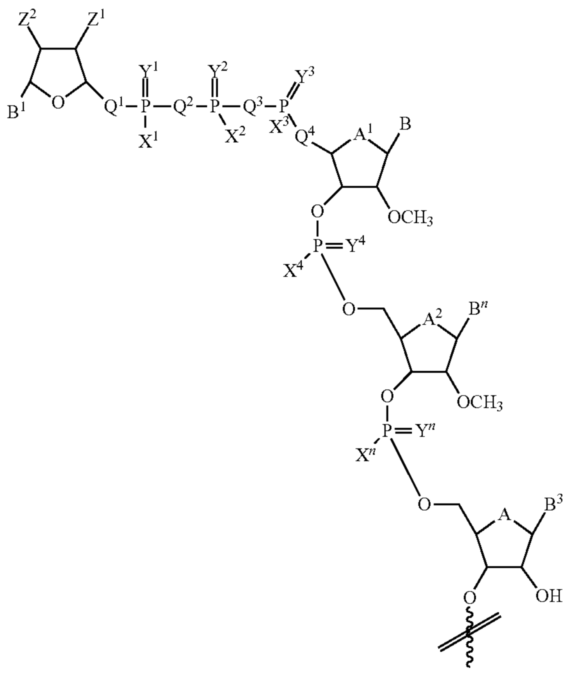

In some embodiments, the mRNA sequence having a 5'-end region motif has a structure of Motif (I'-f):

Motif (I'-f)

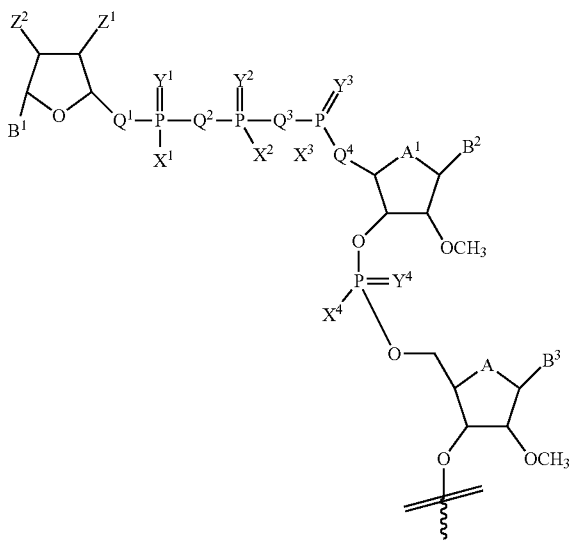

In some embodiments, the mRNA sequence having a 5'-end region motif has a structure of Motif (I'-g):

Motif (I'-g)

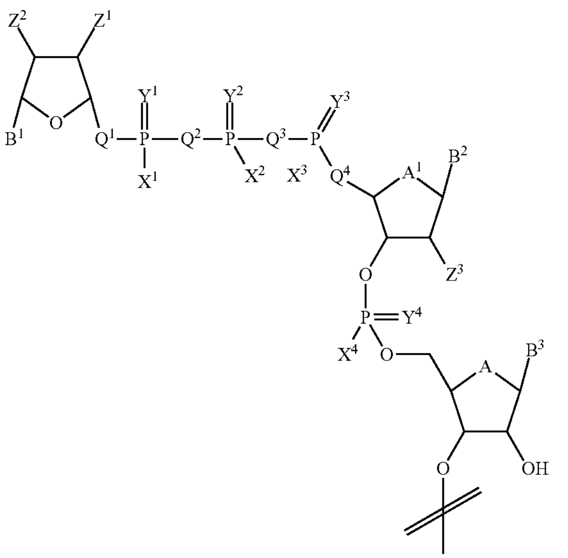

In some embodiments, the mRNA sequence having a 5'-end region motif has a structure of Motif (I'-h):

Motif (I'-h)

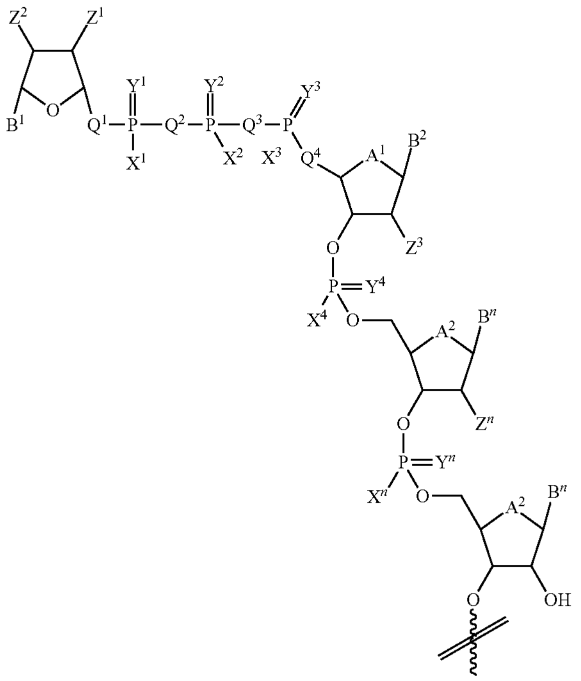

In some embodiments of a compound of Motif (I'), (I'-a), (I'-b), (I'-c), (I'-d), (I'-e), (I'-f), (I'-g) or (I'-h), $Z^1$ is hydrogen, fluorine, —OH, —SH, —$CH_3$, —$CH_2CH_3$, —$OCH_3$, —$OCH_2CH_3$, —$SCH_3$, —$NH_2$, $NHCH_3$, or NHC(═O)$CH_3$. In some embodiments, $Z^1$ is hydrogen. In some embodiments, $Z^1$ is F. In some embodiments, $Z^1$ is —OH. In some embodiments, $Z^1$ is —SH. In some embodiments, $Z^1$ is —$CH_3$. In some embodiments, $Z^1$ is —$CH_2CH_3$. In some embodiments, $Z^1$ is —$OCH_3$. In some embodiments, $Z^1$ is —$OCH_2CH_3$. In some embodiments, $Z^1$ is —$SCH_3$. In some embodiments, $Z^1$ is —$NH_2$. In some embodiments, $Z^1$ is $NHCH_3$. In some embodiments, $Z^1$ is NHC(═O)$CH_3$.

In some embodiments of a compound of Motif (I'), (I'-a), (I'-b), (I'-a), (I'-d), (I'-e), (I'-f), (I'-g) or (I'-h), $Z^2$ is hydrogen, fluorine, —OH, —SH, —$CH_3$, —$CH_2CH_3$, —$OCH_3$, —$OCH_2CH_3$, —$SCH_3$, —$NH_2$, $NHCH_3$, or NHC(═O)$CH_3$. In some embodiments, $Z^2$ is hydrogen. In some embodiments, $Z^2$ is F. In some embodiments, $Z^2$ is —OH. In some embodiments, $Z^2$ is —SH. In some embodiments, $Z^2$ is —$CH_3$. In some embodiments, $Z^2$ is —$CH_2CH_3$. In some embodiments, $Z^2$ is —$OCH_3$. In some embodiments, $Z^2$ is —$OCH_2CH_3$. In some embodiments, $Z^2$ is —$SCH_3$. In some embodiments, $Z^2$ is —$NH_2$. In some embodiments, $Z^2$ is $NHCH_3$. In some embodiments, $Z^2$ is NHC(═O)$CH_3$.

In some embodiments of a compound of Motif (I'), (I'-a), (I'-b), (I'-c), (I'-d), (I'-e), (I'-f), (I'-g) or (I'-h), $Z^3$ is hydrogen, fluorine, —OH, —SH, —$CH_3$, —$CH_2CH_3$, —$OCH_3$, —$NH_2$, —$NHCH_3$, —NH(C(═O)$CH_3$), —$OCH_2CH_3$, —$OCH_2OCH_3$, —$OCH_2CH_2CH_3$, —$OCH(CH_3)_2$, —$SCH_3$, or —$OCH_2CH_2OCH_3$. In some embodiments, $Z^3$ is hydrogen. In some embodiments, $Z^3$ is fluorine. In some embodiments, $Z^3$ is —OH. In some embodiments, $Z^3$ is —SH. In some embodiments, $Z^3$ is —$CH_3$. In some embodiments, $Z^3$ is —$CH_2CH_3$. In some embodiments, $Z^3$ is —$OCH_2OCH_3$. In some embodiments, $Z^3$ is —$OCH_2CH_2CH_3$. In some embodiments, $Z^3$ is —$OCH(CH_3)_2$. In some embodiments, $Z^3$ is —$SCH_3$. In some embodiments, $Z^3$ is —$OCH_2CH_2OCH_3$.

In some embodiments of a compound of Motif (I'), (I'-a), (I'-b), (I'-c), (I'-d), (I'-c), (I'-f), (I'-g) or (I'-h), $Z^4$ is hydrogen, fluorine, —OH, —SH, —$CH_3$, —$CH_2CH_3$, —$OCH_3$, —$NH_2$, —$NHCH_3$, —NH(C(═O)$CH_3$), —$OCH_2CH_3$, —$OCH_2OCH_3$, —$OCH_2CH_2CH_3$, —$OCH(CH_3)_2$, —$SCH_3$, or —$OCH_2CH_2OCH_3$. In some embodiments, $Z^4$ is hydrogen. In some embodiments, $Z^4$ is fluorine. In some embodiments, $Z^4$ is —OH. In some embodiments, $Z^4$ is —SH. In some embodiments, $Z^4$ is —$CH_3$. In some embodiments, $Z^4$ is —$CH_2CH_3$. In some embodiments, $Z^4$ is —$OCH_2OCH_3$. In some embodiments, $Z^4$ is —$OCH_2CH_2CH_3$. In some embodiments, $Z^4$ is —$OCH(CH_3)_2$. In some embodiments, $Z^4$ is —$SCH_3$. In some embodiments, $Z^4$ is —$OCH_2CH_2OCH_3$.

In some embodiments of a compound of Motif (I'), (I'-a), (I'-b), (I'-c), (I'-d), (I'-e), (I'-f), (I'-g) or (I'-h), $Z''$ is hydrogen, fluorine, —OH, —SH, —$CH_3$, —$CH_2CH_3$, —$OCH_3$, —$NH_2$, —$NHCH_3$, —NH(C(═O)$CH_3$), —$OCH_2CH_3$, —$OCH_2OCH_3$, —$OCH_2CH_2CH_3$, —$OCH(CH_3)_2$, —$SCH_3$, or —$OCH_2CH_2OCH_3$. In some embodiments, $Z''$ is hydrogen. In some embodiments, $Z''$ is fluorine. In some embodiments, $Z''$ is —OH. In some embodiments, $Z''$ is —SH. In some embodiments, $Z''$ is —$CH_3$. In some embodiments, $Z''$ is —$CH_2CH_3$. In some embodiments, $Z''$ is —$OCH_2OCH_3$. In some embodiments, $Z''$ is —$OCH_2CH_2CH_3$. In some embodiments, $Z''$ is —$OCH(CH_3)_2$. In some embodiments, $Z''$ is —$SCH_3$. In some embodiments, $Z''$ is —$OCH_2CH_2OCH_3$.

In some embodiments of a compound of Motif (I'), (I'-a), (I'-b), (I'-c), (I'-d), (I'-e), (I'-f), (I'-g) or (I'-h), $B^2$ is independently a natural, a modified, or an unnatural nucleobase. In some embodiments $B^2$ is guanine. In some embodiments $B^2$ is adenine. In some embodiments, $B^2$ is cytosine. In some embodiments, $B^2$ is uracil, In some embodiments, $B^2$ is thymine, In some embodiments, $B^2$ is hypoxanthine. In some embodiments, $B^2$ is purine.

In some embodiments of a compound of Motif (I'), (I'-a), (I'-b), (I'-c), (I'-d), (I'-e), (I'-f), (I'-g) or (I'-h), $B^3$ is independently a natural, a modified, or an unnatural nucleobase. In some embodiments, $B^3$ is guanine. In some embodiments, $B^3$ is adenine. In some embodiments, $B^3$ is cytosine. In some embodiments, $B^3$ is uracil, In some embodiments, $B^3$ is thymine, In some embodiments, $B^3$ is hypoxanthine. In some embodiments, $B^3$ is purine.

In some embodiments of a compound of Motif (I'), (I'-a), (I'-b), (I'-c), (I'-d), (I'-e), (I'-f), (I'-g) or (I'-h), $B''$ is independently a natural, a modified, or an unnatural nucleobase. In some embodiments, $B''$ is guanine. In some embodiments, $B''$ is adenine. In some embodiments, $B''$ is cytosine. In some embodiments, $B''$ is uracil, In some embodiments, $B''$ is thymine, In some embodiments, $B''$ is hypoxanthine. In some embodiments, $B''$ is purine.

In some embodiments of a compound of Motif (I'), (I'-a), (I'-b), (I'-c), (I'-d), (I'-c), (I'-f), (I'-g) or (I'-h), at least one of $B^2$, $B^3$, and $B''$ is adenine. In some embodiments, at least one of $B^2$, $B^3$, and $B''$ is guanine. In some embodiments $B^2$ is adenine. In some embodiments, $B^3$ is adenine In some embodiments of a compound of Motif (I'), (I'-a), (I'-b), (I'-c), (I'-d), (I'-e), (I'-f), (I'-g) or (I'-h), $Q^1$ is —$CH_2$—, —CH═CH—, —$CH_2O$—, —$CH_2S$—, —$CH_2CH_2$—, —$CH_2CF_2$—, —$CH_2NH_2$—, —$CH_2NH(CH_3)$—, or —$CH_2N(C(═O)CH_3)$—. In some embodiments, $Q^1$ is —$CH_2$—. In some embodiments, $Q^1$ is —CH═CH—. In some embodiments, $Q^1$ is —$CH_2O$—. In some embodiments, $Q^1$ is —$CH_2S$—. In some embodiments, $Q^1$ is —$CH_2CH_2$—. In some embodiments, $Q^1$ is —$CH_2CF_2$—. In some embodiments, $Q^1$ is —$CH_2NH_2$—. In some embodiments, $Q^1$ is —$CH_2NH(CH_3)$—. In some embodiments, $Q^1$ is —$CH_2N(C({=}O)CH_3)$—.

In some embodiments of a compound of Motif (I'), (I'-a), (I'-b), (I'-c), (I'-d), (I'-e), (I'-f), (I'-g) or (I'-h), $Q^4$ is —$CH_2$—, —CH═CH—, —$CH_2O$—, —$CH_2S$—, —$CH_2CH_2$—, —$CH_2CF_2$—, —$CH_2NH_2$—, —$CH_2NH(CH_3)$—, or —$CH_2N(C({=}O)CH_3)$—. In some embodiments, $Q^4$ is —$CH_2$—. In some embodiments, $Q^4$ is —CH═CH—. In some embodiments, $Q^4$ is —$CH_2O$—. In some embodiments, $Q^4$ is —$CH_2S$—. In some embodiments, $Q^4$ is —$CH_2CH_2$—. In some embodiments, $Q^4$ is —$CH_2CF_2$—. In some embodiments, $Q^4$ is —$CH_2NH_2$—. In some embodiments, $Q^4$ is —$CH_2NH(CH_3)$—. In some embodiments, $Q^4$ is —$CH_2N(C({=}O)CH_3)$—.

In some embodiments of a compound of Motif (I'), (I'-a), (I'-b), (I'-c), (I'-d), (I'-e), (I'-f), (I'-g) or (I'-h), $Q^2$ is —O—, —S—, —$CH_2$—, —$CF_2$—, —NH—, —$N(CH_3)$—, or —$N(C({=}O)CH_3)$—. In some embodiments, $Q^2$ is —O—. In some embodiments, $Q^2$ is —S—. In some embodiments, $Q^2$ is —$CH_2$—. In some embodiments, $Q^2$ is —$CF_2$—. In some embodiments, $Q^2$ is —NH—. In some embodiments, $Q^2$ is —$N(CH_3)$—. In some embodiments, $Q^2$ is —$N(C({=}O)CH_3)$.

In some embodiments of a compound of Motif (I'), (I'-a), (I'-b), (I'-c), (I'-d), (I'-c), (I'-f), (I'-g) or (I'-h), $Q^3$ is —O—, —S—, —$CH_2$—, —$CF_2$—, —NH—, —$N(CH_3)$—, or —$N(C({=}O)CH_3)$—. In some embodiments, $Q^3$ is —O—. In some embodiments, $Q^3$ is —S—. In some embodiments, $Q^3$ is —$CH_2$—. In some embodiments, $Q^3$ is —$CF_2$—. In some embodiments, $Q^3$ is —NH—. In some embodiments, $Q^3$ is —$N(CH_3)$—. In some embodiments, $Q^3$ is —$N(C({=}O)CH_3)$.

In some embodiments of a compound of Motif (I'), (I'-a), (I'-b), (I'-c), (I'-d), (I'-e), (I'-f), (I'-g) or (I'-h), $X^1$ is —OH, —SH, —O, —S, —$NH_2$, —$NHCH_3$, —$NH(C({=}O)CH_3)$, —$CH_3$, —$CH_2CH_3$, —$CH_2CH_2CH_3$, —$CH(CH_3)_2$, —$OCH_3$, or —$OCH_2CH_3$. In some embodiments, $X^1$ is —OH. In some embodiments, $X^1$ is —SH. In some embodiments, $X^1$ is —O. In some embodiments, $X^1$ is —S—. In some embodiments, $X^1$ is —$NH_2$. In some embodiments, $X^1$ is —$NHCH_3$. In some embodiments, $X^1$ is —$NH(C({=}O)CH_3)$. In some embodiments, $X^1$ is —$CH_3$. In some embodiments, $X^1$ is —$CH_2CH_3$. In some embodiments, $X^1$ is —$CH_2CH_2CH_3$. In some embodiments, $X^1$ is —$CH(CH_3)_2$. In some embodiments, $X^1$ is —$OCH_3$. In some embodiments, $X^1$ is —$OCH_2CH_3$.

In some embodiments of a compound of Motif (I'), (I'-a), (I'-b), (I'-c), (I'-d), (I'-e), (I'-f), (I'-g) or (I'-h), $X^2$ is —OH, —SH, —O, —S, —$NH_2$, —$NHCH_3$, —$NH(C({=}O)CH_3)$, —$CH_3$, —$CH_2CH_3$, —$CH_2CH_2CH_3$, —$CH(CH_3)_2$, —$OCH_3$, or —$OCH_2CH_3$. In some embodiments, $X^2$ is —OH. In some embodiments, $X^2$ is —SH. In some embodiments, $X^2$ is —$O^-$. In some embodiments, $X^2$ is —S—. In some embodiments, $X^2$ is —$NH_2$. In some embodiments, $X^2$ is —$NHCH_3$. In some embodiments, $X^2$ is —$NH(C({=}O)CH_3)$. In some embodiments, $X^2$ is —$CH_3$. In some embodiments, $X^2$ is —$CH_2CH_3$. In some embodiments, $X^2$ is —$CH_2CH_2CH_3$. In some embodiments, $X^2$ is —$CH(CH_3)_2$. In some embodiments, $X^2$ is —$OCH_3$. In some embodiments, $X^2$ is —$OCH_2CH_3$.

In some embodiments of a compound of Motif (I'), (I'-a), (I'-b), (I'-c), (I'-d), (I'-c), (I'-f), (I'-g) or (I'-h), $X^3$ is —OH, —SH, —O, —S, —$NH_2$, —$NHCH_3$, —$NH(C({=}O)CH_3)$, —$CH_3$, —$CH_2CH_3$, —$CH_2CH_2CH_3$, —$CH(CH_3)_2$, —$OCH_3$, or —$OCH_2CH_3$. In some embodiments, $X^3$ is —OH. In some embodiments, $X^3$ is —SH. In some embodiments, $X^3$ is —O. In some embodiments, $X^3$ is —S—. In some embodiments, $X^3$ is —$NH_2$. In some embodiments, $X^3$ is —$NHCH_3$. In some embodiments, $X^3$ is —$NH(C({=}O)CH_3)$. In some embodiments, $X^3$ is —$CH_3$. In some embodiments, $X^3$ is —$CH_2CH_3$. In some embodiments, $X^3$ is —$CH_2CH_2CH_3$. In some embodiments, $X^3$ is —$CH(CH_3)_2$. In some embodiments, $X^3$ is —$OCH_3$. In some embodiments, $X^3$ is —$OCH_2CH_3$.

In some embodiments of a compound of Motif (I'), (I'-a), (I'-b), (I'-c), (I'-d), (I'-e), (I'-f), (I'-g) or (I'-h), $X^4$ is —OH, —SH, —O, —S, —$NH_2$, —$NHCH_3$, —$NH(C({=}O)CH_3)$, —$CH_3$, —$CH_2CH_3$, —$CH_2CH_2CH_3$, —$CH(CH_3)_2$, —$OCH_3$, or —$OCH_2CH_3$. In some embodiments, $X^4$ is —OH. In some embodiments, $X^4$ is —SH. In some embodiments, $X^4$ is —$O^-$. In some embodiments, $X^4$ is —S. In some embodiments, $X^4$ is —$NH_2$. In some embodiments, $X^4$ is —$NHCH_3$. In some embodiments, $X^4$ is —$NH(C({=}O)CH_3)$. In some embodiments, $X^4$ is —$CH_3$. In some embodiments, $X^4$ is —$CH_2CH_3$. In some embodiments, $X^4$ is —$CH_2CH_2CH_3$. In some embodiments, $X^4$ is —$CH(CH_3)_2$. In some embodiments, $X^4$ is —$OCH_3$. In some embodiments, $X^4$ is —$OCH_2CH_3$.

In some embodiments of a compound of Motif (I'), (I'-a), (I'-b), (I'-c), (I'-d), (I'-e), (I'-f), (I'-g) or (I'-h), $X''$ is —OH, —SH, —O, —S, —$NH_2$, —$NHCH_3$, —$NH(C({=}O)CH_3)$, —$CH_3$, —$CH_2CH_3$, —$CH_2CH_2CH_3$, —$CH(CH_3)_2$, —$OCH_3$, or —$OCH_2CH_3$. In some embodiments, $X''$ is —OH. In some embodiments, $X''$ is —SH. In some embodiments, $X''$ is —$O^-$. In some embodiments, $X''$ is —S—. In some embodiments, $X''$ is —$NH_2$. In some embodiments, $X''$ is —$NHCH_3$. In some embodiments, $X''$ is —$NH(C({=}O)CH_3)$. In some embodiments, $X''$ is —$CH_3$. In some embodiments, $X''$ is —$CH_2CH_3$. In some embodiments, $X''$ is —$CH_2CH_2CH_3$. In some embodiments, $X''$ is —$CH(CH_3)_2$. In some embodiments, $X''$ is —$OCH_3$. In some embodiments, $X''$ is —$OCH_2CH_3$.

In some embodiments of a compound of Motif (I'), (I'-a), (I'-b), (I'-c), (I'-d), (I'-c), (I'-f), (I'-g) or (I'-h), $Y^1$ is ═O, ═S, ═NH, or ═$NCH_3$. In some embodiments, $Y^1$ is ═O. In some embodiments, $Y^1$ is ═S. In some embodiments, $Y^1$ is ═NH. In some embodiments, $Y^1$ is ═$NHCH_3$.

In some embodiments of a compound of Motif (I'), (I'-a), (I'-b), (I'-c), (I'-d), (I'-e), (I'-f), (I'-g) or (I'-h), $Y^2$ is ═O, ═S, ═NH, or ═$NCH_3$. In some embodiments, $Y^2$ is ═O. In some embodiments, $Y^2$ is ═S. In some embodiments, $Y^2$ is ═NH. In some embodiments, $Y^2$ is ═$NHCH_3$.

In some embodiments of a compound of Motif (I'), (I'-a), (I'-b), (I'-c), (I'-d), (I'-c), (I'-f), (I'-g) or (I'-h), $Y^3$ is ═O, ═S, ═NH, or ═$NCH_3$. In some embodiments, $Y^3$ is ═O. In some embodiments, $Y^3$ is ═S. In some embodiments, $Y^3$ is ═NH. In some embodiments, $Y^3$ is ═$NHCH_3$.

In some embodiments of a compound of Motif (I'), (I'-a), (I'-b), (I'-c), (I'-d), (I'-c), (I'-f), (I'-g) or (I'-h), $Y^4$ is ═O, ═S, ═NH, or ═$NCH_3$. In some embodiments, $Y^4$ is ═O. In some embodiments, $Y^4$ is ═S. In some embodiments, $Y^4$ is ═NH. In some embodiments, $Y^4$ is ═$NHCH_3$.

In some embodiments of a compound of Motif (I'), (I'-a), (I'-b), (I'-c), (I'-d), (I'-e), (I'-f), (I'-g) or (I'-h), $Y''$ is ═O, ═S, ═NH, or ═$NCH_3$. In some embodiments, $Y''$ is ═O. In some embodiments, $Y''$ is ═S. In some embodiments, $Y''$ is ═NH. In some embodiments, $Y''$ is ═$NHCH_3$.

In some embodiments of a compound of Motif (I'), (I'-a), (I'-b), (I'-c), (I'-d), (I'-e), (I'-f), (I'-g) or (I'-h), A is —O—, —S—, —$CH_2$—, —NH—, —$N(CH_3)$— or —$N(C(=O)$ $CH_3$)—. In some embodiments, A is —O—. In some embodiments, A is —S—. In some embodiments, A is —$CH_2$—. In some embodiments, A is —NH—. In some embodiments, A is —N($CH_3$)—. In some embodiments, A is —N(C(=O)$CH_3$)—.

In some embodiments of a compound of Motif (I'), (I'-a), (I'-b), (I'-c), (I'-d), (I'-e), (I'-f), (I'-g) or (I'-h), $A^1$ is —O—, —S—, —$CH_2$—, —NH—, —N($CH_3$)— or —N(C(=O)$CH_3$)—. In some embodiments, $A^1$ is —O—. In some embodiments, $A^1$ is —S—. In some embodiments, $A^1$ is —$CH_2$—. In some embodiments, $A^1$ is —NH—. In some embodiments, $A^1$ is —N($CH_3$)—. In some embodiments, $A^1$ is —N(C(=O)$CH_3$)—.

In some embodiments of a compound of Motif (I'), (I'-a), (I'-b), (I'-c), (I'-d), (I'-e), (I'-f), (I'-g) or (I'-h), $A^2$ is —O—, —S—, —$CH_2$—, —NH—, —N($CH_3$)— or —N(C(=O)$CH_3$)—. In some embodiments, $A^2$ is —O—. In some embodiments, $A^2$ is —S—. In some embodiments, $A^2$ is —$CH_2$—. In some embodiments, $A^2$ is —NH—. In some embodiments, $A^2$ is —N($CH_3$)—. In some embodiments, $A^2$ is —N(C(=O)$CH_3$)—.

In some embodiments of a compound of Motif (I'), (I'-a), (I'-b), (I'-c), (I'-d), (I'-c), (I'-f), (I'-g) or (I'-h), p is 0, 1, 2, 3, 4, 5 or 6. In some embodiments, p is 0. In some embodiments, p is 1. In some embodiments, p is 2. In some embodiments, p is 3. In some embodiments, p is 4. In some embodiments, p is 5. In some embodiments, p is 6.

In some embodiments of a compound of Motif (I'), at least one of $X^1$, $X^2$, $X^3$, $X^4$, and $X''$ is —SH.

In some embodiments of a compound of Motif (I'), at least one of $X^1$, $X^2$, $X^3$, $X^4$, and $X''$ is —S—.

In some embodiments of a compound of Motif (I'), at least one of $Y^1$, $Y^2$, $Y^3$, $Y^4$, and $Y''$ is =S.

In some embodiments of a compound of Motif (I'), at least one of A, $A^1$, and $A^2$ is —S—.

In some embodiments of a compound of Motif (I'), at least one of $Z^1$, $Z^2$, $Z^3$, $Z^4$, and $Z''$ is —$OCH_3$. In some embodiments, $Z^3$ is —$OCH_3$. In some embodiments, $Z^3$ and $Z^1$ are —$OCH_3$. In some embodiments of a compound of Motif (I'), at least one of $Z^1$, $Z^2$, $Z^3$, $Z^4$, and $Z''$ is —OH. In some embodiments, $Z^1$, $Z^2$, and $Z^4$ are —OH. In some embodiments, $Z^2$ and $Z^4$ are —OH.

In some embodiments of a compound of Motif (I'), at least one of $Q^1$, $Q^2$, $Q^3$, and $Q^4$ is —$OCH_3$. In some embodiments of a compound of Formula (I), at least one of $Q^1$, $Q^2$, $Q^3$, and $Q^4$ is —O—. In some embodiments, $Q^1$ and $Q^4$ are —$OCH_3$. In some embodiments, $Q^2$ and $Q^3$ are —O—.

In some embodiments of a compound o Motif (I'), at least one of $Y^1$, $Y^2$, $Y^3$, $Y^4$, and $Y''$ is =O. In some embodiments, $Y^1$, $Y^2$, $Y^3$, and $Y^4$ is are =O. In some embodiments, $Y^1$, $Y^2$, $Y^3$, $Y^4$, and $Y''$ is =S. In some embodiments, $Y^2$ is =S. In some embodiments, $Y^4$ is =S.

In some embodiments of a compound of Motif (I'), at least one of $X^1$, $X^2$, $X^3$, $X^4$, and $X''$ is —$O^-$. In Some embodiments, $X^1$, $X^2$, $X^3$, and $X^4$ are —$O^-$. In some embodiments, $X^1$ is —S. In some embodiments, $X^2$ is —S—. In some embodiments, $X^3$ is —S—. In some embodiments, $X^4$ is —S—.

In some embodiments of a compound of Motif (I'), In some embodiments of a compound of Motif (I'), at least one of A, A', and $A^2$ is —O—. In some embodiments, A, $A^1$, and $A^2$ are —O—.

In one aspect, described herein is an mRNA sequence initiator comprising a compound of Formula (II) or a salt or solvate thereof:

Formula (II)

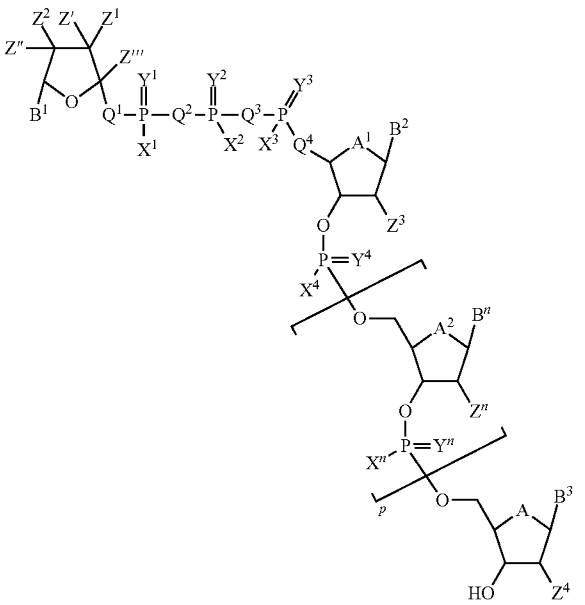

wherein $B^1$ is

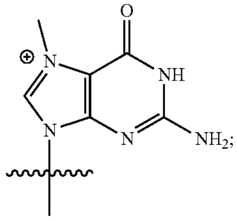 [SMILES: *n1c[n+](C)c2c(=O)[nH]c(N)nc21]

each $B^2$, $B^3$, and $B''$ is independently a natural, a modified, or an unnatural nucleobase;

each $Z^1$ and Z' is independently is hydrogen, fluorine, —OH, —SH, —$CH_3$, —$CH_2CH_3$, —$OCH_3$, —NH($CH_3$), —$NH_2$, —NH(C(=O)$CH_3$), or —$SCH_3$;

each $Z^2$ and Z" is independently fluorine, —OH, —SH, —$CH_3$, —$CH_2CH_3$, —$OCH_3$, —$SCH_3$, —$OCH_2CH_3$, —$NH_2$, $NHCH_3$, or NHC(=O)$CH_3$;

Z''' is hydrogen, fluorine, —$CH_3$, —$CH_2CH_3$, —$OCH_3$, or —$OCH_2CH_3$;

each $Z^3$, $Z^4$, and Z" is independently hydrogen, fluorine, —OH, —$CH_3$, —$CH_2CH_3$, —$OCH_3$, —$NH_2$, —$NHCH_3$, —NH(C(=O)$CH_3$), —$OCH_2CH_3$, —$OCH_2OCH_3$, —$OCH_2CH_2CH_3$, —$OCH(CH_3)_2$, —$SCH_3$, or —$OCH_2CH_2OCH_3$;

each $Q^1$ and $Q^4$ is independently —CH=CH—, —$CH_2$—, —$CH_2O$—, —$CH_2S$—, —$CH_2CH_2$—, —$CH_2CF_2$—, —$CH_2NH_2$—, —$CH_2NH(CH_3)$—, or —$CH_2$N(C(=O)$CH_3$)—;

each $Q^2$ and $Q^3$ is independently —O—, —S—, —$CH_2$—, —$CF_2$—, —NH—, —N($CH_3$)—, or —N(C(=O)$CH_3$)—;

each $X^1$, $X^2$, $X^3$, $X^4$, and $X''$ is independently —OH, —SH, —O, —S, —$NH_2$, —$NHCH_3$, —NH(C(=O)$CH_3$), —$CH_3$, —$CH_2CH_3$, —$CH_2CH_2CH_3$, —CH($CH_3$)$_2$, —$OCH_3$ or —$OCH_2CH_3$;

each $Y^1$, $Y^2$, $Y^3$, $Y^4$, and $Y''$ is independently =O, =S, =NH, or $=NCH_3$;

each A, $A^1$, and $A^2$ is independently —O—, —S—, $—CH_2—$, —NH—, $—N(CH_3)—$ or $—N(C(=O)CH_3)—$; and p=0, 1, 2, 3, 4, 5 or 6.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $B^2$ independently a natural, a modified, or an unnatural nucleobase. In some embodiments, $B^2$ is adenine. In some embodiments, $B^2$ is guanine. In some embodiments, $B^2$ is cytosine. In some embodiments, $B^2$ is uracil, In some embodiments, $B^2$ is thymine, In some embodiments, $B^2$ is hypoxanthine. In some embodiments, $B^2$ is purine.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $B^3$ independently a natural, a modified, or an unnatural nucleobase. In some embodiments, $B^3$ is adenine. In some embodiments, $B^3$ is guanine. In some embodiments, $B^3$ is cytosine. In some embodiments, $B^3$ is uracil, In some embodiments, $B^3$ is thymine, In some embodiments, $B^3$ is hypoxanthine. In some embodiments, $B^3$ is purine.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $B''$ independently a natural, a modified, or an unnatural nucleobase. In some embodiments, $B''$ is adenine. In some embodiments, $B''$ is guanine. In some embodiments, $B''$ is cytosine. In some embodiments, $B''$ is uracil, In some embodiments, $B''$ is thymine, In some embodiments, $B''$ is hypoxanthine. In some embodiments, $B''$ is purine.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $Z^1$ is hydrogen, fluorine, —OH, —SH, $—CH_3$, $—CH_2CH_3$, $—OCH_3$, $—NH(CH_3)$, $—NH_2$, $—NH(C(=O)CH_3)$, or $—SCH_3$. In some embodiments, $Z^1$ is hydrogen. In some embodiments, $Z^1$ is fluorine. In some embodiments, $Z^1$ is —OH. In some embodiments, $Z^1$ is —SH. In some embodiments, $Z^1$ is $—CH_3$. In some embodiments, $Z^1$ is $—CH_2CH_3$. In some embodiments, $Z^1$ is $—OCH_3$. In some embodiments, $Z^1$ is $—NH(CH_3)$, In some embodiments, $Z^1$ is $—NH_2—$. In some embodiments, $Z^1$ is $—NH(C(=O)CH_3)$. In some embodiments, $Z^1$ is $—SCH_3$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $Z^1$ is hydrogen, fluorine, —OH, —SH, $—CH_3$, $—CH_2CH_3$, $—OCH_3$, $—NH(CH_3)$, $—NH_2$, $—NH(C(=O)CH_3)$, or $—SCH_3$. In some embodiments, $Z^1$ is hydrogen. In some embodiments, $Z^1$ is fluorine. In some embodiments, $Z^1$ is —OH. In some embodiments, $Z^1$ is —SH. In some embodiments, $Z^1$ is $—CH_3$. In some embodiments, $Z^1$ is $—CH_2CH_3$. In some embodiments, $Z^1$ is $—OCH_3$. In some embodiments, $Z^1$ is $—NH(CH_3)$, In some embodiments, $Z^1$ is $—NH_2—$. In some embodiments, $Z^1$ is $—NH(C(=O)CH_3)$. In some embodiments, $Z^1$ is $—SCH_3$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $Z^2$ is fluorine, —OH, —SH, $—CH_3$, $—CH_2CH_3$, $—OCH_3$, $—SCH_3$, $—OCH_2CH_3$, $—NH_2$, $NHCH_3$, or $NHC(=O)CH_3$. In some embodiments, $Z^2$ is fluorine. In some embodiments, $Z^2$ is —OH. In some embodiments, $Z^2$ is —SH. In some embodiments, $Z^2$ is $—CH_3$. In some embodiments, $Z^2$ is $—CH_2CH_3$. In some embodiments, $Z^2$ is $—OCH_3$. In some embodiments, $Z^2$ is $—SCH_3$. In some embodiments, $Z^2$ is $—OCH_2CH_3$. In some embodiments, $Z^2$ is $—NH_2$. In some embodiments, $Z^2$ is $NHCH_3$. In some embodiments, $Z^2$ is $NHC(=O)CH_3$.

In some embodiments of a compound of Formula (II), (II-a), (II-b), (II-c), (II-d), (II-c), (II-f), (II-g), (II-h), (II-i), (II-j), (II-k), (II-l), (II-m), (II-n), (II-o), (II-p), (II-q), (II-r), (II-s), (II-t), or (II-u), Z" is fluorine, —OH, —SH, $—CH_3$, $—CH_2CH_3$, $—OCH_3$, $—SCH_3$, $—OCH_2CH_3$, $—NH_2$, $NHCH_3$, or $NHC(=O)CH_3$. In some embodiments, Z" is fluorine. In some embodiments, Z" is —OH. In some embodiments, Z" is —SH. In some embodiments, Z" is $—CH_3$. In some embodiments, Z" is $—CH_2CH_3$. In some embodiments, Z" is $—OCH_3$. In some embodiments, Z" is $—SCH_3$. In some embodiments, Z" is $—OCH_2CH_3$. In some embodiments, Z" is $—NH_2$. In some embodiments, Z" is $NHCH_3$. In some embodiments, Z" is $NHC(=O)CH_3$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), Z'" is hydrogen, fluorine, $—CH_3$, $—CH_2CH_3$, $—OCH_3$, or $—OCH_2CH_3$. In some embodiments, Z'" is hydrogen. In some embodiments, Z'" is fluorine. In some embodiments, Z'" is $—CH_3$. In some embodiments, Z'" is $—CH_2CH_3$. In some embodiments, Z'" is $—OCH_3$. In some embodiments, Z'" is $—OCH_2CH_3$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $Z^3$ is hydrogen, fluorine, —OH, $—CH_3$, $—CH_2CH_3$, $—OCH_3$, $—NH_2$, $—NHCH_3$, $—NH(C(=O)CH_3)$, $—OCH_2CH_3$, $—OCH_2OCH_3$, $—OCH_2CH_2CH_3$, $—OCH(CH_3)_2$, $—SCH_3$, or $—OCH_2CH_2OCH_3$. In some embodiments, $Z^3$ is hydrogen. In some embodiments, $Z^3$ is fluorine. In some embodiments, $Z^3$ is —OH. In some embodiments, $Z^3$ is $—CH_3$. In some embodiments, $Z^3$ is $—CH_2CH_3$. In some embodiments, $Z^3$ is $—OCH_3$. In some embodiments, $Z^3$ is $—NH_2$. In some embodiments, $Z^3$ is $—NHCH_3$. In some embodiments, $Z^3$ is $—NH(C(=O)CH_3)$. In some embodiments, $Z^3$ is $—OCH_2CH_3$. In some embodiments, $Z^3$ is $—OCH_2OCH_3$. In some embodiments, $Z^3$ is $—OCH_2CH_2CH_3$. In some embodiments, $Z^3$ is $—OCH(CH_3)_2$. In some embodiments, $Z^3$ is $—SCH_3$. In some embodiments, $Z^3$ is $—OCH_2CH_2OCH_3$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $Z^4$ is hydrogen, fluorine, —OH, $—CH_3$, $—CH_2CH_3$, $—OCH_3$, $—NH_2$, $—NHCH_3$, $—NH(C(=O)CH_3)$, $—OCH_2CH_3$, $—OCH_2OCH_3$, $—OCH_2CH_2CH_3$, $—OCH(CH_3)_2$, $—SCH_3$, or $—OCH_2CH_2OCH_3$. In some embodiments, $Z^4$ is hydrogen. In some embodiments, $Z^4$ is fluorine. In some embodiments, $Z^4$ is —OH. In some embodiments, $Z^4$ is $—CH_3$. In some embodiments, $Z^4$ is $—CH_2CH_3$. In some embodiments, $Z^4$ is $—OCH_3$. In some embodiments, $Z^4$ is $—NH_2$. In some embodiments, $Z^4$ is $—NHCH_3$. In some embodiments, $Z^4$ is $—NH(C(=O)CH_3)$. In some embodiments, $Z^4$ is $—OCH_2CH_3$. In some embodiments, $Z^4$ is $—OCH_2OCH_3$. In some embodiments, $Z^4$ is $—OCH_2CH_2CH_3$. In some embodiments, $Z^4$ is $—OCH(CH_3)_2$. In some embodiments, $Z^4$ is $—SCH_3$. In some embodiments, $Z^4$ is $—OCH_2CH_2OCH_3$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), Z″ is hydrogen, fluorine, —OH, $—CH_3$, $—CH_2CH_3$, $—OCH_3$, $—NH_2$, $—NHCH_3$, $—NH(C(=O)CH_3)$, $—OCH_2CH_3$, $—OCH_2OCH_3$, $—OCH_2CH_2CH_3$, $—OCH(CH_3)_2$, $—SCH_3$, or $—OCH_2CH_2OCH_3$. In some embodiments, Z″ is hydrogen. In some embodiments, Z″ is fluorine. In some embodiments, Z″ is —OH. In some embodiments, Z″ is $—CH_3$. In some embodiments, Z″ is $—CH_2CH_3$. In some embodiments, Z″ is $—OCH_3$. In some embodiments, Z″ is $—NH_2$. In some embodiments, Z″ is $—NHCH_3$. In some embodiments, Z″ is $—NH(C(=O)CH_3)$. In some embodiments, Z″ is $—OCH_2CH_3$. In some embodiments, Z″ is $—OCH_2OCH_3$. In some embodiments, Z″ is $—OCH_2CH_2CH_3$. In some embodiments, Z″ is $—OCH(CH_3)_2$. In some embodiments, Z″ is $—SCH_3$. In some embodiments, Z″ is $—OCH_2CH_2OCH_3$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $Q^1$ is —CH=CH—, $—CH_2—$, $—CH_2O—$, $—CH_2S—$, $—CH_2CH_2—$, $—CH_2CF_2—$, $—CH_2NH_2—$, $—CH_2NH(CH_3)—$, or $—CH_2N(C(=O)CH_3)—$. In some embodiments, $Q^1$ is —CH=CH—. In some embodiments, $Q^1$ is $—CH_2—$. In some embodiments, $Q^1$ is $—CH_2O—$. In some embodiments, $Q^1$ is $—CH_2S—$. In some embodiments, $Q^1$ is $—CH_2CH_2—$. In some embodiments, $Q^1$ is $—CH_2CF_2—$. In some embodiments, $Q^1$ is $—CH_2NH_2—$. In some embodiments, $Q^1$ is $—CH_2NH(CH_3)—$. In some embodiments, $Q^1$ is $—CH_2N(C(=O)CH_3)—$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $Q^4$ is —CH=CH—, $—CH_2—$, $—CH_2O—$, $—CH_2S—$, $—CH_2CH_2—$, $—CH_2CF_2—$, $—CH_2NH_2—$, $—CH_2NH(CH_3)—$, or $—CH_2N(C(=O)CH_3)—$. In some embodiments, $Q^1$ is —CH=CH—. In some embodiments, $Q^4$ is $—CH_2—$. In some embodiments, $Q^4$ is $—CH_2O—$. In some embodiments, $Q^4$ is $—CH_2S—$. In some embodiments, $Q^4$ is $—CH_2CH_2—$. In some embodiments, $Q^4$ is $—CH_2CF_2—$. In some embodiments, $Q^4$ is $—CH_2NH_2—$. In some embodiments, $Q^4$ is $—CH_2NH(CH_3)—$. In some embodiments, $Q^4$ is $—CH_2N(C(=O)CH_3)—$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $Q^2$ is —O—, —S—, $—CH_2—$, $—CF_2—$, —NH—, $—N(CH_3)—$, or $—N(C(=O)CH_3)—$. In some embodiments $Q^2$ is —O—. In some embodiments $Q^2$ is —S—. In some embodiments $Q^2$ is $—CH_2—$. In some embodiments $Q^2$ is $—CF_2—$. In some embodiments $Q^2$ is —NH—. In some embodiments $Q^2$ is $—N(CH_3)—$. In some embodiments $Q^2$ is $—N(C(=O)CH_3)—$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $Q^3$ is —O—, —S—, $—CH_2—$, $—CF_2—$, —NH—, $—N(CH_3)—$, or $—N(C(=O)CH_3)—$. In some embodiments $Q^3$ is —O—. In some embodiments $Q^3$ is —S—. In some embodiments $Q^3$ is $—CH_2—$. In some embodiments $Q^3$ is $—CF_2—$. In some embodiments $Q^3$ is —NH—. In some embodiments $Q^3$ is $—N(CH_3)—$. In some embodiments $Q^3$ is $—N(C(=O)CH_3)—$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $X^1$ is —OH, —SH, —O, —S, $—NH_2$, $—NHCH_3$, $—NH(C(=O)CH_3)$, $—CH_3$, $—CH_2CH_3$, $—CH_2CH_2CH_3$, $—CH(CH_3)_2$, $—OCH_3$ or $—OCH_2CH_3$. In some embodiments, $X^1$ is —OH. In some embodiments, $X^1$ is —SH. In some embodiments, $X^1$ is $—O^-$. In some embodiments, $X^1$ is —S. In some embodiments, $X^1$ is $—NH_2$. In some embodiments, $X^1$ is $—NHCH_3$. In some embodiments, $X^1$ is $—NH(C(=O)CH_3)$. In some embodiments, $X^1$ is $—CH_3$. In some embodiments, X' is $—CH_2CH_3$. In some embodiments, $X^1$ is $—CH_2CH_2CH_3$. In some embodiments, $X^1$ is $—CH(CH_3)_2$. In some embodiments, $X^1$ is $—OCH_3$. In some embodiments, $X^1$ is $—OCH_2CH_3$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $X^2$ is —OH, —SH, —O, —S, $—NH_2$, $—NHCH_3$, $—NH(C(=O)CH_3)$, $—CH_3$, $—CH_2CH_3$, $—CH_2CH_2CH_3$, $—CH(CH_3)_2$, $—OCH_3$ or $—OCH_2CH_3$. In some embodiments, $X^2$ is —OH. In some embodiments, $X^2$ is —SH. In some embodiments, $X^2$ is $—O^-$. In some embodiments, $X^2$ is —S. In some embodiments, $X^2$ is $—NH_2$. In some embodiments, $X^2$ is $—NHCH_3$. In some embodiments, $X^2$ is $—NH(C(=O)CH_3)$. In some embodiments, $X^2$ is $—CH_3$. In some embodiments, $X^2$ is $—CH_2CH_3$. In some embodiments, $X^2$ is $—CH_2CH_2CH_3$. In some embodiments, $X^2$ is $—CH(CH_3)_2$. In some embodiments, $X^2$ is $—OCH_3$. In some embodiments, $X^2$ is $—OCH_2CH_3$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $X^3$ is —OH, —SH, —O, —S, $—NH_2$, $—NHCH_3$, $—NH(C(=O)CH_3)$, $—CH_3$, $—CH_2CH_3$, $—CH_2CH_2CH_3$, $—CH(CH_3)_2$, $—OCH_3$ or $—OCH_2CH_3$. In some embodiments, $X^3$ is —OH. In some embodiments, $X^3$ is —SH. In some embodiments, $X^3$ is —O. In some embodiments, $X^3$ is —S. In some embodiments, $X^3$ is $—NH_2$. In some embodiments, $X^3$ is $—NHCH_3$. In some embodiments, $X^3$ is $—NH(C(=O)CH_3)$. In some embodiments, $X^3$ is $—CH_3$. In some embodiments, $X^3$ is $—CH_2CH_3$. In some embodiments, $X^3$ is $—CH_2CH_2CH_3$. In some embodiments, $X^3$ is $—CH(CH_3)_2$. In some embodiments, $X^3$ is $—OCH_3$. In some embodiments, $X^3$ is $—OCH_2CH_3$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $X^4$ is —OH, —SH, —O, —S, $—NH_2$, $—NHCH_3$, $—NH(C(=O)CH_3)$, $—CH_3$, $—CH_2CH_3$, $—CH_2CH_2CH_3$, $—CH(CH_3)_2$, $—OCH_3$ or $—OCH_2CH_3$. In some embodiments, $X^4$ is —OH. In some embodiments, $X^4$ is —SH. In some embodiments, $X^4$ is $—O^-$. In some embodiments, $X^4$ is —S. In some embodiments, $X^4$ is $—NH_2$. In some embodiments, $X^4$ is $—NHCH_3$. In some embodiments, $X^4$ is $—NH(C(=O)CH_3)$. In some embodiments, $X^4$ is $—CH_3$. In some embodiments, $X^4$ is $—CH_2CH_3$. In some embodiments, $X^4$ is $—CH_2CH_2CH_3$. In some embodiments, $X^4$ is $—CH(CH_3)_2$. In some embodiments, $X^4$ is $—OCH_3$. In some embodiments, $X^4$ is $—OCH_2CH_3$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), X″ is —OH, —SH, —O, —S, —$NH_2$, —$NHCH_3$, —NH(C(═O)$CH_3$), —$CH_3$, —$CH_2CH_3$, —$CH_2CH_2CH_3$, —CH($CH_3$)$_2$, —$OCH_3$ or —$OCH_2CH_3$. In some embodiments, X″ is —OH. In some embodiments, X″ is —SH. In some embodiments, X″ is —$O^-$. In some embodiments, X″ is —S. In some embodiments, X″ is —$NH_2$. In some embodiments, X″ is —$NHCH_3$. In some embodiments, X″ is —NH(C(═O)$CH_3$). In some embodiments, X″ is —$CH_3$. In some embodiments, X″ is —$CH_2CH_3$. In some embodiments, X″ is —$CH_2CH_2CH_3$. In some embodiments, X″ is —CH($CH_3$)$_2$. In some embodiments, X″ is —$OCH_3$. In some embodiments, X″ is —$OCH_2CH_3$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $Y^1$ is ═O, ═S, ═NH, or ═$NCH_3$. In some embodiments, $Y^1$ is ═O. In some embodiments, $Y^1$ is ═S. In some embodiments, $Y^1$ is ═NH. In some embodiments, $Y^1$ is ═$NCH_3$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $Y^2$ is ═O, ═S, ═NH, or ═$NCH_3$. In some embodiments, $Y^2$ is ═O. In some embodiments, $Y^2$ is ═S. In some embodiments, $Y^2$ is ═NH. In some embodiments, $Y^2$ is ═$NCH_3$.

In some embodiments of a compound of Formula (II), (II-a), (II-b), (II-c), (II-d), (II-c), (II-f), (II-g), (II-h), (II-i), (II-j), (II-k), (II-l), (II-m), (II-n), (II-o), (II-p), (II-q), (II-r), (II-s), (II-t), or (II-u), $Y^3$ is ═O, ═S, ═NH, or ═$NCH_3$. In some embodiments, $Y^3$ is ═O. In some embodiments, $Y^3$ is ═S. In some embodiments, $Y^3$ is ═NH. In some embodiments, $Y^3$ is ═$NCH_3$.

In some embodiments of a compound of Formula (II), (II-a), (II-b), (II-c), (II-d), (II-c), (II-f), (II-g), (II-h), (II-i), (II-j), (II-k), (II-l), (II-m), (II-n), (II-o), (II-p), (II-q), (II-r), (II-s), (II-t), or (II-u), $Y^4$ is ═O, ═S, ═NH, or ═$NCH_3$. In some embodiments, $Y^4$ is ═O. In some embodiments, $Y^4$ is ═S. In some embodiments, $Y^4$ is ═NH. In some embodiments, $Y^4$ is ═$NCH_3$.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), Y″ is ═O, ═S, ═NH, or ═$NCH_3$. In some embodiments, Y″ is ═O. In some embodiments, Y″ is ═S. In some embodiments, Y″ is ═NH. In some embodiments, Y″ is ═$NCH_3$.

In some embodiments of a compound of Formula (II), (II-a), (II-b), (II-c), (II-d), (II-c), (II-f), (II-g), (II-h), (II-i), (II-j), (II-k), (II-l), (II-m), (II-n), (II-o), (II-p), (II-q), (II-r), (II-s), (II-t), or (II-u), A is —O—, —S—, —$CH_2$—, —NH—, —N($CH_3$)— or —N(C(═O)$CH_3$)—. In some embodiments, A is —O—. In some embodiments, A is —S—. In some embodiments, A is —$CH_2$—. In some embodiments, A is —NH—. In some embodiments, A is —N($CH_3$)—. In some embodiments, A is —N(C(═O)$CH_3$)—.

In some embodiments of a compound of Formula (II), (II-a), (II-b), (II-c), (II-d), (II-c), (II-f), (II-g), (II-h), (II-i), (II-j), (II-k), (II-l), (II-m), (II-n), (II-o), (II-p), (II-q), (II-r), (II-s), (II-t), or (II-u), $A^1$ is —O—, —S—, —$CH_2$—, —NH—, —N($CH_3$)— or —N(C(═O)$CH_3$)—. In some embodiments, $A^1$ is —O—. In some embodiments, $A^1$ is —S—. In some embodiments, $A^1$ is —$CH_2$—. In some embodiments, $A^1$ is —NH—. In some embodiments, $A^1$ is —N($CH_3$)—. In some embodiments, $A^1$ is —N(C(═O)$CH_3$)—.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), $A^2$ is —O—, —S—, —$CH_2$—, —NH—, —N($CH_3$)— or —N(C(═O)$CH_3$)—. In some embodiments, $A^2$ is —O—. In some embodiments, $A^2$ is —S—. In some embodiments, $A^2$ is —$CH_2$—. In some embodiments, $A^2$ is —NH—. In some embodiments, $A^2$ is —N($CH_3$)—. In some embodiments, $A^2$ is —N(C(═O)$CH_3$)—.

In some embodiments of a compound of Formula (II), (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-s), (II-t), or (II-u), p is 0, 1, 2, 3, 4, 5 or 6. In some embodiments, p is 0. In some embodiments, p is 1. In some embodiments, p is 2. In some embodiments, p is 3. In some embodiments, p is 4. In some embodiments, p is 5. In some embodiments, p is 6.

In some embodiments, $B^1$ is

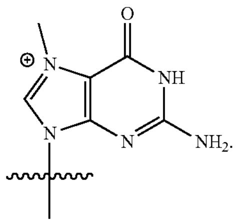 [SMILES: *n1c[n+](C)c2c(=O)[nH]c(N)nc21]

In some embodiments, each $B^2$ and $B^3$ is independently adenine or guanine. In some embodiments, $B^2$ is adenine. In some embodiments, $B^3$ is guanine.

In some embodiments, each $Z^1$, $Z^2$, $Z^3$, and $Z^4$ is independently —OH or —$OCH_3$. In some embodiments, $Z^3$ is —$OCH_3$. In some embodiments, $Z^1$ is —$OCH_3$. In some embodiments $Z^2$ is —OH. In some embodiments, $Z^1$, $Z^2$, and $Z^4$ are —OH and $Z^3$ is —$OCH_3$. In some embodiments, $Z^1$ and $Z^3$ are —$OCH_3$ and $Z^2$ and $Z^4$ are —OH. In some embodiments, Z', Z'', and Z''' are hydrogen.

In some embodiments, $Q^1$ and $Q^4$ are —$OCH_2$—. In some embodiments $Q^2$ and $Q^3$ are —O—.

In some embodiments, $X^1$, $X^2$, $X^3$, and $X^4$ are —O—. In some embodiments, $X^1$, $X^2$, $X^3$, and $X^4$ are —S—. In some embodiments, $X^1$, $X^3$, $X^4$ are —O— and $X^2$ is —S—.

In some embodiments, $Y^1$, $Y^2$, $Y^3$, and $Y^4$ are ═O. In some embodiments, $Y^1$, $Y^2$, $Y^3$, and $Y^4$ are ═S. In some embodiments, $Y^1$, $Y^3$, and $Y^4$ are ═O and $Y^2$ is ═S. In some embodiments, $Y^1$, $Y^2$, $Y^3$ are ═O and $Y^4$ is ═S.

In some embodiments, A, $A^1$, and $A^2$ are —O—.

In some embodiments, p is 0.

In one aspect, described herein is an mRNA sequence having a 5'-end region motif (Motif (II'):

Motif (II')

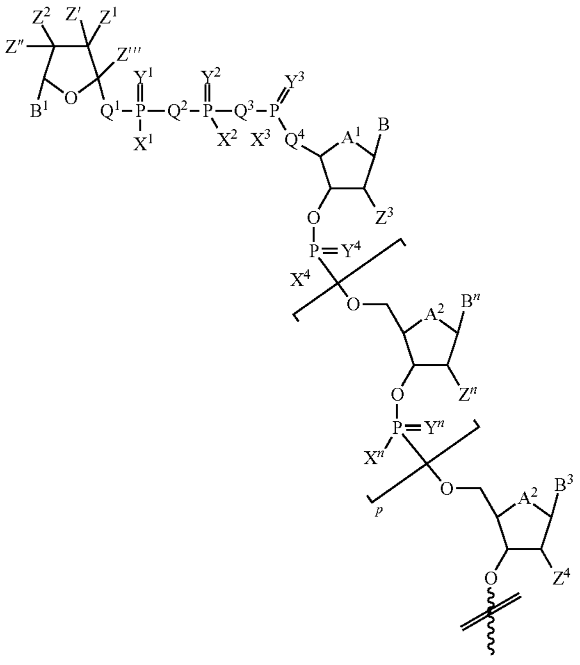

wherein $B^1$ is

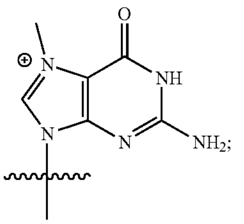 [SMILES: *n1c[n+](C)c2c(=O)[nH]c(N)nc21]

each $B^2$, $B^3$, and $B''$ is independently a natural, a modified, or an unnatural nucleobase;

each $Z^1$ and $Z^1$ is independently is hydrogen, fluorine, —OH, —SH, —$CH_3$, —$CH_2CH_3$, —$OCH_3$, —NH($CH_3$), —$NH_2$, —NH(C(═O)$CH_3$), or —$SCH_3$;

each $Z^2$ and Z" is independently fluorine, —OH, —SH, —$CH_3$, —$CH_2CH_3$, —$OCH_3$, —$SCH_3$, —$OCH_2CH_3$, —$NH_2$, $NHCH_3$, or NHC(═O)$CH_3$;

Z''' is hydrogen, fluorine, —$CH_3$, —$CH_2CH_3$, —$OCH_3$, or —$OCH_2CH_3$;

each $Z^3$, $Z^4$, and $Z''$ is independently hydrogen, fluorine, —OH, —$CH_3$, —$CH_2CH_3$, —$OCH_3$, —$NH_2$, —$NHCH_3$, —NH(C(═O)$CH_3$), —$OCH_2CH_3$, —$OCH_2OCH_3$, —$OCH_2CH_2CH_3$, —OCH$(CH_3)_2$, —$SCH_3$, or —$OCH_2CH_2OCH_3$;

each $Q^1$ and $Q^4$ is independently —CH═CH—, —$CH_2$—, —$CH_2O$—, —$CH_2S$—, —$CH_2CH_2$—, —$CH_2CF_2$—, —$CH_2NH_2$—, —$CH_2NH(CH_3)$—, or —$CH_2N(C(═O)CH_3)$—;

each $Q^2$ and $Q^3$ is independently —O—, —S—, —$CH_2$—, —$CF_2$—, —NH—, —N($CH_3$)—, or —N(C(═O)$CH_3$)—;

each $X^1$, $X^2$, $X^3$, $X^4$, and $X''$ is independently —OH, —SH, —O, —S, —$NH_2$, —$NHCH_3$, —NH(C(═O)$CH_3$), —$CH_3$, —$CH_2CH_3$, —$CH_2CH_2CH_3$, —CH$(CH_3)_2$, —$OCH_3$ or —$OCH_2CH_3$;

each $Y^1$, $Y^2$, $Y^3$, $Y^4$, and $Y''$ is independently ═O, ═S, ═NH, or ═$NCH_3$;

each A, $A^1$, and $A^2$ is independently —O—, —S—, —$CH_2$—, —NH—, —N($CH_3$)— or —N(C(═O)$CH_3$)—; and p=0, 1, 2, 3, 4, 5 or 6.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $B^2$ independently a natural, a modified, or an unnatural nucleobase. In some embodiments, $B^2$ is adenine. In some embodiments, $B^2$ is guanine. In some embodiments, $B^2$ is cytosine. In some embodiments, $B^2$ is uracil, In some embodiments, $B^2$ is thymine, In some embodiments, $B^2$ is hypoxanthine. In some embodiments, $B^2$ is purine.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $B^3$ independently a natural, a modified, or an unnatural nucleobase. In some embodiments, $B^3$ is adenine. In some embodiments, $B^3$ is guanine. In some embodiments, $B^3$ is cytosine. In some embodiments, $B^3$ is uracil, In some embodiments, $B^3$ is thymine, In some embodiments, $B^3$ is hypoxanthine. In some embodiments, $B^3$ is purine.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $B''$ independently a natural, a modified, or an unnatural nucleobase. In some embodiments, $B''$ is adenine. In some embodiments, $B''$ is guanine. In some embodiments, $B''$ is cytosine. In some embodiments, $B''$ is uracil, In some embodiments, $B''$ is thymine, In some embodiments, $B''$ is hypoxanthine. In some embodiments, $B''$ is purine.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $Z^1$ is hydrogen, fluorine, —OH, —SH, —$CH_3$, —$CH_2CH_3$, —$OCH_3$, —NH($CH_3$), —$NH_2$, —NH(C(═O)$CH_3$), or —$SCH_3$. In some embodiments, $Z^1$ is hydrogen. In some embodiments, $Z^1$ is fluorine. In some embodiments, $Z^1$ is —OH. In some embodiments, $Z^1$ is —SH. In some embodiments, $Z^1$ is —$CH_3$. In some embodiments, $Z^1$ is —$CH_2CH_3$. In some embodiments, $Z^1$ is —$OCH_3$. In some embodiments, $Z^1$ is —NH($CH_3$), In some embodiments, $Z^1$ is —$NH_2$—. In some embodiments, $Z^1$ is —NH(C(═O)$CH_3$). In some embodiments, $Z^1$ is —$SCH_3$.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $Z^1$ is hydrogen, fluorine, —OH, —SH, —$CH_3$, —$CH_2CH_3$, —$OCH_3$, —NH($CH_3$), —$NH_2$, —NH(C(═O)$CH_3$), or —$SCH_3$. In some embodiments, $Z^1$ is hydrogen. In some embodiments, $Z^1$ is fluorine. In some embodiments, Z' is —OH. In some embodiments, $Z^1$ is —SH. In some embodiments, $Z^1$ is —$CH_3$. In some embodiments, $Z^1$ is —$CH_2CH_3$. In some embodiments, $Z^1$ is —$OCH_3$. In some embodiments, $Z^1$ is —$NH(CH_3)$, In some embodiments, $Z^1$ is —$NH_2$—. In some embodiments, Z' is —$NH(C(=O)CH_3)$. In some embodiments, $Z^1$ is —$SCH_3$.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $Z^2$ is fluorine, —OH, —SHI, —$CH_3$, —$CH_2CH_3$, —$OCH_3$, —$SCH_3$, —$OCH_2CH_3$, —$NH_2$, $NHCH_3$, or $NHC(=O)CH_3$. In some embodiments, $Z^2$ is fluorine. In some embodiments, $Z^2$ is —OH. In some embodiments, $Z^2$ is —SH. In some embodiments, $Z^2$ is —$CH_3$. In some embodiments, $Z^2$ is —$CH_2CH_3$. In some embodiments, $Z^2$ is —$OCH_3$. In some embodiments, $Z^2$ is —$SCH_3$. In some embodiments, $Z^2$ is —$OCH_2CH_3$. In some embodiments, $Z^2$ is —$NH_2$. In some embodiments, $Z^2$ is $NHCH_3$. In some embodiments, $Z^2$ is $NHC(=O)CH_3$.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), Z" is fluorine, —OH, —SH, —$CH_3$, —$CH_2CH_3$, —$OCH_3$, —$SCH_3$, —$OCH_2CH_3$, —$NH_2$, $NHCH_3$, or $NHC(=O)CH_3$. In some embodiments, Z" is fluorine. In some embodiments, Z" is —OH. In some embodiments, Z" is —SH. In some embodiments, Z" is —$CH_3$. In some embodiments, Z" is —$CH_2CH_3$. In some embodiments, Z" is —$OCH_3$. In some embodiments, Z" is —$SCH_3$. In some embodiments, Z" is —$OCH_2CH_3$. In some embodiments, Z" is —$NH_2$. In some embodiments, Z" is $NHCH_3$. In some embodiments, Z" is $NHC(=O)CH_3$.

In some embodiments of a compound of Motif (II'), (II'-a), (II'-b), (II'-c), (II'-d), (II'-c), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), Z‴ is hydrogen, fluorine, —$CH_3$, —$CH_2CH_3$, —$OCH_3$, or —$OCH_2CH_3$. In some embodiments, Z‴ is hydrogen. In some embodiments, Z‴ is fluorine. In some embodiments, Z‴ is —$CH_3$. In some embodiments, Z‴ is —$CH_2CH_3$. In some embodiments, Z‴ is —$OCH_3$. In some embodiments, Z‴ is —$OCH_2CH_3$.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $Z^3$ is hydrogen, fluorine, —OH, —$CH_3$, —$CH_2CH_3$, —$OCH_3$, —$NH_2$, —$NHCH_3$, —$NH(C(=O)CH_3)$, —$OCH_2CH_3$, —$OCH_2OCH_3$, —$OCH_2CH_2CH_3$, —$OCH(CH_3)_2$, —$SCH_3$, or —$OCH_2CH_2OCH_3$.

In some embodiments, $Z^3$ is hydrogen. In some embodiments, $Z^3$ is fluorine. In some embodiments, $Z^3$ is —OH. In some embodiments, $Z^3$ is —$CH_3$. In some embodiments, $Z^3$ is —$CH_2CH_3$. In some embodiments, $Z^3$ is —$OCH_3$. In some embodiments, $Z^3$ is —$NH_2$. In some embodiments, $Z^3$ is —$NHCH_3$. In some embodiments, $Z^3$ is —$NH(C(=O)CH_3)$. In some embodiments, $Z^3$ is —$OCH_2CH_3$. In some embodiments, $Z^3$ is —$OCH_2OCH_3$. In some embodiments, $Z^3$ is —$OCH_2CH_2CH_3$. In some embodiments, $Z^3$ is —$OCH(CH_3)_2$. In some embodiments, $Z^3$ is —$SCH_3$. In some embodiments, $Z^3$ is —$OCH_2CH_2OCH_3$.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $Z^4$ is hydrogen, fluorine, —OH, —$CH_3$, —$CH_2CH_3$, —$OCH_3$, —$NH_2$, —$NHCH_3$, —$NH(C(=O)CH_3)$, —$OCH_2CH_3$, —$OCH_2OCH_3$, —$OCH_2CH_2CH_3$, —$OCH(CH_3)_2$, —$SCH_3$, or —$OCH_2CH_2OCH_3$.

In some embodiments, $Z^4$ is hydrogen. In some embodiments, $Z^4$ is fluorine. In some embodiments, $Z^4$ is —OH. In some embodiments, $Z^4$ is —$CH_3$. In some embodiments, $Z^4$ is —$CH_2CH_3$. In some embodiments, $Z^4$ is —$OCH_3$. In some embodiments, $Z^4$ is —$NH_2$. In some embodiments, $Z^4$ is —$NHCH_3$. In some embodiments, $Z^4$ is —$NH(C(=O)CH_3)$. In some embodiments, $Z^4$ is —$OCH_2CH_3$. In some embodiments, $Z^4$ is —$OCH_2OCH_3$. In some embodiments, $Z^4$ is —$OCH_2CH_2CH_3$. In some embodiments, $Z^4$ is —$OCH(CH_3)_2$. In some embodiments, $Z^4$ is —$SCH_3$. In some embodiments, $Z^4$ is —$OCH_2CH_2OCH_3$.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), Z" is hydrogen, fluorine, —OH, —$CH_3$, —$CH_2CH_3$, —$OCH_3$, —$NH_2$, —$NHCH_3$, —$NH(C(=O)CH_3)$, —$OCH_2CH_3$, —$OCH_2OCH_3$, —$OCH_2CH_2CH_3$, —$OCH(CH_3)_2$, —$SCH_3$, or —$OCH_2CH_2OCH_3$.

In some embodiments, Z" is hydrogen. In some embodiments, Z" is fluorine. In some embodiments, Z" is —OH. In some embodiments, Z" is —$CH_3$. In some embodiments, Z" is —$CH_2CH_3$. In some embodiments, Z" is —$OCH_3$. In some embodiments, Z" is —$NH_2$. In some embodiments, Z" is —$NHCH_3$. In some embodiments, Z" is —$NH(C(=O)CH_3)$. In some embodiments, Z" is —$OCH_2CH_3$. In some embodiments, Z" is —$OCH_2OCH_3$. In some embodiments, Z" is —$OCH_2CH_2CH_3$. In some embodiments, Z" is —$OCH(CH_3)_2$. In some embodiments, Z" is —$SCH_3$. In some embodiments, Z" is —$OCH_2CH_2OCH_3$.

In some embodiments of a compound of Motif (II'), (II'-a), (II'-b), (II'-c), (II'-d), (II'-c), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $Q^1$ is —CH=CH—, —$CH_2$—, —$CH_2O$—, —$CH_2S$—, —$CH_2CH_2$—, —$CH_2CF_2$—, —$CH_2NH_2$—, —$CH_2NH(CH_3)$—, or —$CH_2N(C(=O)CH_3)$—. In some embodiments, $Q^1$ is —CH=CH—. In some embodiments, $Q^1$ is —$CH_2$—. In some embodiments, $Q^1$ is —$CH_2O$—. In some embodiments, $Q^1$ is —$CH_2S$—. In some embodiments, $Q^1$ is —$CH_2CH_2$—. In some embodiments, $Q^1$ is —$CH_2CF_2$—. In some embodiments, $Q^1$ is —$CH_2NH_2$—. In some embodiments, $Q^1$ is —$CH_2NH(CH_3)$—. In some embodiments, $Q^1$ is —$CH_2N(C(=O)CH_3)$—.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $Q^4$ is —CH=CH—, —$CH_2$—, —$CH_2O$—, —$CH_2S$—, —$CH_2CH_2$—, —$CH_2CF_2$—, —$CH_2NH_2$—, —$CH_2NH(CH_3)$—, or —$CH_2N(C(=O)CH_3)$—. In some embodiments, $Q^1$ is —CH=CH—. In some embodiments, $Q^4$ is —$CH_2$—. In some embodiments, $Q^4$ is —$CH_2O$—. In some embodiments, $Q^4$ is —$CH_2S$—. In some embodiments, $Q^4$ is —$CH_2CH_2$—. In some embodiments, $Q^4$ is —$CH_2CF_2$—. In some embodiments, $Q^4$ is —$CH_2NH_2$—. In some embodiments, $Q^4$ is —$CH_2NH(CH_3)$—. In some embodiments, $Q^4$ is —$CH_2N(C(=O)CH_3)$—.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $Q^2$ is —O—, —S—, —$CH_2$—, —$CF_2$—, —NH—, —$N(CH_3)$—, or —$N(C(=O)CH_3)$—. In some embodiments $Q^2$ is —O—. In some embodiments $Q^2$ is —S—. In some embodiments $Q^2$ is —$CH_2$—. In some embodiments $Q^2$ is —$CF_2$—. In some embodiments $Q^2$ is —NH—. In some embodiments $Q^2$ is —N($CH_3$)—. In some embodiments $Q^2$ is —N(C(=O)$CH_3$)—.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $Q^3$ is —O—, —S—, —$CH_2$—, —$CF_2$—, —NH—, —N($CH_3$)—, or —N(C(=O)$CH_3$)—. In some embodiments $Q^3$ is —O—. In some embodiments $Q^3$ is —S—. In some embodiments $Q^3$ is —$CH_2$—. In some embodiments $Q^3$ is —$CF_2$—. In some embodiments $Q^3$ is —NH—. In some embodiments $Q^3$ is —N($CH_3$)—. In some embodiments $Q^3$ is —N(C(=O)$CH_3$)—.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $X^1$ is —OH, —SH, —O, —S—, —$NH_2$, —$NHCH_3$, —NH(C(=O)$CH_3$), —$CH_3$, —$CH_2CH_3$, —$CH_2CH_2CH_3$, —$CH(CH_3)_2$, —$OCH_3$ or —$OCH_2CH_3$. In some embodiments, $X^1$ is —OH. In some embodiments, $X^1$ is —SH. In some embodiments, $X^1$ is —$O^-$. In some embodiments, $X^1$ is —S—. In some embodiments, $X^1$ is —$NH_2$. In some embodiments, $X^1$ is —$NHCH_3$. In some embodiments, $X^1$ is —NH(C(=O)$CH_3$). In some embodiments, $X^1$ is —$CH_3$. In some embodiments, $X^1$ is —$CH_2CH_3$. In some embodiments, $X^1$ is —$CH_2CH_2CH_3$. In some embodiments, $X^1$ is —$CH(CH_3)_2$. In some embodiments, $X^1$ is —$OCH_3$. In some embodiments, $X^1$ is —$OCH_2CH_3$.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $X^2$ is —OH, —SH, —O, —S, —$NH_2$, —$NHCH_3$, —NH(C(=O)$CH_3$), —$CH_3$, —$CH_2CH_3$, —$CH_2CH_2CH_3$, —$CH(CH_3)_2$, —$OCH_3$ or —$OCH_2CH_3$. In some embodiments, $X^2$ is —OH. In some embodiments, $X^2$ is —SH. In some embodiments, $X^2$ is —$O^-$. In some embodiments, $X^2$ is —S—. In some embodiments, $X^2$ is —$NH_2$. In some embodiments, $X^2$ is —$NHCH_3$. In some embodiments, $X^2$ is —NH(C(=O)$CH_3$). In some embodiments, $X^2$ is —$CH_3$. In some embodiments, $X^2$ is —$CH_2CH_3$. In some embodiments, $X^2$ is —$CH_2CH_2CH_3$. In some embodiments, $X^2$ is —$CH(CH_3)_2$. In some embodiments, $X^2$ is —$OCH_3$. In some embodiments, $X^2$ is —$OCH_2CH_3$.

In some embodiments of a compound of Motif (II'), (II'-a), (II'-b), (II'-c), (II'-d), (II'-c), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $X^3$ is —OH, —SH, —O, —S, —$NH_2$, —$NHCH_3$, —NH(C(=O)$CH_3$), —$CH_3$, —$CH_2CH_3$, —$CH_2CH_2CH_3$, —$CH(CH_3)_2$, —$OCH_3$ or —$OCH_2CH_3$. In some embodiments, $X^3$ is —OH. In some embodiments, $X^3$ is —SH. In some embodiments, $X^3$ is —O. In some embodiments, $X^3$ is —S. In some embodiments, $X^3$ is —$NH_2$. In some embodiments, $X^3$ is —$NHCH_3$. In some embodiments, $X^3$ is —NH(C(=O)$CH_3$). In some embodiments, $X^3$ is —$CH_3$. In some embodiments, $X^3$ is —$CH_2CH_3$. In some embodiments, $X^3$ is —$CH_2CH_2CH_3$. In some embodiments, $X^3$ is —$CH(CH_3)_2$. In some embodiments, $X^3$ is —$OCH_3$. In some embodiments, $X^3$ is —$OCH_2CH_3$.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $X^4$ is —OH, —SH, —$O^-$, —$S^-$, —$NH_2$, —$NHCH_3$, —NH(C(=O)$CH_3$), —$CH_3$, —$CH_2CH_3$, —$CH_2CH_2CH_3$, —$CH(CH_3)_2$, —$OCH_3$ or —$OCH_2CH_3$. In some embodiments, $X^4$ is —OH. In some embodiments, $X^4$ is —SH. In some embodiments, $X^4$ is —$O^-$. In some embodiments, $X^4$ is —S—. In some embodiments, $X^4$ is —$NH_2$. In some embodiments, $X^4$ is —$NHCH_3$. In some embodiments, $X^4$ is —NH(C(=O)$CH_3$). In some embodiments, $X^4$ is —$CH_3$. In some embodiments, $X^4$ is —$CH_2CH_3$. In some embodiments, $X^4$ is —$CH_2CH_2CH_3$. In some embodiments, $X^4$ is —$CH(CH_3)_2$. In some embodiments, $X^4$ is —$OCH_3$. In some embodiments, $X^4$ is —$OCH_2CH_3$.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), X″ is —OH, —SH, —O, —S, —$NH_2$, —$NHCH_3$, —NH(C(=O)$CH_3$), —$CH_3$, —$CH_2CH_3$, —$CH_2CH_2CH_3$, —$CH(CH_3)_2$, —$OCH_3$ or —$OCH_2CH_3$. In some embodiments, X″ is —OH. In some embodiments, X″ is —SH. In some embodiments, X″ is —$O^-$. In some embodiments, X″ is —S. In some embodiments, X″ is —$NH_2$. In some embodiments, X″ is —$NHCH_3$. In some embodiments, X″ is —NH(C(=O)$CH_3$). In some embodiments, X″ is —$CH_3$. In some embodiments, X″ is —$CH_2CH_3$. In some embodiments, X″ is —$CH_2CH_2CH_3$. In some embodiments, X″ is —$CH(CH_3)_2$. In some embodiments, X" is —$OCH_3$. In some embodiments, X″ is —$OCH_2CH_3$.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $Y^1$ is =O, =S, =NH, or =$NCH_3$. In some embodiments, $Y^1$ is =O. In some embodiments, $Y^1$ is =S. In some embodiments, $Y^1$ is =NH. In some embodiments, $Y^1$ is =$NCH_3$.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $Y^2$ is —O, =S, =NH, or =$NCH_3$. In some embodiments, $Y^2$ is =O. In some embodiments, $Y^2$ is =S. In some embodiments, $Y^2$ is =NH. In some embodiments, $Y^2$ is =$NCH_3$.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $Y^3$ is =O, =S, =NH, or =$NCH_3$. In some embodiments, $Y^3$ is =O. In some embodiments, $Y^3$ is =S. In some embodiments, $Y^3$ is =NH. In some embodiments, $Y^3$ is =$NCH_3$.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $Y^4$ is =O, =S, =NH, or =$NCH_3$. In some embodiments, $Y^4$ is =O. In some embodiments, $Y^4$ is =S. In some embodiments, $Y^4$ is =NH. In some embodiments, $Y^4$ is =$NCH_3$.

In some embodiments of a compound of Motif (II'), (II'-a), (II'-b), (II'-c), (II'-d), (II'-c), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), Y″ is =O, =S, =NH, or =$NCH_3$. In some embodiments, Y″ is =O. In some embodiments, Y″ is =S. In some embodiments, Y″ is =NH. In some embodiments, Y″ is =$NCH_3$.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), A is —O—, —S—, —$CH_2$—, —NH—, —N($CH_3$)— or —N(C(=O)$CH_3$)—.

In some embodiments, A is —O—. In some embodiments, A is —S—. In some embodiments, A is —$CH_2$—. In some embodiments, A is —NH—. In some embodiments, A is —$N(CH_3)$—. In some embodiments, A is —N(C(=O)$CH_3$)—.

In some embodiments of a compound of Motif (II'), (II'-a), (II'-b), (II'-c), (II'-d), (II'-c), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $A^1$ is —O—, —S—, —$CH_2$—, —NH—, —$N(CH_3)$— or —N(C(=O)$CH_3$)—. In some embodiments, $A^1$ is —O—. In some embodiments, $A^1$ is —S—. In some embodiments, $A^1$ is —$CH_2$—. In some embodiments, $A^1$ is —NH—. In some embodiments, $A^1$ is —$N(CH_3)$—. In some embodiments, $A^1$ is —N(C(=O)$CH_3$)—.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), $A^2$ is —O—, —S—, —$CH_2$—, —NH—, —$N(CH_3)$— or —N(C(=O)$CH_3$)—. In some embodiments, $A^2$ is —O—. In some embodiments, $A^2$ is —S—. In some embodiments, $A^2$ is —$CH_2$—. In some embodiments, $A^2$ is —NH—. In some embodiments, $A^2$ is —$N(CH_3)$—. In some embodiments, $A^2$ is —N(C(=O)$CH_3$)—.

In some embodiments of a compound of Motif (II'), (II'-a), (II'-b), (II'-c), (II'-d), (II'-e), (II'-f), (II'-g), (II'-h), (II'-i), (II'-j), (II'-k), (II'-l), (II'-m), (II'-n), (II'-o), (II'-p), (II'-q), (II'-r), (II'-s), (II'-t), or (II'-u), p is 0, 1, 2, 3, 4, 5 or 6. In some embodiments, p is 0. In some embodiments, p is 1. In some embodiments, p is 2. In some embodiments, p is 3. In some embodiments, p is 4. In some embodiments, p is 5. In some embodiments, p is 6.

In some embodiments, $B^1$ is

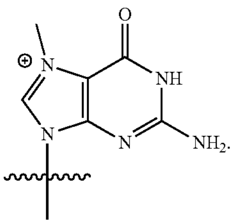 [SMILES: *n1c[n+](C)c2c(=O)[nH]c(N)nc21]

In some embodiments, each $B^2$ and $B^3$ is independently adenine or guanine. In some embodiments, $B^2$ is adenine. In some embodiments, $B^3$ is guanine.

In some embodiments, each $Z^1$, $Z^2$. $Z^3$, and $Z^4$ is independently —OH or —$OCH_3$. In some embodiments, $Z^3$ is —$OCH_3$. In some embodiments, $Z^1$ is —$OCH_3$. In some embodiments $Z^2$ is —OH. In some embodiments, $Z^1$, $Z^2$, and $Z^4$ are —OH and $Z^3$ is —$OCH_3$. In some embodiments, $Z^1$ and $Z^3$ are —$OCH_3$ and $Z^2$ and $Z^4$ are —OH. In some embodiments, Z', Z'', and Z''' are hydrogen.

In some embodiments, $Q^1$ and $Q^4$ are —$OCH_2$—. In some embodiments $Q^2$ and $Q^3$ are —O—.

In some embodiments, $X^1$, $X^2$, $X^3$, and $X^4$ are —O—. In some embodiments, $X^1$, $X^2$, $X^3$, and $X^4$ are —S—. In some embodiments, $X^1$, $X^3$, $X^4$ are —O- and $X^2$ is —S—.

In some embodiments, $Y^1$, $Y^2$, $Y^3$, and $Y^4$ are =O. In some embodiments, $Y^1$, $Y^2$, $Y^3$, and $Y^4$ are =S. In some embodiments, $Y^1$, $Y^3$, and $Y^4$ are =O and $Y^2$ is =S. In some embodiments, $Y^1$, $Y^2$, $Y^3$ are =O and $Y^4$ is =S.

In some embodiments, A, $A^1$, and $A^2$ are —O—.

In some embodiments, p is 0.

In one aspect, described herein is an mRNA sequence initiator comprising a compound of Formula (II) or a salt or solvate thereof:

Formula (II)

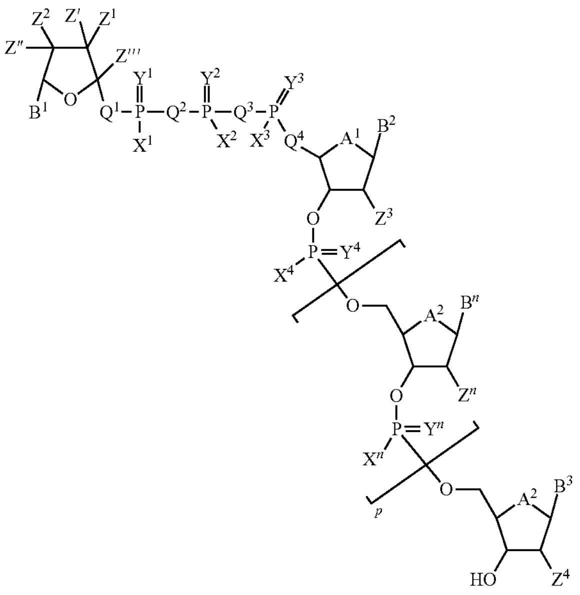

wherein $B^1$ is

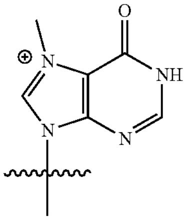

or;

each $B^2$, $B^3$, and B'' is independently a natural, a modified, or an unnatural nucleobase;

each $Z^1$ and Z'' is independently is hydrogen, fluorine, —OH, —SH, —$CH_3$, —$CH_2CH_3$, —$OCH_3$, —NH($CH_3$), —$NH_2$, —NH(C(=O)$CH_3$), or —$SCH_3$;

Z''' is hydrogen, fluorine, —$CH_3$, —$CH_2CH_3$, —$OCH_3$, or —$OCH_2CH_3$;

each $Z^1$ and $Z^2$ is independently hydrogen, fluorine, —OH, —SH, —$CH_3$, —$CH_2CH_3$, —$OCH_3$, —$SCH_3$, —$OCH_2CH_3$, —$NH_2$, $NHCH_3$, or NHC(=O)$CH_3$;

each $Z^3$, $Z^4$, and Z'' is independently hydrogen, fluorine, —OH, —$CH_3$, —$CH_2CH_3$, —$OCH_3$, —$NH_2$, —$NHCH_3$, —NH(C(=O)$CH_3$), —$OCH_2CH_3$, —$OCH_2OCH_3$, —$OCH_2CH_2CH_3$, —$OCH(CH_3)_2$, —$SCH_3$, or —$OCH_2CH_2OCH_3$;

each $Q^1$ and $Q^4$ is independently —CH=CH—, —$CH_2$—, —$CH_2O$—, —$CH_2S$—, —$CH_2CH_2$—, —$CH_2CF_2$—, —$CH_2NH_2$—, —$CH_2NH(CH_3)$—, or —$CH_2N$(C(=O)$CH_3$)—;

each $Q^2$ and $Q^3$ is independently —O—, —S—, —$CH_2$—, —$CF_2$—, —NH—, —$N(CH_3)$—, or —N(C(=O)$CH_3$)—;

each $X^1$, $X^2$, $X^3$, $X^4$, and X'' is independently —OH, —SH, —$O^-$, —$S^-$, —$NH_2$, —$NHCH_3$, —NH(C(=O)

$CH_3$), $—CH_3$, $—CH_2CH_3$, $—CH_2CH_2CH_3$, $—CH(CH_3)_2$, $—OCH_3$ or $—OCH_2CH_3$;

each $Y^1$, $Y^2$, $Y^3$, $Y^4$, and $Y''$ is independently =O, =S, =NH, or $=NCH_3$;

each A, $A^1$, and $A^2$ is independently —O—, —S—, $—CH_2—$, —NH—, $—N(CH_3)—$ or $—N(C(=O)CH_3)—$; and p=0, 1, 2, 3, 4, 5 or 6.

In some embodiments of a compound of Formula (II), (II-a'), (II-b'), (II-c'), (II-d'), (II-c'), (II-f), (II-g'), (II-h'), (II-i'), (II-j'), (II-k'), (II-I'), (II-m'), (II-n'), (II-o'), (II-p'), (II-q'), (II-r'), (II-s'), (II-t'), or (II-u'), $B^1$ is

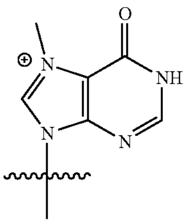
or
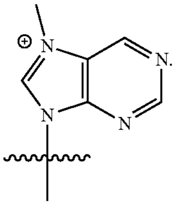

In some embodiments, $B^1$ is

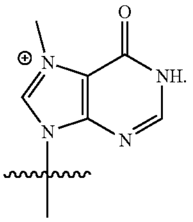 [SMILES: *n1c[n+](C)c2c(=O)[nH]cnc21]

In some embodiments, $B^1$ is

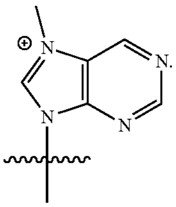 [SMILES: *n1c[n+](C)c2cncnc21]

In some embodiments of a compound of Formula (II), (II-a'), (II-b'), (II-c'), (II-d'), (II-e'), (II-f'), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $B^2$ independently a natural, a modified, or an unnatural nucleobase. In some embodiments, $B^2$ is adenine. In some embodiments, $B^2$ is guanine. In some embodiments, $B^2$ is cytosine. In some embodiments, $B^2$ is uracil, In some embodiments, $B^2$ is thymine, In some embodiments, $B^2$ is hypoxanthine. In some embodiments, $B^2$ is purine.

In some embodiments of a compound of Formula (II), (II-a'), (II-b'), (II-c'), (II-d'), (II-e'), (II-f), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $B^3$ independently a natural, a modified, or an unnatural nucleobase. In some embodiments, $B^3$ is adenine. In some embodiments, $B^3$ is guanine. In some embodiments, $B^3$ is cytosine. In some embodiments, $B^3$ is uracil, In some embodiments, $B^3$ is thymine, In some embodiments, $B^3$ is hypoxanthine. In some embodiments, $B^3$ is purine.

In some embodiments of a compound of Formula (II), (II-a'), (II-b'), (II-c'), (II-d'), (II-e'), (II-f''), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $B''$ independently a natural, a modified, or an unnatural nucleobase. In some embodiments, $B''$ is adenine. In some embodiments, $B''$ is guanine. In some embodiments, $B''$ is cytosine. In some embodiments, $B''$ is uracil, In some embodiments, $B''$ is thymine, In some embodiments, $B''$ is hypoxanthine. In some embodiments, $B''$ is purine.

In some embodiments of a compound of Formula (II), (II-a'), (II-b'), (II-c'), (II-d'), (II-c'), (II-f''), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $Z^1$ is hydrogen, fluorine, —OH, —SH, $—CH_3$, $—CH_2CH_3$, $—OCH_3$, $—NH(CH_3)$, $—NH_2$, $—NH(C(=O)CH_3)$, or $—SCH_3$. In some embodiments, $Z^1$ is hydrogen. In some embodiments, $Z^1$ is fluorine. In some embodiments, Z' is —OH. In some embodiments, Z' is —SH. In some embodiments, Z' is $—CH_3$. In some embodiments, Z' is $—CH_2CH_3$. In some embodiments, Z' is $—OCH_3$. In some embodiments, Z' is $—NH(CH_3)$, In some embodiments, Z' is $—NH_2—$. In some embodiments, Z' is $—NH(C(=O)CH_3)$. In some embodiments, Z' is $—SCH_3$.

In some embodiments of a compound of Formula (II), (II-a'), (II-b'), (II-c'), (II-d'), (II-e'), (II-f'), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), Z" is hydrogen, fluorine, —OH, —SH, $—CH_3$, $—CH_2CH_3$, $—OCH_3$, $—NH(CH_3)$, $—NH_2$, $—NH(C(=O)CH_3)$, or $—SCH_3$. In some embodiments, Z" is hydrogen. In some embodiments, Z" is fluorine. In some embodiments, Z" is —OH. In some embodiments, Z" is —SH. In some embodiments, Z" is $—CH_3$. In some embodiments, Z" is $—CH_2CH_3$. In some embodiments, Z" is $—OCH_3$. In some embodiments, Z" is $—NH(CH_3)$, In some embodiments, Z" is $—NH_2—$. In some embodiments, Z" is $—NH(C(=O)CH_3)$. In some embodiments, Z" is $—SCH_3$.

In some embodiments of a compound of Formula (II), (II-a'), (II-b'), (II-c'), (II-d'), (II-e'), (II-f''), (II-g'), (II-h'), (II-i'), (II-j'), (II-k'), (II-I'), (II-m'), (II-n'), (II-o'), (II-p'), (II-q'), (II-r'), (II-s'), (II-t'), or (II-u'), Z''' is hydrogen, fluorine, $—CH_3$, $—CH_2CH_3$, $—OCH_3$, or $—OCH_2CH_3$. In some embodiments, Z''' is hydrogen. In some embodiments, Z''' is fluorine. In some embodiments, Z''' is $—CH_3$. In some embodiments, Z''' is $—CH_2CH_3$. In some embodiments, Z''' is $—OCH_3$. In some embodiments, Z''' is $—OCH_2CH_3$.

In some embodiments of a compound of Formula (II), (II-a'), (II-b'), (II-c'), (II-d'), (II-e'), (II-f'), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $Z^1$ is hydrogen, fluorine, —OH, —SH, $—CH_3$, $—CH_2CH_3$, $—OCH_3$, $—SCH_3$, $—OCH_2CH_3$, $—NH_2$, $NHCH_3$, or $NHC(=O)CH_3$. In some embodiments, $Z^1$ is hydrogen. In some embodiments, $Z^1$ is fluorine. In some embodiments, $Z^1$ is —OH. In some embodiments, $Z^1$ is —SH. In some embodiments, $Z^1$ is $—CH_3$. In some embodiments, $Z^1$ is $—CH_2CH_3$. In some embodiments, $Z^1$ is $—OCH_3$. In some embodiments, $Z^1$ is $—SCH_3$. In some embodiments, $Z^1$ is $—OCH_2CH_3$. In some embodiments, $Z^1$ is $—NH_2$. In some embodiments, $Z^1$ is $NHCH_3$. In some embodiments, $Z^1$ is $NHC(=O)CH_3$.

In some embodiments of a compound of Formula (II), (II-a'), (II-b'), (II-c'), (II-d'), (II-e'), (II-f'), (II-g'), (II-h'), (II-i'), (II-j'), (II-k'), (II-I'), (II-m'), (II-n'), (II-o'), (II-p'), (II-q'), (II-r'), (II-s'), (II-t'), or (II-u'), $Z^2$ is hydrogen, fluorine, —OH, —SH, —$CH_3$, —$CH_2CH_3$, —$OCH_3$, —$SCH_3$, —$OCH_2CH_3$, —$NH_2$, $NHCH_3$, or $NHC(=O)CH_3$. In some embodiments, $Z^2$ is hydrogen. In some embodiments, $Z^2$ is fluorine. In some embodiments, $Z^2$ is —OH. In some embodiments, $Z^2$ is —SH. In some embodiments, $Z^2$ is —$CH_3$. In some embodiments, $Z^2$ is —$CH_2CH_3$. In some embodiments, $Z^2$ is —$OCH_3$. In some embodiments, $Z^2$ is —$SCH_3$. In some embodiments, $Z^2$ is —$OCH_2CH_3$. In some embodiments, $Z^2$ is —$NH_2$. In some embodiments, $Z^2$ is $NHCH_3$. In some embodiments, $Z^2$ is $NHC(=O)CH_3$.

In some embodiments of a compound of Formula (II), (II-a'), (II-b'), (II-c'), (II-d'), (II-e'), (II-f'), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $Z^3$ is hydrogen, fluorine, —OH, —$CH_3$, —$CH_2CH_3$, —$OCH_3$, —$NH_2$, —$NHCH_3$, —$NH(C(=O)CH_3)$, —$OCH_2CH_3$, —$OCH_2OCH_3$, —$OCH_2CH_2CH_3$, —$OCH(CH_3)_2$, —$SCH_3$, or —$OCH_2CH_2OCH_3$.

In some embodiments, $Z^3$ is hydrogen. In some embodiments, $Z^3$ is fluorine. In some embodiments, $Z^3$ is —OH. In some embodiments, $Z^3$ is —$CH_3$. In some embodiments, $Z^3$ is —$CH_2CH_3$. In some embodiments, $Z^3$ is —$OCH_3$. In some embodiments, $Z^3$ is —$NH_2$. In some embodiments, $Z^3$ is —$NHCH_3$. In some embodiments, $Z^3$ is —$NH(C(=O)CH_3)$. In some embodiments, $Z^3$ is —$OCH_2CH_3$. In some embodiments, $Z^3$ is —$OCH_2OCH_3$. In some embodiments, $Z^3$ is —$OCH_2CH_2CH_3$. In some embodiments, $Z^3$ is —$OCH(CH_3)_2$. In some embodiments, $Z^3$ is —$SCH_3$. In some embodiments, $Z^3$ is —$OCH_2CH_2OCH_3$.

In some embodiments of a compound of Formula (II), (II-a'), (II-b'), (II-c'), (II-d'), (II-c'), (II-f''), (II-g'), (II-h'), (II-i'), (II-j'), (II-k'), (II-I'), (II-m'), (II-n'), (II-o'), (II-p'), (II-q'), (II-r'), (II-s'), (II-t'), or (II-u'), $Z^4$ is hydrogen, fluorine, —OH, —$CH_3$, —$CH_2CH_3$, —$OCH_3$, —$NH_2$, —$NHCH_3$, —$NH(C(=O)CH_3)$, —$OCH_2CH_3$, —$OCH_2OCH_3$, —$OCH_2CH_2CH_3$, —$OCH(CH_3)_2$, —$SCH_3$, or —$OCH_2CH_2OCH_3$.

In some embodiments, $Z^4$ is hydrogen. In some embodiments, $Z^4$ is fluorine. In some embodiments, $Z^4$ is —OH. In some embodiments, $Z^4$ is —$CH_3$. In some embodiments, $Z^4$ is —$CH_2CH_3$. In some embodiments, $Z^4$ is —$OCH_3$. In some embodiments, $Z^4$ is —$NH_2$. In some embodiments, $Z^4$ is —$NHCH_3$. In some embodiments, $Z^4$ is —$NH(C(=O)CH_3)$. In some embodiments, $Z^4$ is —$OCH_2CH_3$. In some embodiments, $Z^4$ is —$OCH_2OCH_3$. In some embodiments, $Z^4$ is —$OCH_2CH_2CH_3$. In some embodiments, $Z^4$ is —$OCH(CH_3)_2$. In some embodiments, $Z^4$ is —$SCH_3$. In some embodiments, $Z^4$ is —$OCH_2CH_2OCH_3$.

In some embodiments of a compound of Formula (II), (II-a'), (II-b'), (II-c'), (II-d'), (II-e'), (II-f), (II-g'), (II-h'), (II-i'), (II-j'), (II-k'), (II-I'), (II-m'), (II-n'), (II-o'), (II-p'), (II-q'), (II-r'), (II-s'), (II-t'), or (II-u'), $Z''$ is hydrogen, fluorine, —OH, —$CH_3$, —$CH_2CH_3$, —$OCH_3$, —$NH_2$, —$NHCH_3$, —$NH(C(=O)CH_3)$, —$OCH_2CH_3$, —$OCH_2OCH_3$, —$OCH_2CH_2CH_3$, —$OCH(CH_3)_2$, —$SCH_3$, or —$OCH_2CH_2OCH_3$. In some embodiments, $Z''$ is hydrogen. In some embodiments, $Z''$ is fluorine. In some embodiments, $Z''$ is —OH. In some embodiments, $Z''$ is —$CH_3$. In some embodiments, $Z''$ is —$CH_2CH_3$. In some embodiments, $Z''$ is —$OCH_3$. In some embodiments, $Z''$ is —$NH_2$. In some embodiments, $Z''$ is —$NHCH_3$. In some embodiments, $Z''$ is —$NH(C(=O)CH_3)$. In some embodiments, $Z''$ is —$OCH_2CH_3$. In some embodiments, $Z''$ is —$OCH_2OCH_3$. In some embodiments, $Z''$ is —$OCH_2CH_2CH_3$. In some embodiments, $Z''$ is —$OCH(CH_3)_2$. In some embodiments, $Z''$ is —$SCH_3$. In some embodiments, $Z''$ is —$OCH_2CH_2OCH_3$.

In some embodiments of a compound of Formula (II), (II-a'), (II-b'), (II-c'), (II-d'), (II-e'), (II-f'), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $Q^1$ is —CH=CH—, —$CH_2$—, —$CH_2O$—, —$CH_2S$—, —$CH_2CH_2$—, —$CH_2CF_2$—, —$CH_2NH_2$—, —$CH_2NH(CH_3)$—, or —$CH_2N(C(=O)CH_3)$—. In some embodiments, $Q^1$ is —CH=CH—. In some embodiments, $Q^1$ is —$CH_2$—. In some embodiments, $Q^1$ is —$CH_2O$—. In some embodiments, $Q^1$ is —$CH_2S$—. In some embodiments, $Q^1$ is —$CH_2CH_2$—. In some embodiments, $Q^1$ is —$CH_2CF_2$—. In some embodiments, $Q^1$ is —$CH_2NH_2$—. In some embodiments, $Q^1$ is —$CH_2NH(CH_3)$—. In some embodiments, $Q^1$ is —$CH_2N(C(=O)CH_3)$—.

In some embodiments of a compound of Formula (II), (II-a'), (II-b'), (II-c'), (II-d'), (II-e'), (II-f''), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $Q^4$ is —CH=CH—, —$CH_2$—, —$CH_2O$—, —$CH_2S$—, —$CH_2CH_2$—, —$CH_2CF_2$—, —$CH_2NH_2$—, —$CH_2NH(CH_3)$—, or —$CH_2N(C(=O)CH_3)$—. In some embodiments, $Q^1$ is —CH=CH—. In some embodiments, $Q^4$ is —$CH_2$—. In some embodiments, $Q^4$ is —$CH_2O$—. In some embodiments, $Q^4$ is —$CH_2S$—. In some embodiments, $Q^4$ is —$CH_2CH_2$—. In some embodiments, $Q^4$ is —$CH_2CF_2$—. In some embodiments, $Q^4$ is —$CH_2NH_2$—. In some embodiments, $Q^4$ is —$CH_2NH(CH_3)$—. In some embodiments, $Q^4$ is —$CH_2N(C(=O)CH_3)$—.

In some embodiments of a compound of Formula (II), (II-a'), (II-b'), (II-c'), (II-d'), (II-e'), (II-f'), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $Q^2$ is —O—, —S—, —$CH_2$—, —$CF_2$—, —NH—, —$N(CH_3)$—, or —$N(C(=O)CH_3)$—. In some embodiments $Q^2$ is —O—. In some embodiments $Q^2$ is —S—. In some embodiments $Q^2$ is —$CH_2$—. In some embodiments $Q^2$ is —$CF_2$—. In some embodiments $Q^2$ is —NH—. In some embodiments $Q^2$ is —$N(CH_3)$—. In some embodiments $Q^2$ is —$N(C(=O)CH_3)$—.

In some embodiments of a compound of Formula (II), (II-a'), (II-b'), (II-c'), (II-d'), (II-e'), (II-f), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $Q^3$ is —O—, —S—, —$CH_2$—, —$CF_2$—, —NH—, —$N(CH_3)$—, or —$N(C(=O)CH_3)$—. In some embodiments $Q^3$ is —O—. In some embodiments $Q^3$ is —S—. In some embodiments $Q^3$ is —$CH_2$—. In some embodiments $Q^3$ is —$CF_2$—. In some embodiments $Q^3$ is —NH—. In some embodiments $Q^3$ is —$N(CH_3)$—. In some embodiments $Q^3$ is —$N(C(=O)CH_3)$—.

In some embodiments of a compound of Formula (II), (II-a'), (II-b'), (II-c'), (II-d'), (II-e'), (II-f), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $X^1$ is —OH, —SH, —O, —S, —$NH_2$, —$NHCH_3$, —$NH(C(=O)CH_3)$, —$CH_3$, —$CH_2CH_3$, —$CH_2CH_2CH_3$, —$CH(CH_3)_2$, —$OCH_3$ or —$OCH_2CH_3$. In some embodiments, $X^1$ is —OH. In some embodiments, $X^1$ is —SH. In some embodiments, $X^1$ is —$O^-$. In some embodiments, $X^1$ is —S. In some embodiments, $X^1$ is —$NH_2$. In some embodiments, $X^1$ is —$NHCH_3$. In some embodiments, $X^1$ is —$NH(C(=O)CH_3)$. In some embodiments, $X^1$ is —$CH_3$. In some embodiments, $X^1$ is —$CH_2CH_3$. In some embodiments, $X^1$ is —$CH_2CH_2CH_3$. In some embodiments, $X^1$ is —$CH(CH_3)_2$. In some embodiments, $X^1$ is —$OCH_3$. In some embodiments, $X^1$ is —$OCH_2CH_3$.

In some embodiments of a compound of Formula (II), (II-a'), (II-b'), (II-c'), (II-d'), (II-c'), (II-f'), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $X^2$ is —OH, —SH, —O, —S, —$NH_2$, —$NHCH_3$, —NH(C(═O)$CH_3$), —$CH_3$, —$CH_2CH_3$, —$CH_2CH_2CH_3$, —CH($CH_3$)$_2$, —$OCH_3$ or —$OCH_2CH_3$. In some embodiments, $X^2$ is —OH. In some embodiments, $X^2$ is —SH. In some embodiments, $X^2$ is —O. In some embodiments, $X^2$ is —S. In some embodiments, $X^2$ is —$NH_2$. In some embodiments, $X^2$ is —$NHCH_3$. In some embodiments, $X^2$ is —NH(C(═O)$CH_3$). In some embodiments, $X^2$ is —$CH_3$. In some embodiments, $X^2$ is —$CH_2CH_3$. In some embodiments, $X^2$ is —$CH_2CH_2CH_3$. In some embodiments, $X^2$ is —CH($CH_3$)$_2$. In some embodiments, $X^2$ is —$OCH_3$. In some embodiments, $X^2$ is —$OCH_2CH_3$.

In some embodiments of a compound of Formula (II), (II-a'), (II-b'), (II-c'), (II-d'), (II-e'), (II-f), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $X^3$ is —OH, —SH, —O, —S, —$NH_2$, —$NHCH_3$, —NH(C(═O)$CH_3$), —$CH_3$, —$CH_2CH_3$, —$CH_2CH_2CH_3$, —CH($CH_3$)$_2$, —$OCH_3$ or —$OCH_2CH_3$. In some embodiments, $X^3$ is —OH. In some embodiments, $X^3$ is —SH. In some embodiments, $X^3$ is —$O^-$. In some embodiments, $X^3$ is —S. In some embodiments, $X^3$ is —$NH_2$. In some embodiments, $X^3$ is —$NHCH_3$. In some embodiments, $X^3$ is —NH(C(═O)$CH_3$). In some embodiments, $X^3$ is —$CH_3$. In some embodiments, $X^3$ is —$CH_2CH_3$. In some embodiments, $X^3$ is —$CH_2CH_2CH_3$. In some embodiments, $X^3$ is —CH($CH_3$)$_2$. In some embodiments, $X^3$ is —$OCH_3$. In some embodiments, $X^3$ is —$OCH_2CH_3$.

In some embodiments of a compound of Formula (II), (II-a'), (II-b'), (II-c'), (II-d'), (II-e'), (II-f'), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $X^4$ is —OH, —SH, —O, —S, —$NH_2$, —$NHCH_3$, —NH(C(═O)$CH_3$), —$CH_3$, —$CH_2CH_3$, —$CH_2CH_2CH_3$, —CH($CH_3$)$_2$, —$OCH_3$ or —$OCH_2CH_3$. In some embodiments, $X^4$ is —OH. In some embodiments, $X^4$ is —SH. In some embodiments, $X^4$ is —O. In some embodiments, $X^4$ is —S. In some embodiments, $X^4$ is —$NH_2$. In some embodiments, $X^4$ is —$NHCH_3$. In some embodiments, $X^4$ is —NH(C(═O)$CH_3$). In some embodiments, $X^4$ is —$CH_3$. In some embodiments, $X^4$ is —$CH_2CH_3$. In some embodiments, $X^4$ is —$CH_2CH_2CH_3$. In some embodiments, $X^4$ is —CH($CH_3$)$_2$. In some embodiments, $X^4$ is —$OCH_3$. In some embodiments, $X^4$ is —$OCH_2CH_3$.

In some embodiments of a compound of Formula (II), (II-a'), (II-b'), (II-c'), (II-d'), (II-e'), (II-f), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $X''$ is —OH, —SH, —O, —S—, —$NH_2$, —$NHCH_3$, —NH(C(═O)$CH_3$), —$CH_3$, —$CH_2CH_3$, —$CH_2CH_2CH_3$, —CH($CH_3$)$_2$, —$OCH_3$ or —$OCH_2CH_3$. In some embodiments, $X''$ is —OH. In some embodiments, $X''$ is —SH. In some embodiments, $X''$ is —$O^-$. In some embodiments, $X''$ is —S. In some embodiments, $X''$ is —$NH_2$. In some embodiments, $X''$ is —$NHCH_3$. In some embodiments, $X''$ is —NH(C(═O)$CH_3$). In some embodiments, $X''$ is —$CH_3$. In some embodiments, $X''$ is —$CH_2CH_3$. In some embodiments, $X''$ is —$CH_2CH_2CH_3$. In some embodiments, $X''$ is —CH($CH_3$)$_2$. In some embodiments, X" is —$OCH_3$. In some embodiments, $X''$ is —$OCH_2CH_3$.

In some embodiments of a compound of Formula (II), (II-a'), (II-b'), (II-c'), (II-d'), (II-e'), (II-f'), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $Y^1$ is ═O, ═S, ═NH, or ═$NCH_3$. In some embodiments, $Y^1$ is ═O. In some embodiments, $Y^1$ is ═S. In some embodiments, $Y^1$ is ═NH. In some embodiments, $Y^1$ is ═$NCH_3$.

In some embodiments of a compound of Formula (II), (II-a'), (II-b'), (II-c'), (II-d'), (II-e'), (II-f'), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $Y^2$ is ═O, ═S, ═NH, or ═$NCH_3$. In some embodiments, $Y^2$ is ═O. In some embodiments, $Y^2$ is ═S. In some embodiments, $Y^2$ is ═NH. In some embodiments, $Y^2$ is ═$NCH_3$.

In some embodiments of a compound of Formula (II), (II-a'), (II-b'), (II-c'), (II-d'), (II-e'), (II-f'), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $Y^3$ is ═O, ═S, —NH, or ═$NCH_3$. In some embodiments, $Y^3$ is ═O. In some embodiments, $Y^3$ is ═S. In some embodiments, $Y^3$ is ═NH. In some embodiments, $Y^3$ is ═$NCH_3$.

In some embodiments of a compound of Formula (II), (II-a'), (II-b'), (II-c'), (II-d'), (II-e'), (II-f''), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $Y^4$ is ═O, ═S, ═NH, or ═$NCH_3$. In some embodiments, $Y^4$ is ═O. In some embodiments, $Y^4$ is ═S. In some embodiments, $Y^4$ is ═NH. In some embodiments, $Y^4$ is ═$NCH_3$.

In some embodiments of a compound of Formula (II), (II-a'), (II-b'), (II-c'), (II-d'), (II-e'), (II-f), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $Y''$ is ═O, ═S, ═NH, or ═$NCH_3$. In some embodiments, $Y''$ is ═O. In some embodiments, $Y''$ is ═S. In some embodiments, $Y''$ is ═NH. In some embodiments, $Y''$ is ═$NCH_3$.

In some embodiments of a compound of Formula (II), (II-a'), (II-b'), (II-c'), (II-d'), (II-e'), (II-f'), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), A is —O—, —S—, —$CH_2$—, —NH—, —N($CH_3$)— or —N(C(═O)$CH_3$)—. In some embodiments, A is —O—. In some embodiments, A is —S—. In some embodiments, A is —$CH_2$—. In some embodiments, A is —NH—. In some embodiments, A is —N($CH_3$)—. In some embodiments, A is —N(C(═O)$CH_3$)—.

In some embodiments of a compound of Formula (II), (II-a'), (II-b'), (II-c'), (II-d'), (II-e'), (II-f''), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $A^1$ is —O—, —S—, —$CH_2$—, —NH—, —N($CH_3$)— or —N(C(═O)$CH_3$)—. In some embodiments, $A^1$ is —O—. In some embodiments, $A^1$ is —S—. In some embodiments, $A^1$ is —$CH_2$—. In some embodiments, $A^1$ is —NH—. In some embodiments, $A^1$ is —N($CH_3$)—. In some embodiments, $A^1$ is —N(C(═O)$CH_3$)—.

In some embodiments of a compound of Formula (II), (II-a'), (II-b'), (II-c'), (II-d'), (II-c'), (II-f''), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), $A^2$ is —O—, —S—, —$CH_2$—, —NH—, —N($CH_3$)— or —N(C(═O)$CH_3$)—. In some embodiments, $A^2$ is —O—. In some embodiments, $A^2$ is —S—. In some embodiments, $A^2$ is —$CH_2$—. In some embodiments, $A^2$ is —NH—. In some embodiments, $A^2$ is —N($CH_3$)—. In some embodiments, $A^2$ is —N(C(═O)$CH_3$)—.

In some embodiments of a compound of Formula (II), (II-a'), (II-b'), (II-c'), (II-d'), (II-e'), (II-f), (II-g'), (II-h'), (II-i'), (II-j'), (II-k'), (II-l'), (II-m'), (II-n'), (II-o'), (II-p'), (II-q'), (II-r'), (II-s'), (II-t'), or (II-u'), p is 0, 1, 2, 3, 4, 5 or 6. In some embodiments, p is 0. In some embodiments, p is 1. In some embodiments, p is 2. In some embodiments, p is 3. In some embodiments, p is 4. In some embodiments, p is 5. In some embodiments, p is 6.

In some embodiments, $B^1$ is

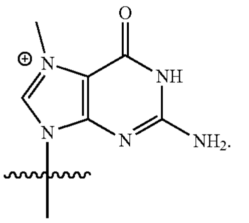 [SMILES: *n1c[n+](C)c2c(=O)[nH]c(N)nc21]

In some embodiments, each $B^2$ and $B^3$ is independently adenine or guanine. In some embodiments, $B^2$ is adenine. In some embodiments, $B^3$ is guanine.

In some embodiments, each $Z^1$, $Z^2$. $Z^3$, and $Z^4$ is independently —OH or —$OCH_3$. In some embodiments, $Z^3$ is —$OCH_3$. In some embodiments, $Z^1$ is —$OCH_3$. In some embodiments $Z^2$ is —OH. In some embodiments, $Z^1$, $Z^2$, and $Z^4$ are —OH and $Z^3$ is —$OCH_3$. In some embodiments, $Z^1$ and $Z^3$ are —$OCH_3$ and $Z^2$ and $Z^4$ are —OH. In some embodiments, Z', Z'', and Z''' are hydrogen.

In some embodiments, $Q^1$ and $Q^4$ are —$OCH_2$—. In some embodiments $Q^2$ and $Q^3$ are —O—.

In some embodiments, $X^1$, $X^2$, $X^3$, and $X^4$ are —O—. In some embodiments, $X^1$, $X^2$, $X^3$, and $X^4$ are —S—. In some embodiments, $X^1$, $X^3$, $X^4$ are —O- and $X^2$ is —S—.

In some embodiments, $Y^1$, $Y^2$, $Y^3$, and $Y^4$ are =O. In some embodiments, $Y^1$, $Y^2$, $Y^3$, and $Y^4$ are =S. In some embodiments, $Y^1$, $Y^3$, and $Y^4$ are —O and $Y^2$ is =S. In some embodiments, $Y^1$, $Y^2$, $Y^3$ are =O and $Y^4$ is =S.

In some embodiments, A, A', and $A^2$ are —O—.

In some embodiments, p is 0.

In some embodiments, the IVT mRNA sequence initiator has a structure of Formula (II-a):

Formula (II-a)

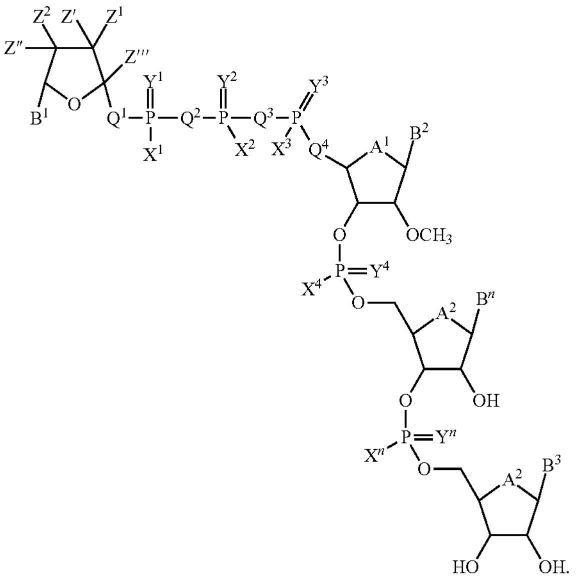

In some embodiments, the IVT mRNA sequence initiator has a structure of Formula (II-a'):

Formula (II-a')

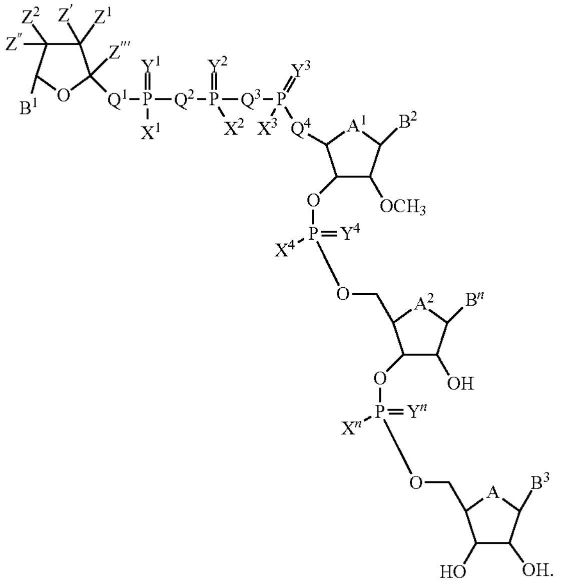

In some embodiments, the IVT mRNA sequence initiator has a structure of Formula (II-b):

Formula (II-b)

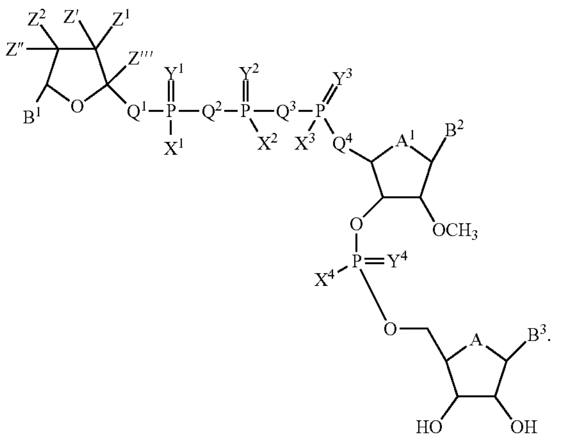

| In some embodiments, the IVT mRNA sequence initiator has a structure of Formula (II-b'):

Formula (II-b')

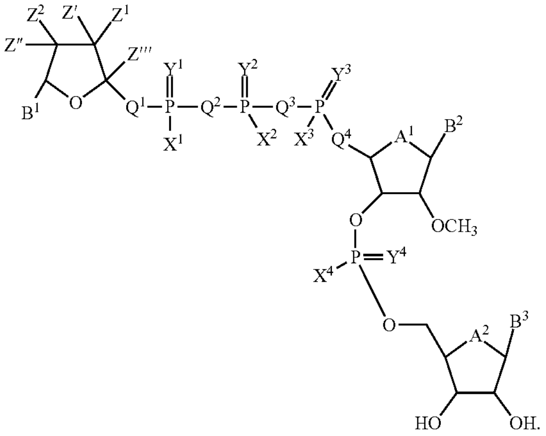

In some embodiments, the IVT mRNA sequence initiator has a structure of Formula (II-c):

Formula (II-c)

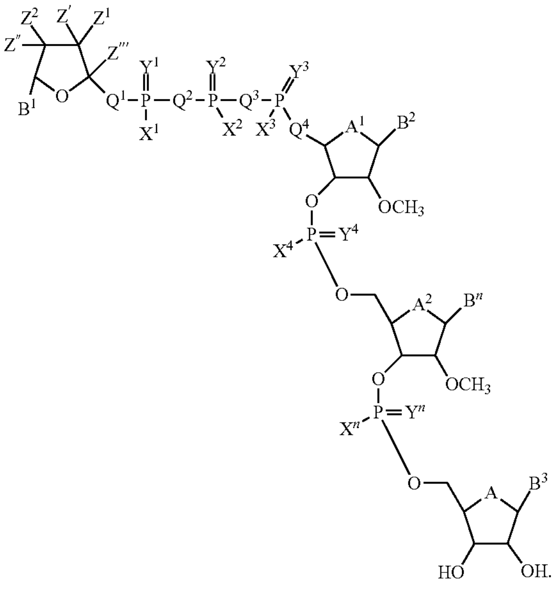

In some embodiments, the IVT mRNA sequence initiator has a structure of Formula (II-c'):

Formula (II-c')

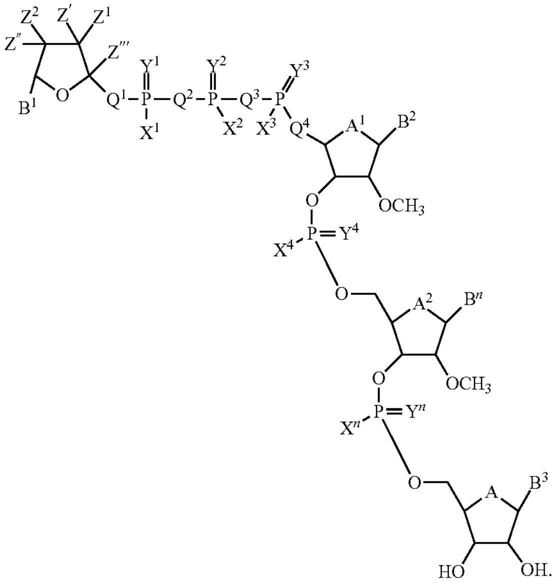

In some embodiments, the IVT mRNA sequence initiator has a structure of Formula (II-d):

Formula (II-d)

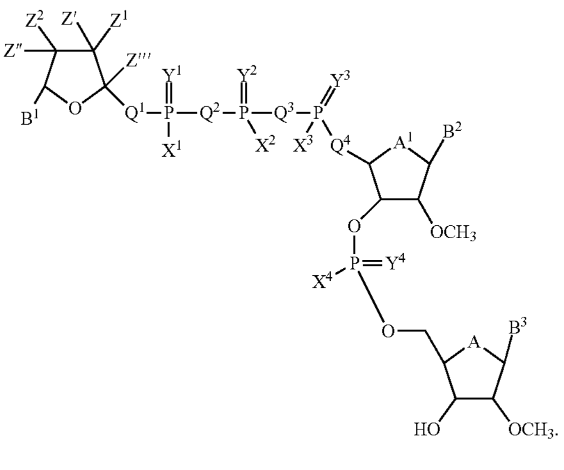

In some embodiments, the IVT mRNA sequence initiator has a structure of Formula (II-d'):

Formula (II-d')

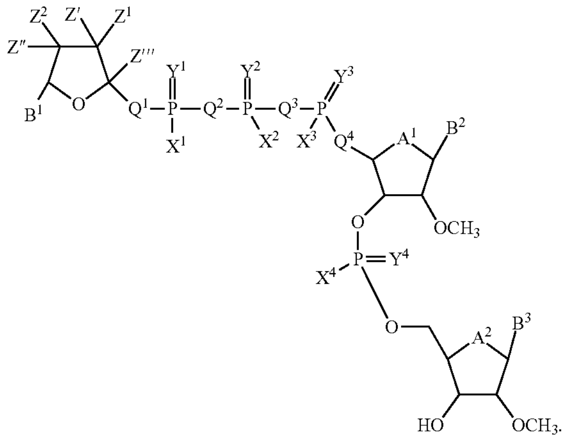

In some embodiments, the IVT mRNA sequence initiator has a structure of Formula (II-e):

Formula (II-e)

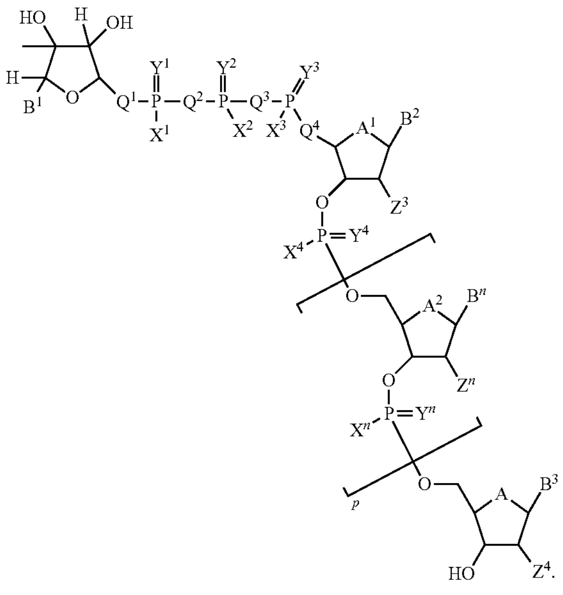

In some embodiments, the IVT mRNA sequence initiator has a structure of Formula (II-e'):

Formula (II-e')

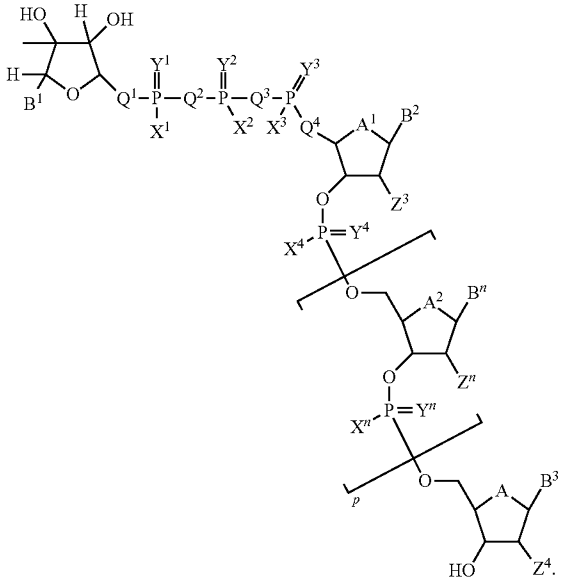

In some embodiments, the IVT mRNA sequence initiator has a structure of Formula (II-f):

Formula (II-f)

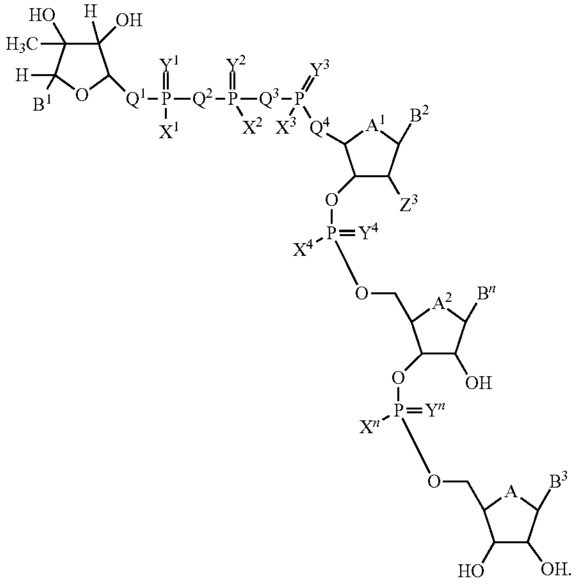

In some embodiments, the IVT mRNA sequence initiator has a structure of Formula (II-g):

Formula (II-g)

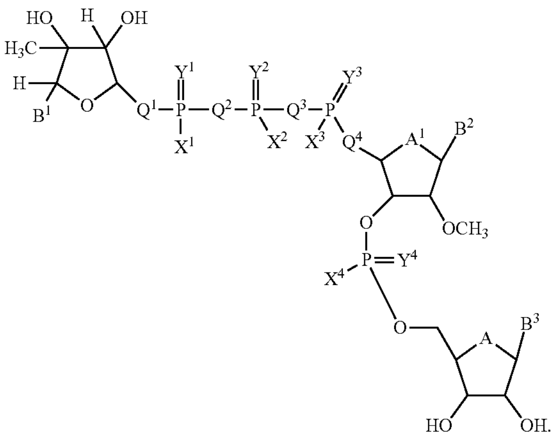

In some embodiments, the IVT mRNA sequence initiator has a structure of Formula (II-g'):

Formula (II-g')

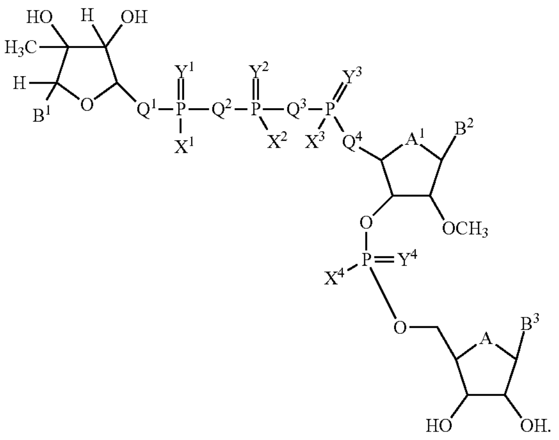

In some embodiments, the IVT mRNA sequence initiator has a structure of Formula (II-h):

Formula (II-h)

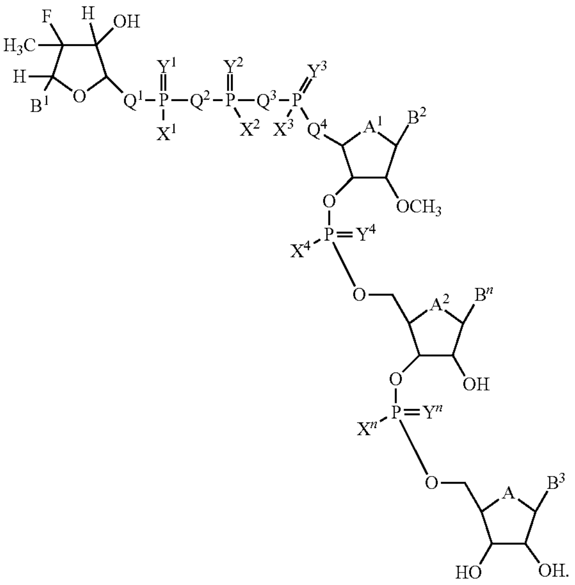

In some embodiments, the IVT mRNA sequence initiator has a structure of Formula (II-h'):

Formula (II-h')

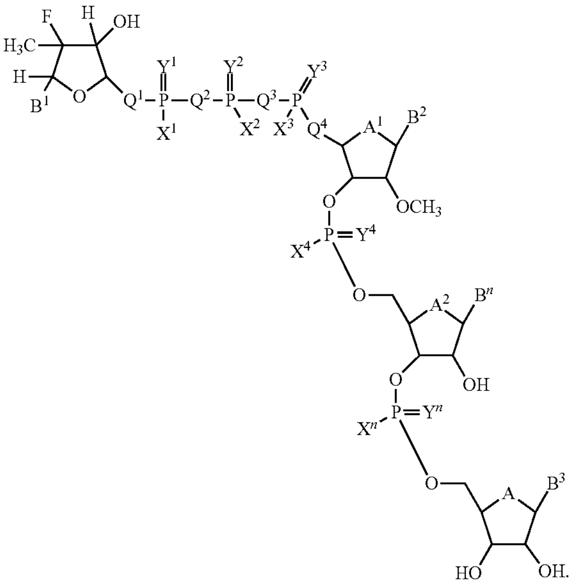

In some embodiments, the IVT mRNA sequence initiator has a structure of Formula (II-i)

Formula (II-i)

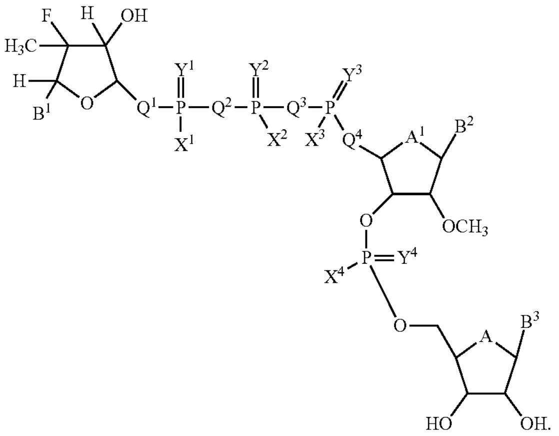

In some embodiments, the IVT mRNA sequence initiator has a structure of Formula (II-I')

Formula (II-I')

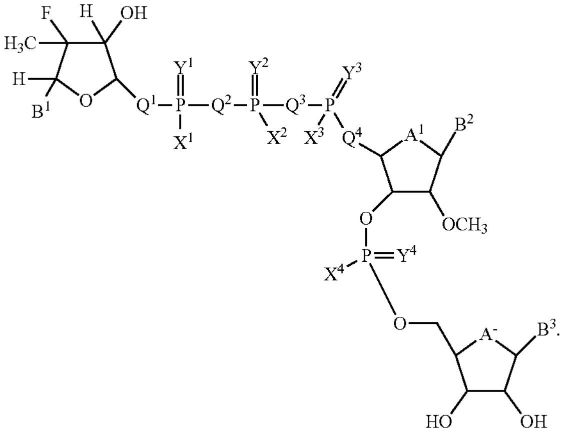

In some embodiments, the IVT mRNA sequence initiator has a structure of Formula (II-j):

Formula (II-j)

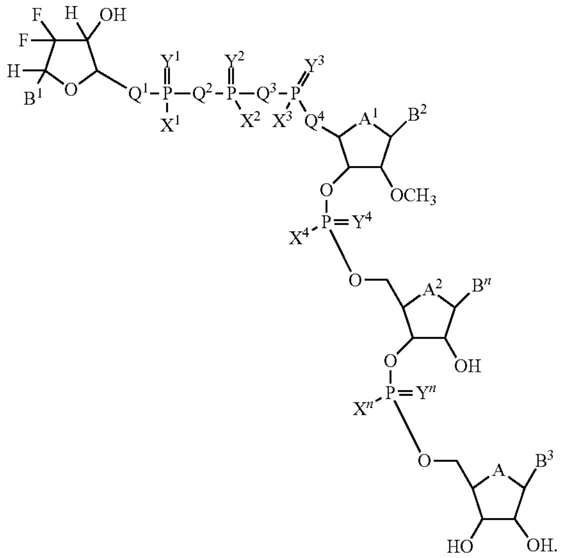

In some embodiments, the IVT mRNA sequence initiator has a structure of Formula (II-j'):

Formula (II-j')

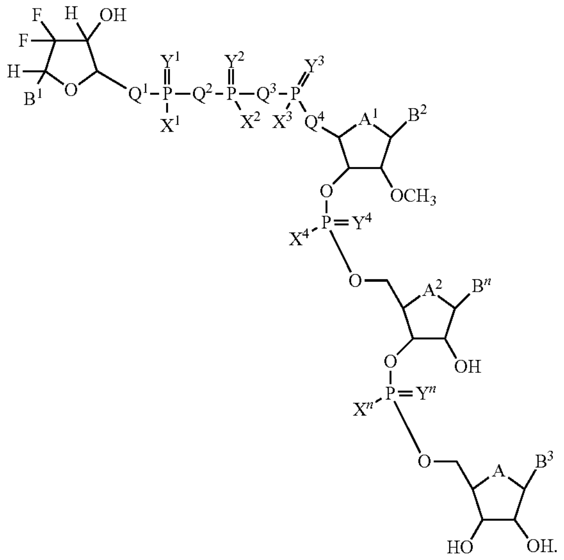

In some embodiments, the IVT mRNA sequence initiator has a structure of Formula (II-k):

Formula (II-k)

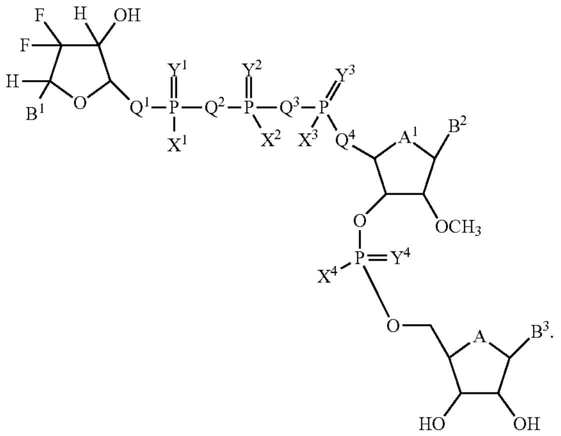

In some embodiments, the IVT mRNA sequence initiator has a structure of Formula (II-k'):

Formula (II-k')

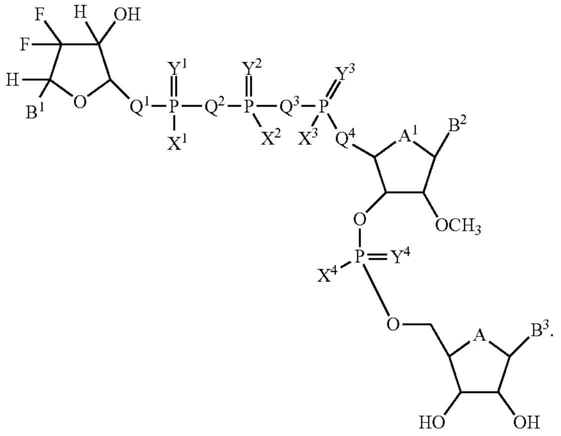

In some embodiments, the IVT mRNA sequence initiator has a structure of Formula (II-l):

Formula (II-1)

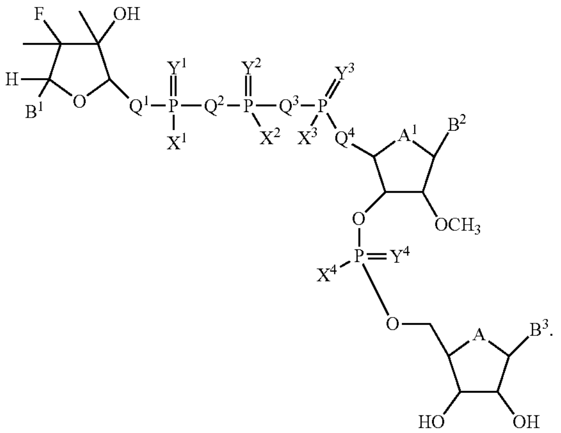

In some embodiments, the IVT mRNA sequence initiator has a structure of Formula (II-l'):

Formula (II-1')

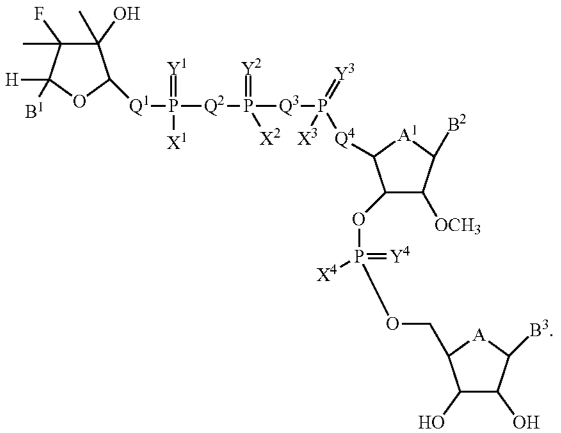

In some embodiments, the IVT mRNA sequence initiator has a structure of Formula (II-m):

Formula (II-m)

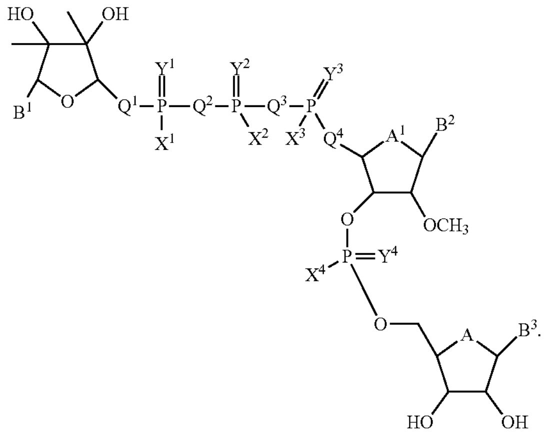

In some embodiments, the IVT mRNA sequence initiator has a structure of Formula (II-m')

Formula (II-m′)

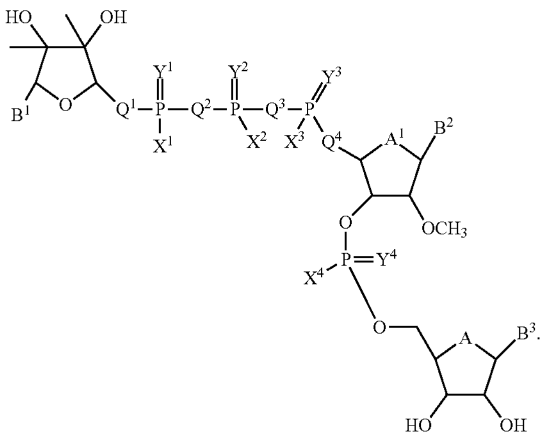

In some embodiments, the IVT mRNA sequence initiator has a structure of Formula (II-n):

Formula (II-n)

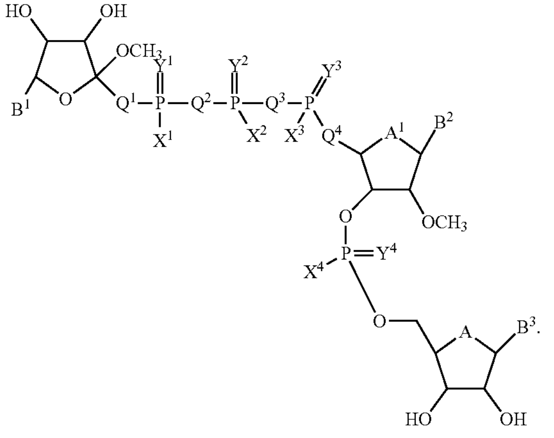

In some embodiments, the IVT mRNA sequence initiator has a structure of Formula (II-n'):

Formula (II-n′)

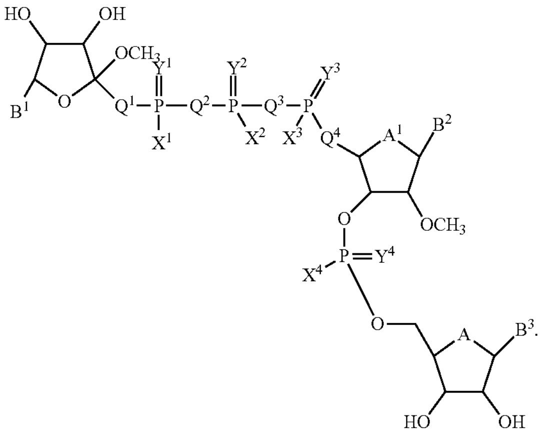

In some embodiments, the IVT mRNA sequence initiator has a structure of Formula (II-o):

Formula (II-o)

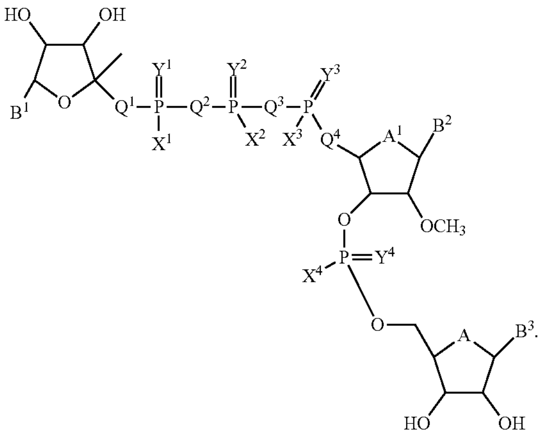

In some embodiments, the IVT mRNA sequence initiator has a structure of Formula (II-o'):

Formula (II-o′)

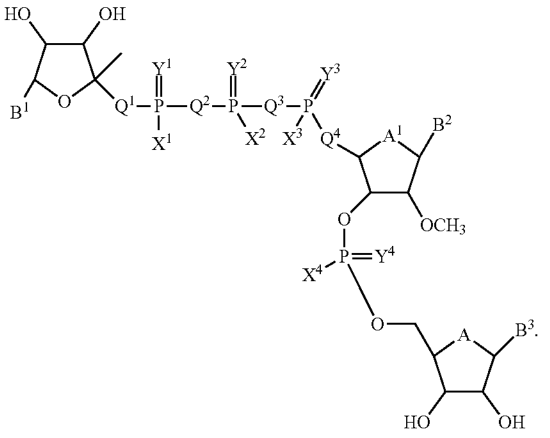

In some embodiments, the IVT mRNA sequence initiator has a structure of Formula (II-p):

Formula (II-p)

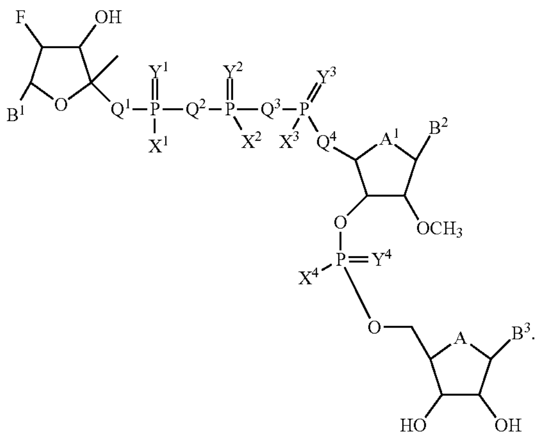

In some embodiments, the IVT mRNA sequence initiator has a structure of Formula (II-p'):

Formula (II-p′)

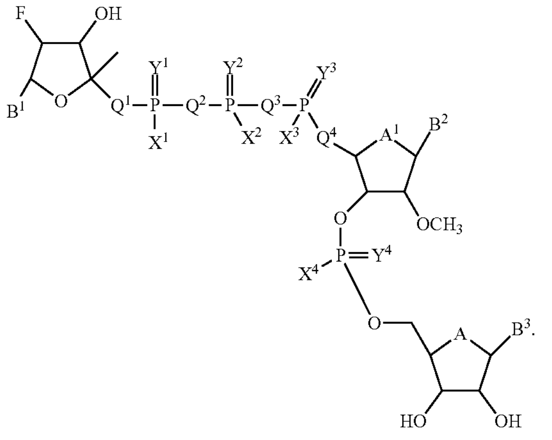

In some embodiments, the IVT mRNA sequence initiator has a structure of Formula (II-q):

Formula (II-q)

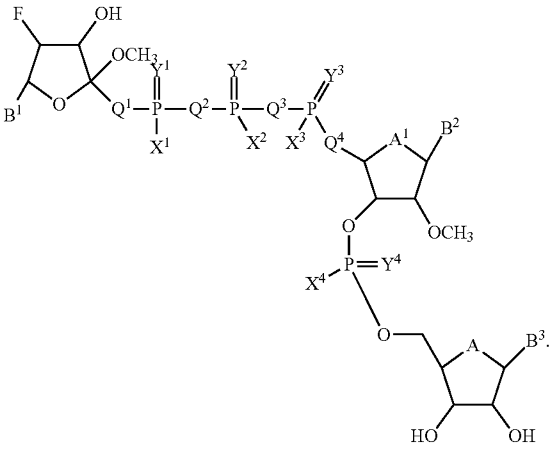

In some embodiments, the IVT mRNA sequence initiator has a structure of Formula (II-q'):

Formula (II-q′)

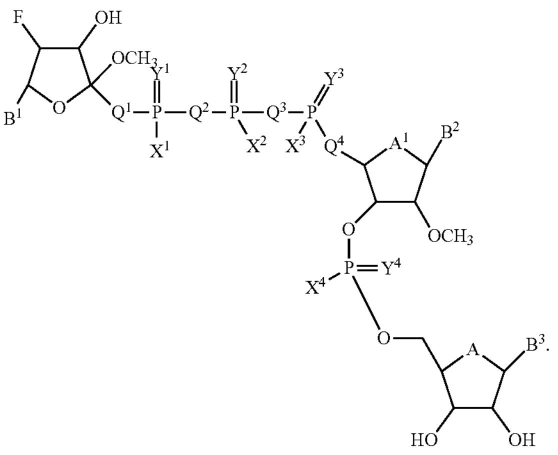

In some embodiments, the IVT mRNA sequence initiator has a structure of Formula (II-r):

Formula (II-r)

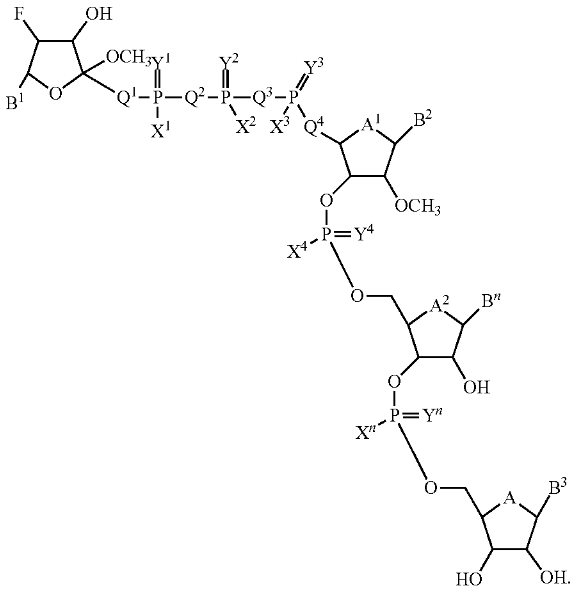

In some embodiments, the IVT mRNA sequence initiator has a structure of Formula (II-r'):

Formula (II-r')

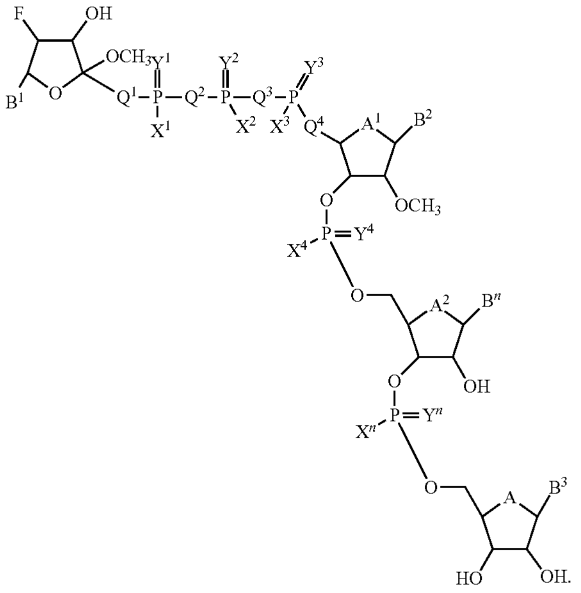

In some embodiments, the IVT mRNA sequence initiator has a structure of Formula (II-s):

Formula (II-s)

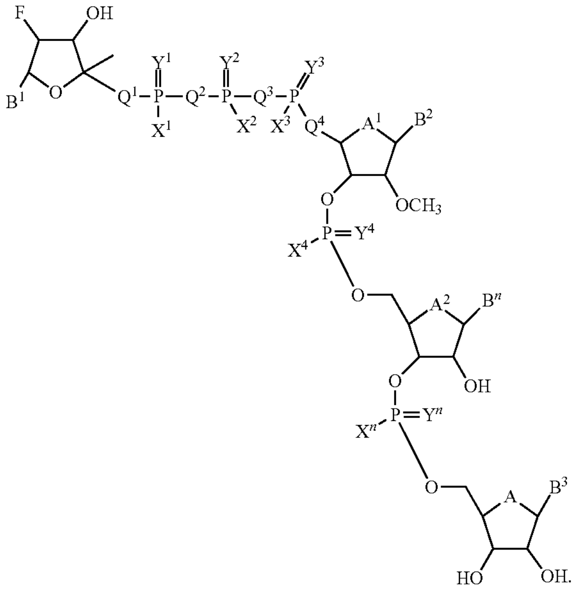

In some embodiments, the IVT mRNA sequence initiator has a structure of Formula (II-s'):

Formula (II-s')

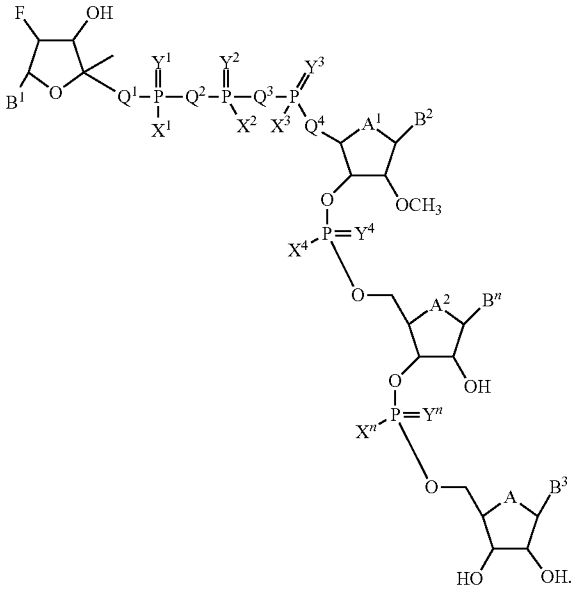

In some embodiments, the IVT mRNA sequence initiator has a structure of Formula (II-t):

Formula (II-t).

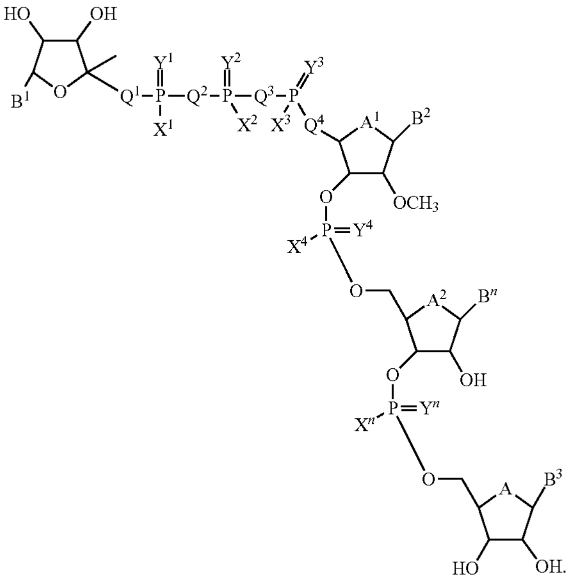

In some embodiments, the IVT mRNA sequence initiator has a structure of Formula (II-t'):

Formula (II-t')

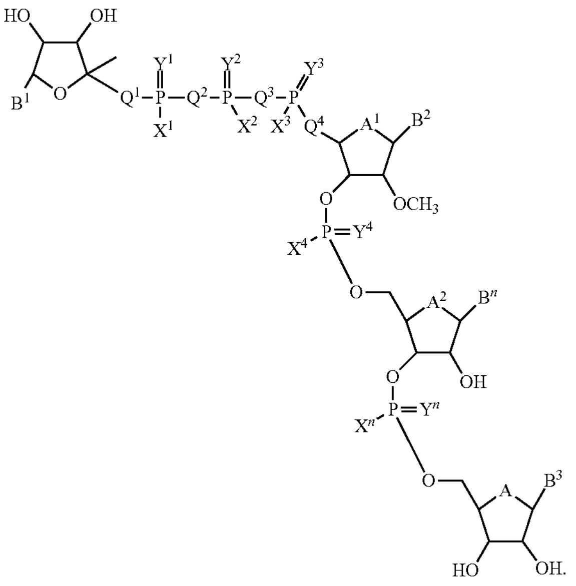

In some embodiments, the IVT mRNA sequence initiator has a structure of Formula (II-u):

Formula (II-u)

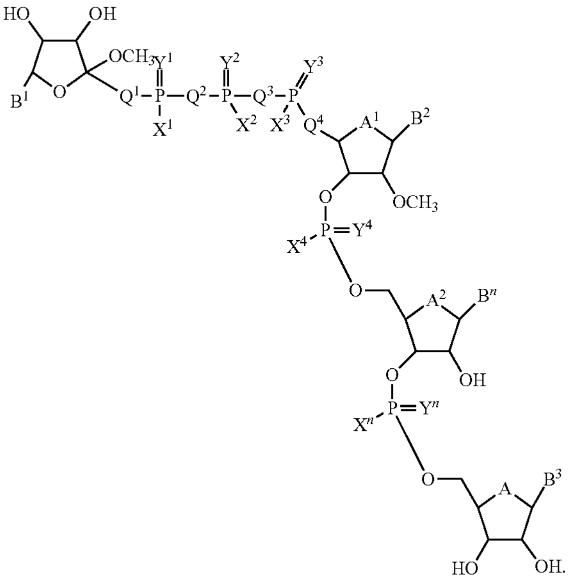

In some embodiments, the IVT mRNA sequence initiator has a structure of Formula (II-u'):

Formula (II-u')

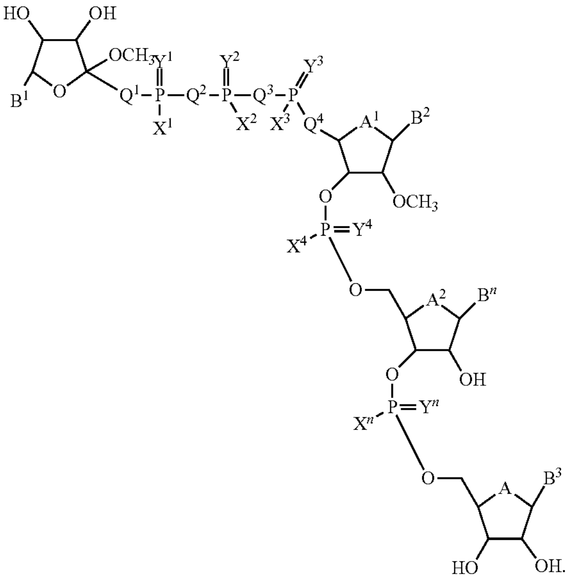

In some embodiments of Formula (II) or Formulas (II-a) to (II-u'), each B independently is a natural nucleobase. In some embodiments of Formula (II) or Formulas (II-a) to (II-u'), each B independently is a modified nucleobase. In some embodiments of Formula (II) or Formulas (II-a) to (II-u'), each B independently is an unnatural nucleobase.

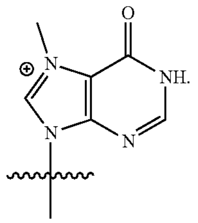 [SMILES: *n1c[n+](C)c2c(=O)[nH]cnc21]

In some embodiments of Formula (II) or Formulas (II-a) to (II-u'), $B^1$ is

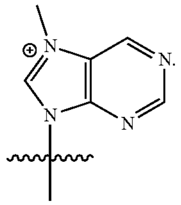 [SMILES: *n1c[n+](C)c2cncnc21]

In some embodiments of Formula (II) or Formulas (II-a) to (II-u'), $B^1$ is

In some embodiments of Formula (II) or Formulas (II-a) to (II-u'), $Z^1$ is fluorine.

In some embodiments of Formula (II) or Formulas (II-a) to (II-u'), $Z^1$ is —OH.

In some embodiments of Formula (II) or Formulas (II-a) to (II-u'), $Z^1$ is —$OCH_3$.

In some embodiments of Formula (II) or Formulas (II-a) to (II-u'), $Z^2$ is fluorine.

In some embodiments of Formula (II) or Formulas (II-a) to (II-u'), $Z^2$ is —OH.

In some embodiments of Formula (II) or Formulas (II-a) to (II-u'), $Z^2$ is —$OCH_3$.

In some embodiments of Formula (II) or Formulas (II-a) to (II-u'), $Q^1$ is —$CH_2O$—.

In some embodiments of Formula (II) or Formulas (II-a) to (II-u'), $Q^1$ is —O—.

In some embodiments of Formula (II) or Formulas (II-a) to (II-u'), $Q^4$ is —$CH_2O$—.

In some embodiments of Formula (II) or Formulas (II-a) to (II-u'), $Q^4$ is —O—.

In some embodiments of Formula (II) or Formulas (II-a) to (II-u'), $Q^2$ is —O—.

In some embodiments of Formula (II) or Formulas (II-a) to (II-u'), $Q^3$ is —O—.

In some embodiments of Formula (II) or Formulas (II-a) to (II-u'), $Y^1$ is =O.

In some embodiments of Formula (II) or Formulas (II-a) to (II-u'), $Y^3$ is —O.

In some embodiments of Formula (II) or Formulas (II-a) to (II-u'), $Y^2$ is =O.

In some embodiments of Formula (II) or Formulas (II-a) to (II-u'), $Y^4$ is =O.

In some embodiments of Formula (II) or Formulas (II-a) to (II-u'), $Y''$ is =O.

In some embodiments of Formula (II) or Formulas (II-a) to (II-u'), one or more of $Y^1$, $Y^2$, $Y^3$, $Y^4$, and $Y''$ is =S.

In some embodiments of Formula (II) or Formulas (II-a) to (II-u'), $Y^2$ is =S.

In some embodiments of Formula (II) or Formulas (II-a) to (II-u'), $Y^4$ is =S.

In some embodiments of Formula (II) or Formulas (II-a) to (II-u'), $Y''$ is =S.

In some embodiments of Formula (II) or Formulas (II-a) to (II-u'), each $Y^1$, $Y^2$, $Y^3$, $Y^4$, and $Y''$ is =O.

In some embodiments of Formula (II) or Formulas (II-a) to (II-u'), each $X^1$, $X^4$, and $X''$ is —
0.

In some embodiments of Formula (II) or Formulas (II-a) to (II-u'), $X^2$ is —O—.

In some embodiments of Formula (II) or Formulas (II-a) to (II-u'), $X^3$ is —$O^-$.

In some embodiments of Formula (II) or Formulas (II-a) to (II-u'), one or more of $X^1$, $X^2$, $X^3$, $X^4$, and $X''$ is —S.

In some embodiments of Formula (II) or Formulas (II-a) to (II-u'), $X^2$ is —S—.

In some embodiments of Formula (II) or Formulas (II-a) to (II-u'), $X^4$ is —S—.

In some embodiments of Formula (II) or Formulas (II-a) to (II-u'), $X^3$ is —S—.

In some embodiments of Formula (II) or Formulas (II-a) to (II-u'), each $X^1$, $X^2$, $X^3$, $X^4$, and $X''$ is —O.

In some embodiments of Formula (II) or Formulas (II-a) to (II-u'), each A, $A^1$, and $A^2$ is —O—.

In some embodiments of Formula (II) or Formulas (II-a) to (II-u'), one or more of A, $A^1$, and $A^2$ is —S—. In some embodiments, A is —S—. In some embodiments, $A^1$ is —O—. In some embodiments, $A^2$ is —O—. In some embodiments, $A^2$ is —S—. In some embodiments, A is —O—. In some embodiments, $A^1$ is —O—.

In some embodiments of Formula (II) or Formulas (II-a) to (II-u'), p is 0. In some embodiments, p is 1. In some embodiments, p is 2.

In some embodiments of Formula (II) or Formulas (II-a) to (II-u'), $B^2$ is adenine, cytosine, guanine, uracil, thymine, hypoxanthine, or purine.

In some embodiments of Formula (II) or Formulas (II-a) to (II-u'), $B^3$ is adenine, cytosine, guanine, uracil, thymine, hypoxanthine, or purine.

In some embodiments of Formula (II) or Formulas (II-a) to (II-u'), $B''$ is adenine, cytosine, guanine, uracil, thymine, hypoxanthine, or purine.

In some embodiments of Formula (II) or Formulas (II-a) to (II-u'), $Q^1$ is —$CH_2O$—. In some embodiments, $Q^4$ is —$CH_2O$—.

In some embodiments of Formula (II) or Formulas (II-a) to (II-u'), $Q^2$ is —O—. In some embodiments, $Q^3$ is —O—.

In some embodiments of Formula (II) or Formulas (II-a) to (II-u'), each $X''$ is independently —OH, —SH, O', or S.

In some embodiments of Formula (II) or Formulas (II-a) to (II-u'), each $Y''$ is independently =O or =S.

In some embodiments of Formula (II) or Formulas (II-a) to (II-u'), $B^1$ is

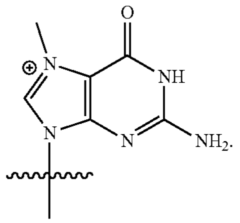 [SMILES: *n1c[n+](C)c2c(=O)[nH]c(N)nc21]

In some embodiments of Formula (II) or Formulas (II-a) to (II-u'), $Q^1$ is $—CH_2O—$; $Q^4$ is $—CH_2O—$; $Q^2$ is —O—; $Q^3$ is —O—; each X″ is independently —OH, —SH, O', or S; each Y″ is independently ═O or ═S; $B^1$ is

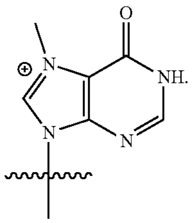 [SMILES: *n1c[n+](C)c2c(=O)[nH]cnc21]

In some embodiments of Formula (II) or Formulas (II-a) to (II-u'), $Q^1$ is $—CH_2O—$; $Q^4$ is $—CH_2O—$; $Q^2$ is —O—; $Q^3$ is —O-'each X″ is independently —OH, —SH, O', or S; each Y″ is independently ═O or ═S; $B^1$ is

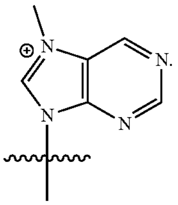 [SMILES: *n1c[n+](C)c2cncnc21]

In some embodiments of Formula (II) or Formulas (II-a) to (II-u'), $B^2$ is adenine. In some embodiments of Formula (II) or Formulas (II-a) to (II-u'), $B^3$ is guanine.

In one aspect, described herein is a mRNA sequence having a 5'-end region motif (Motif (II″):

Motif (II″)

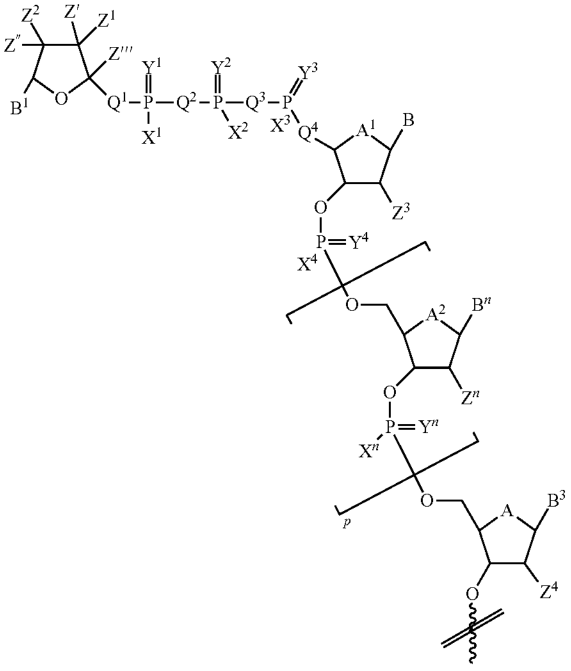

wherein $B^1$ is

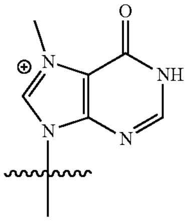

or

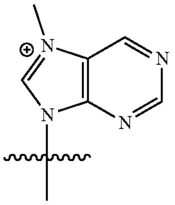

;

each $B^2$, $B^3$, and B″ is independently a natural, a modified, or an unnatural nucleobase;

each Z' and Z" is independently is hydrogen, fluorine, —OH, —SH, $—CH_3$, $—CH_2CH_3$, $—OCH_3$, —NH($CH_3$), $—NH_2$, $—NH(C(═O)CH_3)$, or $—SCH_3$;

Z'" is hydrogen, fluorine, $—CH_3$, $—CH_2CH_3$, $—OCH_3$, or $—OCH_2CH_3$;

each $Z^1$ and $Z^2$ is independently hydrogen, fluorine, —OH, —SH, $—CH_3$, $—CH_2CH_3$, $—OCH_3$, $—SCH_3$, $—OCH_2CH_3$, $—NH_2$, $NHCH_3$, or $NHC(═O)CH_3$;

each $Z^3$, $Z^4$, and Z″ is independently hydrogen, fluorine, —OH, $—CH_3$, $—CH_2CH_3$, $—OCH_3$, $—NH_2$, $—NHCH_3$, $—NH(C(═O)CH_3)$, $—OCH_2CH_3$, $—OCH_2OCH_3$, $—OCH_2CH_2CH_3$, $—OCH(CH_3)_2$, $—SCH_3$, or $—OCH_2CH_2OCH_3$;

each $Q^1$ and $Q^4$ is independently —CH═CH—, $—CH_2—$, $—CH_2O—$, $—CH_2S—$, $—CH_2CH_2—$, $—CH_2CF_2—$, $—CH_2NH_2—$, $—CH_2NH(CH_3)—$, or $—CH_2N(C(═O)CH_3)—$;

each $Q^2$ and $Q^3$ is independently —O—, —S—, $—CH_2—$, $—CF_2—$, —NH—, $—N(CH_3)—$, or $—N(C(═O)CH_3)—$;

each $X^1$, $X^2$, $X^3$, $X^4$, and X″ is independently —OH, —SH, —O, —S, $—NH_2$, $—NHCH_3$, $—NH(C(═O)CH_3)$, $—CH_3$, $—CH_2CH_3$, $—CH_2CH_2CH_3$, $—CH(CH_3)_2$, $—OCH_3$ or $—OCH_2CH_3$;

each $Y^1$, $Y^2$, $Y^3$, $Y^4$, and Y″ is independently ═O, ═S, ═NH, or $═NCH_3$;

each A, $A^1$, and $A^2$ is independently —O—, —S—, $—CH_2—$, —NH—, $—N(CH_3)—$ or $—N(C(═O)CH_3)—$; and p=0, 1, 2, 3, 4, 5 or 6.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-1'), (II"-m'), (II"-n'), (II"-o'), (II"-p'), (II"-q'), (II"-r'), (II"-s'), (II"-t'), or (II"-u'), $B^1$ is

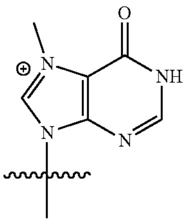

or

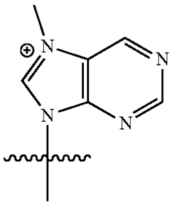

.

In some embodiments, $B^1$ is

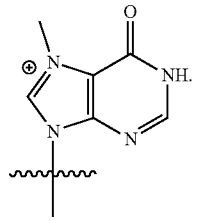 [SMILES: *n1c[n+](C)c2c(=O)[nH]cnc21]

In some embodiments, $B^1$ is

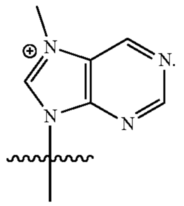 [SMILES: *n1c[n+](C)c2cncnc21]

In some embodiments of a compound of Motif (II"), (II"-a'), (II"-b'), (II"-c'), (II"-d'), (II"-e'), (II"-f'), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $B^2$ independently a natural, a modified, or an unnatural nucleobase. In some embodiments, $B^2$ is adenine. In some embodiments, $B^2$ is guanine. In some embodiments, $B^2$ is cytosine. In some embodiments, $B^2$ is uracil, In some embodiments, $B^2$ is thymine, In some embodiments, $B^2$ is hypoxanthine. In some embodiments, $B^2$ is purine.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $B^3$ independently a natural, a modified, or an unnatural nucleobase. In some embodiments, $B^3$ is adenine. In some embodiments, $B^3$ is guanine. In some embodiments, $B^3$ is cytosine. In some embodiments, $B^3$ is uracil, In some embodiments, $B^3$ is thymine, In some embodiments, $B^3$ is hypoxanthine. In some embodiments, $B^3$ is purine.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-1'), (II"-m'), (II"-n'), (II"-o'), (II"-p'), (II"-q'), (II"-r'), (II"-s'), (II"-t'), or (II"-u'), $B''$ independently a natural, a modified, or an unnatural nucleobase. In some embodiments, $B''$ is adenine. In some embodiments, $B''$ is guanine. In some embodiments, $B''$ is cytosine. In some embodiments, $B''$ is uracil, In some embodiments, $B''$ is thymine, In some embodiments, $B''$ is hypoxanthine. In some embodiments, $B''$ is purine.

In some embodiments of a compound of Motif (II"), (II"-a'), (II"-b'), (II"-c'), (II"-d'), (II"-e'), (II"-f'), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $Z^1$ is hydrogen, fluorine, —OH, —SH, —$CH_3$, —$CH_2CH_3$, —$OCH_3$, —$NH(CH_3)$, —$NH_2$, —$NH(C(=O)CH_3)$, or —$SCH_3$. In some embodiments, $Z^1$ is hydrogen. In some embodiments, $Z^1$ is fluorine. In some embodiments, $Z^1$ is —OH. In some embodiments, $Z^1$ is —SH. In some embodiments, $Z^1$ is —$CH_3$. In some embodiments, $Z^1$ is —$CH_2CH_3$. In some embodiments, $Z^1$ is —$OCH_3$. In some embodiments, $Z^1$ is —$NH(CH_3)$, In some embodiments, $Z^1$ is —$NH_2$—. In some embodiments, $Z^1$ is —$NH(C(=O)CH_3)$. In some embodiments, $Z^1$ is —$SCH_3$.

In some embodiments of a compound of Motif (II"), (II"-a'), (II"-b'), (II"-c'), (II"-d'), (II"-e'), (II"-f'), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), Z" is hydrogen, fluorine, —OH, —SH, —$CH_3$, —$CH_2CH_3$, —$OCH_3$, —$NH(CH_3)$, —$NH_2$, —$NH(C(=O)CH_3)$, or —$SCH_3$. In some embodiments, Z" is hydrogen. In some embodiments, Z" is fluorine. In some embodiments, Z" is —OH. In some embodiments, Z" is —SH. In some embodiments, Z" is —$CH_3$. In some embodiments, Z" is —$CH_2CH_3$. In some embodiments, Z" is —$OCH_3$. In some embodiments, Z" is —$NH(CH_3)$, In some embodiments, Z" is —$NH_2$—. In some embodiments, Z" is —$NH(C(=O)CH_3)$. In some embodiments, Z" is —$SCH_3$.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-1'), (II"-m'), (II"-n'), (II"-o'), (II"-p'), (II"-q'), (II"-r'), (II"-s'), (II"-t'), or (II"-u'), Z''' is hydrogen, fluorine, —$CH_3$, —$CH_2CH_3$, —$OCH_3$, or —$OCH_2CH_3$. In some embodiments, Z''' is hydrogen. In some embodiments, Z''' is fluorine. In some embodiments, Z''' is —$CH_3$. In some embodiments, Z''' is —$CH_2CH_3$. In some embodiments, Z''' is —$OCH_3$. In some embodiments, Z''' is —$OCH_2CH_3$.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $Z^1$ is hydrogen, fluorine, —OH, —SH, —$CH_3$, —$CH_2CH_3$, —$OCH_3$, —$SCH_3$, —$OCH_2CH_3$, —$NH_2$, $NHCH_3$, or $NHC(=O)CH_3$. In some embodiments, $Z^1$ is hydrogen. In some embodiments, $Z^1$ is fluorine. In some embodiments, $Z^1$ is —OH. In some embodiments, $Z^1$ is —SH. In some embodiments, $Z^1$ is —$CH_3$. In some embodiments, $Z^1$ is —$CH_2CH_3$. In some embodiments, $Z^1$ is —$OCH_3$. In some embodiments, $Z^1$ is —$SCH_3$. In some embodiments, $Z^1$ is —$OCH_2CH_3$. In some embodiments, $Z^1$ is —$NH_2$. In some embodiments, $Z^1$ is $NHCH_3$. In some embodiments, $Z^1$ is $NHC(=O)CH_3$.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $Z^2$ is hydrogen, fluorine, —OH, —SH, —$CH_3$, —$CH_2CH_3$, —$OCH_3$, —$SCH_3$, —$OCH_2CH_3$, —$NH_2$, $NHCH_3$, or $NHC(=O)CH_3$. In some embodiments, $Z^2$ is hydrogen. In some embodiments, $Z^2$ is fluorine. In some embodiments, $Z^2$ is —OH. In some embodiments, $Z^2$ is —SH. In some embodiments, $Z^2$ is —$CH_3$. In some embodiments, $Z^2$ is —$CH_2CH_3$. In some embodiments, $Z^2$ is —$OCH_3$. In some embodiments, $Z^2$ is —$SCH_3$. In some embodiments, $Z^2$ is —$OCH_2CH_3$. In some embodiments, $Z^2$ is —$NH_2$. In some embodiments, $Z^2$ is $NHCH_3$. In some embodiments, $Z^2$ is $NHC(=O)CH_3$.

In some embodiments of a compound of Motif (II"), (II"-a'), (II"-b'), (II"-c'), (II"-d'), (II"-e'), (II"-f'), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $Z^3$ is hydrogen, fluorine, —OH, —$CH_3$, —$CH_2CH_3$, —$OCH_3$, —$NH_2$, —$NHCH_3$, —$NH(C(=O)CH_3)$, —$OCH_2CH_3$, —$OCH_2OCH_3$, —$OCH_2CH_2CH_3$, —$OCH(CH_3)_2$, —$SCH_3$, or —$OCH_2CH_2OCH_3$. In some embodiments, $Z^3$ is hydrogen. In some embodiments, $Z^3$ is fluorine. In some embodiments, $Z^3$ is —OH. In some embodiments, $Z^3$ is —$CH_3$. In some embodiments, $Z^3$ is —$CH_2CH_3$. In some embodiments, $Z^3$ is $—OCH_3$. In some embodiments, $Z^3$ is $—NH_2$. In some embodiments, $Z^3$ is $—NHCH_3$. In some embodiments, $Z^3$ is $—NH(C(=O)CH_3)$. In some embodiments, $Z^3$ is $—OCH_2CH_3$. In some embodiments, $Z^3$ is $—OCH_2OCH_3$. In some embodiments, $Z^3$ is $—OCH_2CH_2CH_3$. In some embodiments, $Z^3$ is $—OCH(CH_3)_2$. In some embodiments, $Z^3$ is $—SCH_3$. In some embodiments, $Z^3$ is $—OCH_2CH_2OCH_3$.

In some embodiments of a compound of Motif (II"), (II"-a'), (II"-b'), (II"-c'), (II"-d'), (II"-e'), (II"-f), (II"-g'), (II"-h'), (II"-i'), (II"-j'), (II"-k'), (II"-1'), (II"-m'), (II"-n'), (II"-o'), (II"-p'), (II"-q'), (II"-r'), (II"-s'), (II"-t'), or (II"-u'), $Z^4$ is hydrogen, fluorine, —OH, $—CH_3$, $—CH_2CH_3$, $—OCH_3$, $—NH_2$, $—NHCH_3$, $—NH(C(=O)CH_3)$, $—OCH_2CH_3$, $—OCH_2OCH_3$, $—OCH_2CH_2CH_3$, $—OCH(CH_3)_2$, $—SCH_3$, or $—OCH_2CH_2OCH_3$. In some embodiments, $Z^4$ is hydrogen. In some embodiments, $Z^4$ is fluorine. In some embodiments, $Z^4$ is —OH. In some embodiments, $Z^4$ is $—CH_3$. In some embodiments, $Z^4$ is $—CH_2CH_3$. In some embodiments, $Z^4$ is $—OCH_3$. In some embodiments, $Z^4$ is $—NH_2$. In some embodiments, $Z^4$ is $—NHCH_3$. In some embodiments, $Z^4$ is $—NH(C(=O)CH_3)$. In some embodiments, $Z^4$ is $—OCH_2CH_3$. In some embodiments, $Z^4$ is $—OCH_2OCH_3$. In some embodiments, $Z^4$ is $—OCH_2CH_2CH_3$. In some embodiments, $Z^4$ is $—OCH(CH_3)_2$. In some embodiments, $Z^4$ is $—SCH_3$. In some embodiments, $Z^4$ is $—OCH_2CH_2OCH_3$.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-1'), (II"-m'), (II"-n'), (II"-o'), (II"-p'), (II"-q'), (II"-r'), (II"-s'), (II"-t'), or (II"-u'), Z" is hydrogen, fluorine, —OH, $—CH_3$, $—CH_2CH_3$, $—OCH_3$, $—NH_2$, $—NHCH_3$, $—NH(C(=O)CH_3)$, $—OCH_2CH_3$, $—OCH_2OCH_3$, $—OCH_2CH_2CH_3$, $—OCH(CH_3)_2$, $—SCH_3$, or $—OCH_2CH_2OCH_3$. In some embodiments, Z" is hydrogen. In some embodiments, Z" is fluorine. In some embodiments, Z" is —OH. In some embodiments, Z" is $—CH_3$. In some embodiments, Z" is $—CH_2CH_3$. In some embodiments, Z" is $—OCH_3$. In some embodiments, Z" is $—NH_2$. In some embodiments, Z" is $—NHCH_3$. In some embodiments, Z" is $—NH(C(=O)CH_3)$. In some embodiments, Z" is $—OCH_2CH_3$. In some embodiments, Z" is $—OCH_2OCH_3$. In some embodiments, Z" is $—OCH_2CH_2CH_3$. In some embodiments, Z" is $—OCH(CH_3)_2$. In some embodiments, Z" is $—SCH_3$. In some embodiments, Z" is $—OCH_2CH_2OCH_3$.

In some embodiments of a compound of Motif (II"), (II"-a'), (II"-b'), (II"-c'), (II"-d'), (II"-e'), (II"-f'), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $Q^1$ is —CH=CH—, $—CH_2—$, $—CH_2O—$, $—CH_2S—$, $—CH_2CH_2—$, $—CH_2CF_2—$, $—CH_2NH_2—$, $—CH_2NH(CH_3)—$, or $—CH_2N(C(=O)CH_3)—$. In some embodiments, $Q^1$ is —CH=CH—. In some embodiments, $Q^1$ is $—CH_2—$. In some embodiments, $Q^1$ is $—CH_2O—$. In some embodiments, $Q^1$ is $—CH_2S—$. In some embodiments, $Q^1$ is $—CH_2CH_2—$. In some embodiments, $Q^1$ is $—CH_2CF_2—$. In some embodiments, $Q^1$ is $—CH_2NH_2—$. In some embodiments, $Q^1$ is $—CH_2NH(CH_3)—$. In some embodiments, $Q^1$ is $—CH_2N(C(=O)CH_3)—$.

In some embodiments of a compound of Motif (II"), (II"-a'), (II"-b'), (II"-c'), (II"-d'), (II"-e'), (II"-f), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $Q^4$ is —CH=CH—, $—CH_2—$, $—CH_2O—$, $—CH_2S—$, $—CH_2CH_2—$, $—CH_2CF_2—$, $—CH_2NH_2—$, $—CH_2NH(CH_3)—$, or $—CH_2N(C(=O)CH_3)—$. In some embodiments, $Q^1$ is —CH=CH—. In some embodiments, $Q^4$ is $—CH_2—$. In some embodiments, $Q^4$ is $—CH_2O—$. In some embodiments, $Q^4$ is $—CH_2S—$. In some embodiments, $Q^4$ is $—CH_2CH_2—$. In some embodiments, $Q^4$ is $—CH_2CF_2—$. In some embodiments, $Q^4$ is $—CH_2NH_2—$. In some embodiments, $Q^4$ is $—CH_2NH(CH_3)—$. In some embodiments, $Q^4$ is $—CH_2N(C(=O)CH_3)—$.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-1'), (II"-m'), (II"-n'), (II"-o'), (II"-p'), (II"-q'), (II"-r'), (II"-s'), (II"-t'), or (II"-u'), $Q^2$ is —O—, —S—, $—CH_2—$, $—CF_2—$, —NH—, $—N(CH_3)—$, or $—N(C(=O)CH_3)—$. In some embodiments $Q^2$ is —O—. In some embodiments $Q^2$ is —S—. In some embodiments $Q^2$ is $—CH_2—$. In some embodiments $Q^2$ is $—CF_2—$. In some embodiments $Q^2$ is —NH—. In some embodiments $Q^2$ is $—N(CH_3)—$. In some embodiments $Q^2$ is $—N(C(=O)CH_3)—$.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-1'), (II"-m'), (II"-n'), (II"-o'), (II"-p'), (II"-q'), (II"-r'), (II"-s'), (II"-t'), or (II"-u'), $Q^3$ is —O—, —S—, $—CH_2—$, $—CF_2—$, —NH—, $—N(CH_3)—$, or $—N(C(=O)CH_3)—$. In some embodiments $Q^3$ is —O—. In some embodiments $Q^3$ is —S—. In some embodiments $Q^3$ is $—CH_2—$. In some embodiments $Q^3$ is $—CF_2—$. In some embodiments $Q^3$ is —NH—. In some embodiments $Q^3$ is $—N(CH_3)—$. In some embodiments $Q^3$ is $—N(C(=O)CH_3)—$.

In some embodiments of a compound of Motif (II"), (II"-a'), (II"-b'), (II"-c'), (II"-d'), (II"-c'), (II"-f'), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $X^1$ is —OH, —SH, —O, —S, $—NH_2$, $—NHCH_3$, $—NH(C(=O)CH_3)$, $—CH_3$, $—CH_2CH_3$, $—CH_2CH_2CH_3$, $—CH(CH_3)_2$, $—OCH_3$ or $—OCH_2CH_3$. In some embodiments, $X^1$ is —OH. In some embodiments, $X^1$ is —SH. In some embodiments, $X^1$ is $—O^-$. In some embodiments, $X^1$ is —S. In some embodiments, $X^1$ is $—NH_2$. In some embodiments, $X^1$ is $—NHCH_3$. In some embodiments, $X^1$ is $—NH(C(=O)CH_3)$. In some embodiments, $X^1$ is $—CH_3$. In some embodiments, $X^1$ is $—CH_2CH_3$. In some embodiments, $X^1$ is $—CH_2CH_2CH_3$. In some embodiments, $X^1$ is $—CH(CH_3)_2$. In some embodiments, $X^1$ is $—OCH_3$. In some embodiments, $X^1$ is $—OCH_2CH_3$.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $X^2$ is —OH, —SH, —O, —S—, $—NH_2$, $—NHCH_3$, $—NH(C(=O)CH_3)$, $—CH_3$, $—CH_2CH_3$, $—CH_2CH_2CH_3$, $—CH(CH_3)_2$, $—OCH_3$ or $—OCH_2CH_3$. In some embodiments, $X^2$ is —OH. In some embodiments, $X^2$ is —SH. In some embodiments, $X^2$ is $—O^-$. In some embodiments, $X^2$ is —S. In some embodiments, $X^2$ is $—NH_2$. In some embodiments, $X^2$ is $—NHCH_3$. In some embodiments, $X^2$ is $—NH(C(=O)CH_3)$. In some embodiments, $X^2$ is $—CH_3$. In some embodiments, $X^2$ is $—CH_2CH_3$. In some embodiments, $X^2$ is $—CH_2CH_2CH_3$. In some embodiments, $X^2$ is $—CH(CH_3)_2$. In some embodiments, $X^2$ is $—OCH_3$. In some embodiments, $X^2$ is $—OCH_2CH_3$.

In some embodiments of a compound of Motif (II"), (II"-a'), (II"-b'), (II"-c'), (II"-d'), (II"-€'), (II"-f'), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $X^3$ is —OH, —SH, —O, —S, $—NH_2$, $—NHCH_3$, $—NH(C(=O)CH_3)$, $—CH_3$, $—CH_2CH_3$, $—CH_2CH_2CH_3$, —CH $(CH_3)_2$, —$OCH_3$ or —$OCH_2CH_3$. In some embodiments, $X^3$ is —OH. In some embodiments, $X^3$ is —SH. In some embodiments, $X^3$ is —O. In some embodiments, $X^3$ is —S—. In some embodiments, $X^3$ is —$NH_2$. In some embodiments, $X^3$ is —$NHCH_3$. In some embodiments, $X^3$ is —NH(C(═O)$CH_3$). In some embodiments, $X^3$ is —$CH_3$. In some embodiments, $X^3$ is —$CH_2CH_3$. In some embodiments, $X^3$ is —$CH_2CH_2CH_3$. In some embodiments, $X^3$ is —$CH(CH_3)_2$. In some embodiments, $X^3$ is —$OCH_3$. In some embodiments, $X^3$ is —$OCH_2CH_3$.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $X^4$ is —OH, —SH, —O, —S, —$NH_2$, —$NHCH_3$, —NH(C(═O)$CH_3$), —$CH_3$, —$CH_2CH_3$, —$CH_2CH_2CH_3$, —$CH(CH_3)_2$, —$OCH_3$ or —$OCH_2CH_3$. In some embodiments, $X^4$ is —OH. In some embodiments, $X^4$ is —SH. In some embodiments, $X^4$ is —$O^-$. In some embodiments, $X^4$ is —S—. In some embodiments, $X^4$ is —$NH_2$. In some embodiments, $X^4$ is —$NHCH_3$. In some embodiments, $X^4$ is —NH(C(═O)$CH_3$). In some embodiments, $X^4$ is —$CH_3$. In some embodiments, $X^4$ is —$CH_2CH_3$. In some embodiments, $X^4$ is —$CH_2CH_2CH_3$. In some embodiments, $X^4$ is —$CH(CH_3)_2$. In some embodiments, $X^4$ is —$OCH_3$. In some embodiments, $X^4$ is —$OCH_2CH_3$.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-l'), (II"-m'), (II"-n') (II"-o'), (II"-p'), (II"-q'), (II"-r'), (II"-s'), (II"-t'), or (II"-u'), $X''$ is —OH, —SH, —O, —S, —$NH_2$, —$NHCH_3$, —NH(C(═O)$CH_3$), —$CH_3$, —$CH_2CH_3$, —$CH_2CH_2CH_3$, —$CH(CH_3)_2$, —$OCH_3$ or —$OCH_2CH_3$. In some embodiments, $X''$ is —OH. In some embodiments, $X''$ is —SH. In some embodiments, $X''$ is —$O^-$. In some embodiments, $X''$ is —S. In some embodiments, $X''$ is —$NH_2$. In some embodiments, $X''$ is —$NHCH_3$. In some embodiments, $X''$ is —NH(C(═O)$CH_3$). In some embodiments, $X''$ is —$CH_3$. In some embodiments, $X''$ is —$CH_2CH_3$. In some embodiments, $X''$ is —$CH_2CH_2CH_3$. In some embodiments, $X''$ is —$CH(CH_3)_2$. In some embodiments, X" is —$OCH_3$. In some embodiments, $X''$ is —$OCH_2CH_3$.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-1'), (II"-m'), (II"-n'), (II"-o'), (II"-p'), (II"-q'), (II"-r'), (II"-s'), (II"-t'), or (II"-u'), $Y^1$ is ═O, ═S, ═NH, or ═$NCH_3$. In some embodiments, $Y^1$ is ═O. In some embodiments, $Y^1$ is ═S. In some embodiments, $Y^1$ is ═NH. In some embodiments, $Y^1$ is ═$NCH_3$.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-1'), (II"-m'), (II"-n'), (II"-o'), (II"-p'), (II"-q'), (II"-r'), (II"-s'), (II"-t'), or (II"-u'), $Y^2$ is ═O, ═S, ═NH, or ═$NCH_3$. In some embodiments, $Y^2$ is ═O. In some embodiments, $Y^2$ is ═S. In some embodiments, $Y^2$ is ═NH. In some embodiments, $Y^2$ is ═$NCH_3$.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-1'), (II"-m'), (II"-n'), (II"-o'), (II"-p'), (II"-q'), (II"-r'), (II"-s'), (II"-t'), or (II"-u'), $Y^3$ is ═O, ═S, ═NH, or ═$NCH_3$. In some embodiments, $Y^3$ is ═O. In some embodiments, $Y^3$ is ═S. In some embodiments, $Y^3$ is ═NH. In some embodiments, $Y^3$ is ═$NCH_3$.

In some embodiments of a compound of Motif (II"), (II"-a'), (II"-b'), (II"-c'), (II"-d'), (II"-e'), (II"-f'), (II"-g'), (II"-h'), (II"-i'), (II"-j'), (II"-k'), (II"-1'), (II"-m'), (II"-n'), (II"-o'), (II"-p'), (II"-q'), (II"-r'), (II"-s'), (II"-t'), or (II"-u'), $Y^4$ is ═O, ═S, ═NH, or ═$NCH_3$. In some embodiments, $Y^4$ is ═O. In some embodiments, $Y^4$ is ═S. In some embodiments, $Y^4$ is ═NH. In some embodiments, $Y^4$ is ═$NCH_3$.

In some embodiments of a compound of Motif (II"), (II"-a'), (II"-b'), (II"-c'), (II"-d'), (II"-e'), (II"-f"), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $Y''$ is ═O, ═S, ═NH, or ═$NCH_3$. In some embodiments, $Y''$ is ═O. In some embodiments, $Y''$ is ═S. In some embodiments, $Y''$ is ═NH. In some embodiments, $Y''$ is ═$NCH_3$.

In some embodiments of a compound of Motif (II"), (II"-a'), (II"-b'), (II"-c'), (II"-d'), (II"-e'), (II"-f'), (II"-g'), (II"-h'), (II"-i'), (II"-j'), (II"-k'), (II"-1'), (II"-m'), (II"-n'), (II"-o'), (II"-p'), (II"-q'), (II"-r'), (II"-s'), (II"-t'), or (II"-u'), A is —O—, —S—, —$CH_2$—, —NH—, —N($CH_3$)— or —N(C(═O)$CH_3$)—. In some embodiments, A is —O—. In some embodiments, A is —S—. In some embodiments, A is —$CH_2$—. In some embodiments, A is —NH—. In some embodiments, A is —N($CH_3$)—. In some embodiments, A is —N(C(═O)$CH_3$)—.

In some embodiments of a compound of Motif (II"), (II"-a'), (II"-b'), (II"-c'), (II"-d'), (II"-e'), (II"-f), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $A^1$ is —O—, —S—, —$CH_2$—, —NH—, —N($CH_3$)— or —N(C(═O)$CH_3$)—. In some embodiments, $A^1$ is —O—. In some embodiments, $A^1$ is —S—. In some embodiments, $A^1$ is —$CH_2$—. In some embodiments, $A^1$ is —NH—. In some embodiments, $A^1$ is —N($CH_3$)—. In some embodiments, $A^1$ is —N(C(═O)$CH_3$)—.

In some embodiments of a compound of Motif (II"), (II"-a'), (II"-b'), (II"-c'), (II"-d'), (II"-e'), (II"-f), (II"-g'), (II"-h'), (II"-i'), (II"-j'), (II"-k'), (II"-l'), (II"-m'), (II"-n'), (II"-o'), (II"-p'), (II"-q'), (II"-r'), (II"-s'), (II"-t'), or (II"-u'), $A^2$ is —O—, —S—, —$CH_2$—, —NH—, —N($CH_3$)— or —N(C(═O)$CH_3$)—. In some embodiments, $A^2$ is —O—. In some embodiments, $A^2$ is —S—. In some embodiments, $A^2$ is —$CH_2$—. In some embodiments, $A^2$ is —NH—. In some embodiments, $A^2$ is —N($CH_3$)—. In some embodiments, $A^2$ is —N(C(═O)$CH_3$)—.

In some embodiments of a compound of Motif (II"), (II"-a'), (II"-b'), (II"-c'), (II"-d'), (II"-e'), (II"-f), (II"-g'), (II"-h'), (II"-i'), (II"-j'), (II"-k'), (II"-1'), (II"-m'), (II"-n'), (II"-o'), (II"-p'), (II"-q'), (II"-r'), (II"-s'), (II"-t'), or (II"-u'), p is 0, 1, 2, 3, 4, 5 or 6. In some embodiments, p is 0. In some embodiments, p is 1. In some embodiments, p is 2. In some embodiments, p is 3. In some embodiments, p is 4. In some embodiments, p is 5. In some embodiments, p is 6.

In some embodiments, $B^1$ is

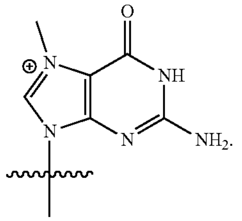 [SMILES: *n1c[n+](C)c2c(=O)[nH]c(N)nc21]

In some embodiments, each $B^2$ and $B^3$ is independently adenine or guanine. In some embodiments, $B^2$ is adenine. In some embodiments, $B^3$ is guanine.

In some embodiments, each $Z^1$, $Z^2$, $Z^3$, and $Z^4$ is independently —OH or —$OCH_3$. In some embodiments, $Z^3$ is —$OCH_3$. In some embodiments, $Z^1$ is —$OCH_3$. In some embodiments $Z^2$ is —OH. In some embodiments, $Z^1$, $Z^2$, and $Z^4$ are —OH and $Z^3$ is —$OCH_3$. In some embodiments, $Z^1$ and $Z^3$ are —$OCH_3$ and $Z^2$ and $Z^4$ are —OH. In some embodiments, Z', Z", and Z'" are hydrogen.

In some embodiments, $Q^1$ and $Q^4$ are —$OCH_2$—. In some embodiments $Q^2$ and $Q^3$ are —O—.

In some embodiments, $X^1$, $X^2$, $X^3$, and $X^4$ are —O—. In some embodiments, $X^1$, $X^2$, $X^3$, and $X^4$ are —S—. In some embodiments, $X^1$, $X^3$, $X^4$ are —O- and $X^2$ is —S—.

In some embodiments, $Y^1$, $Y^2$, $Y^3$, and $Y^4$ are ═O. In some embodiments, $Y^1$, $Y^2$, $Y^3$, and $Y^4$ are ═S. In some embodiments, $Y^1$, $Y^3$, and $Y^4$ are —O and $Y^2$ is ═S. In some embodiments, $Y^1$, $Y^2$, $Y^3$ are ═O and $Y^4$ is ═S.

In some embodiments, A, $A^1$, and $A^2$ are —O—.

In some embodiments, p is 0.

In certain embodiments the sequence initiator compound is as described in Table 1.

TABLE 1

| Compound ID | Name | Chemical Structure |
| --- | --- | --- |
| 1002c | $m^7I(ppp)Am(p)G$ | 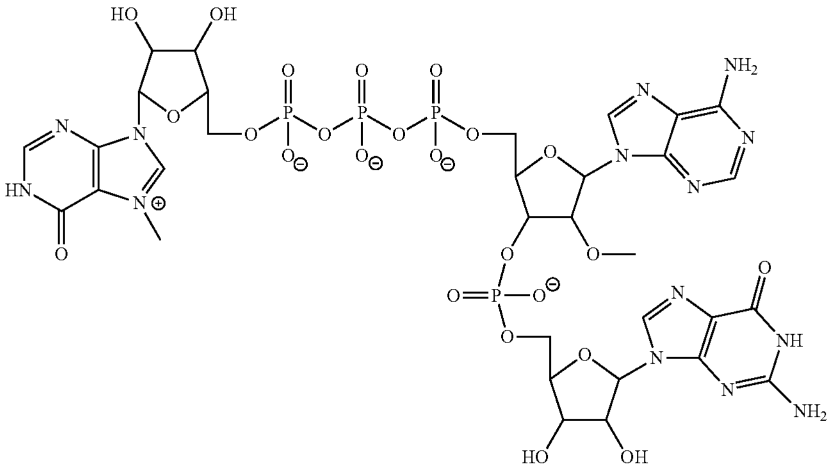 [SMILES: COC1C(OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]cnc43)C(O)C2O)OC1n1cnc2c(N)ncnc21] |
| 1002i | $m^7E(ppp)Am(p)G$ | 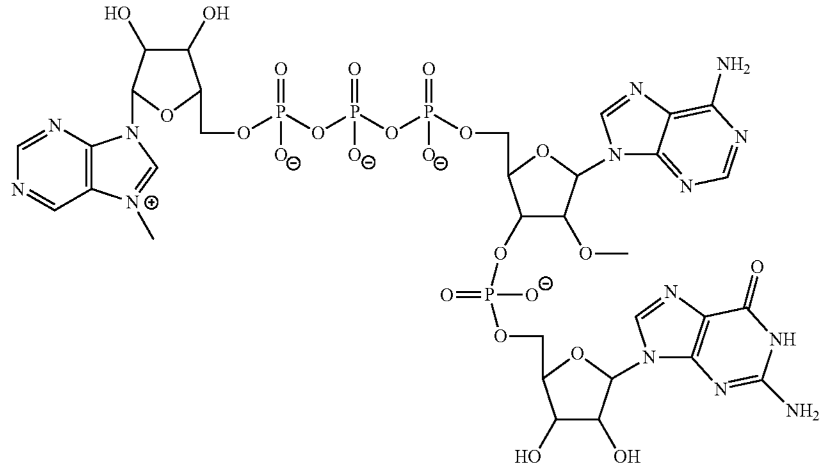 [SMILES: COC1C(OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4cncnc43)C(O)C2O)OC1n1cnc2c(N)ncnc21] |

TABLE 1-continued
| Compound ID | Name | Chemical Structure |
|---|---|---|
| 5201 | $m^7I(ppp)Am(p)G(p)G$ | 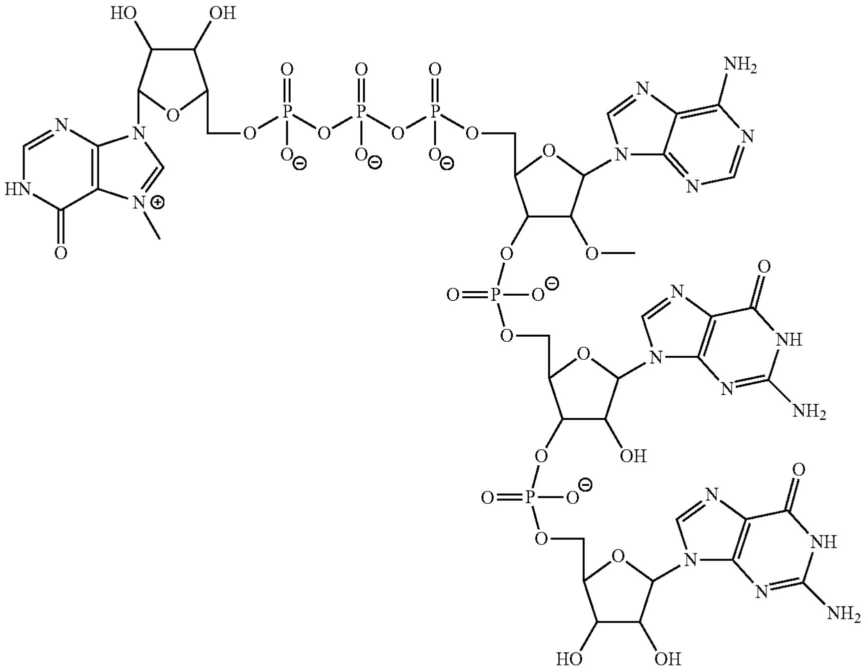 |
| 5202 | $m^7E(ppp)Am(p)G(p)G$ | 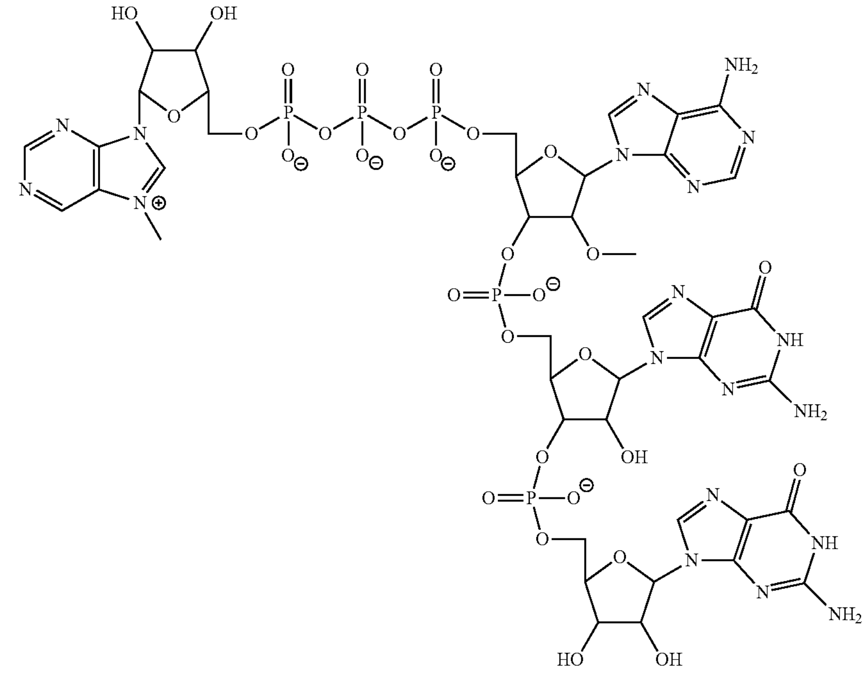 [SMILES: COC1C(OP(=O)([O-])OCC2OC(n3cnc4c(=O)[nH]c(N)nc43)C(O)C2OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4cncnc43)C(O)C2O)OC1n1cnc2c(N)ncnc21] |

TABLE 1-continued
| Compound ID | Name | Chemical Structure |
| --- | --- | --- |
| 1007a | $m^7G(ppp)Am(ps)G$ | 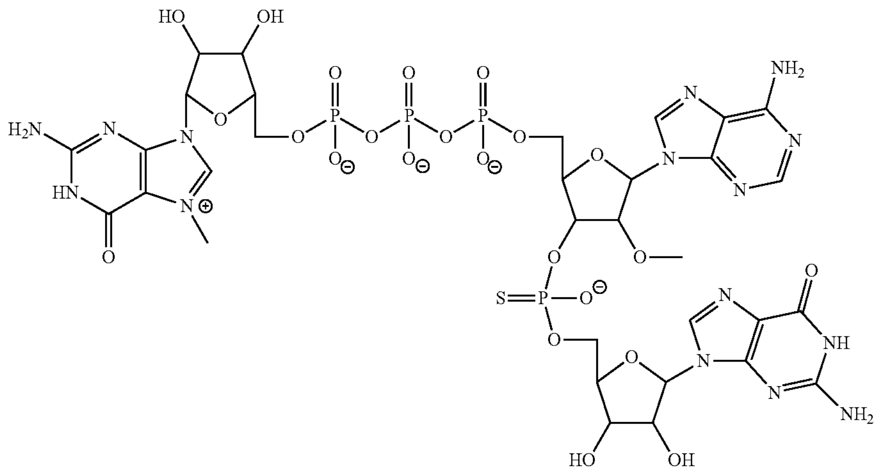 [SMILES: COC1C(OP([O-])(=S)OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(O)C2O)OC1n1cnc2c(N)ncnc21] |
| 5203 | $m^7G(ppp)Am(ps)G(p)G$ | 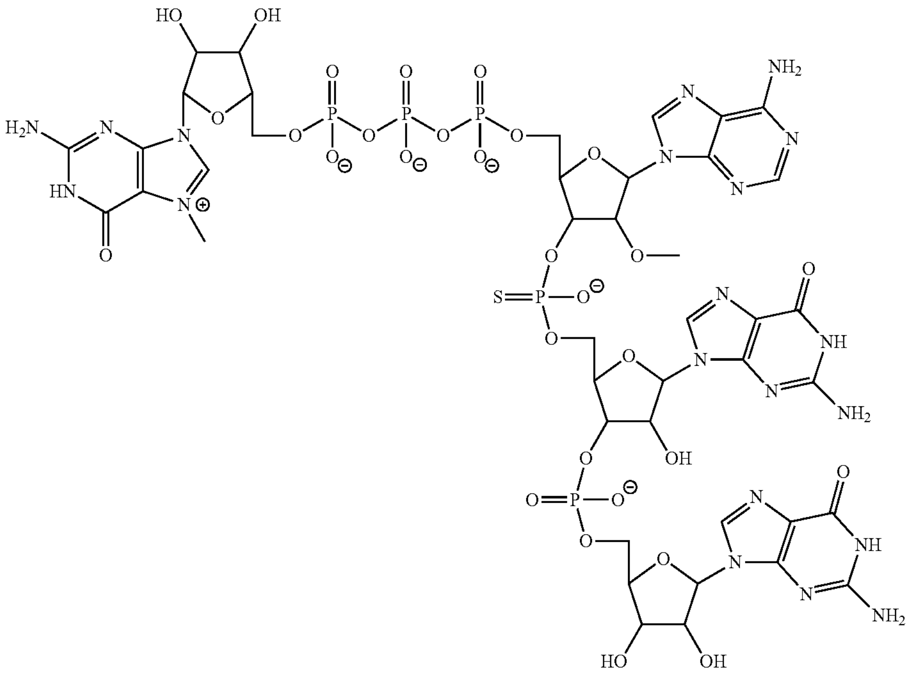 |

TABLE 1-continued
| Compound ID | Name | Chemical Structure |
|---|---|---|
| 5204 | $m^7G(ppp)Am(ps)G(ps)G$ | 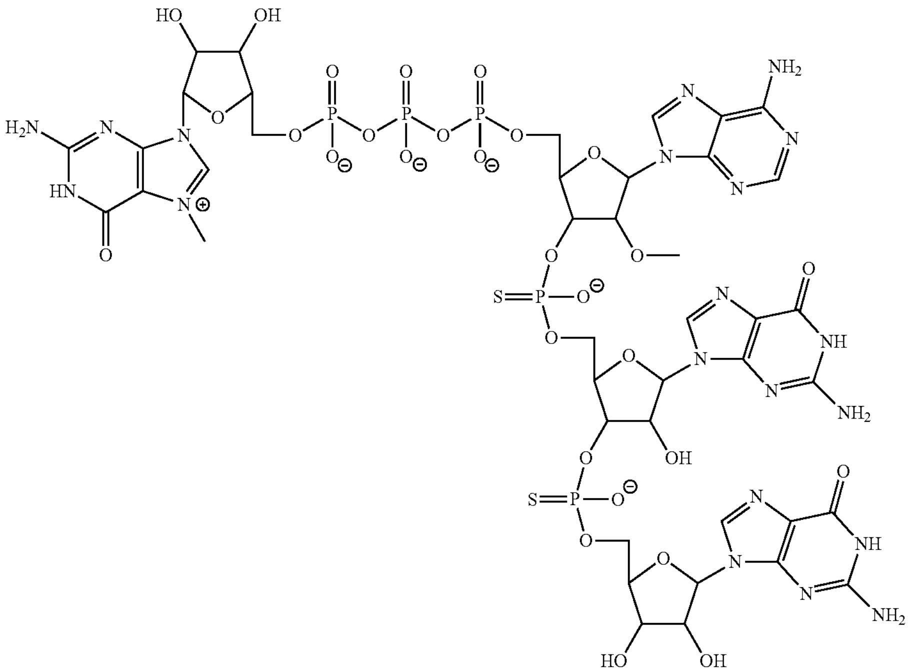 |
| 1007e | $m^7I(ppp)Am(ps)G$ | 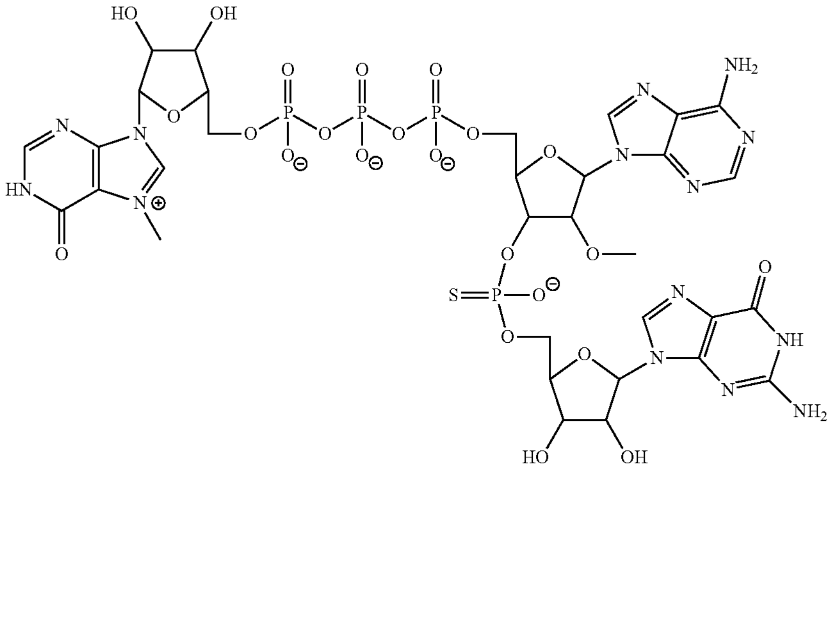 |

TABLE 1-continued
| Compound ID | Name | Chemical Structure |
| --- | --- | --- |
| 5205 | $m^7$I(ppp)Am(ps)G(p)G | 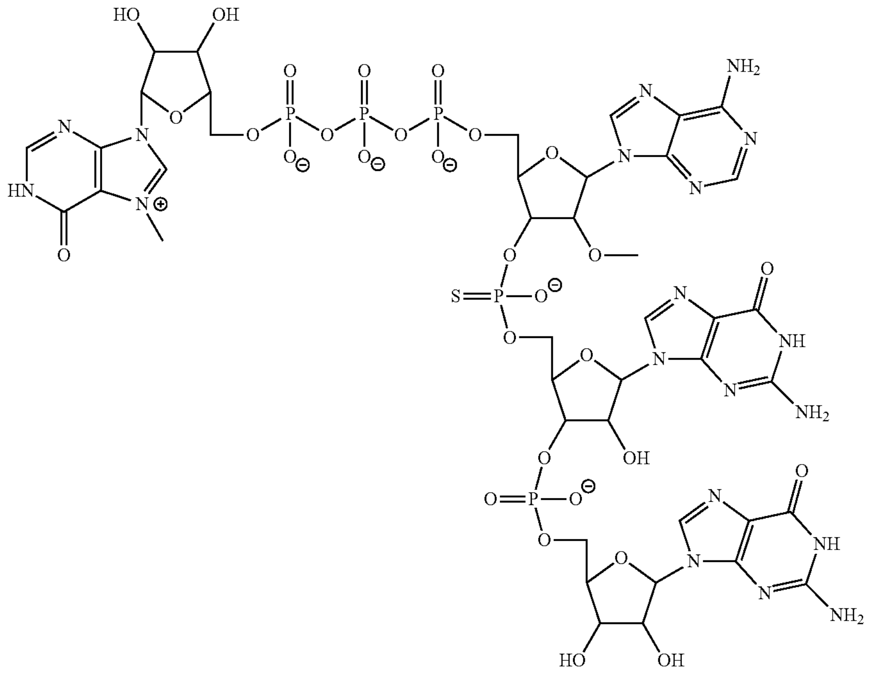 |
| 1007i | $m^7$E(ppp)Am(ps)G | 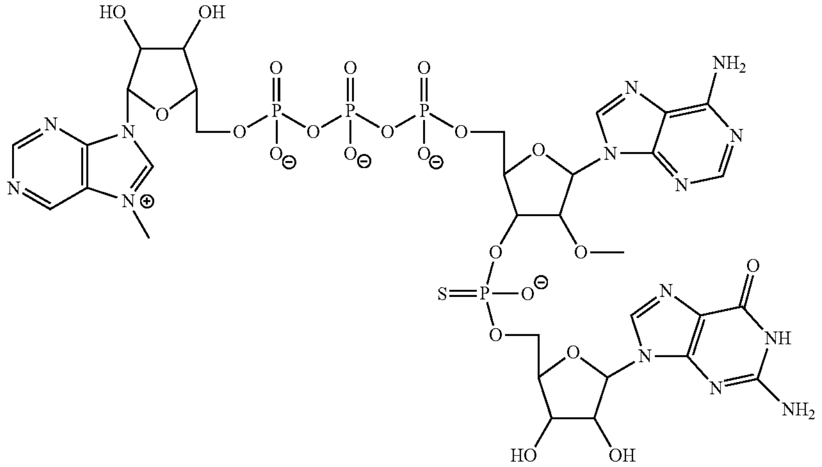 |

TABLE 1-continued
| Compound ID | Name | Chemical Structure |
| --- | --- | --- |
| 5206 | $m^7E(ppp)Am(ps)G(p)G$ | 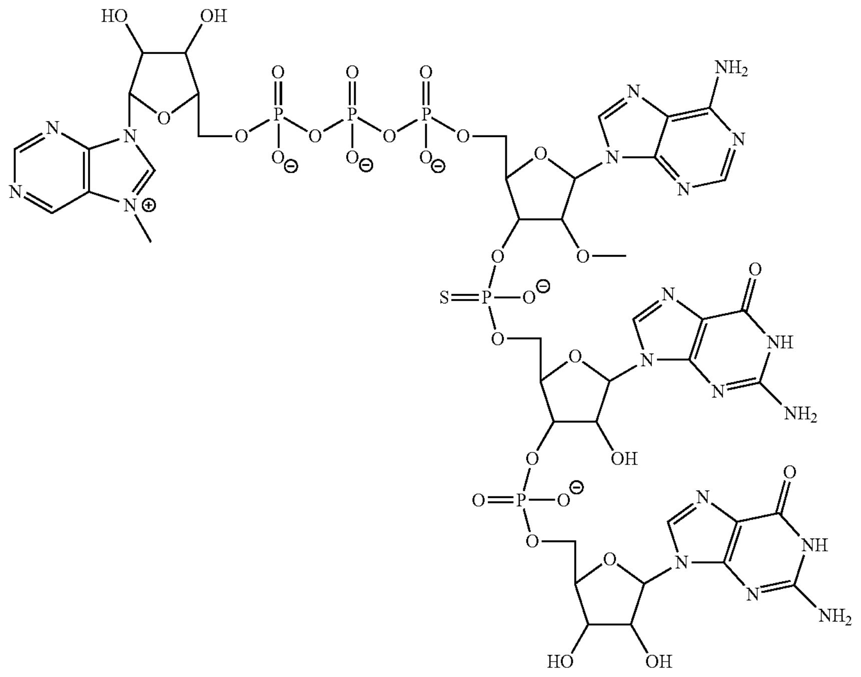 [SMILES: COC1C(OP([O-])(=S)OCC2OC(n3cnc4c(=O)[nH]c(N)nc43)C(O)C2OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4cncnc43)C(O)C2O)OC1n1cnc2c(N)ncnc21] |
| 1032a | $m^7G(ppsps)Am(p)G$ | 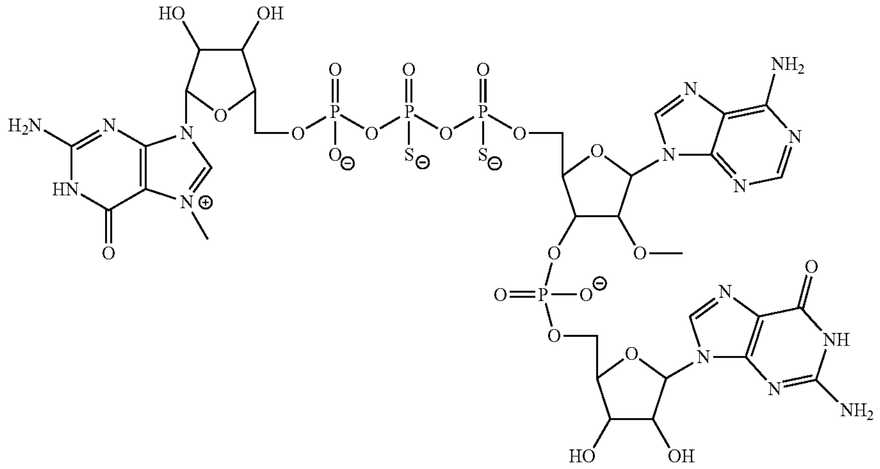 |

TABLE 1-continued
| Compound ID | Name | Chemical Structure |
| --- | --- | --- |
| 1037a | $m^7G(ppsps)Am(ps)G$ | 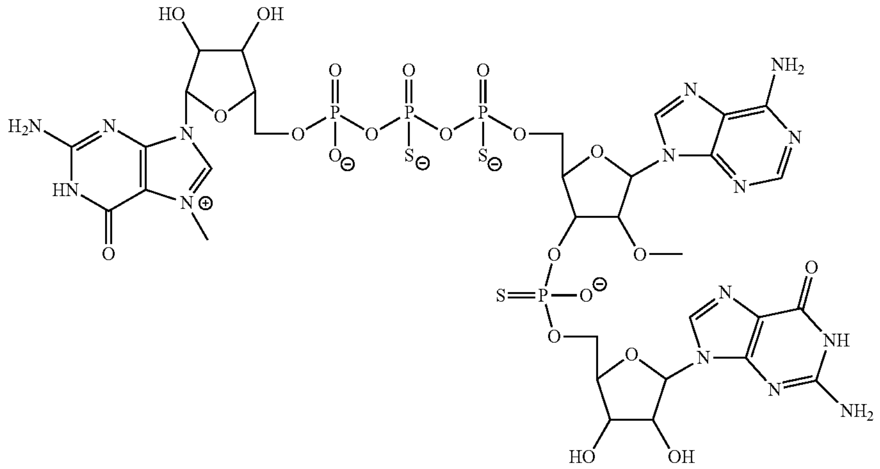 |
| 1107a | $m^7G(ppsp)Am(p)G$ | 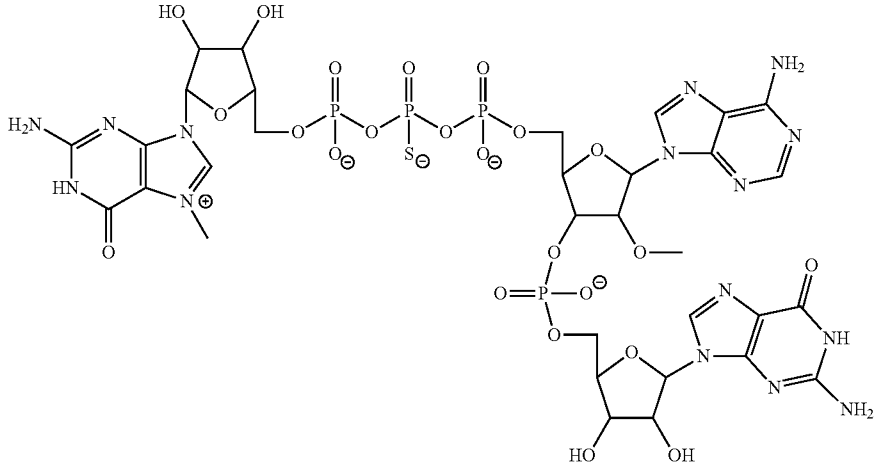 |

TABLE 1-continued
| Compound ID | Name | Chemical Structure |
|---|---|---|
| 5207 | $m^7G(ppsp)Am(p)G(p)G$ | 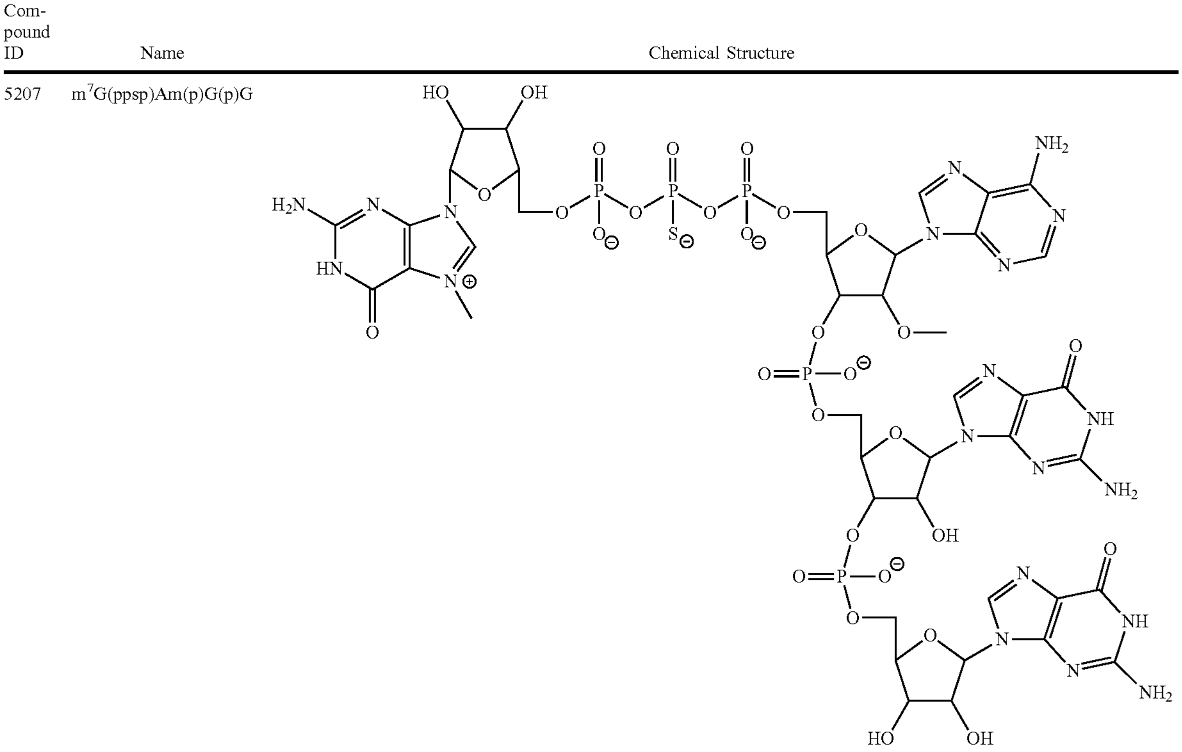 |
| 1112a | $m^7G(ppsp)Am(ps)G$ | 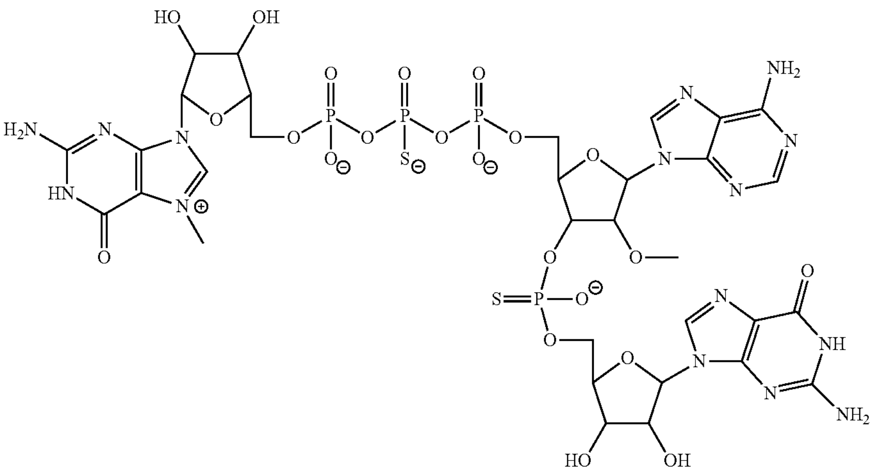 [SMILES: COC1C(OP(=O)([O-])OCC2OC(n3cnc4c(=O)[nH]c(N)nc43)C(O)C2O)C(COP(=O)([O-])OP(=O)([S-])OP(=O)([O-])OCC2OC(n3c[n+](C)c4c(=O)[nH]c(N)nc43)C(O)C2O)OC1n1cnc2c(N)ncnc21] |

TABLE 1-continued
| Compound ID | Name | Chemical Structure |
|---|---|---|
| 1137a | $m^7G(ppssp)Am(p)G$ | 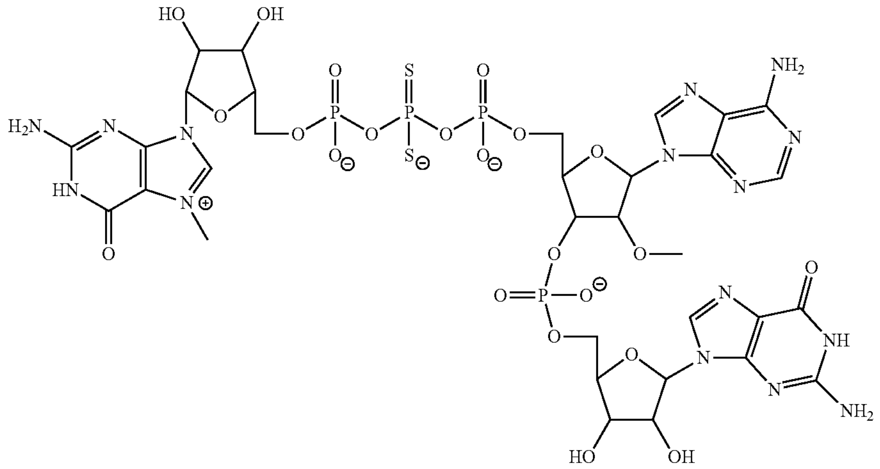 |
| 1141a | $m^7G(ppssp)Am(ps)G$ | 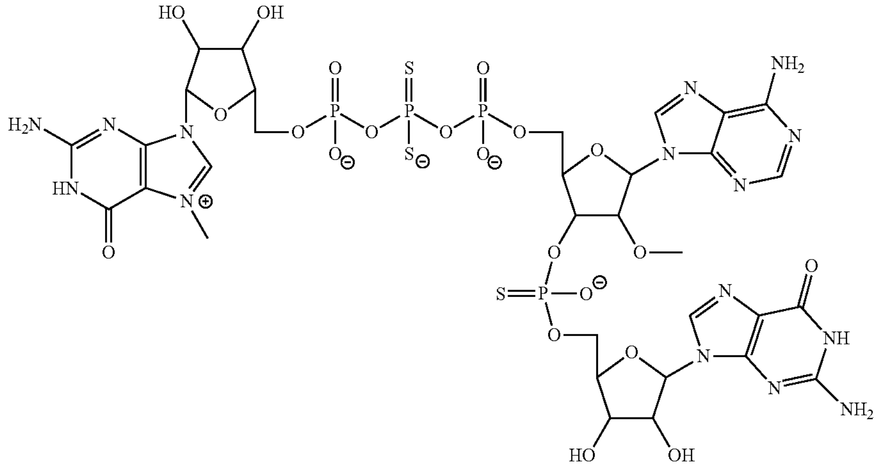 [SMILES: COC1C(OP([O-])(=S)OCC2OC(n3cnc4c(=O)[nH]c(N)nc43)C(O)C2O)C(COP(=O)([O-])OP(=O)([S-])OP(=O)([O-])OCC2OC(n3c[n+](C)c4c(=O)[nH]c(N)nc43)C(O)C2O)OC1n1cnc2c(N)ncnc21] |

TABLE 1-continued
| Compound ID | Name | Chemical Structure |
| --- | --- | --- |
| 5208 | $m^7G(ppssp)Am(p)G(p)G$ | 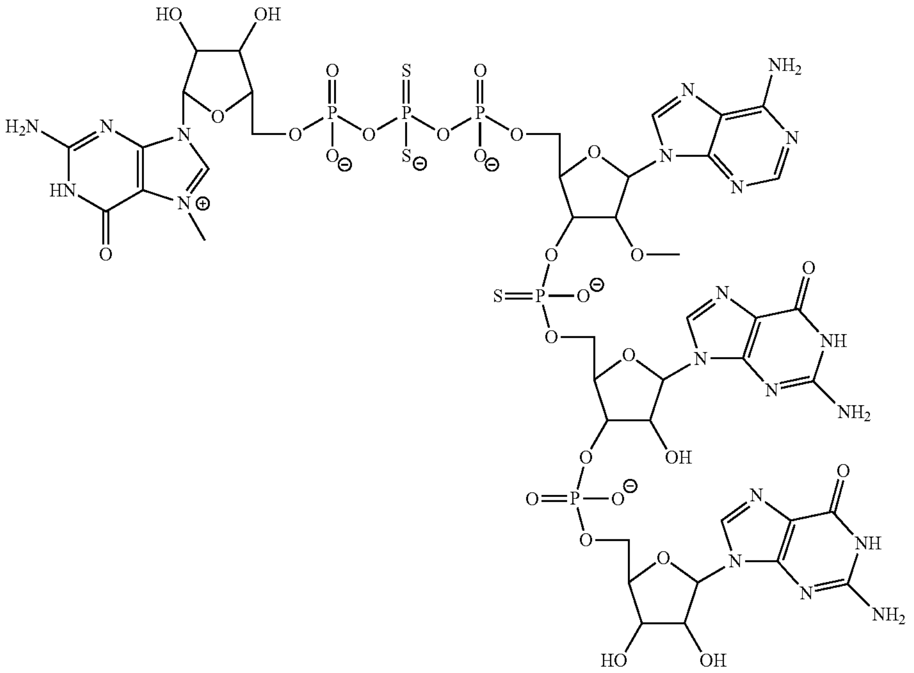 |
| 3102a | $m^7G(ppp)Em(p)G$ | 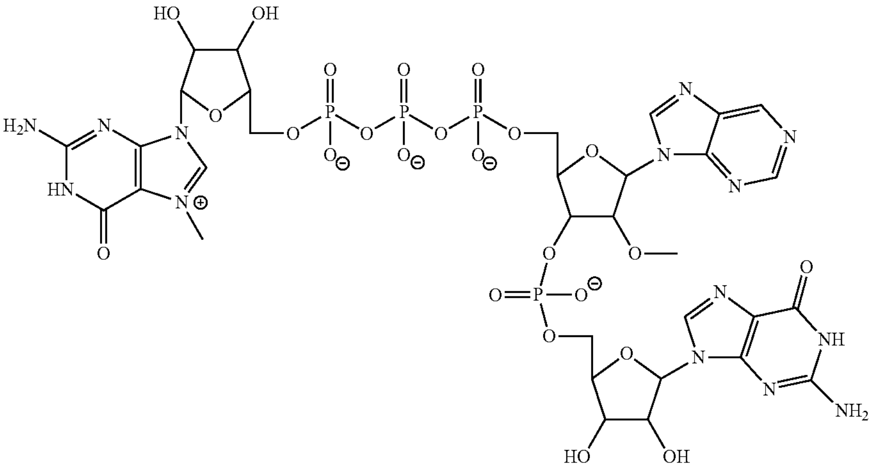 |

TABLE 1-continued
| Compound ID | Name | Chemical Structure |
|---|---|---|
| 3107a | $m^7G(ppp)Em(ps)G$ | 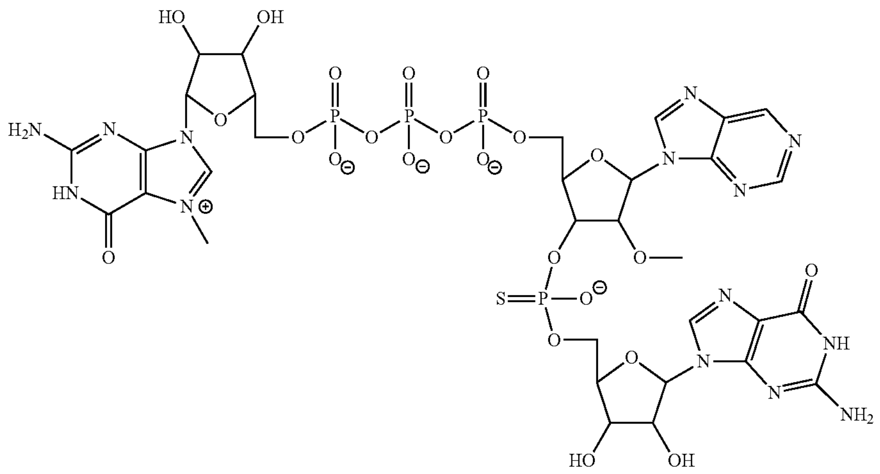 [SMILES: COC1C(OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(O)C2O)OC1n1cnc2cncnc21] |
| 3207a | $m^7G(ppsp)Em(p)G$ | 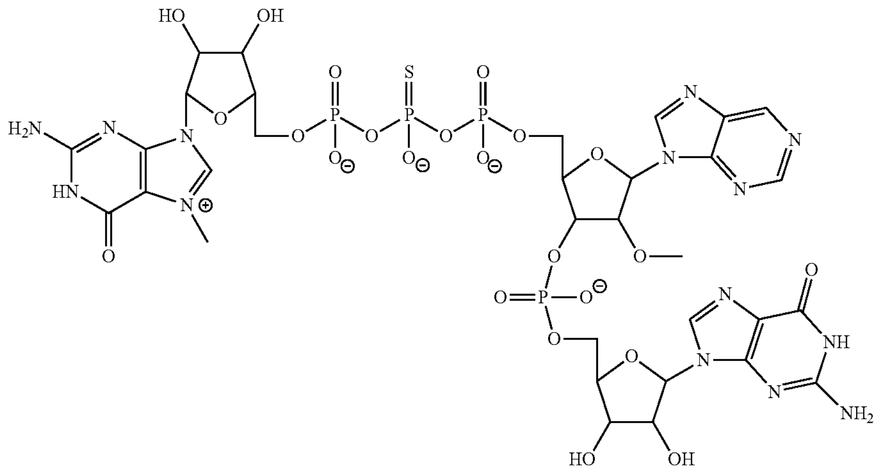 |
| 3212a | $m^7G(ppsp)Em(ps)G$ | 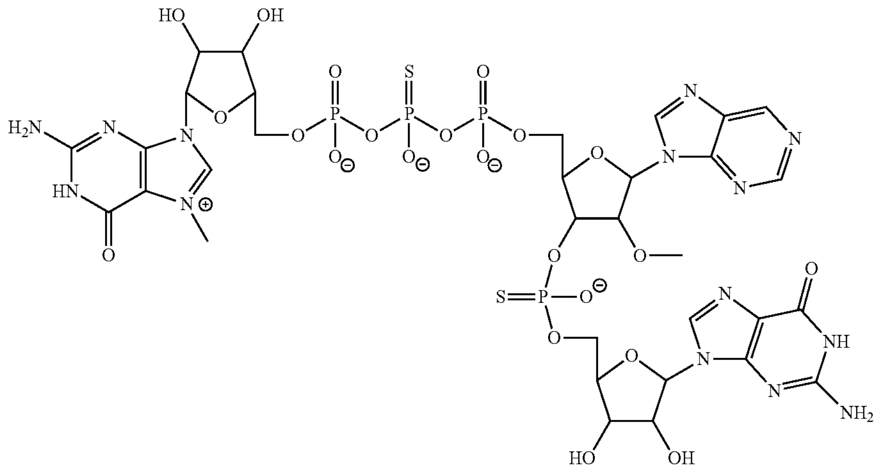 [SMILES: COC1C(OP(=O)([O-])OCC2OC(n3cnc4c(=O)[nH]c(N)nc43)C(O)C2O)C(COP(=O)([O-])OP([O-])(=S)OP(=O)([O-])OCC2OC(n3c[n+](C)c4c(=O)[nH]c(N)nc43)C(O)C2O)OC1n1cnc2cncnc21] |

TABLE 1-continued
| Compound ID | Name | Chemical Structure |
| --- | --- | --- |
| 5209 | $m^7G$(ppp)Em(ps)G(p)G | 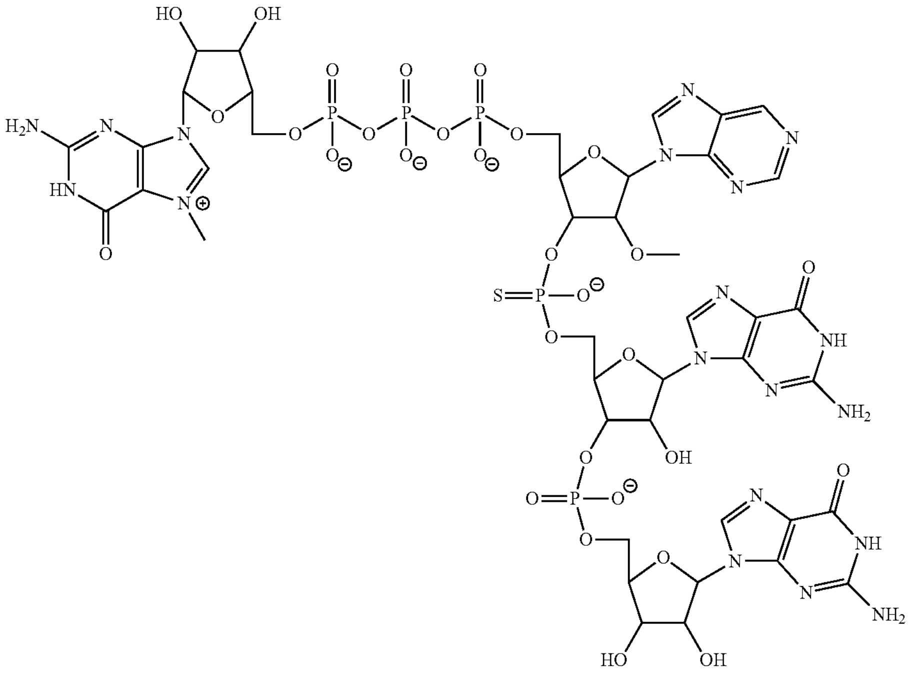 [SMILES: COC1C(OP([O-])(=S)OCC2OC(n3cnc4c(=O)[nH]c(N)nc43)C(O)C2OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(O)C2O)OC1n1cnc2cncnc21] |
| 1007c | $m^7G$(3'OMe)(ppp)Am(ps)G | 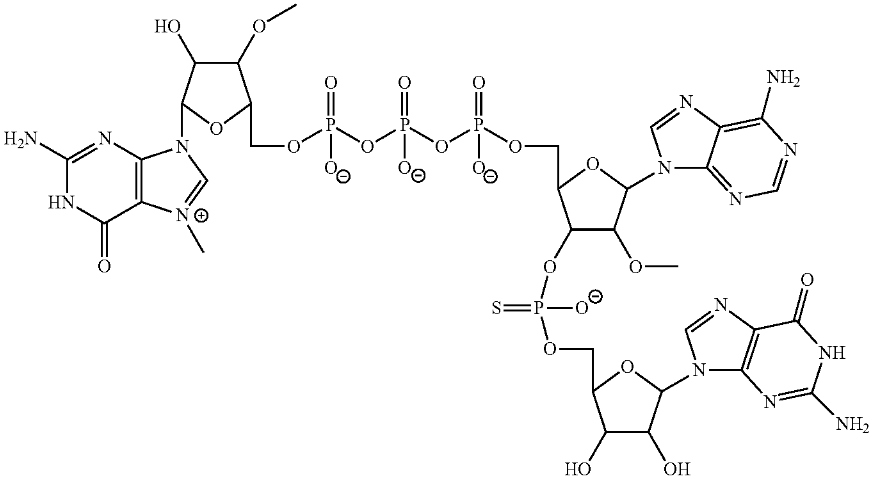 |

TABLE 1-continued
| Compound ID | Name | Chemical Structure |
| --- | --- | --- |
| 1107c | $m^7G$(3'OMe)(ppsp)Am(p)G | 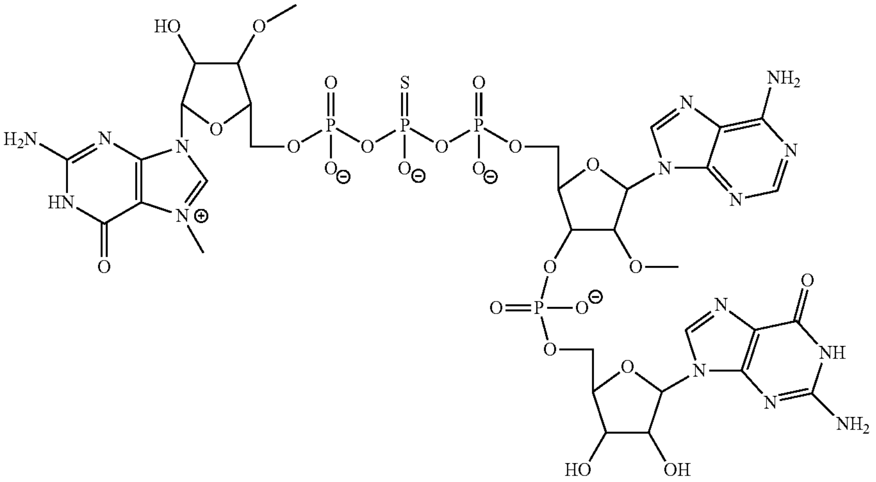 [SMILES: COC1C(COP(=O)([O-])OP([O-])(=S)OP(=O)([O-])OCC2OC(n3cnc4c(N)ncnc43)C(OC)C2OP([O-])(=S)OCC2OC(n3cnc4c(=O)[nH]c(N)nc43)C(O)C2O)OC(n2c[n+](C)c3c(=O)[nH]c(N)nc32)C1O] |
| 1112c | $m^7G$(3'OMe)(ppsp)Am(ps)G | 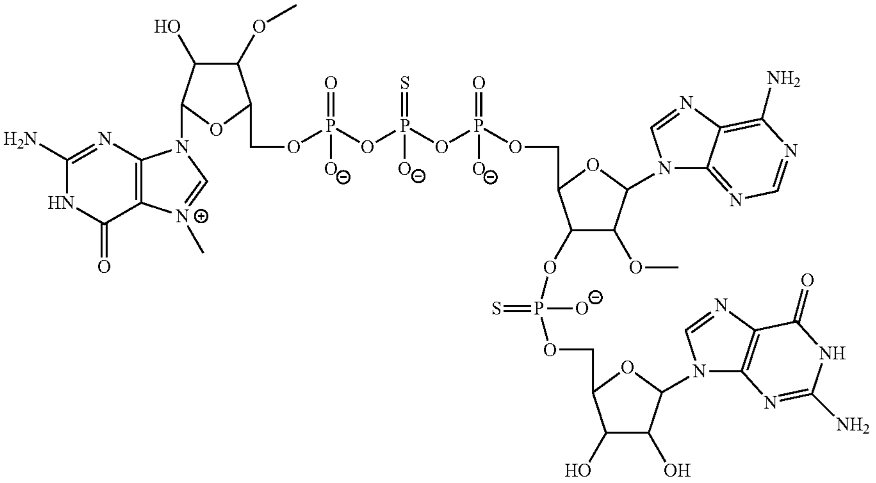 |

TABLE 1-continued
| Compound ID | Name | Chemical Structure |
| --- | --- | --- |
| 5210 | m7G(3'OMe)(ppp)Am(ps) G(p)G | 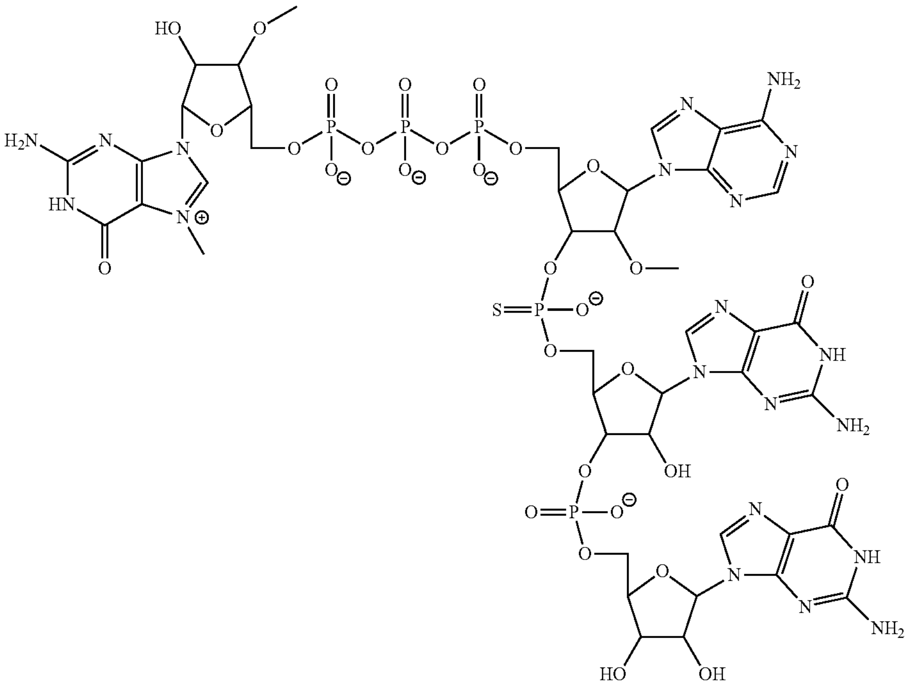 [SMILES: COC1C(COP(=O)([O-])OP(=O)([O-])OP(=O)([O-])OCC2OC(n3cnc4c(N)ncnc43)C(OC)C2OP([O-])(=S)OCC2OC(n3cnc4c(=O)[nH]c(N)nc43)C(O)C2OP(=O)([O-])OCC2OC(n3cnc4c(=O)[nH]c(N)nc43)C(O)C2O)OC(n2c[n+](C)c3c(=O)[nH]c(N)nc32)C1O] |
| 3102c | m7G(3'OMe)(ppp)Em(p)G | 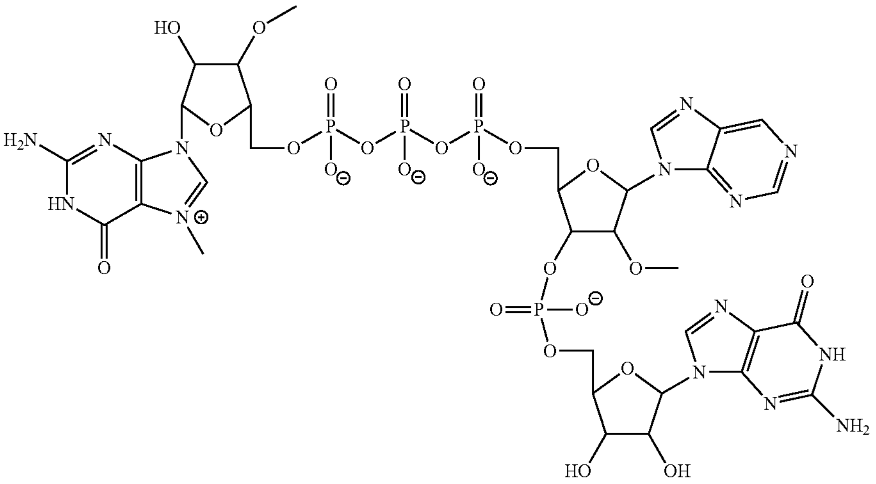 |

TABLE 1-continued
| Compound ID | Name | Chemical Structure |
|---|---|---|
| 3107c | $m^7G(3'OMe)$ (ppp)Em(ps)G | 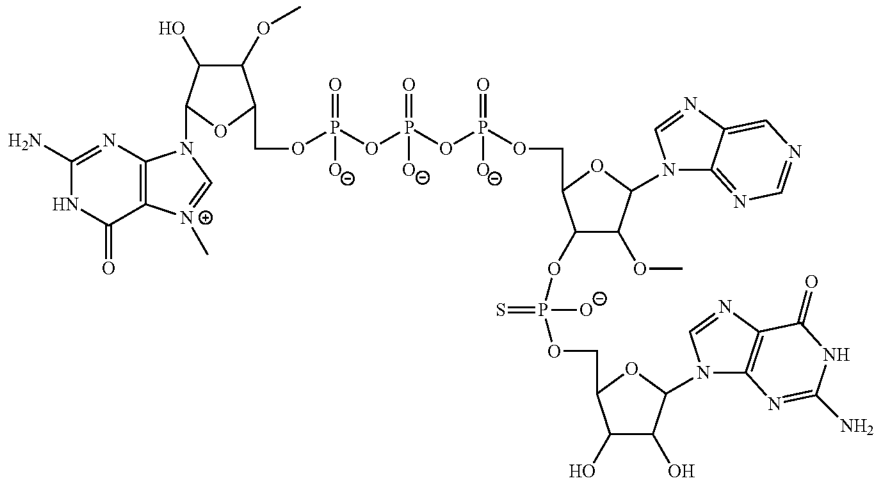 |
| 3207c | $m^7G(3'OMe)$ (ppsp)Em(p)G | 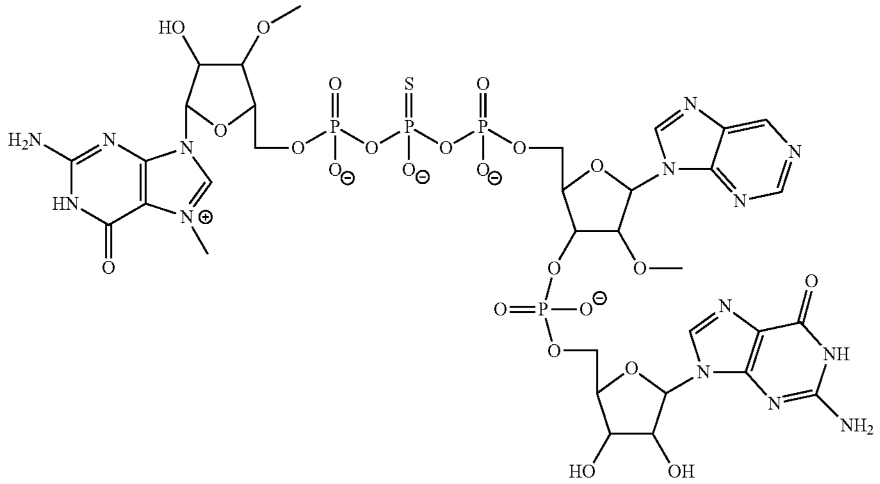 |
| 3212c | $m^7G(3'OMe)$ (ppsp)Em(ps)G | 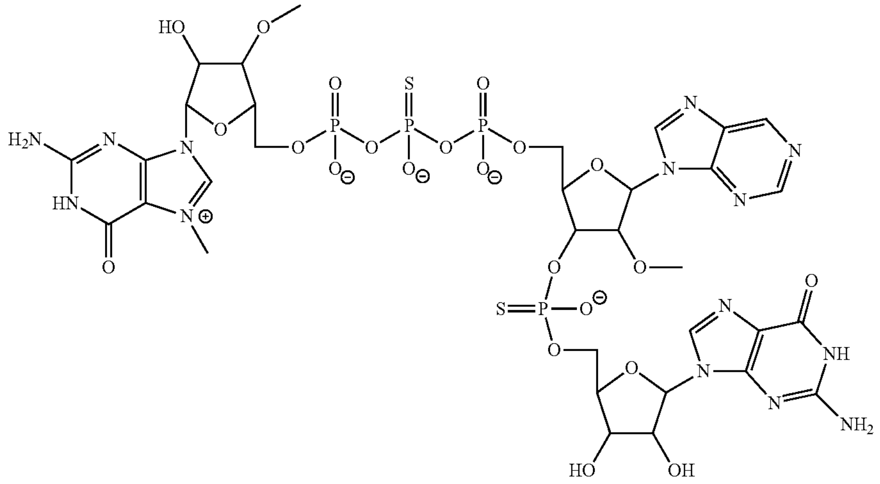 [SMILES: COC1C(COP(=O)([O-])OP(=O)([O-])OP(=O)([O-])OCC2OC(n3cnc4cncnc43)C(OC)C2OP(=O)([O-])OCC2OC(n3cnc4c(=O)[nH]c(N)nc43)C(O)C2O)OC(n2c[n+](C)c3c(=O)[nH]c(N)nc32)C1O] |

TABLE 1-continued
| Compound ID | Name | Chemical Structure |
|---|---|---|
| 5211 | $m^7G$(3'OMe)(ppp)Em(ps) G(p)G | 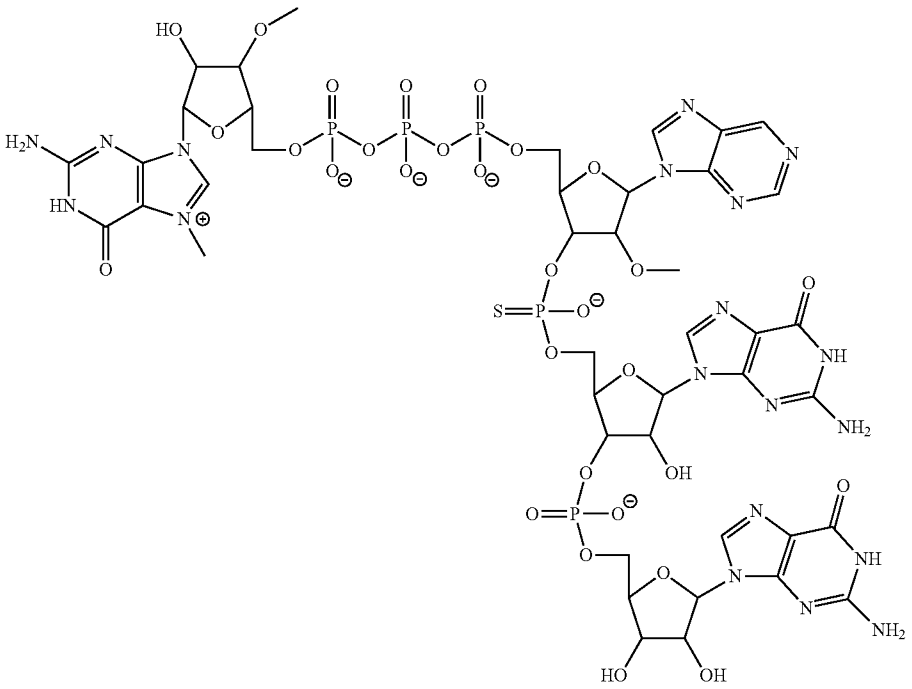 [SMILES: COC1C(COP(=O)([O-])OP(=O)([O-])OP(=O)([O-])OCC2OC(n3cnc4cncnc43)C(OC)C2OP([O-])(=S)OCC2OC(n3cnc4c(=O)[nH]c(N)nc43)C(O)C2OP(=O)([O-])OCC2OC(n3cnc4c(=O)[nH]c(N)nc43)C(O)C2O)OC(n2c[n+](C)c3c(=O)[nH]c(N)nc32)C1O] |
| 5212 | $m^7G$(ppp)Am(p)G(4-thio) | 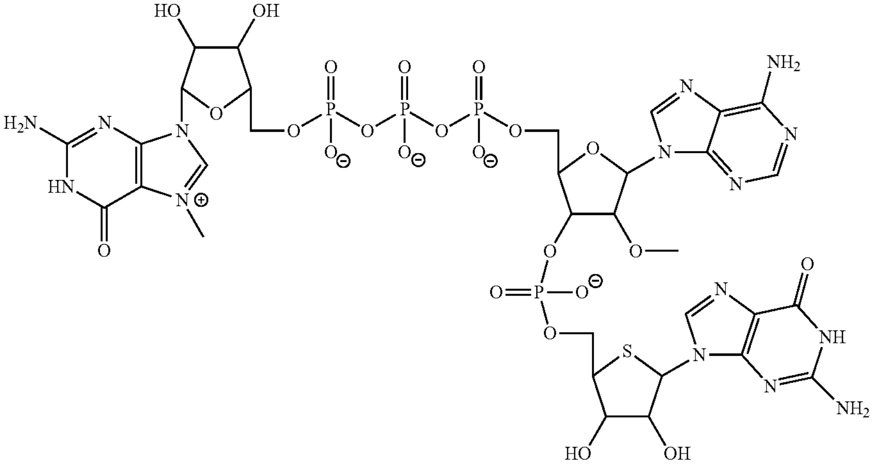 |

TABLE 1-continued
| Compound ID | Name | Chemical Structure |
|---|---|---|
| 5213 | $m^7G$(ppp)Am(p)G(4-thio)(p)G | 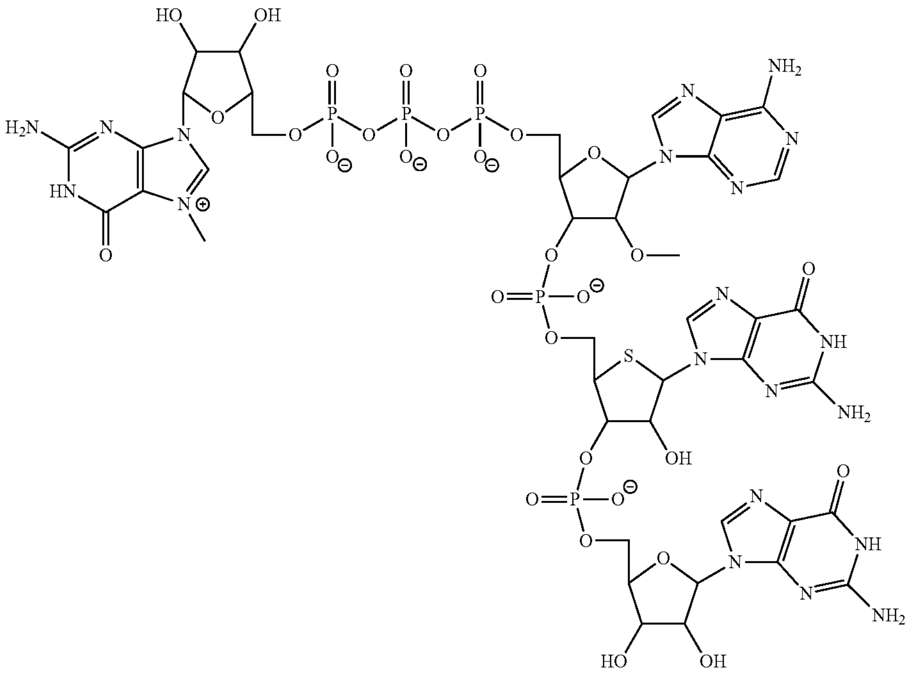 |
| 5214 | $m^7G$(ppp)Am(ps)G(4-thio)(p)G | 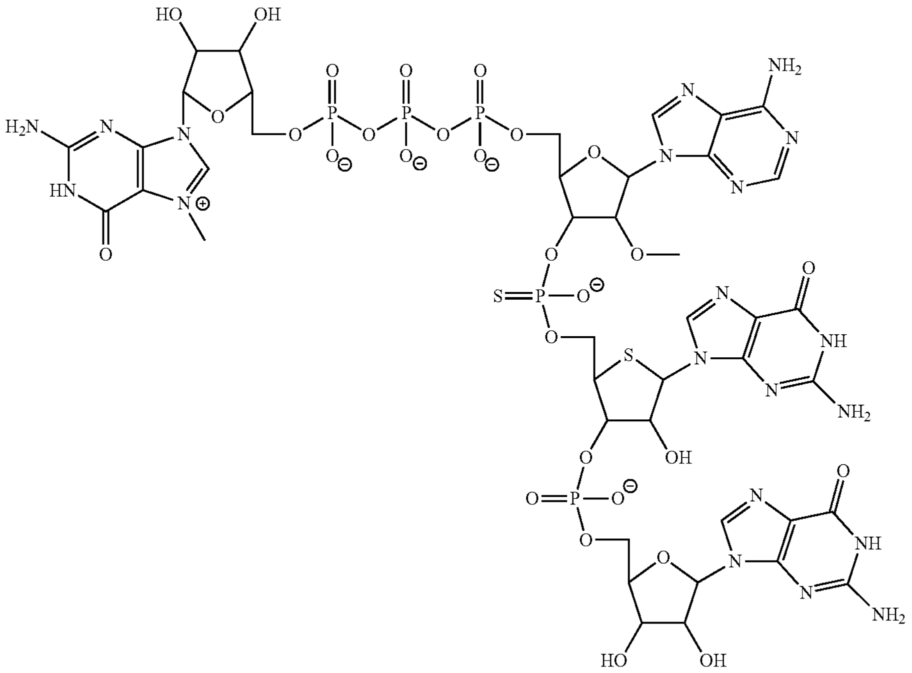 [SMILES: COC1C(OP(=O)([O-])OCC2SC(n3cnc4c(=O)[nH]c(N)nc43)C(O)C2OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(O)C2O)OC1n1cnc2c(N)ncnc21] |

In some embodiments, disclosed herein is a pharmaceutically acceptable salt or pharmaceutically acceptable solvate or a pharmaceutical composition comprising one or more mRNA(s) which is/are produced/manufactured from one or more sequence initiator compound selected from Table 1, wherein the mRNA encode(s) one or more pharmaceutically active protein(s).

In certain embodiments the sequence initiator compound is as described in Table 2.

TABLE 2

| | | |
|---|---|---|
| 5215 | $m^7G$(2'F-2'F)(ppp)Am(p)G | 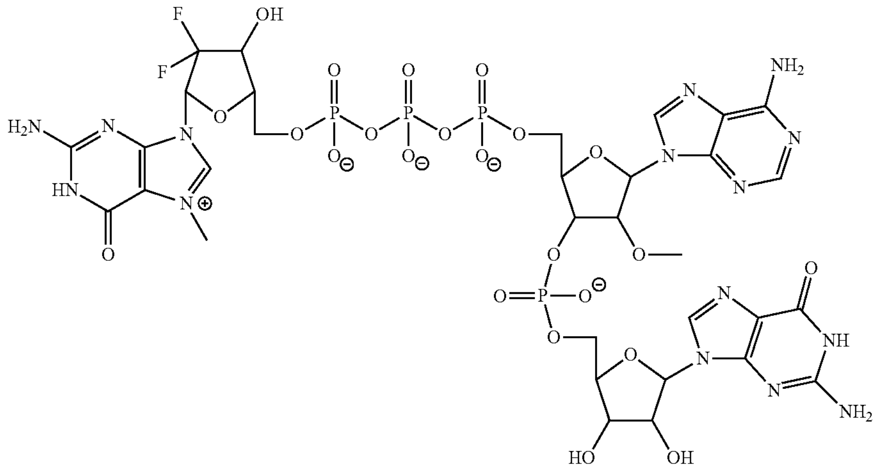 [SMILES: COC1C(OP([O-])(=S)OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(F)(F)C2O)OC1n1cnc2c(N)ncnc21] |
| 5216 | $m^7G$(2'F-2'F)(ppp)Am(ps)G | 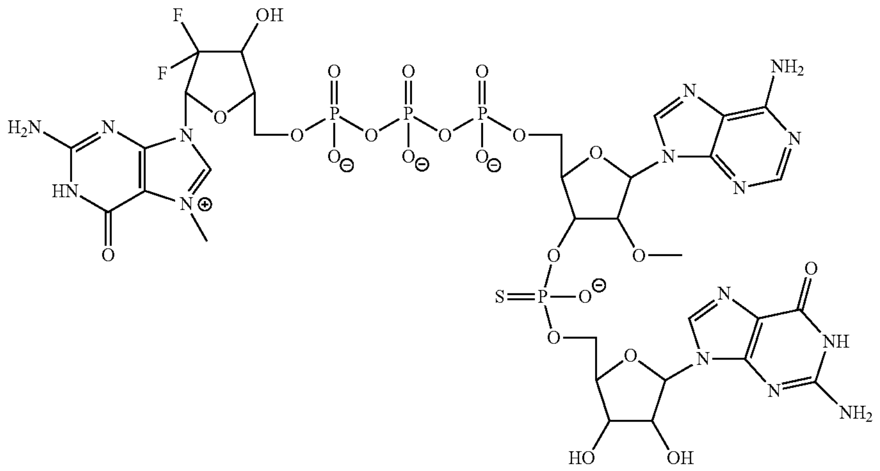 |

TABLE 2-continued
| | | |
|---|---|---|
| 5217 | m7G(2'F-2'F)(ppp) Am(p)G(p)G | 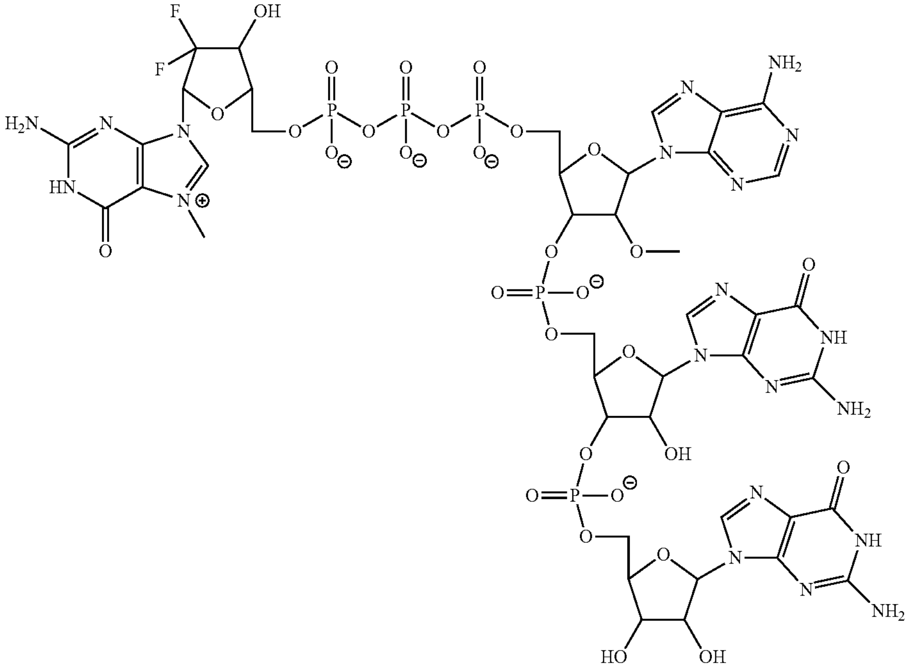 |
| 5218 | m7G(2'F-2'F)(ppp)Am(ps)G(p)G | 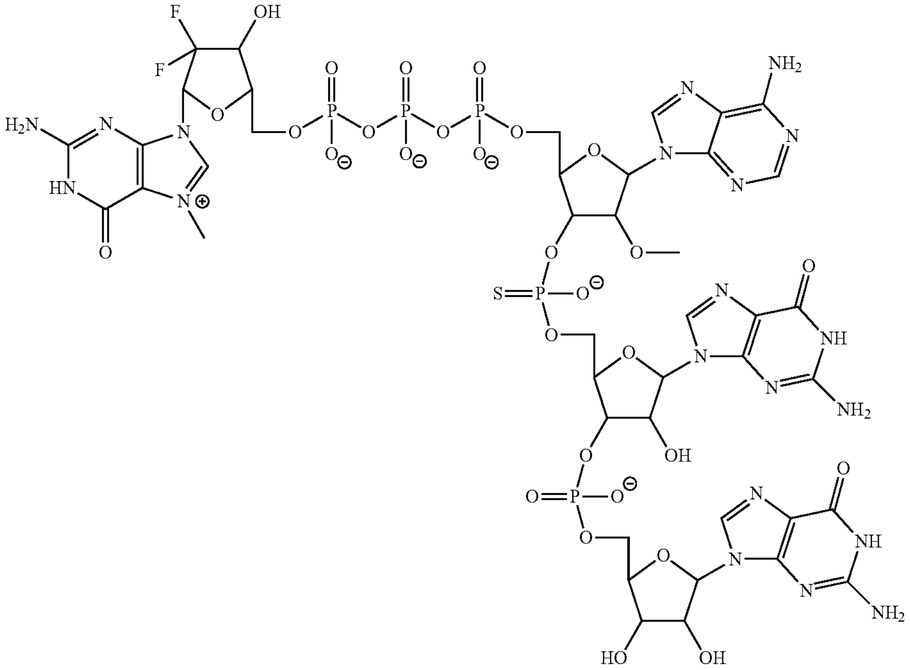 |

TABLE 2-continued
| | | |
|---|---|---|
| 5219 | $m^7G$(2'F-2'Me)(ppp)Am(p)G | 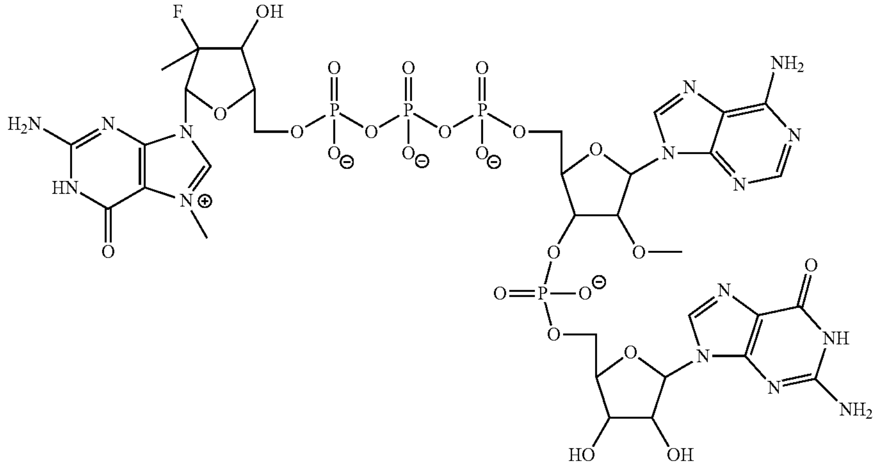 [SMILES: COC1C(OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(C)(F)C2O)OC1n1cnc2c(N)ncnc21] |
| 5220 | $m^7G$(2'F-2'Me)(ppp)Am(ps)G | 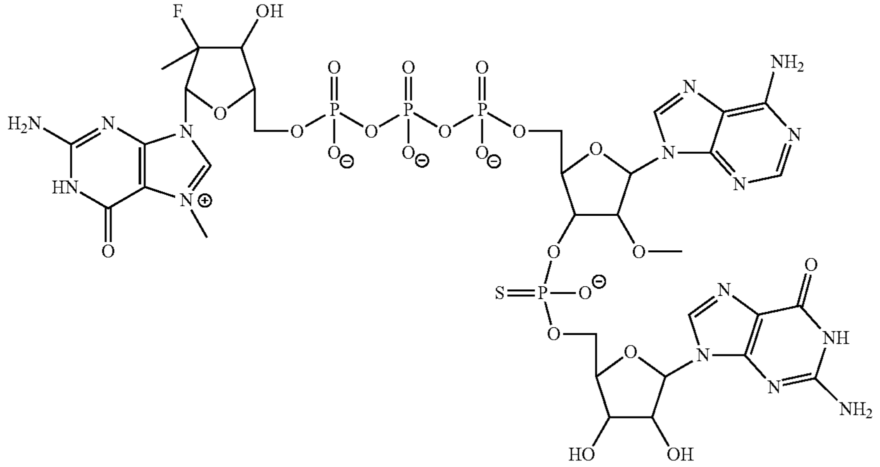 [SMILES: COC1C(OP([O-])(=S)OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(C)(F)C2O)OC1n1cnc2c(N)ncnc21] |
| 5221 | $m^7G$(2'F-2'Me)(ppp)Am(p)G(p)G | 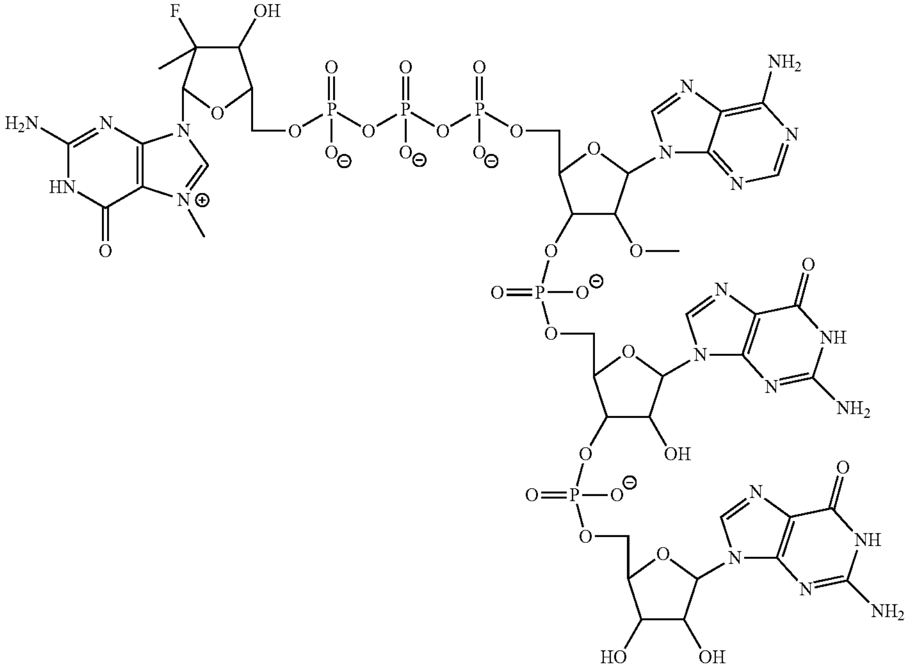 [SMILES: COC1C(OP(=O)([O-])OCC2OC(n3cnc4c(=O)[nH]c(N)nc43)C(O)C2OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(C)(F)C2O)OC1n1cnc2c(N)ncnc21] |

TABLE 2-continued
| | | |
|---|---|---|
| 5222 | m7G(2'F-2'Me)(ppp)Am(ps)G(p)G | 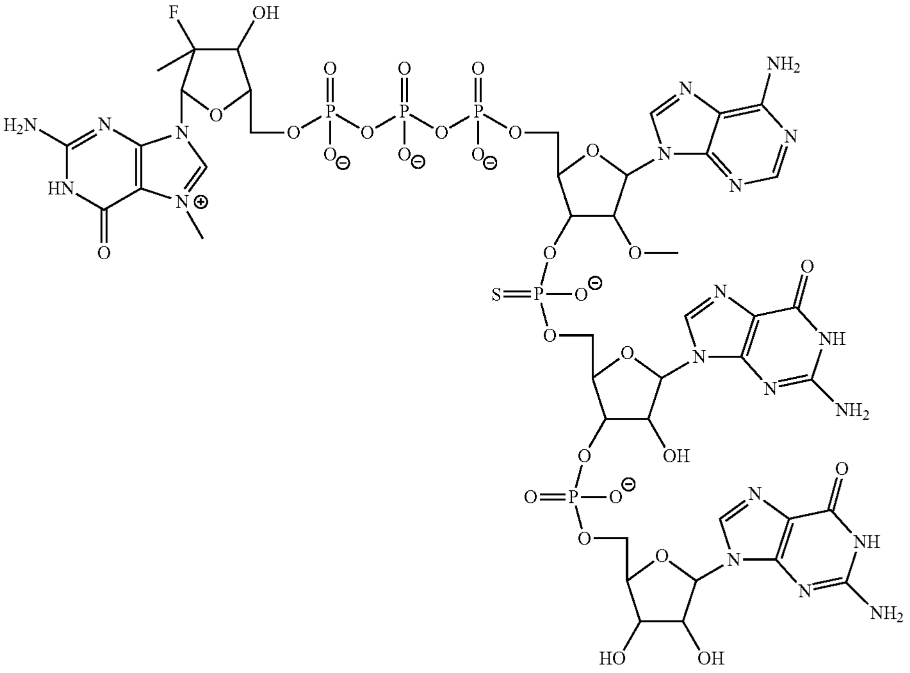 [SMILES: COC1C(OP([O-])(=S)OCC2OC(n3cnc4c(=O)[nH]c(N)nc43)C(O)C2OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(C)(F)C2O)OC1n1cnc2c(N)ncnc21] |
| 5223 | m7G(2'Me-2'OH)(ppp)Am(p)G | 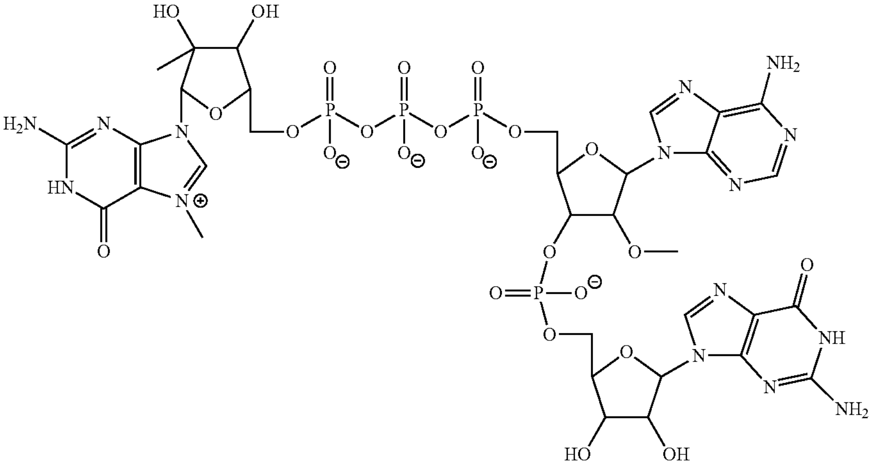 [SMILES: COC1C(OP([O-])(=S)OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(C)(O)C2O)OC1n1cnc2c(N)ncnc21] |
| 5224 | m7G(2'Me-2'OH)(ppp)Am(ps)G | 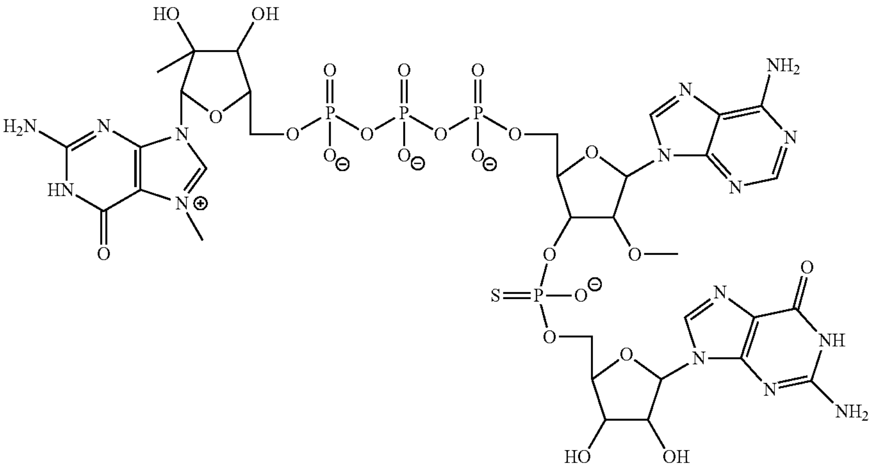 |

TABLE 2-continued
| | | |
|---|---|---|
| 5225 | $m^7G$(2'Me-2'OH)(ppp)Am(p)G(p)G | 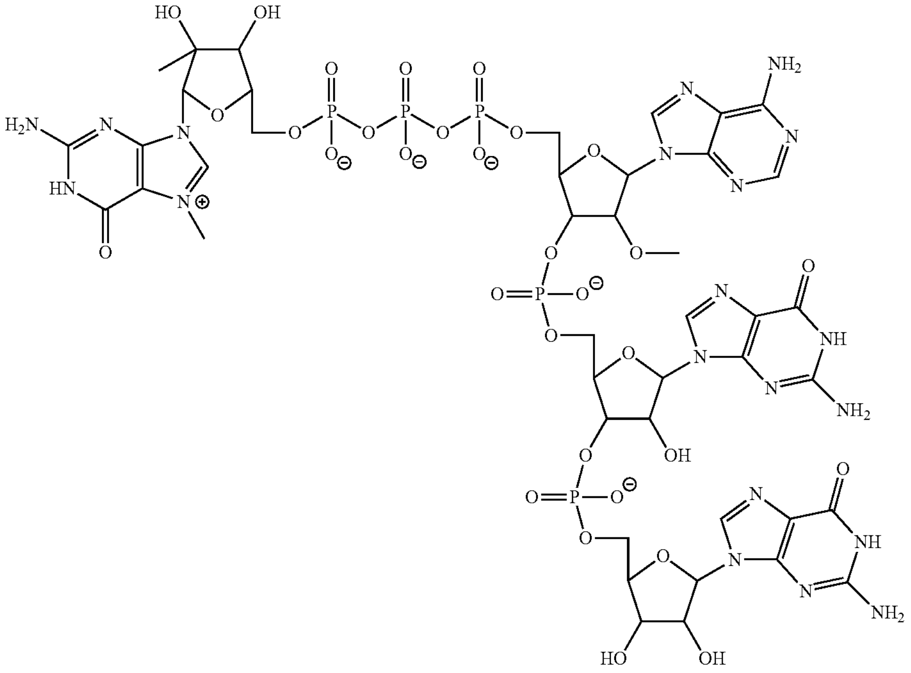 [SMILES: COC1C(OP(=O)([O-])OCC2OC(n3cnc4c(=O)[nH]c(N)nc43)C(O)C2OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(C)(O)C2O)OC1n1cnc2c(N)ncnc21] |
| 5226 | $m^7G$(2'Me-2'OH)(ppp)Am(ps)G(p)G | 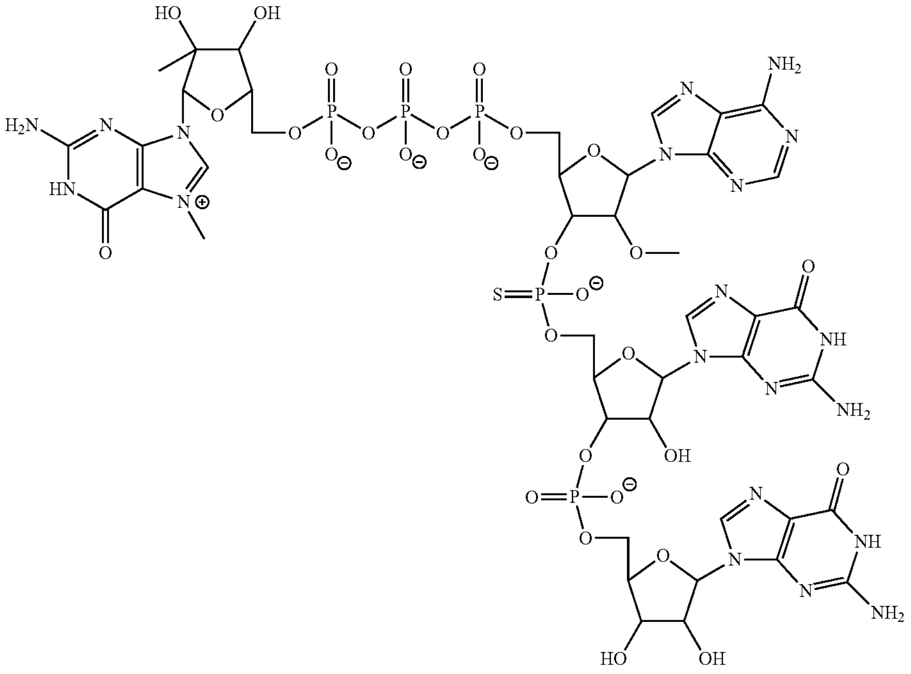 [SMILES: COC1C(OP([O-])(=S)OCC2OC(n3cnc4c(=O)[nH]c(N)nc43)C(O)C2OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(C)(O)C2O)OC1n1cnc2c(N)ncnc21] |

TABLE 2-continued
| | | |
|---|---|---|
| 5227 | $m^7G(4'OMe)$ (ppp)Am(p)G | 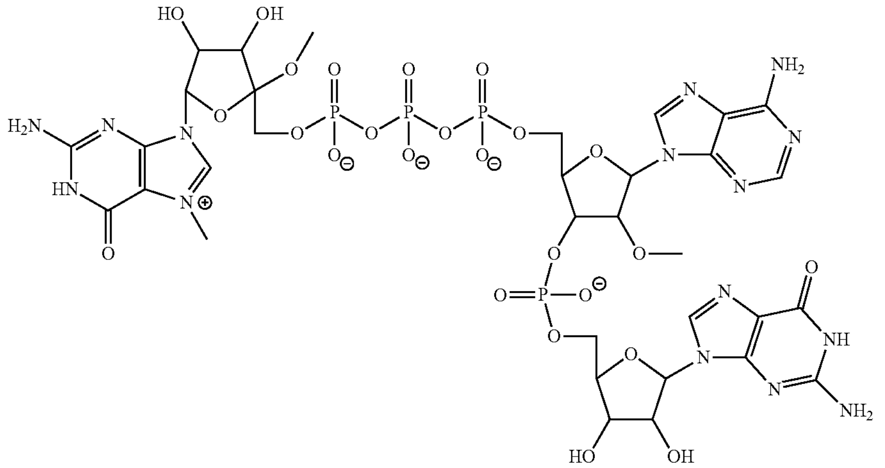 |
| 5228 | $m^7G(4'OMe)$ (ppp)Am(ps)G | 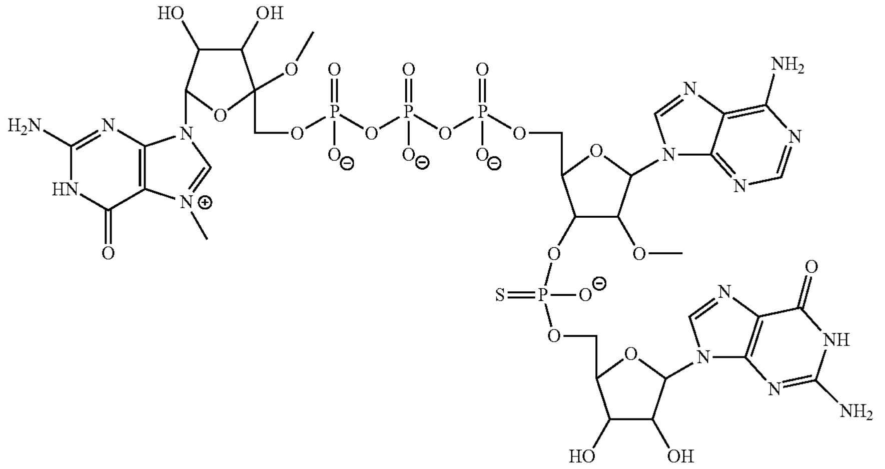 [SMILES: COC1C(OP([O-])(=S)OCC2OC(n3cnc4c(=O)[nH]c(N)nc43)C(O)C2O)C(COP(=O)([O-])OP(=O)([O-])OP(=O)([O-])OCC2(OC)OC(n3c[n+](C)c4c(=O)[nH]c(N)nc43)C(O)C2O)OC1n1cnc2c(N)ncnc21] |
| 5229 | $m^7G(4'OMe)$ (ppp)Am(p)G(p)G | 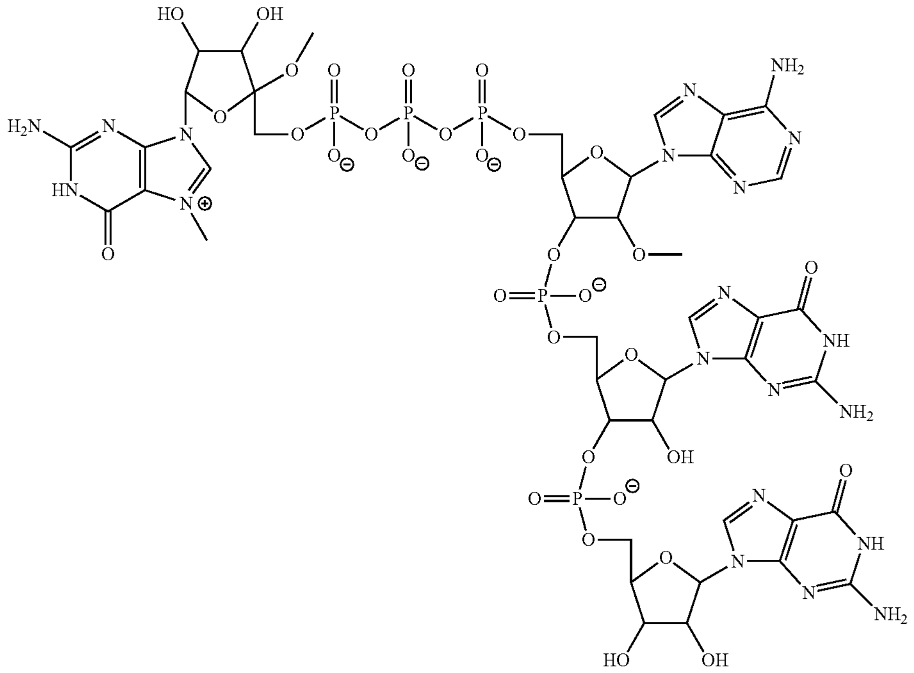 |

TABLE 2-continued

| | | |
|---|---|---|
| 5230 | $m^7G$(4'OMe)(ppp)Am(ps)G(p) | 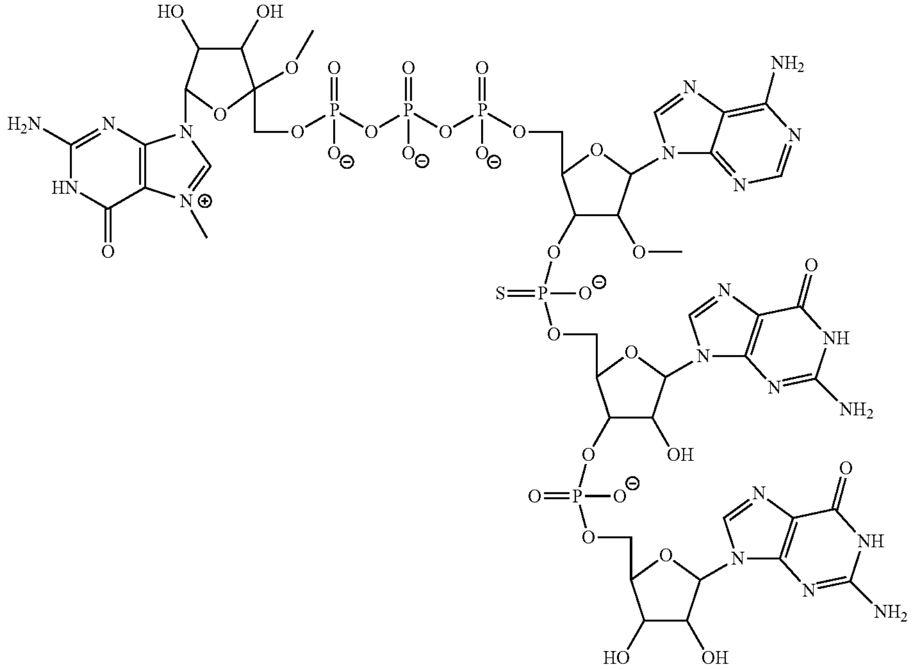 [SMILES: COC1C(OP(=O)([O-])OCC2OC(n3cnc4c(=O)[nH]c(N)nc43)C(O)C2OP(=O)([O-])OCC2OC(n3cnc4c(=O)[nH]c(N)nc43)C(O)C2O)C(COP(=O)([O-])OP(=O)([O-])OP(=O)([O-])OCC2(OC)OC(n3c[n+](C)c4c(=O)[nH]c(N)nc43)C(O)C2O)OC1n1cnc2c(N)ncnc21] |

In some embodiments, disclosed herein is a pharmaceutically acceptable salt or pharmaceutically acceptable solvate or a pharmaceutical composition comprising one or more mRNA(s) which is/are produced/manufactured from one or more sequence initiator compound selected from Table 2, wherein the mRNA encode(s) one or more pharmaceutically active protein(s).

In certain embodiments the sequence initiator compound is as described in Table 3.

TABLE 3

CapA Structures for mRNA preparation

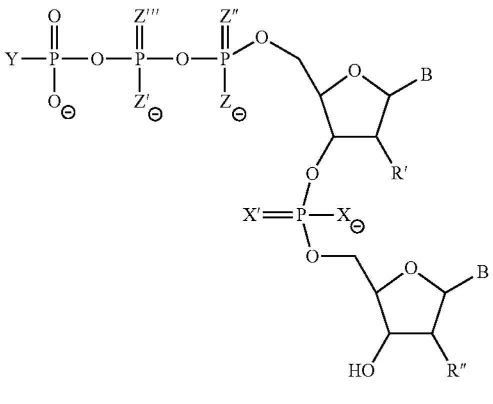

| Compound | Sequence | X | X' | Z | Z' | Z" | Z"' | R' | R" |
|---|---|---|---|---|---|---|---|---|---|
| 1001a-I | Y*AG | O | O | O | O | O | O | OH | OH |
| 1002a-I | Y*AG | O | O | O | O | O | O | OMe | OH |
| 1003a-I | Y*AG | O | O | O | O | O | O | H | OH |
| 1004a-I | Y*AG | O | O | O | O | O | O | F | OH |
| 1005a-I | Y*AG | O | O | O | O | O | O | OEt | OH |
| 1006a-I | Y*AG | S | O | O | O | O | O | OH | OH |
| 1007a-I | Y*AG | S | O | O | O | O | O | OMe | OH |
| 1008a-I | Y*AG | S | O | O | O | O | O | H | OH |
| 1009a-I | Y*AG | S | O | O | O | O | O | F | OH |

TABLE 3-continued

CapA Structures for mRNA preparation

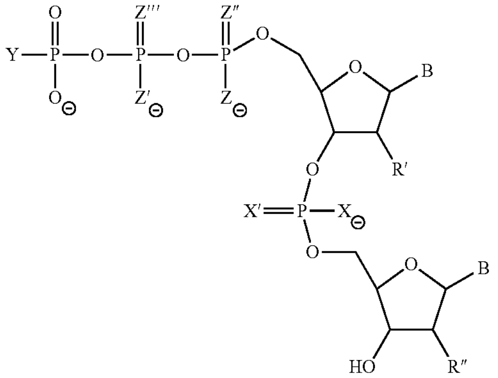

| Compound | Sequence | X | X' | Z | Z' | Z" | Z"' | R' | R" |
|---|---|---|---|---|---|---|---|---|---|
| 1010a-I | Y*AG | S | O | O | O | O | O | OEt | OH |
| 1011a-I | Y*AG | S | S | O | O | O | O | OH | OH |
| 1012a-I | Y*AG | S | S | O | O | O | O | OMe | OH |
| 1013a-I | Y*AG | S | S | O | O | O | O | H | OH |
| 1014a-I | Y*AG | S | S | O | O | O | O | F | OH |
| 1015a-I | Y*AG | S | S | O | O | O | O | OEt | OH |
| 1016a-I | Y*AG | O | O | S | O | O | O | OH | OH |
| 1017a-I | Y*AG | O | O | S | O | O | O | OMe | OH |
| 1018a-I | Y*AG | O | O | S | O | O | O | H | OH |
| 1019a-I | Y*AG | O | O | S | O | O | O | F | OH |
| 1020a-I | Y*AG | O | O | S | O | O | O | OEt | OH |
| 1021a-I | Y*AG | S | O | S | O | O | O | OH | OH |
| 1022a-I | Y*AG | S | O | S | O | O | O | OMe | OH |
| 1023a-I | Y*AG | S | O | S | O | O | O | H | OH |
| 1024a-I | Y*AG | S | O | S | O | O | O | F | OH |
| 1025a-I | Y*AG | S | O | S | O | O | O | OEt | OH |
| 1026a-I | Y*AG | S | S | S | O | O | O | OH | OH |
| 1027a-I | Y*AG | S | S | S | O | O | O | OMe | OH |
| 1028a-I | Y*AG | S | S | S | O | O | O | H | OH |
| 1029a-I | Y*AG | S | S | S | O | O | O | F | OH |
| 1030a-I | Y*AG | S | S | S | O | O | O | OEt | OH |

TABLE 3-continued

CapA Structures for mRNA preparation

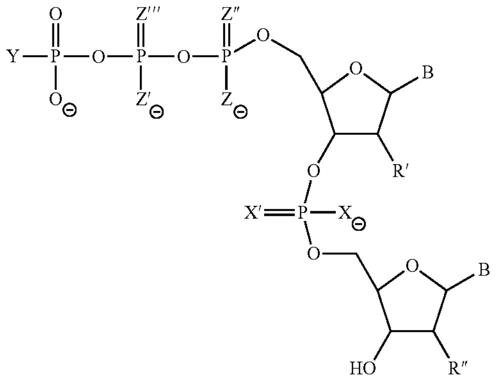

| Compound | Sequence | X | X' | Z | Z' | Z" | Z''' | R' | R" |
|---|---|---|---|---|---|---|---|---|---|
| 1031a-I | Y*AG | O | O | S | S | O | O | OH | OH |
| 1032a-I | Y*AG | O | O | S | S | O | O | OMe | OH |
| 1033a-I | Y*AG | O | O | S | S | O | O | H | OH |
| 1034a-I | Y*AG | O | O | S | S | O | O | F | OH |
| 1035a-I | Y*AG | O | O | S | S | O | O | OEt | OH |
| 1036a-I | Y*AG | S | O | S | S | O | O | OH | OH |
| 1037a-I | Y*AG | S | O | S | S | O | O | OMe | OH |
| 1038a-I | Y*AG | S | O | S | S | O | O | H | OH |
| 1039a-I | Y*AG | S | O | S | S | O | O | F | OH |
| 1040a-I | Y*AG | S | O | S | S | O | O | OEt | OH |
| 1041a-I | Y*AG | S | S | S | S | O | O | OH | OH |
| 1042a-I | Y*AG | S | S | S | S | O | O | OMe | OH |
| 1043a-I | Y*AG | S | S | S | S | O | O | H | OH |
| 1044a-I | Y*AG | S | S | S | S | O | O | F | OH |
| 1045a-I | Y*AG | S | S | S | S | O | O | OEt | OH |
| 1046a-I | Y*AG | O | O | S | S | S | O | OH | OH |
| 1047a-I | Y*AG | O | O | S | S | S | O | OMe | OH |
| 1048a-I | Y*AG | O | O | S | S | S | O | H | OH |
| 1049a-I | Y*AG | O | O | S | S | S | O | F | OH |
| 1050a-I | Y*AG | O | O | S | S | S | O | OEt | OH |
| 1051a-I | Y*AG | S | O | S | S | S | O | OH | OH |
| 1052a-I | Y*AG | S | O | S | S | S | O | OMe | OH |
| 1053a-I | Y*AG | S | O | S | S | S | O | H | OH |
| 1054a-I | Y*AG | S | O | S | S | S | O | F | OH |
| 1055a-I | Y*AG | S | O | S | S | S | O | OEt | OH |
| 1056a-I | Y*AG | S | S | S | S | S | O | OH | OH |
| 1057a-I | Y*AG | S | S | S | S | S | O | OMe | OH |
| 1058a-I | Y*AG | S | S | S | S | S | O | H | OH |
| 1059a-I | Y*AG | S | S | S | S | S | O | F | OH |
| 1060a-I | Y*AG | S | S | S | S | S | O | OEt | OH |
| 1061a-I | Y*AG | O | O | S | S | S | S | OH | OH |
| 1062a-I | Y*AG | O | O | S | S | S | S | OMe | OH |
| 1063a-I | Y*AG | O | O | S | S | S | S | H | OH |
| 1064a-I | Y*AG | O | O | S | S | S | S | F | OH |
| 1065a-I | Y*AG | O | O | S | S | S | S | OEt | OH |
| 1066a-I | Y*AG | S | O | S | S | S | S | OH | OH |
| 1067a-I | Y*AG | S | O | S | S | S | S | OMe | OH |
| 1068a-I | Y*AG | S | O | S | S | S | S | H | OH |
| 1069a-I | Y*AG | S | O | S | S | S | S | F | OH |
| 1070a-I | Y*AG | S | O | S | S | S | S | OEt | OH |
| 1071a-I | Y*AG | S | S | S | S | S | S | OH | OH |
| 1072a-I | Y*AG | S | S | S | S | S | S | OMe | OH |
| 1073a-I | Y*AG | S | S | S | S | S | S | H | OH |
| 1074a-I | Y*AG | S | S | S | S | S | S | F | OH |
| 1075a-I | Y*AG | S | S | S | S | S | S | OEt | OH |
| 1076a-I | Y*AG | O | O | O | S | S | S | OH | OH |
| 1077a-I | Y*AG | O | O | O | S | S | S | OMe | OH |
| 1078a-I | Y*AG | O | O | O | S | S | S | H | OH |
| 1079a-I | Y*AG | O | O | O | S | S | S | F | OH |
| 1080a-I | Y*AG | O | O | O | S | S | S | OEt | OH |
| 1081a-I | Y*AG | S | O | O | S | S | S | OH | OH |
| 1082a-I | Y*AG | S | O | O | S | S | S | OMe | OH |
| 1083a-I | Y*AG | S | O | O | S | S | S | H | OH |
| 1084a-I | Y*AG | S | O | O | S | S | S | F | OH |
| 1085a-I | Y*AG | S | O | O | S | S | S | OEt | OH |
| 1086a-I | Y*AG | S | S | O | S | S | S | OH | OH |
| 1087a-I | Y*AG | S | S | O | S | S | S | OMe | OH |

TABLE 3-continued

CapA Structures for mRNA preparation

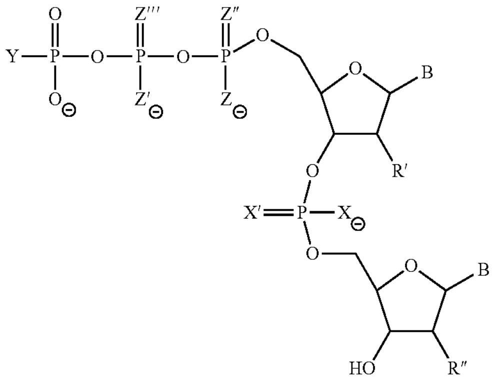

| Compound | Sequence | X | X' | Z | Z' | Z" | Z''' | R' | R" |
|---|---|---|---|---|---|---|---|---|---|
| 1088a-I | Y*AG | S | S | O | S | S | S | H | OH |
| 1089a-I | Y*AG | S | S | O | S | S | S | F | OH |
| 1090a-I | Y*AG | S | S | O | S | S | S | OEt | OH |
| 1091a-I | Y*AG | O | O | O | O | S | S | OH | OH |
| 1092a-I | Y*AG | O | O | O | O | S | S | OMe | OH |
| 1093a-I | Y*AG | O | O | O | O | S | S | H | OH |
| 1094a-I | Y*AG | O | O | O | O | S | S | F | OH |
| 1095a-I | Y*AG | O | O | O | O | S | S | OEt | OH |
| 1096a-I | Y*AG | S | O | O | O | S | S | OH | OH |
| 1097a-I | Y*AG | S | O | O | O | S | S | OMe | OH |
| 1098a-I | Y*AG | S | O | O | O | S | S | H | OH |
| 1099a-I | Y*AG | S | O | O | O | S | S | F | OH |
| 1100a-I | Y*AG | S | O | O | O | S | S | OEt | OH |
| 1101a-I | Y*AG | S | S | O | O | S | S | OH | OH |
| 1102a-I | Y*AG | S | S | O | O | S | S | OMe | OH |
| 1103a-I | Y*AG | S | S | O | O | S | S | H | OH |
| 1104a-I | Y*AG | S | S | O | O | S | S | F | OH |
| 1105a-I | Y*AG | S | S | O | O | S | S | OEt | OH |
| 1106a-I | Y*AG | O | O | O | O | O | S | OH | OH |
| 1107a-I | Y*AG | O | O | O | O | O | S | OMe | OH |
| 1108a-I | Y*AG | O | O | O | O | O | S | H | OH |
| 1109a-I | Y*AG | O | O | O | O | O | S | F | OH |
| 1110a-I | Y*AG | O | O | O | O | O | S | OEt | OH |
| 1111a-I | Y*AG | S | O | O | O | O | S | OH | OH |
| 1112a-I | Y*AG | S | O | O | O | O | S | OMe | OH |
| 1113a-I | Y*AG | S | O | O | O | O | S | H | OH |
| 1114a-I | Y*AG | S | O | O | O | O | S | F | OH |
| 1115a-I | Y*AG | S | O | O | O | O | S | OEt | OH |
| 1116a-I | Y*AG | S | S | O | O | O | S | OH | OH |
| 1117a-I | Y*AG | S | S | O | O | O | S | OMe | OH |
| 1118a-I | Y*AG | S | S | O | O | O | S | H | OH |
| 1119a-I | Y*AG | S | S | O | O | O | S | F | OH |
| 1120a-I | Y*AG | S | S | O | O | O | S | OEt | OH |
| 1121a-I | Y*AG | O | O | S | O | S | O | OH | OH |
| 1122a-I | Y*AG | O | O | S | O | S | O | OMe | OH |
| 1123a-I | Y*AG | O | O | S | O | S | O | H | OH |
| 1124a-I | Y*AG | O | O | S | O | S | O | F | OH |
| 1125a-I | Y*AG | O | O | S | O | S | O | OEt | OH |
| 1126a-I | Y*AG | S | O | S | O | S | O | OH | OH |
| 1127a-I | Y*AG | S | O | S | O | S | O | OMe | OH |
| 1128a-I | Y*AG | S | O | S | O | S | O | H | OH |
| 1129a-I | Y*AG | S | O | S | O | S | O | F | OH |
| 1130a-I | Y*AG | S | O | S | O | S | O | OEt | OH |
| 1131a-I | Y*AG | S | S | S | O | S | O | OH | OH |
| 1132a-I | Y*AG | S | S | S | O | S | O | OMe | OH |
| 1133a-I | Y*AG | S | S | S | O | S | O | H | OH |
| 1134a-I | Y*AG | S | S | S | O | S | O | F | OH |
| 1135a-I | Y*AG | S | S | S | 0 | S | O | OEt | OH |
| 1136a-I | Y*AG | O | O | O | S | O | S | OH | OH |
| 1137a-I | Y*AG | O | O | O | S | O | S | OMe | OH |
| 1138a-I | Y*AG | O | O | O | S | O | S | H | OH |
| 1139a-I | Y*AG | O | O | O | S | O | S | F | OH |
| 1140a-I | Y*AG | O | O | O | S | O | S | OEt | OH |
| 1141a-I | Y*AG | S | O | O | S | O | S | OH | OH |
| 1142a-I | Y*AG | S | O | O | S | O | S | OMe | OH |
| 1143a-I | Y*AG | S | O | O | S | O | S | H | OH |
| 1144a-I | Y*AG | S | O | O | S | O | S | F | OH |

TABLE 3-continued

CapA Structures for mRNA preparation

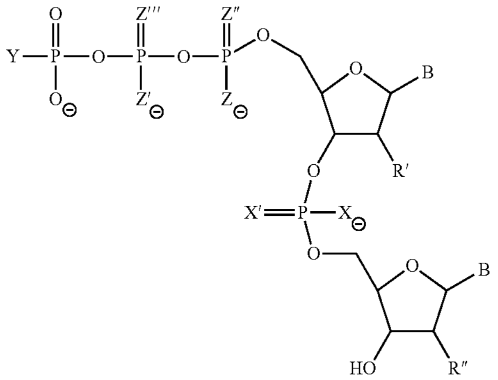

| Compound | Sequence | X | X' | Z | Z' | Z" | Z"' | R' | R" |
|---|---|---|---|---|---|---|---|---|---|
| 1145a-I | Y*AG | S | O | O | S | O | S | OEt | OH |
| 1146a-I | Y*AG | S | S | O | S | O | S | OH | OH |
| 1147a-I | Y*AG | S | S | O | S | O | S | OMe | OH |
| 1148a-I | Y*AG | S | S | O | S | O | S | H | OH |
| 1149a-I | Y*AG | S | S | O | S | O | S | F | OH |
| 1150a-I | Y*AG | S | S | O | S | O | S | OEt | OH |
| 1151a-I | Y*AG | O | O | O | O | O | O | OH | OMe |
| 1152a-I | Y*AG | O | O | O | O | O | O | OMe | OMe |
| 1153a-I | Y*AG | O | O | O | O | O | O | H | OMe |
| 1154a-I | Y*AG | O | O | O | O | O | O | F | OMe |
| 1155a-I | Y*AG | O | O | O | O | O | O | OEt | OMe |
| 1156a-I | Y*AG | S | O | O | O | O | O | OH | OMe |
| 1157a-I | Y*AG | S | O | O | O | O | O | OMe | OMe |
| 1158a-I | Y*AG | S | O | O | O | O | O | H | OMe |
| 1159a-I | Y*AG | S | O | O | O | O | O | F | OMe |
| 1160a-I | Y*AG | S | O | O | O | O | O | OEt | OMe |
| 1161a-I | Y*AG | S | S | O | O | O | O | OH | OMe |
| 1162a-I | Y*AG | S | S | O | O | O | O | OMe | OMe |
| 1163a-I | Y*AG | S | S | O | O | O | O | H | OMe |
| 1164a-I | Y*AG | S | S | O | O | O | O | F | OMe |
| 1165a-I | Y*AG | S | S | O | O | O | O | OEt | OMe |
| 1166a-I | Y*AG | O | O | S | O | O | O | OH | OMe |
| 1167a-I | Y*AG | O | O | S | O | O | O | OMe | OMe |
| 1168a-I | Y*AG | O | O | S | O | O | O | H | OMe |
| 1169a-I | Y*AG | O | O | S | O | O | O | F | OMe |
| 1170a-I | Y*AG | O | O | S | O | O | O | OEt | OMe |
| 1171a-I | Y*AG | S | O | S | O | O | O | OH | OMe |
| 1172a-I | Y*AG | S | O | S | O | O | O | OMe | OMe |
| 1173a-I | Y*AG | S | O | S | O | O | O | H | OMe |
| 1174a-I | Y*AG | S | O | S | O | O | O | F | OMe |
| 1175a-I | Y*AG | S | O | S | O | O | O | OEt | OMe |
| 1176a-I | Y*AG | S | S | S | O | O | O | OH | OMe |
| 1177a-I | Y*AG | S | S | S | O | O | O | OMe | OMe |
| 1178a-I | Y*AG | S | S | S | O | O | O | H | OMe |
| 1179a-I | Y*AG | S | S | S | O | O | O | F | OMe |
| 1180a-I | Y*AG | S | S | S | O | O | O | OEt | OMe |
| 1181a-I | Y*AG | O | O | S | S | O | O | OH | OMe |
| 1182a-I | Y*AG | O | O | S | S | O | O | OMe | OMe |
| 1183a-I | Y*AG | O | O | S | S | O | O | H | OMe |
| 1184a-I | Y*AG | O | O | S | S | O | O | F | OMe |
| 1185a-I | Y*AG | O | O | S | S | O | O | OEt | OMe |
| 1186a-I | Y*AG | S | O | S | S | O | O | OH | OMe |
| 1187a-I | Y*AG | S | O | S | S | O | O | OMe | OMe |
| 1188a-I | Y*AG | S | O | S | S | O | O | H | OMe |
| 1189a-I | Y*AG | S | O | S | S | O | O | F | OMe |
| 1190a-I | Y*AG | S | O | S | S | O | O | OEt | OMe |
| 1191a-I | Y*AG | S | S | S | S | O | O | OH | OMe |
| 1192a-I | Y*AG | S | S | S | S | O | O | OMe | OMe |
| 1193a-I | Y*AG | S | S | S | S | O | O | H | OMe |
| 1194a-I | Y*AG | S | S | S | S | O | O | F | OMe |
| 1195a-I | Y*AG | S | S | S | S | O | O | OEt | OMe |
| 1196a-I | Y*AG | O | O | S | S | S | O | OH | OMe |
| 1197a-I | Y*AG | O | O | S | S | S | O | OMe | OMe |
| 1198a-I | Y*AG | O | O | S | S | S | O | H | OMe |
| 1199a-I | Y*AG | O | O | S | S | S | O | F | OMe |
| 1200a-I | Y*AG | O | O | S | S | S | O | OEt | OMe |
| 1201a-I | Y*AG | S | O | S | S | S | O | OH | OMe |

TABLE 3-continued

CapA Structures for mRNA preparation

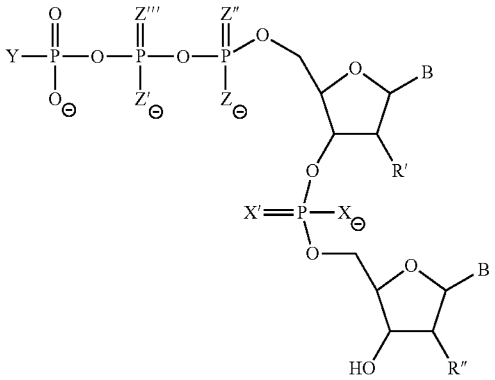

| Compound | Sequence | X | X' | Z | Z' | Z" | Z"' | R' | R" |
|---|---|---|---|---|---|---|---|---|---|
| 1202a-I | Y*AG | S | O | S | S | S | O | OMe | OMe |
| 1203a-I | Y*AG | S | O | S | S | S | O | H | OMe |
| 1204a-I | Y*AG | S | O | S | S | S | O | F | OMe |
| 1205a-I | Y*AG | S | O | S | S | S | O | OEt | OMe |
| 1206a-I | Y*AG | S | S | S | S | S | O | OH | OME |
| 1207a-I | Y*AG | S | S | S | S | S | O | OMe | OMe |
| 1208a-I | Y*AG | S | S | S | S | S | O | H | OMe |
| 1209a-I | Y*AG | S | S | S | S | S | O | F | OMe |
| 1210a-I | Y*AG | S | S | S | S | S | O | OEt | OMe |
| 1211a-I | Y*AG | O | O | S | S | S | S | OH | OMe |
| 1212a-I | Y*AG | O | O | S | S | S | S | OMe | OMe |
| 1213a-I | Y*AG | O | O | S | S | S | S | H | OMe |
| 1214a-I | Y*AG | O | O | S | S | S | S | F | OMe |
| 1215a-I | Y*AG | O | O | S | S | S | S | OEt | OMe |
| 1216a-I | Y*AG | S | O | S | S | S | S | OH | OMe |
| 1217a-I | Y*AG | S | O | S | S | S | S | OMe | OMe |
| 1218a-I | Y*AG | S | O | S | S | S | S | H | OMe |
| 1219a-I | Y*AG | S | O | S | S | S | S | F | OMe |
| 1220a-I | Y*AG | S | O | S | S | S | S | OEt | OMe |
| 1221a-I | Y*AG | S | S | S | S | S | S | OH | OMe |
| 1222a-I | Y*AG | S | S | S | S | S | S | OMe | OMe |
| 1223a-I | Y*AG | S | S | S | S | S | S | H | OMe |
| 1224a-I | Y*AG | S | S | S | S | S | S | F | OMe |
| 1225a-I | Y*AG | S | S | S | S | S | S | OEt | OMe |
| 1226a-I | Y*AG | O | O | O | S | S | S | OH | OMe |
| 1227a-I | Y*AG | O | O | O | S | S | S | OMe | OMe |
| 1228a-I | Y*AG | O | O | O | S | S | S | H | OMe |
| 1229a-I | Y*AG | O | O | O | S | S | S | F | OMe |
| 1230a-I | Y*AG | O | O | O | S | S | S | OEt | OMe |
| 1231a-I | Y*AG | S | O | O | S | S | S | OH | OMe |
| 1232a-I | Y*AG | S | O | O | S | S | S | OMe | OMe |
| 1233a-I | Y*AG | S | O | O | S | S | S | H | OMe |
| 1234a-I | Y*AG | S | O | O | S | S | S | F | OMe |
| 1235a-I | Y*AG | S | O | O | S | S | S | OEt | OMe |
| 1236a-I | Y*AG | S | S | O | S | S | S | OH | OMe |
| 1237a-I | Y*AG | S | S | O | S | S | S | OMe | OMe |
| 1238a-I | Y*AG | S | S | O | S | S | S | H | OMe |
| 1239a-I | Y*AG | S | S | O | S | S | S | F | OMe |
| 1240a-I | Y*AG | S | S | O | S | S | S | OEt | OMe |
| 1241a-I | Y*AG | O | O | O | O | S | S | OH | OMe |
| 1242a-I | Y*AG | O | O | O | O | S | S | OMe | OMe |
| 1243a-I | Y*AG | O | O | O | O | S | S | H | OMe |
| 1244a-I | Y*AG | O | O | O | O | S | S | F | OMe |
| 1245a-I | Y*AG | O | O | O | O | S | S | OEt | OMe |
| 1246a-I | Y*AG | S | O | O | O | S | S | OH | OMe |
| 1247a-I | Y*AG | S | O | O | O | S | S | OMe | OMe |
| 1248a-I | Y*AG | S | O | O | O | S | S | H | OMe |
| 1249a-I | Y*AG | S | O | O | O | S | S | F | OMe |
| 1250a-I | Y*AG | S | O | O | O | S | S | OEt | OMe |
| 1251a-I | Y*AG | S | S | O | O | S | S | OH | OMe |
| 1252a-I | Y*AG | S | S | O | O | S | S | OMe | OMe |
| 1253a-I | Y*AG | S | S | O | O | S | S | H | OMe |
| 1254a-I | Y*AG | S | S | O | O | S | S | F | OMe |
| 1255a-I | Y*AG | S | S | O | O | S | S | OEt | OMe |
| 1256a-I | Y*AG | O | O | O | O | O | S | OH | OMe |
| 1257a-I | Y*AG | O | O | O | O | O | S | OMe | OMe |
| 1258a-I | Y*AG | O | O | O | O | O | S | H | OMe |

TABLE 3-continued

CapA Structures for mRNA preparation

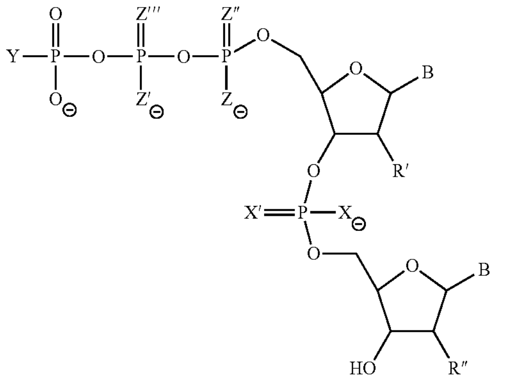

| Compound | Sequence | X | X' | Z | Z' | Z'' | Z''' | R' | R'' |
|---|---|---|---|---|---|---|---|---|---|
| 1259a-I | Y*AG | O | O | O | O | O | S | F | OMe |
| 1260a-I | Y*AG | O | O | O | O | O | S | OEt | OMe |
| 1261a-I | Y*AG | S | O | O | O | O | S | OH | OMe |
| 1262a-I | Y*AG | S | O | O | O | O | S | OMe | OMe |
| 1263a-I | Y*AG | S | O | O | O | O | S | H | OMe |
| 1264a-I | Y*AG | S | O | O | O | O | S | F | OMe |
| 1265a-I | Y*AG | S | O | O | O | O | S | OEt | OMe |
| 1266a-I | Y*AG | S | S | O | O | O | S | OH | OMe |
| 1267a-I | Y*AG | S | S | O | O | O | S | OMe | OMe |
| 1268a-I | Y*AG | S | S | O | O | O | S | H | OMe |
| 1269a-I | Y*AG | S | S | O | O | O | S | F | OMe |
| 1270a-I | Y*AG | S | S | O | O | O | S | OEt | OMe |
| 1271a-I | Y*AG | O | O | S | O | S | O | OH | OMe |
| 1272a-I | Y*AG | O | O | S | O | S | O | OMe | OMe |
| 1273a-I | Y*AG | O | O | S | O | S | O | H | OMe |
| 1274a-I | Y*AG | O | O | S | O | S | O | F | OMe |
| 1275a-I | Y*AG | O | O | S | O | S | O | OEt | OMe |
| 1276a-I | Y*AG | S | O | S | O | S | O | OH | OMe |
| 1277a-I | Y*AG | S | O | S | O | S | O | OMe | OMe |
| 1278a-I | Y*AG | S | O | S | O | S | O | H | OMe |
| 1279a-I | Y*AG | S | O | S | O | S | O | F | OMe |
| 1280a-I | Y*AG | S | O | S | O | S | O | OEt | OMe |
| 1281a-I | Y*AG | S | S | S | O | S | O | OH | OMe |
| 1282a-I | Y*AG | S | S | S | O | S | O | OMe | OMe |
| 1283a-I | Y*AG | S | S | S | O | S | O | H | OMe |
| 1284a-I | Y*AG | S | S | S | O | S | O | F | OMe |
| 1285a-I | Y*AG | S | S | S | O | S | O | OEt | OMe |
| 1286a-I | Y*AG | O | O | O | S | O | S | OH | OMe |
| 1287a-I | Y*AG | O | O | O | S | O | S | OMe | OMe |
| 1288a-I | Y*AG | O | O | O | S | O | S | H | OMe |
| 1289a-I | Y*AG | O | O | O | S | O | S | F | OMe |
| 1290a-I | Y*AG | O | O | O | S | O | S | OEt | OMe |
| 1291a-I | Y*AG | S | O | O | S | O | S | OH | OMe |
| 1292a-I | Y*AG | S | O | O | S | O | S | OMe | OMe |
| 1293a-I | Y*AG | S | O | O | S | O | S | H | OMe |
| 1294a-I | Y*AG | S | O | O | S | O | S | F | OMe |
| 1295a-I | Y*AG | S | O | O | S | O | S | OEt | OMe |
| 1296a-I | Y*AG | S | S | O | S | O | S | OH | OMe |
| 1297a-I | Y*AG | S | S | O | S | O | S | OMe | OMe |
| 1298a-I | Y*AG | S | S | O | S | O | S | H | OMe |
| 1299a-I | Y*AG | S | S | O | S | O | S | F | OMe |
| 1300a-I | Y*AG | S | S | O | S | O | S | OEt | OMe |
| 1301a-I | Y*AA | O | O | O | O | O | O | OH | OH |
| 1302a-I | Y*AA | O | O | O | O | O | O | OMe | OH |
| 1303a-I | Y*AA | O | O | O | O | O | O | H | OH |
| 1304a-I | Y*AA | O | O | O | O | O | O | F | OH |
| 1305a-I | Y*AA | O | O | O | O | O | O | OEt | OH |
| 1306a-I | Y*AA | S | O | O | O | O | O | OH | OH |
| 1307a-I | Y*AA | S | O | O | O | O | O | OMe | OH |
| 1308a-I | Y*AA | S | O | O | O | O | O | H | OH |
| 1309a-I | Y*AA | S | O | O | O | O | O | F | OH |
| 1310a-I | Y*AA | S | O | O | O | O | O | OEt | OH |
| 1311a-I | Y*AA | S | S | O | O | O | O | OH | OH |
| 1312a-I | Y*AA | S | S | O | O | O | O | OMe | OH |
| 1313a-I | Y*AA | S | S | O | O | O | O | H | OH |
| 1314a-I | Y*AA | S | S | O | O | O | O | F | OH |
| 1315a-I | Y*AA | S | S | O | O | O | O | OEt | OH |

TABLE 3-continued

CapA Structures for mRNA preparation

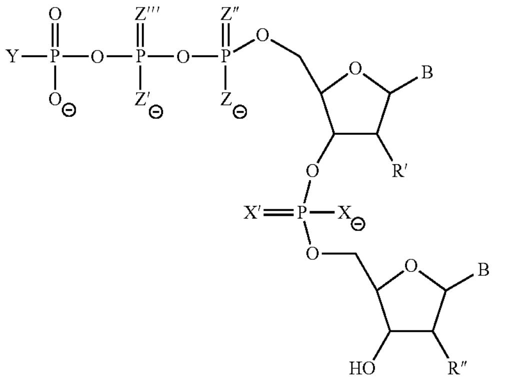

| Compound | Sequence | X | X' | Z | Z' | Z'' | Z''' | R' | R'' |
|---|---|---|---|---|---|---|---|---|---|
| 1316a-I | Y*AA | O | O | S | O | O | O | OH | OH |
| 1317a-I | Y*AA | O | O | S | O | O | O | OMe | OH |
| 1318a-I | Y*AA | O | O | S | O | O | O | H | OH |
| 1319a-I | Y*AA | O | O | S | O | O | O | F | OH |
| 1320a-I | Y*AA | O | O | S | O | O | O | OEt | OH |
| 1321a-I | Y*AA | S | O | S | O | O | O | OH | OH |
| 1322a-I | Y*AA | S | O | S | O | O | O | OMe | OH |
| 1323a-I | Y*AA | S | O | S | O | O | O | H | OH |
| 1324a-I | Y*AA | S | O | S | O | O | O | F | OH |
| 1325a-I | Y*AA | S | O | S | O | O | O | OEt | OH |
| 1326a-I | Y*AA | S | S | S | O | O | O | OH | OH |
| 1327a-I | Y*AA | S | S | S | O | O | O | OMe | OH |
| 1328a-I | Y*AA | S | S | S | O | O | O | H | OH |
| 1329a-I | Y*AA | S | S | S | O | O | O | F | OH |
| 1330a-I | Y*AA | S | S | S | O | O | O | OEt | OH |
| 1331a-I | Y*AA | O | O | S | S | O | O | OH | OH |
| 1332a-I | Y*AA | O | O | S | S | O | O | OMe | OH |
| 1333a-I | Y*AA | O | O | S | S | O | O | H | OH |
| 1334a-I | Y*AA | O | O | S | S | O | O | F | OH |
| 1335a-I | Y*AA | O | O | S | S | O | O | OEt | OH |
| 1336a-I | Y*AA | S | O | S | S | O | O | OH | OH |
| 1337a-I | Y*AA | S | O | S | S | O | O | OMe | OH |
| 1338a-I | Y*AA | S | O | S | S | O | O | H | OH |
| 1339a-I | Y*AA | S | O | S | S | O | O | F | OH |
| 1340a-I | Y*AA | S | O | S | S | O | O | OEt | OH |
| 1341a-I | Y*AA | S | S | S | S | O | O | OH | OH |
| 1342a-I | Y*AA | S | S | S | S | O | O | OMe | OH |
| 1343a-I | Y*AA | S | S | S | S | O | O | H | OH |
| 1344a-I | Y*AA | S | S | S | S | O | O | F | OH |
| 1345a-I | Y*AA | S | S | S | S | O | O | OEt | OH |
| 1346a-I | Y*AA | O | O | S | S | S | O | OH | OH |
| 1347a-I | Y*AA | O | O | S | S | S | O | OMe | OH |
| 1348a-I | Y*AA | O | O | S | S | S | O | H | OH |
| 1349a-I | Y*AA | O | O | S | S | S | O | F | OH |
| 1350a-I | Y*AA | O | O | S | S | S | O | OEt | OH |
| 1351a-I | Y*AA | S | O | S | S | S | O | OH | OH |
| 1352a-I | Y*AA | S | O | S | S | S | O | OMe | OH |
| 1353a-I | Y*AA | S | O | S | S | S | O | H | OH |
| 1354a-I | Y*AA | S | O | S | S | S | O | F | OH |
| 1355a-I | Y*AA | S | O | S | S | S | O | OEt | OH |
| 1356a-I | Y*AA | S | S | S | S | S | O | OH | OH |
| 1357a-I | Y*AA | S | S | S | S | S | O | OMe | OH |
| 1358a-I | Y*AA | S | S | S | S | S | O | H | OH |
| 1359a-I | Y*AA | S | S | S | S | S | O | F | OH |
| 1360a-I | Y*AA | S | S | S | S | S | O | OEt | OH |
| 1361a-I | Y*AA | O | O | S | S | S | S | OH | OH |
| 1362a-I | Y*AA | O | O | S | S | S | S | OMe | OH |
| 1363a-I | Y*AA | O | O | S | S | S | S | H | OH |
| 1364a-I | Y*AA | O | O | S | S | S | S | F | OH |
| 1365a-I | Y*AA | O | O | S | S | S | S | OEt | OH |
| 1366a-I | Y*AA | S | O | S | S | S | S | OH | OH |
| 1367a-I | Y*AA | S | O | S | S | S | S | OMe | OH |
| 1368a-I | Y*AA | S | O | S | S | S | S | H | OH |
| 1369a-I | Y*AA | S | O | S | S | S | S | F | OH |
| 1370a-I | Y*AA | S | O | S | S | S | S | OEt | OH |
| 1371a-I | Y*AA | S | S | S | S | S | S | OH | OH |
| 1372a-I | Y*AA | S | S | S | S | S | S | OMe | OH |

TABLE 3-continued

CapA Structures for mRNA preparation

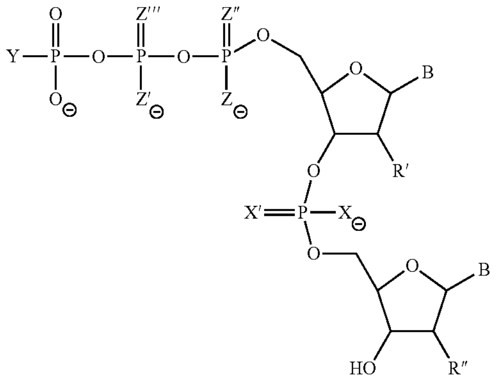

| Compound | Sequence | X | X' | Z | Z' | Z" | Z'" | R' | R" |
|---|---|---|---|---|---|---|---|---|---|
| 1373a-I | Y*AA | S | S | S | S | S | S | H | OH |
| 1374a-I | Y*AA | S | S | S | S | S | S | F | OH |
| 1375a-I | Y*AA | S | S | S | S | S | S | OEt | OH |
| 1376a-I | Y*AA | O | O | O | S | S | S | OH | OH |
| 1377a-I | Y*AA | O | O | O | S | S | S | OMe | OH |
| 1378a-I | Y*AA | O | O | O | S | S | S | H | OH |
| 1379a-I | Y*AA | O | O | O | S | S | S | F | OH |
| 1380a-I | Y*AA | O | O | O | S | S | S | OEt | OH |
| 1381a-I | Y*AA | S | O | O | S | S | S | OH | OH |
| 1382a-I | Y*AA | S | O | O | S | S | S | OMe | OH |
| 1383a-I | Y*AA | S | O | O | S | S | S | H | OH |
| 1384a-I | Y*AA | S | O | O | S | S | S | F | OH |
| 1385a-I | Y*AA | S | O | O | S | S | S | OEt | OH |
| 1386a-I | Y*AA | S | S | O | S | S | S | OH | OH |
| 1387a-I | Y*AA | S | S | O | S | S | S | OMe | OH |
| 1388a-I | Y*AA | S | S | O | S | S | S | H | OH |
| 1389a-I | Y*AA | S | S | O | S | S | S | F | OH |
| 1390a-I | Y*AA | S | S | O | S | S | S | OEt | OH |
| 1391a-I | Y*AA | O | O | O | O | S | S | OH | OH |
| 1392a-I | Y*AA | O | O | O | O | S | S | OMe | OH |
| 1393a-I | Y*AA | O | O | O | O | S | S | H | OH |
| 1394a-I | Y*AA | O | O | O | O | S | S | F | OH |
| 1395a-I | Y*AA | O | O | O | O | S | S | OEt | OH |
| 1396a-I | Y*AA | S | O | O | O | S | S | OH | OH |
| 1397a-I | Y*AA | S | O | O | O | S | S | OMe | OH |
| 1398a-I | Y*AA | S | O | O | O | S | S | H | OH |
| 1399a-I | Y*AA | S | O | O | O | S | S | F | OH |
| 1400a-I | Y*AA | S | O | O | O | S | S | OEt | OH |
| 1401a-I | Y*AA | S | S | O | O | S | S | OH | OH |
| 1402a-I | Y*AA | S | S | O | O | S | S | OMe | OH |
| 1403a-I | Y*AA | S | S | O | O | S | S | H | OH |
| 1404a-I | Y*AA | S | S | O | O | S | S | F | OH |
| 1405a-I | Y*AA | S | S | O | O | S | S | OEt | OH |
| 1406a-I | Y*AA | O | O | O | O | O | S | OH | OH |
| 1407a-I | Y*AA | O | O | O | O | O | S | OMe | OH |
| 1408a-I | Y*AA | O | O | O | O | O | S | H | OH |
| 1409a-I | Y*AA | O | O | O | O | O | S | F | OH |
| 1410a-I | Y*AA | O | O | O | O | O | S | OEt | OH |
| 1411a-I | Y*AA. | S | O | O | O | O | S | OH | OH |
| 1412a-I | Y*AA | S | O | O | O | O | S | OMe | OH |
| 1413a-I | Y*AA | S | O | O | O | O | S | H | OH |
| 1414a-I | Y*AA | S | O | O | O | O | S | F | OH |
| 1415a-I | Y*AA | S | O | O | O | O | S | OEt | OH |
| 1416a-I | Y*AA | S | S | O | O | O | S | OH | OH |
| 1417a-I | Y*AA | S | S | O | O | O | S | OMe | OH |
| 1418a-I | Y*AA | S | S | O | O | O | S | H | OH |
| 1419a-I | Y*AA | S | S | O | O | O | S | F | OH |
| 1420a-I | Y*AA | S | S | O | O | O | S | OEt | OH |
| 1421a-I | Y*AA | O | O | S | O | S | O | OH | OH |
| 1422a-I | Y*AA | O | O | S | O | S | O | OMe | OH |
| 1423a-I | Y*AA | O | O | S | O | S | O | H | OH |
| 1424a-I | Y*AA | O | O | S | O | S | O | F | OH |
| 1425a-I | Y*AA | O | O | S | O | S | O | OEt | OH |
| 1426a-I | Y*AA | S | O | S | O | S | O | OH | OH |
| 1427a-I | Y*AA | S | O | S | O | S | O | OMe | OH |
| 1428a-I | Y*AA | S | O | S | O | S | O | H | OH |
| 1429a-I | Y*AA | S | O | S | O | S | O | F | OH |

TABLE 3-continued

CapA Structures for mRNA preparation

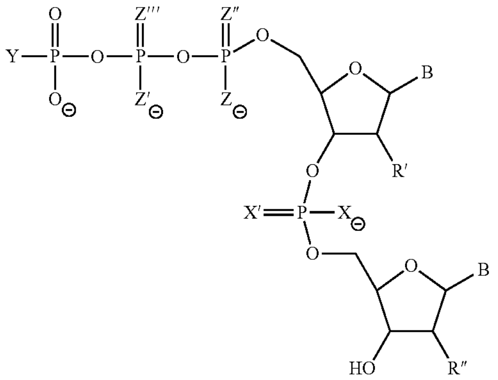

| Compound | Sequence | X | X' | Z | Z' | Z" | Z'" | R' | R" |
|---|---|---|---|---|---|---|---|---|---|
| 1430a-I | Y*AA | S | O | S | O | S | O | OEt | OH |
| 1431a-I | Y*AA | S | S | S | O | S | O | OH | OH |
| 1432a-I | Y*AA | S | S | S | O | S | O | OMe | OH |
| 1433a-I | Y*AA | S | S | S | O | S | O | H | OH |
| 1434a-I | Y*AA | S | S | S | O | S | O | F | OH |
| 1435a-I | Y*AA | S | S | S | O | S | O | OEt | OH |
| 1436a-I | Y*AA | O | O | O | S | O | S | OH | OH |
| 1437a-I | Y*AA | O | O | O | S | O | S | OMe | OH |
| 1438a-I | Y*AA | O | O | O | S | O | S | H | OH |
| 1439a-I | Y*AA | O | O | O | S | O | S | F | OH |
| 1440a-I | Y*AA | O | O | O | S | O | S | OEt | OH |
| 1441a-I | Y*AA | S | O | O | S | O | S | OH | OH |
| 1442a-I | Y*AA | S | O | O | S | O | S | OMe | OH |
| 1443a-I | Y*AA | S | O | O | S | O | S | H | OH |
| 1444a-I | Y*AA | S | O | O | S | O | S | F | OH |
| 1445a-I | Y*AA | S | O | O | S | O | S | OEt | OH |
| 1446a-I | Y*AA | S | S | O | S | O | S | OH | OH |
| 1447a-I | Y*AA | S | S | O | S | O | S | OMe | OH |
| 1448a-I | Y*AA | S | S | O | S | O | S | H | OH |
| 1449a-I | Y*AA | S | S | O | S | O | S | F | OH |
| 1450a-I | Y*AA | S | S | O | S | O | S | OEt | OH |
| 1451a-I | Y*AA | O | O | O | O | O | O | OH | OMe |
| 1452a-I | Y*AA | O | O | O | O | O | O | OMe | OMe |
| 1453a-I | Y*AA | O | O | O | O | O | O | H | OMe |
| 1454a-I | Y*AA | O | O | O | O | O | O | F | OMe |
| 1455a-I | Y*AA | O | O | O | O | O | O | OEt | OMe |
| 1456a-I | Y*AA | S | O | O | O | O | O | OH | OMe |
| 1457a-I | Y*AA | S | O | O | O | O | O | OMe | OMe |
| 1458a-I | Y*AA | S | O | O | O | O | O | H | OMe |
| 1459a-I | Y*AA | S | O | O | O | O | O | F | OMe |
| 1460a-I | Y*AA | S | O | O | O | O | O | OEt | OMe |
| 1461a-I | Y*AA | S | S | O | O | O | O | OH | OMe |
| 1462a-I | Y*AA | S | S | O | O | O | O | OMe | OMe |
| 1463a-I | Y*AA | S | S | O | O | O | O | H | OMe |
| 1464a-I | Y*AA | S | S | O | O | O | O | F | OMe |
| 1465a-I | Y*AA | S | S | O | O | O | O | OEt | OMe |
| 1466a-I | Y*AA | O | O | S | O | O | O | OH | OMe |
| 1467a-I | Y*AA | O | O | S | O | O | O | OMe | OMe |
| 1468a-I | Y*AA | O | O | S | O | O | O | H | OMe |
| 1469a-I | Y*AA | O | O | S | O | O | O | F | OMe |
| 1470a-I | Y*AA | O | O | S | O | O | O | OEt | OMe |
| 1471a-I | Y*AA | S | O | S | O | O | O | OH | OMe |
| 1472a-I | Y*AA | S | O | S | O | O | O | OMe | OMe |
| 1473a-I | Y*AA | S | O | S | O | O | O | H | OMe |
| 1474a-I | Y*AA | S | O | S | O | O | O | F | OMe |
| 1475a-I | Y*AA | S | O | S | O | O | O | OEt | OMe |
| 1476a-I | Y*AA | S | S | S | O | O | O | OH | OMe |
| 1477a-I | Y*AA | S | S | S | O | O | O | OMe | OMe |
| 1478a-I | Y*AA | S | S | S | O | O | O | H | OMe |
| 1479a-I | Y*AA | S | S | S | O | O | O | F | OMe |
| 1480a-I | Y*AA | S | S | S | O | O | O | OEt | OMe |
| 1481a-I | Y*AA | O | O | S | S | O | O | OH | OMe |
| 1482a-I | Y*AA | O | O | S | S | O | O | OMe | OMe |
| 1483a-I | Y*AA | O | O | S | S | O | O | H | OMe |
| 1484a-I | Y*AA | O | O | S | S | O | O | F | OMe |
| 1485a-I | Y*AA | O | O | S | S | O | O | OEt | OMe |
| 1486a-I | Y*AA | S | O | S | S | O | O | OH | OMe |

TABLE 3-continued

CapA Structures for mRNA preparation

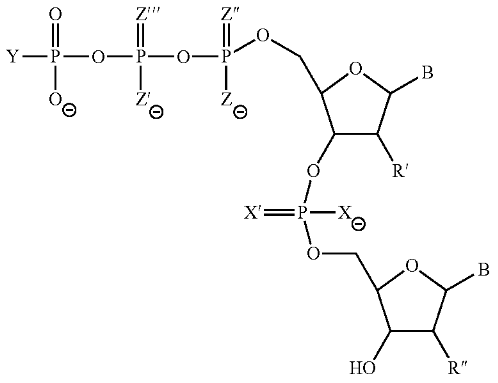

| Compound | Sequence | X | X' | Z | Z' | Z" | Z"' | R' | R" |
|---|---|---|---|---|---|---|---|---|---|
| 1487a-I | Y*AA | S | O | S | S | O | O | OMe | OMe |
| 1488a-I | Y*AA | S | O | S | S | O | O | H | OMe |
| 1489a-I | Y*AA | S | O | S | S | O | O | F | OMe |
| 1490a-I | Y*AA | S | O | S | S | O | O | OEt | OMe |
| 1491a-I | Y*AA | S | S | S | S | O | O | OH | OMe |
| 1492a-I | Y*AA | S | S | S | S | O | O | OMe | OMe |
| 1493a-I | Y*AA | S | S | S | S | O | O | H | OMe |
| 1494a-I | Y*AA | S | S | S | S | O | O | F | OMe |
| 1495a-I | Y*AA | S | S | S | S | O | O | OEt | OMe |
| 1496a-I | Y*AA | O | O | S | S | S | O | OH | OMe |
| 1497a-I | Y*AA | O | O | S | S | S | O | OMe | OMe |
| 1498a-I | Y*AA | O | O | S | S | S | O | H | OMe |
| 1499a-I | Y*AA | O | O | S | S | S | O | F | OMe |
| 1500a-I | Y*AA | O | O | S | S | S | O | OEt | OMe |
| 1501a-I | Y*AA | S | O | S | S | S | O | OH | OMe |
| 1502a-I | Y*AA | S | O | S | S | S | O | OMe | OMe |
| 1503a-I | Y*AA | S | O | S | S | S | O | H | OMe |
| 1504a-I | Y*AA | S | O | S | S | S | O | F | OMe |
| 1505a-I | Y*AA | S | O | S | S | S | O | OEt | OMe |
| 1506a-I | Y*AA | S | S | S | S | S | O | OH | OMe |
| 1507a-I | Y*AA | S | S | S | S | S | O | OMe | OMe |
| 1508a-I | Y*AA | S | S | S | S | S | O | H | OMe |
| 1509a-I | Y*AA | S | S | S | S | S | O | F | OMe |
| 1510a-I | Y*AA | S | S | S | S | S | O | OEt | OMe |
| 1511a-I | Y*AA | O | O | S | S | S | S | OH | OMe |
| 1512a-I | Y*AA | O | O | S | S | S | S | OMe | OMe |
| 1513a-I | Y*AA | O | O | S | S | S | S | H | OMe |
| 1514a-I | Y*AA | O | O | S | S | S | S | F | OMe |
| 1515a-I | Y*AA | O | O | S | S | S | S | OEt | OMe |
| 1516a-I | Y*AA | S | O | S | S | S | S | OH | OMe |
| 1517a-I | Y*AA | S | O | S | S | S | S | OMe | OMe |
| 1518a-I | Y*AA | S | O | S | S | S | S | H | OMe |
| 1519a-I | Y*AA | S | O | S | S | S | S | F | OMe |
| 1520a-I | Y*AA | S | O | S | S | S | S | OEt | OMe |
| 1521a-I | Y*AA | S | S | S | S | S | S | OH | OMe |
| 1522a-I | Y*AA | S | 5 | S | S | S | S | OMe | OMe |
| 1523a-I | Y*AA | S | S | S | S | S | S | H | OMe |
| 1524a-I | Y*AA | S | S | S | S | S | S | F | OMe |
| 1525a-I | Y*AA | S | S | S | S | S | S | OEt | OMe |
| 1526a-I | Y*AA | O | O | O | S | S | S | OH | OMe |
| 1527a-I | Y*AA | O | O | O | S | S | S | OMe | OMe |
| 1528a-I | Y*AA | O | O | O | S | S | S | H | OMe |
| 1529a-I | Y*AA | O | O | O | S | S | S | F | OMe |
| 1530a-I | Y*AA | O | O | O | S | S | S | OEt | OMe |
| 1531a-I | Y*AA | S | O | O | S | S | S | OH | OMe |
| 1532a-I | Y*AA | S | O | O | S | S | S | OMe | OMe |
| 1533a-I | Y*AA | S | O | O | S | S | S | H | OMe |
| 1534a-I | Y*AA | S | O | O | S | S | S | F | OMe |
| 1535a-I | Y*AA | S | O | O | S | S | S | OEt | OMe |
| 1536a-I | Y*AA | S | S | O | S | S | S | OH | OMe |
| 1537a-I | Y*AA | S | S | O | S | S | S | OMe | OMe |
| 1538a-I | Y*AA | S | S | O | S | S | S | H | OMe |
| 1539a-I | Y*AA | S | S | O | S | S | S | F | OMe |
| 1540a-I | Y*AA | S | S | O | S | S | S | OEt | OMe |
| 1541a-I | Y*AA | O | O | O | O | S | S | OH | OMe |
| 1542a-I | Y*AA | O | O | O | O | S | S | OMe | OMe |
| 1543a-I | Y*AA | O | O | O | O | S | S | H | OMe |

TABLE 3-continued

CapA Structures for mRNA preparation

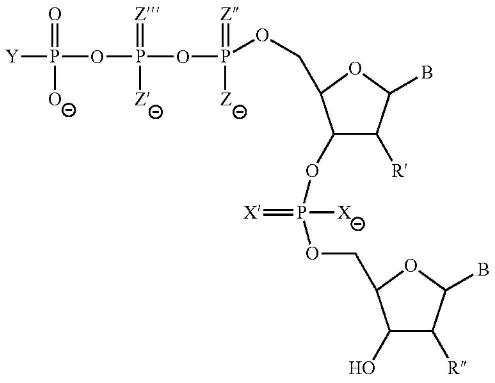

| Compound | Sequence | X | X' | Z | Z' | Z" | Z"' | R' | R" |
|---|---|---|---|---|---|---|---|---|---|
| 1544a-I | Y*AA | O | O | O | O | S | S | F | OMe |
| 1545a-I | Y*AA | O | O | O | O | S | S | OEt | OMe |
| 1546a-I | Y*AA | S | O | O | O | S | S | OH | OMe |
| 1547a-I | Y*AA | S | O | O | O | S | S | OMe | OMe |
| 1548a-I | Y*AA | S | O | O | O | S | S | H | OMe |
| 1549a-I | Y*AA | S | O | O | O | S | S | F | OMe |
| 1550a-I | Y*AA | S | O | O | O | S | S | OEt | OMe |
| 1551a-I | Y*AA | S | S | O | O | S | S | OH | OMe |
| 1552a-I | Y*AA | S | S | O | O | S | S | OMe | OMe |
| 1553a-I | Y*AA | S | S | O | O | S | S | H | OMe |
| 1554a-I | Y*AA | S | S | O | O | S | S | F | OMe |
| 1555a-I | Y*AA | S | S | O | O | S | S | OEt | OMe |
| 1556a-I | Y*AA | O | O | O | O | O | S | OH | OMe |
| 1557a-I | Y*AA | O | O | O | O | O | S | OMe | OMe |
| 1558a-I | Y*AA | O | O | O | O | O | S | H | OMe |
| 1559a-I | Y*AA | O | O | O | O | O | S | F | OMe |
| 1560a-I | Y*AA | O | O | O | O | O | S | OEt | OMe |
| 1561a-I | Y*AA | S | O | O | O | O | S | OH | OMe |
| 1562a-I | Y*AA | S | O | O | O | O | S | OMe | OMe |
| 1563a-I | Y*AA | S | O | O | O | O | S | H | OMe |
| 1564a-I | Y*AA | S | O | O | O | O | S | F | OMe |
| 1565a-I | Y*AA | S | O | O | O | O | S | OEt | OMe |
| 1566a-I | Y*AA | S | S | O | O | O | S | OH | OMe |
| 1567a-I | Y*AA | S | S | O | O | O | S | OMe | OMe |
| 1568a-I | Y*AA | S | S | O | O | O | S | H | OMe |
| 1569a-I | Y*AA | S | S | O | O | O | S | F | OMe |
| 1570a-I | Y*AA | S | S | O | O | O | S | OEt | OMe |
| 1571a-I | Y*AA | O | O | S | O | S | O | OH | OMe |
| 1572a-I | Y*AA | O | O | S | O | S | O | OMe | OMe |
| 1573a-I | Y*AA | O | O | S | O | S | O | H | OMe |
| 1574a-I | Y*AA | O | O | S | O | S | O | F | OMe |
| 1575a-I | Y*AA | O | O | S | O | S | O | OEt | OMe |
| 1576a-I | Y*AA | S | O | S | O | S | O | OH | OMe |
| 1577a-I | Y*AA | S | O | S | O | S | O | OMe | OMe |
| 1578a-I | Y*AA | S | O | S | O | S | O | H | OMe |
| 1579a-I | Y*AA | S | O | S | O | S | O | F | OMe |
| 1580a-I | Y*AA | S | O | S | O | S | O | OEt | OMe |
| 1581a-I | Y*AA | S | S | S | O | S | O | OH | OMe |
| 1582a-I | Y*AA | S | S | S | O | S | O | OMe | OMe |
| 1583a-I | Y*AA | S | S | S | O | S | O | H | OMe |
| 1584a-I | Y*AA | S | S | S | O | S | O | F | OMe |
| 1585a-I | Y*AA | S | S | S | O | S | O | OEt | OMe |
| 1586a-I | Y*AA | O | O | O | S | O | S | OH | OMe |
| 1587a-I | Y*AA | O | O | O | S | O | S | OMe | OMe |
| 1588a-I | Y*AA | O | O | O | S | O | S | H | OMe |
| 1589a-I | Y*AA | O | O | O | S | O | S | F | OMe |
| 1590a-I | Y*AA | O | O | O | S | O | S | OEt | OMe |
| 1591a-I | Y*AA | S | O | O | S | O | S | OH | OMe |
| 1592a-I | Y*AA | S | O | O | S | O | S | OMe | OMe |
| 1593a-I | Y*AA | S | O | O | S | O | S | H | OMe |
| 1594a-I | Y*AA | S | O | O | S | O | S | F | OMe |
| 1595a-I | Y*AA | S | O | O | S | O | S | OEt | OMe |
| 1596a-I | Y*AA | S | S | O | S | O | S | OH | OMe |
| 1597a-I | Y*AA | S | S | O | S | O | S | OMe | OMe |
| 1598a-I | Y*AA | S | S | O | S | O | S | H | OMe |
| 1599a-I | Y*AA | S | S | O | S | O | S | F | OMe |
| 1600a-I | Y*AA | S | S | O | S | O | S | OEt | OMe |

TABLE 3-continued

CapA Structures for mRNA preparation

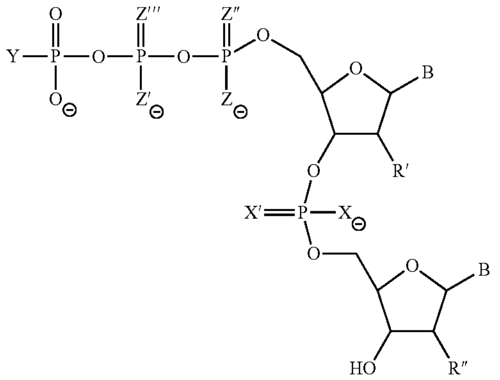

| Compound | Sequence | X | X' | Z | Z' | Z" | Z'" | R' | R" |
|---|---|---|---|---|---|---|---|---|---|
| 1601a-I | Y*AC | O | O | O | O | O | O | OH | OH |
| 1602a-I | Y*AC | O | O | O | O | O | O | OMe | OH |
| 1603a-I | Y*AC | O | O | O | O | O | O | H | OH |
| 1604a-I | Y*AC | O | O | O | O | O | O | F | OH |
| 1605a-I | Y*AC | O | O | O | O | O | O | OEt | OH |
| 1606a-I | Y*AC | S | O | O | O | O | O | OH | OH |
| 1607a-I | Y*AC | S | O | O | O | O | O | OMe | OH |
| 1608a-I | Y*AC | S | O | O | O | O | O | H | OH |
| 1609a-I | Y*AC | S | O | O | O | O | O | F | OH |
| 1610a-I | Y*AC | S | O | O | O | O | O | OEt | OH |
| 1611a-I | Y*AC | S | S | O | O | O | O | OH | OH |
| 1612a-I | Y*AC | S | S | O | O | O | O | OMe | OH |
| 1613a-I | Y*AC | S | S | O | O | O | O | H | OH |
| 1614a-I | Y*AC | S | S | O | O | O | O | F | OH |
| 1615a-I | Y*AC | S | S | O | O | O | O | OEt | OH |
| 1616a-I | Y*AC | O | O | S | O | O | O | OH | OH |
| 1617a-I | Y*AC | O | O | S | O | O | O | OMe | OH |
| 1618a-I | Y*AC | O | O | S | O | O | O | H | OH |
| 1619a-I | Y*AC | O | O | S | O | O | O | F | OH |
| 1620a-I | Y*AC | O | O | S | O | O | O | OEt | OH |
| 1621a-I | Y*AC | S | O | S | O | O | O | OH | OH |
| 1622a-I | Y*AC | S | O | S | O | O | O | OMe | OH |
| 1623a-I | Y*AC | S | O | S | O | O | O | H | OH |
| 1624a-I | Y*AC | S | O | S | O | O | O | F | OH |
| 1625a-I | Y*AC | S | O | S | O | O | O | OEt | OH |
| 1626a-I | Y*AC | S | S | S | O | O | O | OH | OH |
| 1627a-I | Y*AC | S | S | S | O | O | O | OMe | OH |
| 1628a-I | Y*AC | S | S | S | O | O | O | H | OH |
| 1629a-I | Y*AC | S | S | S | O | O | O | F | OH |
| 1630a-I | Y*AC | S | S | S | O | O | O | OEt | OH |
| 1631a-I | Y*AC | O | O | S | S | O | O | OH | OH |
| 1632a-I | Y*AC | O | O | S | S | O | O | OMe | OH |
| 1633a-I | Y*AC | O | O | S | S | O | O | H | OH |
| 1634a-I | Y*AC | O | O | S | S | O | O | F | OH |
| 1635a-I | Y*AC | O | O | S | S | O | O | OEt | OH |
| 1636a-I | Y*AC | S | O | S | S | O | O | OH | OH |
| 1637a-I | Y*AC | S | O | S | S | O | O | OMe | OH |
| 1638a-I | Y*AC | S | O | S | S | O | O | H | OH |
| 1639a-I | Y*AC | S | O | S | S | O | O | F | OH |
| 1640a-I | Y*AC | S | O | S | S | O | O | OEt | OH |
| 1641a-I | Y*AC | S | S | S | S | O | O | OH | OH |
| 1642a-I | Y*AC | S | S | S | S | O | O | OMe | OH |
| 1643a-I | Y*AC | S | S | S | S | O | O | H | OH |
| 1644a-I | Y*AC | S | S | S | S | O | O | F | OH |
| 1645a-I | Y*AC | S | S | S | S | O | O | OEt | OH |
| 1646a-I | Y*AC | O | O | S | S | S | O | OH | OH |
| 1647a-I | Y*AC | O | O | S | S | S | O | OMe | OH |
| 1648a-I | Y*AC | O | O | S | S | S | O | H | OH |
| 1649a-I | Y*AC | O | O | S | S | S | O | F | OH |
| 1650a-I | Y*AC | O | O | S | S | S | O | OEt | OH |
| 1651a-I | Y*AC | S | O | S | S | S | O | OH | OH |
| 1652a-I | Y*AC | S | O | S | S | S | O | OMe | OH |
| 1653a-I | Y*AC | S | O | S | S | S | O | H | OH |
| 1654a-I | Y*AC | S | O | S | S | S | O | F | OH |
| 1655a-I | Y*AC | S | O | S | S | 5 | O | OEt | OH |
| 1656a-I | Y*AC | S | S | S | S | S | O | OH | OH |
| 1657a-I | Y*AC | S | S | S | S | S | O | OMe | OH |

TABLE 3-continued

CapA Structures for mRNA preparation

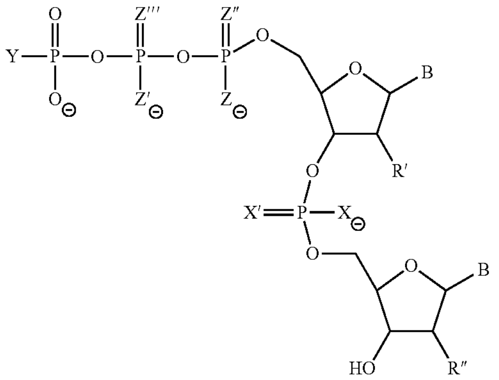

| Compound | Sequence | X | X' | Z | Z' | Z" | Z'" | R' | R" |
|---|---|---|---|---|---|---|---|---|---|
| 1658a-I | Y*AC | S | S | S | S | S | O | H | OH |
| 1659a-I | Y*AC | S | S | S | S | S | O | F | OH |
| 1660a-I | Y*AC | S | S | S | S | S | O | OEt | OH |
| 1661a-I | Y*AC | O | O | S | S | S | S | OH | OH |
| 1662a-I | Y*AC | O | O | S | S | S | S | OMe | OH |
| 1663a-I | Y*AC | O | O | S | S | S | S | H | OH |
| 1664a-I | Y*AC | O | O | S | S | S | S | F | OH |
| 1665a-I | Y*AC | O | O | S | S | S | S | OEt | OH |
| 1666a-I | Y*AC | S | O | S | S | S | S | OH | OH |
| 1667a-I | Y*AC | S | O | S | S | S | S | OMe | OH |
| 1668a-I | Y*AC | S | O | S | S | S | S | H | OH |
| 1669a-I | Y*AC | S | O | S | S | S | S | F | OH |
| 1670a-I | Y*AC | S | O | S | S | S | S | OEt | OH |
| 1671a-I | Y*AC | S | S | S | S | S | S | OH | OH |
| 1672a-I | Y*AC | S | S | S | S | S | S | OMe | OH |
| 1673a-I | Y*AC | S | S | S | S | S | S | H | OH |
| 1674a-I | Y*AC | S | S | S | S | S | S | F | OH |
| 1675a-I | Y*AC | S | S | S | S | S | S | OEt | OH |
| 1676a-I | Y*AC | O | O | O | S | S | S | OH | OH |
| 1677a-I | Y*AC | O | O | O | S | S | S | OMe | OH |
| 1678a-I | Y*AC | O | O | O | S | S | S | H | OH |
| 1679a-I | Y*AC | O | O | O | S | S | S | F | OH |
| 1680a-I | Y*AC | O | O | O | S | S | S | OEt | OH |
| 1681a-I | Y*AC | S | O | O | S | S | S | OH | OH |
| 1682a-I | Y*AC | S | O | O | S | S | S | OMe | OH |
| 1683a-I | Y*AC | S | O | O | S | S | S | H | OH |
| 1684a-I | Y*AC | S | O | O | S | S | S | F | OH |
| 1685a-I | Y*AC | S | O | O | S | S | S | OEt | OH |
| 1686a-I | Y*AC | S | S | O | S | S | S | OH | OH |
| 1687a-I | Y*AC | S | S | O | S | S | S | OMe | OH |
| 1688a-I | Y*AC | S | S | O | S | S | S | H | OH |
| 1689a-I | Y*AC | S | S | O | S | S | S | F | OH |
| 1690a-I | Y*AC | S | S | O | S | S | S | OEt | OH |
| 1691a-I | Y*AC | O | O | O | O | S | S | OH | OH |
| 1692a-I | Y*AC | O | O | O | O | S | S | OMe | OH |
| 1693a-I | Y*AC | O | O | O | O | S | S | H | OH |
| 1694a-I | Y*AC | O | O | O | O | S | S | F | OH |
| 1695a-I | Y*AC | O | O | O | O | S | S | OEt | OH |
| 1696a-I | Y*AC | S | O | O | O | S | S | OH | OH |
| 1697a-I | Y*AC | S | O | O | O | S | S | OMe | OH |
| 1698a-I | Y*AC | S | O | O | O | S | S | H | OH |
| 1699a-I | Y*AC | S | O | O | O | S | S | F | OH |
| 1700a-I | Y*AC | S | O | O | O | S | S | OEt | OH |
| 1701a-I | Y*AC | S | S | O | O | S | S | OH | OH |
| 1702a-I | Y*AC | S | S | O | O | S | S | OMe | OH |
| 1703a-I | Y*AC | S | S | O | O | S | S | H | OH |
| 1704a-I | Y*AC | S | S | O | O | S | S | F | OH |
| 1705a-I | Y*AC | S | S | O | O | S | S | OEt | OH |
| 1706a-I | Y*AC | O | O | O | O | O | S | OH | OH |
| 1707a-I | Y*AC | O | O | O | O | O | S | OMe | OH |
| 1708a-I | Y*AC | O | O | O | O | O | S | H | OH |
| 1709a-I | Y*AC | O | O | O | O | O | S | F | OH |
| 1710a-I | Y*AC | O | O | O | O | O | S | OEt | OH |
| 1711a-I | Y*AC | S | O | O | O | O | S | OH | OH |
| 1712a-I | Y*AC | S | O | O | O | O | S | OMe | OH |
| 1713a-I | Y*AC | S | O | O | O | O | S | H | OH |
| 1714a-I | Y*AC | S | O | O | O | O | S | F | OH |

TABLE 3-continued

CapA Structures for mRNA preparation

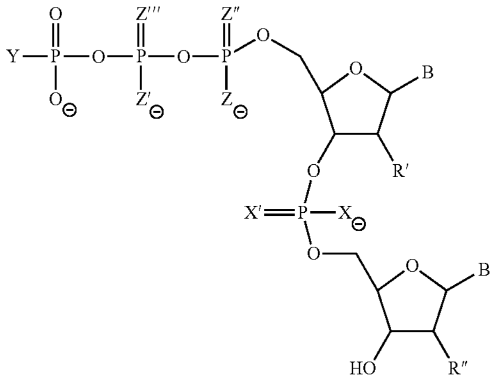

| Compound | Sequence | X | X' | Z | Z' | Z'' | Z''' | R' | R'' |
|---|---|---|---|---|---|---|---|---|---|
| 1715a-I | Y*AC | S | O | O | O | O | S | OEt | OH |
| 1716a-I | Y*AC | S | S | O | O | O | S | OH | OH |
| 1717a-I | Y*AC | S | S | O | O | O | S | OMe | OH |
| 1718a-I | Y*AC | S | S | O | O | O | S | H | OH |
| 1719a-I | Y*AC | S | S | O | O | O | S | F | OH |
| 1720a-I | Y*AC | S | S | O | O | O | S | OEt | OH |
| 1721a-I | Y*AC | O | O | S | O | S | O | OH | OH |
| 1722a-I | Y*AC | O | O | S | O | S | O | OMe | OH |
| 1723a-I | Y*AC | O | O | S | O | S | O | H | OH |
| 1724a-I | Y*AC | O | O | S | O | S | O | F | OH |
| 1725a-I | Y*AC | O | O | S | O | S | O | OEt | OH |
| 1726a-I | Y*AC | S | O | S | O | S | O | OH | OH |
| 1727a-I | Y*AC | S | O | S | O | S | O | OMe | OH |
| 1728a-I | Y*AC | S | O | S | O | S | O | H | OH |
| 1729a-I | Y*AC | S | O | S | O | S | O | F | OH |
| 1730a-I | Y*AC | S | O | S | O | S | O | OEt | OH |
| 1731a-I | Y*AC | S | S | S | O | S | O | OH | OH |
| 1732a-I | Y*AC | S | S | S | O | S | O | OMe | OH |
| 1733a-I | Y*AC | S | 5 | S | O | S | O | H | OH |
| 1734a-I | Y*AC | S | S | S | O | S | O | F | OH |
| 1735a-I | Y*AC | S | S | S | O | S | O | OEt | OH |
| 1736a-I | Y*AC | O | O | O | S | O | S | OH | OH |
| 1737a-I | Y*AC | O | O | O | S | O | S | OMe | OH |
| 1738a-I | Y*AC | O | O | O | S | O | S | H | OH |
| 1739a-I | Y*AC | O | O | O | S | O | S | F | OH |
| 1740a-I | Y*AC | O | O | O | S | O | S | OEt | OH |
| 1741a-I | Y*AC | S | O | O | S | O | S | OH | OH |
| 1742a-I | Y*AC | S | O | O | S | O | S | OMe | OH |
| 1743a-I | Y*AC | S | O | O | S | O | S | H | OH |
| 1744a-I | Y*AC | S | O | O | S | O | S | F | OH |
| 1745a-I | Y*AC | S | O | O | S | O | S | OEt | OH |
| 1746a-I | Y*AC | S | S | O | S | O | S | OH | OH |
| 1747a-I | Y*AC | S | S | O | S | O | S | OMe | OH |
| 1748a-I | Y*AC | S | S | O | S | O | S | H | OH |
| 1749a-I | Y*AC | S | S | O | S | O | S | F | OH |
| 1750a-I | Y*AC | S | S | O | S | O | S | OEt | OH |
| 1751a-I | Y*AC | O | O | O | O | O | O | OH | OMe |
| 1752a-I | Y*AC | O | O | O | O | O | O | OMe | OMe |
| 1753a-I | Y*AC | O | O | O | O | O | O | H | OMe |
| 1754a-I | Y*AC | O | O | O | O | O | O | F | OMe |
| 1755a-I | Y*AC | O | O | O | O | O | O | OEt | OMe |
| 1756a-I | Y*AC | S | O | O | O | O | O | OH | OMe |
| 1757a-I | Y*AC | S | O | O | O | O | O | OMe | OMe |
| 1758a-I | Y*AC | S | O | O | O | O | O | H | OMe |
| 1759a-I | Y*AC | S | O | O | O | O | O | F | OMe |
| 1760a-I | Y*AC | S | O | O | O | O | O | OEt | OMe |
| 1761a-I | Y*AC | S | S | O | O | O | O | OH | OMe |
| 1762a-I | Y*AC | S | S | O | O | O | O | OMe | OMe |
| 1763a-I | Y*AC | S | S | O | O | O | O | H | OMe |
| 1764a-I | Y*AC | S | S | O | O | O | O | F | OMe |
| 1765a-I | Y*AC | S | S | O | O | O | O | OEt | OMe |
| 1766a-I | Y*AC | O | O | S | O | O | O | OH | OMe |
| 1767a-I | Y*AC | O | O | S | O | O | O | OMe | OMe |
| 1768a-I | Y*AC | O | O | S | O | O | O | H | OMe |
| 1769a-I | Y*AC | O | O | S | O | O | O | F | OMe |
| 1770a-I | Y*AC | O | O | S | O | O | O | OEt | OMe |
| 1771a-I | Y*AC | S | O | S | O | O | O | OH | OMe |
| 1772a-I | Y*AC | S | O | S | O | O | O | OMe | OMe |
| 1773a-I | Y*AC | S | O | S | O | O | O | H | OMe |
| 1774a-I | Y*AC | S | O | S | O | O | O | F | OMe |
| 1775a-I | Y*AC | S | O | S | O | O | O | OEt | OMe |
| 1776a-I | Y*AC | S | S | S | O | O | O | OH | OMe |
| 1777a-I | Y*AC | S | S | S | O | O | O | OMe | OMe |
| 1778a-I | Y*AC | S | S | S | O | O | O | H | OMe |
| 1779a-I | Y*AC | S | S | S | O | O | O | F | OMe |
| 1780a-I | Y*AC | S | S | S | O | O | O | OEt | OMe |
| 1781a-I | Y*AC | O | O | S | S | O | O | OH | OMe |
| 1782a-I | Y*AC | O | O | S | S | O | O | OMe | OMe |
| 1783a-I | Y*AC | O | O | S | S | O | O | H | OMe |
| 1784a-I | Y*AC | O | O | S | S | O | O | F | OMe |
| 1785a-I | Y*AC | O | O | S | S | O | O | OEt | OMe |
| 1786a-I | Y*AC | S | O | S | S | O | O | OH | OMe |
| 1787a-I | Y*AC | S | O | S | S | O | O | OMe | OMe |
| 1788a-I | Y*AC | S | O | S | S | O | O | H | OMe |
| 1789a-I | Y*AC | S | O | S | S | O | O | F | OMe |
| 1790a-I | Y*AC | S | O | S | S | O | O | OEt | OMe |
| 1791a-I | Y*AC | S | S | S | S | O | O | OH | OMe |
| 1792a-I | Y*AC | S | S | S | S | O | O | OMe | OMe |
| 1793a-I | Y*AC | S | S | S | S | O | O | H | OMe |
| 1794a-I | Y*AC | S | S | S | S | O | O | F | OMe |
| 1795a-I | Y*AC | S | S | S | S | O | O | OEt | OMe |
| 1796a-I | Y*AC | O | O | S | S | S | O | OH | OMe |
| 1797a-I | Y*AC | O | O | S | S | S | O | OMe | OMe |
| 1798a-I | Y*AC | O | O | S | S | S | O | H | OMe |
| 1799a-I | Y*AC | O | O | S | S | S | O | F | OMe |
| 1800a-I | Y*AC | O | O | S | S | S | O | OEt | OMe |
| 1801a-I | Y*AC | S | O | S | S | S | O | OH | OMe |
| 1802a-I | Y*AC | S | O | S | S | S | O | OMe | OMe |
| 1803a-I | Y*AC | S | O | S | S | S | O | H | OMe |
| 1804a-I | Y*AC | S | O | S | S | S | O | F | OMe |
| 1805a-I | Y*AC | S | O | S | S | S | O | OEt | OMe |
| 1806a-I | Y*AC | S | S | S | S | S | O | OH | OMe |
| 1807a-I | Y*AC | S | S | S | S | S | O | OMe | OMe |
| 1808a-I | Y*AC | S | S | S | S | S | O | H | OMe |
| 1809a-I | Y*AC | S | S | S | S | S | O | F | OMe |
| 1810a-I | Y*AC | S | S | S | S | S | O | OEt | OMe |
| 1811a-I | Y*AC | O | O | S | S | S | S | OH | OMe |
| 1812a-I | Y*AC | O | O | S | S | S | S | OMe | OMe |
| 1813a-I | Y*AC | O | O | S | S | S | S | H | OMe |
| 1814a-I | Y*AC | O | O | S | S | S | S | F | OMe |
| 181Sa-I | Y*AC | O | O | S | S | S | S | OEt | OMe |
| 1816a-I | Y*AC | S | O | S | S | S | S | OH | OMe |
| 1817a-I | Y*AC | S | O | S | S | S | S | OMe | OMe |
| 1818a-I | Y*AC | S | O | S | S | S | S | H | OMe |
| 1819a-I | Y*AC | S | O | S | S | S | S | F | OMe |
| 1820a-I | Y*AC | S | O | S | S | S | S | OEt | OMe |
| 1821a-I | Y*AC | S | S | S | S | S | S | OH | OMe |
| 1822a-I | Y*AC | S | S | S | S | S | S | OMe | OMe |
| 1823a-I | Y*AC | S | S | S | S | S | S | H | OMe |
| 1824a-I | Y*AC | S | S | S | S | S | S | F | OMe |
| 1825a-I | Y*AC | S | S | S | S | S | S | OEt | OMe |
| 1826a-I | Y*AC | O | O | O | S | S | S | OH | OMe |
| 1827a-I | Y*AC | O | O | O | S | S | S | OMe | OMe |
| 1828a-I | Y*AC | O | O | O | S | S | S | H | OMe |

TABLE 3-continued

CapA Structures for mRNA preparation

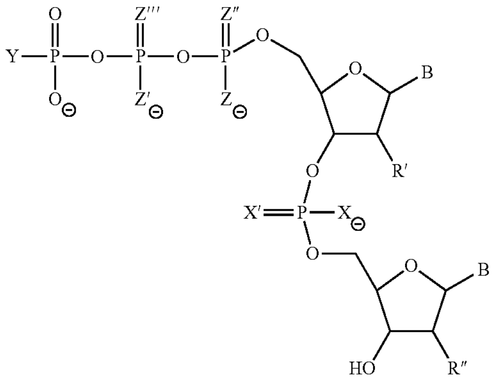

TABLE 3-continued

CapA Structures for mRNA preparation

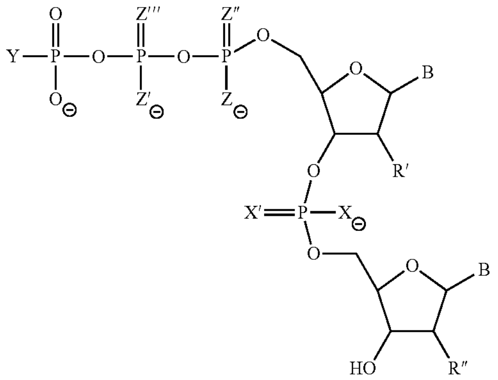

| Compound | Sequence | X | X' | Z | Z' | Z" | Z"' | R' | R" |
|---|---|---|---|---|---|---|---|---|---|
| 1829a-I | Y*AC | O | O | O | S | S | S | F | OMe |
| 1830a-I | Y*AC | O | O | O | S | S | S | OEt | OMe |
| 1831a-I | Y*AC | S | O | O | S | S | S | OH | OMe |
| 1832a-I | Y*AC | S | O | O | S | S | S | OMe | OMe |
| 1833a-I | Y*AC | S | O | O | S | S | S | H | OMe |
| 1834a-I | Y*AC | S | O | O | S | S | S | F | OMe |
| 1835a-I | Y*AC | S | O | O | S | S | S | OEt | OMe |
| 1836a-I | Y*AC | S | S | O | S | S | S | OH | OMe |
| 1837a-I | Y*AC | S | S | O | S | S | S | OMe | OMe |
| 1838a-I | Y*AC | S | S | O | S | S | S | H | OMe |
| 1839a-I | Y*AC | S | S | O | S | S | S | F | OMe |
| 1840a-I | Y*AC | S | S | O | S | S | S | OEt | OMe |
| 1841a-I | Y*AC | O | O | O | O | S | S | OH | OMe |
| 1842a-I | Y*AC | O | O | O | O | S | S | OMe | OMe |
| 1843a-I | Y*AC | O | O | O | O | S | S | H | OMe |
| 1844a-I | Y*AC | O | O | O | O | S | S | F | OMe |
| 1845a-I | Y*AC | O | O | O | O | S | S | OEt | OMe |
| 1846a-I | Y*AC | S | O | O | O | S | S | OH | OMe |
| 1847a-I | Y*AC | S | O | O | O | S | S | OMe | OMe |
| 1848a-I | Y*AC | S | O | O | O | S | S | H | OMe |
| 1849a-I | Y*AC | S | O | O | O | S | S | F | OMe |
| 1850a-I | Y*AC | S | O | O | O | S | S | OEt | OMe |
| 1851a-I | Y*AC | S | S | O | O | S | S | OH | OMe |
| 1852a-I | Y*AC | S | S | O | O | S | S | OMe | OMe |
| 1853a-I | Y*AC | S | S | O | O | S | S | H | OMe |
| 1854a-I | Y*AC | S | S | O | O | S | S | F | OMe |
| 1855a-I | Y*AC | S | S | O | O | S | S | OEt | OMe |
| 1856a-I | Y*AC | O | O | O | O | O | S | OH | OMe |
| 1857a-I | Y*AC | O | O | O | O | O | S | OMe | OMc |
| 1858a-I | Y*AC | O | O | O | O | O | S | H | OMe |
| 1859a-I | Y*AC | O | O | O | O | O | S | F | OMe |
| 1860a-I | Y*AC | O | O | O | O | O | S | OEt | OMe |
| 1861a-I | Y*AC | S | O | O | O | O | S | OH | OMe |
| 1862a-I | Y*AC | S | O | O | O | O | S | OMe | OMe |
| 1863a-I | Y*AC | S | O | O | O | O | S | H | OMe |
| 1864a-I | Y*AC | S | O | O | O | O | S | F | OMe |
| 1865a-I | Y*AC | S | O | O | O | O | S | OEt | OMe |
| 1866a-I | Y*AC | S | S | O | O | O | S | OH | OMe |
| 1867a-I | Y*AC | S | S | O | O | O | S | OMe | OMe |
| 1868a-I | Y*AC | S | S | O | O | O | S | H | OMe |
| 1869a-I | Y*AC | S | S | O | O | O | S | F | OMe |
| 1870a-I | Y*AC | S | S | O | O | O | S | OEt | OMe |
| 1871a-I | Y*AC | O | O | S | O | S | O | OH | OMe |
| 1872a-I | Y*AC | O | O | S | O | S | O | OMe | OMe |
| 1873a-I | Y*AC | O | O | S | O | S | O | H | OMe |
| 1874a-I | Y*AC | O | O | S | O | S | O | F | OMe |
| 1875a-I | Y*AC | O | O | S | O | S | O | OEt | OMe |
| 1876a-I | Y*AC | S | O | S | O | S | O | OH | OMe |
| 1877a-I | Y*AC | S | O | S | O | S | O | OMe | OMe |
| 1878a-I | Y*AC | S | O | S | O | S | O | H | OMe |
| 1879a-I | Y*AC | S | O | S | O | S | O | F | OMe |
| 1880a-I | Y*AC | S | O | S | O | S | O | OEt | OMe |
| 1881a-I | Y*AC | S | S | S | O | S | O | OH | OMe |
| 1882a-I | Y*AC | S | S | S | O | S | O | OMe | OMe |
| 1883a-I | Y*AC | S | S | S | O | S | O | H | OMe |
| 1884a-I | Y*AC | S | S | S | O | S | O | F | OMe |
| 1885a-I | Y*AC | S | S | S | O | S | O | OEt | OMe |

TABLE 3-continued

CapA Structures for mRNA preparation

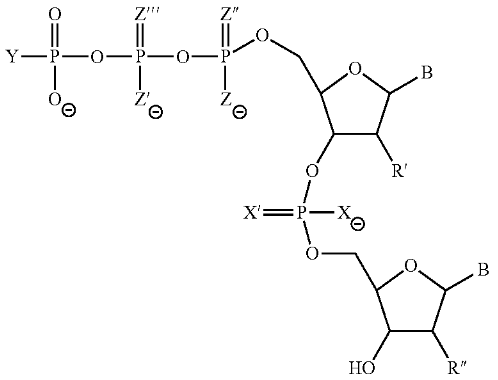

| Compound | Sequence | X | X' | Z | Z' | Z" | Z"' | R' | R" |
|---|---|---|---|---|---|---|---|---|---|
| 1886a-I | Y*AC | O | O | O | S | O | S | OH | OMe |
| 1887a-I | Y*AC | O | O | O | S | O | S | OMe | OMe |
| 1888a-I | Y*AC | O | O | O | S | O | S | H | OMe |
| 1889a-I | Y*AC | O | O | O | S | O | S | F | OMe |
| 1890a-I | Y*AC | O | O | O | S | O | S | OEt | OMe |
| 1891a-I | Y*AC | S | O | O | S | O | S | OH | OMe |
| 1892a-I | Y*AC | S | O | O | S | O | S | OMe | OMe |
| 1893a-I | Y*AC | S | O | O | S | O | S | H | OMe |
| 1894a-I | Y*AC | S | O | O | S | O | S | F | OMe |
| 1895a-I | Y*AC | S | O | O | S | O | S | OEt | OMe |
| 1896a-I | Y*AC | S | S | O | S | O | S | OH | OMe |
| 1897a-I | Y*AC | S | S | O | S | O | S | OMe | OMe |
| 1898a-I | Y*AC | S | S | O | S | O | S | H | OMe |
| 1899a-I | Y*AC | S | S | O | S | O | S | F | OMe |
| 1900a-I | Y*AC | S | S | O | S | O | S | OEt | OMe |
| 1901a-I | Y*AU | O | O | O | O | O | O | OH | OH |
| 1902a-I | Y*AU | O | O | O | O | O | O | OMe | OH |
| 1903a-I | Y*AU | O | O | O | O | O | O | H | OH |
| 1904a-I | Y*AU | O | O | O | O | O | O | F | OH |
| 1905a-I | Y*AU | O | O | O | O | O | O | OEt | OH |
| 1906a-I | Y*AU | S | O | O | O | O | O | OH | OH |
| 1907a-I | Y*AU | S | O | O | O | O | O | OMe | OH |
| 1908a-I | Y*AU | S | O | O | O | O | O | H | OH |
| 1909a-I | Y*AU | S | O | O | O | O | O | F | OH |
| 1910a-I | Y*AU | S | O | O | O | O | O | OEt | OH |
| 1911a-I | Y*AU | S | S | O | O | O | O | OH | OH |
| 1912a-I | Y*AU | S | S | O | O | O | O | OMe | OH |
| 1913a-I | Y*AU | S | S | O | O | O | O | H | OH |
| 1914a-I | Y*AU | S | S | O | O | O | O | F | OH |
| 1915a-I | Y*AU | S | S | O | O | O | O | OEt | OH |
| 1916a-I | Y*AU | O | O | S | O | O | O | OH | OH |
| 1917a-I | Y*AU | O | O | S | O | O | O | OMe | OH |
| 1918a-I | Y*AU | O | O | S | O | O | O | H | OH |
| 1919a-I | Y*AU | O | O | S | O | O | O | F | OH |
| 1920a-I | Y*AU | O | O | S | O | O | O | OEt | OH |
| 1921a-I | Y*AU | S | O | S | O | O | O | OH | OH |
| 1922a-I | Y*AU | S | O | S | O | O | O | OMe | OH |
| 1923a-I | Y*AU | S | O | S | O | O | O | H | OH |
| 1924a-I | Y*AU | S | O | S | O | O | O | F | OH |
| 1925a-I | Y*AU | S | O | S | O | O | O | OEt | OH |
| 1926a-I | Y*AU | S | S | S | O | O | O | OH | OH |
| 1927a-I | Y*AU | S | S | S | O | O | O | OMe | OH |
| 1928a-I | Y*AU | S | S | S | O | O | O | H | OH |
| 1929a-I | Y*AU | S | S | S | O | O | O | F | OH |
| 1930a-I | Y*AU | S | S | S | O | O | O | OEt | OH |
| 1931a-I | Y*AU | O | O | S | S | O | O | OH | OH |
| 1932a-I | Y*AU | O | O | S | S | O | O | OMe | OH |
| 1933a-I | Y*AU | O | O | S | S | O | O | H | OH |
| 1934a-I | Y*AU | O | O | S | S | O | O | F | OH |
| 1935a-I | Y*AU | O | O | S | S | O | O | OEt | OH |
| 1936a-I | Y*AU | S | O | S | S | O | O | OH | OH |
| 1937a-I | Y*AU | S | O | S | S | O | O | OMe | OH |
| 1938a-I | Y*AU | S | O | S | S | O | O | H | OH |
| 1939a-I | Y*AU | S | O | S | S | O | O | F | OH |
| 1940a-I | Y*AU | S | O | S | S | O | O | OEt | OH |
| 1941a-I | Y*AU | S | S | S | S | O | O | OH | OH |
| 1942a-I | Y*AU | S | S | S | S | O | O | OMe | OH |

TABLE 3-continued

CapA Structures for mRNA preparation

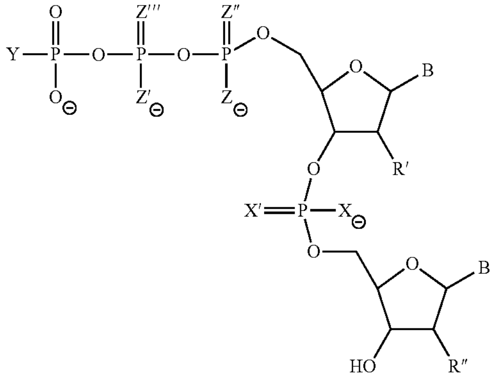

| Compound | Sequence | X | X' | Z | Z' | Z" | Z"' | R' | R" |
|---|---|---|---|---|---|---|---|---|---|
| 1943a-I | Y*AU | S | S | S | S | O | O | H | OH |
| 1944a-I | Y*AU | S | S | S | S | O | O | F | OH |
| 1945a-I | Y*AU | S | S | S | S | O | O | OEt | OH |
| 1946a-I | Y*AU | O | O | S | S | S | O | OH | OH |
| 1947a-I | Y*AU | O | O | S | S | S | O | OMe | OH |
| 1948a-I | Y*AU | O | O | S | S | S | O | H | OH |
| 1949a-I | Y*AU | O | O | S | S | S | O | F | OH |
| 1950a-I | Y*AU | O | O | S | S | S | O | OEt | OH |
| 1951a-I | Y*AU | S | O | S | S | S | O | OH | OH |
| 1952a-I | Y*AU | S | O | S | S | S | O | OMe | OH |
| 1953a-I | Y*AU | S | O | S | S | S | O | H | OH |
| 1954a-I | Y*AU | S | O | S | S | S | O | F | OH |
| 1955a-I | Y*AU | S | O | S | S | S | O | OEt | OH |
| 1956a-I | Y*AU | S | S | S | S | S | O | OH | OH |
| 1957a-I | Y*AU | S | S | S | S | S | O | OMe | OH |
| 1958a-I | Y*AU | S | S | S | S | S | O | H | OH |
| 1959a-I | Y*AU | S | S | S | S | S | O | F | OH |
| 1960a-I | Y*AU | S | S | S | S | S | O | OEt | OH |
| 1961a-I | Y*AU | O | O | S | S | S | S | OH | OH |
| 1962a-I | Y*AU | O | O | S | S | S | S | OMe | OH |
| 1963a-I | Y*AU | O | O | S | S | S | S | H | OH |
| 1964a-I | Y*AU | O | O | S | S | S | S | F | OH |
| 1965a-I | Y*AU | O | O | S | S | S | S | OEt | OH |
| 1966a-I | Y*AU | S | O | S | S | S | S | OH | OH |
| 1967a-I | Y*AU | S | O | S | S | S | S | OMe | OH |
| 1968a-I | Y*AU | S | O | S | S | S | S | H | OH |
| 1969a-I | Y*AU | S | O | S | S | S | S | F | OH |
| 1970a-I | Y*AU | S | O | S | S | S | S | OEt | OH |
| 1971a-I | Y*AU | S | S | S | S | S | S | OH | OH |
| 1972a-I | Y*AU | S | S | S | S | S | S | OMe | OH |
| 1973a-I | Y*AU | S | S | S | S | S | S | H | OH |
| 1974a-I | Y*AU | S | S | S | S | S | S | F | OH |
| 1975a-I | Y*AU | S | S | S | S | S | S | OEt | OH |
| 1976a-I | Y*AU | O | O | O | S | S | S | OH | OH |
| 1977a-I | Y*AU | O | O | O | S | S | S | OMe | OH |
| 1978a-I | Y*AU | O | O | O | S | S | S | H | OH |
| 1979a-I | Y*AU | O | O | O | S | S | S | F | OH |
| 1980a-I | Y*AU | O | O | O | S | S | S | OEt | OH |
| 1981a-I | Y*AU | S | O | O | S | S | S | OH | OH |
| 1982a-I | Y*AU | S | O | O | S | S | S | OMe | OH |
| 1983a-I | Y*AU | S | O | O | S | S | S | H | OH |
| 1984a-I | Y*AU | S | O | O | S | S | S | F | OH |
| 1985a-I | Y*AU | S | O | O | S | S | S | OEt | OH |
| 1986a-I | Y*AU | S | S | O | S | S | S | OH | OH |
| 1987a-I | Y*AU | S | S | O | S | S | S | OMe | OH |
| 1988a-I | Y*AU | S | S | O | S | S | S | H | OH |
| 1989a-I | Y*AU | S | S | O | S | S | S | F | OH |
| 1990a-I | Y*AU | S | S | O | S | S | S | OEt | OH |
| 1991a-I | Y*AU | O | O | O | O | S | S | OH | OH |
| 1992a-I | Y*AU | O | O | O | O | S | S | OMe | OH |
| 1993a-I | Y*AU | O | O | O | O | S | S | H | OH |
| 1994a-I | Y*AU | O | O | O | O | S | S | F | OH |
| 1995a-I | Y*AU | O | O | O | O | S | S | OEt | OH |
| 1996a-I | Y*AU | S | O | O | O | S | S | OH | OH |
| 1997a-I | Y*AU | S | O | O | O | S | S | OMe | OH |
| 1998a-I | Y*AU | S | O | O | O | S | S | H | OH |
| 1999a-I | Y*AU | S | O | O | O | S | S | F | OH |

TABLE 3-continued

CapA Structures for mRNA preparation

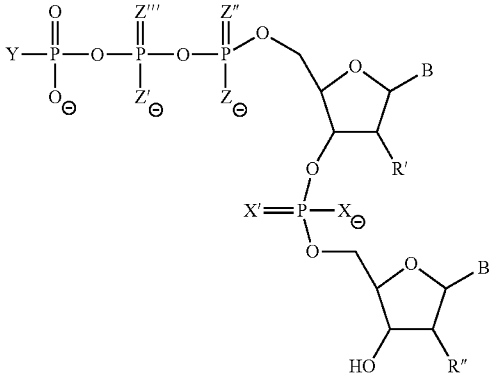

| Compound | Sequence | X | X' | Z | Z' | Z" | Z"' | R' | R" |
|---|---|---|---|---|---|---|---|---|---|
| 2000a-I | Y*AU | S | O | O | O | S | S | OE | OH |
| 2001a-I | Y*AU | S | S | O | O | S | S | OH | OH |
| 2002a-I | Y*AU | S | S | O | O | S | S | OMe | OH |
| 2003a-I | Y*AU | S | S | O | O | S | S | H | OH |
| 2004a-I | Y*AU | S | S | O | O | S | S | F | OH |
| 2005a-I | Y*AU | S | S | O | O | S | S | OEt | OH |
| 2006a-I | Y*AU | O | O | O | O | O | S | OH | OH |
| 2007a-I | Y*AU | O | O | O | O | O | S | OMe | OH |
| 2008a-I | Y*AU | O | O | O | O | O | S | H | OH |
| 2009a-I | Y*AU | O | O | O | O | O | S | F | OH |
| 2010a-I | Y*AU | O | O | O | O | O | S | OEt | OH |
| 2011a-I | Y*AU | S | O | O | O | O | S | OH | OH |
| 2012a-I | Y*AU | S | O | O | O | O | S | OMe | OH |
| 2013a-I | Y*AU | S | O | O | O | O | S | H | OH |
| 2014a-I | Y*AU | S | O | O | O | O | S | F | OH |
| 2015a-I | Y*AU | S | O | O | O | O | S | OEt | OH |
| 2016a-I | Y*AU | S | S | O | O | O | S | OH | OH |
| 2017a-I | Y*AU | S | S | O | O | O | S | OMe | OH |
| 2018a-I | Y*AU | S | S | O | O | O | S | H | OH |
| 2019a-I | Y*AU | S | S | O | O | O | S | F | OH |
| 2020a-I | Y*AU | S | S | O | O | O | S | OEt | OH |
| 2021a-I | Y*AU | O | O | S | O | S | O | OH | OH |
| 2022a-I | Y*AU | O | O | S | O | S | O | OMe | OH |
| 2023a-I | Y*AU | O | O | S | O | S | O | H | OH |
| 2024a-I | Y*AU | O | O | S | O | S | O | F | OH |
| 2025a-I | Y*AU | O | O | S | O | S | O | OEt | OH |
| 2026a-I | Y*AU | S | O | S | O | S | O | OH | OH |
| 2027a-I | Y*AU | S | O | S | O | S | O | OMe | OH |
| 2028a-I | Y*AU | S | O | S | O | S | O | H | OH |
| 2029a-I | Y*AU | S | O | S | O | S | O | F | OH |
| 2030a-I | Y*AU | S | O | S | O | S | O | OEt | OH |
| 2031a-I | Y*AU | S | S | S | O | S | O | OH | OH |
| 2032a-I | Y*AU | S | S | S | O | S | O | OMe | OH |
| 2033a-I | Y*AU | S | S | S | O | S | O | H | OH |
| 2034a-I | Y*AU | S | S | S | O | S | O | F | OH |
| 2035a-I | Y*AU | S | S | S | O | S | O | OEt | OH |
| 2036a-I | Y*AU | O | O | O | S | O | S | OH | OH |
| 2037a-I | Y*AU | O | O | O | S | O | S | OMe | OH |
| 2038a-I | Y*AU | O | O | O | S | O | S | H | OH |
| 2039a-I | Y*AU | O | O | O | S | O | S | F | OH |
| 2040a-I | Y*AU | O | O | O | S | O | S | OEt | OH |
| 2041a-I | Y*AU | S | O | O | S | O | S | OH | OH |
| 2042a-I | Y*AU | S | O | O | S | O | S | OMe | OH |
| 2043a-I | Y*AU | S | O | O | S | O | S | H | OH |
| 2044a-I | Y*AU | S | O | O | S | O | S | F | OH |
| 2045a-I | Y*AU | S | O | O | S | O | S | OEt | OH |
| 2046a-I | Y*AU | S | S | O | S | O | S | OH | OH |
| 2047a-I | Y*AU | S | S | O | S | O | S | OMe | OH |
| 2048a-I | Y*AU | S | S | O | S | O | S | H | OH |
| 2049a-I | Y*AU | S | S | O | S | O | S | F | OH |
| 2050a-I | Y*AU | S | S | O | S | O | S | OEt | OH |
| 2051a-I | Y*AU | O | O | O | O | O | O | OH | OMe |
| 2052a-I | Y*AU | O | O | O | O | O | O | OMe | OMe |
| 2053a-I | Y*AU | O | O | O | O | O | O | H | OMe |
| 2054a-I | Y*AU | O | O | O | O | O | O | F | OMe |
| 2055a-I | Y*AU | O | O | O | O | O | O | OEt | OMe |
| 2056a-I | Y*AU | S | O | O | O | O | O | OH | OMe |

TABLE 3-continued

CapA Structures for mRNA preparation

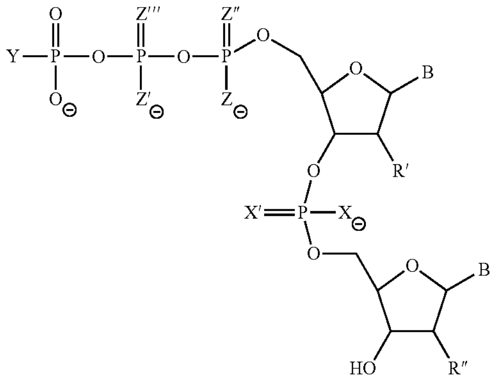

| Compound | Sequence | X | X' | Z | Z' | Z'' | Z''' | R' | R'' |
|---|---|---|---|---|---|---|---|---|---|
| 2057a-I | Y*AU | S | O | O | O | O | O | OMe | OMe |
| 2058a-I | Y*AU | S | O | O | O | O | O | H | OMe |
| 2059a-I | Y*AU | S | O | O | O | O | O | F | OMe |
| 2060a-I | Y*AU | S | O | O | O | O | O | OEt | OMe |
| 2061a-I | Y*AU | S | S | O | O | O | O | OH | OMe |
| 2062a-I | Y*AU | S | S | O | O | O | O | OMe | OMe |
| 2063a-I | Y*AU | S | S | O | O | O | O | H | OMe |
| 2064a-I | Y*AU | S | S | O | O | O | O | F | OMe |
| 2065a-I | Y*AU | S | S | O | O | O | O | OEt | OMe |
| 2066a-I | Y*AU | O | O | S | O | O | O | OH | OMe |
| 2067a-I | Y*AU | O | O | S | O | O | O | OMe | OMe |
| 2068a-I | Y*AU | O | O | S | O | O | O | H | OMe |
| 2069a-I | Y*AU | O | O | S | O | O | O | F | OMe |
| 2070a-I | Y*AU | O | O | S | O | O | O | OEt | OMe |
| 2071a-I | Y*AU | S | O | S | O | O | O | OH | OMe |
| 2072a-I | Y*AU | S | O | S | O | O | O | OMe | OMe |
| 2073a-I | Y*AU | S | O | S | O | O | O | H | OMe |
| 2074a-I | Y*AU | S | O | S | O | O | O | F | OMe |
| 2075a-I | Y*AU | S | O | S | O | O | O | OEt | OMe |
| 2076a-I | Y*AU | S | S | S | O | O | O | OH | OMe |
| 2077a-I | Y*AU | S | S | S | O | O | O | OMe | OMe |
| 2078a-I | Y*AU | S | S | S | O | O | O | H | OMe |
| 2079a-I | Y*AU | S | S | S | O | O | O | F | OMe |
| 2080a-I | Y*AU | S | S | S | O | O | O | OEt | OMe |
| 2081a-I | Y*AU | O | O | S | S | O | O | OH | OMe |
| 2082a-I | Y*AU | O | O | S | S | O | O | OMe | OMe |
| 2083a-I | Y*AU | O | O | S | S | O | O | H | OMe |
| 2084a-I | Y*AU | O | O | S | S | O | O | F | OMe |
| 2085a-I | Y*AU | O | O | S | S | O | O | OEt | OMe |
| 2086a-I | Y*AU | S | O | S | S | O | O | OH | OMe |
| 2087a-I | Y*AU | S | O | S | S | O | O | OMe | OMe |
| 2088a-I | Y*AU | S | O | S | S | O | O | H | OMe |
| 2089a-I | Y*AU | S | O | S | S | O | O | F | OMe |
| 2090a-I | Y*AU | S | O | S | S | O | O | OEt | OMe |
| 2091a-I | Y*AU | S | S | S | S | O | O | OH | OMe |
| 2092a-I | Y*AU | S | S | S | S | O | O | OMe | OMe |
| 2093a-I | Y*AU | S | S | S | S | O | O | H | OMe |
| 2094a-I | Y*AU | S | S | S | S | O | O | F | OMe |
| 2095a-I | Y*AU | S | S | S | S | O | O | OEt | OMe |
| 2096a-I | Y*AU | O | O | S | S | S | O | OH | OMe |
| 2097a-I | Y*AU | O | O | S | S | S | O | OMe | OMe |
| 2098a-I | Y*AU | O | O | S | S | S | O | H | OMe |
| 2099a-I | Y*AU | O | O | S | S | S | O | F | OMe |
| 2100a-I | Y*AU | O | O | S | S | S | O | OEt | OMe |
| 2101a-I | Y*AU | S | O | S | S | S | O | OH | OMe |
| 2102a-I | Y*AU | S | O | S | S | S | O | OMe | OMe |
| 2103a-I | Y*AU | S | O | S | S | S | O | H | OMe |
| 2104a-I | Y*AU | S | O | S | S | S | O | F | OMe |
| 2105a-I | Y*AU | S | O | S | S | S | O | OEt | OMe |
| 2106a-I | Y*AU | S | S | S | S | S | O | OH | OMe |
| 2107a-I | Y*AU | S | S | S | S | S | O | OMe | OMe |
| 2108a-I | Y*AU | S | S | S | S | S | O | H | OMe |
| 2109a-I | Y*AU | S | S | S | S | S | O | F | OMe |
| 2110a-I | Y*AU | S | S | S | S | S | O | OEt | OMe |
| 2111a-I | Y*AU | O | O | S | S | S | S | OH | OMe |
| 2112a-I | Y*AU | O | O | S | S | S | S | OMe | OMe |
| 2113a-I | Y*AU | O | O | S | S | S | S | H | OMe |

TABLE 3-continued

CapA Structures for mRNA preparation

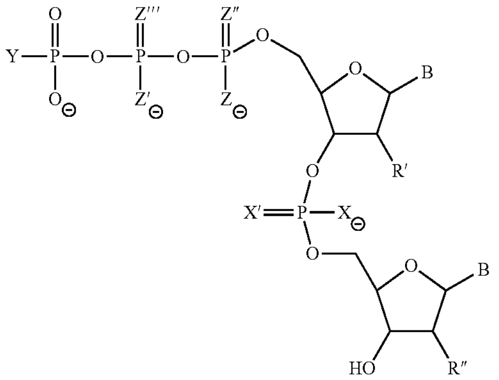

| Compound | Sequence | X | X' | Z | Z' | Z'' | Z''' | R' | R'' |
|---|---|---|---|---|---|---|---|---|---|
| 2114a-I | Y*AU | O | O | S | S | S | S | F | OMe |
| 2115a-I | Y*AU | O | O | S | S | S | S | OEt | OMe |
| 2116a-I | Y*AU | S | O | S | S | S | S | OH | OMe |
| 2117a-I | Y*AU | S | O | S | S | S | S | OMe | OMe |
| 2118a-I | Y*AU | S | O | S | S | S | S | H | OMe |
| 2119a-I | Y*AU | S | O | S | S | S | S | F | OMe |
| 2120a-I | Y*AU | S | O | S | S | S | S | OEt | OMe |
| 2121a-I | Y*AU | S | S | S | S | S | S | OH | OMe |
| 2122a-I | Y*AU | S | S | S | S | S | S | OMe | OMe |
| 2123a-I | Y*AU | S | S | S | S | S | S | H | OMe |
| 2124a-I | Y*AU | S | S | S | S | S | S | F | OMe |
| 2125a-I | Y*AU | S | S | S | S | S | S | OEt | OMe |
| 2126a-I | Y*AU | O | O | O | S | S | S | OH | OMe |
| 2127a-I | Y*AU | O | O | O | S | S | S | OMe | OMe |
| 2128a-I | Y*AU | O | O | O | S | S | S | H | OMe |
| 2129a-I | Y*AU | O | O | O | S | S | S | F | OMe |
| 2130a-I | Y*AU | O | O | O | S | S | S | OEt | OMe |
| 2131a-I | Y*AU | S | O | O | S | S | S | OH | OMe |
| 2132a-I | Y*AU | S | O | O | S | S | S | OMe | OMe |
| 2133a-I | Y*AU | S | O | O | S | S | S | H | OMe |
| 2134a-I | Y*AU | S | O | O | S | S | S | F | OMe |
| 2135a-I | Y*AU | S | O | O | S | S | S | OEt | OMe |
| 2136a-I | Y*AU | S | S | O | S | S | S | OH | OMe |
| 2137a-I | Y*AU | S | S | O | S | S | S | OMe | OMe |
| 2138a-I | Y*AU | S | S | O | S | S | S | H | OMe |
| 2139a-I | Y*AU | S | S | O | S | S | S | F | OMe |
| 2140a-I | Y*AU | S | S | O | S | S | S | OEt | OMe |
| 2141a-I | Y*AU | O | O | O | O | S | S | OH | OMe |
| 2142a-I | Y*AU | O | O | O | O | S | S | OMe | OMe |
| 2143a-I | Y*AU | O | O | O | O | S | S | H | OMe |
| 2144a-I | Y*AU | O | O | O | O | S | S | F | OMe |
| 2145a-I | Y*AU | O | O | O | O | S | S | OEt | OMe |
| 2146a-I | Y*AU | S | O | O | O | S | S | OH | OMe |
| 2147a-I | Y*AU | S | O | O | O | S | S | OMe | OMe |
| 2148a-I | Y*AU | S | O | O | O | S | S | H | OMe |
| 2149a-I | Y*AU | S | O | O | O | S | S | F | OMe |
| 2150a-I | Y*AU | S | O | O | O | S | S | OEt | OMe |
| 2151a-I | Y*AU | S | S | O | O | S | S | OH | OMe |
| 2152a-I | Y*AU | S | S | O | O | S | S | OMe | OMe |
| 2153a-I | Y*AU | S | S | O | O | S | S | H | OMe |
| 2154a-I | Y*AU | S | S | O | O | S | S | F | OMe |
| 2155a-I | Y*AU | S | S | O | O | S | S | OEt | OMe |
| 2156a-I | Y*AU | O | O | O | O | O | S | OH | OMe |
| 2157a-I | Y*AU | O | O | O | O | O | S | OMe | OMe |
| 2158a-I | Y*AU | O | O | O | O | O | S | H | OMe |
| 2159a-I | Y*AU | O | O | O | O | O | S | F | OMe |
| 2160a-I | Y*AU | O | O | O | O | O | S | OEt | OMe |
| 2161a-I | Y*AU | S | O | O | O | O | S | OH | OMe |
| 2162a-I | Y*AU | S | O | O | O | O | S | OMe | OMe |
| 2163a-I | Y*AU | S | O | O | O | O | S | H | OMe |
| 2164a-I | Y*AU | S | O | O | O | O | S | F | OMe |
| 2165a-I | Y*AU | S | O | O | O | O | S | OEt | OMe |
| 2166a-I | Y*AU | S | S | O | O | O | S | OH | OMe |
| 2167a-I | Y*AU | S | S | O | O | O | S | OMe | OMe |
| 2168a-I | Y*AU | S | S | O | O | O | S | H | OMe |
| 2169a-I | Y*AU | S | S | O | O | O | S | F | OMe |
| 2170a-I | Y*AU | S | S | O | O | O | S | OEt | OMe |

TABLE 3-continued

CapA Structures for mRNA preparation

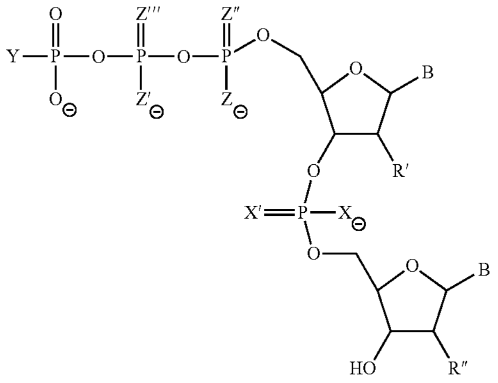

| Compound | Sequence | X | X' | Z | Z' | Z" | Z"' | R' | R" |
|---|---|---|---|---|---|---|---|---|---|
| 2171a-I | Y*AU | O | O | S | O | S | O | OH | OMe |
| 2172a-I | Y*AU | O | O | S | O | S | O | OMe | OMe |
| 2173a-I | Y*AU | O | O | S | O | S | O | H | OMe |
| 2174a-I | Y*AU | O | O | S | O | S | O | F | OMe |
| 2175a-I | Y*AU | O | O | S | O | S | O | OEt | OMe |
| 2176a-I | Y*AU | S | O | S | O | S | O | OH | OMe |
| 2177a-I | Y*AU | S | O | S | O | S | O | OMe | OMe |
| 2178a-I | Y*AU | S | O | S | O | S | O | H | OMe |
| 2179a-I | Y*AU | S | O | S | O | S | O | F | OMe |
| 2180a-I | Y*AU | S | O | S | O | S | O | OEt | OMe |
| 2181a-I | Y*AU | S | S | S | O | S | O | OH | OMe |
| 2182a-I | Y*AU | S | S | S | O | S | O | OMe | OMe |
| 2183a-I | Y*AU | S | S | S | O | S | O | H | OMe |
| 2184a-I | Y*AU | S | S | S | O | S | O | F | OMe |
| 2185a-I | Y*AU | S | S | S | O | S | O | OEt | OMe |
| 2186a-I | Y*AU | O | O | O | S | O | S | OH | OMe |
| 2187a-I | Y*AU | O | O | O | S | O | S | OMe | OMe |
| 2188a-I | Y*AU | O | O | O | S | O | S | H | OMe |
| 2189a-I | Y*AU | O | O | O | S | O | S | F | OMe |
| 2190a-I | Y*AU | O | O | O | S | O | S | OEt | OMe |
| 2191a-I | Y*AU | S | O | O | S | O | S | OH | OMe |
| 2192a-I | Y*AU | S | O | O | S | O | S | OMe | OMe |
| 2193a-I | Y*AU | S | O | O | S | O | S | H | OMe |
| 2194a-I | Y*AU | S | O | O | S | O | S | F | OMe |
| 2195a-I | Y*AU | S | O | O | S | O | S | OEt | OMe |
| 2196a-I | Y*AU | S | S | O | S | O | S | OH | OMe |
| 2197a-I | Y*AU | S | S | O | S | O | S | OMe | OMe |
| 2198a-I | Y*AU | S | S | O | S | O | S | H | OMe |
| 2199a-I | Y*AU | S | S | O | S | O | S | F | OMe |
| 2200a-I | Y*AU | S | S | O | S | O | S | OEt | OMe |
| 2201a-I | Y*AI | O | O | O | O | O | O | OH | OH |
| 2202a-I | Y*AI | O | O | O | O | O | O | OMe | OH |
| 2203a-I | Y*AI | O | O | O | O | O | O | H | OH |
| 2204a-I | Y*AI | O | O | O | O | O | O | F | OH |
| 2205a-I | Y*AI | O | O | O | O | O | O | OEt | OH |
| 2206a-I | Y*AI | S | O | O | O | O | O | OH | OH |
| 2207a-I | Y*AI | S | O | O | O | O | O | OMe | OH |
| 2208a-I | Y*AI | S | O | O | O | O | O | H | OH |
| 2209a-I | Y*AI | S | O | O | O | O | O | F | OH |
| 2210a-I | Y*AI | S | O | O | O | O | O | OEt | OH |
| 2211a-I | Y*AI | S | S | O | O | O | O | OH | OH |
| 2212a-I | Y*AI | S | S | O | O | O | O | OMe | OH |
| 2213a-I | Y*AI | S | S | O | O | O | O | H | OH |
| 2214a-I | Y*AI | S | S | O | O | O | O | F | OH |
| 2215a-I | Y*AI | S | S | O | O | O | O | OEt | OH |
| 2216a-I | Y*AI | O | O | S | O | O | O | OH | OH |
| 2217a-I | Y*AI | O | O | S | O | O | O | OMe | OH |
| 2218a-I | Y*AI | O | O | S | O | O | O | H | OH |
| 2219a-I | Y*AI | O | O | S | O | O | O | F | OH |
| 2220a-I | Y*AI | O | O | S | O | O | O | OEt | OH |
| 2221a-I | Y*AI | S | O | S | O | O | O | OH | OH |
| 2222a-I | Y*AI | S | O | S | O | O | O | OMe | OH |
| 2223a-I | Y*AI | S | O | S | O | O | O | H | OH |
| 2224a-I | Y*AI | S | O | S | O | O | O | F | OH |
| 2225a-I | Y*AI | S | O | S | O | O | O | OEt | OH |
| 2226a-I | Y*AI | S | S | S | O | O | O | OH | OH |
| 2227a-I | Y*AI | S | S | S | O | O | O | OMe | OH |

TABLE 3-continued

CapA Structures for mRNA preparation

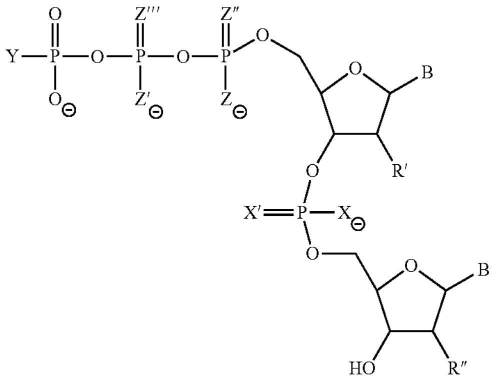

| Compound | Sequence | X | X' | Z | Z' | Z" | Z"' | R' | R" |
|---|---|---|---|---|---|---|---|---|---|
| 2228a-I | Y*AI | S | S | S | O | O | O | H | OH |
| 2229a-I | Y*AI | S | S | S | O | O | O | F | OH |
| 2230a-I | Y*AI | S | S | S | O | O | O | OEt | OH |
| 2231a-I | Y*AI | O | O | S | S | O | O | OH | OH |
| 2232a-I | Y*AI | O | O | S | S | O | O | OMe | OH |
| 2233a-I | Y*AI | O | O | S | S | O | O | H | OH |
| 2234a-I | Y*AI | O | O | S | S | O | O | F | OH |
| 2235a-I | Y*AI | O | O | S | S | O | O | OEt | OH |
| 2236a-I | Y*AI | S | O | S | S | O | O | OH | OH |
| 2237a-I | Y*AI | S | O | S | S | O | O | OMe | OH |
| 2238a-I | Y*AI | S | O | S | S | O | O | H | OH |
| 2239a-I | Y*AI | S | O | S | S | O | O | F | OH |
| 2240a-I | Y*AI | S | O | S | S | O | O | OEt | OH |
| 2241a-I | Y*AI | S | S | S | S | O | O | OH | OH |
| 2242a-I | Y*AI | S | S | S | S | O | O | OMe | OH |
| 2243a-I | Y*AI | S | S | S | S | O | O | H | OH |
| 2244a-I | Y*AI | S | S | S | S | O | O | F | OH |
| 2245a-I | Y*AI | S | S | S | S | O | O | OEt | OH |
| 2246a-I | Y*AI | O | O | S | S | S | O | OH | OH |
| 2247a-I | Y*AI | O | O | S | S | S | O | OMe | OH |
| 2248a-I | Y*AI | O | O | S | S | S | O | H | OH |
| 2249a-I | Y*AI | O | O | S | S | S | O | F | OH |
| 2250a-I | Y*AI | O | O | S | S | S | O | OEt | OH |
| 2251a-I | Y*AI | S | O | S | S | S | O | OH | OH |
| 2252a-I | Y*AI | S | O | S | S | S | O | OMe | OH |
| 2253a-I | Y*AI | S | O | S | S | S | O | H | OH |
| 2254a-I | Y*AI | S | O | S | S | S | O | F | OH |
| 2255a-I | Y*AI | S | O | S | S | S | O | OEt | OH |
| 2256a-I | Y*AI | S | S | S | S | S | O | OH | OH |
| 2257a-I | Y*AI | S | S | S | S | S | O | OMe | OH |
| 2258a-I | Y*AI | S | S | S | S | S | O | H | OH |
| 2259a-I | Y*AI | S | S | S | S | S | O | F | OH |
| 2260a-I | Y*AI | S | S | S | S | S | O | OEt | OH |
| 2261a-I | Y*AI | O | O | S | S | S | S | OH | OH |
| 2262a-I | Y*AI | O | O | S | S | S | S | OMe | OH |
| 2263a-I | Y*AI | O | O | S | S | S | S | H | OH |
| 2264a-I | Y*AI | O | O | S | S | S | S | F | OH |
| 2265a-I | Y*AI | O | O | S | S | S | S | OEt | OH |
| 2266a-I | Y*AI | S | O | S | S | S | S | OH | OH |
| 2267a-I | Y*AI | S | O | S | S | S | S | OMe | OH |
| 2268a-I | Y*AI | S | O | S | S | S | S | H | OH |
| 2269a-I | Y*AI | S | O | S | S | S | S | F | OH |
| 2270a-I | Y*AI | S | O | S | S | S | S | OEt | OH |
| 2271a-I | Y*AI | S | S | S | S | S | S | OH | OH |
| 2272a-I | Y*AI | S | S | S | S | S | S | OMe | OH |
| 2273a-I | Y*AI | S | S | S | S | S | S | H | OH |
| 2274a-I | Y*AI | S | S | S | S | S | S | F | OH |
| 2275a-I | Y*AI | S | S | S | S | S | S | OEt | OH |
| 2276a-I | Y*AI | O | O | O | S | S | S | OH | OH |
| 2277a-I | Y*AI | O | O | O | S | S | S | OMe | OH |
| 2278a-I | Y*AI | O | O | O | S | S | S | H | OH |
| 2279a-I | Y*AI | O | O | O | S | S | S | F | OH |
| 2280a-I | Y*AI | O | O | O | S | S | S | OEt | OH |
| 2281a-I | Y*AI | S | O | O | S | S | S | OH | OH |
| 2282a-I | Y*AI | S | O | O | S | S | S | OMe | OH |
| 2283a-I | Y*AI | S | O | O | S | S | S | H | OH |
| 2284a-I | Y*AI | S | O | O | S | S | S | F | OH |

TABLE 3-continued

CapA Structures for mRNA preparation

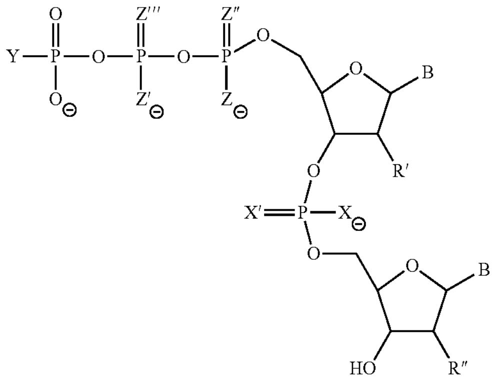

| Compound | Sequence | X | X' | Z | Z' | Z" | Z"' | R' | R" |
|---|---|---|---|---|---|---|---|---|---|
| 2285a-I | Y*AI | S | O | O | S | S | S | OEt | OH |
| 2286a-I | Y*AI | S | S | O | S | S | S | OH | OH |
| 2287a-I | Y*AI | S | S | O | S | S | S | OMe | OH |
| 2288a-I | Y*AI | S | S | O | S | S | S | H | OH |
| 2289a-I | Y*AI | S | S | O | S | S | S | F | OH |
| 2290a-I | Y*AI | S | S | O | S | S | S | OEt | OH |
| 2291a-I | Y*AI | O | O | O | O | S | S | OH | OH |
| 2292a-I | Y*AI | O | O | O | O | S | S | OMe | OH |
| 2293a-I | Y*AI | O | O | O | O | S | S | H | OH |
| 2294a-I | Y*AI | O | O | O | O | S | S | F | OH |
| 2295a-I | Y*AI | O | O | O | O | S | S | OEt | OH |
| 2296a-I | Y*AI | S | O | O | O | S | S | OH | OH |
| 2297a-I | Y*AI | S | O | O | O | S | S | OMe | OH |
| 2298a-I | Y*AI | S | O | O | O | S | S | H | OH |
| 2299a-I | Y*AI | S | O | O | O | S | S | F | OH |
| 2300a-I | Y*AI | S | O | O | O | S | S | OEt | OH |
| 2301a-I | Y*AI | S | S | O | O | S | S | OH | OH |
| 2302a-I | Y*AI | S | S | O | O | S | S | OMe | OH |
| 2303a-I | Y*AI | S | S | O | O | S | S | H | OH |
| 2304a-I | Y*AI | S | S | O | O | S | S | F | OH |
| 2305a-I | Y*AI | S | S | O | O | S | S | OEt | OH |
| 2306a-I | Y*AI | O | O | O | O | O | S | OH | OH |
| 2307a-I | Y*AI | O | O | O | O | O | S | OMe | OH |
| 2308a-I | Y*AI | O | O | O | O | O | S | H | OH |
| 2309a-I | Y*AI | O | O | O | O | O | S | F | OH |
| 2310a-I | Y*AI | O | O | O | O | O | S | OEt | OH |
| 2311a-I | Y*AI | S | O | O | O | O | S | OH | OH |
| 2312a-I | Y*AI | S | O | O | O | O | S | OMe | OH |
| 2313a-I | Y*AI | S | O | O | O | O | S | H | OH |
| 2314a-I | Y*AI | S | O | O | O | O | S | F | OH |
| 2315a-I | Y*AI | S | O | O | O | O | S | OEt | OH |
| 2316a-I | Y*AI | S | S | O | O | O | S | OH | OH |
| 2317a-I | Y*AI | S | S | O | O | O | S | OMe | OH |
| 2318a-I | Y*AI | S | S | O | O | O | S | H | OH |
| 2319a-I | Y*AI | S | S | O | O | O | S | F | OH |
| 2320a-I | Y*AI | S | S | O | O | O | S | OEt | OH |
| 2321a-I | Y*AI | O | O | S | O | S | O | OH | OH |
| 2322a-I | Y*AI | O | O | S | O | S | O | OMe | OH |
| 2323a-I | Y*AI | O | O | S | O | S | O | H | OH |
| 2324a-I | Y*AI | O | O | S | O | S | O | F | OH |
| 2325a-I | Y*AI | O | O | S | O | S | O | OEt | OH |
| 2326a-I | Y*AI | S | O | S | O | S | O | OH | OH |
| 2327a-I | Y*AI | S | O | S | O | S | O | OMe | OH |
| 2328a-I | Y*AI | S | O | S | O | S | O | H | OH |
| 2329a-I | Y*AI | S | O | S | O | S | O | F | OH |
| 2330a-I | Y*AI | S | O | S | O | S | O | OEt | OH |
| 2331a-I | Y*AI | S | S | S | O | S | O | OH | OH |
| 2332a-I | Y*AI | S | S | S | O | S | O | OMe | OH |
| 2333a-I | Y*AI | S | S | S | O | S | O | H | OH |
| 2334a-I | Y*AI | S | S | S | O | S | O | F | OH |
| 2335a-I | Y*AI | S | S | S | O | S | O | OEt | OH |
| 2336a-I | Y*AI | O | O | O | S | O | S | OH | OH |
| 2337a-I | Y*AI | O | O | O | S | O | S | OMe | OH |
| 2338a-I | Y*AI | O | O | O | S | O | S | H | OH |
| 2339a-I | Y*AI | O | O | O | S | O | S | F | OH |
| 2340a-I | Y*AI | O | O | O | S | O | S | OEt | OH |
| 2341a-I | Y*AI | S | O | O | S | O | S | OH | OH |

TABLE 3-continued

CapA Structures for mRNA preparation

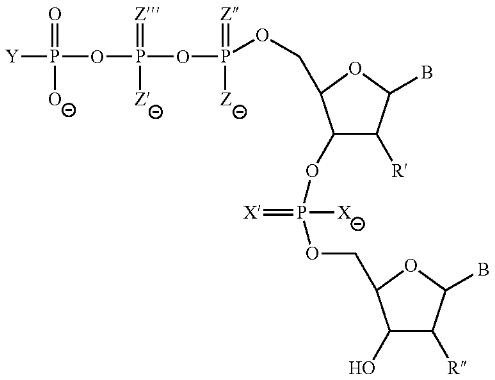

| Compound | Sequence | X | X' | Z | Z' | Z" | Z"' | R' | R" |
|---|---|---|---|---|---|---|---|---|---|
| 2342a-I | Y*AI | S | O | O | S | O | S | OMe | OH |
| 2343a-I | Y*AI | S | O | O | S | O | S | H | OH |
| 2344a-I | Y*AI | S | O | O | S | O | S | F | OH |
| 2345a-I | Y*AI | S | O | O | S | O | S | OEt | OH |
| 2346a-I | Y*AI | S | S | O | S | O | S | OH | OH |
| 2347a-I | Y*AI | S | S | O | S | O | S | OMe | OH |
| 2348a-I | Y*AI | S | S | O | S | O | S | H | OH |
| 2349a-I | Y*AI | S | S | O | S | O | S | F | OH |
| 2350a-I | Y*AI | S | S | O | S | O | S | OEt | OH |
| 2351a-I | Y*AI | O | O | O | O | O | O | OH | OMe |
| 2352a-I | Y*AI | O | O | O | O | O | O | OMe | OMe |
| 2353a-I | Y*AI | O | O | O | O | O | O | H | OMe |
| 2354a-I | Y*AI | O | O | O | O | O | O | F | OMe |
| 2355a-I | Y*AI | O | O | O | O | O | O | OEt | OMe |
| 2356a-I | Y*AI | S | O | O | O | O | O | OH | OMe |
| 2357a-I | Y*AI | S | O | O | O | O | O | OMe | OMe |
| 2358a-I | Y*AI | S | O | O | O | O | O | H | OMe |
| 2359a-I | Y*AI | S | O | O | O | O | O | F | OMe |
| 2360a-I | Y*AI | S | O | O | O | O | O | OEt | OMe |
| 2361a-I | Y*AI | S | S | O | O | O | O | OH | OMe |
| 2362a-I | Y*AI | S | S | O | O | O | O | OMe | OMe |
| 2363a-I | Y*AI | S | S | O | O | O | O | H | OMe |
| 2364a-I | Y*AI | S | S | O | O | O | O | F | OMe |
| 2365a-I | Y*AI | S | S | O | O | O | O | OEt | OMe |
| 2366a-I | Y*AI | O | O | S | O | O | O | OH | OMe |
| 2367a-I | Y*AI | O | O | S | O | O | O | OMe | OMe |
| 2368a-I | Y*AI | O | O | S | O | O | O | H | OMe |
| 2369a-I | Y*AI | O | O | S | O | O | O | F | OMe |
| 2370a-I | Y*AI | O | O | S | O | O | O | OEt | OMe |
| 2371a-I | Y*AI | S | O | S | O | O | O | OH | OMe |
| 2372a-I | Y*AI | S | O | S | O | O | O | OMe | OMe |
| 2373a-I | Y*AI | S | O | S | O | O | O | H | OMe |
| 2374a-I | Y*AI | S | O | S | O | O | O | F | OMe |
| 2375a-I | Y*AI | S | O | S | O | O | O | OEt | OMe |
| 2376a-I | Y*AI | S | S | S | O | O | O | OH | OMe |
| 2377a-I | Y*AI | S | S | S | O | O | O | OMe | OMe |
| 2378a-I | Y*AI | S | S | S | O | O | O | H | OMe |
| 2379a-I | Y*AI | S | S | S | O | O | O | F | OMe |
| 2380a-I | Y*AI | S | S | S | O | O | O | OEt | OMe |
| 2381a-I | Y*AI | O | O | S | S | O | O | OH | OMe |
| 2382a-I | Y*AI | O | O | S | S | O | O | OMe | OMe |
| 2383a-I | Y*AI | O | O | S | S | O | O | H | OMe |
| 2384a-I | Y*AI | O | O | S | S | O | O | F | OMe |
| 2385a-I | Y*AI | O | O | S | S | O | O | OEt | OMe |
| 2386a-I | Y*AI | S | O | S | S | O | O | OH | OMe |
| 2387a-I | Y*AI | S | O | S | S | O | O | OMe | OMe |
| 2388a-I | Y*AI | S | O | S | S | O | O | H | OMe |
| 2389a-I | Y*AI | S | O | S | S | O | O | F | OMe |
| 2390a-I | Y*AI | S | O | S | S | O | O | OEt | OMe |
| 2391a-I | Y*AI | S | S | S | S | O | O | OH | OMe |
| 2392a-I | Y*AI | S | S | S | S | O | O | OMe | OMe |
| 2393a-I | Y*AI | S | S | S | S | O | O | H | OMe |
| 2394a-I | Y*AI | S | S | S | S | O | O | F | OMe |
| 2395a-I | Y*AI | S | S | S | S | O | O | OEt | OMe |
| 2396a-I | Y*AI | O | O | S | S | S | O | OH | OMe |
| 2397a-I | Y*AI | O | O | S | S | S | O | OMe | OMe |
| 2398a-I | Y*AI | O | O | S | S | S | O | H | OMe |

TABLE 3-continued

CapA Structures for mRNA preparation

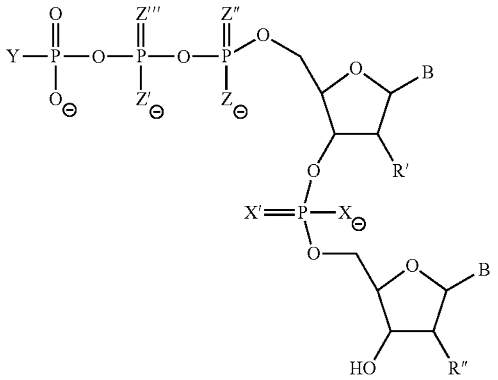

| Compound | Sequence | X | X' | Z | Z' | Z" | Z"' | R' | R" |
|---|---|---|---|---|---|---|---|---|---|
| 2399a-I | Y*AI | O | O | S | S | S | O | F | OMe |
| 2400a-I | Y*AI | O | O | S | S | S | O | OEt | OMe |
| 2401a-I | Y*AI | S | O | S | S | S | O | OH | OMe |
| 2402a-I | Y*AI | S | O | S | S | S | O | OMe | OMe |
| 2403a-I | Y*AI | S | O | S | S | S | O | H | OMe |
| 2404a-I | Y*AI | S | O | S | S | S | O | F | OMe |
| 2405a-I | Y*AI | S | O | S | S | S | O | OEt | OMe |
| 2406a-I | Y*AI | S | S | S | S | S | O | OH | OMe |
| 2407a-I | Y*AI | S | S | S | S | S | O | OMe | OMe |
| 2408a-I | Y*AI | S | S | S | S | S | O | H | OMe |
| 2409a-I | Y*AI | S | S | S | S | S | O | F | OMe |
| 2410a-I | Y*AI | S | S | S | S | S | O | OEt | OMe |
| 2411a-I | Y*AI | O | O | S | S | S | S | OH | OMe |
| 2412a-I | Y*AI | O | O | S | S | S | S | OMe | OMe |
| 2413a-I | Y*AI | O | O | S | S | S | S | H | OMe |
| 2414a-I | Y*AI | O | O | S | S | S | S | F | OMe |
| 2415a-I | Y*AI | O | O | S | S | S | S | OEt | OMe |
| 2416a-I | Y*AI | S | O | S | S | S | S | OH | OMe |
| 2417a-I | Y*AI | S | O | S | S | S | S | OMe | OMe |
| 2418a-I | Y*AI | S | O | S | S | S | S | H | OMe |
| 2419a-I | Y*AI | S | O | S | S | S | S | F | OMe |
| 2420a-I | Y*AI | S | O | S | S | S | S | OE | OMe |
| 2421a-I | Y*AI | S | S | S | S | S | S | OH | OMe |
| 2422a-I | Y*AI | S | S | S | S | S | S | OMe | OMe |
| 2423a-I | Y*AI | S | S | S | S | S | S | H | OMe |
| 2424a-I | Y*AI | S | S | S | S | S | S | F | OMe |
| 2425a-I | Y*AI | S | S | S | S | S | S | OEt | OMe |
| 2426a-I | Y*AI | O | O | O | S | S | S | OH | OMe |
| 2427a-I | Y*AI | O | O | O | S | S | S | OMe | OMe |
| 2428a-I | Y*AI | O | O | O | S | S | S | H | OMe |
| 2429a-I | Y*AI | O | O | O | S | S | S | F | OMe |
| 2430a-I | Y*AI | O | O | O | S | S | S | OEt | OMe |
| 2431a-I | Y*AI | S | O | O | S | S | S | OH | OMe |
| 2432a-I | Y*AI | S | O | O | S | S | S | OMe | OMe |
| 2433a-I | Y*AI | S | O | O | S | S | S | H | OMe |
| 2434a-I | Y*AI | S | O | O | S | S | S | F | OMe |
| 2435a-I | Y*AI | S | O | O | S | S | S | OEt | OMe |
| 2436a-I | Y*AI | S | S | O | S | S | S | OH | OMe |
| 2437a-I | Y*AI | S | S | O | S | S | S | OMe | OMe |
| 2438a-I | Y*AI | S | S | O | S | S | S | H | OMe |
| 2439a-I | Y*AI | S | S | O | S | S | S | F | OMe |
| 2440a-I | Y*AI | S | S | O | S | S | S | OEt | OMe |
| 2441a-I | Y*AI | O | O | O | O | S | S | OH | OMe |
| 2442a-I | Y*AI | O | O | O | O | S | S | OMe | OMe |
| 2443a-I | Y*AI | O | O | O | O | S | S | H | OMe |
| 2444a-I | Y*AI | O | O | O | O | S | S | F | OMe |
| 2445a-I | Y*AI | O | O | O | O | S | S | OEt | OMe |
| 2446a-I | Y*AI | S | O | O | O | S | S | OH | OMe |
| 2447a-I | Y*AI | S | O | O | O | S | S | OMe | OMe |
| 2448a-I | Y*AI | S | O | O | O | S | S | H | OMe |
| 2449a-I | Y*AI | S | O | O | O | S | S | F | OMe |
| 2450a-I | Y*AI | S | O | O | O | S | S | OEt | OMe |
| 2451a-I | Y*AI | S | S | O | O | S | S | OH | OMe |
| 2452a-I | Y*AI | S | S | O | O | S | S | OMe | OMe |
| 2453a-I | Y*AI | S | S | O | O | S | S | H | OMe |
| 2454a-I | Y*AI | S | S | O | O | S | S | F | OMe |
| 2455a-I | Y*AI | S | S | O | O | S | S | OEt | OMc |

TABLE 3-continued

CapA Structures for mRNA preparation

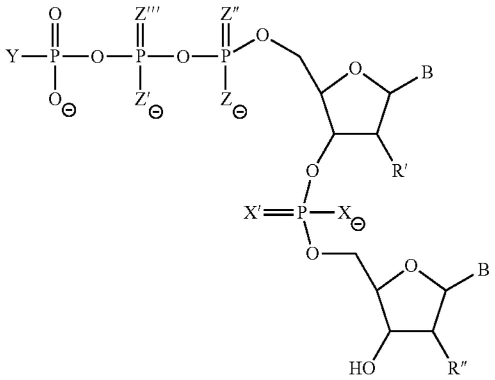

| Compound | Sequence | X | X' | Z | Z' | Z" | Z"' | R' | R" |
|---|---|---|---|---|---|---|---|---|---|
| 2456a-I | Y*AI | O | O | O | O | O | S | OH | OMe |
| 2457a-I | Y*AI | O | O | O | O | O | S | OMe | OMe |
| 2458a-I | Y*AI | O | O | O | O | O | S | H | OMe |
| 2459a-I | Y*AI | O | O | O | O | O | S | F | OMe |
| 2460a-I | Y*AI | O | O | O | O | O | S | OEt | OMe |
| 2461a-I | Y*AI | S | O | O | O | O | S | OH | OMe |
| 2462a-I | Y*AI | S | O | O | O | O | S | OMe | OMe |
| 2463a-I | Y*AI | S | O | O | O | O | S | H | OMe |
| 2464a-I | Y*AI | S | O | O | O | O | S | F | OMe |
| 2465a-I | Y*AI | S | O | O | O | O | S | OEt | OMe |
| 2466a-I | Y*AI | S | S | O | O | O | S | OH | OMe |
| 2467a-I | Y*AI | S | S | O | O | O | S | OMe | OMe |
| 2468a-I | Y*AI | S | S | O | O | O | S | H | OMe |
| 2469a-I | Y*AI | S | S | O | O | O | S | F | OMe |
| 2470a-I | Y*AI | S | S | O | O | O | S | OEt | OMe |
| 2471a-I | Y*AI | O | O | S | O | S | O | OH | OMe |
| 2472a-I | Y*AI | O | O | S | O | S | O | OMe | OMe |
| 2473a-I | Y*AI | O | O | S | O | S | O | H | OMe |
| 2474a-I | Y*AI | O | O | S | O | S | O | F | OMe |
| 2475a-I | Y*AI | O | O | S | O | S | O | OEt | OMe |
| 2476a-I | Y*AI | S | O | S | O | S | O | OH | OMe |
| 2477a-I | Y*AI | S | O | S | O | S | O | OMe | OMe |
| 2478a-I | Y*AI | S | O | S | O | S | O | H | OMe |
| 2479a-I | Y*AI | S | O | S | O | S | O | F | OMe |
| 2480a-I | Y*AI | S | O | S | O | S | O | OEt | OMe |
| 2481a-I | Y*AI | S | S | S | O | S | O | OH | OMe |
| 2482a-I | Y*AI | S | S | S | O | S | O | OMe | OMe |
| 2483a-I | Y*AI | S | S | S | O | S | O | H | OMe |
| 2484a-I | Y*AI | S | S | S | O | S | O | F | OMe |
| 2485a-I | Y*AI | S | S | S | O | S | O | OEt | OMe |
| 2486a-I | Y*AI | O | O | O | S | O | S | OH | OMe |
| 2487a-I | Y*AI | O | O | O | S | O | S | OMe | OMe |
| 2488a-I | Y*AI | O | O | O | S | O | S | H | OMe |
| 2489a-I | Y*AI | O | O | O | S | O | S | F | OMe |
| 2490a-I | Y*AI | O | O | O | S | O | S | OEt | OMe |
| 2491a-I | Y*AI | S | O | O | S | O | S | OH | OMe |
| 2492a-I | Y*AI | S | O | O | S | O | S | OMe | OMe |
| 2493a-I | Y*AI | S | O | O | S | O | S | H | OMe |
| 2494a-I | Y*AI | S | O | O | S | O | S | F | OMe |
| 2495a-I | Y*AI | S | O | O | S | O | S | OEt | OMe |
| 2496a-I | Y*AI | S | S | O | S | O | S | OH | OMe |
| 2497a-I | Y*AI | S | S | O | S | O | S | OMe | OMe |
| 2498a-I | Y*AI | S | S | O | S | O | S | H | OMe |
| 2499a-I | Y*AI | S | S | O | S | O | S | F | OMe |
| 2500a-I | Y*AI | S | S | O | S | O | S | OEt | OMe |
| 2501a-I | Y*AT | O | O | O | O | O | O | OH | OH |
| 2502a-I | Y*AT | O | O | O | O | O | O | OMe | OH |
| 2503a-I | Y*AT | O | O | O | O | O | O | H | OH |
| 2504a-I | Y*AT | O | O | O | O | O | O | F | OH |
| 2505a-I | Y*AT | O | O | O | O | O | O | OEt | OH |
| 2506a-I | Y*AT | S | O | O | O | O | O | OH | OH |
| 2507a-I | Y*AT | S | O | O | O | O | O | OMe | OH |
| 2508a-I | Y*AT | S | O | O | O | O | O | H | OH |
| 2509a-I | Y*AT | S | O | O | O | O | O | F | OH |
| 2510a-I | Y*AT | S | O | O | O | O | O | OEt | OH |
| 2511a-I | Y*AT | S | S | O | O | O | O | OH | OH |
| 2512a-I | Y*AT | S | S | O | O | O | O | OMe | OH |

TABLE 3-continued

CapA Structures for mRNA preparation

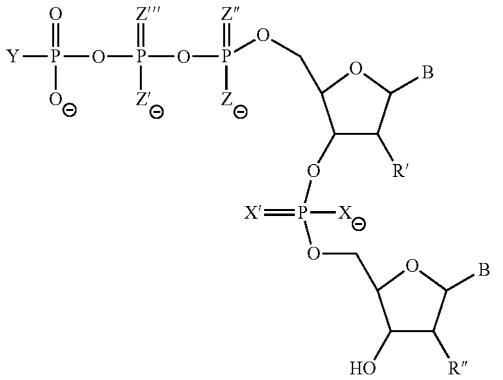

| Compound | Sequence | X | X' | Z | Z' | Z'' | Z''' | R' | R'' |
|---|---|---|---|---|---|---|---|---|---|
| 2513a-I | Y*AT | S | S | O | O | O | O | H | OH |
| 2514a-I | Y*AT | S | S | O | O | O | O | F | OH |
| 2515a-I | Y*AT | S | S | O | O | O | O | OEt | OH |
| 2516a-I | Y*AT | O | O | S | O | O | O | OH | OH |
| 2517a-I | Y*AT | O | O | S | O | O | O | OMe | OH |
| 2518a-I | Y*AT | O | O | S | O | O | O | H | OH |
| 2519a-I | Y*AT | O | O | S | O | O | O | F | OH |
| 2520a-I | Y*AT | O | O | S | O | O | O | OEt | OH |
| 2521a-I | Y*AT | S | O | S | O | O | O | OH | OH |
| 2522a-I | Y*AT | S | O | S | O | O | O | OMe | OH |
| 2523a-I | Y*AT | S | O | S | O | O | O | H | OH |
| 2524a-I | Y*AT | S | O | S | O | O | O | F | OH |
| 2525a-I | Y*AT | S | O | S | O | O | O | OEt | OH |
| 2526a-I | Y*AT | S | S | S | O | O | O | OH | OH |
| 2527a-I | Y*AT | S | S | S | O | O | O | OMe | OH |
| 2528a-I | Y*AT | S | S | S | O | O | O | H | OH |
| 2529a-I | Y*AT | S | S | S | O | O | O | F | OH |
| 2530a-I | Y*AT | S | S | S | O | O | O | OEt | OH |
| 2531a-I | Y*AT | O | O | S | S | O | O | OH | OH |
| 2532a-I | Y*AT | O | O | S | S | O | O | OMe | OH |
| 2533a-I | Y*AT | O | O | S | S | O | O | H | OH |
| 2534a-I | Y*AT | O | O | S | S | O | O | F | OH |
| 2535a-I | Y*AT | O | O | S | S | O | O | OEt | OH |
| 2536a-I | Y*AT | S | O | S | S | O | O | OH | OH |
| 2537a-I | Y*AT | S | O | S | S | O | O | OMe | OH |
| 2538a-I | Y*AT | S | O | S | S | O | O | H | OH |
| 2539a-I | Y*AT | S | O | S | S | O | O | F | OH |
| 2540a-I | Y*AT | S | O | S | S | O | O | OEt | OH |
| 2541a-I | Y*AT | S | S | S | S | O | O | OH | OH |
| 2542a-I | Y*AT | S | S | S | S | O | O | OMe | OH |
| 2543a-I | Y*AT | S | S | S | S | O | O | H | OH |
| 2544a-I | Y*AT | S | S | S | S | O | O | F | OH |
| 2545a-I | Y*AT | S | S | S | S | O | O | OEt | OH |
| 2546a-I | Y*AT | O | O | S | S | S | O | OH | OH |
| 2547a-I | Y*AT | O | O | S | S | S | O | OMe | OH |
| 2548a-I | Y*AT | O | O | S | S | S | O | H | OH |
| 2549a-I | Y*AT | O | O | S | S | S | O | F | OH |
| 2550a-I | Y*AT | O | O | S | S | S | O | OEt | OH |
| 2551a-I | Y*AT | S | O | S | S | S | O | OH | OH |
| 2552a-I | Y*AT | S | O | S | S | S | O | OMe | OH |
| 2553a-I | Y*AT | S | O | S | S | S | O | H | OH |
| 2554a-I | Y*AT | S | O | S | S | S | O | F | OH |
| 2555a-I | Y*AT | S | O | S | S | S | O | OEt | OH |
| 2556a-I | Y*AT | S | S | S | S | S | O | OH | OH |
| 2557a-I | Y*AT | S | S | S | S | S | O | OMe | OH |
| 2558a-I | Y*AT | S | S | S | S | S | O | H | OH |
| 2559a-I | Y*AT | S | S | S | S | S | O | F | OH |
| 2560a-I | Y*AT | S | S | S | S | S | O | OEt | OH |
| 2561a-I | Y*AI | O | O | S | S | S | S | OH | OH |
| 2562a-I | Y*AT | O | O | S | S | S | S | OMe | OH |
| 2563a-I | Y*AT | O | O | S | S | S | S | H | OH |
| 2564a-I | Y*AT | O | O | S | S | S | S | F | OH |
| 2565a-I | Y*AT | O | O | S | S | S | S | OEt | OH |
| 2566a-I | Y*AT | S | O | S | S | S | S | OH | OH |
| 2567a-I | Y*AT | S | O | S | S | S | S | OMe | OH |
| 2568a-I | Y*AT | S | O | S | S | S | S | H | OH |
| 2569a-I | Y*AT | S | O | S | S | S | S | F | OH |

TABLE 3-continued

CapA Structures for mRNA preparation

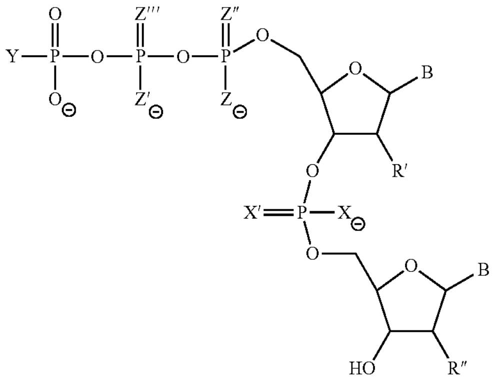

| Compound | Sequence | X | X' | Z | Z' | Z'' | Z''' | R' | R'' |
|---|---|---|---|---|---|---|---|---|---|
| 2570a-I | Y*AT | S | O | S | S | S | S | OEt | OH |
| 2571a-I | Y*AT | S | S | S | S | S | S | OH | OH |
| 2572a-I | Y*AT | S | S | S | S | S | S | OMe | OH |
| 2573a-I | Y*AT | S | S | S | S | S | S | H | OH |
| 2574a-I | Y*AT | S | S | S | S | S | S | F | OH |
| 2575a-I | Y*AT | S | S | S | S | S | S | OEt | OH |
| 2576a-I | Y*AT | O | O | O | S | S | S | OH | OH |
| 2577a-I | Y*AT | O | O | O | S | S | S | OMe | OH |
| 2578a-I | Y*AT | O | O | O | S | S | S | H | OH |
| 2579a-I | Y*AT | O | O | O | S | S | S | F | OH |
| 2580a-I | Y*AT | O | O | O | S | S | S | OEt | OH |
| 2581a-I | Y*AT | S | O | O | S | S | S | OH | OH |
| 2582a-I | Y*AT | S | O | O | S | S | S | OMe | OH |
| 2583a-I | Y*AT | S | O | O | S | S | S | H | OH |
| 2584a-I | Y*AT | S | O | O | S | S | S | F | OH |
| 2585a-I | Y*AT | S | O | O | S | S | S | OEt | OH |
| 2586a-I | Y*AT | S | O | O | S | S | S | OH | OH |
| 2587a-I | Y*AT | S | S | O | S | S | S | OMe | OH |
| 2588a-I | Y*AT | S | S | O | S | S | S | H | OH |
| 2589a-I | Y*AT | S | S | O | S | S | S | F | OH |
| 2590a-I | Y*AT | S | S | O | S | S | S | OEt | OH |
| 2591a-I | Y*AT | O | O | O | O | S | S | OH | OH |
| 2592a-I | Y*AT | O | O | O | O | S | S | OMe | OH |
| 2593a-I | Y*AT | O | O | O | O | S | S | H | OH |
| 2594a-I | Y*AT | O | O | O | O | S | S | F | OH |
| 2595a-I | Y*AT | O | O | O | O | S | S | OEt | OH |
| 2596a-I | Y*AT | S | O | O | O | S | S | OH | OH |
| 2597a-I | Y*AT | S | O | O | O | S | S | OMe | OH |
| 2598a-I | Y*AT | S | O | O | O | S | S | H | OH |
| 2599a-I | Y*AT | S | O | O | O | S | S | F | OH |
| 2600a-I | Y*AT | S | O | O | O | S | S | OEt | OH |
| 2601a-I | Y*AT | S | S | O | O | S | S | OH | OH |
| 2602a-I | Y*AT | S | S | O | O | S | S | OMe | OH |
| 2603a-I | Y*AT | S | S | O | O | S | S | H | OH |
| 2604a-I | Y*AT | S | S | O | O | S | S | F | OH |
| 2605a-I | Y*AT | S | S | O | O | S | S | OEt | OH |
| 2606a-I | Y*AT | O | O | O | O | O | S | OH | OH |
| 2607a-I | Y*AT | O | O | O | O | O | S | OMe | OH |
| 2608a-I | Y*AT | O | O | O | O | O | S | H | OH |
| 2609a-I | Y*AT | O | O | O | O | O | S | F | OH |
| 2610a-I | Y*AT | O | O | O | O | O | S | OEt | OH |
| 2611a-I | Y*AT | S | O | O | O | O | S | OH | OH |
| 2612a-I | Y*AT | S | O | O | O | O | S | OMe | OH |
| 2613a-I | Y*AT | S | O | O | O | O | S | H | OH |
| 2614a-I | Y*AT | S | O | O | O | O | S | F | OH |
| 2615a-I | Y*AT | S | O | O | O | O | S | OEt | OH |
| 2616a-I | Y*AT | S | S | O | O | O | S | OH | OH |
| 2617a-I | Y*AT | S | S | O | O | O | S | OMe | OH |
| 2618a-I | Y*AT | S | S | O | O | O | S | H | OH |
| 2619a-I | Y*AT | S | S | O | O | O | S | F | OH |
| 2620a-I | Y*AT | S | S | O | O | O | S | OEt | OH |
| 2621a-I | Y*AT | O | O | S | O | S | O | OH | OH |
| 2622a-I | Y*AT | O | O | S | O | S | O | OMe | OH |
| 2623a-I | Y*AT | O | O | S | O | S | O | H | OH |
| 2624a-I | Y*AT | O | O | S | O | S | O | F | OH |
| 2625a-I | Y*AT | O | O | S | O | S | O | OEt | OH |
| 2626a-I | Y*AT | S | O | S | O | S | O | OH | OH |

TABLE 3-continued

CapA Structures for mRNA preparation

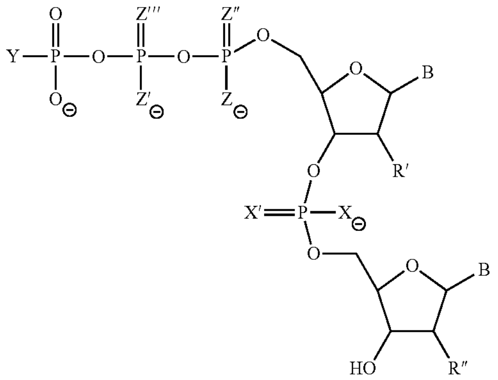

| Compound | Sequence | X | X' | Z | Z' | Z" | Z''' | R' | R" |
|---|---|---|---|---|---|---|---|---|---|
| 2627a-I | Y*AT | S | O | S | O | S | O | OMe | OH |
| 2628a-I | Y*AT | S | O | S | O | S | O | H | OH |
| 2629a-I | Y*AT | S | O | S | O | S | O | F | OH |
| 2630a-I | Y*AT | S | O | S | O | S | O | OEt | OH |
| 2631a-I | Y*AT | S | S | S | O | S | O | OH | OH |
| 2632a-I | Y*AT | S | S | S | O | S | O | OMe | OH |
| 2633a-I | Y*AT | S | S | S | O | S | O | H | OH |
| 2634a-I | Y*AT | S | S | S | O | S | O | F | OH |
| 2635a-I | Y*AT | S | S | S | O | S | O | OEt | OH |
| 2636a-I | Y*AT | O | O | O | S | O | S | OH | OH |
| 2637a-I | Y*AT | O | O | O | S | O | S | OMe | OH |
| 2638a-I | Y*AT | O | O | O | S | O | S | H | OH |
| 2639a-I | Y*AT | O | O | O | S | O | S | F | OH |
| 2640a-I | Y*AT | O | O | O | S | O | S | OEt | OH |
| 2641a-I | Y*AT | S | O | O | S | O | S | OH | OH |
| 2642a-I | Y*AT | S | O | O | S | O | S | OMe | OH |
| 2643a-I | Y*AT | S | O | O | S | O | S | H | OH |
| 2644a-I | Y*AT | S | O | O | S | O | S | F | OH |
| 2645a-I | Y*AT | S | O | O | S | O | S | OEt | OH |
| 2646a-I | Y*AT | S | S | O | S | O | S | OH | OH |
| 2647a-I | Y*AT | S | S | O | S | O | S | OMe | OH |
| 2648a-I | Y*AT | S | S | O | S | O | S | H | OH |
| 2649a-I | Y*AT | S | S | O | S | O | S | F | OH |
| 2650a-I | Y*AT | S | S | O | S | O | S | OEt | OH |
| 2651a-I | Y*AT | O | O | O | O | O | O | OH | OMe |
| 2652a-I | Y*AT | O | O | O | O | O | O | OMe | OMe |
| 2653a-I | Y*AT | O | O | O | O | O | O | H | OMe |
| 2654a-I | Y*AT | O | O | O | O | O | O | F | OMe |
| 2655a-I | Y*AT | O | O | O | O | O | O | OEt | OMe |
| 2656a-I | Y*AT | S | O | O | O | O | O | OH | OMe |
| 2657a-I | Y*AT | S | O | O | O | O | O | OMe | OMe |
| 2658a-I | Y*AT | S | O | O | O | O | O | H | OMe |
| 2659a-I | Y*AT | S | O | O | O | O | O | F | OMe |
| 2660a-I | Y*AT | S | O | O | O | O | O | OEt | OMe |
| 2661a-I | Y*AT | S | S | O | O | O | O | OH | OMe |
| 2662a-I | Y*AT | S | S | O | O | O | O | OMe | OMe |
| 2663a-I | Y*AT | S | S | O | O | O | O | H | OMe |
| 2664a-I | Y*AT | S | S | O | O | O | O | F | OMe |
| 2665a-I | Y*AT | S | S | O | O | O | O | OEt | OMe |
| 2666a-I | Y*AT | O | O | S | O | O | O | OH | OMe |
| 2667a-I | Y*AT | O | O | S | O | O | O | OMe | OMe |
| 2668a-I | Y*AT | O | O | S | O | O | O | H | OMe |
| 2669a-I | Y*AT | O | O | S | O | O | O | F | OMe |
| 2670a-I | Y*AT | O | O | S | O | O | O | OEt | OMe |
| 2671a-I | Y*AT | S | O | S | O | O | O | OH | OMe |
| 2672a-I | Y*AT | S | O | S | O | O | O | OMe | OMe |
| 2673a-I | Y*AT | S | O | S | O | O | O | H | OMe |
| 2674a-I | Y*AT | S | O | S | O | O | O | F | OMe |
| 2675a-I | Y*AT | S | O | S | O | O | O | OEt | OMe |
| 2676a-I | Y*AT | S | S | S | O | O | O | OH | OMe |
| 2677a-I | Y*AT | S | S | S | O | O | O | OMe | OMe |
| 2678a-I | Y*AT | S | S | S | O | O | O | H | OMe |
| 2679a-I | Y*AT | S | S | S | O | O | O | F | OMe |
| 2680a-I | Y*AT | S | S | S | O | O | O | OEt | OMe |
| 2681a-I | Y*AT | O | O | S | S | O | O | OH | OMe |
| 2682a-I | Y*AT | O | O | S | S | O | O | OMe | OMe |
| 2683a-I | Y*AT | O | O | S | S | O | O | H | OMe |

TABLE 3-continued

CapA Structures for mRNA preparation

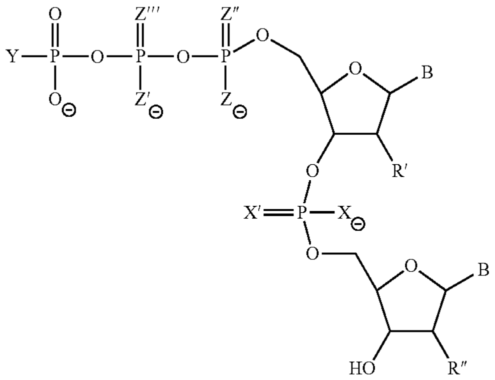

| Compound | Sequence | X | X' | Z | Z' | Z" | Z''' | R' | R" |
|---|---|---|---|---|---|---|---|---|---|
| 2684a-I | Y*AT | O | O | S | S | O | O | F | OMe |
| 2685a-I | Y*AT | O | O | S | S | O | O | OEt | OMe |
| 2686a-I | Y*AT | S | O | S | S | O | O | OH | OMe |
| 2687a-I | Y*AT | S | O | S | S | O | O | OMe | OMe |
| 2688a-I | Y*AT | S | O | S | S | O | O | H | OMe |
| 2689a-I | Y*AT | S | O | S | S | O | O | F | OMe |
| 2690a-I | Y*AT | S | O | S | S | O | O | OEt | OMe |
| 2691a-I | Y*AT | S | S | S | S | O | O | OH | OMe |
| 2692a-I | Y*AT | S | S | S | S | O | O | OMe | OMe |
| 2693a-I | Y*AT | S | S | S | S | O | O | H | OMe |
| 2694a-I | Y*AT | S | S | S | S | O | O | F | OMe |
| 2695a-I | Y*AT | S | S | S | S | O | O | OEt | OMe |
| 2696a-I | Y*AT | O | O | S | S | S | O | OH | OMe |
| 2697a-I | Y*AT | O | O | S | S | S | O | OMe | OMe |
| 2698a-I | Y*AT | O | O | S | S | S | O | H | OMe |
| 2699a-I | Y*AT | O | O | S | S | S | O | F | OMe |
| 2700a-I | Y*AT | O | O | S | S | S | O | OEt | OMe |
| 2701a-I | Y*AT | S | O | S | S | S | O | OH | OMe |
| 2702a-I | Y*AT | S | O | S | S | S | O | OMe | OMe |
| 2703a-I | Y*AT | S | O | S | S | S | O | H | OMe |
| 2704a-I | Y*AT | S | O | S | S | S | O | F | OMe |
| 2705a-I | Y*AT | S | O | S | S | S | O | OEt | OMe |
| 2706a-I | Y*AT | S | S | S | S | S | O | OH | OMe |
| 2707a-I | Y*AT | S | S | S | S | S | O | OMe | OMe |
| 2708a-I | Y*AT | S | S | S | S | S | O | H | OMe |
| 2709a-I | Y*AT | S | S | S | S | S | O | F | OMe |
| 2710a-I | Y*AT | S | S | S | S | S | O | OEt | OMe |
| 2711a-I | Y*AT | O | O | S | S | S | S | OH | OMe |
| 2712a-I | Y*AT | O | O | S | S | S | S | OMe | OMe |
| 2713a-I | Y*AT | O | O | S | S | S | S | H | OMe |
| 2714a-I | Y*AT | O | O | S | S | S | S | F | OMe |
| 2715a-I | Y*AT | O | O | S | S | S | S | OEt | OMe |
| 2716a-I | Y*AT | S | O | S | S | S | S | OH | OMe |
| 2717a-I | Y*AT | S | O | S | S | S | S | OMe | OMe |
| 2718a-I | Y*AT | S | O | S | S | S | S | H | OMe |
| 2719a-I | Y*AT | S | O | S | S | S | S | F | OMe |
| 2720a-I | Y*AT | S | O | S | S | S | S | OEt | OMe |
| 2721a-I | Y*AT | S | S | S | S | S | S | OH | OMe |
| 2722a-1 | Y*AT | S | S | S | S | S | S | OMe | OMe |
| 2723a-I | Y*AT | S | S | S | S | S | S | H | OMe |
| 2724a-I | Y*AT | S | S | S | S | S | S | F | OMe |
| 2725a-I | Y*AT | S | S | S | S | S | S | OEt | OMe |
| 2726a-I | Y*AT | O | O | O | S | S | S | OH | OMe |
| 2727a-I | Y*AT | O | O | O | S | S | S | OMe | OMe |
| 2728a-I | Y*AT | O | O | O | S | S | S | H | OMe |
| 2729a-I | Y*AT | O | O | O | S | S | S | F | OMe |
| 2730a-I | Y*AT | O | O | O | S | S | S | OEt | OMe |
| 2731a-I | Y*AT | S | O | O | S | S | S | OH | OMe |
| 2732a-I | Y*AT | S | O | O | S | S | S | OMe | OMe |
| 2733a-I | Y*AT | S | O | O | S | S | S | H | OMe |
| 2734a-I | Y*AT | S | O | O | S | S | S | F | OMe |
| 2735a-I | Y*AT | S | O | O | S | S | S | OEt | OMe |
| 2736a-I | Y*AT | S | S | O | S | S | S | OH | OMe |
| 2737a-I | Y*AT | S | S | O | S | S | S | OMe | OMe |
| 2738a-I | Y*AT | S | S | O | S | S | S | H | OMe |
| 2739a-I | Y*AT | S | S | O | S | S | S | F | OMe |
| 2740a-I | Y*AT | S | S | O | S | S | S | OEt | OMc |

TABLE 3-continued

CapA Structures for mRNA preparation

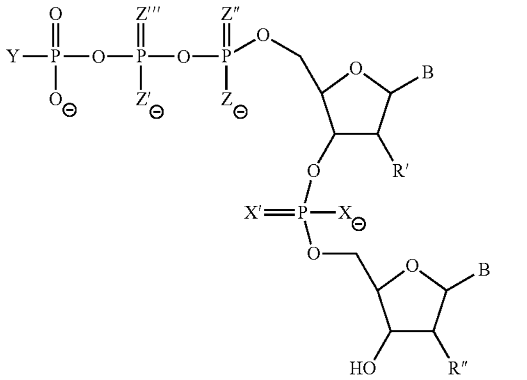

| Compound | Sequence | X | X' | Z | Z' | Z'' | Z''' | R' | R'' |
|---|---|---|---|---|---|---|---|---|---|
| 2741a-I | Y*AT | O | O | O | O | S | S | OH | OMe |
| 2742a-I | Y*AT | O | O | O | O | S | S | OMe | OMe |
| 2743a-I | Y*AT | O | O | O | O | S | S | H | OMe |
| 2744a-I | Y*AT | O | O | O | O | S | S | F | OMe |
| 2745a-I | Y*AT | O | O | O | O | S | S | OEt | OMe |
| 2746a-I | Y*AT | S | O | O | O | S | S | OH | OMe |
| 2747a-I | Y*AT | S | O | O | O | S | S | OMe | OMe |
| 2748a-I | Y*AT | S | O | O | O | S | S | H | OMe |
| 2749a-I | Y*AT | S | O | O | O | S | S | F | OMe |
| 2750a-I | Y*AT | S | O | O | O | S | S | OEt | OMe |
| 2751a-I | Y*AT | S | S | O | O | S | S | OH | OMe |
| 2752a-I | Y*AT | S | S | O | O | S | S | OMe | OMe |
| 2753a-I | Y*AT | S | S | O | O | S | S | H | OMe |
| 2754a-I | Y*AT | S | S | O | O | S | S | F | OMe |
| 2755a-I | Y*AT | S | S | O | O | S | S | OEt | OMe |
| 2756a-I | Y*AT | O | O | O | O | O | S | OH | OMe |
| 2757a-I | Y*AT | O | O | O | O | O | S | OMe | OMe |
| 2758a-I | Y*AT | O | O | O | O | O | S | H | OMe |
| 2759a-I | Y*AT | O | O | O | O | O | S | F | OMe |
| 2760a-I | Y*AT | O | O | O | O | O | S | OEt | OMe |
| 2761a-I | Y*AT | S | O | O | O | O | S | OH | OMe |
| 2762a-I | Y*AT | S | O | O | O | O | S | OMe | OMe |
| 2763a-I | Y*AT | S | O | O | O | O | S | H | OMe |
| 2764a-I | Y*AT | S | O | O | O | O | S | F | OMe |
| 2765a-I | Y*AT | S | O | O | O | O | S | OEt | OMe |
| 2766a-I | Y*AT | S | S | O | O | O | S | OH | OMe |
| 2767a-I | Y*AT | S | S | O | O | O | S | OMe | OMe |
| 2768a-I | Y*AT | S | S | O | O | O | S | H | OMe |
| 2769a-I | Y*AT | S | S | O | O | O | S | F | OMe |
| 2770a-I | Y*AT | S | S | O | O | O | S | OEt | OMe |
| 2771a-I | Y*AT | O | O | S | O | S | O | OH | OMe |
| 2772a-I | Y*AT | O | O | S | O | S | O | OMe | OMe |
| 2773a-I | Y*AT | O | O | S | O | S | O | H | OMe |
| 2774a-I | Y*AT | O | O | S | O | S | O | F | OMe |
| 2775a-I | Y*AT | O | O | S | O | S | O | OEt | OMe |
| 2776a-I | Y*AT | S | O | S | O | S | O | OH | OMe |
| 2777a-I | Y*AT | S | O | S | O | S | O | OMe | OMe |
| 2778a-I | Y*AT | S | O | S | O | S | O | H | OMe |
| 2779a-I | Y*AT | S | O | S | O | S | O | F | OMe |
| 2780a-I | Y*AT | S | O | S | O | S | O | OEt | OMe |
| 2781a-I | Y*AT | S | S | S | O | S | O | OH | OMe |
| 2782a-I | Y*AT | S | S | S | O | S | O | OMe | OMe |
| 2783a-I | Y*AT | S | S | S | O | S | O | H | OMe |
| 2784a-I | Y*AT | S | S | S | O | S | O | F | OMe |
| 2785a-I | Y*AT | S | S | S | O | S | O | OEt | OMe |
| 2786a-I | Y*AT | O | O | O | S | O | S | OH | OMe |
| 2787a-I | Y*AT | O | O | O | S | O | S | OMe | OMe |
| 2788a-I | Y*AT | O | O | O | S | O | S | H | OMe |
| 2789a-I | Y*AT | O | O | O | S | O | S | F | OMe |
| 2790a-I | Y*AT | O | O | O | S | O | S | OEt | OMe |
| 2791a-I | Y*AT | S | O | O | S | O | S | OH | OMe |
| 2792a-I | Y*AT | S | O | O | S | O | S | OMe | OMe |
| 2793a-I | Y*AT | S | O | O | S | O | S | H | OMe |
| 2794a-I | Y*AT | S | O | O | S | O | S | F | OMe |
| 2795a-I | Y*AT | S | O | O | S | O | S | OEt | OMe |
| 2796a-I | Y*AT | S | S | O | S | O | S | OH | OMe |
| 2797a-I | Y*AT | S | S | O | S | O | S | OMe | OMe |

TABLE 3-continued

CapA Structures for mRNA preparation

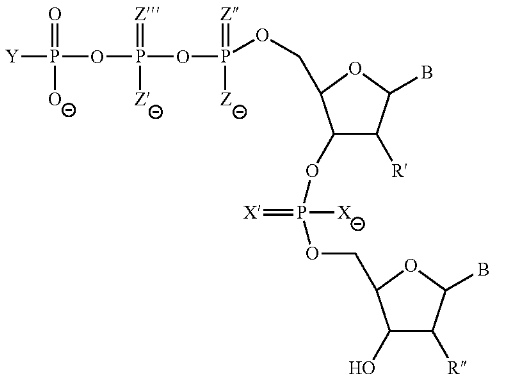

| Compound | Sequence | X | X' | Z | Z' | Z'' | Z''' | R' | R'' |
|---|---|---|---|---|---|---|---|---|---|
| 2798a-I | Y*AT | S | S | O | S | O | S | H | OMe |
| 2799a-I | Y*AT | S | S | O | S | O | S | F | OMe |
| 2800a-I | Y*AT | S | S | O | S | O | S | OEt | OMe |
| 2801a-I | Y*AE | O | O | O | O | O | O | OH | OH |
| 2802a-I | Y*AE | O | O | O | O | O | O | OMe | OH |
| 2803a-I | Y*AE | O | O | O | O | O | O | H | OH |
| 2804a-I | Y*AE | O | O | O | O | O | O | F | OH |
| 2805a-I | Y*AE | O | O | O | O | O | O | OEt | OH |
| 2806a-I | Y*AE | S | O | O | O | O | O | OH | OH |
| 2807a-I | Y*AE | S | O | O | O | O | O | OMe | OH |
| 2808a-I | Y*AE | S | O | O | O | O | O | H | OH |
| 2809a-I | Y*AE | S | O | O | O | O | O | F | OH |
| 2810a-I | Y*AE | S | O | O | O | O | O | OEt | OH |
| 2811a-I | Y*AE | S | S | O | O | O | O | OH | OH |
| 2812a-I | Y*AE | S | S | O | O | O | O | OMe | OH |
| 2813a-I | Y*AE | S | S | O | O | O | O | H | OH |
| 2814a-I | Y*AE | S | S | O | O | O | O | F | OH |
| 2815a-I | Y*AE | S | S | O | O | O | O | OEt | OH |
| 2816a-I | Y*AE | O | O | S | O | O | O | OH | OH |
| 2817a-I | Y*AE | O | O | S | O | O | O | OMe | OH |
| 2818a-I | Y*AE | O | O | S | O | O | O | H | OH |
| 2819a-I | Y*AE | O | O | S | O | O | O | F | OH |
| 2820a-I | Y*AE | O | O | S | O | O | O | OEt | OH |
| 2821a-I | Y*AE | S | O | S | O | O | O | OH | OH |
| 2822a-I | Y*AE | S | O | S | O | O | O | OMe | OH |
| 2823a-I | Y*AE | S | O | S | O | O | O | H | OH |
| 2824a-I | Y*AE | S | O | S | O | O | O | F | OH |
| 2825a-I | Y*AE | S | O | S | O | O | O | OEt | OH |
| 2826a-I | Y*AE | S | S | S | O | O | O | OH | OH |
| 2827a-I | Y*AE | S | S | S | O | O | O | OMe | OH |
| 2828a-I | Y*AE | S | S | S | O | O | O | H | OH |
| 2829a-I | Y*AE | S | S | S | O | O | O | F | OH |
| 2830a-I | Y*AE | S | S | S | O | O | O | OEt | OH |
| 2831a-I | Y*AE | O | O | S | S | O | O | OH | OH |
| 2832a-I | Y*AE | O | O | S | S | O | O | OMe | OH |
| 2833a-I | Y*AE | O | O | S | S | O | O | H | OH |
| 2834a-I | Y*AE | O | O | S | S | O | O | F | OH |
| 2835a-I | Y*AE | O | O | S | S | O | O | OEt | OH |
| 2836a-I | Y*AE | S | O | S | S | O | O | OH | OH |
| 2837a-I | Y*AE | S | O | S | S | O | O | OMe | OH |
| 2838a-I | Y*AE | S | O | S | S | O | O | H | OH |
| 2839a-I | Y*AE | S | O | S | S | O | O | F | OH |
| 2840a-I | Y*AE | S | O | S | S | O | O | OEt | OH |
| 2841a-1 | Y*AE | S | S | S | S | O | O | OH | OH |
| 2842a-I | Y*AE | S | S | S | S | O | O | OMe | OH |
| 2843a-I | Y*AE | S | S | S | S | O | O | H | OH |
| 2844a-I | Y*AE | S | S | S | S | O | O | F | OH |
| 2845a-I | Y*AE | S | S | S | S | O | O | OEt | OH |
| 2846a-I | Y*AE | O | O | S | S | S | O | OH | OH |
| 2847a-I | Y*AE | O | O | S | S | S | O | OMe | OH |
| 2848a-I | Y*AE | O | O | S | S | S | O | H | OH |
| 2849a-I | Y*AE | O | O | S | S | S | O | F | OH |
| 2850a-I | Y*AE | O | O | S | S | S | O | OEt | OH |
| 2851a-I | Y*AE | S | O | S | S | S | O | OH | OH |
| 2852a-I | Y*AE | S | O | S | S | S | O | OMe | OH |
| 2853a-I | Y*AE | S | O | S | S | S | O | H | OH |
| 2854a-I | Y*AE | S | O | S | S | S | O | F | OH |

TABLE 3-continued

CapA Structures for mRNA preparation

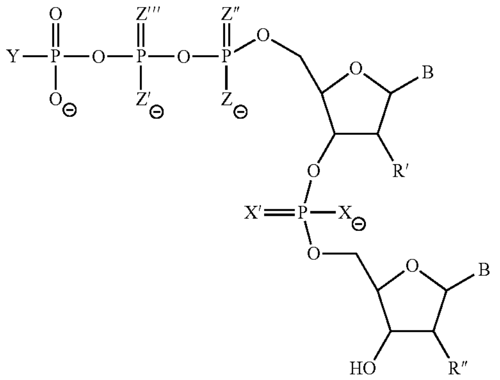

| Compound | Sequence | X | X' | Z | Z' | Z" | Z'" | R' | R" |
|---|---|---|---|---|---|---|---|---|---|
| 2855a-I | Y*AE | S | O | S | S | S | O | OEt | OH |
| 2856a-I | Y*AE | S | S | S | S | S | O | OH | OH |
| 2857a-I | Y*AE | S | S | S | S | S | O | OMe | OH |
| 2858a-I | Y*AE | S | S | S | S | S | O | H | OH |
| 2859a-I | Y*AE | S | S | S | S | S | O | F | OH |
| 2860a-I | Y*AE | S | S | S | S | S | O | OEt | OH |
| 2861a-I | Y*AE | O | O | S | S | S | S | OH | OH |
| 2862a-I | Y*AE | O | O | S | S | S | S | OMe | OH |
| 2863a-I | Y*AE | O | O | S | S | S | S | H | OH |
| 2864a-I | Y*AE | O | O | S | S | S | S | F | OH |
| 2865a-I | Y*AE | O | O | S | S | S | S | OEt | OH |
| 2866a-I | Y*AE | S | O | S | S | S | S | OH | OH |
| 2867a-I | Y*AE | S | O | S | S | S | S | OMe | OH |
| 2868a-I | Y*AE | S | O | S | S | S | S | H | OH |
| 2869a-I | Y*AE | S | O | S | S | S | S | F | OH |
| 2870a-I | Y*AE | S | O | S | S | S | S | OEt | OH |
| 2871a-I | Y*AE | S | S | S | S | S | S | OH | OH |
| 2872a-I | Y*AE | S | S | S | S | S | S | OMe | OH |
| 2873a-I | Y*AE | S | S | S | S | S | S | H | OH |
| 2874a-I | Y*AE | S | S | S | S | S | S | F | OH |
| 2875a-I | Y*AE | S | S | S | S | S | S | OEt | OH |
| 2876a-I | Y*AE | O | O | O | S | S | S | OH | OH |
| 2877a-I | Y*AE | O | O | O | S | S | S | OMe | OH |
| 2878a-I | Y*AE | O | O | O | S | S | S | H | OH |
| 2879a-I | Y*AE | O | O | O | S | S | S | F | OH |
| 2880a-I | Y*AE | O | O | O | S | S | S | OEt | OH |
| 2881a-I | Y*AE | S | O | O | S | S | S | OH | OH |
| 2882a-I | Y*AE | S | O | O | S | S | S | OMe | OH |
| 2883a-I | Y*AE | S | O | O | S | S | S | H | OH |
| 2884a-I | Y*AE | S | O | O | S | S | S | F | OH |
| 2885a-I | Y*AE | S | O | O | S | S | S | OEt | OH |
| 2886a-I | Y*AB | S | S | O | S | S | S | OH | OH |
| 2887a-I | Y*AE | S | S | O | S | S | S | OMe | OH |
| 2888a-I | Y*AE | S | S | O | S | S | S | H | OH |
| 2889a-I | Y*AE | S | S | O | S | S | S | F | OH |
| 2890a-I | Y*AE | S | S | O | S | S | S | OEt | OH |
| 2891a-I | Y*AE | O | O | O | O | S | S | OH | OH |
| 2892a-I | Y*AE | O | O | O | O | S | S | OMe | OH |
| 2893a-I | Y*AE | O | O | O | O | S | S | H | OH |
| 2894a-I | Y*AE | O | O | O | O | S | S | F | OH |
| 2895a-I | Y*AE | O | O | O | O | S | S | OEt | OH |
| 2896a-I | Y*AE | S | O | O | O | S | S | OH | OH |
| 2897a-I | Y*AE | S | O | O | O | S | S | OMe | OH |
| 2898a-I | Y*AE | S | O | O | O | S | S | H | OH |
| 2899a-I | Y*AE | S | O | O | O | S | S | F | OH |
| 2900a-I | Y*AE | S | O | O | O | S | S | OEt | OH |
| 2901a-I | Y*AE | S | S | O | O | S | S | OH | OH |
| 2902a-I | Y*AE | S | S | O | O | S | S | OMe | OH |
| 2903a-I | Y*AE | S | S | O | O | S | S | H | OH |
| 2904a-I | Y*AE | S | S | O | O | S | S | F | OH |
| 2905a-I | Y*AE | S | S | O | O | S | S | OEt | OH |
| 2906a-I | Y*AE | O | O | O | O | O | S | OH | OH |
| 2907a-I | Y*AE | O | O | O | O | O | S | OMe | OH |
| 2908a-I | Y*AE | O | O | O | O | O | S | H | OH |
| 2909a-I | Y*AE | O | O | O | O | O | S | F | OH |
| 2910a-I | Y*AE | O | O | O | O | O | S | OEt | OH |
| 2911a-I | Y*AE | S | O | O | O | O | S | OH | OH |

TABLE 3-continued

CapA Structures for mRNA preparation

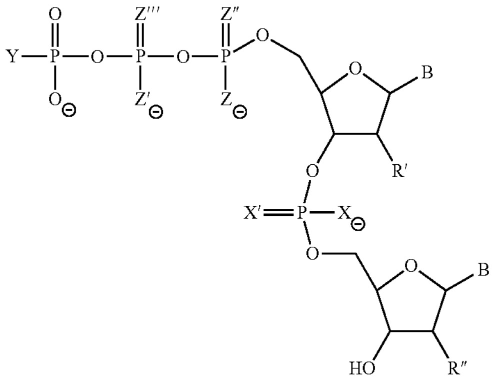

| Compound | Sequence | X | X' | Z | Z' | Z" | Z'" | R' | R" |
|---|---|---|---|---|---|---|---|---|---|
| 2912a-I | Y*AE | S | O | O | O | O | S | OMe | OH |
| 2913a-I | Y*AE | S | O | O | O | O | S | H | OH |
| 2914a-I | Y*AE | S | O | O | O | O | S | F | OH |
| 2915a-I | Y*AE | S | O | O | O | O | S | OEt | OH |
| 2916a-I | Y*AE | S | S | O | O | O | S | OH | OH |
| 2917a-I | Y*AE | S | S | O | O | O | S | OMe | OH |
| 2918a-I | Y*AE | S | S | O | O | O | S | H | OH |
| 2919a-I | Y*AE | S | S | O | O | O | S | F | OH |
| 2920a-I | Y*AE | S | S | O | O | O | S | OEt | OH |
| 2921a-I | Y*AE | O | O | S | O | S | O | OH | OH |
| 2922a-I | Y*AE | O | O | S | O | S | O | OMe | OH |
| 2923a-I | Y*AE | O | O | S | O | S | O | H | OH |
| 2924a-I | Y*AE | O | O | S | O | S | O | F | OH |
| 2925a-I | Y*AE | O | O | S | O | S | O | OEt | OH |
| 2926a-I | Y*AE | S | O | S | O | S | O | OH | OH |
| 2927a-I | Y*AE | S | O | S | O | S | O | OMe | OH |
| 2928a-I | Y*AE | S | O | S | O | S | O | H | OH |
| 2929a-I | Y*AE | S | O | S | O | S | O | F | OH |
| 2930a-I | Y*AE | S | O | S | O | S | O | OEt | OH |
| 2931a-I | Y*AE | S | S | S | O | S | O | OH | OH |
| 2932a-I | Y*AE | S | S | S | O | S | O | OMe | OH |
| 2933a-I | Y*AE | S | S | S | O | S | O | H | OH |
| 2934a-I | Y*AE | S | S | S | O | S | O | F | OH |
| 2935a-I | Y*AE | S | S | S | O | S | O | OEt | OH |
| 2936a-I | Y*AE | O | O | O | S | O | S | OH | OH |
| 2937a-I | Y*AE | O | O | O | S | O | S | OMe | OH |
| 2938a-I | Y*AE | O | O | O | S | O | S | H | OH |
| 2939a-I | Y*AE | O | O | O | S | O | S | F | OH |
| 2940a-I | Y*AE | O | O | O | S | O | S | OEt | OH |
| 2941a-I | Y*AE | S | O | O | S | O | S | OH | OH |
| 2942a-I | Y*AE | S | O | O | S | O | S | OMe | OH |
| 2943a-I | Y*AE | S | O | O | S | O | S | H | OH |
| 2944a-I | Y*AE | S | O | O | S | O | S | F | OH |
| 2945a-I | Y*AE | S | O | O | S | O | S | OEt | OH |
| 2946a-I | Y*AE | S | S | O | S | O | S | OH | OH |
| 2947a-I | Y*AE | S | S | O | S | O | S | OMe | OH |
| 2948a-I | Y*AE | S | S | O | S | O | S | H | OH |
| 2949a-I | Y*AE | S | S | O | S | O | S | F | OH |
| 2950a-I | Y*AE | S | S | O | S | O | S | OEt | OH |
| 2951a-I | Y*AE | O | O | O | O | O | O | OH | OMe |
| 2952a-I | Y*AE | O | O | O | O | O | O | OMe | OMe |
| 2953a-I | Y*AE | O | O | O | O | O | O | H | OMe |
| 2954a-I | Y*AE | O | O | O | O | O | O | F | OMe |
| 2955a-I | Y*AE | O | O | O | O | O | O | OEt | OMe |
| 2956a-I | Y*AE | S | O | O | O | O | O | OH | OMe |
| 2957a-I | Y*AE | S | O | O | O | O | O | OMe | OMe |
| 2958a-I | Y*AE | S | O | O | O | O | O | H | OMe |
| 2959a-I | Y*AE | S | O | O | O | O | O | F | OMe |
| 2960a-I | Y*AE | S | O | O | O | O | O | OEt | OMe |
| 2961a-I | Y*AE | S | S | O | O | O | O | OH | OMe |
| 2962a-I | Y*AE | S | S | O | O | O | O | OMe | OMe |
| 2963a-I | Y*AE | S | S | O | O | O | O | H | OMe |
| 2964a-I | Y*AE | S | S | O | O | O | O | F | OMe |
| 2965a-I | Y*AE | S | S | O | O | O | O | OEt | OMe |
| 2966a-I | Y*AE | O | O | S | O | O | O | OH | OMe |
| 2967a-I | Y*AE | O | O | S | O | O | O | OMe | OMe |
| 2968a-I | Y*AE | O | O | S | O | O | O | H | OMe |

TABLE 3-continued

CapA Structures for mRNA preparation

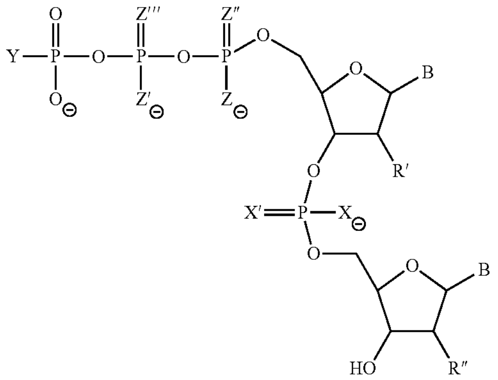

| Compound | Sequence | X | X' | Z | Z' | Z'' | Z''' | R' | R'' |
|---|---|---|---|---|---|---|---|---|---|
| 2969a-I | Y*AE | O | O | S | O | O | O | F | OMe |
| 2970a-I | Y*AE | O | O | S | O | O | O | OEt | OMe |
| 2971a-I | Y*AE | S | O | S | O | O | O | OH | OMe |
| 2972a-I | Y*AE | S | O | S | O | O | O | OMe | OMe |
| 2973a-I | Y*AE | S | O | S | O | O | O | H | OMe |
| 2974a-I | Y*AE | S | O | S | O | O | O | F | OMe |
| 2975a-I | Y*AE | S | O | S | O | O | O | OEt | OMe |
| 2976a-I | Y*AE | S | S | S | O | O | O | OH | OMe |
| 2977a-I | Y*AE | S | S | S | O | O | O | OMe | OMe |
| 2978a-I | Y*AE | S | S | S | O | O | O | H | OMe |
| 2979a-I | Y*AE | S | S | S | O | O | O | F | OMe |
| 2980a-I | Y*AE | S | S | S | O | O | O | OEt | OMe |
| 2981a-I | Y*AE | O | O | S | S | O | O | OH | OMe |
| 2982a-I | Y*AE | O | O | S | S | O | O | OMe | OMe |
| 2983a-I | Y*AE | O | O | S | S | O | O | H | OMe |
| 2984a-I | Y*AE | O | O | S | S | O | O | F | OMe |
| 2985a-I | Y*AE | O | O | S | S | O | O | OEt | OMe |
| 2986a-I | Y*AE | S | O | S | S | O | O | OH | OMe |
| 2987a-I | Y*AE | S | O | S | S | O | O | OMe | OMe |
| 2988a-I | Y*AE | S | O | S | S | O | O | H | OMe |
| 2989a-I | Y*AE | S | O | S | S | O | O | F | OMe |
| 2990a-I | Y*AE | S | O | S | S | O | O | OEt | OMe |
| 2991a-I | Y*AE | S | S | S | S | O | O | OH | OMe |
| 2992a-I | Y*AE | S | S | S | S | O | O | OMe | OMe |
| 2993a-I | Y*AE | S | S | S | S | O | O | H | OMe |
| 2994a-I | Y*AE | S | S | S | S | O | O | F | OMe |
| 2995a-I | Y*AE | S | S | S | S | O | O | OEt | OMe |
| 2996a-I | Y*AE | O | O | S | S | S | O | OH | OMe |
| 2997a-I | Y*AE | O | O | S | S | S | O | OMe | OMe |
| 2998a-I | Y*AE | O | O | S | S | S | O | H | OMe |
| 2999a-I | Y*AE | O | O | S | S | S | O | F | OMe |
| 3000a-I | Y*AE | O | O | S | S | S | O | OEt | OMe |
| 3001a-I | Y*AE | S | O | S | S | S | O | OH | OMe |
| 3002a-I | Y*AE | S | O | S | S | S | O | OMe | OMe |
| 3003a-I | Y*AE | S | O | S | S | S | O | H | OMe |
| 3004a-I | Y*AE | S | O | S | S | S | O | F | OMe |
| 3005a-I | Y*AE | S | O | S | S | S | O | OEt | OMe |
| 3006a-I | Y*AE | S | S | S | S | S | O | OH | OMe |
| 3007a-I | Y*AE | S | S | S | S | S | O | OMe | OMe |
| 3008a-I | Y*AE | S | S | S | S | S | O | H | OMe |
| 3009a-I | Y*AE | S | S | S | S | S | O | F | OMe |
| 3010a-I | Y*AE | S | S | S | S | S | O | OEt | OMe |
| 3011a-I | Y*AE | O | O | S | S | S | S | OH | OMe |
| 3012a-I | Y*AE | O | O | S | S | S | S | OMe | OMe |
| 3013a-I | Y*AE | O | O | S | S | S | S | H | OMe |
| 3014a-I | Y*AE | O | O | S | S | S | S | F | OMe |
| 3015a-I | Y*AE | O | O | S | S | S | S | OE | OMe |
| 3016a-I | Y*AE | S | O | S | S | S | S | OH | OMe |
| 3017a-I | Y*AE | S | O | S | S | S | S | OMe | OMe |
| 3018a-I | Y*AE | S | O | S | S | S | S | H | OMe |
| 3019a-I | Y*AE | S | O | S | S | S | S | F | OMe |
| 3020a-I | Y*AE | S | O | S | S | S | S | OEt | OMe |
| 3021a-I | Y*AE | S | S | S | S | S | S | OH | OMe |
| 3022a-I | Y*AE | S | S | S | S | S | S | OMe | OMe |
| 3023a-I | Y*AE | S | S | S | S | S | S | H | OMe |
| 3024a-I | Y*AE | S | S | S | S | S | S | F | OMe |
| 3025a-I | Y*AE | S | S | S | S | S | S | OEt | OMe |

TABLE 3-continued

CapA Structures for mRNA preparation

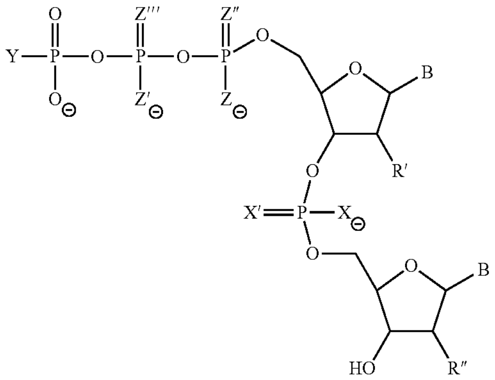

| Compound | Sequence | X | X' | Z | Z' | Z'' | Z''' | R' | R'' |
|---|---|---|---|---|---|---|---|---|---|
| 3026a-I | Y*AE | O | O | O | S | S | S | OH | OMe |
| 3027a-I | Y*AE | O | O | O | S | S | S | OMe | OMe |
| 3028a-I | Y*AE | O | O | O | S | S | S | H | OMe |
| 3029a-I | Y*AE | O | O | O | S | S | S | F | OMe |
| 3030a-I | Y*AE | O | O | O | S | S | S | OEt | OMe |
| 3031a-I | Y*AE | S | O | O | S | S | S | OH | OMe |
| 3032a-I | Y*AE | S | O | O | S | S | S | OMe | OMe |
| 3033a-I | Y*AE | S | O | O | S | S | S | H | OMe |
| 3034a-I | Y*AE | S | O | O | S | S | S | F | OMe |
| 3035a-I | Y*AE | S | O | O | S | S | S | OEt | OMe |
| 3036a-I | Y*AE | S | S | O | S | S | S | OH | OMe |
| 3037a-I | Y*AE | S | S | O | S | S | S | OMe | OMe |
| 3038a-I | Y*AE | S | S | O | S | S | S | H | OMe |
| 3039a-I | Y*AE | S | S | O | S | S | S | F | OMe |
| 3040a-I | Y*AE | S | S | O | S | S | S | OEt | OMe |
| 3041a-I | Y*AE | O | O | O | O | S | S | OH | OMe |
| 3042a-I | Y*AE | O | O | O | O | S | S | OMe | OMe |
| 3043a-I | Y*AE | O | O | O | O | S | S | H | OMe |
| 3044a-I | Y*AE | O | O | O | O | S | S | F | OMe |
| 3045a-I | Y*AE | O | O | O | O | S | S | OEt | OMe |
| 3046a-I | Y*AE | S | O | O | O | S | S | OH | OMe |
| 3047a-I | Y*AE | S | O | O | O | S | S | OMe | OMe |
| 3048a-I | Y*AE | S | O | O | O | S | S | H | OMe |
| 3049a-I | Y*AE | S | O | O | O | S | S | F | OMe |
| 3050a-I | Y*AE | S | O | O | O | S | S | OEt | OMe |
| 3051a-I | Y*AE | S | S | O | O | S | S | OH | OMe |
| 3052a-I | Y*AE | S | S | O | O | S | S | OMe | OMe |
| 3053a-I | Y*AE | S | S | O | O | S | S | H | OMc |
| 3054a-I | Y*AE | S | S | O | O | S | S | F | OMe |
| 3055a-I | Y*AE | S | S | O | O | S | S | OEt | OMe |
| 3056a-I | Y*AE | O | O | O | O | O | S | OH | OMe |
| 3057a-I | Y*AE | O | O | O | O | O | S | OMe | OMe |
| 3058a-I | Y*AE | O | O | O | O | O | S | H | OMe |
| 3059a-I | Y*AE | O | O | O | O | O | S | F | OMe |
| 3060a-I | Y*AE | O | O | O | O | O | S | OEt | OMe |
| 3061a-I | Y*AE | S | O | O | O | O | S | OH | OMe |
| 3062a-I | Y*AE | S | O | O | O | O | S | OMe | OMc |
| 3063a-I | Y*AE | S | O | O | O | O | S | H | OMe |
| 3064a-I | Y*AE | S | O | O | O | O | S | F | OMe |
| 3065a-I | Y*AE | S | O | O | O | O | S | OEt | OMe |
| 3066a-I | Y*AE | S | S | O | O | O | S | OH | OMe |
| 3067a-I | Y*AE | S | S | O | O | O | S | OMe | OMe |
| 3068a-I | Y*AE | S | S | O | O | O | S | H | OMe |
| 3069a-I | Y*AE | S | S | O | O | O | S | F | OMe |
| 3070a-I | Y*AE | S | S | O | O | O | S | OEt | OMe |
| 3071a-I | Y*AE | O | O | S | O | S | O | OH | OMe |
| 3072a-I | Y*AE | O | O | S | O | S | O | OMe | OMe |
| 3073a-I | Y*AE | O | O | S | O | S | O | H | OMe |
| 3074a-I | Y*AE | O | O | S | O | S | O | F | OMe |
| 3075a-I | Y*AE | O | O | S | O | S | O | OEt | OMe |
| 3076a-I | Y*AE | S | O | S | O | S | O | OH | OMe |
| 3077a-I | Y*AE | S | O | S | O | S | O | OMe | OMe |
| 3078a-I | Y*AE | S | O | S | O | S | O | H | OMe |
| 3079a-I | Y*AE | S | O | S | O | S | O | F | OMe |
| 3080a-I | Y*AE | S | O | S | O | S | O | OEt | OMe |
| 3081a-I | Y*AE | S | S | S | O | S | O | OH | OMe |
| 3082a-I | Y*AE | S | S | S | O | S | O | OMe | OMe |

TABLE 3-continued

CapA Structures for mRNA preparation

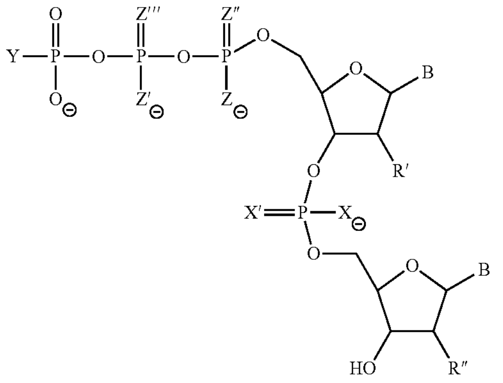

| Compound | Sequence | X | X' | Z | Z' | Z'' | Z''' | R' | R'' |
|---|---|---|---|---|---|---|---|---|---|
| 3083a-I | Y*AE | S | S | S | O | S | O | H | OMe |
| 3084a-I | Y*AE | S | S | S | O | S | O | F | OMe |
| 3085a-I | Y*AE | S | S | S | O | S | O | OEt | OMe |
| 3086a-I | Y*AE | O | O | O | S | O | S | OH | OMe |
| 3087a-I | Y*AE | O | O | O | S | O | S | OMe | OMe |
| 3088a-I | Y*AE | O | O | O | S | O | S | H | OMe |
| 3089a-I | Y*AE | O | O | O | S | O | S | F | OMe |
| 3090a-I | Y*AE | O | O | O | S | O | S | OEt | OMe |
| 3091a-I | Y*AE | S | O | O | S | O | S | OH | OMe |
| 3092a-I | Y*AE | S | O | O | S | O | S | OMe | OMe |
| 3093a-I | Y*AE | S | O | O | S | O | S | H | OMe |
| 3094a-I | Y*AE | S | O | O | S | O | S | F | OMe |
| 3095a-I | Y*AE | S | O | O | S | O | S | OEt | OMe |
| 3096a-I | Y*AE | S | S | O | S | O | S | OH | OMe |
| 3097a-I | Y*AE | S | S | O | S | O | S | OMe | OMe |
| 3098a-I | Y*AE | S | S | O | S | O | S | H | OMe |
| 3099a-I | Y*AE | S | S | O | S | O | S | F | OMe |
| 3100a-I | Y*AE | S | S | O | S | O | S | OEt | OMe |
| 3101a-I | Y*EG | O | O | O | O | O | O | OH | OH |
| 3102a-I | Y*EG | O | O | O | O | O | O | OMe | OH |
| 3103a-I | Y*EG | O | O | O | O | O | O | H | OH |
| 3104a-I | Y*EG | O | O | O | O | O | O | F | OH |
| 3105a-I | Y*EG | O | O | O | O | O | O | OEt | OH |
| 3106a-I | Y*EG | S | O | O | O | O | O | OH | OH |
| 3107a-I | Y*EG | S | O | O | O | O | O | OMe | OH |
| 3108a-I | Y*EG | S | O | O | O | O | O | H | OH |
| 3109a-I | Y*EG | S | O | O | O | O | O | F | OH |
| 3110a-I | Y*EG | S | O | O | O | O | O | OEt | OH |
| 3111a-I | Y*EG | S | S | O | O | O | O | OH | OH |
| 3112a-I | Y*EG | S | S | O | O | O | O | OMe | OH |
| 3113a-I | Y*EG | S | S | O | O | O | O | H | OH |
| 3114a-I | Y*EG | S | S | O | O | O | O | F | OH |
| 3115a-I | Y*EG | S | S | O | O | O | O | OEt | OH |
| 3116a-I | Y*EG | O | O | S | O | O | O | OH | OH |
| 3117a-I | Y*EG | O | O | S | O | O | O | OMe | OH |
| 3118a-I | Y*EG | O | O | S | O | O | O | H | OH |
| 3119a-I | Y*EG | O | O | S | O | O | O | F | OH |
| 3120a-I | Y*EG | O | O | S | O | O | O | OEt | OH |
| 3121a-I | Y*EG | S | O | S | O | O | O | OH | OH |
| 3122a-I | Y*EG | S | O | S | O | O | O | OMe | OH |
| 3123a-I | Y*EG | S | O | S | O | O | O | H | OH |
| 3124a-I | Y*EG | S | O | S | O | O | O | F | OH |
| 3125a-I | Y*EG | S | O | S | O | O | O | OEt | OH |
| 3126a-I | Y*EG | S | S | S | O | O | O | OH | OH |
| 3127a-I | Y*EG | S | S | S | O | O | O | OMe | OH |
| 3128a-I | Y*EG | S | S | S | O | O | O | H | OH |
| 3129a-I | Y*EG | S | S | S | O | O | O | F | OH |
| 3130a-I | Y*EG | S | S | S | O | O | O | OEt | OH |
| 3131a-I | Y*EG | O | O | S | S | O | O | OH | OH |
| 3132a-I | Y*EG | O | O | S | S | O | O | OMe | OH |
| 3133a-I | Y*EG | O | O | S | S | O | O | H | OH |
| 3134a-I | Y*EG | O | O | S | S | O | O | F | OH |
| 3135a-I | Y*EG | O | O | S | S | O | O | OEt | OH |
| 3136a-I | Y*EG | S | O | S | S | O | O | OH | OH |
| 3137a-I | Y*EG | S | O | S | S | O | O | OMe | OH |
| 3138a-I | Y*EG | S | O | S | S | O | O | H | OH |
| 3139a-I | Y*EG | S | O | S | S | O | O | F | OH |

TABLE 3-continued

CapA Structures for mRNA preparation

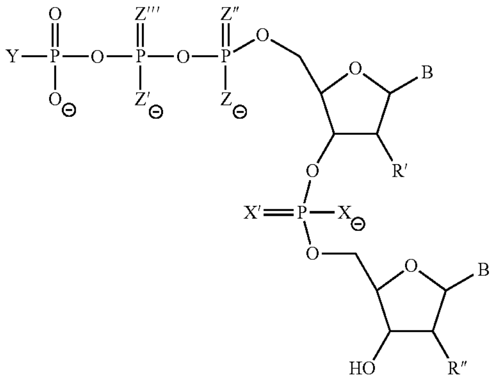

| Compound | Sequence | X | X' | Z | Z' | Z'' | Z''' | R' | R'' |
|---|---|---|---|---|---|---|---|---|---|
| 3140a-I | Y*EG | S | O | S | S | O | O | OEt | OH |
| 3141a-I | Y*EG | S | S | S | S | O | O | OH | OH |
| 3142a-I | Y*EG | S | S | S | S | O | O | OMe | OH |
| 3143a-I | Y*EG | S | S | S | S | O | O | H | OH |
| 3144a-I | Y*EG | S | S | S | S | O | O | F | OH |
| 3145a-I | Y*EG | S | S | S | S | O | O | OEt | OH |
| 3146a-I | Y*EG | O | O | S | S | S | O | OH | OH |
| 3147a-I | Y*EG | O | O | S | S | S | O | OMe | OH |
| 3148a-I | Y*EG | O | O | S | S | S | O | H | OH |
| 3149a-I | Y*EG | O | O | S | S | S | O | F | OH |
| 3150a-I | Y*EG | O | O | S | S | S | O | OEt | OH |
| 3151a-I | Y*EG | S | O | S | S | S | O | OH | OH |
| 3152a-I | Y*EG | S | O | S | S | S | O | OMe | OH |
| 3153a-I | Y*EG | S | O | S | S | S | O | H | OH |
| 3154a-I | Y*EG | S | O | S | S | S | O | F | OH |
| 3155a-I | Y*EG | S | O | S | S | S | O | OEt | OH |
| 3156a-I | Y*EG | S | S | S | S | S | O | OH | OH |
| 3157a-I | Y*EG | S | S | S | S | S | O | OMe | OH |
| 3158a-I | Y*EG | S | S | S | S | S | O | H | OH |
| 3159a-I | Y*EG | S | S | S | S | S | O | F | OH |
| 3160a-I | Y*EG | S | S | S | S | S | O | OEt | OH |
| 3161a-I | Y*EG | O | O | S | S | S | S | OH | OH |
| 3162a-I | Y*EG | O | O | S | S | S | S | OMe | OH |
| 3163a-I | Y*EG | O | O | S | S | S | S | H | OH |
| 3164a-I | Y*EG | O | O | S | S | S | S | F | OH |
| 3165a-I | Y*EG | O | O | S | S | S | S | OEt | OH |
| 3166a-I | Y*EG | S | O | S | S | S | S | OH | OH |
| 3167a-I | Y*EG | S | O | S | S | S | S | OMe | OH |
| 3168a-I | Y*EG | S | O | S | S | S | S | H | OH |
| 3169a-I | Y*EG | S | O | S | S | S | S | F | OH |
| 3170a-I | Y*EG | S | O | S | S | S | S | OEt | OH |
| 3171a-I | Y*EG | S | S | S | S | S | S | OH | OH |
| 3172a-I | Y*EG | S | S | S | S | S | S | OMe | OH |
| 3173a-I | Y*EG | S | S | S | S | S | S | H | OH |
| 3174a-I | Y*EG | S | S | S | S | S | S | F | OH |
| 3175a-I | Y*EG | S | S | S | S | S | S | OEt | OH |
| 3176a-I | Y*EG | O | O | O | S | S | S | OH | OH |
| 3177a-I | Y*EG | O | O | O | S | S | S | OMe | OH |
| 3178a-I | Y*EG | O | O | O | S | S | S | H | OH |
| 3179a-I | Y*EG | O | O | O | S | S | S | F | OH |
| 3180a-I | Y*EG | O | O | O | S | S | S | OEt | OH |
| 3181a-I | Y*EG | S | O | O | S | S | S | OH | OH |
| 3182a-I | Y*EG | S | O | O | S | S | S | OMe | OH |
| 3183a-I | Y*EG | S | O | O | S | S | S | H | OH |
| 3184a-I | Y*EG | S | O | O | S | S | S | F | OH |
| 3185a-I | Y*EG | S | O | O | S | S | S | OEt | OH |
| 3186a-I | Y*EG | S | S | O | S | S | S | OH | OH |
| 3187a-I | Y*EG | S | S | O | S | S | S | OMe | OH |
| 3188a-I | Y*EG | S | S | O | S | S | S | H | OH |
| 3189a-I | Y*EG | S | S | O | S | S | S | F | OH |
| 3190a-I | Y*EG | S | S | O | S | S | S | OEt | OH |
| 3191a-I | Y*EG | O | O | O | O | S | S | OH | OH |
| 3192a-I | Y*EG | O | O | O | O | S | S | OMe | OH |
| 3193a-I | Y*EG | O | O | O | O | S | S | H | OH |
| 3194a-I | Y*EG | O | O | O | O | S | S | F | OH |
| 3195a-I | Y*EG | O | O | O | O | S | S | OEt | OH |
| 3196a-I | Y*EG | S | O | O | O | S | S | OH | OH |

TABLE 3-continued

CapA Structures for mRNA preparation

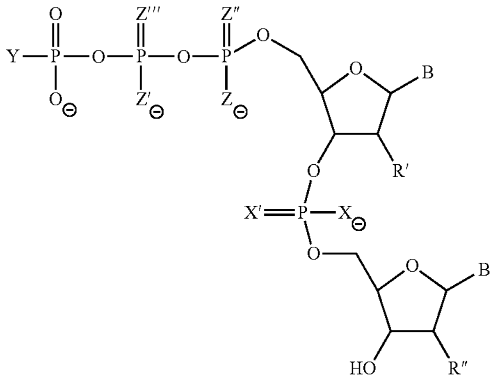

| Compound | Sequence | X | X' | Z | Z' | Z" | Z'" | R' | R" |
|---|---|---|---|---|---|---|---|---|---|
| 3197a-I | Y*EG | S | O | O | O | S | S | OMe | OH |
| 3198a-I | Y*EG | S | O | O | O | S | S | H | OH |
| 3199a-I | Y*EG | S | O | O | O | S | S | F | OH |
| 3200a-I | Y*EG | S | O | O | O | S | S | OEt | OH |
| 3201a-I | Y*EG | S | S | O | O | S | S | OH | OH |
| 3202a-I | Y*EG | S | S | O | O | S | S | OMe | OH |
| 3203a-I | Y*EG | S | S | O | O | S | S | H | OH |
| 3204a-I | Y*EG | S | S | O | O | S | S | F | OH |
| 3205a-I | Y*EG | S | S | O | O | S | S | OEt | OH |
| 3206a-I | Y*EG | O | O | O | O | O | S | OH | OH |
| 3207a-I | Y*EG | O | O | O | O | O | S | OMe | OH |
| 3208a-I | Y*EG | O | O | O | O | O | S | H | OH |
| 3209a-I | Y*EG | O | O | O | O | O | S | F | OH |
| 3210a-I | Y*EG | O | O | O | O | O | S | OEt | OH |
| 3211a-I | Y*EG | S | O | O | O | O | S | OH | OH |
| 3212a-I | Y*EG | S | O | O | O | O | S | OMe | OH |
| 3213a-I | Y*EG | S | O | O | O | O | S | H | OH |
| 3214a-I | Y*EG | S | O | O | O | O | S | F | OH |
| 3215a-I | Y*EG | S | O | O | O | O | S | OEt | OH |
| 3216a-I | Y*EG | S | S | O | O | O | S | OH | OH |
| 3217a-I | Y*EG | S | S | O | O | O | S | OMe | OH |
| 3218a-I | Y*EG | S | S | O | O | O | S | H | OH |
| 3219a-I | Y*EG | S | S | O | O | O | S | F | OH |
| 3220a-I | Y*EG | S | S | O | O | O | S | OEt | OH |
| 3221a-I | Y*EG | O | O | S | O | S | O | OH | OH |
| 3222a-I | Y*EG | O | O | S | O | S | O | OMe | OH |
| 3223a-I | Y*EG | O | O | S | O | S | O | H | OH |
| 3224a-I | Y*EG | O | O | S | O | S | O | F | OH |
| 3225a-I | Y*EG | O | O | S | O | S | O | OEt | OH |
| 3226a-I | Y*EG | S | O | S | O | S | O | OH | OH |
| 3227a-I | Y*EG | S | O | S | O | S | O | OMe | OH |
| 3228a-I | Y*EG | S | O | S | O | S | O | H | OH |
| 3229a-I | Y*EG | S | O | S | O | S | O | F | OH |
| 3230a-I | Y*EG | S | O | S | O | S | O | OEt | OH |
| 3231a-I | Y*EG | S | S | S | O | S | O | OH | OH |
| 3232a-I | Y*EG | S | S | S | O | S | O | OMe | OH |
| 3233a-I | Y*EG | S | S | S | O | S | O | H | OH |
| 3234a-I | Y*EG | S | S | S | O | S | O | F | OH |
| 3235a-I | Y*EG | S | S | S | O | S | O | OEt | OH |
| 3236a-I | Y*EG | O | O | O | S | O | S | OH | OH |
| 3237a-I | Y*EG | O | O | O | S | O | S | OMe | OH |
| 3238a-I | Y*EG | O | O | O | S | O | S | H | OH |
| 3239a-I | Y*EG | O | O | O | S | O | S | F | OH |
| 3240a-I | Y*EG | O | O | O | S | O | S | OEt | OH |
| 3241a-I | Y*EG | S | O | O | S | O | S | OH | OH |
| 3242a-I | Y*EG | S | O | O | S | O | S | OMe | OH |
| 3243a-I | Y*EG | S | O | O | S | O | S | H | OH |
| 3244a-I | Y*EG | S | O | O | S | O | S | F | OH |
| 3245a-I | Y*EG | S | O | O | S | O | S | OEt | OH |
| 3246a-I | Y*EG | S | S | O | S | O | S | OH | OH |
| 3247a-I | Y*EG | S | S | O | S | O | S | OMe | OH |
| 3248a-I | Y*EG | S | S | O | S | O | S | H | OH |
| 3249a-I | Y*EG | S | S | O | S | O | S | F | OH |
| 3250a-I | Y*EG | S | S | O | S | O | S | OEt | OH |
| 3251a-I | Y*EG | O | O | O | O | O | O | OH | OMe |
| 3252a-I | Y*EG | O | O | O | O | O | O | OMe | OMe |
| 3253a-I | Y*EG | O | O | O | O | O | O | H | OMe |

TABLE 3-continued

CapA Structures for mRNA preparation

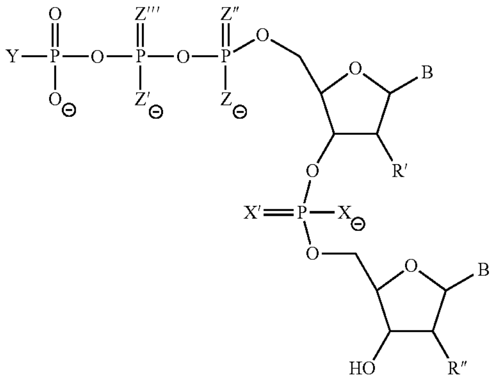

| Compound | Sequence | X | X' | Z | Z' | Z" | Z'" | R' | R" |
|---|---|---|---|---|---|---|---|---|---|
| 3254a-I | Y*EG | O | O | O | O | O | O | F | OMe |
| 3255a-I | Y*EG | O | O | O | O | O | O | OEt | OMe |
| 3256a-I | Y*EG | S | O | O | O | O | O | OH | OMe |
| 3257a-I | Y*EG | S | O | O | O | O | O | OMe | OMe |
| 3258a-I | Y*EG | S | O | O | O | O | O | H | OMe |
| 3259a-I | Y*EG | S | O | O | O | O | O | F | OMe |
| 3260a-I | Y*EG | S | O | O | O | O | O | OEt | OMe |
| 3261a-I | Y*EG | S | S | O | O | O | O | OH | OMe |
| 3262a-I | Y*EG | S | S | O | O | O | O | OMe | OMe |
| 3263a-I | Y*EG | S | S | O | O | O | O | H | OMe |
| 3264a-I | Y*EG | S | S | O | O | O | O | F | OMe |
| 3265a-I | Y*EG | S | S | O | O | O | O | OEt | OMe |
| 3266a-I | Y*EG | O | O | S | O | O | O | OH | OMe |
| 3267a-I | Y*EG | O | O | S | O | O | O | OMe | OMe |
| 3268a-I | Y*EG | O | O | S | O | O | O | H | OMe |
| 3269a-I | Y*EG | O | O | S | O | O | O | F | OMe |
| 3270a-I | Y*EG | O | O | S | O | O | O | OEt | OMe |
| 3271a-I | Y*EG | S | O | S | O | O | O | OH | OMe |
| 3272a-I | Y*EG | S | O | S | O | O | O | OMe | OMe |
| 3273a-I | Y*EG | S | O | S | O | O | O | H | OMe |
| 3274a-I | Y*EG | S | O | S | O | O | O | F | OMe |
| 3275a-I | Y*EG | S | O | S | O | O | O | OEt | OMe |
| 3276a-I | Y*EG | S | S | S | O | O | O | OH | OMe |
| 3277a-I | Y*EG | S | S | S | O | O | O | OMe | OMe |
| 3278a-I | Y*EG | S | S | S | O | O | O | H | OMe |
| 3279a-I | Y*EG | S | S | S | O | O | O | F | OMe |
| 3280a-I | Y*EG | S | S | S | O | O | O | OEt | OMe |
| 3281a-I | Y*EG | O | O | S | S | O | O | OH | OMe |
| 3282a-I | Y*EG | O | O | S | S | O | O | OMe | OMe |
| 3283a-I | Y*EG | O | O | S | S | O | O | H | OMe |
| 3284a-I | Y*EG | O | O | S | S | O | O | F | OMe |
| 3285a-I | Y*EG | O | O | S | S | O | O | OEt | OMe |
| 3286a-I | Y*EG | S | O | S | S | O | O | OH | OMe |
| 3287a-I | Y*EG | S | O | S | S | O | O | OMe | OMe |
| 3288a-I | Y*EG | S | O | S | S | O | O | H | OMe |
| 3289a-I | Y*EG | S | O | S | S | O | O | F | OMe |
| 3290a-I | Y*EG | S | O | S | S | O | O | OEt | OMe |
| 3291a-I | Y*EG | S | S | S | S | O | O | OH | OMe |
| 3292a-I | Y*EG | S | S | S | S | O | O | OMe | OMe |
| 3293a-I | Y*EG | S | S | S | S | O | O | H | OMe |
| 3294a-I | Y*EG | S | S | S | S | O | O | F | OMe |
| 3295a-I | Y*EG | S | S | S | S | O | O | OEt | OMe |
| 3296a-I | Y*EG | O | O | S | S | S | O | OH | OMe |
| 3297a-I | Y*EG | O | O | S | S | S | O | OMe | OMe |
| 3298a-I | Y*EG | O | O | S | S | S | O | H | OMe |
| 3299a-I | Y*EG | O | O | S | S | S | O | F | OMe |
| 3300a-I | Y*EG | O | O | S | S | S | O | OEt | OMe |
| 3301a-I | Y*EG | S | O | S | S | S | O | OH | OMe |
| 3302a-I | Y*EG | S | O | S | S | S | O | OMe | OMe |
| 3303a-I | Y*EG | S | O | S | S | S | O | H | OMe |
| 3304a-I | Y*EG | S | O | S | S | S | O | F | OMe |
| 3305a-I | Y*EG | S | O | S | S | S | O | OEt | OMe |
| 3306a-I | Y*EG | S | S | S | S | S | O | OH | OMe |
| 3307a-I | Y*EG | S | S | S | S | S | O | OMe | OMe |
| 3308a-I | Y*EG | S | S | S | S | S | O | H | OMe |
| 3309a-I | Y*EG | S | S | S | S | S | O | F | OMe |
| 3310a-I | Y*EG | S | S | S | S | S | O | OEt | OMe |

TABLE 3-continued

CapA Structures for mRNA preparation

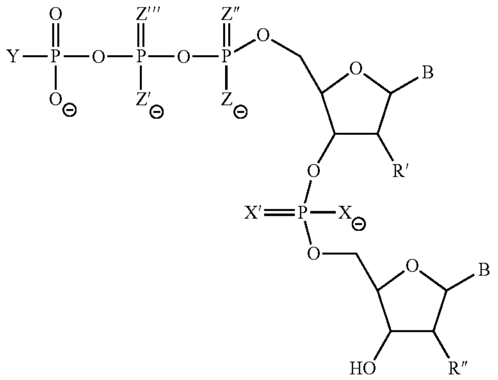

| Compound | Sequence | X | X' | Z | Z' | Z'' | Z''' | R' | R'' |
|---|---|---|---|---|---|---|---|---|---|
| 3311a-I | Y*EG | O | O | S | S | S | S | OH | OMe |
| 3312a-I | Y*EG | O | O | S | S | S | S | OMe | OMe |
| 3313a-I | Y*EG | O | O | S | S | S | S | H | OMe |
| 3314a-I | Y*EG | O | O | S | S | S | S | F | OMe |
| 3315a-I | Y*EG | O | O | S | S | S | S | OEt | OMe |
| 3316a-I | Y*EG | S | O | S | S | S | S | OH | OMe |
| 3317a-I | Y*EG | S | O | S | S | S | S | OMe | OMe |
| 3318a-I | Y*EG | S | O | S | S | S | S | H | OMc |
| 3319a-I | Y*EG | S | O | S | S | S | S | F | OMe |
| 3320a-I | Y*EG | S | O | S | S | S | S | OEt | OMe |
| 3321a-I | Y*EG | S | S | S | S | S | S | OH | OMe |
| 3322a-I | Y*EG | S | S | S | S | S | S | OMe | OMe |
| 3323a-I | Y*EG | S | S | S | S | S | S | H | OMe |
| 3324a-I | Y*EG | S | S | S | S | S | S | F | OMe |
| 3325a-I | Y*EG | S | S | S | S | S | S | OEt | OMe |
| 3326a-I | Y*EG | O | O | O | S | S | S | OH | OMe |
| 3327a-I | Y*EG | O | O | O | S | S | S | OMe | OMe |
| 3328a-I | Y*EG | O | O | O | S | S | S | H | OMe |
| 3329a-I | Y*EG | O | O | O | S | S | S | F | OMe |
| 3330a-I | Y*EG | O | O | O | S | S | S | OEt | OMe |
| 3331a-I | Y*EG | S | O | O | S | S | S | OH | OMe |
| 3332a-I | Y*EG | S | O | O | S | S | S | OMe | OMe |
| 3333a-I | Y*EG | S | O | O | S | S | S | H | OMe |
| 3334a-I | Y*EG | S | O | O | S | S | S | F | OMe |
| 3335a-I | Y*EG | S | O | O | S | S | S | OEt | OMe |
| 3336a-I | Y*EG | S | S | O | S | S | S | OH | OMe |
| 3337a-I | Y*EG | S | S | O | S | S | S | OMe | OMe |
| 3338a-I | Y*EG | S | S | O | S | S | S | H | OMe |
| 3339a-I | Y*EG | S | S | O | S | S | S | F | OMe |
| 3340a-I | Y*EG | S | S | O | S | S | S | OEt | OMe |
| 3341a-I | Y*EG | O | O | O | O | S | S | OH | OMe |
| 3342a-I | Y*EG | O | O | O | O | S | S | OMe | OMe |
| 3343a-I | Y*EG | O | O | O | O | S | S | H | OMe |
| 3344a-I | Y*EG | O | O | O | O | S | S | F | OMe |
| 3345a-I | Y*EG | O | O | O | O | S | S | OEt | OMe |
| 3346a-I | Y*EG | S | O | O | O | S | S | OH | OMe |
| 3347a-I | Y*EG | S | O | O | O | S | S | OMe | OMe |
| 3348a-I | Y*EG | S | O | O | O | S | S | H | OMe |
| 3349a-I | Y*EG | S | O | O | O | S | S | F | OMe |
| 3350a-I | Y*EG | S | O | O | O | S | S | OEt | OMe |
| 3351a-I | Y*EG | S | S | O | O | S | S | OH | OMe |
| 3352a-I | Y*EG | S | S | O | O | S | S | OMe | OMe |
| 3353a-I | Y*EG | S | S | O | O | S | S | H | OMe |
| 3354a-I | Y*EG | S | S | O | O | S | S | F | OMe |
| 3355a-I | Y*EG | S | S | O | O | S | S | OEt | OMe |
| 3356a-I | Y*EG | O | O | O | O | O | S | OH | OMe |
| 3357a-I | Y*EG | O | O | O | O | O | S | OMe | OMe |
| 3358a-I | Y*EG | O | O | O | O | O | S | H | OMe |
| 3359a-I | Y*EG | O | O | O | O | O | S | F | OMe |
| 3360a-I | Y*EG | O | O | O | O | O | S | OEt | OMe |
| 3361a-I | Y*EG | S | O | O | O | O | S | OH | OMe |
| 3362a-I | Y*EG | S | O | O | O | O | S | OMe | OMe |
| 3363a-I | Y*EG | S | O | O | O | O | S | H | OMe |
| 3364a-I | Y*EG | S | O | O | O | O | S | F | OMe |
| 3365a-I | Y*EG | S | O | O | O | O | S | OEt | OMe |
| 3366a-1 | Y*EG | S | S | O | O | O | S | OH | OMe |
| 3367a-I | Y*EG | S | S | O | O | O | S | OMe | OMe |

TABLE 3-continued

CapA Structures for mRNA preparation

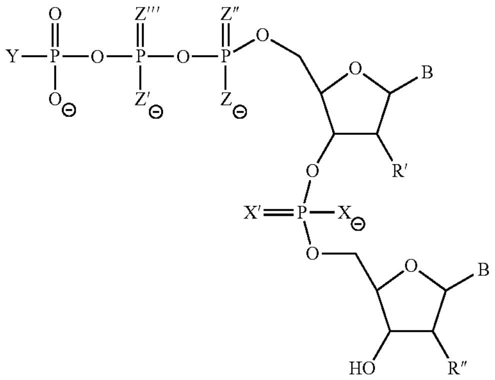

| Compound | Sequence | X | X' | Z | Z' | Z'' | Z''' | R' | R'' |
|---|---|---|---|---|---|---|---|---|---|
| 3368a-I | Y*EG | S | S | O | O | O | S | H | OMe |
| 3369a-I | Y*EG | S | S | O | O | O | S | F | OMe |
| 3370a-I | Y*EG | S | S | O | O | O | S | OEt | OMe |
| 3371a-I | Y*EG | O | O | S | O | S | O | OH | OMe |
| 3372a-I | Y*EG | O | O | S | O | S | O | OMe | OMe |
| 3373a-I | Y*EG | O | O | S | O | S | O | H | OMe |
| 3374a-I | Y*EG | O | O | S | O | S | O | F | OMe |
| 3375a-I | Y*EG | O | O | S | O | S | O | OEt | OMc |
| 3376a-I | Y*EG | S | O | S | O | S | O | OH | OMe |
| 3377a-I | Y*EG | S | O | S | O | S | O | OMe | OMe |
| 3378a-I | Y*EG | S | O | S | O | S | O | H | OMe |
| 3379a-I | Y*EG | S | O | S | O | S | O | F | OMe |
| 3380a-I | Y*EG | S | O | S | O | S | O | OEt | OMe |
| 3381a-I | Y*EG | S | S | S | O | S | O | OH | OMe |
| 3382a-I | Y*EG | S | S | S | O | S | O | OMe | OMe |
| 3383a-I | Y*EG | S | S | S | O | S | O | H | OMe |
| 3384a-I | Y*EG | S | S | S | O | S | O | F | OMe |
| 3385a-I | Y*EG | S | S | S | O | S | O | OEt | OMe |
| 3386a-I | Y*EG | O | O | O | S | O | S | OH | OMe |
| 3387a-I | Y*EG | O | O | O | S | O | S | OMe | OMe |
| 3388a-I | Y*EG | O | O | O | S | O | S | H | OMe |
| 3389a-I | Y*EG | O | O | O | S | O | S | F | OMe |
| 3390a-I | Y*EG | O | O | O | S | O | S | OEt | OMe |
| 3391a-I | Y*EG | S | O | O | S | O | S | OH | OMe |
| 3392a-I | Y*EG | S | O | O | S | O | S | OMe | OMe |
| 3393a-I | Y*EG | S | O | O | S | O | S | H | OMe |
| 3394a-I | Y*EG | S | O | O | S | O | S | F | OMe |
| 3395a-I | Y*EG | S | O | O | S | O | S | OEt | OMe |
| 3396a-I | Y*EG | S | S | O | S | O | S | OH | OMe |
| 3397a-I | Y*EG | S | S | O | S | O | S | OMe | OMe |
| 3398a-I | Y*EG | S | S | O | S | O | S | H | OMe |
| 3399a-I | Y*EG | S | S | O | S | O | S | F | OMe |
| 3400a-I | Y*EG | S | S | O | S | O | S | OEt | OMe |
| 3401a-I | Y*EA | O | O | O | O | O | O | OH | OH |
| 3402a-I | Y*EA | O | O | O | O | O | O | OMe | OH |
| 3403a-I | Y*EA | O | O | O | O | O | O | H | OH |
| 3404a-I | Y*EA | O | O | O | O | O | O | F | OH |
| 3405a-I | Y*EA | O | O | O | O | O | O | OEt | OH |
| 3406a-I | Y*EA | S | O | O | O | O | O | OH | OH |
| 3407a-I | Y*EA | S | O | O | O | O | O | OMe | OH |
| 3408a-I | Y*EA | S | O | O | O | O | O | H | OH |
| 3409a-I | Y*EA | S | O | O | O | O | O | F | OH |
| 3410a-I | Y*EA | S | O | O | O | O | O | OEt | OH |
| 3411a-I | Y*EA | S | S | O | O | O | O | OH | OH |
| 3412a-I | Y*EA | S | S | O | O | O | O | OMe | OH |
| 3413a-I | Y*EA | S | S | O | O | O | O | H | OH |
| 3414a-I | Y*EA | S | S | O | O | O | O | F | OH |
| 3415a-I | Y*EA | S | S | O | O | O | O | OEt | OH |
| 3416a-I | Y*EA | O | O | S | O | O | O | OH | OH |
| 3417a-I | Y*EA | O | O | S | O | O | O | OMe | OH |
| 3418a-I | Y*EA | O | O | S | O | O | O | H | OH |
| 3419a-I | Y*EA | O | O | S | O | O | O | F | OH |
| 3420a-I | Y*EA | O | O | S | O | O | O | OEt | OH |
| 3421a-I | Y*EA | S | O | S | O | O | O | OH | OH |
| 3422a-I | Y*EA | S | O | S | O | O | O | OMe | OH |
| 3423a-I | Y*EA | S | O | S | O | O | O | H | OH |
| 3424a-I | Y*EA | S | O | S | O | O | O | F | OH |

TABLE 3-continued

CapA Structures for mRNA preparation

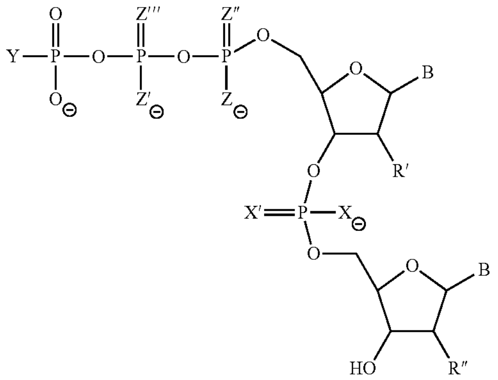

| Compound | Sequence | X | X' | Z | Z' | Z'' | Z''' | R' | R'' |
|---|---|---|---|---|---|---|---|---|---|
| 3425a-I | Y*EA | S | O | S | O | O | O | OEt | OH |
| 3426a-I | Y*EA | S | S | S | O | O | O | OH | OH |
| 3427a-I | Y*EA | S | S | S | O | O | O | OMe | OH |
| 3428a-I | Y*EA | S | S | S | O | O | O | H | OH |
| 3429a-I | Y*EA | S | S | S | O | O | O | F | OH |
| 3430a-I | Y*EA | S | S | S | O | O | O | OEt | OH |
| 3431a-I | Y*EA | O | O | S | S | O | O | OH | OH |
| 3432a-I | Y*EA | O | O | S | S | O | O | OMe | OH |
| 3433a-I | Y*EA | O | O | S | S | O | O | H | OH |
| 3434a-I | Y*EA | O | O | S | S | O | O | F | OH |
| 3435a-I | Y*EA | O | O | S | S | O | O | OEt | OH |
| 3436a-I | Y*EA | S | O | S | S | O | O | OH | OH |
| 3437a-I | Y*EA | S | O | S | S | O | O | OMe | OH |
| 3438a-I | Y*EA | S | O | S | S | O | O | H | OH |
| 3439a-I | Y*EA | S | O | S | S | O | O | F | OH |
| 3440a-I | Y*EA | S | O | S | S | O | O | OEt | OH |
| 3441a-I | Y*EA | S | S | S | S | O | O | OH | OH |
| 3442a-I | Y*EA | S | S | S | S | O | O | OMe | OH |
| 3443a-I | Y*EA | S | S | S | S | O | O | H | OH |
| 3444a-I | Y*EA | S | S | S | S | O | O | F | OH |
| 3445a-I | Y*EA | S | S | S | S | O | O | OEt | OH |
| 3446a-I | Y*EA | O | O | S | S | S | O | OH | OH |
| 3447a-I | Y*EA | O | O | S | S | S | O | OMe | OH |
| 3448a-I | Y*EA | O | O | S | S | S | O | H | OH |
| 3449a-I | Y*EA | O | O | S | S | S | O | F | OH |
| 3450a-I | Y*EA | O | O | S | S | S | O | OEt | OH |
| 3451a-I | Y*EA | S | O | S | S | S | O | OH | OH |
| 3452a-I | Y*EA | S | O | S | S | S | O | OMe | OH |
| 3453a-I | Y*EA | S | O | S | S | S | O | H | OH |
| 3454a-I | Y*EA | S | O | S | S | S | O | F | OH |
| 3455a-I | Y*EA | S | O | S | S | S | O | OEt | OH |
| 3456a-I | Y*EA | S | S | S | S | S | O | OH | OH |
| 3457a-I | Y*EA | S | S | S | S | S | O | OMe | OH |
| 3458a-I | Y*EA | S | S | S | S | S | O | H | OH |
| 3459a-I | Y*EA | S | S | S | S | S | O | F | OH |
| 3460a-I | Y*EA | S | S | S | S | S | O | OEt | OH |
| 3461a-I | Y*EA | O | O | S | S | S | S | OH | OH |
| 3462a-I | Y*EA | O | O | S | S | S | S | OMe | OH |
| 3463a-I | Y*EA | O | O | S | S | S | S | H | OH |
| 3464a-I | Y*EA | O | O | S | S | S | S | F | OH |
| 3465a-I | Y*EA | O | O | S | S | S | S | OEt | OH |
| 3466a-I | Y*EA | S | O | S | S | S | S | OH | OH |
| 3467a-I | Y*EA | S | O | S | S | S | S | OMe | OH |
| 3468a-I | Y*EA | S | O | S | S | S | S | H | OH |
| 3469a-I | Y*EA | S | O | S | S | S | S | F | OH |
| 3470a-I | Y*EA | S | O | S | S | S | S | OEt | OH |
| 3471a-I | Y*EA | S | S | S | S | S | S | OH | OH |
| 3472a-I | Y*EA | S | S | S | S | S | S | OMe | OH |
| 3473a-I | Y*EA | S | S | S | S | S | S | H | OH |
| 3474a-I | Y*EA | S | S | S | S | S | S | F | OH |
| 3475a-I | Y*EA | S | S | S | S | S | S | OEt | OH |
| 3476a-I | Y*EA | O | O | O | S | S | S | OH | OH |
| 3477a-I | Y*EA | O | O | O | S | S | S | OMe | OH |
| 3478a-I | Y*EA | O | O | O | S | S | S | H | OH |
| 3479a-I | Y*EA | O | O | O | S | S | S | F | OH |
| 3480a-I | Y*EA | O | O | O | S | S | S | OEt | OH |
| 3481a-I | Y*EA | S | O | O | S | S | S | OH | OH |

TABLE 3-continued

CapA Structures for mRNA preparation

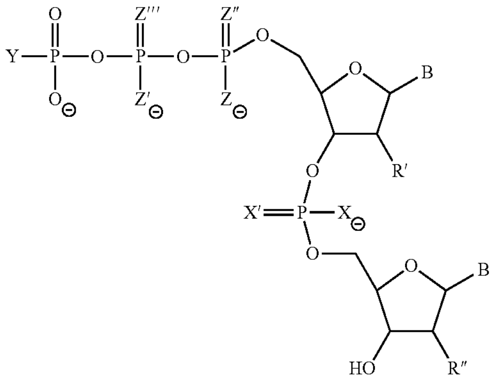

| Compound | Sequence | X | X' | Z | Z' | Z'' | Z''' | R' | R'' |
|---|---|---|---|---|---|---|---|---|---|
| 3482a-I | Y*EA | S | O | O | S | S | S | OMe | OH |
| 3483a-I | Y*EA | S | O | O | S | S | S | H | OH |
| 3484a-I | Y*EA | S | O | O | S | S | S | F | OH |
| 3485a-I | Y*EA | S | O | O | S | S | S | OEt | OH |
| 3486a-I | Y*EA | S | S | O | S | S | S | OH | OH |
| 3487a-I | Y*EA | S | S | O | S | S | S | OMe | OH |
| 3488a-I | Y*EA | S | S | O | S | S | S | H | OH |
| 3489a-I | Y*EA | S | S | O | S | S | S | F | OH |
| 3490a-I | Y*EA | S | S | O | S | S | S | OEt | OH |
| 3491a-I | Y*EA | O | O | O | O | S | $ | OH | OH |
| 3492a-I | Y*EA | O | O | O | O | S | S | OMe | OH |
| 3493a-I | Y*EA | O | O | O | O | S | S | H | OH |
| 3494a-I | Y*EA | O | O | O | O | S | S | F | OH |
| 3495a-I | Y*EA | O | O | O | O | S | S | OEt | OH |
| 3496a-I | Y*EA | S | O | O | O | S | 5 | OH | OH |
| 3497a-I | Y*EA | S | O | O | O | S | S | OMe | OH |
| 3498a-I | Y*EA | S | O | O | O | S | S | H | OH |
| 3499a-I | Y*EA | S | O | O | O | S | S | F | OH |
| 3500a-I | Y*EA | S | O | O | O | S | S | OEt | OH |
| 3501a-I | Y*EA | S | S | O | O | S | S | OH | OH |
| 3502a-I | Y*EA | S | S | O | O | S | S | OMe | OH |
| 3503a-I | Y*EA | S | S | O | O | S | S | H | OH |
| 3504a-I | Y*EA | S | S | O | O | S | S | F | OH |
| 3505a-I | Y*EA | S | S | O | O | S | S | OEt | OH |
| 3506a-I | Y*EA | O | O | O | O | O | S | OH | OH |
| 3507a-I | Y*EA | O | O | O | O | O | S | OMe | OH |
| 3508a-I | Y*EA | O | O | O | O | O | S | H | OH |
| 3509a-I | Y*EA | O | O | O | O | O | S | F | OH |
| 3510a-I | Y*EA | O | O | O | O | O | S | OEt | OH |
| 3511a-I | Y*EA | S | O | O | O | O | S | OH | OH |
| 3512a-I | Y*EA | S | O | O | O | O | S | OMe | OH |
| 3513a-I | Y*EA | S | O | O | O | O | S | H | OH |
| 3514a-I | Y*EA | S | O | O | O | O | S | F | OH |
| 3515a-I | Y*EA | S | O | O | O | O | S | OEt | OH |
| 3516a-I | Y*EA | S | S | O | O | O | S | OH | OH |
| 3517a-I | Y*EA | S | S | O | O | O | S | OMe | OH |
| 3518a-I | Y*EA | S | S | O | O | O | S | H | OH |
| 3519a-I | Y*EA | S | S | O | O | O | S | F | OH |
| 3520a-I | Y*EA | S | S | O | O | O | S | OEt | OH |
| 3521a-I | Y*EA | O | O | S | O | S | O | OH | OH |
| 3522a-I | Y*EA | O | O | S | O | S | O | OMe | OH |
| 3523a-I | Y*EA | O | O | S | O | S | O | H | OH |
| 3524a-I | Y*EA | O | O | S | O | S | O | F | OH |
| 3525a-I | Y*EA | O | O | S | O | S | O | OEt | OH |
| 3526a-I | Y*EA | S | O | S | O | S | O | OH | OH |
| 3527a-I | Y*EA | S | O | S | O | S | O | OMe | OH |
| 3528a-I | Y*EA | S | O | S | O | S | O | H | OH |
| 3529a-I | Y*EA | S | O | S | O | S | O | F | OH |
| 3530a-I | Y*EA | S | O | S | O | S | O | OEt | OH |
| 3531a-I | Y*EA | S | S | S | O | S | O | OH | OH |
| 3532a-I | Y*EA | S | S | S | O | S | O | OMe | OH |
| 3533a-I | Y*EA | S | S | S | O | S | O | H | OH |
| 3534a-I | Y*EA | S | S | S | O | S | O | F | OH |
| 3535a-I | Y*EA | S | S | S | O | S | O | OEt | OH |
| 3536a-I | Y*EA | O | O | O | S | O | S | OH | OH |
| 3537a-I | Y*EA | O | O | O | S | O | S | OMe | OH |
| 3538a-I | Y*EA | O | O | O | S | O | S | H | OH |

TABLE 3-continued

CapA Structures for mRNA preparation

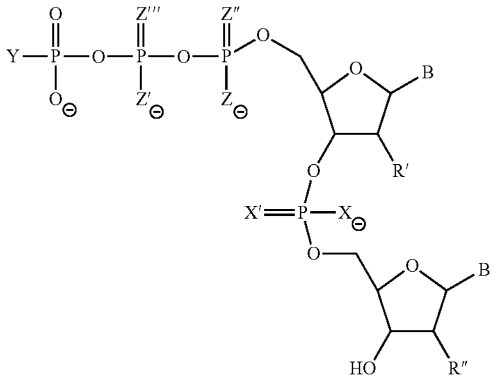

| Compound | Sequence | X | X' | Z | Z' | Z'' | Z''' | R' | R'' |
|---|---|---|---|---|---|---|---|---|---|
| 3539a-I | Y*EA | O | O | O | S | O | S | F | OH |
| 3540a-I | Y*EA | O | O | O | S | O | S | OEt | OH |
| 3541a-I | Y*EA | S | O | O | S | O | S | OH | OH |
| 3542a-I | Y*EA | S | O | O | S | O | S | OMe | OH |
| 3543a-I | Y*EA | S | O | O | S | O | S | H | OH |
| 3544a-I | Y*EA | S | O | O | S | O | S | F | OH |
| 3545a-I | Y*EA | S | O | O | S | O | S | OEt | OH |
| 3546a-I | Y*EA | S | S | O | S | O | S | OH | OH |
| 3547a-I | Y*EA | S | S | O | S | O | S | OMe | OH |
| 3548a-I | Y*EA | S | S | O | S | O | S | H | OH |
| 3549a-I | Y*EA | S | S | O | S | O | S | F | OH |
| 3550a-I | Y*EA | S | S | O | S | O | S | OEt | OH |
| 3551a-I | Y*EA | O | O | O | O | O | O | OH | OMe |
| 3552a-I | Y*EA | O | O | O | O | O | O | OMe | OMe |
| 3553a-I | Y*EA | O | O | O | O | O | O | H | OMe |
| 3554a-I | Y*EA | O | O | O | O | O | O | F | OMe |
| 3555a-I | Y*EA | O | O | O | O | O | O | OEt | OMe |
| 3556a-I | Y*EA | S | O | O | O | O | O | OH | OMe |
| 3557a-I | Y*EA | S | O | O | O | O | O | OMe | OMe |
| 3558a-I | Y*EA | S | O | O | O | O | O | H | OMe |
| 3559a-I | Y*EA | S | O | O | O | O | O | F | OMe |
| 3560a-I | Y*EA | S | O | O | O | O | O | OEt | OMe |
| 3561a-I | Y*EA | S | S | O | O | O | O | OH | OMe |
| 3562a-I | Y*EA | S | S | O | O | O | O | OMe | OMe |
| 3563a-I | Y*EA | S | S | O | O | O | O | H | OMe |
| 3564a-I | Y*EA | S | S | O | O | O | O | F | OMe |
| 3565a-I | Y*EA | S | S | O | O | O | O | OEt | OMe |
| 3566a-I | Y*EA | O | O | S | O | O | O | OH | OMe |
| 3567a-I | Y*EA | O | O | S | O | O | O | OMe | OMe |
| 3568a-I | Y*EA | O | O | S | O | O | O | H | OMe |
| 3569a-I | Y*EA | O | O | S | O | O | O | F | OMe |
| 3570a-I | Y*EA | O | O | S | O | O | O | OEt | OMe |
| 3571a-I | Y*EA | S | O | S | O | O | O | OH | OMe |
| 3572a-I | Y*EA | S | O | S | O | O | O | OMe | OMe |
| 3573a-I | Y*EA | S | O | S | O | O | O | H | OMe |
| 3574a-I | Y*EA | S | O | S | O | O | O | F | OMe |
| 3575a-I | Y*EA | S | O | S | O | O | O | OEt | OMe |
| 3576a-I | Y*EA | S | S | S | O | O | O | OH | OMe |
| 3577a-I | Y*EA | S | S | S | O | O | O | OMe | OMe |
| 3578a-I | Y*EA | S | S | S | O | O | O | H | OMe |
| 3579a-I | Y*EA | S | S | S | O | O | O | F | OMe |
| 3580a-I | Y*EA | S | S | S | O | O | O | OEt | OMe |
| 3581a-I | Y*EA | O | O | S | S | O | O | OH | OMe |
| 3582a-I | Y*EA | O | O | S | S | O | O | OMe | OMe |
| 3583a-I | Y*EA | O | O | S | S | O | O | H | OMe |
| 3584a-I | Y*EA | O | O | S | S | O | O | F | OMe |
| 3585a-I | Y*EA | O | O | S | S | O | O | OEt | OMe |
| 3586a-I | Y*EA | S | O | S | S | O | O | OH | OMe |
| 3587a-I | Y*EA | S | O | S | S | O | O | OMe | OMe |
| 3588a-I | Y*EA | S | O | S | S | O | O | H | OMe |
| 3589a-I | Y*EA | S | O | S | S | O | O | F | OMe |
| 3590a-I | Y*EA | S | O | S | S | O | O | OEt | OMe |
| 3591a-I | Y*EA | S | S | S | S | O | O | OH | OMe |
| 3592a-I | Y*EA | S | S | S | S | O | O | OMe | OMe |
| 3593a-I | Y*EA | S | S | S | S | O | O | H | OMe |
| 3594a-I | Y*EA | S | S | S | S | O | O | F | OMe |
| 3595a-I | Y*EA | S | S | S | S | O | O | OEt | OMe |

TABLE 3-continued

CapA Structures for mRNA preparation

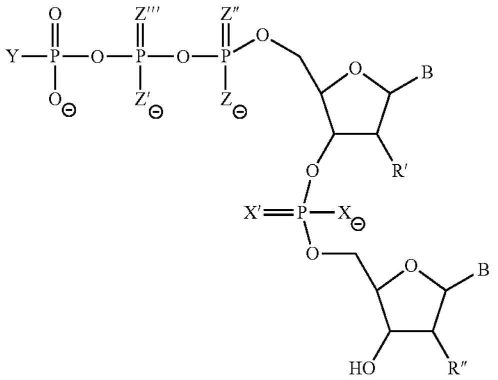

| Compound | Sequence | X | X' | Z | Z' | Z'' | Z''' | R' | R'' |
|---|---|---|---|---|---|---|---|---|---|
| 3596a-I | Y*EA | O | O | S | S | S | O | OH | OMe |
| 3597a-I | Y*EA | O | O | S | S | S | O | OMe | OMe |
| 3598a-I | Y*EA | O | O | S | S | S | O | H | OMe |
| 3599a-I | Y*EA | O | O | S | S | S | O | F | OMe |
| 3600a-I | Y*EA | O | O | S | S | S | O | OEt | OMe |
| 3601a-I | Y*EA | S | O | S | S | S | O | OH | OMe |
| 3602a-I | Y*EA | S | O | S | S | S | O | OMe | OMe |
| 3603a-I | Y*BA | S | O | S | S | S | O | H | OMe |
| 3604a-I | Y*EA | S | O | S | S | S | O | F | OMe |
| 3605a-I | Y*EA | S | O | S | S | S | O | OEt | OME |
| 3606a-I | Y*EA | S | S | S | S | S | O | OH | OMe |
| 3607a-I | Y*EA | S | S | S | S | S | O | OMe | OMe |
| 3608a-I | Y*EA | S | S | S | S | S | O | H | OMe |
| 3609a-I | Y*EA | S | S | S | S | S | O | F | OMe |
| 3610a-I | Y*EA | S | S | S | S | S | O | OEt | OMe |
| 3611a-I | Y*EA | O | O | S | S | S | S | OH | OMe |
| 3612a-I | Y*EA | O | O | S | S | S | S | OMe | OMe |
| 3613a-I | Y*EA | O | O | S | S | S | S | H | OMe |
| 3614a-I | Y*EA | O | O | S | S | S | S | F | OMe |
| 3615a-I | Y*EA | O | O | S | S | S | S | OEt | OMe |
| 3616a-I | Y*EA | S | O | S | S | S | S | OH | OMe |
| 3617a-I | Y*EA | S | O | S | S | S | S | OMe | OMe |
| 3618a-I | Y*EA | S | O | S | S | S | S | H | OMe |
| 3619a-I | Y*EA | S | O | S | S | S | S | F | OMe |
| 3620a-I | Y*EA | S | O | S | S | S | S | OEt | OMe |
| 3621a-I | Y*EA | S | S | S | S | S | S | OH | OMe |
| 3622a-I | Y*EA | S | S | S | S | S | S | OMe | OMe |
| 3623a-I | Y*EA | S | S | S | S | S | S | H | OMe |
| 3624a-I | Y*EA | S | S | S | S | S | S | F | OMe |
| 3625a-I | Y*EA | S | S | S | S | S | S | OEt | OMe |
| 3626a-I | Y*EA | O | O | O | S | S | S | OH | OMe |
| 3627a-I | Y*EA | O | O | O | S | S | S | OMe | OMe |
| 3628a-I | Y*EA | O | O | O | S | S | S | H | OMe |
| 3629a-I | Y*EA | O | O | O | S | S | S | F | OMe |
| 3630a-I | Y*EA | O | O | O | S | S | S | OEt | OMe |
| 3631a-I | Y*EA | S | O | O | S | S | S | OH | OMe |
| 3632a-I | Y*EA | S | O | O | S | S | S | OMe | OMe |
| 3633a-I | Y*EA | S | O | O | S | S | S | H | OMe |
| 3634a-I | Y*EA | S | O | O | S | S | S | F | OMe |
| 3635a-I | Y*EA | S | O | O | S | S | S | OEt | OMe |
| 3636a-I | Y*EA | S | S | O | S | S | S | OH | OMe |
| 3637a-I | Y*EA | S | S | O | S | S | S | OMe | OMe |
| 3638a-I | Y*EA | S | S | O | S | S | S | H | OMe |
| 3639a-I | Y*EA | S | S | O | S | S | S | F | OMe |
| 3640a-I | Y*EA | S | S | O | S | S | S | OEt | OMe |
| 3641a-I | Y*EA | O | O | O | O | S | S | OH | OMe |
| 3642a-I | Y*EA | O | O | O | O | S | S | OMe | OMe |
| 3643a-I | Y*EA | O | O | O | O | S | S | H | OMe |
| 3644a-I | Y*EA | O | O | O | O | S | S | F | OMe |
| 3645a-I | Y*EA | O | O | O | O | S | S | OEt | OMe |
| 3646a-I | Y*EA | S | O | O | O | S | S | OH | OMe |
| 3647a-I | Y*EA | S | O | O | O | S | S | OMe | OMe |
| 3648a-I | Y*EA | S | O | O | O | S | S | H | OMe |
| 3649a-I | Y*EA | S | O | O | O | S | S | F | OMe |
| 3650a-I | Y*EA | S | O | O | O | S | S | OEt | OMe |
| 3651a-I | Y*EA | S | S | O | O | S | S | OH | OMe |
| 3652a-I | Y*EA | S | S | O | O | S | S | OMe | OMe |

TABLE 3-continued

CapA Structures for mRNA preparation

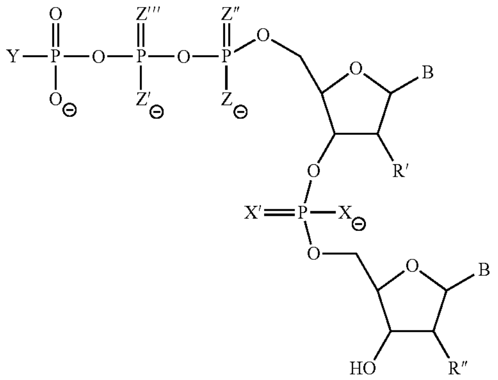

| Compound | Sequence | X | X' | Z | Z' | Z'' | Z''' | R' | R'' |
|---|---|---|---|---|---|---|---|---|---|
| 3653a-I | Y*EA | S | S | O | O | S | S | H | OMe |
| 3654a-I | Y*EA | S | S | O | O | S | S | F | OMe |
| 3655a-I | Y*EA | S | S | O | O | S | S | OEt | OMe |
| 3656a-I | Y*EA | O | O | O | O | O | S | OH | OMe |
| 3657a-I | Y*EA | O | O | O | O | O | S | OMe | OMe |
| 3658a-I | Y*EA | O | O | O | O | O | S | H | OMe |
| 3659a-I | Y*EA | O | O | O | O | O | S | F | OMe |
| 3660a-I | Y*EA | O | O | O | O | O | S | OEt | OMe |
| 3661a-I | Y*EA | S | O | O | O | O | S | OH | OMe |
| 3662a-I | Y*EA | S | O | O | O | O | S | OMe | OMe |
| 3663a-I | Y*EA | S | O | O | O | O | S | H | OMe |
| 3664a-I | Y*EA | S | O | O | O | O | S | F | OMe |
| 3665a-I | Y*EA | S | O | O | O | O | S | OEt | OMe |
| 3666a-I | Y*EA | S | S | O | O | O | S | OH | OMe |
| 3667a-I | Y*EA | S | S | O | O | O | S | OMe | OMe |
| 3668a-I | Y*EA | S | S | O | O | O | S | H | OMe |
| 3669a-I | Y*EA | S | S | O | O | O | S | F | OMe |
| 3670a-I | Y*EA | S | S | O | O | O | S | OEt | OMe |
| 3671a-I | Y*EA | O | O | S | O | S | O | OH | OMe |
| 3672a-I | Y*EA | O | O | S | O | S | O | OMe | OMe |
| 3673a-I | Y*EA | O | O | S | O | S | O | H | OMe |
| 3674a-I | Y*EA | O | O | S | O | S | O | F | OMe |
| 3675a-I | Y*EA | O | O | S | O | S | O | OEt | OMe |
| 3676a-I | Y*EA | S | O | S | O | S | O | OH | OMe |
| 3677a-I | Y*EA | S | O | S | O | S | O | OMe | OMe |
| 3678a-I | Y*EA | S | O | S | O | S | O | H | OMe |
| 3679a-I | Y*EA | S | O | S | O | S | O | F | OMe |
| 3680a-I | Y*EA | S | O | S | O | S | O | OEt | OMe |
| 3681a-I | Y*EA | S | S | S | O | S | O | OH | OMe |
| 3682a-I | Y*EA | S | S | S | O | S | O | OMe | OMe |
| 3683a-I | Y*EA | S | S | S | O | S | O | H | OMe |
| 3684a-I | Y*EA | S | S | S | O | S | O | F | OMe |
| 3685a-I | Y*EA | S | S | S | O | S | O | OEt | OMe |
| 3686a-I | Y*EA | O | O | O | S | O | S | OH | OMe |
| 3687a-I | Y*EA | O | O | O | S | O | S | OMe | OMe |
| 3688a-I | Y*EA | O | O | O | S | O | S | H | OMe |
| 3689a-I | Y*EA | O | O | O | S | O | S | F | OMe |
| 3690a-I | Y*EA | O | O | O | S | O | S | OEt | OMe |
| 3691a-I | Y*EA | S | O | O | S | O | S | OH | OMe |
| 3692a-I | Y*EA | S | O | O | S | O | S | OMe | OMe |
| 3693a-I | Y*EA | S | O | O | S | O | S | H | OMe |
| 3694a-I | Y*EA | S | O | O | S | O | S | F | OMe |
| 3695a-I | Y*EA | S | O | O | S | O | S | OEt | OMe |
| 3696a-I | Y*EA | S | S | O | S | O | S | OH | OMe |
| 3697a-I | Y*EA | S | S | O | S | O | S | OMe | OMe |
| 3698a-I | Y*EA | S | S | O | S | O | S | H | OMe |
| 3699a-I | Y*EA | S | S | O | S | O | S | F | OMe |
| 3700a-I | Y*EA | S | S | O | S | O | S | OE | OMe |
| 3701a-I | Y*EC | O | O | O | O | O | O | OH | OH |
| 3702a-I | Y*EC | O | O | O | O | O | O | OMe | OH |
| 3703a-I | Y*EC | O | O | O | O | O | O | H | OH |
| 3704a-I | Y*EC | O | O | O | O | O | O | F | OH |
| 3705a-I | Y*EC | O | O | O | O | O | O | OEt | OH |
| 3706a-I | Y*EC | S | O | O | O | O | O | OH | OH |
| 3707a-I | Y*EC | S | O | O | O | O | O | OMe | OH |
| 3708a-I | Y*EC | S | O | O | O | O | O | H | OH |
| 3709a-I | Y*EC | S | O | O | O | O | O | F | OH |

TABLE 3-continued

CapA Structures for mRNA preparation

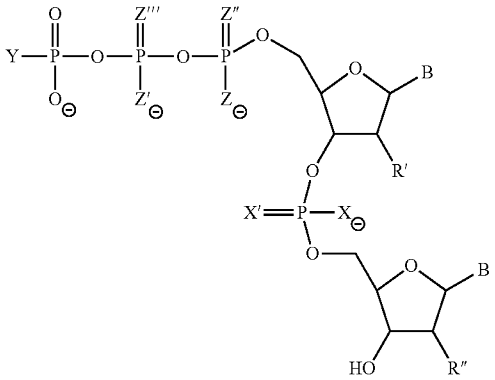

| Compound | Sequence | X | X' | Z | Z' | Z'' | Z''' | R' | R'' |
|---|---|---|---|---|---|---|---|---|---|
| 3710a-I | Y*EC | S | O | O | O | O | O | OEt | OH |
| 3711a-I | Y*EC | S | S | O | O | O | O | OH | OH |
| 3712a-I | Y*EC | S | S | O | O | O | O | OMe | OH |
| 3713a-I | Y*EC | S | S | O | O | O | O | H | OH |
| 3714a-I | Y*EC | S | S | O | O | O | O | F | OH |
| 3715a-I | Y*EC | S | S | O | O | O | O | OEt | OH |
| 3716a-I | Y*EC | O | O | S | O | O | O | OH | OH |
| 3717a-I | Y*EC | O | O | S | O | O | O | OMe | OH |
| 3718a-I | Y*EC | O | O | S | O | O | O | H | OH |
| 3719a-I | Y*EC | O | O | S | O | O | O | F | OH |
| 3720a-I | Y*EC | O | O | S | O | O | O | OEt | OH |
| 3721a-I | Y*EC | S | O | S | O | O | O | OH | OH |
| 3722a-I | Y*EC | S | O | S | O | O | O | OMe | OH |
| 3723a-I | Y*EC | S | O | S | O | O | O | H | OH |
| 3724a-I | Y*EC | S | O | S | O | O | O | F | OH |
| 3725a-I | Y*EC | S | O | S | O | O | O | OEt | OH |
| 3726a-I | Y*EC | S | S | S | O | O | O | OH | OH |
| 3727a-I | Y*EC | S | S | S | O | O | O | OMe | OH |
| 3728a-I | Y*EC | S | S | S | O | O | O | H | OH |
| 3729a-I | Y*EC | S | S | S | O | O | O | F | OH |
| 3730a-I | Y*EC | S | S | S | O | O | O | OEt | OH |
| 3731a-I | Y*EC | O | O | S | S | O | O | OH | OH |
| 3732a-I | Y*EC | O | O | S | S | O | O | OMe | OH |
| 3733a-I | Y*EC | O | O | S | S | O | O | H | OH |
| 3734a-I | Y*EC | O | O | S | S | O | O | F | OH |
| 3735a-I | Y*EC | O | O | S | S | O | O | OEt | OH |
| 3736a-I | Y*EC | S | O | S | S | O | O | OH | OH |
| 3737a-I | Y*EC | S | O | S | S | O | O | OMe | OH |
| 3738a-I | Y*EC | S | O | S | S | O | O | H | OH |
| 3739a-I | Y*EC | S | O | S | S | O | O | F | OH |
| 3740a-I | Y*EC | S | O | S | S | O | O | OEt | OH |
| 3741a-I | Y*EC | S | S | S | S | O | O | OH | OH |
| 3742a-I | Y*EC | S | S | S | S | O | O | OMe | OH |
| 3743a-I | Y*EC | S | S | S | S | O | O | H | OH |
| 3744a-I | Y*EC | S | S | S | S | O | O | F | OH |
| 3745a-I | Y*EC | S | S | S | S | O | O | OEt | OH |
| 3746a-I | Y*EC | O | O | S | S | S | O | OH | OH |
| 3747a-I | Y*EC | O | O | S | S | S | O | OMe | OH |
| 3748a-I | Y*EC | O | O | S | S | S | O | H | OH |
| 3749a-I | Y*EC | O | O | S | S | S | O | F | OH |
| 3750a-I | Y*EC | O | O | S | S | S | O | OEt | OH |
| 3751a-I | Y*EC | S | O | S | S | S | O | OH | OH |
| 3752a-I | Y*EC | S | O | S | S | S | O | OMe | OH |
| 3753a-I | Y*EC | S | O | S | S | S | O | H | OH |
| 3754a-I | Y*EC | S | O | S | S | S | O | F | OH |
| 3755a-I | Y*EC | S | O | S | S | S | O | OEt | OH |
| 3756a-I | Y*EC | S | S | S | S | S | O | OH | OH |
| 3757a-I | Y*EC | S | S | S | S | S | O | OMe | OH |
| 3758a-I | Y*EC | S | S | S | S | S | O | H | OH |
| 3759a-I | Y*EC | S | S | S | S | S | O | F | OH |
| 3760a-I | Y*EC | S | S | S | S | S | O | OEt | OH |
| 3761a-I | Y*EC | O | O | S | S | S | S | OH | OH |
| 3762a-I | Y*EC | O | O | S | S | S | S | OMe | OH |
| 3763a-I | Y*EC | O | O | S | S | S | S | H | OH |
| 3764a-I | Y*EC | O | O | S | S | S | S | F | OH |
| 3765a-I | Y*EC | O | O | S | S | S | S | OEt | OH |
| 3766a-I | Y*EC | S | O | S | S | S | S | OH | OH |

TABLE 3-continued

CapA Structures for mRNA preparation

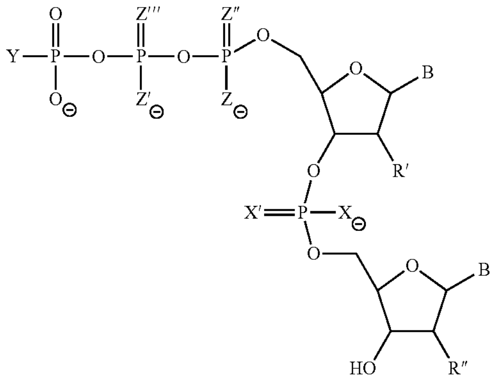

| Compound | Sequence | X | X' | Z | Z' | Z" | Z''' | R' | R" |
|---|---|---|---|---|---|---|---|---|---|
| 3767a-I | Y*EC | S | O | S | S | S | S | OMe | OH |
| 3768a-I | Y*EC | S | O | S | S | S | S | H | OH |
| 3769a-I | Y*EC | S | O | S | S | S | S | F | OH |
| 3770a-I | Y*EC | S | O | S | S | S | S | OEt | OH |
| 3771a-I | Y*EC | S | S | S | S | S | S | OH | OH |
| 3772a-I | Y*EC | S | S | S | S | S | S | OMe | OH |
| 3773a-I | Y*EC | S | S | S | S | S | S | H | OH |
| 3774a-I | Y*EC | S | S | S | S | S | S | F | OH |
| 3775a-I | Y*EC | S | S | S | S | S | S | OEt | OH |
| 3776a-I | Y*EC | O | O | O | S | S | S | OH | OH |
| 3777a-I | Y*EC | O | O | O | S | S | S | OMe | OH |
| 3778a-I | Y*EC | O | O | O | S | S | S | H | OH |
| 3779a-I | Y*EC | O | O | O | S | S | S | F | OH |
| 3780a-I | Y*EC | O | O | O | S | S | S | OEt | OH |
| 3781a-I | Y*EC | S | O | O | S | S | S | OH | OH |
| 3782a-I | Y*EC | S | O | O | S | S | S | OMe | OH |
| 3783a-I | Y*EC | S | O | O | S | S | S | H | OH |
| 3784a-I | Y*EC | S | O | O | S | S | S | F | OH |
| 3785a-I | Y*EC | S | O | O | S | S | S | OEt | OH |
| 3786a-I | Y*EC | S | S | O | S | S | S | OH | OH |
| 3787a-I | Y*EC | S | S | O | S | S | S | OMe | OH |
| 3788a-I | Y*EC | S | S | O | S | S | S | H | OH |
| 3789a-I | Y*EC | S | S | O | S | S | S | F | OH |
| 3790a-I | Y*EC | S | S | O | S | S | S | OEt | OH |
| 3791a-I | Y*EC | O | O | O | O | S | S | OH | OH |
| 3792a-I | Y*EC | O | O | O | O | S | S | OMe | OH |
| 3793a-I | Y*EC | O | O | O | O | S | S | H | OH |
| 3794a-I | Y*EC | O | O | O | O | S | S | F | OH |
| 3795a-I | Y*EC | O | O | O | O | S | S | OEt | OH |
| 3796a-I | Y*EC | S | O | O | O | S | S | OH | OH |
| 3797a-I | Y*EC | S | O | O | O | S | S | OMe | OH |
| 3798a-I | Y*EC | S | O | O | O | S | S | H | OH |
| 3799a-I | Y*EC | S | O | O | O | S | S | F | OH |
| 3800a-I | Y*EC | S | O | O | O | S | S | OEt | OH |
| 3801a-I | Y*EC | S | S | O | O | S | S | OH | OH |
| 3802a-I | Y*EC | S | S | O | O | S | S | OMe | OH |
| 3803a-I | Y*EC | S | S | O | O | S | S | H | OH |
| 3804a-I | Y*EC | S | S | O | O | S | S | F | OH |
| 3805a-I | Y*EC | S | S | O | O | S | S | OEt | OH |
| 3806a-I | Y*EC | O | O | O | O | O | S | OH | OH |
| 3807a-I | Y*EC | O | O | O | O | O | S | OMe | OH |
| 3808a-I | Y*EC | O | O | O | O | O | S | H | OH |
| 3809a-I | Y*EC | O | O | O | O | O | S | F | OH |
| 3810a-I | Y*EC | O | O | O | O | O | S | OEt | OH |
| 3811a-I | Y*EC | S | O | O | O | O | S | OH | OH |
| 3812a-I | Y*EC | S | O | O | O | O | S | OMe | OH |
| 3813a-I | Y*EC | S | O | O | O | O | S | H | OH |
| 3814a-I | Y*EC | S | O | O | O | O | S | F | OH |
| 3815a-I | Y*EC | S | O | O | O | O | S | OEt | OH |
| 3816a-I | Y*EC | S | S | O | O | O | S | OH | OH |
| 3817a-I | Y*EC | S | S | O | O | O | S | OMe | OH |
| 3818a-I | Y*EC | S | S | O | O | O | S | H | OH |
| 3819a-I | Y*EC | S | S | O | O | O | S | F | OH |
| 3820a-I | Y*EC | S | S | O | O | O | S | OEt | OH |
| 3821a-I | Y*EC | O | O | S | O | S | O | OH | OH |
| 3822a-I | Y*EC | O | O | S | O | S | O | OMe | OH |
| 3823a-I | Y*EC | O | O | S | O | S | O | H | OH |

TABLE 3-continued

CapA Structures for mRNA preparation

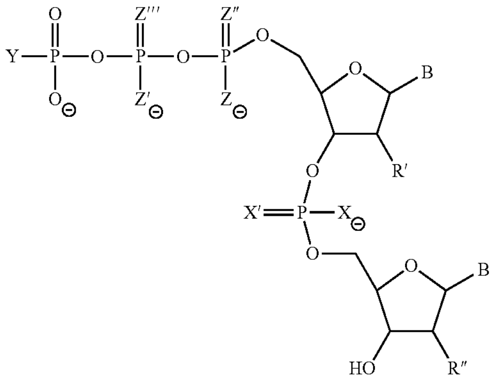

| Compound | Sequence | X | X' | Z | Z' | Z" | Z''' | R' | R" |
|---|---|---|---|---|---|---|---|---|---|
| 3824a-I | Y*EC | O | O | S | O | S | O | F | OH |
| 3825a-I | Y*EC | O | O | S | O | S | O | OEt | OH |
| 3826a-I | Y*EC | S | O | S | O | S | O | OH | OH |
| 3827a-I | Y*EC | S | O | S | O | S | O | OMe | OH |
| 3828a-I | Y*EC | S | O | S | O | S | O | H | OH |
| 3829a-I | Y*EC | S | O | S | O | S | O | F | OH |
| 3830a-I | Y*EC | S | O | S | O | S | O | OEt | OH |
| 3831a-I | Y*EC | S | S | S | O | S | O | OH | OH |
| 3832a-I | Y*EC | S | S | S | O | S | O | OMe | OH |
| 3833a-I | Y*EC | S | S | S | O | S | O | H | OH |
| 3834a-I | Y*EC | S | S | S | O | S | O | F | OH |
| 3835a-I | Y*EC | S | S | S | O | S | O | OEt | OH |
| 3836a-I | Y*EC | O | O | O | S | O | S | OH | OH |
| 3837a-I | Y*EC | O | O | O | S | O | S | OMe | OH |
| 3838a-I | Y*EC | O | O | O | S | O | S | H | OH |
| 3839a-I | Y*EC | O | O | O | S | O | S | F | OH |
| 3840a-I | Y*EC | O | O | O | S | O | S | OEt | OH |
| 3841a-I | Y*EC | S | O | O | S | O | S | OH | OH |
| 3842a-I | Y*EC | S | O | O | S | O | S | OMe | OH |
| 3843a-I | Y*EC | S | O | O | S | O | S | H | OH |
| 3844a-I | Y*EC | S | O | O | S | O | S | F | OH |
| 3845a-I | Y*EC | S | O | O | S | O | S | OEt | OH |
| 3846a-I | Y*EC | S | S | O | S | O | S | OH | OH |
| 3847a-I | Y*EC | S | S | O | S | O | S | OMe | OH |
| 3848a-I | Y*EC | S | S | O | S | O | S | H | OH |
| 3849a-I | Y*EC | S | S | O | S | O | S | F | OH |
| 3850a-I | Y*EC | S | S | O | S | O | S | OEt | OH |
| 3851a-I | Y*EC | O | O | O | O | O | O | OH | OMe |
| 3852a-I | Y*EC | O | O | O | O | O | O | OMe | OMe |
| 3853a-I | Y*EC | O | O | O | O | O | O | H | OMe |
| 3854a-I | Y*EC | O | O | O | O | O | O | F | OMe |
| 3855a-I | Y*EC | O | O | O | O | O | O | OEt | OMe |
| 3856a-I | Y*EC | S | O | O | O | O | O | OH | OMe |
| 3857a-I | Y*EC | S | O | O | O | O | O | OMe | OMe |
| 3858a-I | Y*EC | S | O | O | O | O | O | H | OMe |
| 3859a-I | Y*EC | S | O | O | O | O | O | F | OMe |
| 3860a-I | Y*EC | S | O | O | O | O | O | OEt | OMe |
| 3861a-I | Y*EC | S | S | O | O | O | O | OH | OMe |
| 3862a-I | Y*EC | S | S | O | O | O | O | OMe | OMe |
| 3863a-I | Y*EC | S | S | O | O | O | O | H | OMe |
| 3864a-I | Y*EC | S | S | O | O | O | O | F | OMe |
| 3865a-I | Y*EC | S | S | O | O | O | O | OEt | OMe |
| 3866a-I | Y*EC | O | O | S | O | O | O | OH | OMe |
| 3867a-I | Y*EC | O | O | S | O | O | O | OMe | OMe |
| 3868a-I | Y*EC | O | O | S | O | O | O | H | OMe |
| 3869a-I | Y*EC | O | O | S | O | O | O | F | OMe |
| 3870a-I | Y*EC | O | O | S | O | O | O | OEt | OMe |
| 3871a-I | Y*EC | S | O | S | O | O | O | OH | OMe |
| 3872a-I | Y*EC | S | O | S | O | O | O | OMe | OMe |
| 3873a-I | Y*EC | S | O | S | O | O | O | H | OMe |
| 3874a-I | Y*EC | S | O | S | O | O | O | F | OMe |
| 3875a-I | Y*EC | S | O | S | O | O | O | OEt | OMe |
| 3876a-I | Y*EC | S | S | S | O | O | O | OH | OMe |
| 3877a-I | Y*EC | S | S | S | O | O | O | OMe | OMe |
| 3878a-I | Y*EC | S | S | S | O | O | O | H | OMe |
| 3879a-I | Y*EC | S | S | S | O | O | O | F | OMe |
| 3880a-I | Y*EC | S | S | S | O | O | O | OEt | OMe |

TABLE 3-continued

CapA Structures for mRNA preparation

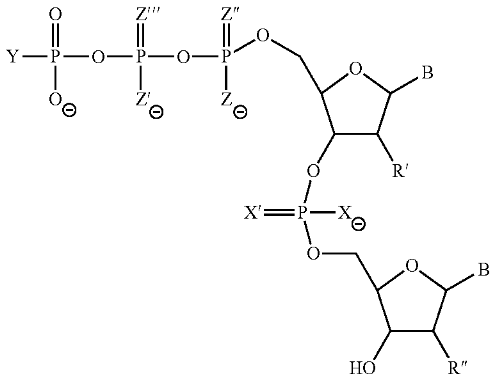

| Compound | Sequence | X | X' | Z | Z' | Z'' | Z''' | R' | R'' |
|---|---|---|---|---|---|---|---|---|---|
| 3881a-I | Y*EC | O | O | S | S | O | O | OH | OMe |
| 3882a-I | Y*EC | O | O | S | S | O | O | OMe | OMe |
| 3883a-I | Y*EC | O | O | S | S | O | O | H | OMe |
| 3884a-I | Y*EC | O | O | S | S | O | O | F | OMe |
| 3885a-I | Y*EC | O | O | S | S | O | O | OEt | OMe |
| 3886a-I | Y*EC | S | O | S | S | O | O | OH | OMe |
| 3887a-I | Y*EC | S | O | S | S | O | O | OMe | OMe |
| 3888a-I | Y*EC | S | O | S | S | O | O | H | OMe |
| 3889a-I | Y*EC | S | O | S | S | O | O | F | OMe |
| 3890a-I | Y*EC | S | O | S | S | O | O | OEt | OMe |
| 3891a-I | Y*EC | S | S | S | S | O | O | OH | OMe |
| 3892a-I | Y*EC | S | S | S | S | O | O | OMe | OMe |
| 3893a-I | Y*EC | S | S | S | S | O | O | H | OMe |
| 3894a-I | Y*EC | S | S | S | S | O | O | F | OMe |
| 3895a-I | Y*EC | S | S | S | S | O | O | OEt | OMe |
| 3896a-I | Y*EC | O | O | S | S | S | O | OH | OMe |
| 3897a-I | Y*EC | O | O | S | S | S | O | OMe | OMe |
| 3898a-I | Y*EC | O | O | S | S | S | O | H | OMe |
| 3899a-I | Y*EC | O | O | S | S | S | O | F | OMe |
| 3900a-I | Y*EC | O | O | S | S | S | O | OEt | OMe |
| 3901a-I | Y*EC | S | O | S | S | S | O | OH | OMe |
| 3902a-I | Y*EC | S | O | S | S | S | O | OMe | OMe |
| 3903a-I | Y*EC | S | O | S | S | S | O | H | OMe |
| 3904a-I | Y*EC | S | O | S | S | S | O | F | OMe |
| 3905a-I | Y*EC | S | O | S | S | S | O | OEt | OMe |
| 3906a-I | Y*EC | S | S | S | S | S | O | OH | OMe |
| 3907a-I | Y*EC | S | S | S | S | S | O | OMe | OMe |
| 3908a-I | Y*EC | S | S | S | S | S | O | H | OMe |
| 3909a-I | Y*EC | S | S | S | S | S | O | F | OMe |
| 3910a-I | Y*EC | S | S | S | S | S | O | OEt | OMe |
| 3911a-I | Y*EC | O | O | S | S | S | S | OH | OMe |
| 3912a-I | Y*EC | O | O | S | S | S | S | OMe | OMe |
| 3913a-I | Y*EC | O | O | S | S | S | S | H | OMe |
| 3914a-I | Y*EC | O | O | S | S | S | S | F | OMe |
| 3915a-I | Y*EC | O | O | S | S | S | S | OEt | OMe |
| 3916a-I | Y*EC | S | O | S | S | S | S | OH | OMe |
| 3917a-I | Y*EC | S | O | S | S | S | S | OMe | OMe |
| 3918a-I | Y*EC | S | O | S | S | S | S | H | OMe |
| 3919a-I | Y*EC | S | O | S | S | S | S | F | OMe |
| 3920a-I | Y*EC | S | O | S | S | S | S | OEt | OMe |
| 3921a-I | Y*EC | S | S | S | S | S | S | OH | OMe |
| 3922a-I | Y*EC | S | S | S | S | S | S | OMe | OMe |
| 3923a-I | Y*EC | S | S | S | S | S | S | H | OMe |
| 3924a-I | Y*EC | S | S | S | S | S | S | F | OMe |
| 3925a-I | Y*EC | S | S | S | S | S | S | OEt | OMe |
| 3926a-I | Y*EC | O | O | O | S | S | S | OH | OMe |
| 3927a-I | Y*EC | O | O | O | S | S | S | OMe | OMe |
| 3928a-I | Y*EC | O | O | O | S | S | S | H | OMe |
| 3929a-I | Y*EC | O | O | O | S | S | S | F | OMe |
| 3930a-I | Y*EC | O | O | O | S | S | S | OEt | OMe |
| 3931a-I | Y*EC | S | O | O | S | S | S | OH | OMe |
| 3932a-I | Y*EC | S | O | O | S | S | S | OMe | OMe |
| 3933a-I | Y*EC | S | O | O | S | S | S | H | OMe |
| 3934a-I | Y*EC | S | O | O | S | S | S | F | OMe |
| 3935a-I | Y*EC | S | O | O | S | S | S | OEt | OMe |
| 3936a-I | Y*EC | S | S | O | S | S | S | OH | OMe |
| 3937a-I | Y*EC | S | S | O | S | S | S | OMe | OMe |

TABLE 3-continued

CapA Structures for mRNA preparation

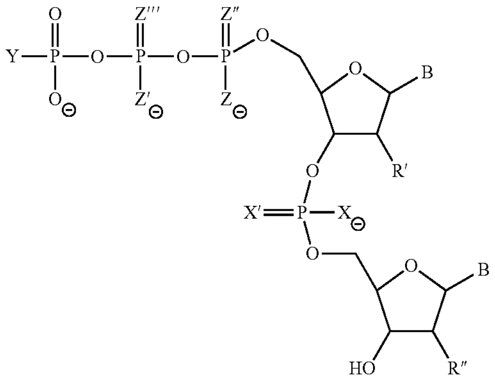

| Compound | Sequence | X | X' | Z | Z' | Z'' | Z''' | R' | R'' |
|---|---|---|---|---|---|---|---|---|---|
| 3938a-I | Y*EC | S | S | O | S | S | S | H | OMe |
| 3939a-I | Y*EC | S | S | O | S | S | S | F | OMe |
| 3940a-I | Y*EC | S | S | O | S | S | S | OEt | OMe |
| 3941a-I | Y*EC | O | O | O | O | S | S | OH | OMe |
| 3942a-I | Y*EC | O | O | O | O | S | S | OMe | OMe |
| 3943a-I | Y*EC | O | O | O | O | S | S | H | OMe |
| 3944a-I | Y*EC | O | O | O | O | S | S | F | OMe |
| 3945a-I | Y*EC | O | O | O | O | S | S | OEt | OMe |
| 3946a-I | Y*EC | S | O | O | O | S | S | OH | OMe |
| 3947a-I | Y*EC | S | O | O | O | S | S | OMe | OMe |
| 3948a-I | Y*EC | S | O | O | O | S | S | H | OMe |
| 3949a-I | Y*EC | S | O | O | O | S | S | F | OMe |
| 3950a-I | Y*EC | S | O | O | O | S | S | OEt | OMe |
| 3951a-I | Y*EC | S | S | O | O | S | S | OH | OMe |
| 3952a-I | Y*EC | S | S | O | O | S | S | OMe | OMe |
| 3953a-I | Y*EC | S | S | O | O | S | S | H | OMe |
| 3954a-I | Y*EC | S | S | O | O | S | S | F | OMe |
| 3955a-I | Y*EC | S | S | O | O | S | S | OEt | OMe |
| 3956a-I | Y*EC | O | O | O | O | S | S | OH | OMe |
| 3957a-I | Y*EC | O | O | O | O | O | S | OMe | OMe |
| 3958a-I | Y*EC | O | O | O | O | O | S | H | OMe |
| 3959a-I | Y*BC | O | O | O | O | O | S | F | OMe |
| 3960a-I | Y*EC | O | O | O | O | O | S | OEt | OMe |
| 3961a-I | Y*EC | S | O | O | O | O | S | OH | OMe |
| 3962a-I | Y*EC | S | O | O | O | O | S | OMe | OMe |
| 3963a-I | Y*EC | S | O | O | O | O | S | H | OMe |
| 3964a-I | Y*EC | S | O | O | O | O | S | F | OMe |
| 3965a-I | Y*EC | S | O | O | O | O | S | OEt | OMe |
| 3966a-I | Y*EC | S | S | O | O | O | S | OH | OMe |
| 3967a-I | Y*EC | S | S | O | O | O | S | OMe | OMe |
| 3968a-I | Y*EC | S | S | O | O | O | S | H | OMe |
| 3969a-I | Y*EC | S | S | O | O | O | S | F | OMe |
| 3970a-I | Y*EC | S | S | O | O | O | S | OEt | OMe |
| 3971a-I | Y*EC | O | O | S | O | S | O | OH | OMe |
| 3972a-I | Y*EC | O | O | S | O | S | O | OMe | OMe |
| 3973a-I | Y*EC | O | O | S | O | S | O | H | OMe |
| 3974a-I | Y*EC | O | O | S | O | S | O | F | OMe |
| 3975a-I | Y*EC | O | O | S | O | S | O | OEt | OMe |
| 3976a-I | Y*EC | S | O | S | O | S | O | OH | OMe |
| 3977a-I | Y*EC | S | O | S | O | S | O | OMe | OMe |
| 3978a-I | Y*EC | S | O | S | O | S | O | H | OMe |
| 3979a-I | Y*EC | S | O | S | O | S | O | F | OMe |
| 3980a-I | Y*EC | S | O | S | O | S | O | OEt | OMe |
| 3981a-I | Y*EC | S | S | S | O | S | O | OH | OMe |
| 3982a-I | Y*EC | S | S | S | O | S | O | OMe | OMe |
| 3983a-I | Y*EC | S | S | S | O | S | O | H | OMe |
| 3984a-I | Y*EC | S | S | S | O | S | O | F | OMe |
| 3985a-I | Y*EC | S | S | S | O | S | O | OEt | OMe |
| 3986a-I | Y*EC | O | O | O | S | O | S | OH | OMe |
| 3987a-I | Y*EC | O | O | O | S | O | S | OMe | OMe |
| 3988a-I | Y*EC | O | O | O | S | O | S | H | OMe |
| 3989a-I | Y*EC | O | O | O | S | O | S | F | OMe |
| 3990a-I | Y*EC | O | O | O | S | O | S | OEt | OMe |
| 3991a-I | Y*EC | S | O | O | S | O | S | OH | OMe |
| 3992a-I | Y*EC | S | O | O | S | O | S | OMe | OMe |
| 3993a-I | Y*EC | S | O | O | S | O | S | H | OMe |
| 3994a-I | Y*EC | S | O | O | S | O | S | F | OMe |

TABLE 3-continued

CapA Structures for mRNA preparation

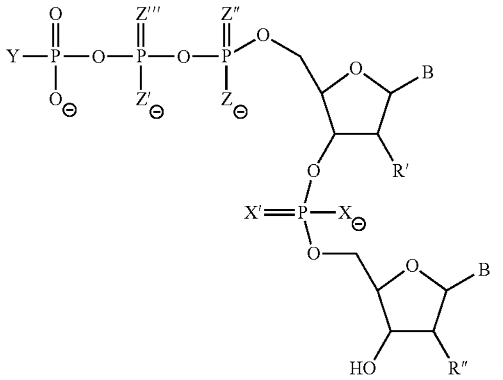

| Compound | Sequence | X | X' | Z | Z' | Z" | Z''' | R' | R" |
|---|---|---|---|---|---|---|---|---|---|
| 3995a-I | Y*EC | S | O | O | S | O | S | OEt | OMe |
| 3996a-I | Y*EC | S | S | O | S | O | S | OH | OMe |
| 3997a-I | Y*EC | S | S | O | S | O | S | OMe | OMe |
| 3998a-I | Y*EC | S | S | O | S | O | S | H | OMe |
| 3999a-I | Y*EC | S | S | O | S | O | S | F | OMe |
| 4000a-I | Y*EC | S | S | O | S | O | S | OEt | OMe |
| 4001a-I | Y*EU | O | O | O | O | O | O | OH | OH |
| 4002a-I | Y*EU | O | O | O | O | O | O | OMe | OH |
| 4003a-I | Y*EU | O | O | O | O | O | O | H | OH |
| 4004a-I | Y*EU | O | O | O | O | O | O | F | OH |
| 4005a-I | Y*EU | O | O | O | O | O | O | OEt | OH |
| 4006a-I | Y*EU | S | O | O | O | O | O | OH | OH |
| 4007a-I | Y*EU | S | O | O | O | O | O | OMe | OH |
| 4008a-I | Y*EU | S | O | O | O | O | O | H | OH |
| 4009a-I | Y*EU | S | O | O | O | O | O | F | OH |
| 4010a-I | Y*EU | S | O | O | O | O | O | OEt | OH |
| 4011a-I | Y*EU | S | S | O | O | O | O | OH | OH |
| 4012a-I | Y*EU | S | S | O | O | O | O | OMe | OH |
| 4013a-I | Y*EU | S | S | O | O | O | O | H | OH |
| 4014a-I | Y*EU | S | S | O | O | O | O | F | OH |
| 4015a-I | Y*EU | S | S | O | O | O | O | OEt | OH |
| 4016a-I | Y*EU | O | O | S | O | O | O | OH | OH |
| 4017a-I | Y*EU | O | O | S | O | O | O | OMe | OH |
| 4018a-I | Y*EU | O | O | S | O | O | O | H | OH |
| 4019a-I | Y*EU | O | O | S | O | O | O | F | OH |
| 4020a-I | Y*EU | O | O | S | O | O | O | OEt | OH |
| 4021a-I | Y*EU | S | O | S | O | O | O | OH | OH |
| 4022a-I | Y*EU | S | O | S | O | O | O | OMe | OH |
| 4023a-I | Y*EU | S | O | S | O | O | O | H | OH |
| 4024a-I | Y*EU | S | O | S | O | O | O | F | OH |
| 4025a-I | Y*EU | S | O | S | O | O | O | OEt | OH |
| 4026a-I | Y*EU | S | S | S | O | O | O | OH | OH |
| 4027a-I | Y*EU | S | S | S | O | O | O | OMe | OH |
| 4028a-I | Y*EU | S | S | S | O | O | O | H | OH |
| 4029a-I | Y*EU | S | S | S | O | O | O | F | OH |
| 4030a-I | Y*EU | S | S | S | O | O | O | OEt | OH |
| 4031a-I | Y*EU | O | O | S | S | O | O | OH | OH |
| 4032a-I | Y*EU | O | O | S | S | O | O | OMe | OH |
| 4033a-I | Y*EU | O | O | S | S | O | O | H | OH |
| 4034a-I | Y*EU | O | O | S | S | O | O | F | OH |
| 4035a-I | Y*EU | O | O | S | S | O | O | OEt | OH |
| 4036a-I | Y*EU | S | O | S | S | O | O | OH | OH |
| 4037a-I | Y*EU | S | O | S | S | O | O | OMe | OH |
| 4038a-I | Y*EU | S | O | S | S | O | O | H | OH |
| 4039a-I | Y*EU | S | O | S | S | O | O | F | OH |
| 4040a-I | Y*EU | S | O | S | S | O | O | OEt | OH |
| 4041a-I | Y*EU | S | S | S | S | O | O | OH | OH |
| 4042a-I | Y*EU | S | S | S | S | O | O | OMe | OH |
| 4043a-I | Y*EU | S | S | S | S | O | O | H | OH |
| 4044a-I | Y*EU | S | S | S | S | O | O | F | OH |
| 4045a-I | Y*EU | S | S | S | S | O | O | OEt | OH |
| 4046a-I | Y*EU | O | O | S | S | S | O | OH | OH |
| 4047a-I | Y*EU | O | O | S | S | S | O | OMe | OH |
| 4048a-I | Y*EU | O | O | S | S | S | O | H | OH |
| 4049a-I | Y*EU | O | O | S | S | S | O | F | OH |
| 4050a-I | Y*EU | O | O | S | S | S | O | OEt | OH |
| 4051a-I | Y*EU | S | O | S | S | S | O | OH | OH |

TABLE 3-continued

CapA Structures for mRNA preparation

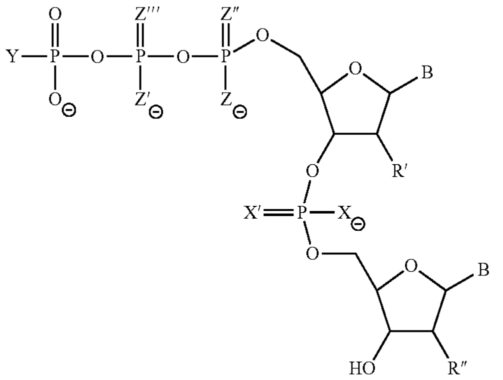

| Compound | Sequence | X | X' | Z | Z' | Z" | Z''' | R' | R" |
|---|---|---|---|---|---|---|---|---|---|
| 4052a-I | Y*EU | S | O | S | S | S | O | OMe | OH |
| 4053a-I | Y*EU | S | O | S | S | S | O | H | OH |
| 4054a-I | Y*EU | S | O | S | S | S | O | F | OH |
| 4055a-I | Y*EU | S | O | S | S | S | O | OEt | OH |
| 4056a-I | Y*EU | S | S | S | S | S | O | OH | OH |
| 4057a-I | Y*EU | S | S | S | S | S | O | OMe | OH |
| 4058a-I | Y*EU | S | S | S | S | S | O | H | OH |
| 4059a-I | Y*EU | S | S | S | S | S | O | F | OH |
| 4060a-I | Y*EU | S | S | S | S | S | O | OEt | OH |
| 4061a-I | Y*EU | O | O | S | S | S | S | OH | OH |
| 4062a-I | Y*EU | O | O | S | S | S | S | OMe | OH |
| 4063a-I | Y*EU | O | O | S | S | S | S | H | OH |
| 4064a-I | Y*EU | O | O | S | S | S | S | F | OH |
| 4065a-I | Y*EU | O | O | S | S | S | S | OEt | OH |
| 4066a-I | Y*EU | S | O | S | S | S | S | OH | OH |
| 4067a-I | Y*EU | S | O | S | S | S | S | OMe | OH |
| 4068a-I | Y*EU | S | O | S | S | S | S | H | OH |
| 4069a-I | Y*EU | S | O | S | S | S | S | F | OH |
| 4070a-I | Y*EU | S | O | S | S | S | S | OEt | OH |
| 4071a-I | Y*EU | S | S | S | S | S | S | OH | OH |
| 4072a-I | Y*EU | S | S | S | S | S | S | OMe | OH |
| 4073a-I | Y*EU | S | S | S | S | S | S | H | OH |
| 4074a-I | Y*EU | S | S | S | S | S | S | F | OH |
| 4075a-I | Y*EU | S | S | S | S | S | S | OEt | OH |
| 4076a-I | Y*EU | O | O | O | S | S | S | OH | OH |
| 4077a-I | Y*EU | O | O | O | S | S | S | OMe | OH |
| 4078a-I | Y*EU | O | O | O | S | S | S | H | OH |
| 4079a-I | Y*EU | O | O | O | S | S | S | F | OH |
| 4080a-I | Y*EU | O | O | O | S | S | S | OEt | OH |
| 4081a-I | Y*EU | S | O | O | S | S | S | OH | OH |
| 4082a-I | Y*EU | S | O | O | S | S | S | OMe | OH |
| 4083a-I | Y*EU | S | O | O | S | S | S | H | OH |
| 4084a-I | Y*EU | S | O | O | S | S | S | F | OH |
| 4085a-I | Y*EU | S | O | O | S | S | S | OEt | OH |
| 4086a-I | Y*EU | S | S | O | S | S | S | OH | OH |
| 4087a-I | Y*EU | S | S | O | S | S | S | OMe | OH |
| 4088a-I | Y*EU | S | S | O | S | S | S | H | OH |
| 4089a-I | Y*EU | S | S | O | S | S | S | F | OH |
| 4090a-I | Y*EU | S | S | O | S | S | S | OEt | OH |
| 4091a-I | Y*EU | O | O | O | O | S | S | OH | OH |
| 4092a-I | Y*EU | O | O | O | O | S | S | OMe | OH |
| 4093a-I | Y*EU | O | O | O | O | S | S | H | OH |
| 4094a-I | Y*EU | O | O | O | O | S | S | F | OH |
| 4095a-I | Y*EU | O | O | O | O | S | S | OEt | OH |
| 4096a-I | Y*EU | S | O | O | O | S | S | OH | OH |
| 4097a-I | Y*EU | S | O | O | O | S | S | OMe | OH |
| 4098a-I | Y*EU | S | O | O | O | S | S | H | OH |
| 4099a-I | Y*EU | S | O | O | O | S | S | F | OH |
| 4100a-I | Y*EU | S | O | O | O | S | S | OEt | OH |
| 4101a-I | Y*EU | S | S | O | O | S | S | OH | OH |
| 4102a-I | Y*EU | S | S | O | O | S | S | OMe | OH |
| 4103a-I | Y*EU | S | S | O | O | S | S | H | OH |
| 4104a-I | Y*EU | S | S | O | O | S | S | F | OH |
| 4105a-I | Y*EU | S | S | O | O | S | S | OEt | OH |
| 4106a-I | Y*EU | O | O | O | O | O | S | OH | OH |
| 4107a-I | Y*EU | O | O | O | O | O | S | OMe | OH |
| 4108a-I | Y*EU | O | O | O | O | O | S | H | OH |

TABLE 3-continued

CapA Structures for mRNA preparation

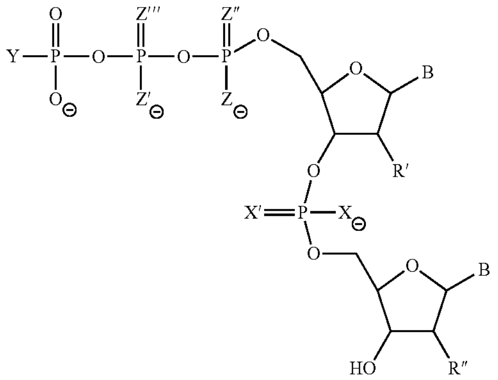

| Compound | Sequence | X | X' | Z | Z' | Z" | Z''' | R' | R" |
|---|---|---|---|---|---|---|---|---|---|
| 4109a-I | Y*EU | O | O | O | O | O | S | F | OH |
| 4110a-I | Y*EU | O | O | O | O | O | S | OEt | OH |
| 4111a-I | Y*EU | S | O | O | O | O | S | OH | OH |
| 4112a-I | Y*EU | S | O | O | O | O | S | OMe | OH |
| 4113a-I | Y*EU | S | O | O | O | O | S | H | OH |
| 4114a-I | Y*EU | S | O | O | O | O | S | F | OH |
| 4115a-I | Y*EU | S | O | O | O | O | S | OEt | OH |
| 4116a-I | Y*EU | S | S | O | O | O | S | OH | OH |
| 4117a-I | Y*EU | S | S | O | O | O | S | OMe | OH |
| 4118a-I | Y*EU | S | S | O | O | O | S | H | OH |
| 4119a-I | Y*EU | S | S | O | O | O | S | F | OH |
| 4120a-I | Y*EU | S | S | O | O | O | S | OEt | OH |
| 4121a-I | Y*EU | O | O | S | O | S | O | OH | OH |
| 4122a-I | Y*EU | O | O | S | O | S | O | OMe | OH |
| 4123a-I | Y*EU | O | O | S | O | S | O | H | OH |
| 4124a-I | Y*EU | O | O | S | O | S | O | F | OH |
| 4125a-I | Y*EU | O | O | S | O | S | O | OEt | OH |
| 4126a-I | Y*EU | S | O | S | O | S | O | OH | OH |
| 4127a-I | Y*EU | S | O | S | O | S | O | OMe | OH |
| 4128a-I | Y*EU | S | O | S | O | S | O | H | OH |
| 4129a-I | Y*EU | S | O | S | O | S | O | F | OH |
| 4130a-I | Y*EU | S | O | S | O | S | O | OEt | OH |
| 4131a-I | Y*EU | S | S | S | O | S | O | OH | OH |
| 4132a-I | Y*EU | S | S | S | O | S | O | OMe | OH |
| 4133a-I | Y*EU | S | S | S | O | S | O | H | OH |
| 4134a-I | Y*EU | S | S | S | O | S | O | F | OH |
| 4135a-I | Y*EU | S | S | S | O | S | O | OEt | OH |
| 4136a-I | Y*EU | O | O | O | S | O | S | OH | OH |
| 4137a-I | Y*EU | O | O | O | S | O | S | OMe | OH |
| 4138a-I | Y*EU | O | O | O | S | O | S | H | OH |
| 4139a-I | Y*EU | O | O | O | S | O | S | F | OH |
| 4140a-I | Y*EU | O | O | O | S | O | S | OEt | OH |
| 4141a-I | Y*EU | S | O | O | S | O | S | OH | OH |
| 4142a-I | Y*EU | S | O | O | S | O | S | OMe | OH |
| 4143a-I | Y*EU | S | O | O | S | O | S | H | OH |
| 4144a-I | Y*EU | S | O | O | S | O | S | F | OH |
| 4145a-I | Y*EU | S | O | O | S | O | S | OEt | OH |
| 4146a-I | Y*EU | S | S | O | S | O | S | OH | OH |
| 4147a-I | Y*EU | S | S | O | S | O | S | OMe | OH |
| 4148a-I | Y*EU | S | S | O | S | O | S | H | OH |
| 4149a-I | Y*EU | S | S | O | S | O | S | F | OH |
| 4150a-I | Y*EU | S | S | O | S | O | S | OEt | OH |
| 4151a-I | Y*EU | O | O | O | O | O | O | OH | OMe |
| 4152a-I | Y*EU | O | O | O | O | O | O | OMe | OMe |
| 4153a-I | Y*EU | O | O | O | O | O | O | H | OMe |
| 4154a-I | Y*EU | O | O | O | O | O | O | F | OMe |
| 4155a-I | Y*EU | O | O | O | O | O | O | OEt | OMe |
| 4156a-I | Y*EU | S | O | O | O | O | O | OH | OMe |
| 4157a-I | Y*EU | S | O | O | O | O | O | OMe | OMe |
| 4158a-I | Y*EU | S | O | O | O | O | O | H | OMe |
| 4159a-I | Y*EU | S | O | O | O | O | O | F | OMe |
| 4160a-I | Y*EU | S | O | O | O | O | O | OEt | OMe |
| 4161a-I | Y*EU | S | S | O | O | O | O | OH | OMe |
| 4162a-I | Y*EU | S | S | O | O | O | O | OMe | OMe |
| 4163a-I | Y*EU | S | S | O | O | O | O | H | OMe |
| 4164a-I | Y*EU | S | S | O | O | O | O | F | OMe |
| 4165a-I | Y*EU | S | S | O | O | O | O | OEt | OMe |

TABLE 3-continued

CapA Structures for mRNA preparation

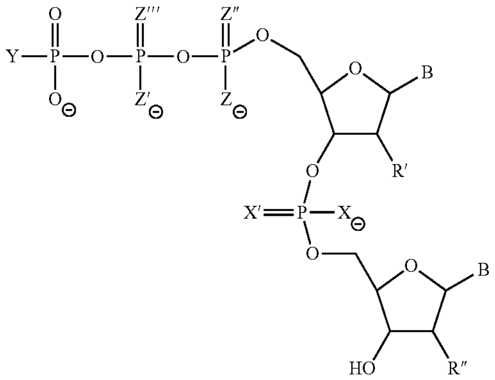

| Compound | Sequence | X | X' | Z | Z' | Z" | Z''' | R' | R" |
|---|---|---|---|---|---|---|---|---|---|
| 4166a-I | Y*EU | O | O | S | O | O | O | OH | OMe |
| 4167a-I | Y*EU | O | O | S | O | O | O | OMe | OMe |
| 4168a-I | Y*EU | O | O | S | O | O | O | H | OMe |
| 4169a-I | Y*EU | O | O | S | O | O | O | F | OMe |
| 4170a-I | Y*EU | O | O | S | O | O | O | OEt | OMe |
| 4171a-I | Y*EU | S | O | S | O | O | O | OH | OMe |
| 4172a-I | Y*EU | S | O | S | O | O | O | OMe | OMe |
| 4173a-I | Y*EU | S | O | S | O | O | O | H | OMe |
| 4174a-I | Y*EU | S | O | S | O | O | O | F | OMe |
| 4175a-I | Y*EU | S | O | S | O | O | O | OEt | OMe |
| 4176a-I | Y*EU | S | S | S | O | O | O | OH | OMe |
| 4177a-I | Y*EU | S | S | S | O | O | O | OMe | OMe |
| 4178a-I | Y*EU | S | S | S | O | O | O | H | OMe |
| 4179a-I | Y*EU | S | S | S | O | O | O | F | OMe |
| 4180a-I | Y*EU | S | S | S | O | O | O | OE | OMe |
| 4181a-I | Y*EU | O | O | S | S | O | O | OH | OMe |
| 4182a-I | Y*EU | O | O | S | S | O | O | OMe | OMe |
| 4183a-I | Y*EU | O | O | S | S | O | O | H | OMe |
| 4184a-I | Y*EU | O | O | S | S | O | O | F | OMe |
| 4185a-I | Y*EU | O | O | S | S | O | O | OEt | OMe |
| 4186a-I | Y*EU | S | O | S | S | O | O | OH | OMe |
| 4187a-I | Y*EU | S | O | S | S | O | O | OMe | OMe |
| 4188a-I | Y*EU | S | O | S | S | O | O | H | OMe |
| 4189a-I | Y*EU | S | O | S | S | O | O | F | OMe |
| 4190a-I | Y*EU | S | O | S | S | O | O | OEt | OMe |
| 4191a-I | Y*EU | S | S | S | S | O | O | OH | OMe |
| 4192a-I | Y*EU | S | S | S | S | O | O | OMe | OMe |
| 4193a-I | Y*EU | S | S | S | S | O | O | H | OMe |
| 4194a-I | Y*EU | S | S | S | S | O | O | F | OMe |
| 4195a-I | Y*EU | S | S | S | S | O | O | OEt | OMe |
| 4196a-I | Y*EU | O | O | S | S | S | O | OH | OMe |
| 4197a-I | Y*EU | O | O | S | S | S | O | OMe | OMe |
| 4198a-I | Y*EU | O | O | S | S | S | O | H | OMe |
| 4199a-I | Y*EU | O | O | S | S | S | O | F | OMe |
| 4200a-I | Y*EU | O | O | S | S | S | O | OEt | OMe |
| 4201a-I | Y*EU | S | O | S | S | S | O | OH | OMe |
| 4202a-I | Y*EU | S | O | S | S | S | O | OMe | OMe |
| 4203a-I | Y*EU | S | O | S | S | S | O | H | OMe |
| 4204a-I | Y*EU | S | O | S | S | S | O | F | OMe |
| 4205a-I | Y*EU | S | O | S | S | S | O | OEt | OMe |
| 4206a-I | Y*EU | S | S | S | S | S | O | OH | OMe |
| 4207a-I | Y*EU | S | S | S | S | S | O | OMe | OMe |
| 4208a-I | Y*EU | S | S | S | S | S | O | H | OMe |
| 4209a-I | Y*EU | S | S | S | S | S | O | F | OMe |
| 4210a-I | Y*EU | S | S | S | S | S | O | OEt | OMe |
| 4211a-I | Y*EU | O | O | S | S | S | S | OH | OMe |
| 4212a-I | Y*EU | O | O | S | S | S | S | OMe | OMe |
| 4213a-I | Y*EU | O | O | S | S | S | S | H | OMe |
| 4214a-I | Y*EU | O | O | S | S | S | S | F | OMe |
| 4215a-I | Y*EU | O | O | S | S | S | S | OEt | OMe |
| 4216a-I | Y*EU | S | O | S | S | S | S | OH | OMe |
| 4217a-I | Y*EU | S | O | S | S | S | S | OMe | OMe |
| 4218a-I | Y*EU | S | O | S | S | S | S | H | OMe |
| 4219a-I | Y*EU | S | O | S | S | S | S | F | OMe |
| 4220a-I | Y*EU | S | O | S | S | S | S | OEt | OMe |
| 4221a-I | Y*EU | S | S | S | S | S | S | OH | OMe |
| 4222a-I | Y*EU | S | S | S | S | S | S | OMe | OMe |

TABLE 3-continued

CapA Structures for mRNA preparation

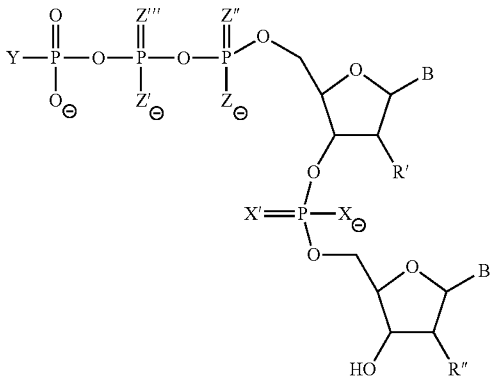

| Compound | Sequence | X | X' | Z | Z' | Z'' | Z''' | R' | R'' |
|---|---|---|---|---|---|---|---|---|---|
| 4223a-I | Y*EU | S | S | S | S | S | S | H | OMe |
| 4224a-I | Y*EU | S | S | S | S | S | S | F | OMe |
| 4225a-I | Y*EU | S | S | S | S | S | S | OEt | OMe |
| 4226a-I | Y*EU | O | O | O | S | S | S | OH | OMe |
| 4227a-I | Y*EU | O | O | O | S | S | S | OMe | OMe |
| 4228a-I | Y*EU | O | O | O | S | S | S | H | OMe |
| 4229a-I | Y*EU | O | O | O | S | S | S | F | OMe |
| 4230a-I | Y*EU | O | O | O | S | S | S | OEt | OMe |
| 4231a-I | Y*EU | S | O | O | S | S | S | OH | OMe |
| 4232a-I | Y*EU | S | O | O | S | S | S | OMe | OMe |
| 4233a-I | Y*EU | S | O | O | S | S | S | H | OMe |
| 4234a-I | Y*EU | S | O | O | S | S | S | F | OMe |
| 4235a-I | Y*EU | S | O | O | S | S | S | OEt | OMe |
| 4236a-I | Y*EU | S | S | O | S | S | S | OH | OMe |
| 4237a-I | Y*EU | S | S | O | S | S | S | OMe | OMe |
| 4238a-I | Y*EU | S | S | O | S | S | S | H | OMe |
| 4239a-I | Y*EU | S | S | O | S | S | S | F | OMe |
| 4240a-I | Y*EU | S | S | O | S | S | S | OEt | OMe |
| 4241a-I | Y*EU | O | O | O | O | S | S | OH | OMe |
| 4242a-I | Y*EU | O | O | O | O | S | S | OMe | OMe |
| 4243a-I | Y*EU | O | O | O | O | S | S | H | OMe |
| 4244a-I | Y*EU | O | O | O | O | S | S | F | OMe |
| 4245a-I | Y*EU | O | O | O | O | S | S | OEt | OMe |
| 4246a-I | Y*EU | S | O | O | O | S | S | OH | OMe |
| 4247a-I | Y*EU | S | O | O | O | S | S | OMe | OMe |
| 4248a-I | Y*EU | S | O | O | O | S | S | H | OMe |
| 4249a-I | Y*EU | S | O | O | O | S | S | F | OMe |
| 4250a-I | Y*EU | S | O | O | O | S | S | OEt | OMe |
| 4251a-I | Y*EU | S | S | O | O | S | S | OH | OMe |
| 4252a-I | Y*EU | S | S | O | O | S | S | OMe | OMe |
| 4253a-I | Y*EU | S | S | O | O | S | S | H | OMe |
| 4254a-I | Y*EU | S | S | O | O | S | S | F | OMe |
| 4255a-I | Y*EU | S | S | O | O | S | S | OEt | OMe |
| 4256a-I | Y*EU | O | O | O | O | O | S | OH | OMe |
| 4257a-I | Y*EU | O | O | O | O | O | S | OMe | OMe |
| 4258a-I | Y*EU | O | O | O | O | O | S | H | OMe |
| 4259a-I | Y*EU | O | O | O | O | O | S | F | OMe |
| 4260a-I | Y*EU | O | O | O | O | O | S | OEt | OMe |
| 4261a-I | Y*EU | S | O | O | O | O | S | OH | OMe |
| 4262a-I | Y*EU | S | O | O | O | O | S | OMe | OMe |
| 4263a-I | Y*EU | S | O | O | O | O | S | H | OMe |
| 4264a-I | Y*EU | S | O | O | O | O | S | F | OMe |
| 4265a-I | Y*EU | S | O | O | O | O | S | OEt | OMe |
| 4266a-I | Y*EU | S | S | O | O | O | S | OH | OMe |
| 4267a-I | Y*EU | S | S | O | O | O | S | OMe | OMe |
| 4268a-I | Y*EU | S | S | O | O | O | S | H | OMe |
| 4269a-I | Y*EU | S | S | O | O | O | S | F | OMe |
| 4270a-I | Y*EU | S | S | O | O | O | S | OEt | OMe |
| 4271a-I | Y*EU | O | O | S | O | S | O | OH | OMe |
| 4272a-I | Y*EU | O | O | S | O | S | O | OMe | OMe |
| 4273a-I | Y*EU | O | O | S | O | S | O | H | OMe |
| 4274a-I | Y*EU | O | O | S | O | S | O | F | OMe |
| 4275a-I | Y*EU | O | O | S | O | S | O | OEt | OMe |
| 4276a-I | Y*EU | S | O | S | O | S | O | OH | OMe |
| 4277a-I | Y*EU | S | O | S | O | S | O | OMe | OMe |
| 4278a-I | Y*EU | S | O | S | O | S | O | H | OMe |
| 4279a-I | Y*EU | S | O | S | O | S | O | F | OMe |

TABLE 3-continued

CapA Structures for mRNA preparation

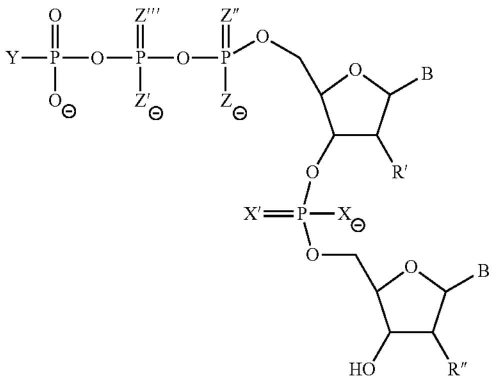

| Compound | Sequence | X | X' | Z | Z' | Z'' | Z''' | R' | R'' |
|---|---|---|---|---|---|---|---|---|---|
| 4280a-I | Y*EU | S | O | S | O | S | O | OEt | OMe |
| 4281a-I | Y*EU | S | S | S | O | S | O | OH | OMe |
| 4282a-I | Y*EU | S | S | S | O | S | O | OMe | OMe |
| 4283a-I | Y*EU | S | S | S | O | S | O | H | OMe |
| 4284a-I | Y*EU | S | S | S | O | S | O | F | OMe |
| 4285a-I | Y*EU | S | S | S | O | S | O | OEt | OMe |
| 4286a-I | Y*EU | O | O | O | S | O | S | OH | OMe |
| 4287a-I | Y*EU | O | O | O | S | O | S | OMe | OMe |
| 4288a-I | Y*EU | O | O | O | S | O | S | H | OMe |
| 4289a-I | Y*EU | O | O | O | S | O | S | F | OMe |
| 4290a-I | Y*EU | O | O | O | S | O | S | OEt | OMe |
| 4291a-I | Y*EU | S | O | O | S | O | S | OH | OMe |
| 4292a-I | Y*EU | S | O | O | S | O | S | OMe | OMe |
| 4293a-I | Y*EU | S | O | O | S | O | S | H | OMe |
| 4294a-I | Y*EU | S | O | O | S | O | S | F | OMe |
| 4295a-I | Y*EU | S | O | O | S | O | S | OEt | OMe |
| 4296a-I | Y*EU | S | S | O | S | O | S | OH | OMe |
| 4297a-I | Y*EU | S | S | O | S | O | S | OMe | OMe |
| 4298a-I | Y*EU | S | S | O | S | O | S | H | OMe |
| 4299a-I | Y*EU | S | S | O | S | O | S | F | OMe |
| 4300a-I | Y*EU | S | S | O | S | O | S | OEt | OMe |
| 4301a-I | Y*EI | O | O | O | O | O | O | OH | OH |
| 4302a-I | Y*EI | O | O | O | O | O | O | OMe | OH |
| 4303a-I | Y*EI | O | O | O | O | O | O | H | OH |
| 4304a-I | Y*EI | O | O | O | O | O | O | F | OH |
| 4305a-I | Y*EI | O | O | O | O | O | O | OEt | OH |
| 4306a-I | Y*EI | S | O | O | O | O | O | OH | OH |
| 4307a-I | Y*EI | S | O | O | O | O | O | OMe | OH |
| 4308a-I | Y*EI | S | O | O | O | O | O | H | OH |
| 4309a-I | Y*EI | S | O | O | O | O | O | F | OH |
| 4310a-I | Y*EI | S | O | O | O | O | O | OEt | OH |
| 4311a-I | Y*EI | S | S | O | O | O | O | OH | OH |
| 4312a-I | Y*EI | S | S | O | O | O | O | OMe | OH |
| 4313a-I | Y*EI | S | S | O | O | O | O | H | OH |
| 4314a-I | Y*EI | S | S | O | O | O | O | F | OH |
| 4315a-I | Y*EI | S | S | O | O | O | O | OEt | OH |
| 4316a-I | Y*EI | O | O | S | O | O | O | OH | OH |
| 4317a-I | Y*EI | O | O | S | O | O | O | OMe | OH |
| 4318a-I | Y*EI | O | O | S | O | O | O | H | OH |
| 4319a-I | Y*EI | O | O | S | O | O | O | F | OH |
| 4320a-I | Y*EI | O | O | S | O | O | O | OEt | OH |
| 4321a-I | Y*EI | S | O | S | O | O | O | OH | OH |
| 4322a-I | Y*EI | S | O | S | O | O | O | OMe | OH |
| 4323a-I | Y*EI | S | O | S | O | O | O | H | OH |
| 4324a-I | Y*EI | S | O | S | O | O | O | F | OH |
| 4325a-I | Y*EI | S | O | S | O | O | O | OEt | OH |
| 4326a-I | Y*EI | S | S | S | O | O | O | OH | OH |
| 4327a-I | Y*EI | S | S | S | O | O | O | OMe | OH |
| 4328a-I | Y*EI | S | S | S | O | O | O | H | OH |
| 4329a-I | Y*EI | S | S | S | O | O | O | F | OH |
| 4330a-I | Y*EI | S | S | S | O | O | O | OEt | OH |
| 4331a-I | Y*EI | O | O | S | S | O | O | OH | OH |
| 4332a-I | Y*EI | O | O | S | S | O | O | OMe | OH |
| 4333a-I | Y*EI | O | O | S | S | O | O | H | OH |
| 4334a-I | Y*EI | O | O | S | S | O | O | F | OH |
| 4335a-I | Y*EI | O | O | S | S | O | O | OEt | OH |
| 4336a-I | Y*EI | S | O | S | S | O | O | OH | OH |

TABLE 3-continued

CapA Structures for mRNA preparation

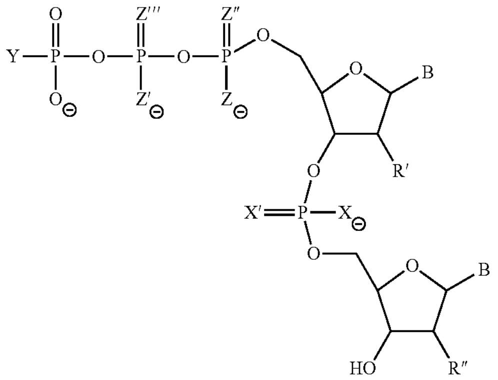

| Compound | Sequence | X | X' | Z | Z' | Z'' | Z''' | R' | R'' |
|---|---|---|---|---|---|---|---|---|---|
| 4337a-I | Y*EI | S | O | S | S | O | O | OMe | OH |
| 4338a-I | Y*EI | S | O | S | S | O | O | H | OH |
| 4339a-I | Y*EI | S | O | S | S | O | O | F | OH |
| 4340a-I | Y*EI | S | O | S | S | O | O | OEt | OH |
| 4341a-I | Y*EI | S | S | S | S | O | O | OH | OH |
| 4342a-I | Y*EI | S | S | S | S | O | O | OMe | OH |
| 4343a-I | Y*EI | S | S | S | S | O | O | H | OH |
| 4344a-I | Y*EI | S | S | S | S | O | O | F | OH |
| 4345a-I | Y*EI | S | S | S | S | O | O | OEt | OH |
| 4346a-I | Y*EI | O | O | S | S | S | O | OH | OH |
| 4347a-I | Y*EI | O | O | S | S | S | O | OMe | OH |
| 4348a-I | Y*EI | O | O | S | S | S | O | H | OH |
| 4349a-I | Y*EI | O | O | S | S | S | O | F | OH |
| 4350a-I | Y*EI | O | O | S | S | S | O | OEt | OH |
| 4351a-I | Y*EI | S | O | S | S | S | O | OH | OH |
| 4352a-I | Y*EI | S | O | S | S | S | O | OMe | OH |
| 4353a-I | Y*EI | S | O | S | S | S | O | H | OH |
| 4354a-I | Y*EI | S | O | S | S | S | O | F | OH |
| 4355a-I | Y*EI | S | O | S | S | S | O | OEt | OH |
| 4356a-I | Y*EI | S | S | S | S | S | O | OH | OH |
| 4357a-I | Y*EI | S | S | S | S | S | O | OMe | OH |
| 4358a-I | Y*EI | S | S | S | S | S | O | H | OH |
| 4359a-I | Y*EI | S | S | S | S | S | O | F | OH |
| 4360a-I | Y*EI | S | S | S | S | S | O | OEt | OH |
| 4361a-I | Y*EI | O | O | S | S | S | S | OH | OH |
| 4362a-I | Y*EI | O | O | S | S | S | S | OMe | OH |
| 4363a-I | Y*EI | O | O | S | S | S | S | H | OH |
| 4364a-I | Y*EI | O | O | S | S | S | S | F | OH |
| 4365a-I | Y*EI | O | O | S | S | S | S | OEt | OH |
| 4366a-I | Y*EI | S | O | S | S | S | S | OH | OH |
| 4367a-I | Y*EI | S | O | S | S | S | S | OMe | OH |
| 4368a-I | Y*EI | S | O | S | S | S | S | H | OH |
| 4369a-I | Y*EI | S | O | S | S | S | S | F | OH |
| 4370a-I | Y*EI | S | O | S | S | S | S | OEt | OH |
| 4371a-I | Y*EI | S | S | S | S | S | S | OH | OH |
| 4372a-I | Y*EI | S | 5 | S | S | S | S | OMe | OH |
| 4373a-I | Y*EI | S | S | S | S | S | S | H | OH |
| 4374a-I | Y*EI | S | S | S | S | S | S | F | OH |
| 4375a-I | Y*EI | S | S | S | S | S | S | OEt | OH |
| 4376a-I | Y*EI | O | O | O | S | S | S | OH | OH |
| 4377a-I | Y*EI | O | O | O | S | S | S | OMe | OH |
| 4378a-I | Y*EI | O | O | O | S | S | S | H | OH |
| 4379a-I | Y*EI | O | O | O | S | S | S | F | OH |
| 4380a-I | Y*EI | O | O | O | S | S | S | OEt | OH |
| 4381a-I | Y*EI | S | O | O | S | S | S | OH | OH |
| 4382a-I | Y*EI | S | O | O | S | S | S | OMe | OH |
| 4383a-I | Y*EI | S | O | O | S | S | S | H | OH |
| 4384a-I | Y*EI | S | O | O | S | S | S | F | OH |
| 4385a-I | Y*EI | S | O | O | S | S | S | OEt | OH |
| 4386a-I | Y*EI | S | S | O | S | S | S | OH | OH |
| 4387a-I | Y*EI | S | S | O | S | S | S | OMe | OH |
| 4388a-I | Y*EI | S | S | O | S | S | S | H | OH |
| 4389a-I | Y*EI | S | S | O | S | S | S | F | OH |
| 4390a-I | Y*EI | S | S | O | S | S | S | OEt | OH |
| 4391a-I | Y*EI | O | O | O | O | S | S | OH | OH |
| 4392a-I | Y*EI | O | O | O | O | S | S | OMe | OH |
| 4393a-I | Y*EI | O | O | O | O | S | S | H | OH |

TABLE 3-continued

CapA Structures for mRNA preparation

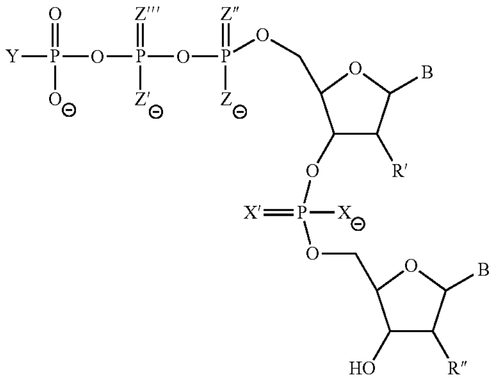

| Compound | Sequence | X | X' | Z | Z' | Z'' | Z''' | R' | R'' |
|---|---|---|---|---|---|---|---|---|---|
| 4394a-I | Y*EI | O | O | O | O | S | S | F | OH |
| 4395a-I | Y*EI | O | O | O | O | S | S | OEt | OH |
| 4396a-I | Y*EI | S | O | O | O | S | S | OH | OH |
| 4397a-I | Y*EI | S | O | O | O | S | S | OMe | OH |
| 4398a-I | Y*EI | S | O | O | O | S | S | H | OH |
| 4399a-I | Y*EI | S | O | O | O | S | S | F | OH |
| 4400a-I | Y*EI | S | O | O | O | S | S | OEt | OH |
| 4401a-I | Y*EI | S | S | O | O | S | S | OH | OH |
| 4402a-I | Y*EI | S | S | O | O | S | S | OMe | OH |
| 4403a-I | Y*EI | S | S | O | O | S | S | H | OH |
| 4404a-I | Y*EI | S | S | O | O | S | S | F | OH |
| 4405a-I | Y*EI | S | S | O | O | S | S | OEt | OH |
| 4406a-I | Y*EI | O | O | O | O | S | S | OH | OH |
| 4407a-I | Y*EI | O | O | O | O | O | S | OMe | OH |
| 4408a-I | Y*EI | O | O | O | O | O | S | H | OH |
| 4409a-I | Y*EI | O | O | O | O | O | S | F | OH |
| 4410a-I | Y*EI | O | O | O | O | O | S | OEt | OH |
| 4411a-I | Y*EI | S | O | O | O | O | S | OH | OH |
| 4412a-I | Y*EI | S | O | O | O | O | S | OMe | OH |
| 4413a-I | Y*EI | S | O | O | O | O | S | H | OH |
| 4414a-I | Y*EI | S | O | O | O | O | S | F | OH |
| 4415a-I | Y*EI | S | O | O | O | O | S | OEt | OH |
| 4416a-I | Y*EI | S | S | O | O | O | S | OH | OH |
| 4417a-I | Y*EI | S | S | O | O | O | S | OMe | OH |
| 4418a-I | Y*EI | S | S | O | O | O | S | H | OH |
| 4419a-I | Y*EI | S | S | O | O | O | S | F | OH |
| 4420a-I | Y*EI | S | S | O | O | O | S | OEt | OH |
| 4421a-I | Y*EI | O | O | S | O | S | O | OH | OH |
| 4422a-I | Y*EI | O | O | S | O | S | O | OMe | OH |
| 4423a-I | Y*EI | O | O | S | O | S | O | H | OH |
| 4424a-I | Y*EI | O | O | S | O | S | O | F | OH |
| 4425a-I | Y*EI | O | O | S | O | S | O | OEt | OH |
| 4426a-I | Y*EI | S | O | S | O | S | O | OH | OH |
| 4427a-I | Y*EI | S | O | S | O | S | O | OMe | OH |
| 4428a-I | Y*EI | S | O | S | O | S | O | H | OH |
| 4429a-I | Y*EI | S | O | S | O | S | O | F | OH |
| 4430a-I | Y*EI | S | O | S | O | S | O | OEt | OH |
| 4431a-I | Y*EI | S | S | S | O | S | O | OH | OH |
| 4432a-I | Y*EI | S | S | S | O | S | O | OMe | OH |
| 4433a-I | Y*EI | S | S | S | O | S | O | H | OH |
| 4434a-I | Y*EI | S | S | S | O | S | O | F | OH |
| 4435a-I | Y*EI | S | S | S | O | S | O | OEt | OH |
| 4436a-I | Y*EI | O | O | O | S | O | S | OH | OH |
| 4437a-I | Y*EI | O | O | O | S | O | S | OMe | OH |
| 4438a-I | Y*EI | O | O | O | S | O | S | H | OH |
| 4439a-I | Y*EI | O | O | O | S | O | S | F | OH |
| 4440a-I | Y*EI | O | O | O | S | O | S | OEt | OH |
| 4441a-I | Y*EI | S | O | O | S | O | S | OH | OH |
| 4442a-I | Y*EI | S | O | O | S | O | S | OMe | OH |
| 4443a-I | Y*EI | S | O | O | S | O | S | H | OH |
| 4444a-I | Y*EI | S | O | O | S | O | S | F | OH |
| 4445a-I | Y*EI | S | O | O | S | O | S | OEt | OH |
| 4446a-I | Y*EI | S | S | O | S | O | S | OH | OH |
| 4447a-I | Y*EI | S | S | O | S | O | S | OMe | OH |
| 4448a-I | Y*EI | S | S | O | S | O | S | H | OH |
| 4449a-I | Y*EI | S | S | O | S | O | S | F | OH |
| 4450a-I | Y*EI | S | S | O | S | O | S | OEt | OH |

TABLE 3-continued

CapA Structures for mRNA preparation

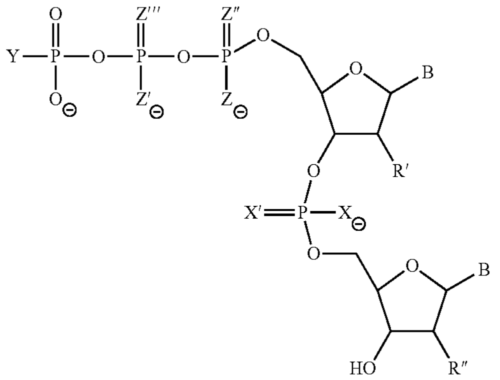

| Compound | Sequence | X | X' | Z | Z' | Z'' | Z''' | R' | R'' |
|---|---|---|---|---|---|---|---|---|---|
| 4451a-I | Y*EI | O | O | O | O | O | O | OH | OMe |
| 4452a-I | Y*EI | O | O | O | O | O | O | OMe | OMe |
| 4453a-I | Y*EI | O | O | O | O | O | O | H | OMe |
| 4454a-I | Y*EI | O | O | O | O | O | O | F | OMe |
| 4455a-I | Y*EI | O | O | O | O | O | O | OEt | OMe |
| 4456a-I | Y*EI | S | O | O | O | O | O | OH | OMe |
| 4457a-I | Y*EI | S | O | O | O | O | O | OMe | OMe |
| 4458a-I | Y*EI | S | O | O | O | O | O | H | OMe |
| 4459a-I | Y*EI | S | O | O | O | O | O | F | OMe |
| 4460a-I | Y*EI | S | O | O | O | O | O | OEt | OMe |
| 4461a-I | Y*EI | S | S | O | O | O | O | OH | OMe |
| 4462a-I | Y*EI | S | S | O | O | O | O | OMe | OMe |
| 4463a-I | Y*EI | S | S | O | O | O | O | H | OMe |
| 4464a-I | Y*EI | S | S | O | O | O | O | F | OMe |
| 4465a-I | Y*EI | S | S | O | O | O | O | OEt | OMe |
| 4466a-I | Y*EI | O | O | S | O | O | O | OH | OMe |
| 4467a-I | Y*EI | O | O | S | O | O | O | OMe | OMe |
| 4468a-I | Y*EI | O | O | S | O | O | O | H | OMe |
| 4469a-I | Y*EI | O | O | S | O | O | O | F | OMe |
| 4470a-I | Y*EI | O | O | S | O | O | O | OEt | OMe |
| 4471a-I | Y*EI | S | O | S | O | O | O | OH | OMe |
| 4472a-I | Y*EI | S | O | S | O | O | O | OMe | OMe |
| 4473a-I | Y*EI | S | O | S | O | O | O | H | OMe |
| 4474a-I | Y*EI | S | O | S | O | O | O | F | OMe |
| 4475a-I | Y*EI | S | O | S | O | O | O | OEt | OMe |
| 4476a-I | Y*EI | S | S | S | O | O | O | OH | OMe |
| 4477a-I | Y*EI | S | S | S | O | O | O | OMe | OMe |
| 4478a-I | Y*EI | S | S | S | O | O | O | H | OMe |
| 4479a-I | Y*EI | S | S | S | O | O | O | F | OMe |
| 4480a-I | Y*EI | S | S | S | O | O | O | OEt | OMe |
| 4481a-I | Y*EI | O | O | S | S | O | O | OH | OMe |
| 4482a-I | Y*EI | O | O | S | S | O | O | OMe | OMe |
| 4483a-I | Y*EI | O | O | S | S | O | O | H | OMe |
| 4484a-I | Y*EI | O | O | S | S | O | O | F | OMe |
| 4485a-I | Y*EI | O | O | S | S | O | O | OEt | OMe |
| 4486a-I | Y*EI | S | O | S | S | O | O | OH | OMe |
| 4487a-I | Y*EI | S | O | S | S | O | O | OMe | OMe |
| 4488a-I | Y*EI | S | O | S | S | O | O | H | OMe |
| 4489a-I | Y*EI | S | O | S | S | O | O | F | OMe |
| 4490a-I | Y*EI | S | O | S | S | O | O | OEt | OMe |
| 4491a-I | Y*EI | S | S | S | S | O | O | OH | OMe |
| 4492a-I | Y*EI | S | S | S | S | O | O | OMe | OMe |
| 4493a-I | Y*EI | S | S | S | S | O | O | H | OMe |
| 4494a-I | Y*EI | S | S | S | S | O | O | F | OMe |
| 4495a-I | Y*EI | S | S | S | S | O | O | OEt | OMe |
| 4496a-I | Y*EI | O | O | S | S | S | O | OH | OMe |
| 4497a-I | Y*EI | O | O | S | S | S | O | OMe | OMe |
| 4498a-I | Y*EI | O | O | S | S | S | O | H | OMe |
| 4499a-I | Y*EI | O | O | S | S | S | O | F | OMe |
| 4500a-I | Y*EI | O | O | S | S | S | O | OEt | OMe |
| 4501a-I | Y*EI | S | O | S | S | S | O | OH | OMe |
| 4502a-I | Y*EI | S | O | S | S | S | O | OMe | OMe |
| 4503a-I | Y*EI | S | O | S | S | S | O | H | OMe |
| 4504a-I | Y*EI | S | O | S | S | S | O | F | OMe |
| 4505a-I | Y*EI | S | O | S | S | S | O | OEt | OMe |
| 4506a-I | Y*EI | S | S | S | S | S | O | OH | OMe |
| 4507a-I | Y*EI | S | S | S | S | S | O | OMe | OMe |

TABLE 3-continued

CapA Structures for mRNA preparation

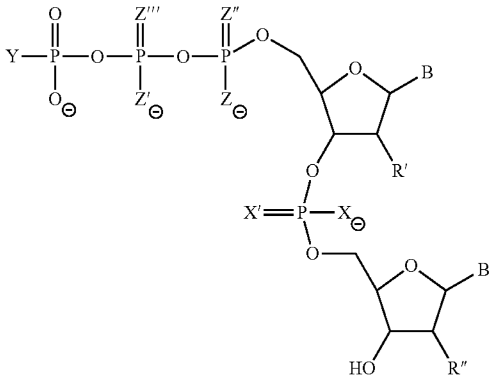

| Compound | Sequence | X | X' | Z | Z' | Z'' | Z''' | R' | R'' |
|---|---|---|---|---|---|---|---|---|---|
| 4508a-I | Y*EI | S | 5 | S | S | S | O | H | OMe |
| 4509a-I | Y*EI | S | S | S | S | S | O | F | OMe |
| 4510a-I | Y*EI | S | S | S | S | S | O | OEt | OMe |
| 4511a-I | Y*EI | O | O | S | S | S | S | OH | OMe |
| 4512a-I | Y*EI | O | O | S | S | S | S | OMe | OMe |
| 4513a-I | Y*EI | O | O | S | S | S | S | H | OMe |
| 4514a-I | Y*EI | O | O | S | S | S | S | F | OMe |
| 4515a-I | Y*EI | O | O | S | S | S | S | OEt | OMe |
| 4516a-I | Y*EI | S | O | S | S | S | S | OH | OMe |
| 4517a-I | Y*EI | S | O | S | S | S | S | OMe | OMe |
| 4518a-I | Y*EI | S | O | S | S | S | S | H | OMe |
| 4519a-I | Y*EI | S | O | S | S | S | S | F | OMe |
| 4520a-I | Y*EI | S | O | S | S | S | S | OEt | OMe |
| 4521a-I | Y*EI | S | S | S | S | S | S | OH | OMe |
| 4522a-I | Y*EI | S | S | S | S | S | S | OMe | OMe |
| 4523a-I | Y*EI | S | S | S | S | S | S | H | OMe |
| 4524a-I | Y*EI | S | S | S | S | S | S | F | OMe |
| 4525a-I | Y*EI | S | S | S | S | S | S | OEt | OMe |
| 4526a-I | Y*EI | O | O | O | S | S | S | OH | OMe |
| 4527a-I | Y*EI | O | O | O | S | S | S | OMe | OMe |
| 4528a-I | Y*EI | O | O | O | S | S | S | H | OMe |
| 4529a-I | Y*EI | O | O | O | S | S | S | F | OMe |
| 4530a-I | Y*EI | O | O | O | S | S | S | OEt | OMe |
| 4531a-I | Y*EI | S | O | O | S | S | S | OH | OMe |
| 4532a-I | Y*EI | S | O | O | S | S | S | OMe | OMe |
| 4533a-I | Y*EI | S | O | O | S | S | S | H | OMe |
| 4534a-I | Y*EI | S | O | O | S | S | S | F | OMe |
| 4535a-I | Y*EI | S | O | O | S | S | S | OEt | OMe |
| 4536a-I | Y*EI | S | S | O | S | S | S | OH | OMe |
| 4537a-I | Y*EI | S | S | O | S | S | S | OMe | OMe |
| 4538a-I | Y*EI | S | S | O | S | S | S | H | OMe |
| 4539a-I | Y*EI | S | S | O | S | S | S | F | OMe |
| 4540a-I | Y*EI | S | S | O | S | S | S | OEt | OMe |
| 4541a-I | Y*EI | O | O | O | O | S | S | OH | OMe |
| 4542a-I | Y*EI | O | O | O | O | S | S | OMe | OMe |
| 4543a-I | Y*EI | O | O | O | O | S | S | H | OMe |
| 4544a-I | Y*EI | O | O | O | O | S | S | F | OMe |
| 4545a-I | Y*EI | O | O | O | O | S | S | OEt | OMe |
| 4546a-I | Y*EI | S | O | O | O | S | S | OH | OMe |
| 4547a-I | Y*EI | S | O | O | O | S | S | OMe | OMe |
| 4548a-I | Y*EI | S | O | O | O | S | S | H | OMe |
| 4549a-I | Y*EI | S | O | O | O | S | S | F | OMe |
| 4550a-I | Y*EI | S | O | O | O | S | S | OEt | OMe |
| 4551a-I | Y*EI | S | S | O | O | S | S | OH | OMe |
| 4552a-I | Y*EI | S | S | O | O | S | S | OMe | OMe |
| 4553a-I | Y*EI | S | S | O | O | S | S | H | OMe |
| 4554a-I | Y*EI | S | S | O | O | S | S | F | OMe |
| 4555a-I | Y*EI | S | S | O | O | S | S | OEt | OMe |
| 4556a-I | Y*EI | O | O | O | O | O | S | OH | OMe |
| 4557a-I | Y*EI | O | O | O | O | O | S | OMe | OMe |
| 4558a-I | Y*EI | O | O | O | O | O | S | H | OMe |
| 4559a-I | Y*EI | O | O | O | O | O | S | F | OMe |
| 4560a-I | Y*EI | O | O | O | O | O | S | OEt | OMe |
| 4561a-I | Y*EI | S | O | O | O | O | S | OH | OMe |
| 4562a-I | Y*EI | S | O | O | O | O | S | OMe | OMe |
| 4563a-I | Y*EI | S | O | O | O | O | S | H | OMe |
| 4564a-I | Y*EI | S | O | O | O | O | S | F | OMe |

TABLE 3-continued

CapA Structures for mRNA preparation

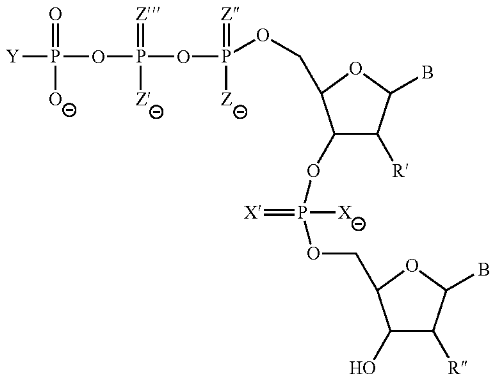

| Compound | Sequence | X | X' | Z | Z' | Z'' | Z''' | R' | R'' |
|---|---|---|---|---|---|---|---|---|---|
| 4565a-I | Y*EI | S | O | O | O | O | S | OEt | OMe |
| 4566a-I | Y*EI | S | S | O | O | O | S | OH | OMe |
| 4567a-I | Y*EI | S | S | O | O | O | S | OMe | OMe |
| 4568a-I | Y*EI | S | S | O | O | O | S | H | OMe |
| 4569a-I | Y*EI | S | S | O | O | O | S | F | OMe |
| 4570a-I | Y*EI | S | S | O | O | O | S | OEt | OMe |
| 4571a-I | Y*EI | O | O | S | O | S | O | OH | OMe |
| 4572a-I | Y*EI | O | O | S | O | S | O | OMe | OMe |
| 4573a-I | Y*EI | O | O | S | O | S | O | H | OMe |
| 4574a-I | Y*EI | O | O | S | O | S | O | F | OMe |
| 4575a-I | Y*EI | O | O | S | O | S | O | OEt | OMe |
| 4576a-I | Y*EI | S | O | S | O | S | O | OH | OMe |
| 4577a-I | Y*EI | S | O | S | O | S | O | OMe | OMe |
| 4578a-I | Y*EI | S | O | S | O | S | O | H | OMe |
| 4579a-I | Y*EI | S | O | S | O | S | O | F | OMe |
| 4580a-I | Y*EI | S | O | S | O | S | O | OEt | OMe |
| 4581a-I | Y*EI | S | S | S | O | S | O | OH | OMe |
| 4582a-I | Y*EI | S | S | S | O | S | O | OMe | OMe |
| 4583a-I | Y*EI | S | S | S | O | S | O | H | OMe |
| 4584a-I | Y*EI | S | S | S | O | S | O | F | OMe |
| 4585a-I | Y*EI | S | S | S | O | S | O | OEt | OMe |
| 4586a-I | Y*EI | O | O | O | S | O | S | OH | OMe |
| 4587a-I | Y*EI | O | O | O | S | O | S | OMe | OMe |
| 4588a-I | Y*EI | O | O | O | S | O | S | H | OMe |
| 4589a-I | Y*EI | O | O | O | S | O | S | F | OMe |
| 4590a-I | Y*EI | O | O | O | S | O | S | OEt | OMe |
| 4591a-I | Y*EI | S | O | O | S | O | S | OH | OMe |
| 4592a-I | Y*EI | S | O | O | S | O | S | OMe | OMe |
| 4593a-I | Y*EI | S | O | O | S | O | S | H | OMe |
| 4594a-I | Y*EI | S | O | O | S | O | S | F | OMe |
| 4595a-I | Y*EI | S | O | O | S | O | S | OEt | OMe |
| 4596a-I | Y*EI | S | S | O | S | O | S | OH | OMe |
| 4597a-I | Y*EI | S | S | O | S | O | S | OMe | OMe |
| 4598a-I | Y*EI | S | S | O | S | O | S | H | OMe |
| 4599a-I | Y*EI | S | S | O | S | O | S | F | OMe |
| 4600a-I | Y*EI | S | S | O | S | O | S | OEt | OMe |
| 4601a-I | Y*ET | O | O | O | O | O | O | OH | OH |
| 4602a-I | Y*ET | O | O | O | O | O | O | OMe | OH |
| 4603a-I | Y*ET | O | O | O | O | O | O | H | OH |
| 4604a-I | Y*ET | O | O | O | O | O | O | F | OH |
| 4605a-I | Y*ET | O | O | O | O | O | O | OEt | OH |
| 4606a-I | Y*ET | S | O | O | O | O | O | OH | OH |
| 4607a-I | Y*ET | S | O | O | O | O | O | OMe | OH |
| 4608a-I | Y*ET | S | O | O | O | O | O | H | OH |
| 4609a-I | Y*ET | S | O | O | O | O | O | F | OH |
| 4610a-I | Y*ET | S | O | O | O | O | O | OEt | OH |
| 4611a-I | Y*ET | S | S | O | O | O | O | OH | OH |
| 4612a-I | Y*ET | S | S | O | O | O | O | OMe | OH |
| 4613a-I | Y*ET | S | S | O | O | O | O | H | OH |
| 4614a-I | Y*ET | S | S | O | O | O | O | F | OH |
| 4615a-I | Y*ET | S | S | O | O | O | O | OEt | OH |
| 4616a-I | Y*ET | O | O | S | O | O | O | OH | OH |
| 4617a-I | Y*ET | O | O | S | O | O | O | OMe | OH |
| 4618a-I | Y*ET | O | O | S | O | O | O | H | OH |
| 4619a-I | Y*ET | O | O | S | O | O | O | F | OH |
| 4620a-I | Y*ET | O | O | S | O | O | O | OEt | OH |
| 4621a-I | Y*ET | S | O | S | O | O | O | OH | OH |

TABLE 3-continued

CapA Structures for mRNA preparation

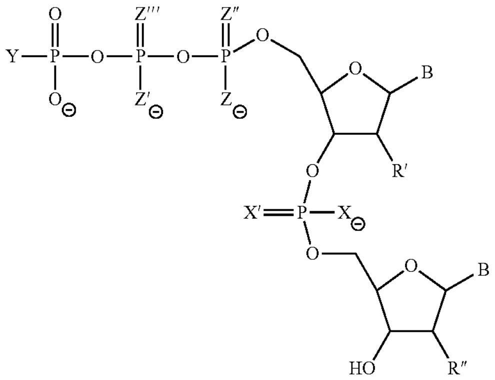

| Compound | Sequence | X | X' | Z | Z' | Z'' | Z''' | R' | R'' |
|---|---|---|---|---|---|---|---|---|---|
| 4622a-I | Y*ET | S | O | S | O | O | O | OMe | OH |
| 4623a-I | Y*ET | S | O | S | O | O | O | H | OH |
| 4624a-I | Y*ET | S | O | S | O | O | O | F | OH |
| 4625a-I | Y*ET | S | O | S | O | O | O | OEt | OH |
| 4626a-I | Y*ET | S | S | S | O | O | O | OH | OH |
| 4627a-I | Y*ET | S | S | S | O | O | O | OMe | OH |
| 4628a-I | Y*ET | S | S | S | O | O | O | H | OH |
| 4629a-I | Y*ET | S | S | S | O | O | O | F | OH |
| 4630a-I | Y*ET | S | S | S | O | O | O | OEt | OH |
| 4631a-I | Y*ET | O | O | S | S | O | O | OH | OH |
| 4632a-I | Y*ET | O | O | S | S | O | O | OMe | OH |
| 4633a-I | Y*ET | O | O | S | S | O | O | H | OH |
| 4634a-I | Y*ET | O | O | S | S | O | O | F | OH |
| 4635a-I | Y*ET | O | O | S | S | O | O | OEt | OH |
| 4636a-I | Y*ET | S | O | S | S | O | O | OH | OH |
| 4637a-I | Y*ET | S | O | S | S | O | O | OMe | OH |
| 4638a-I | Y*ET | S | O | S | S | O | O | H | OH |
| 4639a-I | Y*ET | S | O | S | S | O | O | F | OH |
| 4640a-I | Y*ET | S | O | S | S | O | O | OEt | OH |
| 4641a-I | Y*ET | S | S | S | S | O | O | OH | OH |
| 4642a-I | Y*ET | S | S | S | S | O | O | OMe | OH |
| 4643a-I | Y*ET | S | S | S | S | O | O | H | OH |
| 4644a-I | Y*ET | S | S | S | S | O | O | F | OH |
| 4645a-I | Y*ET | S | S | S | S | O | O | OEt | OH |
| 4646a-I | Y*ET | O | O | S | S | S | O | OH | OH |
| 4647a-I | Y*ET | O | O | S | S | S | O | OMe | OH |
| 4648a-I | Y*ET | O | O | S | S | S | O | H | OH |
| 4649a-I | Y*ET | O | O | S | S | S | O | F | OH |
| 4650a-I | Y*ET | O | O | S | S | S | O | OEt | OH |
| 4651a-I | Y*ET | S | O | S | S | S | O | OH | OH |
| 4652a-I | Y*ET | S | O | S | S | S | O | OMe | OH |
| 4653a-I | Y*ET | S | O | S | S | S | O | H | OH |
| 4654a-I | Y*ET | S | O | S | S | S | O | F | OH |
| 4655a-I | Y*ET | S | O | S | S | S | O | OEt | OH |
| 4656a-I | Y*ET | S | S | S | S | S | O | OH | OH |
| 4657a-I | Y*ET | S | S | S | S | S | O | OMe | OH |
| 4658a-I | Y*ET | S | S | S | S | S | O | H | OH |
| 4659a-I | Y*ET | S | S | S | S | S | O | F | OH |
| 4660a-I | Y*ET | S | S | S | S | S | O | OEt | OH |
| 4661a-I | Y*ET | O | O | S | S | S | S | OH | OH |
| 4662a-I | Y*ET | O | O | S | S | S | S | OMe | OH |
| 4663a-I | Y*ET | O | O | S | S | S | S | H | OH |
| 4664a-I | Y*ET | O | O | S | S | S | S | F | OH |
| 4665a-I | Y*ET | O | O | S | S | S | S | OEt | OH |
| 4666a-I | Y*ET | S | O | S | S | S | S | OH | OH |
| 4667a-I | Y*ET | S | O | S | S | S | S | OMe | OH |
| 4668a-I | Y*ET | S | O | S | S | S | S | H | OH |
| 4669a-I | Y*ET | S | O | S | S | S | S | F | OH |
| 4670a-I | Y*ET | S | O | S | S | S | S | OEt | OH |
| 4671a-I | Y*ET | S | S | S | S | S | S | OH | OH |
| 4672a-I | Y*ET | S | S | S | S | S | S | OMe | OH |
| 4673a-I | Y*ET | S | S | S | S | S | S | H | OH |
| 4674a-I | Y*ET | S | S | S | S | S | S | F | OH |
| 4675a-I | Y*ET | S | S | S | S | S | S | OEt | OH |
| 4676a-I | Y*ET | O | O | O | S | S | S | OH | OH |
| 4677a-I | Y*ET | O | O | O | S | S | S | OMe | OH |
| 4678a-I | Y*ET | O | O | O | S | S | S | H | OH |

TABLE 3-continued

CapA Structures for mRNA preparation

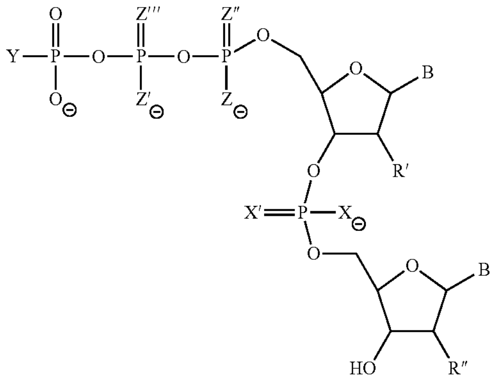

| Compound | Sequence | X | X' | Z | Z' | Z'' | Z''' | R' | R'' |
|---|---|---|---|---|---|---|---|---|---|
| 4679a-I | Y*ET | O | O | O | S | S | S | F | OH |
| 4680a-I | Y*ET | O | O | O | S | S | S | OEt | OH |
| 4681a-I | Y*ET | S | O | O | S | S | S | OH | OH |
| 4682a-I | Y*ET | S | O | O | S | S | S | OMe | OH |
| 4683a-I | Y*ET | S | O | O | S | S | S | H | OH |
| 4684a-I | Y*ET | S | O | O | S | S | S | F | OH |
| 4685a-I | Y*ET | S | O | O | S | S | S | OEt | OH |
| 4686a-I | Y*ET | S | S | O | S | S | S | OH | OH |
| 4687a-I | Y*ET | S | S | O | S | S | S | OMe | OH |
| 4688a-I | Y*EI | S | S | O | S | S | S | H | OH |
| 4689a-I | Y*ET | S | S | O | S | S | S | F | OH |
| 4690a-I | Y*ET | S | S | O | S | S | S | OEt | OH |
| 4691a-I | Y*ET | O | O | O | O | S | S | OH | OH |
| 4692a-I | Y*ET | O | O | O | O | S | S | OMe | OH |
| 4693a-I | Y*ET | O | O | O | O | S | S | H | OH |
| 4694a-I | Y*ET | O | O | O | O | S | S | F | OH |
| 4695a-I | Y*ET | O | O | O | O | S | S | OEt | OH |
| 4696a-I | Y*ET | S | O | O | O | S | S | OH | OH |
| 4697a-I | Y*ET | S | O | O | O | S | S | OMe | OH |
| 4698a-I | Y*ET | S | O | O | O | S | S | H | OH |
| 4699a-I | Y*ET | S | O | O | O | S | S | F | OH |
| 4700a-I | Y*ET | S | O | O | O | S | S | OEt | OH |
| 4701a-I | Y*ET | S | S | O | O | S | S | OH | OH |
| 4702a-I | Y*ET | S | S | O | O | S | S | OMe | OH |
| 4703a-I | Y*ET | S | S | O | O | S | S | H | OH |
| 4704a-I | Y*ET | S | S | O | O | S | S | F | OH |
| 4705a-I | Y*ET | S | S | O | O | S | S | OEt | OH |
| 4706a-I | Y*ET | O | O | O | O | O | S | OH | OH |
| 4707a-I | Y*ET | O | O | O | O | O | S | OMe | OH |
| 4708a-I | Y*ET | O | O | O | O | O | S | H | OH |
| 4709a-I | Y*ET | O | O | O | O | O | S | F | OH |
| 4710a-I | Y*ET | O | O | O | O | O | S | OEt | OH |
| 4711a-I | Y*ET | S | O | O | O | O | S | OH | OH |
| 4712a-I | Y*ET | S | O | O | O | O | S | OMe | OH |
| 4713a-I | Y*ET | S | O | O | O | O | S | H | OH |
| 4714a-I | Y*ET | S | O | O | O | O | S | F | OH |
| 4715a-I | Y*ET | S | O | O | O | O | S | OEt | OH |
| 4716a-I | Y*ET | S | S | O | O | O | S | OH | OH |
| 4717a-I | Y*ET | S | S | O | O | O | S | OMe | OH |
| 4718a-I | Y*ET | S | S | O | O | O | S | H | OH |
| 4719a-I | Y*ET | S | S | O | O | O | S | F | OH |
| 4720a-I | Y*ET | S | S | O | O | O | S | OEt | OH |
| 4721a-I | Y*ET | O | O | S | O | S | O | OH | OH |
| 4722a-I | Y*ET | O | O | S | O | S | O | OMe | OH |
| 4723a-I | Y*EI | O | O | S | O | S | O | H | OH |
| 4724a-I | Y*ET | O | O | S | O | S | O | F | OH |
| 4725a-I | Y*ET | O | O | S | O | S | O | OEt | OH |
| 4726a-I | Y*ET | S | O | S | O | S | O | OH | OH |
| 4727a-I | Y*ET | S | O | S | O | S | O | OMe | OH |
| 4728a-I | Y*ET | S | O | S | O | S | O | H | OH |
| 4729a-I | Y*ET | S | O | S | O | S | O | F | OH |
| 4730a-I | Y*ET | S | O | S | O | S | O | OEt | OH |
| 4731a-I | Y*ET | S | S | S | O | S | O | OH | OH |
| 4732a-I | Y*ET | S | S | S | O | S | O | OMe | OH |
| 4733a-I | Y*ET | S | S | S | O | S | O | H | OH |
| 4734a-I | Y*ET | S | S | S | O | S | O | F | OH |
| 4735a-I | Y*ET | S | S | S | O | S | O | OEt | OH |

TABLE 3-continued

CapA Structures for mRNA preparation

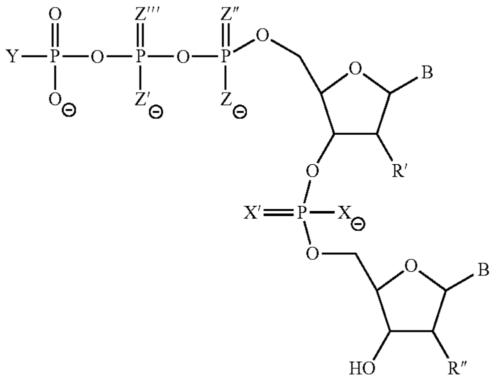

| Compound | Sequence | X | X' | Z | Z' | Z'' | Z''' | R' | R'' |
|---|---|---|---|---|---|---|---|---|---|
| 4736a-I | Y*ET | O | O | O | S | O | S | OH | OH |
| 4737a-I | Y*ET | O | O | O | S | O | S | OMe | OH |
| 4738a-I | Y*ET | O | O | O | S | O | S | H | OH |
| 4739a-I | Y*ET | O | O | O | S | O | S | F | OH |
| 4740a-I | Y*ET | O | O | O | S | O | S | OEt | OH |
| 4741a-I | Y*ET | S | O | O | S | O | S | OH | OH |
| 4742a-I | Y*ET | S | O | O | S | O | S | OMe | OH |
| 4743a-I | Y*ET | S | O | O | S | O | S | H | OH |
| 4744a-I | Y*ET | S | O | O | S | O | S | F | OH |
| 4745a-I | Y*ET | S | O | O | S | O | S | OEt | OH |
| 4746a-I | Y*ET | S | S | O | S | O | S | OH | OH |
| 4747a-I | Y*ET | S | S | O | S | O | S | OMe | OH |
| 4748a-I | Y*ET | S | S | O | S | O | S | H | OH |
| 4749a-I | Y*ET | S | S | O | S | O | S | F | OH |
| 4750a-I | Y*ET | S | S | O | S | O | S | OEt | OH |
| 4751a-I | Y*ET | O | O | O | O | O | O | OH | OMe |
| 4752a-I | Y*ET | O | O | O | O | O | O | OMe | OMe |
| 4753a-I | Y*ET | O | O | O | O | O | O | H | OMe |
| 4754a-I | Y*ET | O | O | O | O | O | O | F | OMe |
| 4755a-I | Y*ET | O | O | O | O | O | O | OEt | OMe |
| 4756a-I | Y*ET | S | O | O | O | O | O | OH | OMe |
| 4757a-I | Y*ET | S | O | O | O | O | O | OMe | OMe |
| 4758a-I | Y*ET | S | O | O | O | O | O | H | OMe |
| 4759a-I | Y*ET | S | O | O | O | O | O | F | OMe |
| 4760a-I | Y*ET | S | O | O | O | O | O | OEt | OMe |
| 4761a-I | Y*ET | S | S | O | O | O | O | OH | OMe |
| 4762a-I | Y*ET | S | S | O | O | O | O | OMe | OMe |
| 4763a-I | Y*ET | S | S | O | O | O | O | H | OMe |
| 4764a-I | Y*ET | S | S | O | O | O | O | F | OMe |
| 4765a-I | Y*ET | S | S | O | O | O | O | OEt | OMe |
| 4766a-I | Y*ET | O | O | S | O | O | O | OH | OMe |
| 4767a-I | Y*ET | O | O | S | O | O | O | OMe | OMe |
| 4768a-I | Y*ET | O | O | S | O | O | O | H | OMe |
| 4769a-I | Y*ET | O | O | S | O | O | O | F | OMe |
| 4770a-I | Y*ET | O | O | S | O | O | O | OEt | OMe |
| 4771a-I | Y*ET | S | O | S | O | O | O | OH | OMe |
| 4772a-I | Y*ET | S | O | S | O | O | O | OMe | OMe |
| 4773a-I | Y*ET | S | O | S | O | O | O | H | OMe |
| 4774a-I | Y*ET | S | O | S | O | O | O | F | OMe |
| 4775a-I | Y*ET | S | O | S | O | O | O | OEt | OMe |
| 4776a-I | Y*ET | S | S | S | O | O | O | OH | OMe |
| 4777a-I | Y*ET | S | S | S | O | O | O | OMe | OMe |
| 4778a-I | Y*ET | S | S | S | O | O | O | H | OMe |
| 4779a-I | Y*ET | S | S | S | O | O | O | F | OMe |
| 4780a-I | Y*ET | S | S | S | O | O | O | OEt | OMe |
| 4781a-I | Y*ET | O | O | S | S | O | O | OH | OMe |
| 4782a-I | Y*ET | O | O | S | S | O | O | OMe | OMe |
| 4783a-I | Y*ET | O | O | S | S | O | O | H | OMe |
| 4784a-I | Y*ET | O | O | S | S | O | O | F | OMe |
| 4785a-I | Y*ET | O | O | S | S | O | O | OEt | OMe |
| 4786a-I | Y*ET | S | O | S | S | O | O | OH | OMe |
| 4787a-I | Y*ET | S | O | S | S | O | O | OMe | OMe |
| 4788a-I | Y*ET | S | O | S | S | O | O | H | OMe |
| 4789a-I | Y*ET | S | O | S | S | O | O | F | OMe |
| 4790a-I | Y*ET | S | O | S | S | O | O | OEt | OMe |
| 4791a-I | Y*ET | S | S | S | S | O | O | OH | OMe |
| 4792a-I | Y*ET | S | S | S | S | O | O | OMe | OMe |

TABLE 3-continued

CapA Structures for mRNA preparation

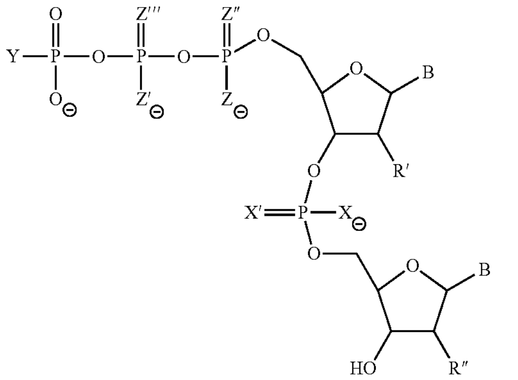

| Compound | Sequence | X | X' | Z | Z' | Z" | Z"' | R' | R" |
|---|---|---|---|---|---|---|---|---|---|
| 4793a-I | Y*ET | S | S | S | S | O | O | H | OMe |
| 4794a-I | Y*ET | S | S | S | S | O | O | F | OMe |
| 4795a-I | Y*ET | S | S | S | S | O | O | OEt | OMe |
| 4796a-I | Y*ET | O | O | S | S | S | O | OH | OMe |
| 4797a-I | Y*ET | O | O | S | S | S | O | OMe | OMe |
| 4798a-I | Y*ET | O | O | S | S | S | O | H | OMe |
| 4799a-I | Y*ET | O | O | S | S | S | O | F | OMe |
| 4800a-I | Y*ET | O | O | S | S | S | O | OEt | OMe |
| 4801a-I | Y*ET | S | O | S | S | S | O | OH | OMe |
| 4802a-I | Y*ET | S | O | S | S | S | O | OMe | OMe |
| 4803a-I | Y*ET | S | O | S | S | S | O | H | OMe |
| 4804a-I | Y*ET | S | O | S | S | S | O | F | OMe |
| 4805a-I | Y*ET | S | O | S | S | S | O | OEt | OMe |
| 4806a-I | Y*ET | S | S | S | S | S | O | OH | OMe |
| 4807a-I | Y*ET | S | S | S | S | S | O | OMe | OMe |
| 4808a-I | Y*ET | S | S | S | S | S | O | H | OMe |
| 4809a-I | Y*ET | S | S | S | S | S | O | F | OMe |
| 4810a-I | Y*ET | S | S | S | S | S | O | OEt | OMe |
| 4811a-I | Y*ET | O | O | S | S | S | S | OH | OMe |
| 4812a-I | Y*ET | O | O | S | S | S | S | OMe | OMe |
| 4813a-I | Y*ET | O | O | S | S | S | S | H | OMe |
| 4814a-I | Y*ET | O | O | S | S | S | S | F | OMe |
| 4815a-I | Y*ET | O | O | S | S | S | S | OEt | OMe |
| 4816a-I | Y*ET | S | O | S | S | S | S | OH | OMe |
| 4817a-I | Y*ET | S | O | S | S | S | S | OMe | OMe |
| 4818a-I | Y*ET | S | O | S | S | S | S | H | OMe |
| 4819a-I | Y*ET | S | O | S | S | S | S | F | OMe |
| 4820a-I | Y*ET | S | O | S | S | S | S | OEt | OMe |
| 4821a-I | Y*ET | S | S | S | S | S | S | OH | OMe |
| 4822a-I | Y*ET | S | S | S | S | S | S | OMe | OMe |
| 4823a-I | Y*ET | S | S | S | S | S | S | H | OMe |
| 4824a-I | Y*ET | S | S | S | S | S | S | F | OMe |
| 4825a-I | Y*ET | S | S | S | S | S | S | OEt | OMe |
| 4826a-I | Y*ET | O | O | O | S | S | S | OH | OMe |
| 4827a-I | Y*ET | O | O | O | S | S | S | OMe | OMe |
| 4828a-I | Y*ET | O | O | O | S | S | S | H | OMe |
| 4829a-I | Y*ET | O | O | O | S | S | S | F | OMe |
| 4830a-I | Y*ET | O | O | O | S | S | S | OEt | OMe |
| 4831a-I | Y*ET | S | O | O | S | S | S | OH | OMe |
| 4832a-I | Y*ET | S | O | O | S | S | S | OMe | OMe |
| 4833a-I | Y*ET | S | O | O | S | S | S | H | OMe |
| 4834a-I | Y*ET | S | O | O | S | S | S | F | OMe |
| 4835a-I | Y*ET | S | O | O | S | S | S | OEt | OMe |
| 4836a-I | Y*ET | S | S | O | S | S | S | OH | OMe |
| 4837a-I | Y*ET | S | S | O | S | S | S | OMe | OMe |
| 4838a-I | Y*ET | S | S | O | S | S | S | H | OMe |
| 4839a-I | Y*ET | S | S | O | S | S | S | F | OMe |
| 4840a-I | Y*ET | S | S | O | S | S | S | OEt | OMe |
| 4841a-I | Y*ET | O | O | O | O | S | S | OH | OMe |
| 4842a-I | Y*ET | O | O | O | O | S | S | OMe | OMe |
| 4843a-I | Y*ET | O | O | O | O | S | S | H | OMe |
| 4844a-I | Y*ET | O | O | O | O | S | S | F | OMe |
| 4845a-I | Y*ET | O | O | O | O | S | S | OEt | OMe |
| 4846a-I | Y*ET | S | O | O | O | S | S | OH | OMe |
| 4847a-I | Y*ET | S | O | O | O | S | S | OMe | OMe |
| 4848a-I | Y*ET | S | O | O | O | S | S | H | OMe |
| 4849a-I | Y*ET | S | O | O | O | S | S | F | OMe |

TABLE 3-continued

CapA Structures for mRNA preparation

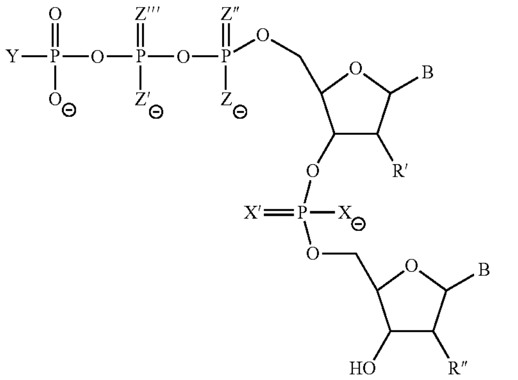

| Compound | Sequence | X | X' | Z | Z' | Z" | Z"' | R' | R" |
|---|---|---|---|---|---|---|---|---|---|
| 4850a-I | Y*ET | S | O | O | O | S | S | OEt | OMe |
| 4851a-I | Y*ET | S | S | O | O | S | S | OH | OMe |
| 4852a-I | Y*ET | S | S | O | O | S | S | OMe | OMe |
| 4853a-I | Y*ET | S | S | O | O | S | S | H | OMe |
| 4854a-I | Y*ET | S | S | O | O | S | S | F | OMe |
| 4855a-I | Y*ET | S | S | O | O | S | S | OEt | OMe |
| 4856a-I | Y*ET | O | O | O | O | O | S | OH | OMe |
| 4857a-I | Y*ET | O | O | O | O | O | S | OMe | OMe |
| 4858a-I | Y*ET | O | O | O | O | O | S | H | OMe |
| 4859a-I | Y*ET | O | O | O | O | O | S | F | OMe |
| 4860a-I | Y*ET | O | O | O | O | O | S | OEt | OMe |
| 4861a-I | Y*ET | S | O | O | O | O | S | OH | OMe |
| 4862a-I | Y*ET | S | O | O | O | O | S | OMe | OMe |
| 4863a-I | Y*ET | S | O | O | O | O | S | H | OMe |
| 4864a-I | Y*ET | S | O | O | O | O | S | F | OMe |
| 4865a-I | Y*ET | S | O | O | O | O | S | OEt | OMe |
| 4866a-I | Y*ET | S | S | O | O | O | S | OH | OMe |
| 4867a-I | Y*ET | S | S | O | O | O | S | OMe | OMe |
| 4868a-I | Y*ET | S | S | O | O | O | S | H | OMe |
| 4869a-I | Y*ET | S | S | O | O | O | S | F | OMe |
| 4870a-I | Y*ET | S | S | O | O | O | S | OEt | OMe |
| 4871a-I | Y*ET | O | O | S | O | S | O | OH | OMe |
| 4872a-I | Y*ET | O | O | S | O | S | O | OMe | OMe |
| 4873a-I | Y*ET | O | O | S | O | S | O | H | OMe |
| 4874a-I | Y*ET | O | O | S | O | S | O | F | OMe |
| 4875a-I | Y*ET | O | O | S | O | S | O | OEt | OMe |
| 4876a-I | Y*ET | S | O | S | O | S | O | OH | OMe |
| 4877a-I | Y*ET | S | O | S | O | S | O | OMe | OMe |
| 4878a-I | Y*ET | S | O | S | O | S | O | H | OMe |
| 4879a-I | Y*ET | S | O | S | O | S | O | F | OMe |
| 4880a-I | Y*ET | S | O | S | O | S | O | OEt | OMe |
| 4881a-I | Y*ET | S | S | S | O | S | O | OH | OMe |
| 4882a-I | Y*ET | S | S | S | O | S | O | OMe | OMe |
| 4883a-I | Y*ET | S | S | S | O | S | O | H | OMe |
| 4884a-I | Y*ET | S | S | S | O | S | O | F | OMe |
| 4885a-I | Y*ET | S | S | S | O | S | O | OEt | OMe |
| 4886a-I | Y*ET | O | O | O | S | O | S | OH | OMe |
| 4887a-I | Y*ET | O | O | O | S | O | S | OMe | OMe |
| 4888a-I | Y*ET | O | O | O | S | O | S | H | OMe |
| 4889a-I | Y*ET | O | O | O | S | O | S | F | OMe |
| 4890a-I | Y*ET | O | O | O | S | O | S | OEt | OMe |
| 4891a-I | Y*ET | S | O | O | S | O | S | OH | OMe |
| 4892a-I | Y*ET | S | O | O | S | O | S | OMe | OMe |
| 4893a-I | Y*ET | S | O | O | S | O | S | H | OMe |
| 4894a-I | Y*ET | S | O | O | S | O | S | F | OMe |
| 4895a-I | Y*ET | S | O | O | S | O | S | OEt | OMe |
| 4896a-I | Y*ET | S | S | O | S | O | S | OH | OMe |
| 4897a-I | Y*ET | S | S | O | S | O | S | OMe | OMe |
| 4898a-I | Y*ET | S | S | O | S | O | S | H | OMe |
| 4899a-I | Y*ET | S | S | O | S | O | S | F | OMe |
| 4900a-I | Y*ET | S | S | O | S | O | S | OEt | OMe |
| 4901a-I | Y*EE | O | O | O | O | O | O | OH | OH |
| 4902a-I | Y*EE | O | O | O | O | O | O | OMe | OH |
| 4903a-I | Y*EE | O | O | O | O | O | O | H | OH |
| 4904a-I | Y*EE | O | O | O | O | O | O | F | OH |
| 4905a-I | Y*EE | O | O | O | O | O | O | OEt | OH |
| 4906a-I | Y*EE | S | O | O | O | O | O | OH | OH |

TABLE 3-continued

CapA Structures for mRNA preparation

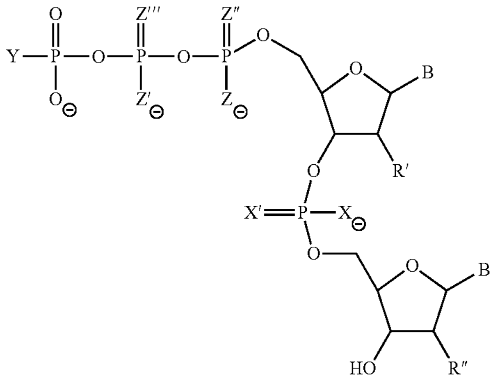

| Compound | Sequence | X | X' | Z | Z' | Z'' | Z''' | R' | R'' |
|---|---|---|---|---|---|---|---|---|---|
| 4907a-I | Y*EE | S | O | O | O | O | O | OMe | OH |
| 4908a-I | Y*EE | S | O | O | O | O | O | H | OH |
| 4909a-I | Y*EE | S | O | O | O | O | O | F | OH |
| 4910a-I | Y*EE | S | O | O | O | O | O | OEt | OH |
| 4911a-I | Y*EE | S | S | O | O | O | O | OH | OH |
| 4912a-I | Y*EE | S | S | O | O | O | O | OMe | OH |
| 4913a-I | Y*EE | S | S | O | O | O | O | H | OH |
| 4914a-I | Y*EE | S | S | O | O | O | O | F | OH |
| 4915a-I | Y*EE | S | S | O | O | O | O | OEt | OH |
| 4916a-I | Y*EE | O | O | S | O | O | O | OH | OH |
| 4917a-I | Y*EE | O | O | S | O | O | O | OMe | OH |
| 4918a-I | Y*EE | O | O | S | O | O | O | H | OH |
| 4919a-I | Y*EE | O | O | S | O | O | O | F | OH |
| 4920a-I | Y*EE | O | O | S | O | O | O | OEt | OH |
| 4921a-I | Y*EE | S | O | S | O | O | O | OH | OH |
| 4922a-I | Y*EE | S | O | S | O | O | O | OMe | OH |
| 4923a-I | Y*EE | S | O | S | O | O | O | H | OH |
| 4924a-I | Y*EE | S | O | S | O | O | O | F | OH |
| 4925a-I | Y*EE | S | O | S | O | O | O | OEt | OH |
| 4926a-I | Y*EE | S | S | S | O | O | O | OH | OH |
| 4927a-I | Y*EE | S | S | S | O | O | O | OMe | OH |
| 4928a-I | Y*EE | S | S | S | O | O | O | H | OH |
| 4929a-I | Y*EE | S | S | S | O | O | O | F | OH |
| 4930a-I | Y*EE | S | S | S | O | O | O | OEt | OH |
| 4931a-I | Y*EE | O | O | S | S | O | O | OH | OH |
| 4932a-I | Y*EE | O | O | S | S | O | O | OMe | OH |
| 4933a-I | Y*EE | O | O | S | S | O | O | H | OH |
| 4934a-I | Y*EE | O | O | S | S | O | O | F | OH |
| 4935a-I | Y*EE | O | O | S | S | O | O | OEt | OH |
| 4936a-I | Y*EE | S | O | S | S | O | O | OH | OH |
| 4937a-I | Y*EE | S | O | S | S | O | O | OMe | OH |
| 4938a-I | Y*EE | S | O | S | S | O | O | H | OH |
| 4939a-I | Y*EE | S | O | S | S | O | O | F | OH |
| 4940a-I | Y*EE | S | O | S | S | O | O | OEt | OH |
| 4941a-I | Y*EE | S | S | S | S | O | O | OH | OH |
| 4942a-I | Y*EE | S | S | S | S | O | O | OMe | OH |
| 4943a-I | Y*EE | S | S | S | S | O | O | H | OH |
| 4944a-I | Y*EE | S | S | S | S | O | O | F | OH |
| 4945a-I | Y*EE | S | S | S | S | O | O | OEt | OH |
| 4946a-I | Y*EE | O | O | S | S | S | O | OH | OH |
| 4947a-I | Y*EE | O | O | S | S | S | O | OMe | OH |
| 4948a-I | Y*EE | O | O | S | S | S | O | H | OH |
| 4949a-I | Y*EE | O | O | S | S | S | O | F | OH |
| 4950a-I | Y*EE | O | O | S | S | S | O | OEt | OH |
| 4951a-I | Y*EE | S | O | S | S | S | O | OH | OH |
| 4952a-I | Y*EE | S | O | S | S | S | O | OMe | OH |
| 4953a-I | Y*EE | S | O | S | S | S | O | H | OH |
| 4954a-I | Y*EE | S | O | S | S | S | O | F | OH |
| 4955a-I | Y*EE | S | O | S | S | S | O | OEt | OH |
| 4956a-I | Y*EE | S | S | S | S | S | O | OH | OH |
| 4957a-I | Y*EE | S | S | S | S | S | O | OMe | OH |
| 4958a-I | Y*EE | S | S | S | S | S | O | H | OH |
| 4959a-I | Y*EE | S | S | S | S | S | O | F | OH |
| 4960a-I | Y*EE | S | S | S | S | S | O | OEt | OH |
| 4961a-I | Y*EE | O | O | S | S | S | S | OH | OH |
| 4962a-I | Y*EE | O | O | S | S | S | S | OMe | OH |
| 4963a-I | Y*EE | O | O | S | S | S | S | H | OH |

TABLE 3-continued

CapA Structures for mRNA preparation

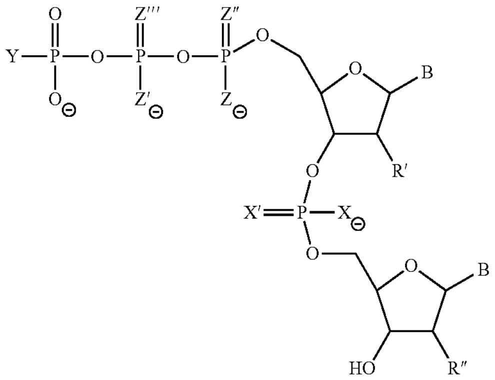

| Compound | Sequence | X | X' | Z | Z' | Z'' | Z''' | R' | R'' |
|---|---|---|---|---|---|---|---|---|---|
| 4964a-I | Y*EE | O | O | S | S | S | S | F | OH |
| 4965a-I | Y*EE | O | O | S | S | S | S | OEt | OH |
| 4966a-I | Y*EE | S | O | S | S | S | S | OH | OH |
| 4967a-I | Y*EE | S | O | S | S | S | S | OMe | OH |
| 4968a-I | Y*EE | S | O | S | S | S | S | H | OH |
| 4969a-I | Y*EE | S | O | S | S | S | S | F | OH |
| 4970a-I | Y*EE | S | O | S | S | S | S | OEt | OH |
| 4971a-I | Y*EE | S | S | S | S | 5 | S | OH | OH |
| 4972a-I | Y*EE | S | S | S | S | S | S | OMe | OH |
| 4973a-I | Y*EE | S | S | S | S | S | S | H | OH |
| 4974a-I | Y*EE | S | S | S | S | S | S | F | OH |
| 4975a-I | Y*EE | S | S | S | S | S | S | OEt | OH |
| 4976a-I | Y*EE | O | O | O | S | S | S | OH | OH |
| 4977a-I | Y*EE | O | O | O | S | S | S | OMe | OH |
| 4978a-I | Y*EE | O | O | O | S | S | S | H | OH |
| 4979a-I | Y*EE | O | O | O | S | S | S | F | OH |
| 4980a-I | Y*EE | O | O | O | S | S | S | OEt | OH |
| 4981a-I | Y*EE | S | O | O | S | S | S | OH | OH |
| 4982a-I | Y*EE | S | O | O | S | S | S | OMe | OH |
| 4983a-I | Y*EE | S | O | O | S | S | S | H | OH |
| 4984a-I | Y*EE | S | O | O | S | S | S | F | OH |
| 4985a-I | Y*EE | S | O | O | S | S | S | OEt | OH |
| 4986a-I | Y*EE | S | S | O | S | S | S | OH | OH |
| 4987a-I | Y*EE | S | S | O | S | S | S | OMe | OH |
| 4988a-I | Y*EE | S | S | O | S | S | S | H | OH |
| 4989a-I | Y*EE | S | S | O | S | S | S | F | OH |
| 4990a-I | Y*EE | S | S | O | S | S | S | OEt | OH |
| 4991a-I | Y*EE | O | O | O | O | S | S | OH | OH |
| 4992a-I | Y*EE | O | O | O | O | S | S | OMe | OH |
| 4993a-I | Y*EE | O | O | O | O | S | S | H | OH |
| 4994a-I | Y*EE | O | O | O | O | S | S | F | OH |
| 4995a-I | Y*EE | O | O | O | O | S | S | OEt | OH |
| 4996a-I | Y*EE | S | O | O | O | S | S | OH | OH |
| 4997a-I | Y*EE | S | O | O | O | S | S | OMe | OH |
| 4998a-I | Y*EE | S | O | O | O | S | S | H | OH |
| 4999a-I | Y*EE | S | O | O | O | S | S | F | OH |
| 5000a-I | Y*EE | S | O | O | O | S | S | OEt | OH |
| 5001a-I | Y*EE | S | S | O | O | S | S | OH | OH |
| 5002a-I | Y*EE | S | S | O | O | S | S | OMe | OH |
| 5003a-I | Y*EE | S | S | O | O | S | S | H | OH |
| 5004a-I | Y*EE | S | S | O | O | S | S | F | OH |
| 5005a-I | Y*EE | S | S | O | O | S | S | OEt | OH |
| 5006a-I | Y*EE | O | O | O | O | O | S | OH | OH |
| 5007a-I | Y*EE | O | O | O | O | O | S | OMe | OH |
| 5008a-I | Y*EE | O | O | O | O | O | S | H | OH |
| 5009a-I | Y*EE | O | O | O | O | O | S | F | OH |
| 5010a-I | Y*EE | O | O | O | O | O | S | OEt | OH |
| 5011a-I | Y*EE | S | O | O | O | O | S | OH | OH |
| 5012a-I | Y*EE | S | O | O | O | O | S | OMe | OH |
| 5013a-I | Y*EE | S | O | O | O | O | S | H | OH |
| 5014a-I | Y*EE | S | O | O | O | O | S | F | OH |
| 5015a-I | Y*EE | S | O | O | O | O | S | OEt | OH |
| 5016a-I | Y*EE | S | S | O | O | O | S | OH | OH |
| 5017a-I | Y*EE | S | S | O | O | O | S | OMe | OH |
| 5018a-I | Y*EE | S | S | O | O | O | S | H | OH |
| 5019a-I | Y*EE | S | S | O | O | O | S | F | OH |
| 5020a-I | Y*EE | S | S | O | O | O | S | OEt | OH |

TABLE 3-continued

CapA Structures for mRNA preparation

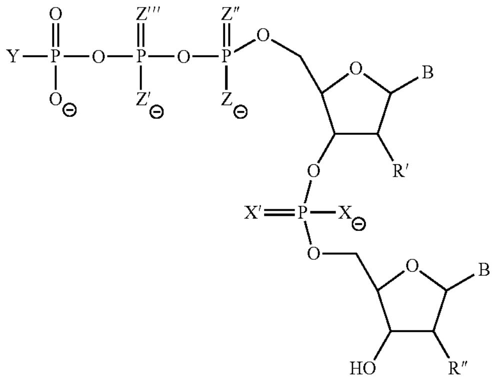

| Compound | Sequence | X | X' | Z | Z' | Z'' | Z''' | R' | R'' |
|---|---|---|---|---|---|---|---|---|---|
| 5021a-I | Y*EE | O | O | S | O | S | O | OH | OH |
| 5022a-I | Y*EE | O | O | S | O | S | O | OMe | OH |
| 5023a-I | Y*EE | O | O | S | O | S | O | H | OH |
| 5024a-I | Y*EE | O | O | S | O | S | O | F | OH |
| 5025a-I | Y*EE | O | O | S | O | S | O | OEt | OH |
| 5026a-I | Y*EE | S | O | S | O | S | O | OH | OH |
| 5027a-I | Y*EE | S | O | S | O | S | O | OMe | OH |
| 5028a-I | Y*EE | S | O | S | O | S | O | H | OH |
| 5029a-I | Y*EE | S | O | S | O | S | O | F | OH |
| 5030a-I | Y*EE | S | O | S | O | S | O | OEt | OH |
| 5031a-I | Y*EE | S | S | S | O | S | O | OH | OH |
| 5032a-I | Y*EE | S | S | S | O | S | O | OMe | OH |
| 5033a-I | Y*EE | S | S | S | O | S | O | H | OH |
| 5034a-I | Y*EE | S | S | S | O | S | O | F | OH |
| 5035a-I | Y*EE | S | S | S | O | S | O | OEt | OH |
| 5036a-I | Y*EE | O | O | O | S | O | S | OH | OH |
| 5037a-I | Y*EE | O | O | O | S | O | S | OMe | OH |
| 5038a-I | Y*EE | O | O | O | S | O | S | H | OH |
| 5039a-I | Y*EE | O | O | O | S | O | S | F | OH |
| 5040a-I | Y*EE | O | O | O | S | O | S | OEt | OH |
| 5041a-I | Y*EE | S | O | O | S | O | S | OH | OH |
| 5042a-I | Y*EE | S | O | O | S | O | S | OMe | OH |
| 5043a-I | Y*EE | S | O | O | S | O | S | H | OH |
| 5044a-I | Y*EE | S | O | O | S | O | S | F | OH |
| 5045a-I | Y*EE | S | O | O | S | O | S | OEt | OH |
| 5046a-I | Y*EE | S | S | O | S | O | S | OH | OH |
| 5047a-I | Y*EE | S | S | O | S | O | S | OMe | OH |
| 5048a-I | Y*EE | S | S | O | S | O | S | H | OH |
| 5049a-I | Y*EE | S | S | O | S | O | S | F | OH |
| 5050a-I | Y*EE | S | S | O | S | O | S | OEt | OH |
| 5051a-I | Y*EE | O | O | O | O | O | O | OH | OMe |
| 5052a-I | Y*EE | O | O | O | O | O | O | OMe | OMe |
| 5053a-I | Y*EE | O | O | O | O | O | O | H | OMe |
| 5054a-I | Y*EE | O | O | O | O | O | O | F | OMe |
| 5055a-I | Y*EE | O | O | O | O | O | O | OEt | OMe |
| 5056a-I | Y*EE | S | O | O | O | O | O | OH | OMe |
| 5057a-I | Y*EE | S | O | O | O | O | O | OMe | OMe |
| 5058a-I | Y*EE | S | O | O | O | O | O | H | OMe |
| 5059a-I | Y*EE | S | O | O | O | O | O | F | OMe |
| 5060a-I | Y*EE | S | O | O | O | O | O | OEt | OMe |
| 5061a-I | Y*EE | S | S | O | O | O | O | OH | OMe |
| 5062a-I | Y*EE | S | S | O | O | O | O | OMe | OMe |
| 5063a-I | Y*EE | S | S | O | O | O | O | H | OMe |
| 5064a-I | Y*EE | S | S | O | O | O | O | F | OMe |
| 5065a-I | Y*EE | S | S | O | O | O | O | OEt | OMe |
| 5066a-I | Y*EE | O | O | S | O | O | O | OH | OMe |
| 5067a-I | Y*EE | O | O | S | O | O | O | OMe | OMe |
| 5068a-I | Y*EE | O | O | S | O | O | O | H | OMe |
| 5069a-I | Y*EE | O | O | S | O | O | O | F | OMe |
| 5070a-I | Y*EE | O | O | S | O | O | O | OEt | OMe |
| 5071a-I | Y*EE | S | O | S | O | O | O | OH | OMe |
| 5072a-I | Y*EE | S | O | S | O | O | O | OMe | OMe |
| 5073a-I | Y*EE | S | O | S | O | O | O | H | OMe |
| 5074a-I | Y*EE | S | O | S | O | O | O | F | OMe |
| 5075a-I | Y*EE | S | O | S | O | O | O | OEt | OMe |
| 5076a-I | Y*EE | S | S | S | O | O | O | OH | OMe |
| 5077a-I | Y*EE | S | S | S | O | O | O | OMe | OMe |

TABLE 3-continued

CapA Structures for mRNA preparation

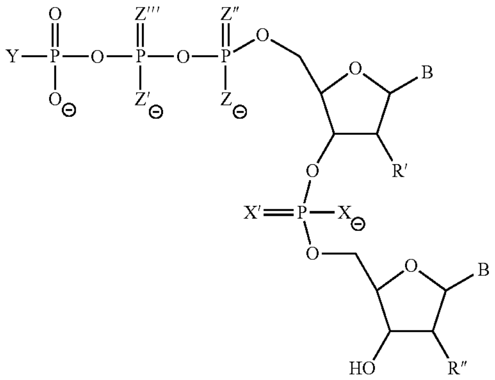

| Compound | Sequence | X | X' | Z | Z' | Z'' | Z''' | R' | R'' |
|---|---|---|---|---|---|---|---|---|---|
| 5078a-I | Y*EE | S | S | S | O | O | O | H | OMe |
| 5079a-I | Y*EE | S | S | S | O | O | O | F | OMe |
| 5080a-I | Y*EE | S | S | S | O | O | O | OEt | OMe |
| 5081a-I | Y*EE | O | O | S | S | O | O | OH | OMe |
| 5082a-I | Y*EE | O | O | S | S | O | O | OMe | OMe |
| 5083a-I | Y*EE | O | O | S | S | O | O | H | OMe |
| 5084a-I | Y*EE | O | O | S | S | O | O | F | OMe |
| 5085a-I | Y*EE | O | O | S | S | O | O | OEt | OMe |
| 5086a-I | Y*EE | S | O | S | S | O | O | OH | OMe |
| 5087a-I | Y*EE | S | O | S | S | O | O | OMe | OMe |
| 5088a-I | Y*EE | S | O | S | S | O | O | H | OMe |
| 5089a-I | Y*EE | S | O | S | S | O | O | F | OMe |
| 5090a-I | Y*EE | S | O | S | S | O | O | OEt | OMe |
| 5091a-I | Y*EE | S | S | S | S | O | O | OH | OMe |
| 5092a-I | Y*EE | S | S | S | S | O | O | OMe | OMe |
| 5093a-I | Y*EE | S | S | S | S | O | O | H | OMe |
| 5094a-I | Y*EE | S | S | S | S | O | O | F | OMe |
| 5095a-I | Y*EE | S | S | S | S | O | O | OEt | OMe |
| 5096a-I | Y*EE | O | O | S | S | S | O | OH | OMe |
| 5097a-I | Y*EE | O | O | S | S | S | O | OMe | OMe |
| 5098a-I | Y*EE | O | O | S | S | S | O | H | OMe |
| 5099a-I | Y*EE | O | O | S | S | S | O | F | OMe |
| 5100a-I | Y*EE | O | O | S | S | S | O | OEt | OMe |
| 5101a-I | Y*EE | S | O | S | S | S | O | OH | OMe |
| 5102a-I | Y*EE | S | O | S | S | S | O | OMe | OMe |
| 5103a-I | Y*EE | S | O | S | S | S | O | H | OMe |
| 5104a-I | Y*EE | S | O | S | S | S | O | F | OMe |
| 5105a-I | Y*EE | S | O | S | S | S | O | OEt | OMe |
| 5106a-I | Y*EE | S | S | S | S | S | O | OH | OMe |
| 5107a-I | Y*EE | S | S | S | S | S | O | OMe | OMe |
| 5108a-I | Y*EE | S | S | S | S | S | O | H | OMe |
| 5109a-I | Y*EE | S | S | S | S | S | O | F | OMe |
| 5110a-I | Y*EE | S | S | S | S | S | O | OEt | OMe |
| 5111a-I | Y*EE | O | O | S | S | S | S | OH | OMe |
| 5112a-I | Y*EE | O | O | S | S | S | S | OMe | OMe |
| 5113a-I | Y*EE | O | O | S | S | S | S | H | OMe |
| 5114a-I | Y*EE | O | O | S | S | S | S | F | OMe |
| 5115a-I | Y*EE | O | O | S | S | S | S | OEt | OMe |
| 5116a-I | Y*EE | S | O | S | S | S | S | OH | OMe |
| 5117a-I | Y*EE | S | O | S | S | S | S | OMe | OMe |
| 5118a-I | Y*EE | S | O | S | S | S | S | H | OMe |
| 5119a-I | Y*EE | S | O | S | S | S | S | F | OMe |
| 5120a-I | Y*EE | S | O | S | S | S | S | OEt | OMe |
| 5121a-I | Y*EE | S | S | S | S | S | S | OH | OMe |
| 5122a-I | Y*EE | S | S | S | S | S | S | OMe | OMe |
| 5123a-I | Y*EE | S | S | S | S | S | S | H | OMe |
| 5124a-I | Y*EE | S | S | S | S | S | S | F | OMe |
| 5125a-I | Y*EE | S | S | S | S | S | S | OEt | OMe |
| 5126a-I | Y*EE | O | O | O | S | S | S | OH | OMe |
| 5127a-I | Y*EE | O | O | O | S | S | S | OMe | OMe |
| 5128a-I | Y*EE | O | O | O | S | S | S | H | OMe |
| 5129a-I | Y*EE | O | O | O | S | S | S | F | OMe |
| 5130a-I | Y*EE | O | O | O | S | S | S | OEt | OMe |
| 5131a-I | Y*EE | S | O | O | S | S | S | OH | OMe |
| 5132a-I | Y*EE | S | O | O | S | S | S | OMe | OMe |
| 5133a-I | Y*EE | S | O | O | S | S | S | H | OMe |
| 5134a-I | Y*EE | S | O | O | S | S | S | F | OMe |

TABLE 3-continued

CapA Structures for mRNA preparation

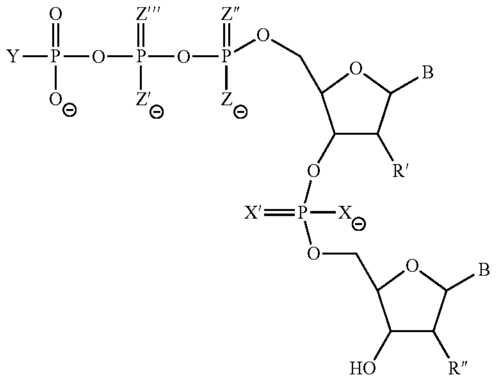

| Compound | Sequence | X | X' | Z | Z' | Z" | Z'" | R' | R" |
|---|---|---|---|---|---|---|---|---|---|
| 5135a-I | Y*EE | S | O | O | S | S | S | OEt | OMe |
| 5136a-I | Y*EE | S | S | O | S | S | S | OH | OMe |
| 5137a-I | Y*EE | S | S | O | S | S | S | OMe | OMe |
| 5138a-I | Y*EE | S | S | O | S | S | S | H | OMe |
| 5139a-I | Y*EE | S | S | O | S | S | S | F | OMe |
| 5140a-I | Y*EE | S | S | O | S | S | S | OEt | OMe |
| 5141a-I | Y*EE | O | O | O | O | S | S | OH | OMe |
| 5142a-I | Y*EE | O | O | O | O | S | S | OMe | OMe |
| 5143a-I | Y*EE | O | O | O | O | S | S | H | OMe |
| 5144a-I | Y*EE | O | O | O | O | S | S | F | OMe |
| 5145a-I | Y*EE | O | O | O | O | S | S | OEt | OMe |
| 5146a-I | Y*EE | S | O | O | O | S | S | OH | OMe |
| 5147a-I | Y*EE | S | O | O | O | S | S | OMe | OMe |
| 5148a-I | Y*EE | S | O | O | O | S | S | H | OMe |
| 5149a-I | Y*EE | S | O | O | O | S | S | F | OMe |
| 5150a-I | Y*EE | S | O | O | O | S | S | OEt | OMe |
| 5151a-I | Y*EE | S | S | O | O | S | S | OH | OMe |
| 5152a-I | Y*EE | S | S | O | O | S | S | OMe | OMe |
| 5153a-I | Y*EE | S | S | O | O | S | S | H | OMe |
| 5154a-I | Y*EE | S | S | O | O | S | S | F | OMe |
| 5155a-I | Y*EE | S | S | O | O | S | S | OEt | OMe |
| 5156a-I | Y*EE | O | O | O | O | O | S | OH | OMe |
| 5157a-I | Y*EE | O | O | O | O | O | S | OMe | OMe |
| 5158a-I | Y*EE | O | O | O | O | O | S | H | OMe |
| 5159a-I | Y*EE | O | O | O | O | O | S | F | OMe |
| 5160a-I | Y*EE | O | O | O | O | O | S | OEt | OMe |
| 5161a-I | Y*EE | S | O | O | O | O | S | OH | OMe |
| 5162a-I | Y*EE | S | O | O | O | O | S | OMe | OMe |
| 5163a-I | Y*EE | S | O | O | O | O | S | H | OMe |
| 5164a-I | Y*EE | S | O | O | O | O | S | F | OMe |
| 5165a-I | Y*EE | S | O | O | O | O | S | OEt | OMe |
| 5166a-I | Y*EE | S | S | O | O | O | S | OH | OMe |
| 5167a-I | Y*EE | S | S | O | O | O | S | OMe | OMe |
| 5168a-I | Y*EE | S | S | O | O | O | S | H | OMe |
| 5169a-I | Y*EE | S | S | O | O | O | S | F | OMe |
| 5170a-I | Y*EE | S | S | O | O | O | S | OEt | OMe |
| 5171a-I | Y*EE | O | O | S | O | S | O | OH | OMe |
| 5172a-I | Y*EE | O | O | S | O | S | O | OMe | OMe |
| 5173a-I | Y*EE | O | O | S | O | S | O | H | OMe |
| 5174a-I | Y*EE | O | O | S | O | S | O | F | OMe |
| 5175a-I | Y*EE | O | O | S | O | S | O | OEt | OMe |
| 5176a-I | Y*EE | S | O | S | O | S | O | OH | OMe |
| 5177a-I | Y*EE | S | O | S | O | S | O | OMe | OMe |
| 5178a-I | Y*EE | S | O | S | O | S | O | H | OMe |
| 5179a-I | Y*EE | S | O | S | O | S | O | F | OMe |
| 5180a-I | Y*EE | S | O | S | O | S | O | OEt | OMe |
| 5181a-I | Y*EE | S | S | S | O | S | O | OH | OMe |
| 5182a-I | Y*EE | S | S | S | O | S | O | OMe | OMe |
| 5183a-I | Y*EE | S | S | S | O | S | O | H | OMe |
| 5184a-I | Y*EE | S | S | S | O | S | O | F | OMe |
| 5185a-I | Y*EE | S | S | S | O | S | O | OEt | OMe |
| 5186a-I | Y*EE | O | O | O | S | O | S | OH | OMe |
| 5187a-I | Y*EE | O | O | O | S | O | S | OMe | OMe |
| 5188a-I | Y*EE | O | O | O | S | O | S | H | OMe |
| 5189a-I | Y*EE | O | O | O | S | O | S | F | OMe |
| 5190a-I | Y*EE | O | O | O | S | O | S | OEt | OMe |
| 5191a-I | Y*EE | S | O | O | S | O | S | OH | OMe |

TABLE 3-continued

CapA Structures for mRNA preparation

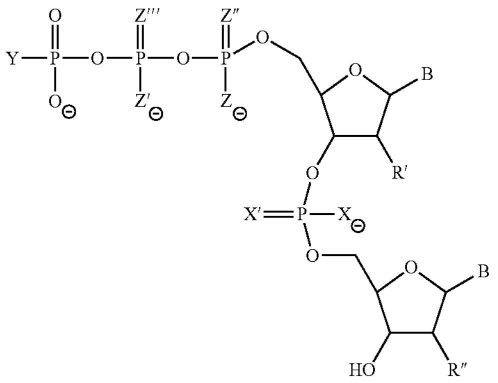

| Compound | Sequence | X | X' | Z | Z' | Z" | Z'" | R' | R" |
|---|---|---|---|---|---|---|---|---|---|
| 5192a-I | Y*EE | S | O | O | S | O | S | OMe | OMe |
| 5193a-I | Y*EE | S | O | O | S | O | S | H | OMe |
| 5194a-I | Y*EE | S | O | O | S | O | S | F | OMe |
| 5195a-I | Y*EE | S | O | O | S | O | S | OEt | OMe |
| 5196a-I | Y*EE | S | S | O | S | O | S | OH | OMe |
| 5197a-I | Y*EE | S | S | O | S | O | S | OMe | OMe |
| 5198a-I | Y*EE | S | S | O | S | O | S | H | OMe |
| 5199a-I | Y*EE | S | S | O | S | O | S | F | OMe |
| 5200a-I | Y*EE | S | S | O | S | O | S | OEt | OMe |

Y*NN (1001a-I to 4360a-I)

B is Adenine (A), Cytosine (C), Guanine (G), Uracil (U), Thymine (T), Hypoxanthine (I) or Purine (E); X is O or S and X' is O or S; Z is O or S and Z' is O or S and Z" is O or S and Z'" is O or S; R' is OH, OMe, H, F, or OEt and R" is OH or OMe Each N in Y*NN indicates nucleotide/nucleoside carrying A, C, G, U, T, I or E, where NN is a dinucleotide moiety of any combination of A, C, G, U, T, I and E

* =

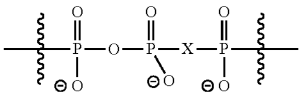

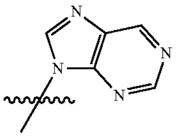 [SMILES: *n1cnc2cncnc21]

Purine (E)

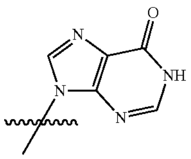 [SMILES: *n1cnc2c(=O)[nH]cnc21]

Hypoxanthine (I)

Y =

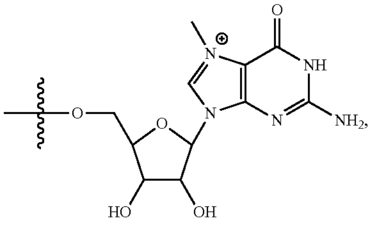

a a

TABLE 3-continued
CapA Structures for mRNA preparation
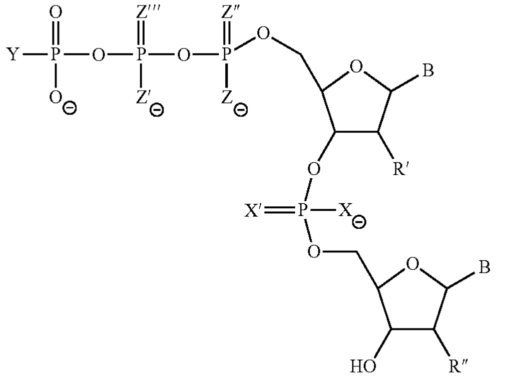
| Compound | Sequence | X | X' | Z | Z' | Z'' | Z''' | R' | R'' |
|---|---|---|---|---|---|---|---|---|---|
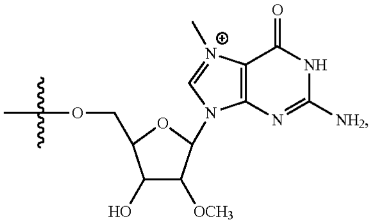
b
b
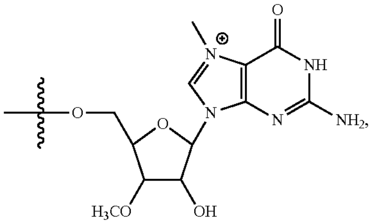
c
c
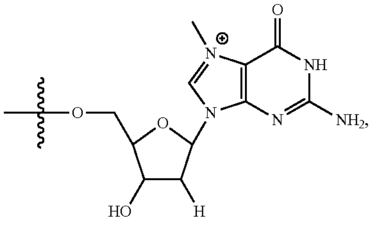
d
d
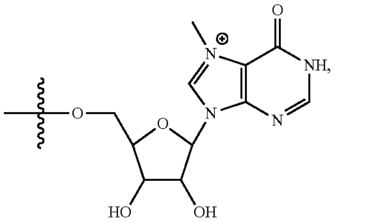
e
e
TABLE 3-continued
CapA Structures for mRNA preparation
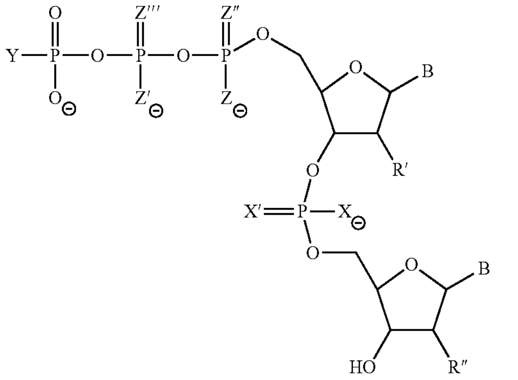
| Compound | Sequence | X | X' | Z | Z' | Z'' | Z''' | R' | R'' |
|---|---|---|---|---|---|---|---|---|---|
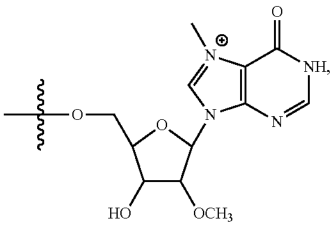
f
f
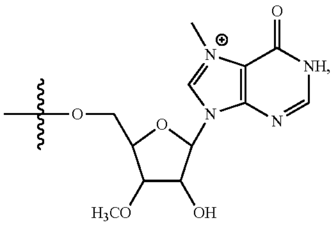
g
g
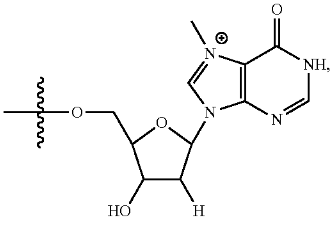
h
h
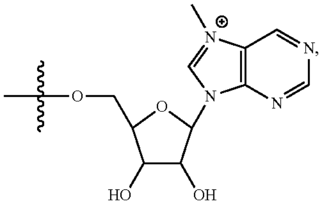
i
i TABLE 3-continued CapA Structures for mRNA preparation

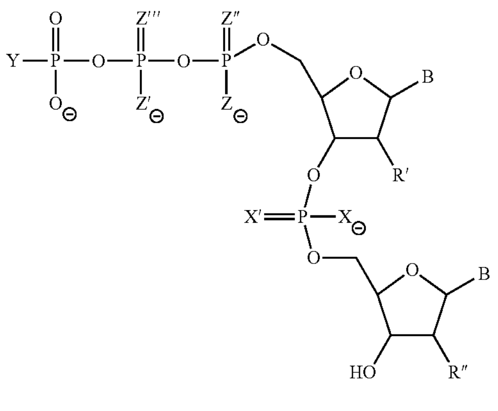

| Compound | Sequence | X | X' | Z | Z' | Z'' | Z''' | R' | R'' |
|---|---|---|---|---|---|---|---|---|---|
| j | 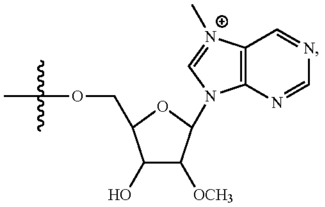 j | | | | | | | | |
| k | 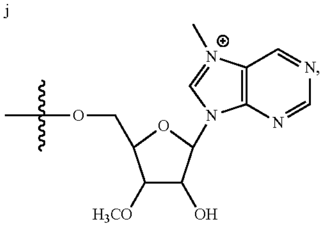 k | | | | | | | | |
| l | 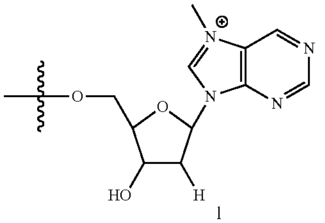 [SMILES: *OCC1OC(n2c[n+](C)c3cncnc32)CC1O] l | | | | | | | | |

In some embodiments, disclosed herein is a pharmaceutically acceptable salt or pharmaceutically acceptable solvate or a pharmaceutical composition comprising one or more mRNA(s) which is/are produced/manufactured from one or more sequence initiator compound selected from Table 3.

In another aspect, described herein is a complex comprising an IVT mRNA sequence initiator and a DNA template, wherein the IVT mRNA sequence initiator comprises a compound described herein, wherein (a) the DNA template comprises a promoter region comprising a transcriptional start site having a first nucleotide at nucleotide position +1, a second nucleotide at nucleotide position +2, and a third nucleotide at nucleotide position +3; and (b) wherein the IVT mRNA sequence initiator is hybridized to the DNA template at least at nucleotide positions +1, +2, and +3.

In another aspect, described herein is a complex comprising an IVT mRNA sequence initiator and a DNA template, wherein the IVT mRNA sequence initiator comprises a compound described herein, wherein (a) the DNA template comprises a promoter region comprising a transcriptional start site having a first nucleotide at nucleotide position +1 and a second nucleotide at nucleotide position +2; and (b) wherein the IVT mRNA sequence initiator is hybridized to the DNA template at least at nucleotide positions +1 and +2.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition can be a mixture of a sequence initiator compound described herein with one or more other chemical components (i.e. pharmaceutically acceptable ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

The compositions described herein can be administered to the subject in a variety of ways, including parenterally, intravenously, intradermally, intramuscularly, colonically, rectally or intraperitoneally. In some embodiments, the sequence initiator compound described herein or a pharmaceutically acceptable salt thereof is administered by intraperitoneal injection, intramuscular injection, subcutaneous injection, or intravenous injection of the subject. In some embodiments, the pharmaceutical compositions can be administered parenterally, intravenously, intramuscularly or orally. The oral agents comprising a sequence initiator compound described herein can be in any suitable form for oral administration, such as liquid, tablets, capsules, or the like. The oral formulations can be further coated or treated to prevent or reduce dissolution in stomach. The compositions of the present disclosure can be administered to a subject using any suitable methods known in the art. Suitable formulations for use in the present disclosure and methods of delivery are generally well known in the art. For example, the sequence initiator compound described herein can be formulated as pharmaceutical compositions with a pharmaceutically acceptable diluent, carrier or excipient. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

Pharmaceutical formulations described herein can be administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the pharmaceutical formulation is in the form of a tablet. In other embodiments, pharmaceutical formulations containing a sequence initiator compound described herein are in the form of a capsule. In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a sequence initiator compound described herein can be formulated for use as an aerosol, a mist or a powder. For buccal or sublingual administration, the compositions may take the form of tablets, lozenges, or gels formulated in a conventional manner. In some embodiments, a sequence initiator compound described herein can be prepared as transdermal dosage forms. In some embodiments, a sequence initiator compound described herein can be formulated into a pharmaceutical composition suitable for intramuscular, subcutaneous, or intravenous injection. In some embodiments, a sequence initiator compound described herein can be administered topically and can be formulated into a variety of topically administrable compositions, such as solutions, suspensions, lotions, gels, pastes, medicated sticks, balms, creams or ointments. In some embodiments, a sequence initiator compound described herein can be formulated in rectal compositions such as enemas, rectal gels, rectal foams, rectal aerosols, suppositories, jelly suppositories, or retention enemas.

In one aspect, described herein is a pharmaceutical composition comprising an RNA molecule comprising the IVT mRNA sequence initiator disclosed herein and one or more of pharmaceutically acceptable excipients. In some embodiments, the pharmaceutical composition comprises lipid nanoparticles. In some embodiments, the RNA is encapsulated in an lipid nanoparticle.

Transcription

In Eukaryotes, transcription of messenger RNAs (mRNAs) is done by RNA polymerase II. This is a complicated multi-subunit enzyme with complex regulation. To carry out large scale transcription in vitro, researches commonly use single subunit phage polymerases derived from T7, T3, SP6, K1-5, K1E, K1F or K11 bacteriophages. This family of polymerases has simple, minimal promoter sequences of ~17 nucleotides which require no accessory proteins and have minimal constraints of the initiating nucleotide sequence. While this application focuses on T7 RNA Polymerase (T7 RNAP), one skilled in the art would understand that this disclosure could be practiced with other RNA polymerases.

T7 RNAP exists in at least two protein states. The first is referred to as the "abortive complex" and is associated with transcriptional initiation. The second is a very processive conformation called the "elongation complex". In vitro transcription can be broken into six steps: 1) binding of the RNA polymerase to the promoter sequence, 2) initiation of transcription, 3) non-processive elongation termed abortive transcription during which the polymerase frequently releases the DNA template and short abortive transcripts 4) conversion of the open complex to the closed complex, 5) processive elongation and 6) transcriptional termination. A significant amount of RNA produced during transcription consists of short abortive fragments of ~2-8 nucleotides in length (Biochemistry 19:3245-3253 (1980); Nucleic Acids Res. 9:31-45 (1981); Nucleic Acids Res. 15:8783-8798 (1987); Biochemistry 27:3966-3974 (1988)). After synthesis of about 10-14 bases, RNA polymerases escape from abortive cycling, at the same time losing sequence-specific contacts with the promoter DNA, and forming a processive elongation complex, in which the RNA chain is extended in a sequence-independent manner (*J. Mol. Biol.* 183:165-177 (1985); *Proc. Natl. Acad. Sci. U.S.A.* 83:3614-3618 (1986); *Mol. Cell Biol.* 7:3371-3379 (1987)).

The consensus sequence for the most active Class III T7 promoters encompasses 17 bp of sequence upstream, and 6 bp downstream, of the transcription start site (Cell 16:815-25. (1979)). The position of the first transcribed nucleotide is commonly referred to as the +1 transcript nucleotide of the RNA, the second transcribed nucleotide as +2 transcript nucleotide and so on (Table 2). During transcription, the two strands are melted to form a transcription bubble and the bottom strand of the duplex (shown 3' to 5' in Table 4) is the template for transcription. For transcript nucleotides +3 and beyond, the template strand defines the identity of the transcribed nucleotides primarily through Watson-Crick base pairing interactions. Here the nucleotide encoding the first RNA transcript nucleotide is defined as the +1 nucleotide of the template. In the example shown in Table 4, the +1 transcript nucleotide is G and the +1 template nucleotide is C. Likewise the +4 transcript nucleotide is A and the +4 template nucleotide is T.

TABLE 4

| | | |
|---|---|---|
| Position in transcript | +1+2+3+4+5+6 | |
| Transcript sequence | pppGGGAGA | |
| Promoter top strand | 5′-TAATACGACTCACTATAGGGAGA...-3′ | SEQ ID NO.1 |
| Promoter bottom strand | 3′-ATTATGCTGAGTGATATCCCTCT...-5′ | SEQ ID NO.2 |
| Position in template | +1+2+3+4+5+6 | |

Unlike DNA polymerases, T7 RNAP initiates RNA synthesis in the absence of a primer. The first step in initiation is called de novo RNA synthesis, in which RNA polymerase recognizes a specific sequence on the DNA template, selects the first pair of nucleotide triphosphates complementary to template residues at positions +1 and +2, and catalyzes the formation of a phosphodiester bond to form a dinucleotide. The initiating nucleotides have lower affinities for the polymerase than those used during elongation. The Kd value is 2 mM for the first initiating NTP and 80 UM for the second, whereas the Kd is approximately 5 μM for NTPs during elongation (J. Mol. Biol. (2007) 370, 256-268). It has been found that de novo synthesis is the rate-limiting step during transcription. T7 RNAP exhibits a strong bias for GTP as the initiating nucleotide (*J. Biol. Chem.* 248:2235-2244 (1973)). Among the 17 T7 promoters in the genome, 15 initiate with GTP (and 13 with pppGpG), whereas there is no obvious NTP preference during transcription elongation (*J. Mol. Biol.* 370:256-268 (2007)). T7 RNA polymerase initiates poorly on promoters encoding A at position +1; transcription instead initiates predominantly with an encoded G at position +2 (*J. Biol. Chem.* 278:2819-2823 (2003)).

During de novo RNA synthesis, binding of the initiating nucleotides is achieved primarily by the free energy created from base stacking, specific interactions between the polymerase residues, the guanine moieties of the initiating nucleotides and base complementarity interactions (J. Mol. Biol. 370:256-268 (2007)).

It is known that T7 RNAP can also initiate with short oligonucleotide primers. For example, it is known that 13 promoters in the T7 genome initiate with pppGpG (*J. Mol. Biol.* 370:256-268 (2007)). Several groups showed that T7 RNAP can initiate from dinucleotide primers (*Biochemistry* 24:5716-5723 (1985)). Axelrod et al. showed that an uncapped GpA dinucleotide could initiate from +1 and +2 template nucleotides that were 2'-deoxycytidine and 2'-deoxythymidine, respectively ("CT" template) Their reaction conditions were 200 micromolar (M) dimer and 100 μM ATP, CTP, GTP and UTP. Their reaction mixture also contained 100 μM 3' dATP, 3' dCTP 3' dUTP or 50 μM 3' dGTP. They observe only GpA initiated RNAs and not a mixture of GpA initiated RNAs and 5' triphosphate RNAs from GTP initiation. This is likely due to the reaction conditions employed. 100 μM GTP is well below the 2 mM Kd of T7 polymerase for the first initiating guanosine (J. Mol. Biol. (2007) 370, 256-268). Since GTP competes for initiation with the initiating oligonucleotide, using a low GTP concentration favors GpA initiation but results in low transcription yield (maximum calculated yield estimated to be <150 μg/mL of reaction). When initiating transcription on "CT" template with ApG, CpG, UpG or GpG, they observed formation of RNA transcripts with an additional untemplated 5' nucleotide (A, C, U or G, respectively).

The methods and compositions provided herein for preparation of 5'-capped RNA include, but are not limited to, mRNA, small nuclear RNA (snRNA), small nucleolar RNA (snoRNA), small cajal body-specific RNA (scaRNA). These methods involve the use of a mRNA sequence initiator, for example, Cap containing oligonucleotide primers, along with nucleoside 5'-triphosphates (NTPs) and RNA polymerase for DNA-templated and promoter controlled synthesis of RNA. In certain aspects, the methods use an initiating capped oligonucleotide primer that provides utility in RNA synthesis, in particular synthesis of capped mRNAs. The exemplary initiating oligonucleotide primer has a structure that resembles Cap 0, Cap 1, Cap 2 or TMG-Cap of natural RNA molecules, which include 2'-O-methylated nucleoside units at, penultimate Cap 1 and next to penultimate Cap 2 5'-positions of RNA. The natural Cap 0 structure does not have 2'-O-methylated nucleoside units.

The methods and compositions for preparation of RNA including, but not limited to, mRNA, snRNA, snoRNA, scaRNA, transfer RNA (tRNA), ribosomal RNA (rRNA), and transfer-messenger RNA (tmRNA) that carry modifications at or near 5'-end of the molecule. These methods involve the use of initiators, e.g. initiating oligonucleotide primers with or without Cap, nucleoside 5'-triphosphates (NTPs) and RNA polymerase for DNA-templated and promoter controlled synthesis of RNA. In certain aspects, the methods use a modified initiating oligonucleotide primer carrying structural modifications that provide utility in RNA synthesis; in particular synthesis of 5'-modified RNAs.

An exemplary initiating capped oligonucleotide primer has an open 3'-OH group that allows for initiation of RNA polymerase mediated synthesis of RNA on a DNA template by adding nucleotide units to the 3'-end of the primer. The initiating capped oligonucleotide primer is substantially complementary to template DNA sequence at the transcription initiation site (i.e., the initiation site is located closer to 3'-terminus of a promoter sequence and may overlap with promoter sequence). In certain embodiments, the initiating capped oligonucleotide primer directs synthesis of RNA predominantly in one direction ("forward") starting from the 3'-end of the primer. In certain aspects and embodiments, the initiating capped oligonucleotide primer outcompetes any nucleoside 5'-triphosphate for initiation of RNA synthesis, thereby maximizing the production of the RNA that starts with initiating capped oligonucleotide primer and minimizing a production of RNA that starts with 5'-triphosphate-nucleoside (typically GTP).

The manufacture of mRNA by in vitro transcription utilizes highly active phage RNA polymerases (T3, T7, SP6 and others). RNA polymerase works under control of specific promoter which is incorporated in DNA plasmid construct in front of a template nucleotide sequence. Transcription process usually starts with purine nucleoside 5'-triphosphate (typically GTP) and continues until the RNA polymerase encounters a terminating sequence or completes the DNA template.

As discussed above, mCAP dinucleotide analogs, $^{7m}G(5')ppp(5')N$, that contain Cap 0 have been used for initiation in vitro transcription (e.g., RNA 1:957-967 (1995)). The capped RNA molecules produced using these dinucleotide analogs contain Cap 0. However only about 50% of synthesized capped RNA molecules have the correct "forward" orientation of Cap 0. To convert RNA with Cap 0 to RNA with Cap 1 an additional enzymatic reaction must be preformed using (nucleoside-2'-O) methyltransferase. However this conversion may be not quantitative; it is not easy to control and it is difficult to separate the remaining Cap 0 RNAs from Cap 1 RNAs. In addition, the competition from NTPs (specifically GTP) for initiation transcription further reduces the quantity of active capped RNA molecules produced.

In addition, modified dinucleotide analogs, such as $^{7m}G_{3'Ome}(5')ppp(5')N$ and other related ARCA analogs, that carry modified 71G residue with blocked 3' and/or 2' position on ribose, have been used for initiation of in vitro transcription (e.g., *RNA* 7:1486-1495 (2001)). These ARCA cap analogs direct RNA synthesis only in the "forward" orientation and therefore produce a RNA molecule with (natural)Cap 0 on the 5'-terminus (having 2' and/or 3' modifications to $^{7m}G$ residue). Such RNAs are more active in translation systems compared to RNAs prepared using standard dinucleotide analogs, $^{7m}G(5')ppp(5')N$. To convert RNA with ARCA Cap 0 to RNA with ARCA Cap 1 an additional enzymatic reaction must be performed with (nucleoside-2'-O) methyltransferase similar to that required for the dinucleotide analogs previously discussed. This method has the same disadvantages as that elaborated for the mCAP dinucleotide analogs; the conversion of RNA with Cap 0 to RNA with ARCA Cap 1 may be not quantitative; the reaction is not easy to control, it is difficult to separate remaining Cap 0 RNAs from Cap 1 RNAs and competition from NTPs (specifically GTP) for initiation of transcription further reduces the quantity of active capped RNA molecules produced.

Short oligonucleotide primers (2 to 6-mer) with 3'-terminal guanosine residue have been used for initiation of in vitro transcription (Pitulle, C. et al., *Gene,* 112:101-105 (1992)). These oligonucleotide primers contained modified and unmodified ribonucleoside residues (e.g., modified ribonucleoside residues included 2'-O-methylated nucleoside residues and 2'-deoxyribonucleoside residues). The shorter oligonucleotide primers (dimers to tetramer) substantially out-compete GTP for initiation of transcription while longer primers (pentamer to hexamer) are much less efficient in initiation of transcription compared to GTP. It may be because these longer primers (as they are designed) have a low percent of complementarity with DNA template at initiation site. In contrast, dimer, AG (as designed), was complementary to the DNA template at initiation site. The RNA molecules produced using oligonucleotide primers, discussed in this section, had internal 2'-O-methylated nucleoside but did not contain 5'-Cap 0, Cap1, Cap 2 or TMG-cap. To convert RNA without cap structure to RNA with Cap 1, Cap 2 or TMG-cap structure an additional enzymatic reactions using capping enzymes would have to be performed. However such conversion has the same disadvantages as those stated above.

Other short RNA oligonucleotides containing cap structures and internal 2'-O-methylated nucleoside residues have been chemically prepared (Ohkubo et al., *Org. Letters* 15:4386-4389 (2013)). These short capped oligonucleotides were ligated with a "decapitated" (without 5'-cap structure) fragment of long RNA using T4 DNA ligase and a complementary DNA splinter oligonucleotide. The final RNA synthesized using this chemical-enzymatic method had both internal 2'-O-methylated nucleoside residues and 5'-TMG-cap structure. However only short capped RNAs (<200-mer) were prepared using this ligation approach. Moreover, the yields were low (15-30%). It is not easy to control and optimize the T4 DNA ligation reaction and it requires a laborious separation process using PolyAcrylamide Gel Electrophoresis and isolation of capped RNAs from remaining uncapped RNAs. Separation of long (500-10000 bases) capped mRNAs from remaining uncapped mRNAs by PAGE method is not feasible.

Finally, 5'-modified nucleoside or 5'-modified mononucleotide or 5'-modified dinucleotide, typically a derivative of guanosine, have been used for initiating in vitro transcription of RNA (*Gene,* 112:101-105 (1992) and Bioconjug. Chem., 10371-378 (1999)). These initiator nucleosides and nucleotides may carry labels or affinity groups (e.g. biotin) and, when incorporated on the 5'-end of RNA, would allow for easy detection, isolation and purification of synthesized RNA. This 5'-labeled or tagged RNAs may be necessary for some applications. However this strategy was not used for the preparation of mRNA with Cap 0, Cap 1, Cap 2 or TMG-cap structures.

In certain aspects of the present disclosure, compositions of the capped mRNA sequence initiators as described herein are provided. In related aspects, are methods in which RNA is synthesized using capped mRNA sequence initiators described herein.

mRNA Sequence Initiators

Provided herein are mRNA sequence initiators that may be used for RNA synthesis. mRNA sequence initiators may have a hybridization sequence which may be complementary to a sequence on DNA template at initiation site. In some embodiments, the length of the hybridization sequence of the initiators for use in the methods and compositions provided herein depends on several factors including the identity of template nucleotide sequence and the temperature at which this initiator is hybridized to DNA template or used during in vitro transcription. Determination of the desired length of a specific nucleotide sequence of a capped initiator for use in transcription can be easily determined by a person of ordinary skill in the art or by routine experimentation. For example, the length of a nucleic acid or oligonucleotide may be determined based on a desired hybridization specificity or selectivity.

mRNA sequence initiators may be capped oligonucleotide primers. In some embodiments, the nucleotide length of initiating capped oligonucleotide primer (including the inverted 5'-5' Cap nucleotide) is between 3 to about 9, in some embodiments the nucleotide length of initiating capped oligonucleotide primer (including Cap) is between 3 to about 7, in some embodiments the nucleotide length of initiating capped oligonucleotide primer (including Cap) is between 3 to about 5, and in some embodiments the nucleotide length of initiating capped oligonucleotide primer (including Cap) is about 3. The length of hybridization sequence within an initiator, e.g., an initiating capped oligonucleotide primer may be equal to or shorter than the total length of the initiating capped oligonucleotide primer.

The presence of hybridization sequence forces an initiator, e.g. an initiating capped oligonucleotide primer, to predominantly align with complementary sequence of the DNA template at the initiation site in only the desired orientation (i.e., the "forward" orientation). In some embodiments, in the forward orientation, the RNA transcript begins with the inverted guanosine residue. The dominance of the forward orientation of primer alignment on DNA template over incorrect "reverse" orientation is maintained by the thermodynamics of the hybridization complex. The latter may be determined by the length of the hybridization sequence of initiating capped oligonucleotide primer and the identity of bases involved in hybridization with DNA template. Hybridization in the desired forward orientation may also depend on the temperature and reaction conditions at which DNA template and initiating capped oligonucleotide primer are hybridized or used during in vitro transcription.

An exemplary initiator, e.g., an initiating capped oligonucleotide primer of the present disclosure enhances efficacy of initiation of transcription compared to efficacy of initiation with standard GTP, ATP, CTP or UTP. In some embodiments, initiation of transcription is considered enhanced when synthesis of RNA starts predominantly from initiating capped oligonucleotide primer and not from any NTP in transcription mixture. The enhanced efficiency of initiation of transcription results in a higher yield of RNA transcript. The enhanced efficiency of initiation of transcription may be increased to about 10%, about 20%, about 40%, about 60%, about 80%, about 90%, about 100%, about 150%, about 200% or about 500% over synthesis of RNA with conventional methods without initiating capped primer. In certain embodiments, a capped mRNA sequence initiator, e.g. an initiating capped oligonucleotide primer, out-competes any NTP (including GTP) for initiation of transcription. One of ordinary skill in the art is able to readily determine the level of substrate activity and efficacy of initiating capped oligonucleotide primers. One example of a method of determining substrate efficacy is illustrated in Example 13). In certain embodiments, initiation takes place from a capped oligonucleotide primer rather than an NTP, which results in a higher level of capping of the transcribed mRNA.

In some aspects, methods are provided in which RNA is synthesized utilizing an initiating capped oligonucleotide primer that has substitutions or modifications. In some aspects, the substitutions and modifications of an initiating capped oligonucleotide primer do not substantially impair the synthesis of RNA. Routine test syntheses can be preformed to determine if desirable synthesis results can be obtained with the modified initiating capped oligonucleotide primers. Those skilled in the art can perform such routine experimentation to determine if desirable results can be obtained. The substitution or modification of initiating capped oligonucleotide primer include for example, one or more modified nucleoside bases, one or more modified sugars, one or more modified internucleotide linkage and/or one or more modified triphosphate bridges.

An initiator, for example, a modified initiating capped oligonucleotide primer, which may include one or more modification groups of the methods and compositions provided herein, can be elongated by RNA polymerase on DNA template by incorporation of NTP onto open 3'-OH group. An initiating capped oligonucleotide primer may include natural RNA and DNA nucleosides, modified nucleosides or nucleoside analogs. The initiating capped oligonucleotide primer may contain natural internucleotide phosphodiester linkages or modifications thereof, or combination thereof.

In one embodiment the modification group may be a thermally labile group which dissociates from a modified initiating capped oligonucleotide primer at an increasing rate as the temperature of the enzyme reaction medium is raised. Examples of thermally labile groups for oligonucleotides and NTPs are described in *Nucleic Acids Res.,* 36:e131 (2008), *Collect. Symp. Ser.,* 10:259-263 (2008) and *Analytical Chemistry,* 81:4955-4962 (2009).

In some aspects, methods are provided in which RNA is synthesized where at least one or more NTP is added to a transcription reaction may have a modification as disclosed herein. In some aspects, the modification of the at least one NTP does not substantially impair RNA polymerase mediated synthesis of RNA. The modification of NTP may include for example, one or more modified nucleoside bases, one or more modified sugars, one or more modified 5'-triphosphate. The modified NTP may incorporate onto the 3'-end of an initiating capped oligonucleotide primer and it does not block transcription and supports further elongation of the primer.

In another embodiment, the modification group of an initiating capped oligonucleotide primer may be a detectable label or detectable marker. Thus, following transcription, the target RNA, containing the detectable label or marker, can be identified by size, mass, color and/or affinity capture. In some embodiments, the detectable label or marker is a fluorescent dye; and the affinity capture label is biotin. In certain embodiments, one or more components of a transcription reaction (initiating capped oligonucleotide primer and/or NTPs) may be labeled with a detectable label or marker. Thus, following transcription, the RNA molecule can be identified, for example, by size, mass, affinity capture or color. In some embodiments, the detectable label is a fluorescent dye; and the affinity capture label is biotin.

Standard chemical and enzymatic synthesis methods may be utilized to synthesize mRNA sequence initiators of the present disclosure and are disclosed herein in the Examples section.

Kits

Kits including mRNA sequence initiators for performing transcription are also contemplated. For example, kits may contain all transcription reagents for synthesis of common RNAs (e.g., FLuc mRNA). More specifically, a kit may contain: a mRNA sequence initiator; a container marked for transcription; instructions for performing RNA synthesis; and one or more reagents selected from the group consisting of one or more modified or unmodified initiating capped oligonucleotide primers, one or more unmodified NTPs, one or more modified NTPs (e.g., pseudouridine 5'-triphosphate), an RNA polymerase, other enzymes, a reaction buffer, magnesium and a DNA template.

mRNA sequence initiators of the present disclosure have a significant advantage over current methods and compositions involving use of various initiating nucleosides, nucleotides and oligonucleotides or use of polyphosphate dinucleotide derivatives containing Cap 0 structure, such as mCAP and ARCA. A mRNA sequence initiator, e.g., an initiating capped oligonucleotide primer may be compatible with existing transcription systems and reagents and no additional enzymes or reagents are required. In addition, the use of initiating capped oligonucleotide primers makes several non-enzymatic and enzymatic steps (such as capping and 2'-O-methylation) unnecessary thus reducing complexity of the process and a cost of RNA synthesis.

While the exemplary methods described herein relate to T7 RNA polymerase mediated transcription reaction, a number of other RNA polymerases known in the art for use in transcription reactions may be utilized with the compositions and methods of the present disclosure. Other enzymes, including natural or mutated variants that may be utilized include, for example, SP6 and T3 RNA polymerases and RNA polymerases from other sources including thermostable RNA polymerases.

Some nucleic acid replication and amplification methods may include transcription as a part of the process. Among these methods are: transcription mediated amplification (TMA) and nucleic acid sequence-based amplification (NASBA), DNA and RNA sequencing and other nucleic acid extension reactions known in the art. The skilled artisan will understand that other methods may be used either in place of, or together with, transcription methods, including variants of transcription reactions developed in the future.

Therapeutic Uses

In one aspect, described herein is a method for reducing the risk of coronary disease in a subject in need thereof, comprising administering to the subject an effective amount of a pharmaceutical composition described herein.

In one aspect, described herein is the production of mRNAs containing a capped mRNA sequence initiator, e.g., an initiation capped oligonucleotide primer for use as therapeutic agents in a pharmaceutical composition, the introduction of RNAs containing the capped intiator into cells to treat a medical condition of the cells or the introduction of RNAs containing the capped initiator into cells that utilize those RNAs to produce proteins that may have a therapeutic affect on the host cells.

One method for treating a condition utilizing an RNA containing capped initiator comprises the step of administering the RNA containing the capped initiator described herein or a composition comprising such RNA to a subject having, or suspected of having a condition whose symptoms/symptomologies may be reduced in severity or eliminated.

An RNA containing a capped initiator as described herein, when formulated in a pharmaceutically acceptable carrier and/or pharmaceutically acceptable salt at a concentration of 4 mg/ml or less, is effective to produce a reduction of the symptoms and/or symptomologies by at least 20%, 30%, 40%, 50%, 60%, 70%, 80%, 90% or greater than an untreated individual with the pharmaceutically acceptable carrier alone.

Pharmaceutical compositions may be formulated for administration by injection or other appropriate routes known to those skilled in the art for treating a particular condition. An injectable composition for parenteral administration typically contains the active compound in a suitable solution and/or pharmaceutical carrier such as sterile physiological saline. The composition may also be formulated as a suspension in a lipid or phospholipid, in a liposomal suspension, or in an aqueous emulsion.

Methods for preparing a variety of compositions and/or formulations are known to those skilled in the art see Remington's Pharmaceutical Sciences ($19^{th}$ Ed., Williams & Wilkins, 1995). The composition to be administered will contain a quantity of the selected compound in a pharmaceutically safe and effective amount for increasing expression of the desired protein in the target cells or tissue.

In some embodiments, the pharmaceutical composition contains at least 0.1% (w/v) of the compound, as described above, in some embodiments, the pharmaceutical composition contains greater than 0.1%, in some embodiments, the pharmaceutical composition contains up to about 10%, in some embodiments, the pharmaceutical composition contains up to about 5%, and in some embodiments, the pharmaceutical composition contains up to about 1% (w/v) of the compound. Choice of a suitable concentration depends on factors such as the desired dose, frequency and method of delivery of the active agent.

For treatment of a subject, such as a mammal or a human, dosages are determined based on factors such as the weight and overall health of the subject, the condition treated, severity of symptoms, etc. Dosages and concentrations are determined to produce the desired benefit while avoiding any undesirable side effects. Typical dosages of the subject compounds are in the range of about 0.0005 to 500 mg/day for a human patient, and ranging in some embodiments between about 1-100 mg/day. For example, higher dose regimens include e.g. 50-100, 75-100, or 50-75 mg/day, and lower dose regimens include e.g. 1-50, 25-50, or 1-25 mg/day.

RNA Modification

Provided herein are RNA molecules modified with initiators, e.g. initiating capped oligonucleotide primers described herein suitable for targeted ex vivo and in vivo delivery systems. A modified RNA molecule may comprise two or more linked ribonucleic acid subunits. Non-limiting exemplary modified RNAs include CRISPR guide RNA, short interfering RNA (siRNA), microRNA (miRNA), short hairpin RNA (shRNA), small nuclear RNA (snRNA), messenger RNA (mRNA), precursor mRNA (pre-mRNA), antisense RNA (asRNA), and heteronuclear RNA (hnRNA). Modified RNAs as described herein encompass both the RNA sequence and any structural embodiment thereof, e.g. single stranded, double stranded, triple stranded, circular, helical, hairpin, stem loop, buldge, etc. A modified RNA may comprise a length of at least about 3, 4, 5, 6, 7, 8, 9, 10, 20, 30, 40, 50, 100, 200, 300, 400, or 500 bases. A modified RNA may comprise a length of at least about 1 kilobase (kb), 2 kb, 3 kb, 4 kb, 5 kb, 10 kb, 20 kb, 50 kb, or more. In some embodiments, the modified RNA is a CRISPR guide RNA (gRNA). A gRNA may be a single guide RNA or a dual guide RNA. In some embodiments, the modified RNA is a mRNA. In some embodiments, a mRNA can be isolated from a cell or a tissue. In some embodiments, a mRNA can be transcribed from a DNA. In some embodiments, a mRNA can be chemically synthesized.

In certain embodiments, modified RNA molecules provided herein are resistant to degradation by RNases or other exonucleases. In certain embodiments, modified RNA molecules provided herein are stabilized to prevent degradation by endonucleases. In some embodiments, modified RNA molecules provided herein are suitable for in vivo delivery and induces less cellular immune receptor activation (e.g. TLR, RIG-I) as compared to unmodified RNA. RNA modifications as described in Diebold (2008) Adv Drug Deliv Rev. April 29; 60(7): 813-23) and Sorrentino (1998)Cell Mol Life Sci. August; 54(8): 785-94, the entirety of both are incorporated herein by reference.

The nucleotides as described herein can be synthetic or chemically modified. For example, guide RNAs provided herein can be synthetic or chemically modified guide RNAs. The nucleotides in the guide RNA that are modified may be those corresponding to one or more nucleotides in the binding region of the guide RNA with Cas9 and/or the nucleotides in the binding region of the guide RNA with the target DNA. Remaining unmodified nucleotides of the guide RNA may be those required to be identified for minimal binding of Cas9 to the 2'-OH location on the bases. In some embodiments, the nucleotides may be modified at the 2' position of the sugar moiety of the nucleotide. In some embodiments, the 2'—OH group of the sugar moiety is replaced by a group selected from H, OR, R, halo, SH, SR, H2, NHR, N(R)2 or CN, wherein R is C1-C6 alkyl, alkenyl or alkynyl and halo is F, CI, Br or I. Other modifications may include, inverted (deoxy) a basics, amino, fluoro, chloro, bromo, CN, CF, methoxy, imidazole, carboxylate, thioate, C1 to C10 lower alkyl, substituted lower alkyl, alkaryl or aralkyl, heterozycloalkyl; heterozycloalkaryl; aminoalkylamino; polyalkylamino or substituted silyl. Methods for making RNAs with specific sequences and modifications are known by those skilled in the art, for example, in Dellinger et al. (2011), J. Am. Chem. Soc, 133, 11540; U.S. Pat. No. 8,202,983; Kumar et al., (2007), J. Am. Chem. Soc, 129, 6859-64; WO2013176844, the entirety of which are incorporated herein by reference.

In some embodiments, polynucleotides or oligonucleotides as provided herein may be synthetic. For example, mRNAs maybe chemically synthesized mRNAs. Synthetic RNA production yield is based on sequences and modifications. 2'-O-methyl modifications have been shown to increase coupling efficacy or efficiency during RNA synthesis and therefore increase yield of chemically synthesized RNA. Furthermore, nucleotides may be modified by phosphorothioates. Phosphothioate (phosphorothioate)(PS) bonds substitute a sulphur atom for a non-bridging oxygen in the phosphate backbone of an oligonucleotide. Accordingly, exemplary nucleotides of the disclosure include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, a-LNA having an a-L-ribo configuration (a diastereomer of LNA), 2'-amino-LNA having a 2'-amino functionalization, and 2'-amino-a-LNA having a 2'-amino functionalization) or hybrids thereof.

Conjugates for Targeted Delivery

Provided herein are conjugates suitable for targeted delivery of agents, such as mRNA, guide RNA, miRNA, siRNA, DNA, peptides, or other micro or macro molecules. A conjugate can contain one or more aptamers, ligands, or moieties for targeted delivery ex vivo or in vivo. In some embodiments, a conjugate comprises a targeting moiety (or ligand), a linker, and an active agent (or payload) that is connected to the targeting moiety. An active agent can be a therapeutic agent, a prophylactic agent, or a diagnostic/prognostic agent. An active agent may have a capability of manipulating a physiological function (e.g., gene expression) in a subject. An active agent maybe a guide RNA, a mRNA, a miRNA, a siRNA, a DNA, or a peptide. The active agent may be connected with the targeting moiety via a linker, via a non-covalent linkage, via nucleobase paring, or any combination thereof. In some embodiments, the conjugate may be a conjugate between a single active agent and a single targeting moiety with the formula: X-Y-Z, wherein X is the targeting moiety; Y is a linker; and Z is the guide RNA. In certain embodiments, one targeting ligand can be conjugated to two or more active agents, wherein the conjugate has the formula: X-(Y-Z)n. For example, the conjugate may comprise a guide RNA and a mRNA. In certain embodiments, one active agent can be linked to two or more targeting ligands wherein the conjugate has the formula: (X-Y) n-Z. In other embodiments, one or more targeting moieties may be connected to one or more active pay loads wherein the conjugate formula may be (X-Y-Z) n. In various combinations, the formula of the conjugates maybe, for example, X-Y-Z-Y-X, (X-Y-Z)n-Y-Z, or X-Y-(X-Y-Z)n, wherein X is a targeting moiety; Y is a linker; Z is an active agent, e.g. a guide RNA. The number of each moiety in the conjugate may vary dependent on types of agents, sizes of the conjugate, delivery targets, particles used to packaging the conjugate, other active agents (e.g., immunologic adjuvants) and routes of administration. Each occurrence of X, Y, and Z can be the same or different, e.g. the conjugate can contain more than one type of targeting moiety, more than one type of linker, and/or more than one type of active agent, n is an integer equal to or greater than 1. In some embodiments, n is an integer between 1 and 50, or between 2 and 20, or between 5 and 40. In some embodiments, n may be an integer of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49 or 50.

In some embodiments, an active agent, e.g., a guide RNA may be delivered to cells and tissues using viral, polymeric and liposomal formulations, cell-penetrating peptides, aptamers, ligands, or conjugates and antibody approaches. A moiety or ligand may direct guide RNAs to particular organ, tissue, or cell, for example, a liver hepatocyte, and may be referred to as a targeting moiety. In some embodiments, targeting moieties modify one or more properties of the attached molecule (e.g., a mRNA or a guide RNA), including but not limited to pharmacodynamic, pharmacokinetic, binding, absorption, cellular distribution, cellular uptake, charge and clearance.

Exemplary moieties that can be attached to a herein described active agent include, but are not limited to, intercalators, reporter molecules, polyamines, polyamides, polyethylene glycols, thiocthers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, dyes, lipid moieties such as a cholesterol moiety (Letsinger et al., Proc. Natl. Acad. Sci. USA, 1989, 86, 6553); cholic acid (Manoharan et al, Bioorg. Med. Chem. Lett., 1994, 4, 1053); a thioether, e.g., hexyl-S-tritylthiol (Manoharan et al, Ann. NY. Acad. Sci., 1992, 660, 306; Manoharan et al, Bioorg. Med. Chem. Let., 1993, 3, 2765); a thiocholesterol (Oberhauser et al., Nucl. Acids Res., 1992, 20, 533); an aliphatic chain, e.g., dodecandiol or undecyl residues (Saison-Behmoaras et al, EMBO J., 1991, 10, 111; Kabanov et al, FEBS Lett., 1990, 259, 327; Svinarchuk et al, Biochimie, 1993, 75, 49); a phospholipid, e.g., di-hexadecyl-rac-glycerol or triethylammonium-1,2-di-O-hexadecyl-rac-glycero-3-H-phosphonate (Manoharan et al, Tetrahedron Lett., 1995, 36, 3651; Shea et al, Nucl. Acids Res., 1990, 18, 3777); a polyamine or a polyethylene glycol chain (Manoharan et al., Nucleosides & Nucleotides, 1995, 14, 969); adamantane acetic acid (Manoharan et al., Tetrahedron Lett., 1995, 36, 3651); a palmityl moiety (Mishra et al, Biochim. Biophys. Acta, 1995, 1264, 229); or an octadecylamine or hexylamino-carbonyl-oxycholesterol moiety (Crooke et al, J. Pharmacol. Exp. Ther., 1996, 277, 923), all references incorporated herein in their entirety. Targeting moieties may include naturally occurring molecules, or recombinant or synthetic molecules, including, but not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG, e.g., PEG-2K, PEG-5K, PEG-10K, PEG-12K, PEG-15K, PEG-20K, PEG-40K), MPEG, [MPEG]2, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acri dines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g, steroids, bile acids, cholesterol, cholic acid, adamantane acetic acid, 1-pyrene butyric acid, dihydrotestosterone, 1,3-Bis-0(hexadecyl) glycerol, geranyloxyhexyl group, hexadecylglycerol, borneol, menthol, 1,3-propanediol, heptadecyl group, palmitic acid, myristic acid,03-(oleoyl) lithocholic acid, 03-(oleoyl) cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent (e.g., a.helical cell-permeation agent), peptide and peptidomimetic ligands, including those having naturally occurring or modified peptides, e.g., D or L peptides; a, B, or y peptides; N-methyl peptides; azapeptides; peptides having one or more amide, i.e., peptide, linkages replaced with one or more urea, thiourea, carbamate, or sulfonyl urea linkages; or cyclic peptides; amphipathic peptides including, but not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, H2A peptides, *Xenopus* peptides, esculentinis-1, and caerins. A peptidomimetic (also referred to herein as an oligopeptidomimetic) is a molecule capable of folding into a defined three-dimensional structure similar to a natural peptide. The peptide or peptidomimetic ligand or moiety can be about 5-50 amino acids long, e.g., about 5, 10, 15, 20, 25, 30, 35, 40, 45, or 50 amino acids long. In some embodiments, the targeting moiety may be other peptides such as somatostatin, octeotide, LHRH (luteinizing hormone releasing hormone), epidermal growth factor receptor (EGFR) binding peptide, aptide or bipodal peptide, RGD-containing peptides, a protein scaffold such as a fibronectin domain, a single domain antibody, a stable scFv, or other homing peptides. As non-limiting examples, a protein or peptide based targeting moiety may be a protein such as thrombospondin, tumor necrosis factors (TNF), annexin V, an interferon, angiostatin, endostatin, cytokine, transferrin, GM-CSF (granulocyte-macrophage colony-stimulating factor), or growth factors such as vascular endothelial growth factor (VEGF), hepatocyte growth factor (HGF), (platelet-derived growth factor (PDGF), basic fibroblast growth factor (bFGF), and epidermal growth factor (EGF). In some embodiments, the targeting moiety maybe an antibody, an antibody fragment, RGD peptide, folic acid or prostate specific membrane antigen (PSMA). In some embodiments, the protein scaffold may be an antibody-derived protein scaffold. Non-limiting examples include single domain antibody (dAbs), nanobody, single-chain variable fragment (scFv), antigen-binding fragment (Fab), Avibody, minibody, CH2D domain, Fcab, and bispecific T-cell engager (BiTE) molecules. In some embodiments, scFv is a stable scFv, wherein the scFv has hyperstable properties. In some embodiments, the nanobody may be derived from the single variable domain (VHH) of camelidae antibody.

In some embodiments, a targeting moiety recognizes or binds a target cell, a marker, or a molecule that is present exclusively or predominantly on the surface of particular cells. For example, a targeting moiety may bind a tumor antigen and direct the activating agent, e.g. a guide RNA-Cas complex to a malignant cell. In some embodiments, the targeting moiety recognizes an intra-cellular protein. In some embodiments, a targeting moiety directs a conjugate to specific tissues, cells, or locations in a cell (for e.g. trivalent N-acetylgalactosamine targets asialoglycoprotein receptor (ASGPR) on the surface of hepatocytes in mammals; Nair et el. J. Am. Chem. Soc. 2014, 136, 16958, see also U.S. Ser. No. 17/192,709). The targeting moiety can direct the conjugate in culture or in a whole organism, or both. In each case, the targeting moiety may bind to a receptor that is present on the surface of or within the targeted cell(s), wherein the targeting moiety binds to the receptor with an effective specificity, affinity and avidity. In other embodiments the targeting moiety targets the conjugate to a specific tissue such as the liver, kidney, lung or pancreas. In other cases, targeting moieties can direct the conjugate to cells of the reticular endothelial or lymphatic system, or to professional phagocytic cells such as macrophages or eosinophils. In some embodiments, the targeting moiety may recognize a RTK receptor, an EGF receptor, a serine or threonine kinase, G-protein coupled receptor, methyl CpG binding protein, cell surface glycoprotein, cancer stem cell antigen or marker, carbonic anhydrase, cytolytic T lymphocyte antigen, DNA methyltransferase, an ectoenzyme, a glycosylphosphatidylinositol-anchored co-receptor, a glypican-related integral membrane proteoglycan, a heat shock protein, a hypoxia induced protein, a multi drug resistant transporter, a Tumor-associated macrophage marker, a tumor associated carbohydrate antigen, a TNF receptor family member, a transmembrane protein, a tumor necrosis factor receptor superfamily member, a tumour differentiation antigen, a zinc dependent metallo-exopeptidase, a zinc transporter, a sodium-dependent transmembrane transport protein, a member of the SIGLEC family of lectins, or a matrix metalloproteinase.

Targeting moieties can be conjugated to nucleobases, sugar moieties, or internucleosidic linkages of a nucleic acid, e.g. a guide RNA or mRNA. Conjugation to purine nucleobases or derivatives thereof can occur at any position including, endocyclic and exocyclic atoms. In some embodiments, the 2-, 6-, 7-, or 8-positions of a purine nucleobase are attached to a moiety. Conjugation to pyrimidine nucleobases or derivatives thereof can also occur at any position. In some embodiments, the 2-, 5-, and 6-positions of a pyrimidine nucleobase can be substituted with a moiety. When a moiety is conjugated to a nucleobase, the preferred position is one that does not interfere with hybridization, i.e., does not interfere with the hydrogen bonding interactions needed for base pairing.

Conjugation to sugar moieties of nucleosides can occur at any carbon atom. Example carbon atoms of a sugar moiety that can be attached to a conjugate moiety include the 2', 3', and 5' carbon atoms. The gamma-position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligonucleotides. Generally, an oligonucleotide is attached to a conjugate moiety by contacting a reactive group (e.g., OH, SH, amine, carboxyl, aldehyde, and the like) on the oligonucleotide with a reactive group on the conjugate moiety. In some embodiments, one reactive group is electrophilic and the other is nucleophilic. For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

A targeting moiety can be attached to an active agent or therapeutic nucleic acid described herein, such as a guide RNA, via RNA-RNA or RNA-DNA base pairing and hybridization. Not intended to be bound by any theories, a targeting moiety can comprise a coupling sequence that is capable of recognizing or binding an active agent, e.g., a guide RNA or a mRNA. In some embodiments, a targeting moiety comprises a coupling sequence capable of hybridizing to a 5' portion, a 3' portion, or a middle portion of a guide RNA. A guide RNA that hybridizes with a coupling sequence may comprise an extension. For example, the coupling sequence may be able to hybridize with the extension sequence of the guide RNA, thereby directing the guide RNA to desired in vivo, ex vivo, intercellular or intracellular locations, while the guide RNA functionality such as interaction with CRISPR enzyme or binding with target sequence(s) is not affected. In some embodiments, the guide RNA comprises an extension that includes a polynucleotide tail. In some embodiments, the guide nucleic acid comprises a poly(A) tail, a poly(U) tail, or a poly(T) tail capable of hybridizing with a poly(U) tail, a poly(A) tail, or a poly(A) tail of the coupling sequence respectively. In some embodiments, the guide nucleic acid may be a guide RNA that comprises the sequence of (A)n or (U)n. In some embodiments, the guide nucleic acid may comprise DNA and may comprise the sequence of (A)n or (T)n. In some embodiments, the coupling sequence may comprise the sequence of (A)n, (U)n or (T)n. As instantly used, n may be any integer between 1 and 200.

A coupling sequence may share sequence identity or complementarity with a nucleic acid active agent, or a portion thereof. In some embodiments, a coupling sequence may share at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% of identity with a guide RNA described herein, or a portion of such guide RNA. In some embodiments, a coupling sequence may share at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% of identity with the complementary sequence of a guide RNA described herein, or the complementary of a portion of such guide RNA. In some embodiments, the coupling sequence may comprise identity or complementarity with at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, or at least 100 contiguous nucleobases of the guide RNA or a complementary thereof.

In some embodiments, a targeting moiety may comprise or be associated with a coupling sequence that is chemically modified. In some embodiments, the coupling sequence comprises an extension that hybridizes with a therapeutic nucleic acid, e.g. a guide RNA, or a portion thereof. In some embodiments, the extension of the coupling sequence may be chemically modified. In some embodiments, the therapeutic nucleic acid, e.g. a guide RNA, may comprise an extension. In some embodiments, the extension of the guide RNA may be chemically modified.

A targeting moiety can be attached to a nucleic acid described herein via a carrier. The carriers may include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier monomer into the backbone, e.g., the phosphate, or modified phosphate, e.g., sulfur containing, backbone, of an oligonucleotide. A "tethering attachment point" (TAP) in refers to an atom of the carrier monomer, e.g., a carbon atom or a heteroatom (distinct from an atom which provides a backbone attachment point), that connects a selected moiety. The selected moiety can be, e.g., a carbohydrate, e.g. monosaccharide, disaccharide, trisaccharide, tetrasaccharide, oligosaccharide and polysaccharide. Optionally, the selected moiety is connected by an intervening tether to the carrier monomer. Thus, the carrier will often include a functional group, e.g., an amino group, or generally, provide a bond, that is suitable for incorporation or tethering of another chemical entity, e.g., a ligand to the constituent atom. Representative U.S. patents that teach the preparation of conjugates of nucleic acids include, but are not limited to, U.S. Pat. Nos. 4,828,979; 4,948,882;

5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,149,782; 5,214,136; 5,245,022; 5,254, 469; 5,258,506; 5,262,536; 5,272,250; 5,292,873; 5,317,098; 5,371,241, 5,391,723; 5,416,203, 5,451,463; 5,510, 475; 5,512,667; 5,514,785; 5,565,552; 5,567,810; 5,574, 142; 5,585,481; 5,587,371; 5,595,726; 5,597,696; 5,599, 923; 5,599,928; 5,672,662; 5,688,941; 5,714,166; 6,153, 737; 6,172,208; 6,300,319; 6,335,434; 6,335,437; 6,395, 437; 6,444,806; 6,486,308; 6,525,031; 6,528,631; 6,559, 279; contents of which are herein incorporated in their entireties by reference.

A targeting moiety can be attached to an active agent, c. g. a guide RNA, via a linker. A linker may be bound to one or more active agents and a targeting moiety ligand to form a conjugate, wherein the conjugate releases at least one active agent, e.g. a guide RNA or guide RNA-Cas complex, upon delivery to a target cell. The linker may be attached to the targeting moiety and the active agent by functional groups independently selected from an ester bond, disulfide, amide, acylhydrazone, ether, carbamate, carbonate, and urea. Alternatively the linker can be attached to either the targeting moiety or the active agent by a non-cleavable group such as provided by the conjugation between a thiol and a maleimide, an azide and an alkyne. In some embodiments, a targeting moiety comprises one or more linkers. In some embodiments, one or more linkers as described herein connect a portion of the targeting moiety to a different portion of the targeting moiety.

The linkers can each independently comprises one or more functional groups selected from the group consisting of ethylene glycol, propylene glycol, amide, ester, ether, alkyl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, wherein each of the carboxyl, carbamoyl, ether, alkoxy, aryloxy, amino, amide, carbamate, alkyl, alkenyl, alkynyl, aryl, arylalkyl, cycloalkyl, heteroaryl, or heterocyclyl is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl. In some embodiments, a linker independently comprises phosphate, phosphorothioate, amide, ether, oxime, hydrazine or carbamate.

In some embodiments, the linker can independently comprise a $C_1$-$C_{10}$ straight chain alkyl, $C_1$-$C_{10}$ straight chain O-alkyl, $C_1$-$C_{10}$ straight chain substituted alkyl, $C_1$-$C_{10}$ straight chain substituted O-alkyl, $C_4$-$C_{13}$ branched chain alkyl, $C_4$-$C_{13}$ branched chain O-alkyl, $C_2$-$C_{12}$ straight chain alkenyl, $C_2$-$C_{12}$ straight chain O-alkenyl, aralkyl, $C_3$-$C_{12}$ straight chain substituted alkenyl, $C_3$-$C_{12}$ straight chain substituted O-alkenyl, polyethylene glycol, polylactic acid, polyglycolic acid, poly(lactide-co-glycolide), polycarprolactone, polycyanoacrylate, ketone, aryl, heterocyclic, succinic ester, amino acid, aromatic group, ether, crown ether, urea, thiourea, amide, purine, pyrimidine, bypiridine, indole derivative acting as a cross linker, chelator, aldehyde, ketone, bisamine, bis alcohol, heterocyclic ring structure, azirine, disulfide, thioether, hydrazone and combinations thereof. For example, the linker can be a C3 straight chain alkyl or a ketone. The alkyl chain of the linker can be substituted with one or more substituents or heteroatoms. In some embodiments, the alkyl chain of the linker may optionally be interrupted by one or more atoms or groups selected from —O—, —C(═O)—, —NR, —O—C(═O)—NR—, —S—, —S—S—.

In some embodiments, the linker may be cleavable and is cleaved to release the active agent. The cleavable functionality may be hydrolyzed in vivo or may be designed to be hydrolyzed enzymatically, for example by Cathepsin B. A "cleavable" linker, as used herein, refers to any linker which can be cleaved physically or chemically. Examples for physical cleavage may be cleavage by light, radioactive emission or heat, while examples for chemical cleavage include cleavage by re-dox-reactions, hydrolysis, pH-dependent cleavage.

Linkers may comprise a direct bond or an atom such as oxygen or sulfur, a unit such as $NR^1$, C(O), C(O)NH, SO, SO2, SO2NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), SO2, N(R'), C(O), substituted or unsubstituted aryl, substituted or unsubstituted heteroaryl, substituted or unsubstituted heterocyclic; where R' is hydrogen, acyl, aliphatic or substituted aliphatic. In one embodiment, the linker is between 1-24 atoms, preferably 4-24 atoms, preferably 6-18 atoms, more preferably 8-18 atoms, and most preferably 8-16 atoms.

In one embodiment, the linker comprises at least one cleavable linking group. In certain embodiments, the linker is a branched linker. The branchpoint of the branched linker may be at least trivalent, but may be a tetravalent, pentavalent or hexavalent atom, or a group presenting such multiple valencies. In certain embodiments, the branchpoint is, —N, —N(O)—C, —O—C, —S—C, —SS—C, —C(O)N(O)—C, —OC(O)N(O)—C, —N(O)C(O)C, or —N(O)C(O)O—C; wherein Q is independently for each occurrence H or optionally substituted alkyl. In other embodiment, the branchpoint is glycerol or glycerol derivative.

In one embodiment, a linker may be cleaved by an enzyme. As a non-limiting example, the linker may be a polypeptide moiety, e.g. AA in WO2010093395 to Govindan, the content of which is incorporated herein by reference in its entirety; that is cleavable by intracellular peptidase. Govindan teaches AA in the linker may be a di, tri, or tetrapeptide such as Ala-Leu, Leu-Ala-Leu, and Ala-Leu-Ala-Leu. In another example, the cleavable linker may be a branched peptide. The branched peptide linker may comprise two or more amino acid moieties that provide an enzyme cleavage site. Any branched peptide linker disclosed in WO 1998019705 to Dubowchik, the content of which is incorporated herein by reference in its entirety, may be used as a linker in the conjugate of the present disclosure. As another example, the linker may comprise a lysosomally cleavable polypeptide disclosed in U.S. Pat. No. 8,877,901 to Govindan et al., the content of which is incorporated herein by reference in its entirety. As another example, the linker may comprise a protein peptide sequence which is selectively enzymatically cleavable by tumor associated proteases, such as any Y and Z structures disclosed in U.S. Pat. No. 6,214,345 to Firestone et al, the content of which is incorporated herein by reference in its entirety.

In some embodiments, a linker may comprise a cleavable linking group. A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum). Cleavable linking groups may be susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular RNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

In some embodiments, a linker may comprise a phosphate based cleavable linking group. Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups (i.e., phosphorus-containing linkages or phosphorus-containing linkers) are —P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. In some embodiments, phosphate-based linking groups are —O—P(O)(OH)—O—, —O—P(S)(OH)O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—S—. In some embodiments, a phosphate-based linker is —O—P(O)(OH)O—.

In some embodiments, a linker may comprise an acid cleavable linking group. Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O) O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

In some embodiments, a linker may comprise a ester based linking group. Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

In some embodiments, a linker may comprise a peptide based linking group. Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

In some embodiments, the MA004 mRNA comprises a mRNA sequence of Seq. ID. 0001 (Table 5). In some embodiments, the degree of similarity between a sequence of MA004 mRNA and another sequence may be at least 50% identical, 55% identical, 60% identical, 65% identical, 70% identical, 75% identical, 80% identical, 85% identical, 90% identical, 95% identical, 97% identical, 98% identical, 99% identical, or 100% identical. As used in Table 5, uppercase nucleotides, A, G, and C, indicate ribonucleotides adenine, guanine, and cytosine, respectively. As used in Table 5, lowercase u' indicates N1-methylpseudouridine.

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The Smith Waterman algorithm can also be used to determine percent identity. Exemplary parameters for amino acid sequence comparison include the following: 1) algorithm from Needleman and Wunsch (J. Mol. Biol., 48:443-453 (1970)); 2) BLOSSUM62 comparison matrix from Hentikoff and Hentikoff (Proc. Nat. Acad. Sci. USA., 89:10915-10919 (1992)) 3) gap penalty=12; and 4) gap length penalty=4. A program useful with these parameters can be publicly available as the "gap" program (Genetics Computer Group, Madison, Wis.). The aforementioned parameters are the default parameters for polypeptide comparisons (with no penalty for end gaps). Alternatively, polypeptide sequence identity can be calculated using the following equation: % identity–(the number of identical residues)/(alignment length in amino acid residues)*100. For this calculation, alignment length includes internal gaps but does not include terminal gaps.

TABLE 5

MA004 mRNA sequences

| Region | Sequence | SEQ ID NO |
|---|---|---|
| Full mRNA sequence | AGGAAAu'AAGAGAGAAAAGAAGAGu'AAGAAGAAAu'<br>Au'AAGAGCCACCAu'GAGCGAGGu'GGAGu'u'CAGCCA<br>CGAGu'ACu'GGAu'GCGGCACGCCCu'GACCCu'GGCCAA<br>GCGGGCCCGGGACGAGCGGGAGGu'GCCCGu'GGGCGC<br>CGu'GCu'GGu'GCu'GAACAACCGGGu'GAu'CGGCGAGG<br>GCu'GGAACCGGGCCAu'CGGCCu'GCACGACCCCACCG<br>CCCACGCCGAGAu'CAu'GGCCCu'GCGGCAGGGCGGCCu<br>'GGu'GAu'GCAGAACu'ACCGGCu'GAu'CGACGCCACCCu<br>'Gu'ACGu'GACCu'u'CGAGCCCu'GCGu'GAu'Gu'GCGCCG<br>GCGCCAu'GAu'CCACAGCCGGAu'CGGCCGGGu'GGu'Gu<br>'u'CGGCGu'GCGGAACGCCAAGACCGGCGCCGCCGGCA<br>GCCu'GAu'GGACGu'GCu'GCACCACCCCGGCAu'GAACC<br>ACCGGGu'GGAGAu'CACCGAGGGCAu'CCu'GGCCGACG<br>AGu'GCGCCGCCCu'GCu'Gu'GCCGGu'u'Cu'u'CCGGAu'G<br>CCCCGGCGGGu'Gu'u'CAACGCCCAGAAGAAGGCCCAG<br>AGCAGCACCGACAGCGGCGGCAGCAGCGGCGGCAGCA<br>GCGGCAGCGAGACACCCGGCACCAGCGAGAGCGCCAC<br>CCCCGAGAGCAGCGGCGGCAGCAGCGGCGGCAGCGAC<br>AAGAAGu'ACAGCAu'CGGCCu'GGCCAu'CGGCACCAAC<br>AGCGu'GGGCu'GGGCCGu'GAu'CACCGACGAGu'ACAA<br>GGu'GCCCAGCAAGAAGu'u'CAAGGu'GCu'GGGCAACA<br>CCGACCGGCACAGCAu'CAAGAAGAACCu'GAu'CGGCG<br>CCCu'GCu'Gu'u'CGACAGCGGCGAGACAGCCGAGGCCA<br>CCCGGCu'GAAGCGGACCGCCCGGCGGCGGu'ACACCC<br>GGCGGAAGAACCGGAu'Cu'GCu'ACCu'GCAGGAGAu'Cu<br>'u'CAGCAACGAGAu'GGCCAAGGu'GGACGACAGCu'u'C<br>u'u'CCACCGGCu'GGAGGAGAGCu'u'CCu'GGu'GGAGGA<br>GGACAAGAAGCACGAGCGGCACCCCAu'Cu'u'CGGCAA | 0001 |

TABLE 5-continued

MA004 mRNA sequences

| Region | Sequence | SEQ ID NO |
| --- | --- | --- |
| | CAu'CGu'GGACGAGGu'GGCCu'ACCACGAGAAGu'ACCC | |
| | CACCAu'Cu'ACCACCu'GCGGAAGAAGCu'GGu'GGACAG | |
| | CACCGACAAGGCCGACCu'GCGGCu'GAu'Cu'ACCu'GGC | |
| | CCu'GGCCCACAu'GAu'CAAGu'u'CCGGGGCCACu'u'CCu | |
| | 'GAu'CGAGGGCGACCu'GAACCCCGACAACAGCGACGu | |
| | GGACAAGCu'Gu'u'CAu'CCAGCu'GGu'GCAGACCu'ACA | |
| | ACCAGCu'Gu'u'CGAGGAGAACCCCAu'CAACGCCAGCG | |
| | GCGu'GGACGCCAAGGCCAu'CCu'GAGCGCCCGGCu'GA | |
| | GCAAGAGCCGGCGGCu'GGAGAACCu'GAu'CGCCCAGC | |
| | u'GCCCGGCGAGAAGAAGAACGGCCu'Gu'u'CGGCAACC | |
| | u'GAu'CGCCCu'GAGCCu'GGGCCu'GACCCCCAACu'u'CA | |
| | AGAGCAACu'u'CGACCu'GGCCGAGGACGCCAAGCu'GC | |
| | AGCu'GAGCAAGGACACCu'ACGACGACGACCu'GGACA | |
| | ACCu'GCu'GGCCCAGAu'CGGCGACCAGu'ACGCCGACC | |
| | u'Gu'u'CCu'GGCCGCCAAGAACCu'GAGCGACGCCAu'CC | |
| | u'GCu'GAGCGACAu'CCu'GCGGGu'GAACACCGAGAu'C | |
| | ACCAAGGCCCCCCu'GAGCGCCAGCAu'GAu'CAAGCGG | |
| | u'ACGACGAGCACCACCAGGACCu'GACCCu'GCu'GAAG | |
| | GCCCu'GGu'GCGGCAGCAGCu'GCCCGAGAAGu'ACAAG | |
| | GAGAU'Cu'uCu'u'CGACCAGAGCAAGAACGGCu'ACGC | |
| | CGGCu'ACAu'CGACGGCGGCGCCAGCCAGGAGGAGu'u' | |
| | Cu'ACAAGu'u'CAu'CAAGCCCAu'CCu'GGAGAAGAu'GG | |
| | ACGGCACCGAGGAGCu'GCu'GGu'GAAGCu'GAACCGGG | |
| | AGGACCUGCuGCGGAAGCAGCGGACCU'uCGACAACG | |
| | GCAGCAu'CCCCCACCAGAu'CCACCu'GGGCGAGCu'GC | |
| | ACGCCAu'CCu'GCGGCGGCAGGAGGACu'u'Cu'ACCCCu' | |
| | u'CCu'GAAGGACAACCGGGAGAAGAu'CGAGAAGAu'CC | |
| | u'GACCu'u'CCGGAu'CCCCu'ACu'ACGu'GGGCCCCCu'G | |
| | GCCCGGGGCAACAGCCGGu'u'CGCCu'GGAu'GACCCGC | |
| | AAGAGCGAGGAGACAAu'CACCCCCu'GGAACu'u'CGAG | |
| | GAGGu'GGu'GGACAAGGGCGCCAGCGCCCAGAGCu'u'C | |
| | Au'CGAGCGGAu'GACCAACu'u'CGACAAGAACCU'GCCC | |
| | AACGAGAAGGu'GCu'GCCCAAGCACAGCCu'GCu'Gu'AC | |
| | GAGu'ACu'u'CACCGu'Gu'ACAACGAGCu'GACCAAGGu' | |
| | GAAGu'ACGu'GACCGAGGGCAu'GCGGAAGCCCGCCu'u' | |
| | CCu'GAGCGGCGAGCAGAAGAAGGCCAu'CGu'GGACCu' | |
| | GCu'Gu'u'CAAGACCAACCGGAAGGu'GACCGu'GAAGC | |
| | AGCu'GAAGGAGGACu'ACu'u'CAAGAAGAu'CGAGu'GC | |
| | u'u'CGACAGCGu'GGAGAu'CAGCGGCGu'GGAGGACCG | |
| | Gu'u'CAACGCCAGCCu'GGGCACCu'ACCACGACCu'GCu' | |
| | GAAGAu'CAu'CAAGGACAAGGACu'u'CCu'GGACAACG | |
| | AGGAGAACGAGGACAu'CCu'GGAGGACAu'CGu'GCu'G | |
| | ACCCu'GACCCu'Gu'u'CGAGGACCGGGAGAu'GAu'CGA | |
| | GGAGCGGCu'GAAGACCu'ACGCCCACCu'Gu'u'CGACGA | |
| | CAAGGu'GAu'GAAGCAGCu'GAAGCGGCGGCGGu'ACAC | |
| | CGGCu'GGGGCCGGCu'GAGCCGGAAGCu'GAu'CAACGG | |
| | CAu'CCGGGACAAGCAGAGCGGCAAGACCAu'CCu'GGA | |
| | Cu'u'CCu'CAAGAGCGACGGCu'u'CGCCAACCGGAACu'u | |
| | 'CAu'GCAGCu'GAu'CCACGACGACAGCCu'GACCu'u'CA | |
| | AGGAGGACAu'CCAGAAGGCCCAGGu'GAGCGGCCAGG | |
| | GCGACAGCCu'GCACGAGCACAu'CGCCAACCu'GGCCG | |
| | GCAGCCCCGCCAu'CAAGAAGGGCAu'CCu'GCAGACCG | |
| | u'GAAGGu'GGu'GGACGAGCu'GGu'GAAGGu'GAu'GGGC | |
| | CGGCACAAGCCCGAGAACAu'CGu'GAu'CGAGAu'GGCC | |
| | CGGGAGAACCAGACCACCCAGAAGGGCCAGAAGAAC | |
| | AGCCGGGAGCGGAu'GAAGCGGAu'CGAGGAGGGCAu'C | |
| | AAGGAGCu'GGGCAGCCAGAu'CCu'GAAGGAGCACCCC | |
| | Gu'GGAGAACACCCAGCu'GCAGAACGAGAAGCuGu'AC | |
| | Cu'Gu'ACu'ACCu'GCAGAACGGCCGGGACAu'Gu'ACGu' | |
| | GGACCAGGAGCu'GGACAu'CAACCGGCu'GAGCGACu'A | |
| | CGACGu'GGACCACAu'CGu'GCCCCAGAGCu'u'CCu'GAA | |
| | GGACGACAGCAu'CGACAACAAGGu'GCu'GACCCGGAG | |
| | CGACAAGAACCGGGGCAAGAGCGACAACGu'GCCCAG | |
| | CGAGGAGGu'GGu'GAAGAAGAu'GAAGAACu'ACu'GGC | |
| | GGCAGCu'GCu'GAACGCCAAGCu'GAu'CACCCAGCGGA | |
| | AGu'u'CGACAACCu'GACCAAGGCCGAGCGGGGCGGCC | |
| | u'GAGCGAGCu'GGACAAGGCCGGCu'u'CAu'CAAGCGGC | |
| | AGCu'GGu'GGAGACACGGCAGAu'CACCAAGCACGu'GG | |
| | CCCAGAu'CCu'GGACAGCCGGAu'GAACACCAAGu'ACG | |
| | ACGAGAACGACAAGCu'GAu'CCGGGAGGu'GAAGGu'G | |
| | Au'CACCCu'CAAGAGCAAGCu'GGu'GAGCGACu'u'CCG | |
| | GAAGGACu'u'CCAGu'u'Cu'ACAAGGu'GCGGGAGAu'CA | |
| | ACAACu'ACCACCACGCCCACGACGCCu'ACCu'GAACG | |
| | CCGu'GGu'GGGCACCGCCCu'GAu'CAAGAAGu'ACCCCA | |
| | AGCu'GGAGAGCGAGu'u'CGu'Gu'ACGGCGACu'ACAAG | |

TABLE 5-continued

| MA004 mRNA sequences | | |
|---|---|---|
| Region | Sequence | SEQ ID NO |
| | Gu'Gu'ACGACGu'GCGGAAGAu'GAu'CGCCAAGAGCGA | |
| | GCAGGAGAu'CGGCAAGGCCACCGCCAAGu'ACu'u'Cu'u | |
| | 'Cu'ACAGCAACAu'CAu'GAACu'u'Cu'u'CAAGACCGAGA | |
| | uCACCCu'GGCCAACGGCGAGAu'CCGGAAGCGGCCCCu | |
| | 'GAU'CGAGACAAACGGCGAGACAGGCGAGAu'CGu'Gu' | |
| | GGGACAAGGGCCGGGACu'u'CGCCACCGu'GCGGAAGG | |
| | u'GCu'GAGCAu'GCCCCAGGu'GAACAu'CGu'GAAGAAG | |
| | ACCGAGGu'GCAGACCGGCGGCu'u'CAGCAAGGAGAGC | |
| | Au'CCu'GCCCAAGCGGAACAGCGACAAGCu'GAu'CGCC | |
| | CGGAAGAAGGACu'GGGACCCCAAGAAGL'ACGGCGGC | |
| | u'u'CGACAGCCCCACCGu'GGCCu'ACAGCGu'GCu'GGu' | |
| | GGu'GGCCAAGGu'GGAGAAGGGCAAGAGCAAGAAGCu | |
| | 'CAAGAGCGu'GAAGGAGCu'GCu'GGGCAu'CACCAu'CA | |
| | u'GGAGCGGAGCAGCu'u'CGAGAAGAACCCCAu'CGACu' | |
| | u'CCu'GGAGGCCAAGGGCu'ACAAGGAGGu'GAAGAAG | |
| | GACCu'GAu'CAu'CAAGCu'GCCCAAGu'ACAGCCu'Gu'u' | |
| | CGAGCu'GGAGAACGGCCGGAAGCGGAu'GCu'GGCCAG | |
| | CGCCGGCGAGCu'GCAGAAGGGCAACGAGCu'GGCCCu' | |
| | GCCCAGCAAGu'ACGu'GAACu'u'CCu'Gu'ACCu'GGCCA | |
| | GCCACu'ACGAGAAGCu'GAAGGGCAGCCCCGAGGACA | |
| | ACGAGCAGAAGCAGCu'Gu'u'CGu'GGAGCAGCACAAGC | |
| | ACu'ACCu'GGACGAGAu'CAu'CGAGCAGAu'CAGCGAGu | |
| | 'u'CAGCAAGCGGGu'GAu'CCu'GGCCGACGCCAACCu'G | |
| | GACAAGGu'GCu'GAGCGCCu'ACAACAAGCACCGGGAC | |
| | AAGCCCAu'CCGGGAGCAGGCCGAGAACAu'CAu'CCAC | |
| | Cu'Gu'u'CACCCu'GACCAACCu'GGGCGCCCCCGCCGCCu | |
| | 'u'CAAGu'ACu'u'CGACACCACCAu'CGACCGGAAGCGGu | |
| | 'ACACCAGCACCAAGGAGGu'GCu'GGACGCCACCCu'GA | |
| | u'CCACCAGAGCAu'CACCGGCCu'Gu'ACGAGACACGGA | |
| | u'CGACCu'GAGCCAGCu'GGGCGGCGACGAGGGCGCCG | |
| | ACAAGCGGACCGCCGACGGCAGCGAGu'u'CGAGAGCC | |
| | CCAAGAAGAAGCGGAAGGu'Gu'GAGCGGCCGCu'u'AAu | |
| | 'u'AAGCu'GCCu'u'Cu'GCGGGGCu'u'GCCu'u'Cu'GGCCAu | |
| | 'GCCCu'u'Cu'u'Cu'Cu'CCCu'u'GCACCu'Gu'ACCu'Cu'u'G | |
| | Gu'Cu'u'u'GAAu'AAAGCCu'GAGu'AGGAAGu'Cu'AGA | |

Target Sequences

The present disclosure provides active agents or therapeutic agents, such as genome editing compositions, and methods and compositions for targeted delivery thereof. The therapeutic agents described herein may comprise genome editing composition directed to and modify, alter, or cleave a target sequence on a target nucleic acid molecule. For example, the active agent may comprise a nucleic acid or a nucleic acid-protein complex capable of effecting a modification to a target sequence.

The target sequence may be a DNA sequence or a RNA sequence. In some embodiments, the active agent or therapeutic agent may comprise a RNA interference factor. In some embodiments, the active agent may comprise a siRNA, shRNA, antisense oligonucleotide, microRNA, anti-microRNA or antimir, supermir, antagomir, ribozyme, triplex-forming oligonucleotide, decoy oligonucleotide, splice-switching oligonucleotide, immunostimulatory oligonucleotide, RNA activator, or a Ul adaptor. The active agent may recognize the target sequence and mediate cleavage and/or degradation of the target sequence. In some embodiments, the active or therapeutic agent may comprise a guide RNA. The guide RNA may be complexed with a nucleic acid guided programmable nuclease, such as a CRISPR enzyme, such as a Cas9, or a fusion protein thereof further comprising a functional domain. The target sequence may be recognized by the nucleic acid guided programmable nuclease domain. The target sequence may be cleaved by the nucleic acid guided programmable nuclease domain and/or modified by the functional domain, such as a deaminase domain, a methylase domain, a methyltransferase domain, an activation domain, a repressor domain, a nuclease domain, a transposase domain, or a recombinase domain. In some embodiments, a Cas9 protein may be directed by a guide RNA to a target sequence of a target nucleic acid molecule, where the guide RNA hybridizes with and the Cas protein cleaves the target sequence. In some embodiments, the target sequence may be complementary to the targeting sequence of the guide RNA. In some embodiments, the degree of complementarity between a targeting sequence of a guide RNA and its corresponding target sequence may be about 50%, 55%, 60%, 65%, 70%, 75%, 80%, 85%, 90%, 95%, 97%, 98%, 99%, or 100%. In some embodiments, the target sequence and the targeting sequence of the guide RNA may be 100% complementary. In other embodiments, the target sequence and the targeting sequence of the guide RNA may contain at least one mismatch. For example, the target sequence and the targeting sequence of the guide RNA may contain 1, 2, 3, 4, 5, 6, 7, 8, 9, or 10 mismatches. In some embodiments, the target sequence and the targeting sequence of the guide RNA may contain 1-6 mismatches. In some embodiments, the target sequence and the targeting sequence of the guide RNA may contain 5 or 6 mismatches.

The length of the target sequence may depend on the nuclease system used. For example, the target sequence for a CRISPR/Cas system may comprise 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the target sequence may comprise 18-24 nucleotides in length. In some embodiments, the target sequence may comprise 19-21 nucleotides in length. In some embodiments, the target sequence may comprise 20 nucleotides in length. When nickases are used, the target sequence may comprise a pair of target sequences recognized by a pair of nickases on opposite strands of the DNA molecule.

In some embodiments, the active or therapeutic agent may comprise a meganuclease system, the target sequence for a meganuclease may comprise 12-40 or more nucleotides in length. When ZFNs are used, the target sequence may comprise two half target sequences recognized by a pair of ZFNs on opposite strands of the DNA molecule, with an interconnecting sequence in between. In some embodiments, each half target sequence for ZFNs may independently comprise 9, 12, 15, 18, or more nucleotides in length. In some embodiments, the interconnecting sequence for ZFNs may comprise 4-20 nucleotides in length. In some embodiments, the interconnecting sequence for ZFNs may comprise 5-7 nucleotides in length.

When TALENs are used, the target sequence may similarly comprise two half target sequences recognized by a pair of TALENs on opposite strands of the DNA molecule, with an interconnecting sequence in between. In some embodiments, each half target sequence for TALENs may independently comprise 10-20 or more nucleotides in length. In some embodiments, the interconnecting sequence for TALENs may comprise 4-20 nucleotides in length. In some embodiments, the interconnecting sequence for TALENs may comprise 12-19 nucleotides in length.

In some embodiments, the target sequence may be adjacent to a protospacer adjacent motif (PAM), a short sequence recognized by a CRISPR/Cas complex. The protospacer adjacent motif, or PAM, is essential for target binding for CRISPR/Cas complexes. Typically, a PAM is a 2-6 base pair DNA sequence immediately following the DNA target sequence of the Cas nuclease. The PAM may be a 5' PAM or a 3' PAM. The exact sequence of PAM depends on the type of Cas protein. For example, a typical SpCas9 binding requires a 3'-NGG-5' PAM, also known as a canonical PAM, where the N is any one of A, G, C, or T. A SpCas9 with certain amino acid substitutions, e.g. D1135E, R1335Q, G1218R, and/or T1337R can recognize a NGA PAM or a NGCG PAM. A SaCas9 binding requires a 3'-NNGRRT-5' PAM. A SaCas9 with certain amino substitutions, e.g., K781E, K697N, H1014R, can recognize a NNNRRT PAM.

Figure 1B:
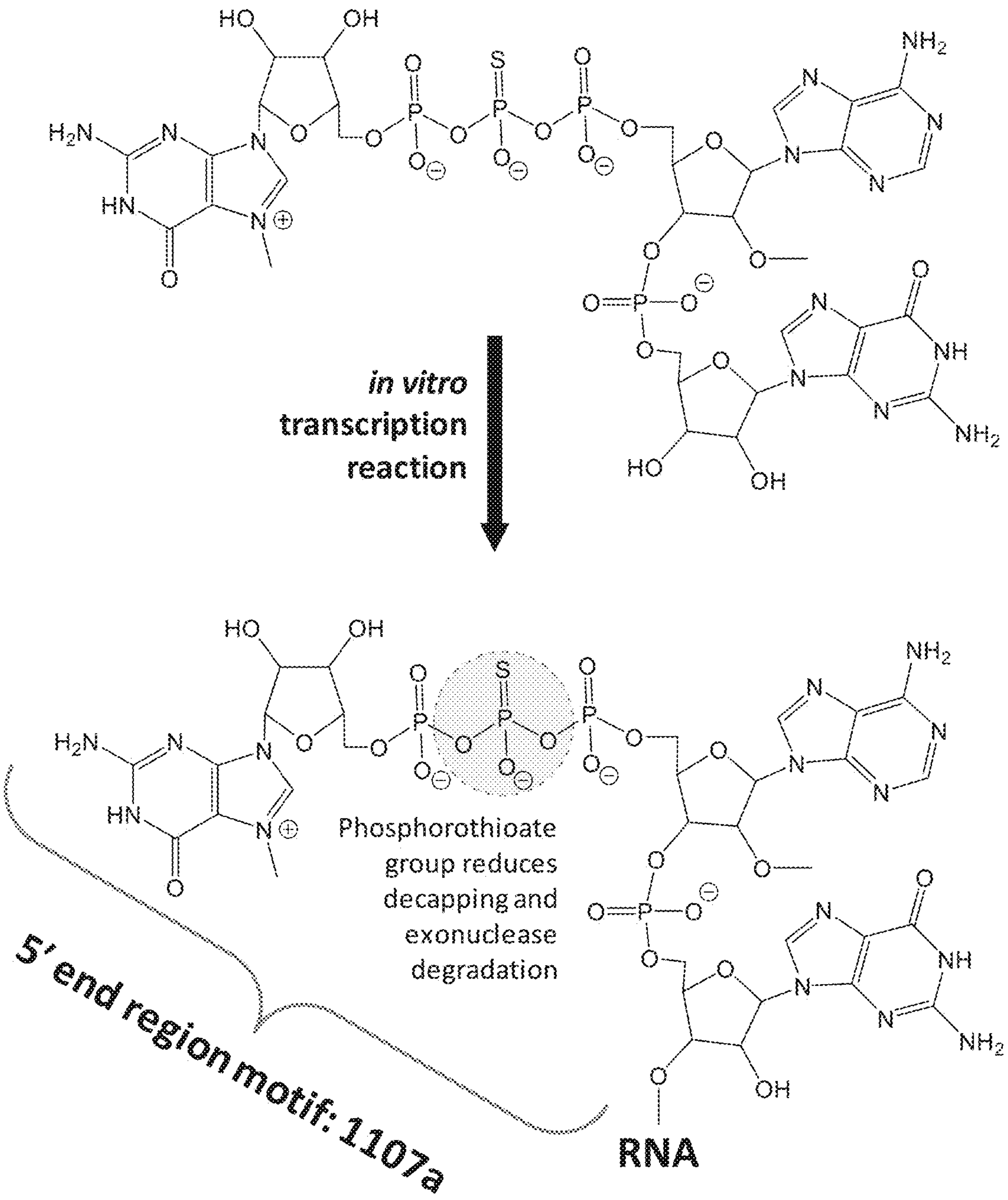

In some embodiments, the PAM may be adjacent to or within 1, 2, 3, or 4, nucleotides of the 3' end of the target sequence. The length and the sequence of the PAM may depend on the Cas9 protein used. For example, the PAM may be selected from a consensus or a particular PAM sequence for a specific Cas9 protein or Cas9 ortholog, including those disclosed in FIG. 1 of Ran et al., Nature, 520:186-191 (2015), which is incorporated herein by reference. In some embodiments, the PAM may comprise 2, 3, 4, 5, 6, 7, 8, 9, or 10 nucleotides in length. Non-limiting exemplary PAM sequences include NGG, NGGNG, NG, NAAAAN, NNAAAAW, NNNNACA, GNNNCNNA, and NNNNGATT (wherein N is defined as any nucleotide, and W is defined as either A or T). In some embodiments, the PAM sequence may be NGG. In some embodiments, the PAM sequence may be NGGNG. In some embodiments, the PAM sequence may be NNAAAAW. Additional evolved Cas variants and PAM sequences as described in Hu et al., Evolved Cas9 variants with broad PAM compatibility and high DNA specificity, Nature 2018 556 (7699): 57-63 is incorporated herein in its entirety.

The target nucleic acid molecule may be any DNA or RNA molecule that is endogenous or exogenous to a cell. As used herein, the term "endogenous sequence" refers to a sequence that is native to the cell. The term "exogenous sequence" refers to a sequence that is not native to a cell, or a sequence whose native location in the genome of the cell is in a different location. In some embodiments, the target nucleic acid molecule may be a plasmid, a genomic DNA, or a chromosome from a cell or in the cell. In some embodiments, the target sequence of the target nucleic acid molecule may be a genomic sequence from a cell or in the cell. In some embodiments, the cell may be a prokaryotic cell. In other embodiments, the cell may be a eukaryotic cell. In some embodiments, the eukaryotic cell may be a mammalian cell. In some embodiments, the eukaryotic cell may be a rodent cell. In some embodiments, the eukaryotic cell may be a human cell. In some embodiments, the eukaryotic cell may be a liver cell. In some embodiments, the eukaryotic cell may be a hepatocyte. In some embodiments, the eukaryotic cell may be a parenchymal cell, a sinusoidal endothelial cell, a phagocytic Kupffer cell, or a stellate cell. In further embodiments, the target sequence may be a viral sequence. In yet other embodiments, the target sequence may be a synthesized sequence. In some embodiments, the target sequence may be on a eukaryotic chromosome, such as a human chromosome.

In some embodiments, the target sequence may be located in a coding sequence of a gene, an intron sequence of a gene, a transcriptional control sequence of a gene, a translational control sequence of a gene, or a non-coding sequence between genes. In some embodiments, the gene may be a protein coding gene. In other embodiments, the gene may be a non-coding RNA gene. In some embodiments, the target sequence may comprise all or a portion of a disease-associated gene. In some embodiments, the target sequence may comprise all or a portion of a gene associated with a coronary disease. In some embodiments, the target sequence may comprise at least a portion of a gene encoding an apolipoprotein. In some embodiments, the target sequence may comprise at least a portion of a gene encoding Proprotein Convertase Subtilisin/Kexin Type 9 (PCSK9), Angiopoietin-like protein 3 (ANGPTL3), Apoliporotein C3 (APOC3), Apolipoprotein A (LPA), LDL Receptor (LDL-R), Myosin regulatory light chain interacting protein or inducible degrader of the LDL receptor (IDOL), Transthyretin (TTR), Antithrombin, AT3, Apolipoprotein B (ApoB), or Hup. The present disclosure also contemplates the use of modification to manipulate expression and activity of target genes, e.g., use of destabilizing mutations to counteract the effect of a gain-of-function PCSK9 variant.

The nucleic acid sequences of exemplary target genes and of other members of the family of human origin and those of a number of animals are publicly available, e.g., from the NCBI website or ENSEMBL website. Examples include, but are not limited to the following sequences: Wild Type PCSK9 Gene (NG_009061.1), *Homo sapiens* proprotein convertase subtilisin/kexin type 9 (PCSK9), RefSeqGene (LRG_275) on chromosome 1; human APOC3 Deposit No. NP_000031.1, GenBank Accession Nos.: NG 008949.1; Mouse, rat and monkey APOC3 nucleic acid sequences Ensembl accession number ENSMUSG00000032081, ENSRNOG00000047503, and ENSMFAG00000001837, respectively; human ANGPTL3 is provided, for example, in NG_028169.1; Mouse, rat, and monkey ANGPTL3 nucleic acid sequences Ensembl accession number ENSMUSG00000028553, ENSRNOG00000008638, and ENSMFAG00000007083, respectively; each of which sequences are incorporated herein its entirety.

In some embodiments, contacting a target sequences with the genome editing composition described herein leads to a base editing event within or adjacent to the target sequence. For example, a target base (e.g. a C base) within or adjacent to a target sequence may be converted to a T base as the result of contact with the genome editing composition as disclosed in the present disclosure comprising a fusion protein comprising a nucleic acid guided nuclease domain and a deaminase domain. In some embodiments, the target base is located upstream (5' end of) of the PAM. In some embodiments, the target base is located at a position 1, 2, 3, 4, 5, 6, 7, 8, 9, 10, 11, 12, 13, 14, 15, 16, 17, 18, 19, 20, 21, 22, 23, 24, 25, 26, 28, 29, 30, 31, 32, 33, 34, 35, 36, 37, 38, 39, 40, 41, 42, 43, 44, 45, 46, 47, 48, 49, or 50 base pairs upstream (5' end of) the PAM. In some embodiments, the target base is located at a position within 13 to 17 base pairs upstream (5' end) of the PAM. In some embodiments, the target base is located at a position outside of 13 to 17 base pairs upstream (5' end) of the PAM. In some embodiments, the target base pair is located at a position 10-15 base pairs upstream (5' end) of the PAM. In some embodiments, the target base is located at a position 11-12 base pairs upstream of the PAM. In some embodiments, the target base is 11 base pairs upstream (5' end) of the PAM. In some embodiments, the target base is located in the coding region (e.g., an exon) of the target sequence, e.g. the ANGPTL3 encoding polynucleotide (e.g., the ANGPTL3 gene locus). For example, conversion of a base in the coding region of the ANGPTL3 gene locus may result in an amino acid change in the ANGPTL3 protein sequence, i.e., a mutation. In some embodiments, the mutation is a loss of function mutation. In some embodiments, a mutation may introduce a pre-mature stop codon into the coding region the target sequence, e.g. coding region of the ANGPTL3 gene. In some embodiments, a loss-of-function mutation is a naturally occurring loss-of-function mutation. In some embodiments, the mutation is located in the coding region of the PCSK9 gene, e.g. a G106R, L253F, A443T, R93C, G24D, S47F, R46H, S 153N, or H193Y mutation. In some embodiments, the loss-of-function mutation introduces a pre-mature stop codon into the coding region of the ANGPTL3 gene. In some embodiments, a loss of function mutation may be introduced into the coding region of a APOC3 gene, e.g. a R19X mutation. In some embodiments, a loss of function mutation may be introduced into a Low-Density Lipoprotein Receptor (LDL-R) protein. In some embodiments, a loss of function mutation may be introduced into a Inducible Degrader of the LDL Receptor (IDOL) protein.

In some embodiments, a target sequence is located in a non-coding region of the target sequence, e.g., in an intron or a splicing site of a target gene. In some embodiments, a target sequence is located in a splicing site and the editing of such target base causes alternative splicing of the target gene mRNA. In some embodiments, the alternative splicing leads to leading to loss-of-function mutants. In some embodiments, the alternative splicing leads to introduction of a premature stop codon or a frameshift in the target mRNA, resulting in truncated, unstable, or folding-defective polypeptides. In some embodiments, stop codons may be introduced into the coding sequence of a apolipoprotein encoding gene upstream of the normal stop codon (referred to as a "premature stop codon"). In some embodiments, stop codons may be introduced into the coding region of the target gene. Premature stop codons cause premature translation termination, in turn resulting in truncated and non-functional proteins and induces rapid degradation of the mRNA via the non-sense mediated mRNA decay pathway. See, e.g., Baker et al., Current Opinion in Cell Biology 16 (3): 293-299, 2004; Chang et al, Annual Review of Biochemistry 76:51-74, 2007; and Behm-Ansmant et ah, Genes & Development 20 (4): 391-398, 2006, each of which is incorporated herein by reference. The genome editing composition described herein may be used to introduce multiple editing events to the target sequence. For example, the genome editing composition may comprise a nucleic acid guide programmable nuclease that induces double strand breaks, deletions, insertions, frameshift, reversions, or other alterations in the target gene. For example, the genome editing composition may comprise a nucleic acid guided programmable nuclease-deaminase fusion protein that can convert several amino acids to create a stop codon (e.g., TAA, TAG, or TGA).

In some embodiments, simultaneous introduction of mutations into more than one protein factors in the LDL-mediated cholesterol clearance pathway are provided. For example, in some embodiments, a mutation may be simultaneously introduced into one or more, preferably at least two, of ANGPTL3, PCSK9, LDLR, APOB, APOE, IDOL, and other LDL-mediated pathway involved genes. In some embodiments, a loss-of-function mutation may be simultaneously introduced into one or more, preferably at least two, of ANGPTL3, PCSK9, APOB, and another LDL-mediated pathway involved gene. In some embodiments, mutations may be simultaneously introduced into ANGPTL3, PCSK9, LDLR, and IDOL. To simultaneously introduce of loss-of-function mutations into more than one protein, multiple guide nucleotide sequences are used.

In some embodiments, the target sequence may be located in a non-genic functional site in the genome that controls aspects of chromatin organization, such as a scaffold site or locus control region. In some embodiments, the target sequence may be a genetic safe harbor site, i.e., a locus that facilitates safe genetic modification.

Templates

In some embodiments, at least one template may be provided as a substrate during the repair of the cleaved target nucleic acid molecule. In some embodiments, the template may be used in homologous recombination, such as, e.g., high-fidelity homologous recombination. In some embodiments, the homologous recombination may result in the integration of the template sequence into the target nucleic acid molecule. In some embodiments, a single template or multiple copies of the same template may be provided. In other embodiments, two or more templates may be provided such that homologous recombination may occur at two or more target sites. For example, different templates may be provided to repair a single gene in a cell, or two different genes in a cell. In some embodiments, the different templates may be provided in independent copy numbers.

In some embodiments, the template may be used in homology-directed repair, requiring DNA strand invasion at the site of the cleavage in the nucleic acid. In some embodiments, the homology-directed repair may result in the copying of the template sequence into the target nucleic acid molecule. In some embodiments, a single template or multiple copies of the same template may be provided. In other embodiments, two or more templates having different sequences may be inserted at two or more sites by homology-directed repair. For example, different templates may be provided to repair a single gene in a cell, or two different genes in a cell. In some embodiments, the different templates may be provided in independent copy numbers.

In some embodiments, the template may be incorporated into the cleaved nucleic acid as an insertion mediated by non-homologous end joining. In some embodiments, the template sequence has no similarity to the nucleic acid sequence near the cleavage site. In some embodiments, the template sequence (e.g., the coding sequence in the template) has no similarity to the nucleic acid sequence near the cleavage site. The template sequence may be flanked by target sequences that may have similar or identical sequence (s) to a target sequence near the cleavage site. In some embodiments, a single template or multiple copies of the same template may be provided. In other embodiments, two or more templates having different sequences may be inserted at two or more sites by non-homologous end joining. For example, different templates may be provided to insert a single template in a cell, or two different templates in a cell. In some embodiments, the different templates may be provided in independent copy numbers.

In some embodiments, the template sequence may correspond to an endogenous sequence of a target cell. In some embodiments, the endogenous sequence may be a genomic sequence of the cell. In some embodiments, the endogenous sequence may be a chromosomal or extrachromosomal sequence. In some embodiments, the endogenous sequence may be a plasmid sequence of the cell. In some embodiments, the template sequence may be substantially identical to a portion of the endogenous sequence in a cell at or near the cleavage site, but comprise at least one nucleotide change. In some embodiments, the repair of the cleaved target nucleic acid molecule with the template may result in a mutation comprising an insertion, deletion, or substitution of one or more nucleotides of the target nucleic acid molecule. In some embodiments, the mutation may result in one or more amino acid changes in a protein expressed from a gene comprising the target sequence. In some embodiments, the mutation may result in one or more nucleotide changes in an RNA expressed from the target gene. In some embodiments, the mutation may alter the expression level of the target gene. In some embodiments, the mutation may result in increased or decreased expression of the target gene. In some embodiments, the mutation may result in gene knockdown. In some embodiments, the mutation may result in gene knockout. In some embodiments, the repair of the cleaved target nucleic acid molecule with the template may result in replacement of an exon sequence, an intron sequence, a transcriptional control sequence, a translational control sequence, or a non-coding sequence of the target gene.

In other embodiments, the template sequence may comprise an exogenous sequence. In some embodiments, the exogenous sequence may comprise a protein or RNA coding sequence operably linked to an exogenous promoter sequence such that, upon integration of the exogenous sequence into the target nucleic acid molecule, the cell is capable of expressing the protein or RNA encoded by the integrated sequence. In other embodiments, upon integration of the exogenous sequence into the target nucleic acid molecule, the expression of the integrated sequence may be regulated by an endogenous promoter sequence. In some embodiments, the exogenous sequence may be a chromosomal or extrachromosomal sequence. In some embodiments, the exogenous sequence may provide a cDNA sequence encoding a protein or a portion of the protein. In yet other embodiments, the exogenous sequence may comprise an exon sequence, an intron sequence, a transcriptional control sequence, a translational control sequence, or a non-coding sequence. In some embodiments, the integration of the exogenous sequence may result in gene knock-in.

The template may be of any suitable length. In some embodiments, the template may comprise 10, 15, 20, 25, 50, 75, 100, 150, 200, 500, 1000, 1500, 2000, 2500, 3000, 3500, 4000, 4500, 5000, 5500, 6000, or more nucleotides in length. In some embodiments, the template may comprise a nucleotide sequence that is complementary to a portion of the target nucleic acid molecule comprising the target sequence (i.e., a "homology arm"). In some embodiments, a homology arm may comprise 10, 15, 20, 25, 50, 75, 100, 150, 200, 500, 1000, 1500, 2000, 2500, 3000 or more nucleotides in length. In some embodiments, the template may comprise a homology arm that is complementary to the sequence located upstream or downstream of the cleavage site on the target nucleic acid molecule. In some embodiments, the template may comprise a first nucleotide sequence and a second homology arm that are complementary to the sequences located upstream and downstream of the cleavage site, respectively. Where a template contains two homology arms, each arm can be the same length or different lengths, and the sequence between the homology arms can be substantially similar or identical to the target sequence between the homology arms, or be entirely unrelated. In some embodiments, the degree of complementarity between the first nucleotide sequence on the template and the sequence upstream of the cleavage site, and between the second nucleotide sequence on the template and the sequence downstream of the cleavage site, may permit homologous recombination, such as, e.g., high-fidelity homologous recombination, between the template and the target nucleic acid molecule. In some embodiments, the degree of complementarity may be about 50%, 55%, 60%, 65%, 70%, 75%, 80%, 85%, 90%, 95%, 97%, 98%, 99%, or 100%. In some embodiments, the degree of complementarity may be about 95%, 97%, 98%, 99%, or 100%. In some embodiments, the degree of complementarity may be about 98%, 99%, or 100%. In some embodiments, the degree of complementarity may be 100%. In some embodiments, for example those described herein where a template is incorporated into the cleaved nucleic acid as an insertion mediated by non-homologous end joining, the template has no homology arms. In some embodiments, a template having no homology arms comprises target sequences flanking one or both ends of the template sequence, e.g., as described herein. In some embodiments, a template having no homology arms comprises target sequences flanking both ends of the template sequence. In some embodiments, a target sequence flanking the end of the template sequence is about 10-50 nucleotides. In some embodiments, a target sequence flanking the end of the template sequence is about 10-20 nucleotides, about 15-20 nucleotides, about 20-25 nucleotides, or about 20-30 nucleotides. In some embodiments, a target sequence flanking the end of the template sequence is about 17-23 nucleotides. In some embodiments, a target sequence flanking the end of the template sequence is about 20 nucleotides.

In some embodiments, a nucleic acid molecule is expressed from the template if homologous recombination occurs between the template and the genomic sequence. In some embodiments, for example, the template does not have a promoter for expressing the nucleic acid molecule and/or the ATG transcriptional start site is removed from the coding sequence.

Delivery

Provided herein are methods and compositions for editing a nucleic acid molecule in a cell with a nuclease system and targeted delivery thereof. In some embodiments, the nucleic acid comprises a nucleic acid sequence encoding a gene. In some embodiments, the nucleic acid comprises a nucleic acid sequence encoding a gene associated with a disease or disorder.

The active agents comprising nucleic acids described herein, e.g. modified guide RNAs, may be conjugated with one or more targeting moieties for targeted delivery to desired in vivo locations. The guide RNA conjugates or guide RNA-protein complex conjugates may be introduced into the cell via any methods known in the art, such as, e.g., viral or bacteriophage infection, transfection, conjugation, protoplast fusion, lipofection, lipid particle or vesicle transduction, electroporation, calcium phosphate precipitation, polyethyleneimine (PEI)-mediated transfection, DEAE-dextran-mediated transfection, liposome-mediated transfection, e.g. transfection mediated by cationic liposomes, particle gun technology, calcium phosphate precipitation, shear-driven cell permeation, fusion to a cell-penetrating peptide followed by cell contact, microinjection, and nanoparticle-mediated delivery. In some embodiments, the nuclease system may be introduced into the cell via viral infection. In some embodiments, the nuclease system may be introduced into the cell via bacteriophage infection. Liposomes may include those formed from 1,2-dioleyloxy-N,N-dimethylaminopropane (DODMA) liposomes, DiLa2 liposomes from Marina Biotech (Bothell, WA), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and liposomes which may deliver small molecule drugs such as, but not limited to, DOXIL® (from Janssen Biotech, Inc. (Horsham, PA)).

In some embodiments, the methods and compositions provided herein may comprise introducing a vector system described herein into a cell. In some embodiments, the vector system encodes the nuclease system in whole or in part. In some embodiments, the vector system comprises one, two, three, or more vectors. In some embodiments, the introduction of the vector system into the cell may result in a stable cell line having the edited nucleic acid molecule while the vectors are lost, e.g., targeted for self-destruction. In some embodiments, the cell is a eukaryotic cell. Non-limiting examples of eukaryotic cells include yeast cells, plant cells, insect cells, cells from an invertebrate animal, cells from a vertebrate animal, mammalian cells, rodent cells, mouse cells, rat cells, and human cells. In some embodiments, the eukaryotic cell may be a mammalian cell. In some embodiments, the eukaryotic cell may be a rodent cell. In some embodiments, the eukaryotic cell may be a human cell. Similarly, the target sequence may be from any such cells or in any such cells.

In some embodiments, the polynucleotides or oligonucleotides provided herein, for example guide RNAs or mRNAs, may be formulated in a lipid vesicle which may have crosslinks between functionalized lipid bilayers, or lipid-polycation complex. The liposome formulation may be influenced by, but not limited to, the selection of the cationic lipid component, the degree of cationic lipid saturation, the nature of the PEGylation, ratio of all components and biophysical parameters such as size, or poly cationic composition. In one embodiment, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo. The lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), respiratory (e.g., nasal, pharyngeal, tracheal and bronchial membranes), genital (e.g., vaginal, cervical and urethral membranes). The formulations may use nanoparticles larger than 10-200 nm which are preferred for higher drug encapsulation efficiency and the ability to provide the sustained delivery of a wide array of drugs which had been thought to be too large to rapidly diffuse through mucosal barriers. The dynamic transport of nanoparticles may be measured using fluorescence recovery after photobleaching (FRAP) and high resolution multiple particle tracking (MPT). The formulations can be made for controlled release and/or targeted delivery. The lipid nanoparticle engineered to penetrate mucus may include surface altering agents such as, but not limited to, mRNA, anionic protein (e.g., bovine serum albumin), surfactants (e.g., cationic surfactants such as for example dimethyldioctadecylammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4, dornase alfa, neltenexine, erdosteine) and various DNases including rhDNase. The surface altering agent may be embedded or enmeshed in the particle's surface or disposed or dispersed (e.g., by coating, adsorption, covalent linkage, or other process) on the surface of the lipid nanoparticle.

In a further embodiment, guide RNA of the present disclosure and the CRISPR system may be formulated as a lipoplex, such as, without limitation, the ATUPLEX™ system, the DACC system, the DBTC system and other siRNA-lipoplex technology. The liposomes, lipoplexes, or lipid nanoparticles may be used to improve the efficacy of the modified guide RNAs for example by increasing cell transfection, increasing the translation of encoded protein or increasing the stability. A cell penetrating peptide may be used with the pharmaceutical formulations of the present disclosure such as a cell-penetrating peptide sequence attached to polycations that facilitates delivery to the intracellular space, e.g., HIV-derived TAT peptide, penetratins, transportans, or hCT derived cell-penetrating peptides. In another embodiment, lipid nanoparticles which target specific cell types may be used. Alternatively, the lipid nanoparticle may be encapsulated into any polymer or hydrogel known in the art which may form a gel when injected into a subject. As another non-limiting example, the lipid nanoparticle may be encapsulated into a polymer matrix which may be biodegradable. In yet another embodiment, the pharmaceutical compositions may be sustained release formulations. In a further embodiment, the sustained release formulations may be for subcutaneous delivery. Sustained release formulations may include, but are not limited to, PLGA microspheres, ethylene vinyl acetate (EVAc), poloxamer, GELSITE® (Nanotherapeutics, Inc. Alachua, FL), HYLENEX® (Halozyme Therapeutics, San Diego, CA), surgical sealants such as fibrinogen polymers (Ethicon Inc. Cornelia, GA), TISSELL® (Baxter International, Inc Deerfield, IL), PEG-based sealants, and COSEAL® (Baxter International, Inc Deerfield, IL).

In some embodiments, the nucleic acids as described herein, such as a guide RNA, may be complexed with a CRISPR enzyme. In some embodiments, a part or all of the complex may be delivered via a vector system comprising one or more vectors. In some embodiments, the vector may be a DNA vector. In other embodiments, the vector may be an RNA vector. In some embodiments, the RNA vector may be an mRNA, e.g. an mRNA that encodes a nuclease such as Cas9. In some embodiments, the vector may be circular. In other embodiments, the vector may be linear. Non-limiting exemplary vectors include plasmids, phagemids, cosmids, artificial chromosomes, minichromosomes, transposons, viral vectors, and expression vectors. In some embodiments, the nuclease is provided by an RNA vector, e.g., as mRNA, and the template is provided by a viral vector. In some embodiments, the vector may be a viral vector. In some embodiments, the viral vector may be genetically modified from its wild-type counterpart. For example, the viral vector may comprise an insertion, deletion, or substitution of one or more nucleotides to facilitate cloning or such that one or more properties of the vector is changed. Such properties may include packaging capacity, transduction efficiency, immunogenicity, genome integration, replication, transcription, and translation. In some embodiments, a portion of the viral genome may be deleted such that the virus is capable of packaging exogenous sequences having a larger size. In some embodiments, the viral vector may have an enhanced transduction efficiency. In some embodiments, the immune response induced by the virus in a host may be reduced. In some embodiments, viral genes (such as, e.g., integrase) that promote integration of the viral sequence into a host genome may be mutated such that the virus becomes non-integrating. In some embodiments, the viral vector may be replication defective. In some embodiments, the viral vector may comprise exogenous transcriptional or translational control sequences to drive expression of coding sequences on the vector. In some embodiments, the virus may be helper-dependent. For example, the virus may need one or more helper virus to supply viral components (such as, e.g., viral proteins) required to amplify and package the vectors into viral particles. In such a case, one or more helper components, including one or more vectors encoding the viral components, may be introduced into a host cell along with the vector system described herein. In other embodiments, the virus may be helper-free. For example, the virus may be capable of amplifying and packaging the vectors without any helper virus. In some embodiments, the vector system described herein may also encode the viral components required for virus amplification and packaging.

Non-limiting exemplary viral vectors include adeno-associated virus (AAV) vector, lentivirus vectors, adenovirus vectors, herpes simplex virus (HSV-1) vectors, bacteriophage T4, baculovirus vectors, and retrovirus vectors. In some embodiments, the viral vector may be an AAV vector. In other embodiments, the viral vector may a lentivirus vector. In some embodiments, the lentivirus may be non-integrating. In some embodiments, the viral vector may be an adenovirus vector. In some embodiments, the adenovirus may be a high-cloning capacity or "gutless" adenovirus, where all coding viral regions apart from the 5' and 3' inverted terminal repeats (ITRs) and the packaging signal (Y) are deleted from the virus to increase its packaging capacity. In yet other embodiments, the viral vector may be an HSV-1 vector. In some embodiments, the HSV-1-based vector is helper dependent, and in other embodiments it is helper independent. For example, an amplicon vector that retains only the packaging sequence requires a helper virus with structural components for packaging, while a 30 kb-deleted HSV-1 vector that removes non-essential viral functions does not require helper virus. In additional embodiments, the viral vector may be bacteriophage T4. In some embodiments, the bacteriophage T4 may be able to package any linear or circular DNA or RNA molecules when the head of the virus is emptied. In further embodiments, the viral vector may be a baculovirus vector. In yet further embodiments, the viral vector may be a retrovirus vector. In embodiments using AAV or lentiviral vectors, which have smaller cloning capacity, it may be necessary to use more than one vector to deliver all the components of a vector system as disclosed herein. For example, one AAV vector may contain sequences encoding a Cas9 protein, while a second AAV vector may contain one or more guide sequences and one or more copies of template.

In certain embodiments, a viral vector may be modified to target a particular tissue or cell type. For example, viral surface proteins may be altered to decrease or eliminate viral protein binding to its natural cell surface receptor(s). In some embodiments, the vector may be modified for liver specific delivery. The surface proteins may also be engineered to interact with a receptor specific to a desired cell type. Viral vectors may have altered host tropism, including limited or redirected tropism. In some embodiments, the viral vector may be engineered to express or display a first binding moiety. The first binding moiety may be fused to a viral surface protein or glycoprotein, conjugated to a virus, chemically crosslinked to a virion, bound to a virus envelope, or joined to a viral vector by any other suitable method. The first binding moiety is capable of binding to a second binding moiety, which may be used to direct the virus to a desired cell type. In some embodiments, the first binding moiety is avidin, streptavidin, neutravidin, captavidin, or another biotin-binding moiety, and the second binding moiety is biotin or an analog thereof. A biotinylated targeting agent may then be bound to the avidin on the viral vector and used to direct the virus to a desired cell type. For example, a T4 vector may be engineered to display a biotin-binding moiety on one or more of its surface proteins. The cell-specificity of such a T4 vector may then be altered by binding a biotinylated antibody or ligand directed to a cell of choice. In alternate embodiments, the first and second binding moieties are hapten and an anti-hapten binding protein; digoxigenin and an anti-digoxigenin binding protein; fluorescein and an anti-fluorescein binding protein; or any other suitable first and second binding moieties that are binding partners.

In some embodiments, the vector may be capable of driving expression of one or more coding sequences in a cell. In some embodiments, the cell may be a prokaryotic cell, such as, e.g., a bacterial cell. In some embodiments, the cell may be a eukaryotic cell, such as, e.g., a yeast, plant, insect, or mammalian cell. In some embodiments, the eukaryotic cell may be a mammalian cell. In some embodiments, the eukaryotic cell may be a rodent cell. In some embodiments, the eukaryotic cell may be a human cell. Suitable promoters to drive expression in different types of cells are known in the art. In some embodiments, the promoter may be wild-type. In other embodiments, the promoter may be modified for more efficient or efficacious expression. In yet other embodiments, the promoter may be truncated yet retain its function. For example, the promoter may have a normal size or a reduced size that is suitable for proper packaging of the vector into a virus.

In some embodiments, the vector may comprise a nucleotide sequence encoding the nuclease described herein. In some embodiments, the vector system may comprise one copy of the nucleotide sequence encoding the nuclease. In other embodiments, the vector system may comprise more than one copy of the nucleotide sequence encoding the nuclease. In some embodiments, the nucleotide sequence encoding the nuclease may be operably linked to at least one transcriptional or translational control sequence. In some embodiments, the nucleotide sequence encoding the nuclease may be operably linked to at least one promoter. In some embodiments, the nucleotide sequence encoding the nuclease may be operably linked to at least one transcriptional or translational control sequence.

In some embodiments, the promoter may be constitutive, inducible, or tissue-specific. In some embodiments, the promoter may be a constitutive promoter. Non-limiting exemplary constitutive promoters include cytomegalovirus immediate early promoter (CMV), simian virus (SV40) promoter, adenovirus major late (MLP) promoter, Rous sarcoma virus (RSV) promoter, mouse mammary tumor virus (MMTV) promoter, phosphoglycerate kinase (PGK) promoter, elongation factor-alpha (EF1α) promoter, ubiquitin promoters, actin promoters, tubulin promoters, immunoglobulin promoters, a functional fragment thereof, or a combination of any of the foregoing. In some embodiments, the promoter may be a CMV promoter. In some embodiments, the promoter may be a truncated CMV promoter. In other embodiments, the promoter may be an EF1α promoter. In some embodiments, the promoter may be an inducible promoter. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On® promoter (Clontech). In some embodiments, the promoter may be a tissue-specific promoter. In some embodiments, the tissue-specific promoter is exclusively or predominantly expressed in liver tissue. Non-limiting exemplary tissue-specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, Nphsl promoter, OG-2 promoter, SP-B promoter, SYN1 promoter, and WASP promoter.

In some embodiments, the vector may encode a Cas protein or a portion of a Cas protein, such as a Cas9 protein or Cpf1 protein. The vector system may further comprise a vector comprising a nucleotide sequence encoding the guide RNA described herein. In some embodiments, the vector system may comprise one copy of the guide RNA. In other embodiments, the vector system may comprise more than one copy of the guide RNA. In embodiments with more than one guide RNA, the guide RNAs may be non-identical such that they target different target sequences, or have other different properties, such as activity or stability within the Cas9 RNP complex. In some embodiments, the nucleotide sequence encoding the guide RNA may be operably linked to at least one transcriptional or translational control sequence. In some embodiments, the nucleotide sequence encoding the guide RNA may be operably linked to at least one promoter. In some embodiments, the promoter may be recognized by RNA polymerase III (Pol III). Non-limiting examples of Pol III promoters include U6, H1 and tRNA promoters. In some embodiments, the nucleotide sequence encoding the guide RNA may be operably linked to a mouse or human U6 promoter. In other embodiments, the nucleotide sequence encoding the guide RNA may be operably linked to a mouse or human H1 promoter. In some embodiments, the nucleotide sequence encoding the guide RNA may be operably linked to a mouse or human tRNA promoter. In embodiments with more than one guide RNA, the promoters used to drive expression may be the same or different. In some embodiments, the nucleotide encoding the crRNA of the guide RNA and the nucleotide encoding the tracr RNA of the guide RNA may be provided on the same vector. In some embodiments, the nucleotide encoding the crRNA and the nucleotide encoding the tracr RNA may be driven by the same promoter. In some embodiments, the crRNA and tracr RNA may be transcribed into a single transcript. For example, the crRNA and tracr RNA may be processed from the single transcript to form a double-molecule guide RNA. Alternatively, the crRNA and tracr RNA may be transcribed into a single-molecule guide RNA. In other embodiments, the crRNA and the tracr RNA may be driven by their corresponding promoters on the same vector. In yet other embodiments, the crRNA and the tracr RNA may be encoded by different vectors.

In some embodiments, the vector system may further comprise a vector comprising the template described herein. In some embodiments, the vector system may comprise one copy of the template. In other embodiments, the vector system may comprise more than one copy of the template. In some embodiments, the vector system may comprise 2, 3, 4, 5, 6, 7, 8, 9, 10, or more copies of the template. In some embodiments, the vector system may comprise 4, 5, 6, 7, 8, or more copies of the template. In some embodiments, the vector system may comprise 5, 6, 7, or more copies of the template. In some embodiments, the vector system may comprise 6 copies of the template. The multiple copies of the template may be located on the same or different vectors. The multiple copies of the template may also be adjacent to one another, or separated by other nucleotide sequences or vector elements. In other embodiments, two or more templates may be provided such that homologous recombination may occur at two or more target sites. For example, different templates may be provided to repair a single gene in a cell, or two different genes in a cell. In some embodiments, the different templates may be provided in independent copy numbers.

A vector system may comprise 1-3 vectors. In some embodiments, the vector system may comprise one single vector. In other embodiments, the vector system may comprise two vectors. In additional embodiments, the vector system may comprise three vectors.

In some embodiments, the nucleotide sequence encoding the nuclease and the template may be located on the same or separate vectors. In some embodiments, the nucleotide sequence encoding the nuclease and the template may be located on the same vector. In some embodiments, the nucleotide sequence encoding the nuclease and the template may be located on separate vectors. The sequences may be oriented in the same or different directions and in any order on the vector.

In some embodiments, the nucleotide sequence encoding a Cas9 protein and a template may be located on the same or separate vectors. In some embodiments, all of the sequences may be located on the same vector. In some embodiments, two or more sequences may be located on the same vector. The sequences may be oriented in the same or different directions and in any order on the vector. In some embodiments, the nucleotide sequence encoding the Cas9 protein and the nucleotide sequence encoding the guide RNA may be located on the same vector. In some embodiments, the nucleotide sequence encoding the Cas9 protein and the template may be located on the same vector. In a particular embodiment, the vector system may comprise a first vector comprising the nucleotide sequence encoding the Cas9 protein, and a second vector comprising the nucleotide sequence encoding the template or multiple copies of the template.

In some embodiments, the template may be released from the vector on which it is located by the nuclease system encoded by the vector system. In some embodiments, the template may be released from the vector by a Cas9 protein provided from an mRNA. The template may comprise at least one target sequence that is recognized by the guide RNA. In some embodiments, the template may be flanked by a target sequence at the 5' and 3' ends of the template. Upon expression of Cas9 protein and delivery of the guide RNA, the guide RNA may hybridize with and the Cas9 protein may cleave the target sequence at both ends of the template such that the template is released from the vector. In additional embodiments, the template may be released from the vector by a nuclease encoded by the vector system by having a target sequence recognized by the nuclease at the 5' and 3' ends of the template. The target sequences at either end of the template may be oriented such that the PAM sequence is closer to the template. In such an orientation, fewer non-template nucleic acids remain on the ends of the template after release from the vector. In some embodiments, the target sequences flanking the template may be the same. In some embodiments, the target sequences flanking the template may be the same as the target sequence found at the cleavage site in which the template is incorporated, e.g., by HR, HDR, or non-homologous end joining. In other embodiments, the target sequences flanking the template may be different. For example, the target sequence at the 5' end of the template may be recognized by one guide RNA or nuclease, and the target sequence at the 3' end of the template may be recognized by another guide RNA or nuclease.

In some embodiments, the vector encoding the nuclease system may comprise at least one target sequence within the vector, to create a self-destroying (or “self-cleaving” or “self-inactivating”) vector system to control the amount of the nuclease system to be expressed. In some embodiments, the self-destroying vector system results in a reduction in the amount of nuclease activity. In further embodiments, the self-destroying vector system results in a reduction in the amount of vector nucleic acid. In embodiments in which the system comprises Cas9, it also comprises guide RNA(s) that recognize the target sequence. In this way, the residence time and/or the level of activity of the nuclease system may be temporally controlled to avoid adverse effects associated with overexpression of the nuclease system. Such adverse effects may include, e.g., an off-target effect by the nuclease. In some embodiments, one or more target sequences may be located at any place on the vector such that, upon expression of the nuclease, the nuclease recognizes and cleaves the target sequence in the vector that contains the nuclease-encoding sequence. The one or more target sequences of the self-destroying vector may be the same. Optionally, the self-destroying vector may comprise multiple target sequences. In some embodiments, the cleavage at a target sequence may reduce the expression of at least one component of the nuclease system, such as, for example, Cas9. In some embodiments, the cleavage may reduce the expression of the nuclease transcript. For example, a target sequence may be located within the nucleotide sequence encoding the nuclease such that the cleavage results in the disruption of the coding region. In other embodiments, a target sequence may be located within a non-coding region on the vector encoding the nuclease. In some embodiments, a target sequence may be located within the promoter that drives the expression of the nuclease such that the cleavage results in the disruption of the promoter sequence. For example, the vector may contain a target sequence (and its corresponding guide RNA) that targets a Cas9 sequence. In certain embodiments, a target sequence may be located between the promoter and the nucleotide sequence encoding the nuclease such that the cleavage results in the separation of the coding sequence from its promoter. In certain embodiments, a target sequence outside the nuclease coding sequence and a target sequence within the nuclease coding sequence are included.

In some embodiments, the vector encoding a Cas9 protein may comprise at least one target sequence that is recognized by a guide RNA. In some embodiments, the target sequence may be located at any place on the vector such that, upon expression of the Cas9 protein and the guide RNA, the guide RNA hybridizes with and the Cas9 protein cleaves the target sequence in the vector encoding the Cas9 protein. In some embodiments, the cleavage at the target sequence may reduce the expression of the Cas9 protein transcript. For example, the target sequence may be located within the nucleotide sequence encoding the Cas9 protein such that the cleavage results in the disruption of the coding region. In other embodiments, the target sequence may be located within a non-coding region on the vector encoding the Cas9 protein. In some embodiments, the target sequence may be located within the promoter that drives the expression of the Cas9 protein such that the cleavage results in the disruption of the promoter sequence. In some embodiments, the target sequence may be located within the nucleotide sequence encoding the Cas9 protein such that the cleavage results in the disruption of the coding sequence. In other embodiments, the target sequence may be located between the promoter and the nucleotide sequence encoding the Cas9 protein such that the cleavage results in the separation of the coding sequence from its promoter.

The target sequences for release of the template, for vector self-destruction, and for targeting by the nuclease system in a cell may be the same or different. For example, the target sequence at the 3' end of the template may be present within the promoter driving the expression of the nuclease (e.g., the Cas9 protein) such that the release of the template simultaneously results in the disruption of the expression of the nuclease (e.g., the Cas9 protein). In some embodiments, both target sequences flanking the template, the target sequences for disrupting the expression of the nuclease (e.g., the Cas9 protein), and the target sequence in the target nucleic acid molecule in a cell may be the same sequence that is recognized by a single guide RNA or nuclease. Thus, in some embodiments, the vector system may comprise only one type of target sequence, and the nuclease system may comprise only one guide RNA. In other embodiments, these target sequences may comprise different sequences that are recognized by different guide RNAs.

In some embodiments, the vector system may comprise inducible promoters to start expression only after it is delivered to a target cell. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On® promoter (Clontech).

In additional embodiments, the vector system may comprise tissue-specific promoters to start expression only after it is delivered into a specific tissue. Non-limiting exemplary tissue-specific promoters include albumin promoter, a-1 antitrypsin promoter, hemopexin promoter, B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, Nphsl promoter, OG-2 promoter, SP-B promoter, SYN1 promoter, and WASP promoter. In particular embodiments, the tissue specific promoter is an albumin promoter, a a-1 antitrypsin promoter, a hepatitis B virus core promoter, or a hemopexin gene promoter. Methods of examining liver specific promoters are described in Kramer et al., Molecular Therapy 7(3): 375-385 (2003), which is incorporated herein in its entirety by reference.

In some embodiments of the present disclosure, the activity of the nuclease system may be temporally regulated by adjusting the residence time, the amount, and/or the activity of the expressed components of the nuclease system. For example, as described herein, the nuclease may be fused with a protein domain that is capable of modifying the intracellular half-life of the nuclease. In certain embodiments involving two or more vectors (e.g., a vector system in which the components described herein are encoded on two or more separate vectors), the activity of the nuclease system may be temporally regulated by controlling the timing in which the vectors are delivered. For example, in some embodiments a vector encoding the nuclease system may deliver the nuclease prior to the vector encoding the template. In other embodiments, the vector encoding the template may deliver the template prior to the vector encoding the nuclease system. In some embodiments, the vectors encoding the nuclease system and template are delivered simultaneously. In certain embodiments, the simultaneously delivered vectors temporally deliver, e.g., the nuclease, template, and/or guide RNA components. In further embodiments, the RNA (such as, e.g., the nuclease transcript) transcribed from the coding sequence on the vectors may further comprise at least one element that is capable of modifying the intracellular half-life of the RNA and/or modulating translational control. In some embodiments, the half-life of the RNA may be increased. In some embodiments, the half-life of the RNA may be decreased. In some embodiments, the element may be capable of increasing the stability of the RNA. In some embodiments, the element may be capable of decreasing the stability of the RNA. In some embodiments, the element may be within the 3' UTR of the RNA. In some embodiments, the element may include a polyadenylation signal (PA). In some embodiments, the element may include a cap, e.g., an upstream mRNA end. In some embodiments, the PA may be added to the 3' UTR of the RNA. In some embodiments, the RNA may comprise no PA such that it is subject to quicker degradation in the cell after transcription. In some embodiments, the element may include at least one AU-rich element (ARE). The AREs may be bound by ARE binding proteins (ARE-BPs) in a manner that is dependent upon tissue type, cell type, timing, cellular localization, and environment. In some embodiments the destabilizing element may promote RNA decay, affect RNA stability, or activate translation. In some embodiments, the ARE may comprise 50 to 150 nucleotides in length. In some embodiments, the ARE may comprise at least one copy of the sequence AUUUA. In some embodiments, at least one ARE may be added to the 3' UTR of the RNA. In some embodiments, the element may be a Woodchuck Hepatitis Virus (WHP) Posttranscriptional Regulatory Element (WPRE), which creates a tertiary structure to enhance expression from the transcript. In further embodiments, the element is a modified and/or truncated WPRE sequence that is capable of enhancing expression from the transcript, as described, for example in Zufferey et al., J Virol, 73 (4): 2886-92 (1999) and Flajolet et al., J Virol, 72 (7): 6175-80 (1998). In some embodiments, the WPRE or equivalent may be added to the 3' UTR of the RNA. In some embodiments, the element may be selected from other RNA sequence motifs that are enriched in either fast- or slow-decaying transcripts.

Embodiments of the disclosure also encompass treating a patient with the vector system described herein. In some embodiments, the method may comprise administering the vector system described herein to the patient. The method may be used as a single therapy or in combination with other therapies available in the art. In some embodiments, the patient may have a mutation (such as, e.g., insertion, deletion, substitution, chromosome translocation) in a disease-associated gene. In some embodiments, administration of the vector system may result in a mutation comprising an insertion, deletion, or substitution of one or more nucleotides of the disease-associated gene in the patient. Certain embodiments may include methods of repairing the patient's mutation in the disease-associated gene. In some embodiments, the mutation may result in one or more amino acid changes in a protein expressed from the disease-associated gene. In some embodiments, the mutation may result in one or more nucleotide changes in an RNA expressed from the disease-associated gene. In some embodiments, the mutation may alter the expression level of the disease-associated gene. In some embodiments, the mutation may result in increased or decreased expression of the gene. In some embodiments, the mutation may result in gene knockdown in the patient. In some embodiments, the administration of the vector system may result in the correction of the patient's mutation in the disease-associated gene. In some embodiments, the administration of the vector system may result in gene knockout in the patient. In some embodiments, the administration of the vector system may result in replacement of an exon sequence, an intron sequence, a transcriptional control sequence, a translational control sequence, or a non-coding sequence of the disease-associated gene.

In some embodiments, the administration of the vector system may result in integration of an exogenous sequence of the template into the patient's genomic DNA. In some embodiments, the exogenous sequence may comprise a protein or RNA coding sequence operably linked to an exogenous promoter sequence such that, upon integration of the exogenous sequence into the patient's genomic DNA, the patient is capable of expressing the protein or RNA encoded by the integrated sequence. The exogenous sequence may provide a supplemental or replacement protein coding or non-coding sequence. For example, the administration of the vector system may result in the replacement of the mutant portion of the disease-associated gene in the patient. In some embodiments, the mutant portion may include an exon of the disease-associated gene. In other embodiments, the integration of the exogenous sequence may result in the expression of the integrated sequence from an endogenous promoter sequence present on the patient's genomic DNA. For example, the administration of the vector system may result in supply of a functional gene product of the disease-associated gene to rectify the patient's mutation. In some embodiments, the administration of the vector system may result in integration of a cDNA sequence encoding a protein or a portion of the protein. In yet other embodiments, the administration of the vector system may result in integration of an exon sequence, an intron sequence, a transcriptional control sequence, a translational control sequence, or a non-coding sequence into the patient's genomic DNA. In some embodiments, the administration of the vector system may result in gene knockin in the patient.

Administration

Provided herein are methods and compositions for editing a target nucleic acid in a cell. Further provided herein are pharmaceutical compositions and methods for modifying the function and activity of a target gene in a cell of a subject. The genome editing compositions described herein may be administered to a subject in need thereof in a therapeutically effective amount, to treat conditions related to high circulating cholesterol levels and/or coronary disease, e.g. hypercholesterolemia, elevated total cholesterol levels, elevated low-density lipoprotein (LDL) levels, elevated LDL-cholesterol levels, reduced high-density lipoprotein levels, liver steatosis, coronary heart disease, ischemia, stroke, peripheral vascular disease, thrombosis, type 2 diabetes, high elevated blood pressure, atherosclerosis, obesity, Alzheimer's disease, neurodegeneration, and combinations thereof can be administered to the subject in a variety of ways, including parenterally, intravenously, intradermally, intramuscularly, colonically, rectally or intraperitoneally. In some embodiments, the pharmaceutical composition may be co-administered with pharmaceutically acceptable salt by intraperitoneal injection, intramuscular injection, subcutaneous injection, or intravenous injection of the subject. In some embodiments, the pharmaceutical composition may be directly injected to a specific tissue, such as the liver tissue. In some embodiments, the pharmaceutical compositions can be administered parenterally, intravenously, intramuscularly or orally. The oral formulations can be further coated or treated to prevent or reduce dissolution in stomach. The compositions of the present disclosure can be administered to a subject using any suitable methods known in the art. Suitable formulations for use in the present disclosure and methods of delivery are generally well known in the art. For example, the composition of the present disclosure can be formulated as pharmaceutical compositions with a pharmaceutically acceptable diluent, carrier or excipient. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

Pharmaceutical formulations described herein can be administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the pharmaceutical formulation is in the form of a tablet. In other embodiments, pharmaceutical formulations containing an composition or inhibitory agent described herein are in the form of a capsule. In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a composition or inhibitory agent described herein can be formulated for use as an aerosol, a mist or a powder. For buccal or sublingual administration, the compositions may take the form of tablets, lozenges, or gels formulated in a conventional manner. In some embodiments, a composition or inhibitory agent described herein can be prepared as transdermal dosage forms. In some embodiments, a composition or inhibitory agent described herein can be formulated into a pharmaceutical composition suitable for intramuscular, subcutaneous, or intravenous injection. In some embodiments, a composition or inhibitory agent described herein can be administered topically and can be formulated into a variety of topically administrable compositions, such as solutions, suspensions, lotions, gels, pastes, medicated sticks, balms, creams or ointments. In some embodiments, a composition or inhibitory agent described herein can be formulated in rectal compositions such as enemas, rectal gels, rectal foams, rectal aerosols, suppositories, jelly suppositories, or retention enemas.

Dosage

Appropriate dosage or effective amounts for administration vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. Factors involved in dosage determination are known to those of ordinary skill in the art without additional experimentation other than routine test. It is generally preferred that a maximum dose of the individual components or combinations thereof be used, that is, the highest safe dose according to sound medical judgment. Empirical considerations, such as the half-life, generally will contribute to the determination of the dosage. For example, therapeutic agents that are compatible with the human immune system, such as polypeptides comprising regions from humanized antibodies or fully human antibodies, may be used to prolong half-life of the polypeptide and to prevent the polypeptide being attacked by the host's immune system.

Frequency of administration may be determined and adjusted over the course of therapy, and is generally, but not necessarily, based on treatment and/or suppression and/or amelioration and/or delay of a disease. Alternatively, sustained continuous release formulations of a polypeptide or a polynucleotide may be appropriate. Various formulations and devices for achieving sustained release are known in the art. In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays.

The dosing regimen can vary over time. In some embodiments, for an adult subject of normal weight, doses ranging from about 0.01 to 1000 mg/kg may be administered. In some embodiments, the dose is between 1 to 200 mg. In some embodiments, the doses may range from about 0.01 to 0.05 mg/kg, between about 0.01 to 0.1 mg/kg, between about 0.01 to 1 mg/kg, between about 0.01 to 10 mg/kg, between about 0.01 to 100 mg/kg, between 0.01 to 500 mg/kg, between about 0.1 to 1 mg/kg, between about 0.1 to 5 mg/kg, between about 0.1 to 10 mg/kg, between about 0.1 to 100 mg/kg, between about 0.1 to 500 mg/kg, between about 0.1 to 1000 mg/kg, between about 1 to 5 mg/kg, between about 1 to 10 mg/kg, between about 1 to 100 mg/kg, between about 1 to 500 mg/kg, between about 1 to 1000 mg/kg, between about 10 to 100 mg/kg, between about 10 to 500 mg/kg, between about 10 to 1000 mg/kg, or between about 100 to 1000 mg/kg. The particular dosage regimen, i.e., dose, timing and repetition, will depend on the particular subject and that subject's medical history, as well as the properties of the polypeptide or the polynucleotide (such as the half-life of the polypeptide or the polynucleotide, and other considerations well known in the art).

As will be apparent to those skilled in the art, the appropriate dosage of a therapeutic agent as described herein will depend on the specific agent (or compositions thereof) employed, the formulation and route of administration, the type and severity of the disease, whether the polypeptide or the polynucleotide is administered for preventive or therapeutic purposes, previous therapy, the subject's clinical history and response to the antagonist, and the discretion of the attending physician. Typically the clinician will administer a polypeptide until a dosage is reached that achieves the desired result.

Administration of one or more therapeutic compositions, e.g. polypeptides, polynucleotides, or RNPs, can be continuous or intermittent, depending, for example, upon the recipient's physiological condition, whether the purpose of the administration is therapeutic or prophylactic, and other factors known to skilled practitioners. The administration of a polypeptide may be essentially continuous over a preselected period of time or may be in a series of spaced dose, e.g., either before, during, or after developing a disease.

Biological Samples

A sample, e.g., a biological sample can be taken from a subject. A biological sample can comprise a plurality of biological samples. The plurality of biological samples can contain two or more biological samples; for examples, about 2-1000, 2-500, 2-250, 2-100, 2-75, 2-50, 2-25, 2-10, 10-1000, 10-500, 10-250, 10-100, 10-75, 10-50, 10-25, 25-1000, 25-500, 25-250, 25-100, 25-75, 25-50, 50-1000, 50-500, 50-250, 50-100, 50-75, 60-70, 100-1000, 100-500, 100-250, 250-1000, 250-500, 500-1000, 2, 3, 4, 5, 6, 7, 8, 9, 10, 11, 12, 13, 14, 15, 16, 17, 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 110, 120, 130, 140, 150, 160, 170, 180, 190, 200, 210, 220, 230, 240, 250, 275, 300, 325, 350, 375, 400, 425, 450, 475, 500, 550, 600, 650, 700, 750, 800, 850, 900, 950, 1000, or more biological samples. The biological samples can be obtained from a plurality of subjects, giving a plurality of sets of a plurality of samples. The biological samples can be obtained from about 2 to about 1000 subjects, or more; for example, about 2-1000, 2-500, 2-250, 2-100, 2-50, 2-25, 2-20, 2-10, 10-1000, 10-500, 10-250, 10-100, 10-50, 10-25, 10-20, 15-20, 25-1000, 25-500, 25-250, 25-100, 25-50, 50-1000, 50-500, 50-250, 50-100, 100-1000, 100-500, 100-250, 250-1000, 250-500, 500-1000, or at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 68, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500, 550, 600, 650, 700, 750, 800, 850, 900, 950, or 1000 or more subjects.

The biological samples can be obtained from human subjects. The biological samples can be obtained from human subjects at different ages. The human subject can be prenatal (e.g., a fetus), a child (e.g., a neonate, an infant, a toddler, a preadolescent), an adolescent, a pubescent, or an adult (e.g., an early adult, a middle aged adult, a senior citizen). The human subject can be between about 0 months and about 120 years old, or older. The human subject can be between about 0 and about 12 months old; for example, about 1, 2, 3, 4, 5, 6, 7, 8, 9, 10, 11, or 12 months old. The human subject can be between about 0 and 12 years old; for example, between about 0 and 30 days old; between about 1 month and 12 months old; between about 1 year and 3 years old; between about 4 years and 5 years old; between about 4 years and 12 years old; about 1, 2, 3, 4, 5, 6, 7, 8, 9, 10, 11, or 12 years old. The human subject can be between about 13 years and 19 years old; for example, about 13, 14, 15, 16, 17, 18, or 19 years old. The human subject can be between about 20 and about 39 year old; for example, about 20, 21, 22, 23, 24, 25, 26, 27, 28, 29, 30, 31, 32, 33, 34, 35, 36, 37, 38, or 39 years old. The human subject can be between about 40 to about 59 years old; for example, about 40, 41, 42, 43, 44, 45, 46, 47, 48, 49, 50, 51, 52, 53, 54, 55, 56, 57, 58, or 59 years old. The human subject can be greater than 59 years old; for example, about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 years old. The human subjects can include living subjects or deceased subjects. The human subjects can include male subjects and/or female subjects.

Biological samples can be obtained from any suitable source that allows determination of expression levels of genes, e.g., from cells, tissues, bodily fluids or secretions, or a gene expression product derived therefrom (e.g., nucleic acids, such as DNA or RNA; polypeptides, such as protein or protein fragments). The nature of the biological sample can depend upon the nature of the subject. If a biological sample is from a subject that is a unicellular organism or a multicellular organism with undifferentiated tissue, the biological sample can comprise cells, such as a sample of a cell culture, an excision of the organism, or the entire organism. If a biological sample is from a multicellular organism, the biological sample can be a tissue sample, a fluid sample, or a secretion.

The biological samples can be obtained from different tissues. The term tissue is meant to include ensembles of cells that are of a common developmental origin and have similar or identical function. The term tissue is also meant to encompass organs, which can be a functional grouping and organization of cells that can have different origins. The biological sample can be obtained from any tissue.

The biological samples can be obtained from different tissue samples from one or more humans or non-human animals. Suitable tissues can include connective tissues, muscle tissues, nervous tissues, epithelial tissues or a portion or combination thereof. Suitable tissues can also include all or a portion of a lung, a heart, a blood vessel (e.g., artery, vein, capillary), a salivary gland, a esophagus, a stomach, a liver, a gallbladder, a pancreas, a colon, a rectum, an anus, a hypothalamus, a pituitary gland, a pineal gland, a thyroid, a parathyroid, an adrenal gland, a kidney, a ureter, a bladder, a urethra, a lymph node, a tonsil, an adenoid, a thymus, a spleen, skin, muscle, a brain, a spinal cord, a nerve, an ovary, a fallopian tube, a uterus, vaginal tissue, a mammary gland, a testicle, a vas deferens, a seminal vesicle, a prostate, penile tissue, a pharynx, a larynx, a trachea, a bronchi, a diaphragm, bone marrow, a hair follicle, or a combination thereof. A biological sample from a human or non-human animal can also include a bodily fluid, secretion, or excretion; for example, a biological sample can be a sample of aqueous humour, vitreous humour, bile, blood, blood serum, breast milk, cerebrospinal fluid, endolymph, perilymph, female ejaculate, amniotic fluid, gastric juice, menses, mucus, peritoneal fluid, pleural fluid, saliva, sebum, semen, sweat, tears, vaginal secretion, vomit, urine, feces, or a combination thereof. The biological sample can be from healthy tissue, diseased tissue, tissue suspected of being diseased, or a combination thereof.

In some embodiments, the biological sample is a fluid sample, for example a sample of blood, serum, sputum, urine, semen, or other biological fluid. In certain embodiments the sample is a blood sample. In some embodiments the biological sample is a tissue sample, such as a tissue sample taken to determine the presence or absence of disease in the tissue. In certain embodiments the sample is a sample of thyroid tissue.

The biological samples can be obtained from subjects in different stages of disease progression or different conditions. Different stages of disease progression or different conditions can include healthy, at the onset of primary symptom, at the onset of secondary symptom, at the onset of tertiary symptom, during the course of primary symptom, during the course of secondary symptom, during the course of tertiary symptom, at the end of the primary symptom, at the end of the secondary symptom, at the end of tertiary symptom, after the end of the primary symptom, after the end of the secondary symptom, after the end of the tertiary symptom, or a combination thereof. Different stages of disease progression can be a period of time after being diagnosed or suspected to have a disease; for example, at least about, or at least, 1, 2, 3, 4, 5, 6, 7, 8, 9, 10, 11, 12, 13, 14, 15, 16, 17, 18, 19, 20, 21, 22, 23 or 24 hours; 1, 2, 3, 4, 5, 6, 7, 8, 9, 10, 11, 12, 13, 14, 15, 16, 17, 18, 19, 20, 21, 22, 23, 24, 25, 26, 27 or 28 days; 1, 2, 3, 4, 5, 6, 7, 8, 9, 10, 11, 12, 13, 14, 15, 16, 17, 18, 19 or 20 weeks; 1, 2, 3, 4, 5, 6, 7, 8, 9, 10, 11 or 12 months; 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 years after being diagnosed or suspected to have a disease. Different stages of disease progression or different conditions can include before, during or after an action or state; for example, treatment with drugs, treatment with a surgery, treatment with a procedure, performance of a standard of care procedure, resting, sleeping, eating, fasting, walking, running, performing a cognitive task, sexual activity, thinking, jumping, urinating, relaxing, being immobilized, being emotionally traumatized, being shock, and the like.

The methods of the present disclosure provide for analysis of a biological sample from a subject or a set of subjects. The subject(s) may be, e.g., any animal (e.g., a mammal), including but not limited to humans, non-human primates, rodents, dogs, cats, pigs, fish, and the like. The present methods and compositions can apply to biological samples from humans, as described herein.

A biological sample can be obtained by methods known in the art such as the biopsy methods provided herein, swabbing, scraping, phlebotomy, or any other suitable method. The biological sample can be obtained, stored, or transported using components of a kit of the present disclosure. In some cases, multiple biological samples, such as multiple thyroid samples, can be obtained for analysis, characterization, or diagnosis according to the methods of the present disclosure. In some cases, multiple biological samples, such as one or more samples from one tissue type (e.g., thyroid) and one or more samples from another tissue type (e.g., buccal) can be obtained for diagnosis or characterization by the methods of the present disclosure. In some cases, multiple samples, such as one or more samples from one tissue type (e.g., thyroid) and one or more samples from another tissue (e.g., buccal) can be obtained at the same or different times. In some cases, the samples obtained at different times are stored and/or analyzed by different methods. For example, a sample can be obtained and analyzed by cytological analysis (e.g., using routine staining). In some cases, a further sample can be obtained from a subject based on the results of a cytological analysis. The diagnosis of a disease or condition, e.g. a coronary disease can include examination of a subject by a physician, nurse or other medical professional. The examination can be part of a routine examination, or the examination can be due to a specific complaint including, but not limited to, one of the following: pain, illness, anticipation of illness, presence of a suspicious lump or mass, a disease, or a condition. The subject may or may not be aware of the disease or condition. The medical professional can obtain a biological sample for testing. In some cases the medical professional can refer the subject to a testing center or laboratory for submission of the biological sample. The methods of obtaining provided herein include methods of biopsy including fine needle aspiration, core needle biopsy, vacuum assisted biopsy, incisional biopsy, excisional biopsy, punch biopsy, shave biopsy or skin biopsy. In some cases, the methods and compositions provided herein are applied to data only from biological samples obtained by FNA. In some cases, the methods and compositions provided herein are applied to data only from biological samples obtained by FNA or surgical biopsy. In some cases, the methods and compositions provided herein are applied to data only from biological samples obtained by surgical biopsy. A biological sample can be obtained by non-invasive methods, such methods including, but not limited to: scraping of the skin or cervix, swabbing of the cheek, saliva collection, urine collection, feces collection, collection of menses, tears, or semen. The biological sample can be obtained by an invasive procedure, such procedures including, but not limited to: biopsy, alveolar or pulmonary lavage, needle aspiration, or phlebotomy. The method of biopsy can further include incisional biopsy, excisional biopsy, punch biopsy, shave biopsy, or skin biopsy. The method of needle aspiration can further include fine needle aspiration, core needle biopsy, vacuum assisted biopsy, or large core biopsy. Multiple biological samples can be obtained by the methods herein to ensure a sufficient amount of biological material. Generic methods for obtaining biological samples are also known in the art and further described in for example Ramzy, Ibrahim *Clinical Cytopathology and Aspiration Biopsy* 2001 which is herein incorporated by reference in its entirety. The biological sample can be a fine needle aspirate of a thyroid nodule or a suspected thyroid tumor. The fine needle aspirate sampling procedure can be guided by the use of an ultrasound, X-ray, or other imaging device.

In some cases, the subject can be referred to a specialist such as an oncologist, surgeon, or endocrinologist for further diagnosis. The specialist can likewise obtain a biological sample for testing or refer the individual to a testing center or laboratory for submission of the biological sample. In any case, the biological sample can be obtained by a physician, nurse, or other medical professional such as a medical technician, endocrinologist, cytologist, phlebotomist, radiologist, or a pulmonologist. The medical professional can indicate the appropriate test or assay to perform on the sample, or the molecular profiling business of the present disclosure can consult on which assays or tests are most appropriately indicated. The molecular profiling business can bill the individual or medical or insurance provider thereof for consulting work, for sample acquisition and or storage, for materials, or for all products and services rendered.

A medical professional need not be involved in the initial diagnosis or sample acquisition. An individual can alternatively obtain a sample through the use of an over the counter kit. The kit can contain a means for obtaining said sample as described herein, a means for storing the sample for inspection, and instructions for proper use of the kit. In some cases, molecular profiling services are included in the price for purchase of the kit. In other cases, the molecular profiling services are billed separately.

A biological sample suitable for use by the molecular profiling business can be any material containing tissues, cells, nucleic acids, genes, gene fragments, expression products, gene expression products, and/or gene expression product fragments of an individual to be tested. Methods for determining sample suitability and/or adequacy are provided. The biological sample can include, but is not limited to, tissue, cells, and/or biological material from cells or derived from cells of an individual. The sample can be a heterogeneous or homogeneous population of cells or tissues. The biological sample can be obtained using any method known to the art that can provide a sample suitable for the analytical methods described herein.

Obtaining a biological sample can be aided by the use of a kit. A kit can be provided containing materials for obtaining, storing, and/or shipping biological samples. The kit can contain, for example, materials and/or instruments for the collection of the biological sample (e.g., sterile swabs, sterile cotton, disinfectant, needles, syringes, scalpels, anesthetic swabs, knives, curette blade, liquid nitrogen, etc.). The kit can contain, for example, materials and/or instruments for the storage and/or preservation of biological samples (e.g., containers; materials for temperature control such as ice, ice packs, cold packs, dry ice, liquid nitrogen; chemical preservatives or buffers such as formaldehyde, formalin, paraformaldehyde, glutaraldehyde, alcohols such as ethanol or methanol, acetone, acetic acid, HOPE fixative (Hepes-glutamic acid buffer-mediated organic solvent protection effect), heparin, saline, phosphate buffered saline, TAPS, bicine, Tris, tricine, TAPSO, HEPES, TES, MOPS, PIPES, cadodylate, SSC, MES, phosphate buffer; protease inhibitors such as aprotinin, bestatin, calpain inhibitor I and II, chymostatin, E-64, leupeptin, alpha-2-macroglobulin, pefabloc SC, pepstatin, phenylmethanesufonyl fluoride, trypsin inhibitors; DNAse inhibitors such as 2-mercaptoethanol, 2-nitro-5-thicyanobenzoic acid, calcium, EGTA, EDTA, sodium dodecyl sulfate, iodoacetate, etc.; RNAse inhibitors such as ribonuclease inhibitor protein; double-distilled water; DEPC (diethyprocarbonate) treated water, etc.). The kit can contain instructions for use. The kit can be provided as, or contain, a suitable container for shipping. The shipping container can be an insulated container. The shipping container can be self-addressed to a collection agent (e.g., laboratory, medical center, genetic testing company, etc.). The kit can be provided to a subject for home use or use by a medical professional. Alternatively, the kit can be provided directly to a medical professional.

One or more biological samples can be obtained from a given subject. In some cases, between about 1 and about 50 biological samples are obtained from the given subject; for example, about 1-50, 1-40, 1-30, 1-25, 1-20, 1-15, 1-10, 1-7, 1-5, 5-50, 5-40, 5-30, 5-25, 5-15, 5-10, 10-50, 10-40, 10-25, 10-20, 25-50, 25-40, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 biological samples can be obtained from the given subject. Multiple biological samples from the given subject can be obtained from the same source (e.g., the same tissue), e.g., multiple blood samples, or multiple tissue samples, or from multiple sources (e.g., multiple tissues). Multiple biological samples from the given subject can be obtained at the same time or at different times. Multiple biological samples from the given subject can be obtained at the same condition or different condition. Multiple biological samples from the given subject can be obtained at the same disease progression or different disease progression of the subject. If multiple biological samples are collected from the same source (e.g., the same tissue) from the particular subject, the samples can be combined into a single sample. Combining samples in this way can ensure that enough material is obtained for testing and/or analysis.

Also described herein is an RNA molecule comprising the IVT mRNA sequence initiator described herein. In some embodiments, the RNA comprises a guide RNA or a nuclease mRNA.

Also described herein is a cell containing an RNA molecule comprising the IVT mRNA sequence initiator described herein.

Also described herein is a cell containing a polypeptide translated from an RNA molecule comprising the IVT mRNA sequence initiator described herein.

Also described herein is a method for synthesizing an RNA molecule comprising:

a. introducing the IVT mRNA sequence initiator described herein into a mixture comprising an RNA polymerase, and
b. incubating the mixture for a time sufficient to allow for transcription of the RNA molecule.

Also described herein is a method of gene editing comprising introducing into a cell an RNA molecule described herein, or pharmaceutical composition described herein, wherein the RNA molecule comprises guide RNA or a nuclease mRNA, wherein the RNA molecule is translated in the cell.

EXAMPLES

The following examples are provided to better illustrate the present disclosure and are not to be interpreted as limiting the scope of the disclosure. To the extent that specific materials are mentioned, it is merely for purposes of illustration and is not intended to limit the disclosure. One skilled in the art may develop equivalent means or reactants without the exercise of inventive capacity and without departing from the scope of the disclosure.

Synthesis of Cap Structures
Example 1. Preparation of Trinucleotide Caps 1007a, 1032a, 1037a, 1107a, 1112a, 1137a, 1141a, 3102a, 3107a, 3207a, 3212a, 1007c, 1112c, 3102c, 3107c, 3207c, and 3212c
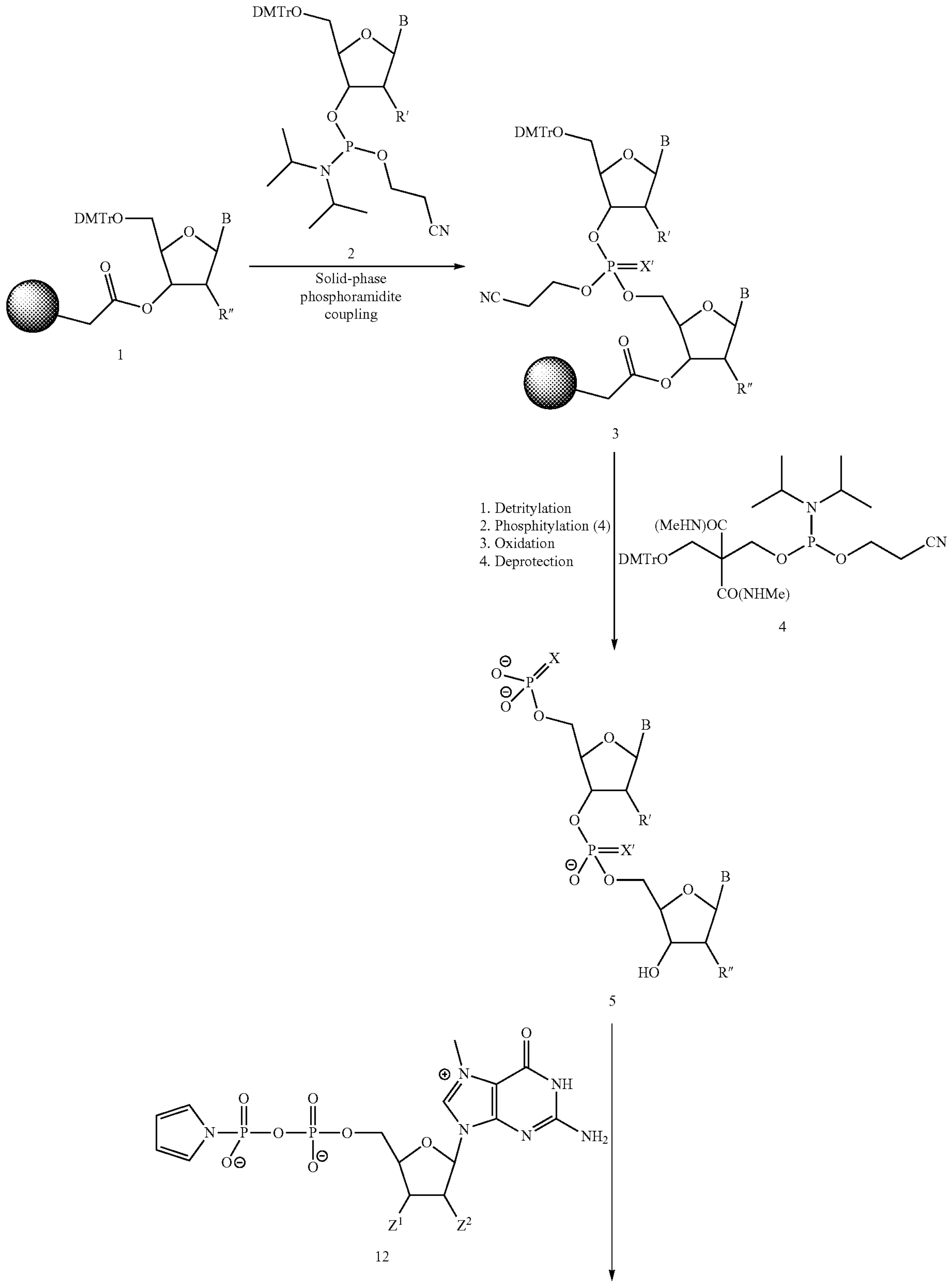
1 2 3 4 5 12

-continued

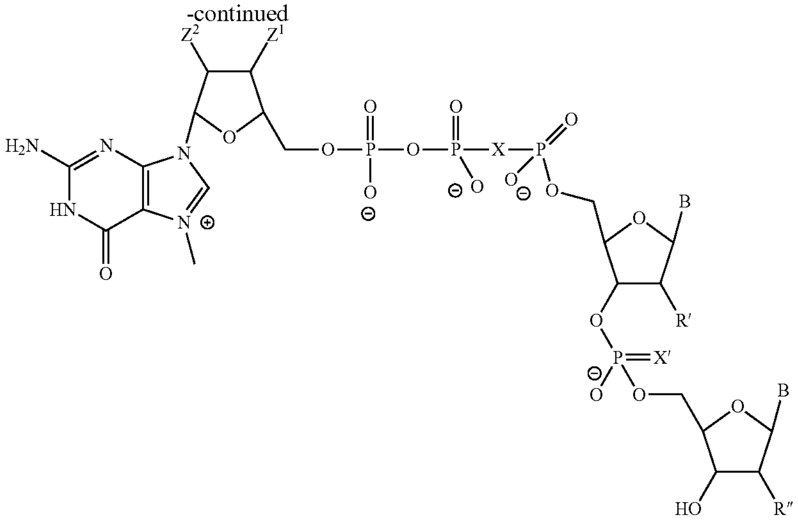

1007a, 1032a, 1037a, 1107a, 1112a, 1137a, 1141a, 3102a, 3107a, 3207a, 3212a, 1007c, 1112c, 3102c, 3107c, 3207c, and 3212c The dinucleotide 5'-phosphate 7 is prepared from the solid support 1 and phosphoramidite 3 by following standard solid phase oligonucleotide synthesis and deprotection protocol (Methods in Molecular Biology, 1993, 20, 81-114; ACS Chem. Biol. 2015, 10, 1181-1187, incorporated herein by reference in its entirety). The phosphoramidite 2 are purchased from commercial sources and/or custom synthesized. The detritylation of support bound fully protected dinucleotide 3 affords the 5'-deprotected dinucleotide intermediate on the support. The intermediate thus obtained is reared the 5'-phosphorylating agent 4 according to reported procedures (EP 816368 A1, https://www.glenresearch.com/solid-chemical-phosphorylation-reagent-ii.html, The Glen Report, 2011, 23, 10-11). After coupling and oxidation, the 5'-phosphorylated dinucleotide is treated with base followed by HPLC purification to obtain the fully deprotected dinucleotide 5'-phosphate 5 (https://www.glenresearch.com/solid-chemical-phosphorylation-reagent-ii.html).

Compound 12 is prepared from guanosine or 2' and/or 3' sugar-modified guanosine according to reported procedure (*Nucleic Acids Research,* 2016, 44, 9578; RNA, 2001, 7, 1486; WO 2017/053297 A1). Compound 12 is coupled with the dinucleotide 5'-monophosphate 5 as described in the literature (Nucleic Acids Research, 2016, 44, 9578, WO 2017/053297 A1) to afford the desired compounds 1007a, 1032a, 1037a, 1107a, 1112a, 1137a, 1141a, 3102a, 3107a, 3207a, 3212a, 1007c, 1112c, 3102c, 3107c, 3207c, and 3212c.

As generally described here in Example 1, compounds 1007a and 1107a (FIG. 1) were synthesized. A final amount of about 1 gram of compound 1007a was produced; this material was characterized by mass spectrometry and HPLC to have an actual mass of 1161 daltons and purity of 98.4%. Additionally, a final amount of about 250 milligrams of compound 1107a was produced; this material was characterized by mass spectrometry and HPLC to have an actual mass of 1161 daltons and purity of 97.5%. These compounds were used as mRNA initiators, as described in Example 5.

Example 2. Preparation of Trinucleotide Caps 1002e and 1007e

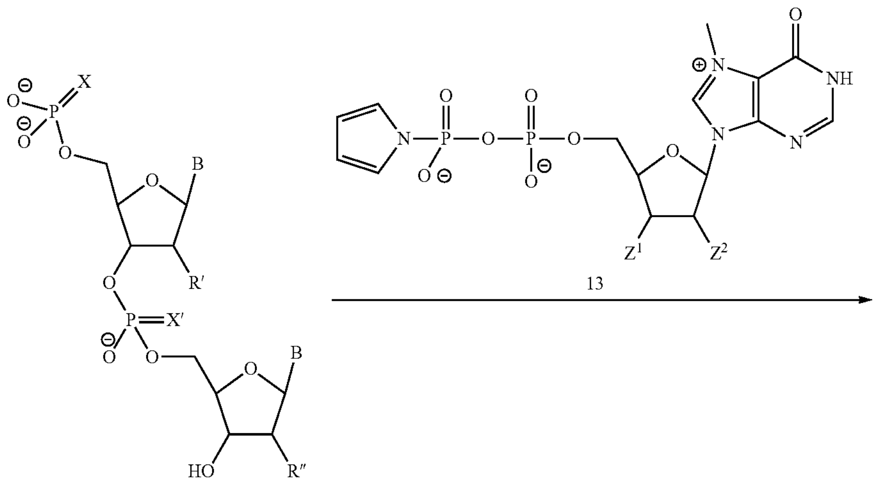

13

5

-continued
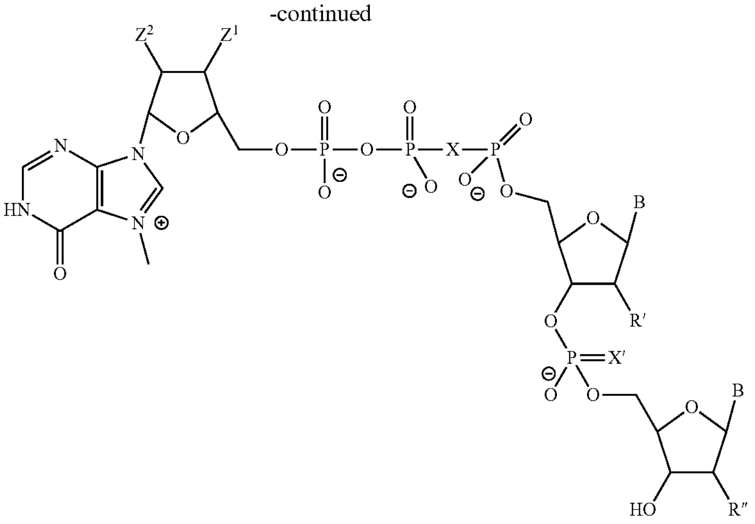
1002e and 1007e
Compound 13 is prepared from inosine or 2' and/or 3' sugar-modified inosine (*Nucleic Acids Research,* 2016, 44, 9578; RNA, 2001, 7, 1486; WO 2017/053297 A1). Compound 13 is then coupled with dinucleotide 5'-monophosphate 5 to afford compounds 1002e and 1007e as described above in Example 1
Example 3. Preparation of Trinucleotide Caps 1002i and 1007i
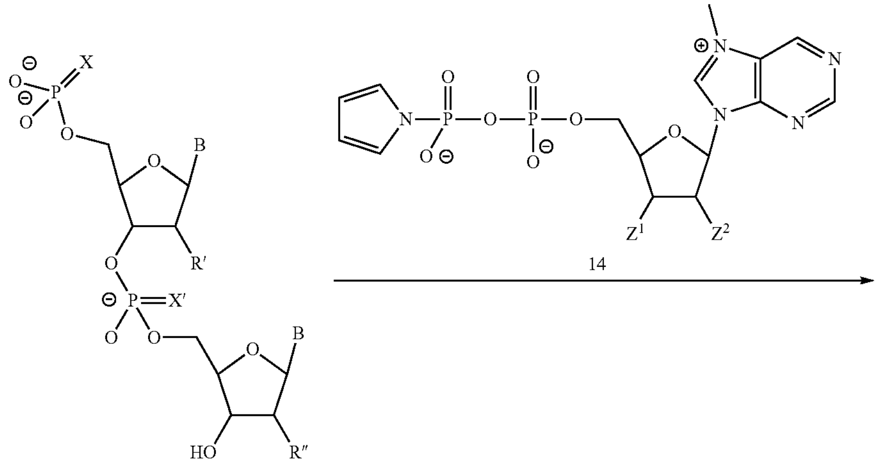
5

-continued
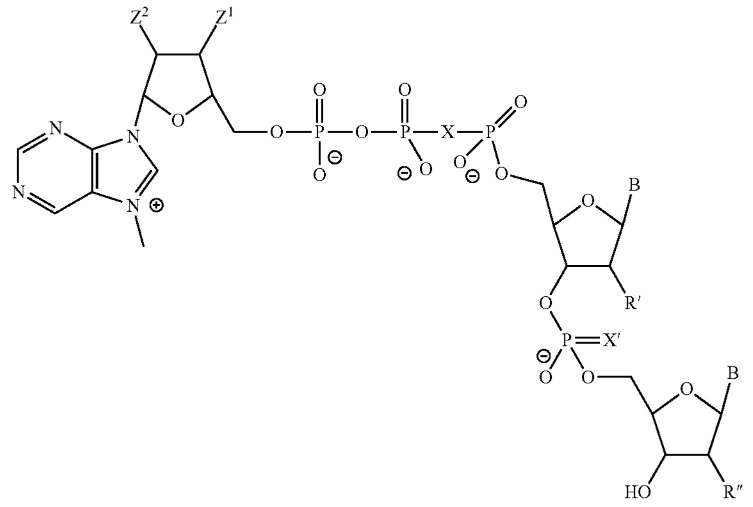
1002i and 1007i
Compound 14 is prepared from nebularine or 2' and/or 3' sugar-modified nebularine. Compound 13 is then coupled with dinucleotide 5'-monophosphate 5 to afford compounds 1002i and 1007i as described above in Example 1.
Example 4. Preparation of Tetranucleotide Caps 5203, 5204, 5267, 5288, 5209, 5210, and 5211
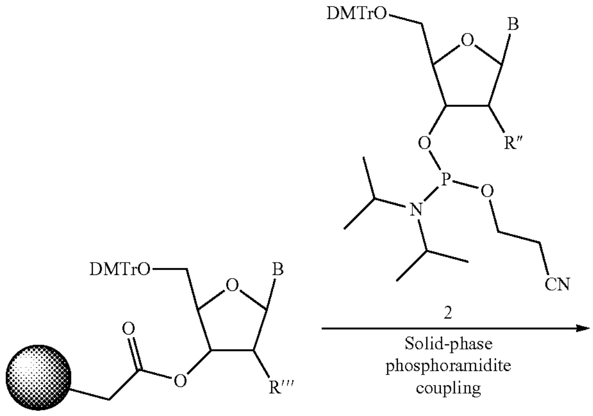
1

-continued
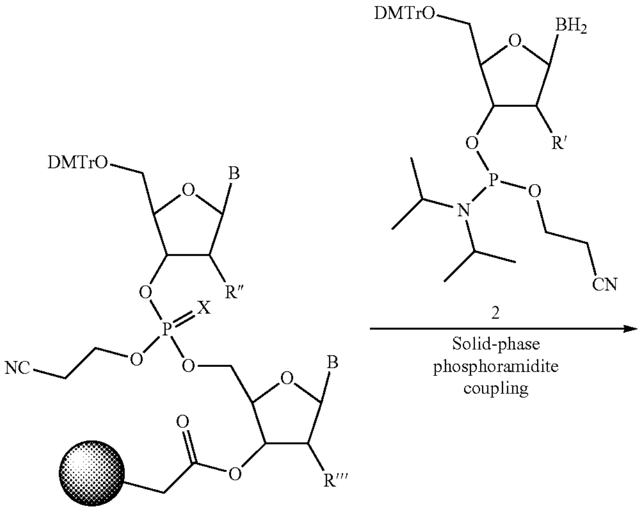
3
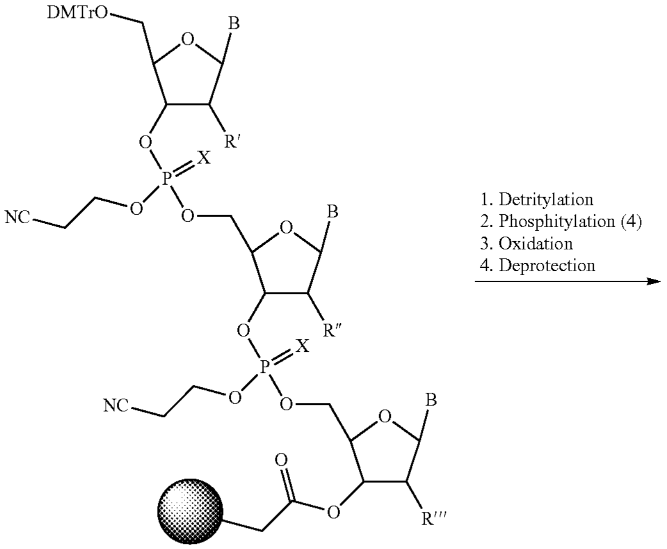
6

-continued
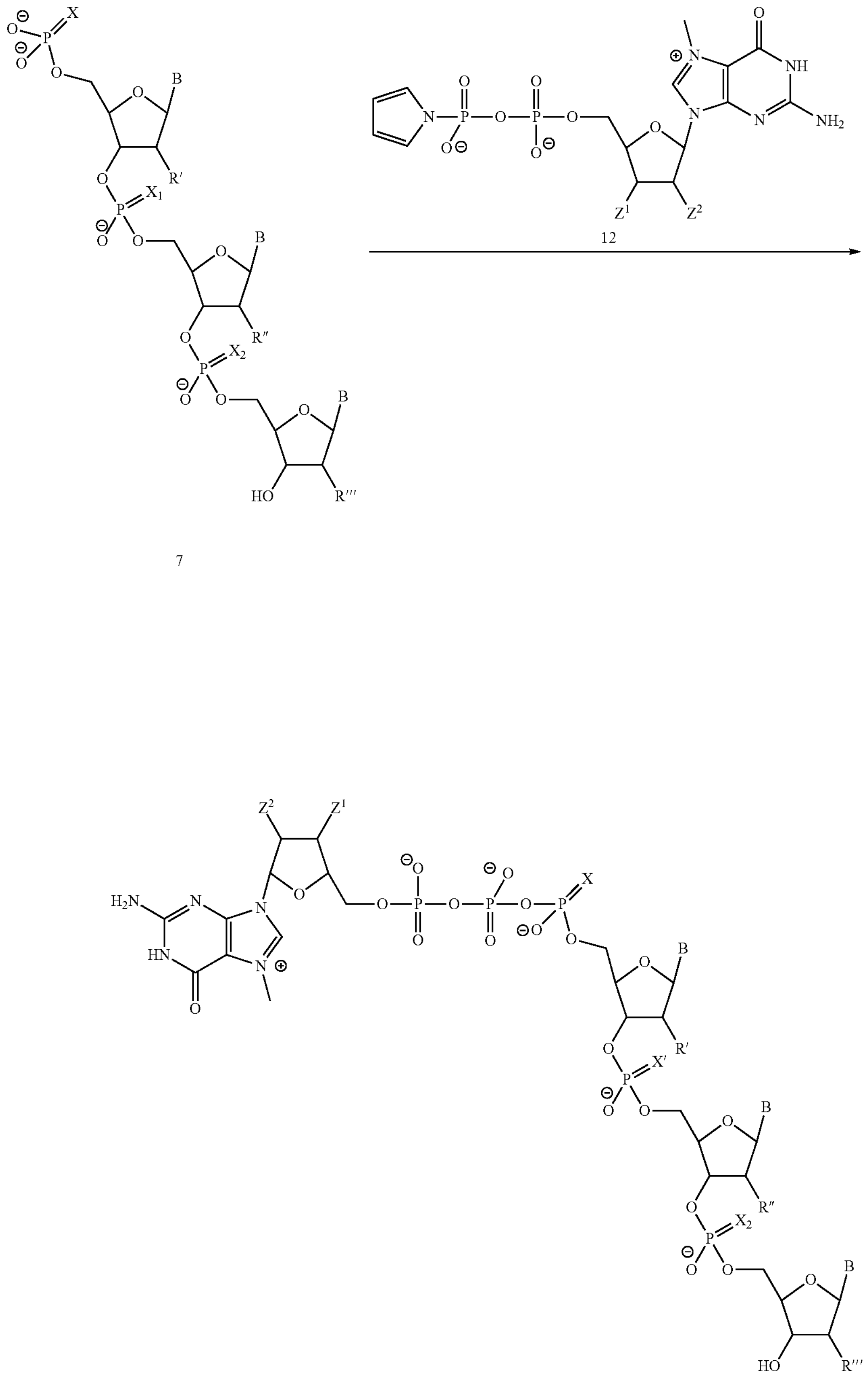
7
12
5203, 5204, 5207, 5208, 5209, 5210, and 5211

The trinucleotide 5'-monophosphate 7 is prepared form the solid support 1 by following a similar procedure described in Example 1 for the synthesis of the dinucleotide 5'-monophosphate. An additional phosphoramidite is coupled to the 5'-end of the fully-protected solid support bound dinucleotide under standard solid phase oligonucleotide conditions prior to reacting with the 5'-phosphorylating agent 4. Compound 7 thus obtained is then reacted with compound 12 to afford compounds 5203, 5204, 5207, 5208, 5209, 5210, and 5211.

Example 5. Preparation of Tetranucleotide Caps 5201 and 5205

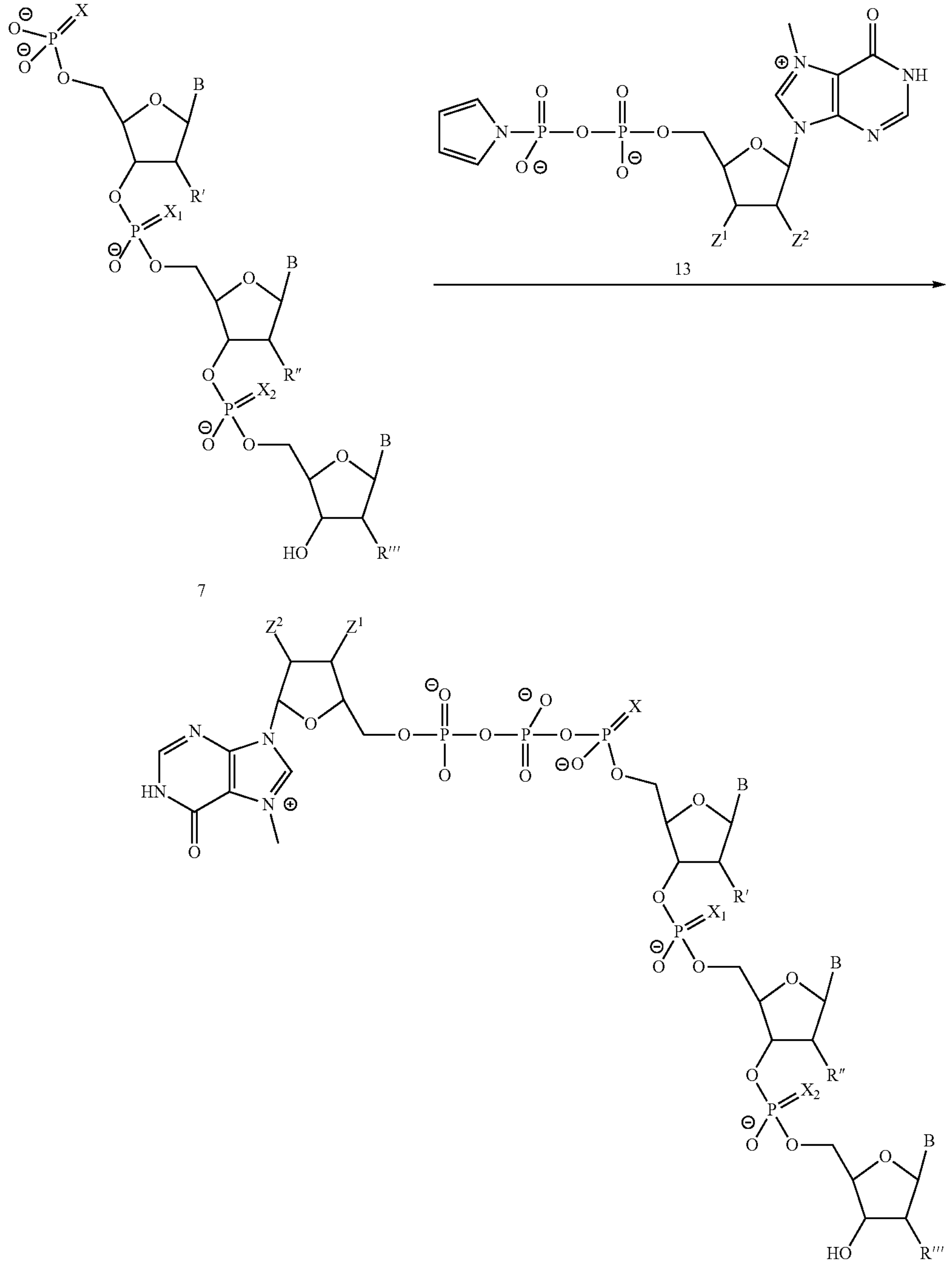

13

7

5201 and 5205

The desired compounds 5201 and 5205 are prepared from compound 7 and compound 13 as described in Examples 1-4.
Example 6. Preparation of Tetranucleotide Caps 5202 and 5206
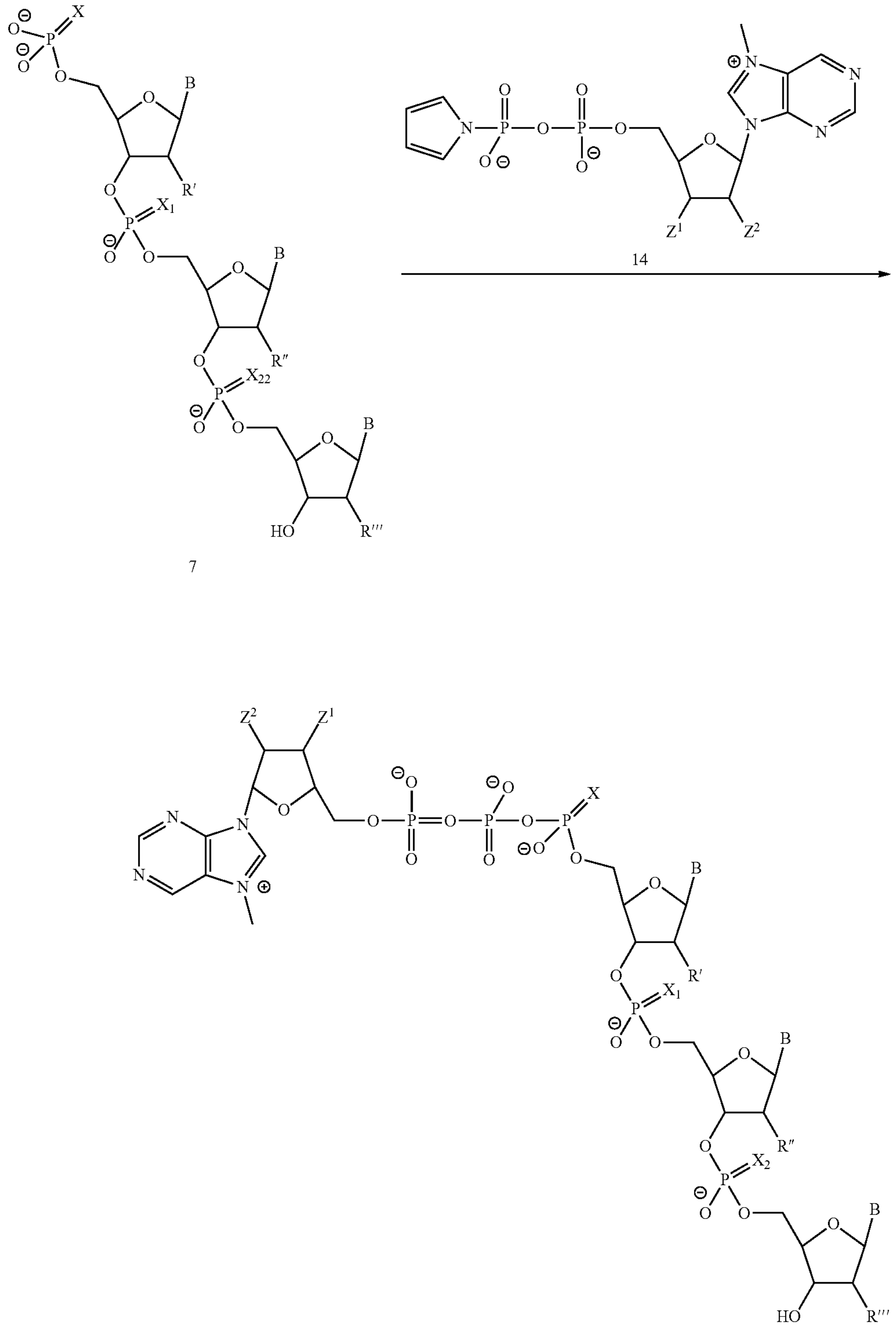
7
14
5202 and 5206

The desired compounds 5202 and 5206 are prepared from compound 7 and compound 14 as described in Examples 1-4.

Example 7. One-Pot Preparation of 5' Capped mRNA

A. mRNA Production

Figure 2:
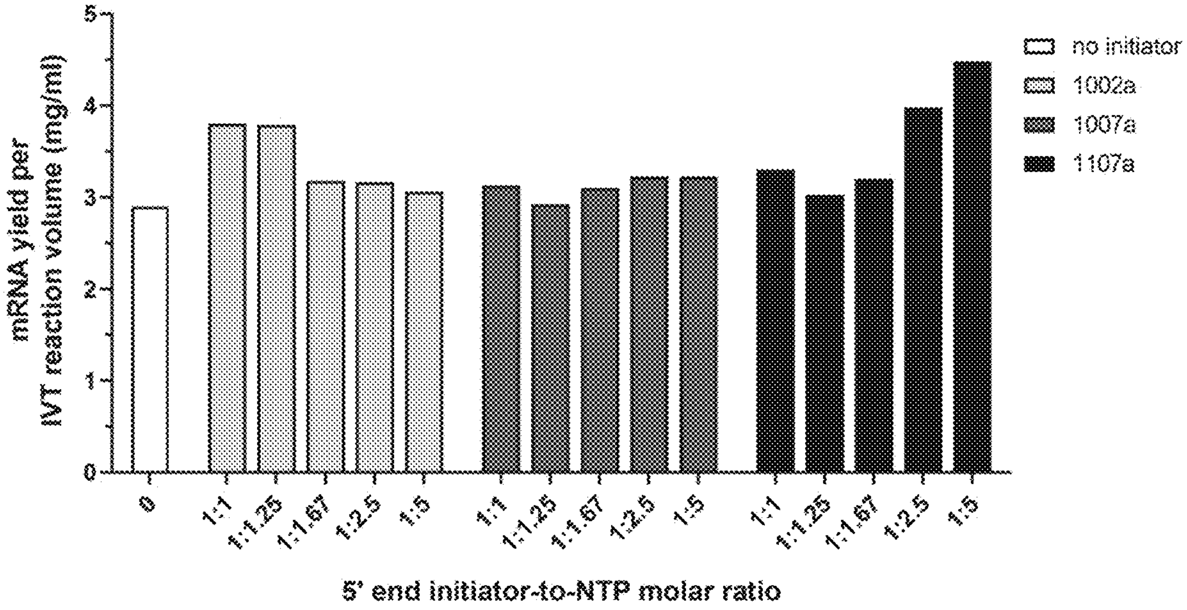
FIG. 2 illustrates a comparison of production yields for mRNAs that were prepared using different 5' end initiators.
Figure 3:
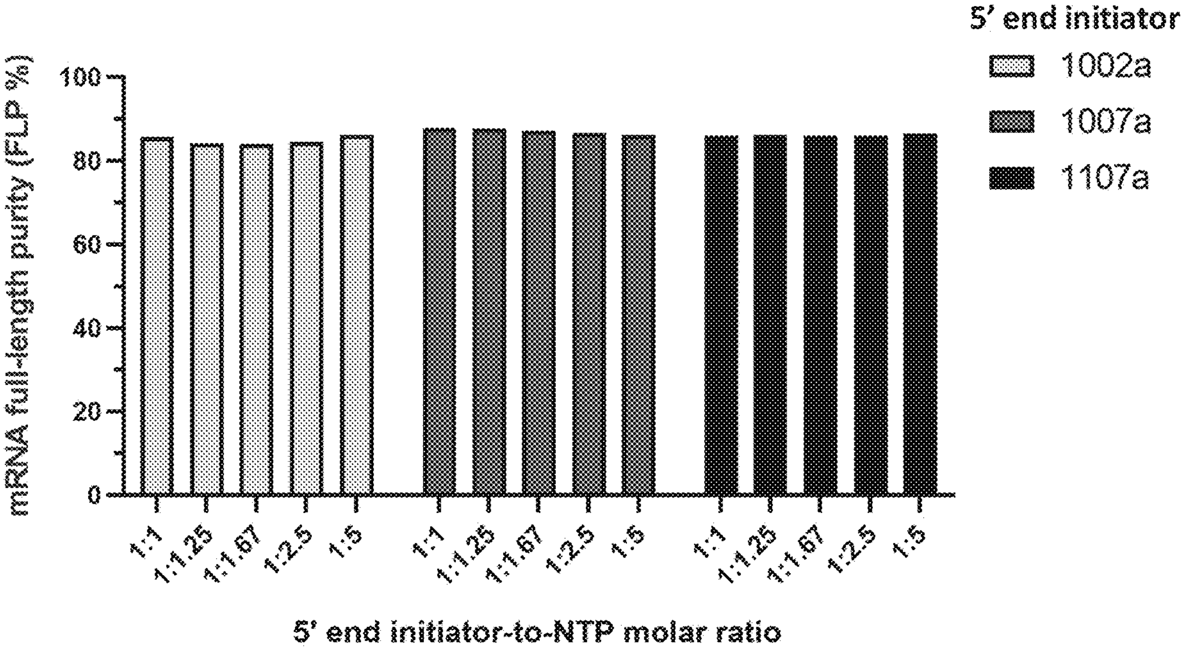
FIG. 3 illustrates a comparison of mRNA full-length purity between mRNAs that were prepared using different 5' end initiators.

The 5' end initiator, 1007a, (FIG. 1A) was used to prepare capped mRNAs that encode for ABE and luciferase proteins. In this Example and for all others described herein, the ABE mRNA sequence was MA004 (SEQ. 0001) and the luciferase mRNA sequence was the Photinus pyralis (Firefly) luciferase sequence described in NCBI reference sequence XM_031473197.1. These mRNA can be produced by different methods well known in the art. One of such methods used herein was in vitro transcription (IVT) using T7 polymerase; or in other embodiments, additional RNA polymerase variants. This IVT reaction to produce mRNA used a linearized DNA template that comprised a T7 polymerase promoter and associated regulatory sequences, mRNA coding sequence (CDS), 3' and 5' untranslated regions (UTRs), poly A tail, and additional sequence elements to facilitate and modulate mRNA stability and in vivo performance. Prior to IVT, the DNA template was in the form of a plasmid; in other embodiments the DNA template is in the form of a PCR product, synthetic DNA product, or any other double-stranded DNA construct. Linearization of the DNA template with a restriction digestion enzyme was performed in order to promote run-off transcription. The typical IVT reaction included T7 polymerase, DNA template, RNase inhibitor, cap analog, inorganic pyrophosphatase, and the naturally occurring ribonucleoside triphosphates (NTPs) such as GTP, ATP, CTP, and N1-methyl pseudouridine triphosphosphate; in some embodiments NTPs include UTP or modified NTPs such as pseudouridine, 5'methyl cytidine, 5-methoxy uridine, N6-methyl adenosine, and N4-acetyl cytidine. The 1007a 5' end initiator was added to the IVT reaction along with ATP, GTP, CTP, and N1-methyl pseudouridine triphosphate at a 1:1 initiator-to-NTP molar ratio and additional ratios described in Example 5 (B). Poly A tail was encoded in the DNA template that was added to the mRNA during transcription; in some instances, poly A tail is added to the mRNA after the IVT reaction using an RNA ligase enzyme. Finally, T7 RNA polymerase was added to the mixture and the IVT reaction was run at 37° C. for about 1-4 hours. After IVT, DNase was added to the transcription mixture to remove DNA template; in some instances, residual DNA is removed with chromatography. This mRNA was purified to remove residual reaction products and impurities, and stored in 1 mM citrate buffer. Characterization of production yield and mRNA full-length purity was performed by UV spectrometry and capillary gel electrophoresis methods, which are known in the art. The final production yield for ABE encoding mRNA with 5' end region motif, 1007a, was about 3.3 mg per 1 ml of IVT reaction (FIG. 2) and the mRNA had a full-length purity of about 88% (FIG. 3). As a comparison, the production yield for ABE encoding mRNA with 5' end motif, 1002a, a commercially available capping compound known in the art, was about 3.8 mg per 1 ml of IVT reaction (FIG. 2) and the mRNA had a full-length purity of about 86% (FIG. 3). Similar IVT and purification process are used to produce mRNA encoding SpCas9, Cas12b, CBE, and other ABEs; in all cases the DNA template, reaction conditions, and purification parameters are optimized for the specific gene of interest.

Similarly, ABE encoding mRNA with 5' end region, 1107a, (FIG. 1B) was produced and characterized as described in the paragraph above. The final production yield for mRNA with 5' end region, 1107a, was about 3.3 mg per 1 ml of IVT reaction (FIG. 2) and had a full-length purity of about 86% (FIG. 3).

Similarly, exemplary trinucleotide 5' end initiators 1007e, 1007i, 1002e, 1002i, 1032a, 1037a, 1112a, 1137a, 1141a, 3102a, 3107a, 3207a, 3212a, 1007c, 1107c, 1112c, 3102c, 3107c, 3207c, 3212c, 5212, 5213, and 5214 (described in Table 1) that include additional modifications to the triphosphate bridge, phosphodiester linkages, ribose ring functional groups, and tetranucleotide bases and other modifications are used to produce 5' capped mRNA as described above.

Similarly, exemplary tetranucleotide 5' end initiators 5201, 5202, 5203, 5204, 5205, 5206, 5207, 5208, 5209, 5210, and 5211 (described in Table 1) are used to produce 5' capped mRNA as described above.

Similarly, in other embodiments, trinucleotide and tetranucleotide 5' end initiators shown in Table 1 can be used to produce 5' capped mRNA as described in the paragraph above, and As noted by this example and the data generated, these will exhibit similar properties based on the results of this example.

B. Adjustment of mRNA 5' End Initiator-to-NTP Molar Ratio

The amount of capped mRNA produced in an IVT reaction is directly proportional to the ratio of cap to NTPs in the reaction mixture (Stepinski, J. et al., *RNA.* 2006, 7, 1486-1495). The 5' end initiator-to-NTP ratio in an IVT reaction impacts the amount of mRNA that becomes capped primarily because cap can compete with NTPs for insertion at the 5' end of mRNA. A typical initiator-to-NTP ratio for a dinucleotide cap structure is 4:1 and a typical molar initiator-to-NTP ratio for a trinucleotide cap structure is 1:1; where NTP represents either GTP, ATP, CTP, UTP, or modified NTPs such as N1-methyl pseudouridine. At both a 4:1 ratio for a dinucleotide cap and 1:1 ratio for a trinucleotide cap, the resultant mRNA will have a mixture of transcripts of which at least 80% are capped at the 5' end and up to 20% are uncapped, this is also described as a capping efficiency of 80%. Capping efficiency is the measured amount of capped mRNA divided by the total amount of capped mRNA plus uncapped mRNA. Therefore, trinucleotide caps can be considered more efficient capping compounds than dinucleotide caps since less input cap is required to produce a final mRNA product that contains a similar amount of capped 5' ends. The ability of trinucleotide caps to produce a high (>90%) capping efficiency at a lower initiator-to-NTP ratio than dinucleotide caps, in some instances, can be attributed to the increased affinity of a trinucleotide cap for the DNA template. In some cases, the optimal cap-to-NTP ratio may vary with the composition of the cap structure, wherein modification of cap structures may affect capping efficiency. For example, cap structures with phosphorothioate backbones modifications may exhibit reduced capping efficiency at a 1:1 initiator-to-NTP ratio compared to conventional phosphodiester backbones since phosphorothioate groups can weaken hybridization strength of complementary nucleic acids. Unexpectedly, mRNA capped with phosphorothioate-containing compound 1007a had a capping efficiency of greater than 90% at an initiator-to-NTP ratio ranging from 1:1 down to 1:2.5 (FIG. 4); this was similar to the capping efficiency of mRNA capped with the conventional phosphodiester-containing 5' end initiator, 1002a, using similar production conditions. Similarly, trinucleotide initiators, 1007e, 1007i, 1037a, 1112a, 1141a, 3107a, 3212a, 1007c, 1112c, 3107c, 3212c, 5214 and other trinucleotide cap structures described in Table 1 with phosphorothioate linkage between the first two initiating nucleotides are expected to also have similar capping efficiencies as compared to compound 1002a based on the observations seen in the previous example.

Figure 4:
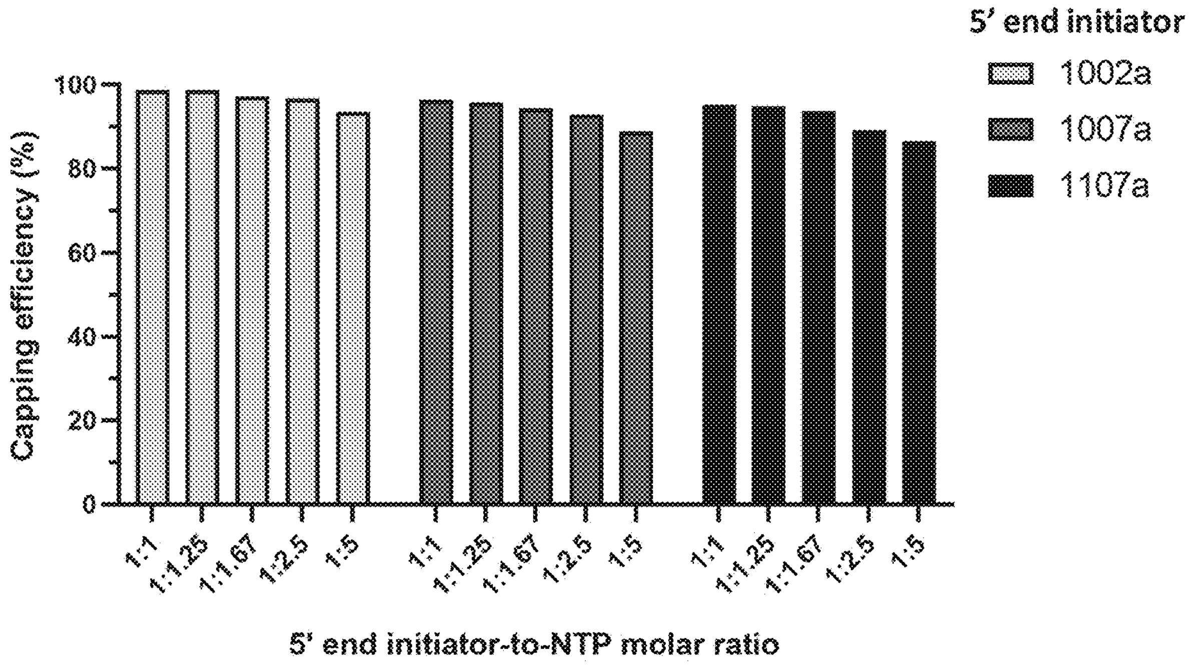
FIG. 4 illustrates a comparison of mRNA capping efficiency between mRNAs that were prepared using different 5' end initiators.

Phosphorothioate modification of the triphosphate bridge in a cap structure is not expected to reduce capping efficiency and production of mRNA containing triphosphate bridge-modified dinucleotide caps is well known in the art. Interestingly, mRNA was produced with cap compound 1107a (FIG. 2), which demonstrated that trinucleotide caps containing phosphorothioate modification of the triphosphate bridge can be incorporated into mRNA with >90% capping efficiency at an initiator-to-NTP ratio ranging from 1:1 down to 1:1.67 (FIG. 4). Similarly, trinucleotide cap structures with triphosphate bridge phosphorothioate modifications described in Table 1 are expected to have similar capping efficiencies as compared to 5' end initiator, 1107a, based on the observations seen in the previous example.

Additionally, tetranucleotide cap compounds 5201, 5202, 5203, 5204, 5205, 5206, 5207, 5208, 5209, 5210, 5211, and other cap structures described in Table 1 may also produce mRNA with >90% capping efficiency at an initiator-to-NTP ratio of 1:1 and below due to the increased hybridization strength of the tetranucleotide cap compared to trinucleotide and dinucleotide caps.

Furthermore, as seen with mRNA made with compounds 1007a and 1107a, an initiator-to-NTP ratio ranging from 1:1 down to 1:5 did not reduce the amount of full-length mRNA produced (FIG. 3), and so the chemically modified cap compounds described herein were able to function as mRNA initiators across a, range of reaction conditions. As noted by this example and the data generated, it is contemplated that the remaining compounds described in Table 1 will exhibit similar properties based on the results of this example.

C. Determination of mRNA Capping Efficiency

The amount of capped mRNA relative to the total amount of mRNA that is present, i.e. capping efficiency, can be measured by numerous methods well known in the art. One of such methods is digestion of the mRNA into small fragments followed by chromatographic separation and detection. In some cases, digestion is performed with sequence-specific RNA or DNA nucleases or cleavage enzymes. Chromatographic separation and measurement of capped RNA is typically performed by HPLC, FPLC, thin layer chromatography, gel electrophoresis, or capillary gel electrophoresis techniques. Identity of capped RNA and uncapped mRNA is verified by mass spectrometry.

Example 8. Measurement of Capped mRNA Stability

Removal of the cap from mRNA, i.e. decapping, is a common initiating step in the degradation of mRNA within cells. Reported methods for measuring decapping and mRNA degradation are used to evaluate the stability of capped mRNA (Grudzien, E. et al., *J. Biol. Chem.* 2006, 281, 1857-1867). Cap structures that prevent the interaction of decapping enzymes may improve mRNA stability and half-life in cells. For example, mRNA with 5' end region motifs, 1032a, 1037a, 1107a, 5207a, 1112a, 1137a, 1141a, 5208, 3207a, 3212a, 1107c, 1112c, 3207c, and 3212c, contain phosphorothioate modifications in the triphosphate linkage that may inhibit the activity of dcp2 decapping enzyme. Similarly, other compounds as described in Table 1 containing phosphorothioate modifications in the triphosphate linkage may also inhibit the activity of dcp2 decapping enzyme based on the results of the previous examples. Stability of mRNA may also be improved with cap modifications that inhibit exonuclease activity. For example, introduction of phosphorothioate modifications between the first two or three initiating nucleotides in the cap structure, as present in mRNA with 5' end region motifs, 1007a, 1007e, 1007i, 1037a, 1112a, 1141a, 3107a, 3212a, 1007c, 1112c, 3107c, 3212c, 5203, 5204, 5205, 5206, 5209, 5210, 5211, 5214, may reduce the rate of mRNA degradation in cells. Similarly, other compounds as described in Table 1 with a phosphorothioate modification between the first two or three initiating nucleotides in the cap structure may also reduce the rate of mRNA degradation in cells as seen by the previous example.

Example 9. Translation of Capped Luciferase mRNA in Hela Cells and Lysates

Figure 5:
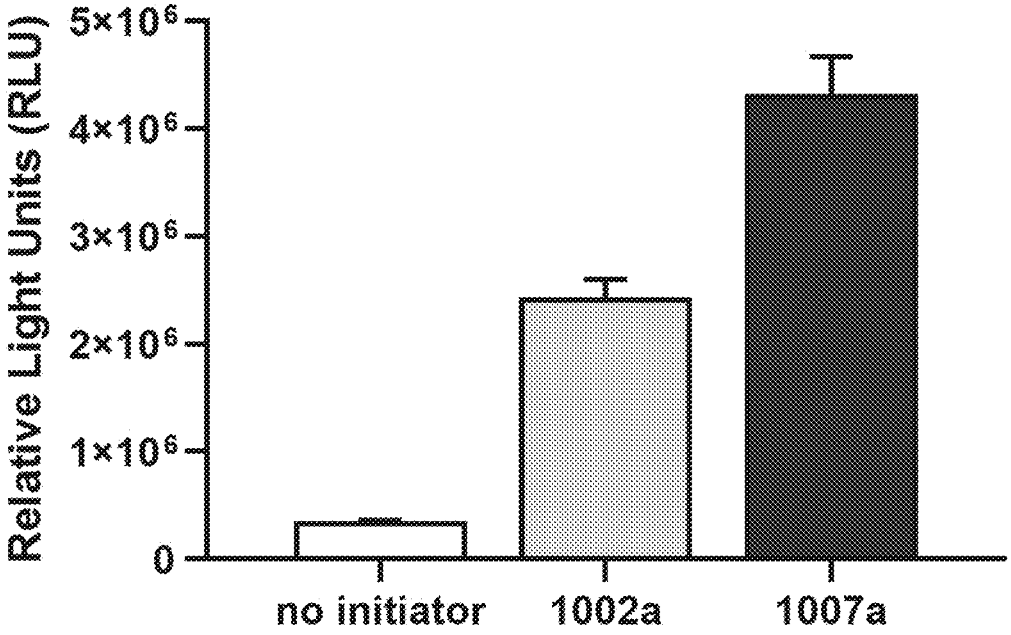
FIG. 5 illustrates protein expression of mRNAs comprising different 5' end region motifs in HeLa cell lysate.

HeLa cells are cultured in RPMI with 10% FBS at 37° C. under 5% $CO_2$ atmosphere. Cells are plated into an appropriately sized well plate per manufacturer's recommended seeding conditions. After overnight incubation, cells are checked for monolayer formation and then transfected using a transfection agent such as MessengerMAX. Solution A: the desired amount of luciferase mRNA is diluted in OptiMEM and mixed with Solution B: MessengerMAX in OptiMEM. After mixing solutions A and B, the mixture is incubated at room temperature for 20 minutes, and then added dropwise to each well of cells. The cells are then incubated at 37° C. for 12-72 hours to allow for expression of mRNA into protein. Cells are harvested and prepared for measuring luciferase protein levels per Promega luciferase assay system protocol. In some instances, mRNA is directly administered to HeLa lysates that contain the cellular components for protein expression, this approach does not require the use of a transfection agent. For example, luciferase encoding mRNA with 5' end region motif, 1007a, was added to a commercially available HeLa lysate in vitro translation kit to produce luciferase protein. Luciferase protein activity as measured by luminescent light production in the presence of a luciferin substrate, was measured with a luminescence-detecting plate reader. Relative light units measured per this assay are proportional to the amount of luciferase protein translated from mRNA. The results of this Example were compared using a mRNA made with a commercially available 5' end initiator, 1002a, as a reference. In this example, the mRNA with initiator 1007a produced around 2x greater luciferase activity than the mRNA with initiator 1002a (FIG. 5). As noted by this example and the data generated, it is contemplated that the remaining compounds described in Table 1 will exhibit similar properties based on the results of this example.

Figure 6:
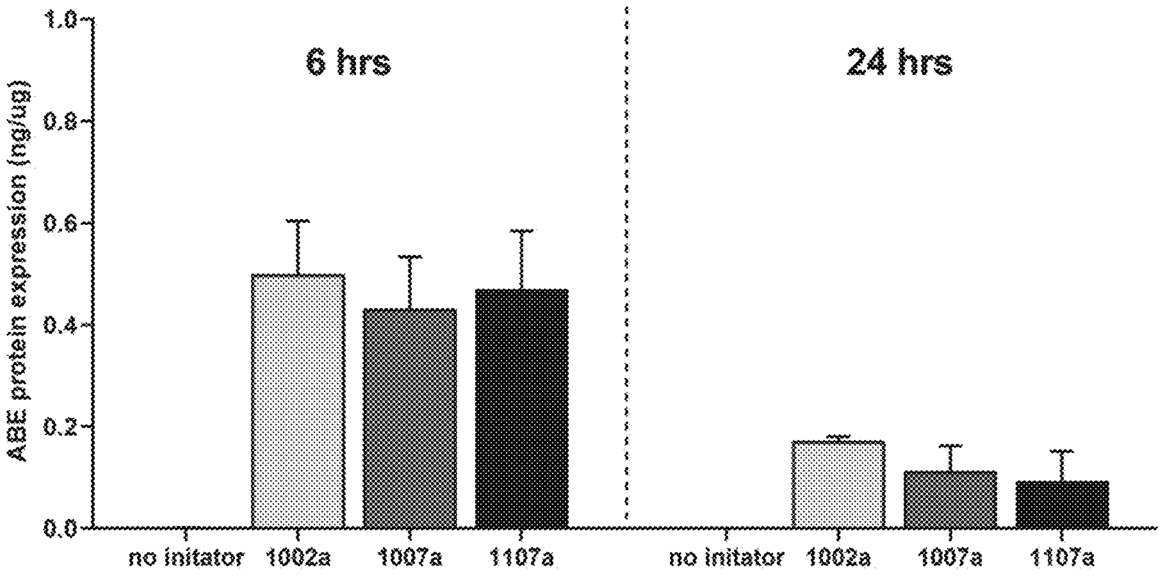
FIG. 6 illustrates protein expression of mRNAs comprising different 5' end region motifs in primary human hepatocyte cells.

Example 10. Translation of Capped mRNA in Primary Hepatocyte Cells for Genome Editing Primary human liver hepatocytes (hPH), primary cynomolgus liver hepatocytes (cPH), or primary mouse liver hepatocytes (mPH) are cultured per the manufacturer's protocol. In brief, the cells are thawed and resuspended in hepatocyte thawing medium followed by centrifugation at 100 g for 10 min at 4° C. The supernatant is discarded, and the pelleted cells resuspended in hepatocyte plating medium. Each vial contains ~5 million cells that are used for plating one 24-well plate. Plated cells are allowed to settle and adhere for 4-6 h in a tissue culture incubator at 37° C. under 5% $CO_2$ atmosphere. After incubation, cells are checked for monolayer formation. The incubating media is then replaced with fresh hepatocyte maintenance media The cells thus are ready for transfection using a transfection agent such as MessengerMAX. Solution A: desired amount of single guide RNA (sgRNA) is mixed with 1:1 wt ratio of mRNA in OptiMEM. Solution B: MessengerMAX in OptiMEM. After mixing solutions A and B, the mixture is incubated at room temperature for 20 minutes, and then the incubated solution is added dropwise to each well of cells. The cells are then allowed to remain at 37° C. for 3 days. Cells are harvested and prepared for genomic DNA extraction using Thermo Kingfisher instrument. Extracted genomic DNA is processed by PCR, and amplified PCR product was then subjected to NGS (MiSeq) to analyze genome editing. In some instances, hPH are transfected with ABE encoding mRNA as described above and the levels of translated ABE protein are used to assess the mRNA function. For example, mRNA with 5' end region motifs, 1007a and 1107a, were transfected to hPH cells as described above, the cells were lysed, and ABE protein levels were measured by ELISA. The results of this example were compared using ABE mRNA made with a commercially available initiator, 1002a, as a reference. In this example, the mRNAs with 5' end region motifs, 1007a and 1107a, produced similar ABE protein levels as compared to the mRNA with 5' end region motif, 1002a (FIG. 6). As noted by this example and the data generated, it is contemplated that the remaining compounds described in Table 1 will exhibit similar properties based on the results of this example.

Example 11. Translation of Capped mRNA In Vivo in Mouse for Genome Editing

A. LNP Preparation for In Vitro Transfection and In Vivo Evaluation

Lipid nanoparticles (LNPs) are generated by microfluidic mixing using the Precision Nanosystems NanoAssemblr system according to the manufacturer's protocol, with some optimization for individual payloads. The resulting LNPs are filtered using 0.2-micron filters and stored at 4° C. or frozen at 80° C.

B. In Vivo Evaluation in Mice

LNPs used in these studies are prepared as described above in Example 6 (A), comprising chemically synthesized sgRNAs targeting the mouse ANGPTL3 (mANGPTL3) and/or mouse PCSK9 (mPCSK9) genes and SpCas9 or ABE8.8 mRNA in a 1:1 weight ratio, are administered to C57BL/6 mice (n=5) intravenously via the lateral tail vein or retro-orbital sinus in a total volume of 5-10 ml/kg. 4 or 5 days post dose at necropsy, livers and blood are collected for NGS measurements of editing efficiency, and serum PCSK9, triglyceride and cholesterol analyses.

C. Genomic DNA Isolation

Genomic DNA is isolated from approximately 20 microliters of whole mouse liver lysate using a bead-based extraction kit, MagMAX-96 DNA Multi-Sample Kit on the KingFisher Flex automated extraction instrument according to the manufacturer's protocols. Mouse whole liver is lysed using the FastPrep-24 system according the to manufacturer's protocol. Livers are loaded into 2 mL lysing matrix tubes with 0.5 mL of PBS. Extracted genomic DNA is stored at 4° C. until further use or at −80° C. for long term storage.

D. Next Generation Sequencing (NGS) and Analysis of Editing Efficiency

Next generation sequencing, or deep sequencing, is performed on the region of interest to determine the extent of gene editing. Samples are prepared using the Nextera XT DNA library preparation kit (Illumina) according to the manufacturer's protocol. Briefly, two rounds of PCR are performed first to amplify the region of interest and second to add DNA sequences required for deep sequencing and sample identification to the initial product. The final amplicon is sequenced on the Illumina MiSeq instrument according to the manufacturer's protocol.

Paired-end reads are analyzed with the CRISPResso2 pipeline (Clement, K. et al., *Nat. Biotech.* 2019, 37, 224-226). Briefly, low-quality reads are filtered out, adapter sequences are trimmed from the reads, and the paired-end reads are merged and aligned to the amplicon sequence. The editing percentage is calculated as the number of reads supporting an insertion or a deletion, over the total number of aligned reads. For ABE, the editing percentage is calculated as the number of reads supporting an insertion or a deletion, over the total number of aligned reads.

Figure 7:
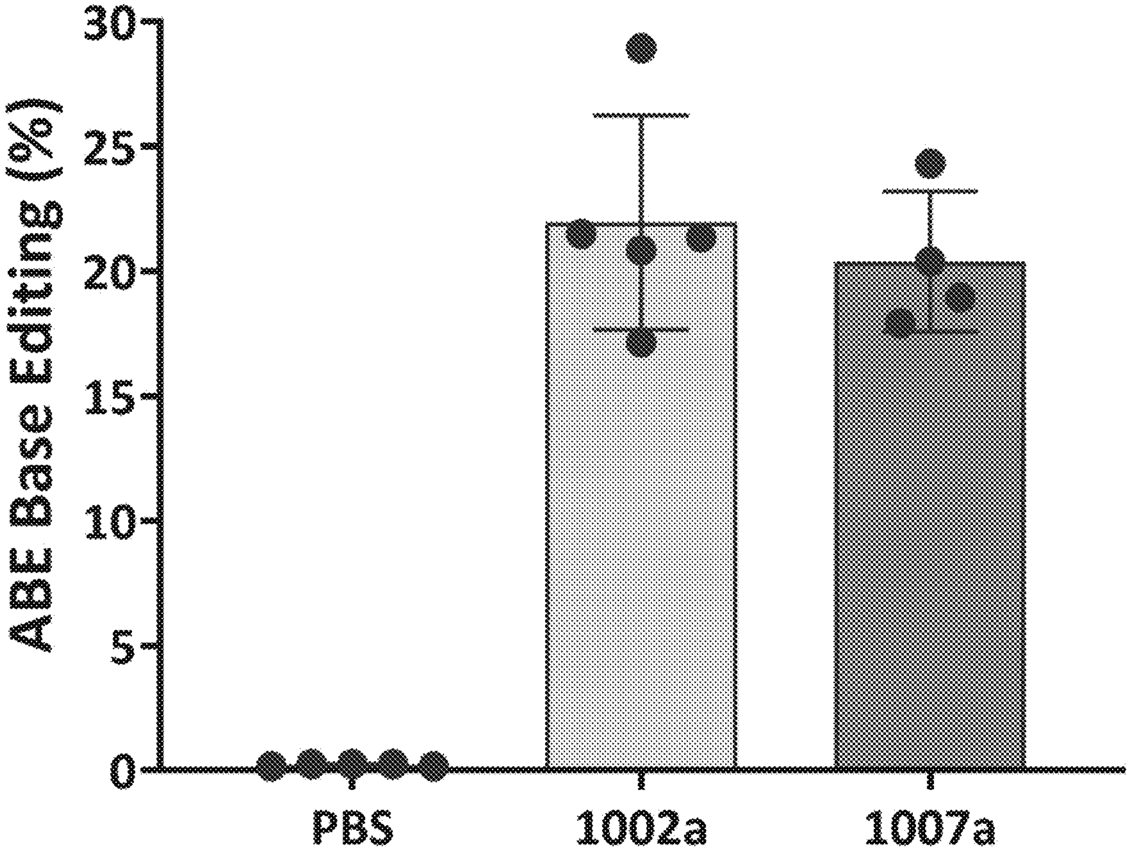
FIG. 7 illustrates a comparison of ABE base editing using the protein encoded by mRNAs comprising different 5' end-region motifs in vivo in mouse.

In some instances, LNPs were formulated with sgRNA targeting mPCSK9 and ABE encoding mRNAs with 5' end region motif, 1007a, administered in vivo to mice, and editing efficiency was assessed as described in Example 11. The results of this example were compared using ABE encoding mRNA made with a commercially available 5' end initiator, 1002a, as a reference. In this example, the mRNA with 5' end region motif, 1007a, produced similar hepatocyte editing levels as compared to the mRNA with 5' end region motif, 1002a (FIG. 7). As noted by this example and the data generated, it is contemplated that the remaining compounds in Table 1 will exhibit similar properties based on the results of this example.

Figure 8:
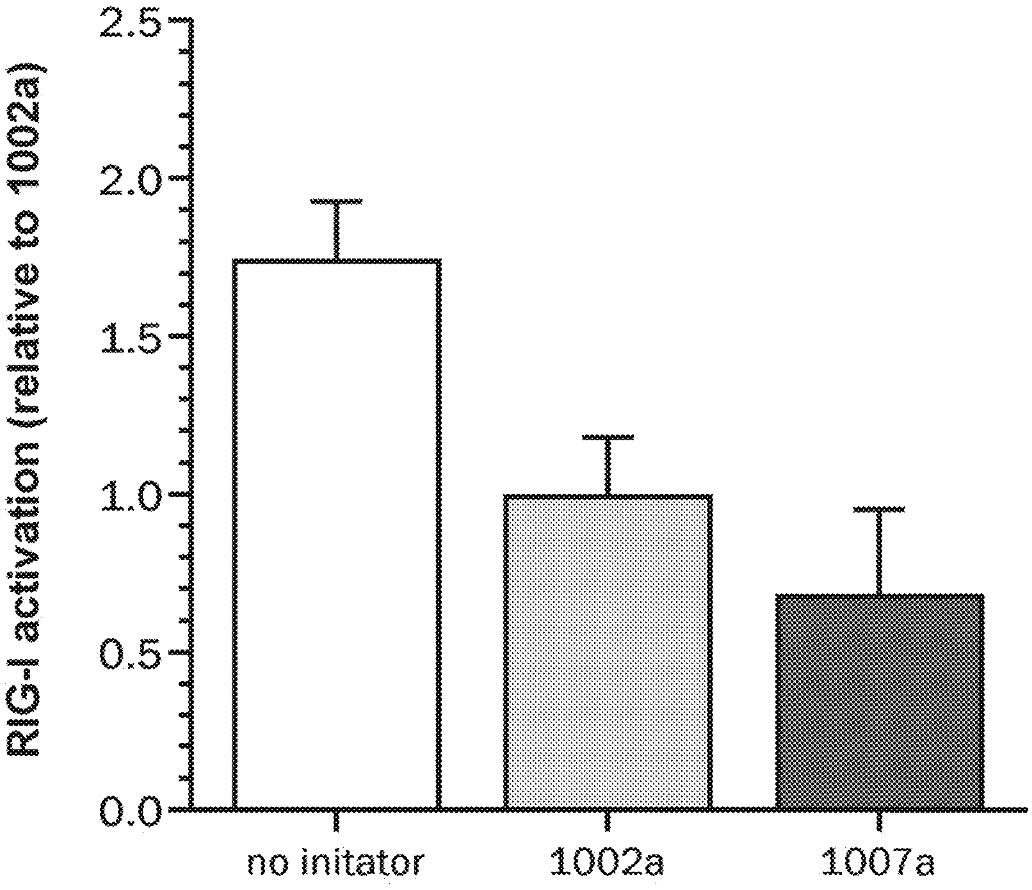
FIG. 8 illustrates immune stimulation of mRNA comprising different 5' end-regions motifs in HEK293 cells.

Example 12. Determination of Immune Stimulation of Capped mRNA In Vivo in Mouse or in an In Vitro HEK293 Cell Model LNPs are prepared and administered in vivo to mice as in Example 11(A,B). Blood is collected at appropriate time points, typically at intervals between 1-48 hours post-dose and terminal end point, and processed to serum or plasma per techniques well known in the art. Serum or plasma cytokine and chemokine levels are measured using V-PLEX cytokine and chemokine detection kits. Cytokine and chemokine levels are compared to animals treated with buffer alone as well as pre-dose sampling of the treatment animals. In some instances, the immune stimulation of capped mRNA is assessed after in vitro transfection to reporter cell lines such as HEK-Lucia RIG-I cell reporter model, which produces luciferase signal in the presence of IFN-stimulated response elements such as uncapped mRNA. This cell model is cultured and transfected as described in Example 7, and luciferase activity is measured using a luciferase activity kit and plate reader. It is known in the art that uncapped mRNA produces a RIG-I-dependent IFN immune response, and capped mRNA lessens this immune stimulation. In this example, mRNA with 5' end region motif, 1007a, showed reduced RIG-I activity as compared to uncapped mRNA using the HEK-Lucia RIG-I cell reporter model (FIG. 8). Furthermore, mRNA with 5' end region motif, 1007a, did not appear to increase RIG-I activation as a result of the chemical modifications to the cap structure. The results of this example were compared using mRNA made with a commercially available 5' end initiator, 1002a, as a reference. As noted by this example and the data generated, it is contemplated that the remaining compounds in Table 1 will exhibit similar properties based on the results of this example.

Other Embodiments

From the foregoing description, it will be apparent that variations and modifications may be made to the disclosure described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

While specific examples and numerous embodiments have been provided to illustrate aspects and combinations of aspects of the foregoing, it should be appreciated and understood that any aspect, or combination thereof, of an exemplary or disclosed embodiment may be excluded therefrom to constitute another embodiment without limitation and that it is contemplated that any such embodiment can constitute a separate and independent claim. Similarly, it should be appreciated and understood that any aspect or combination of aspects of one or more embodiments may also be included or combined with any aspect or combination of aspects of of one or more embodiments and that it is contemplated herein that all such combinations thereof fall within the scope of this disclosure and can be presented as separate and independent claims without limitation. Accordingly, it should be appreciated that any feature presented in one claim may be included in another claim; any feature presented in one claim may be removed from the claim to constitute a claim without that feature; and any feature presented in one claim may be combined with any feature in another claim, each of which is contemplated herein. The following enumerated clauses are further illustrative examples of aspects and combination of aspects of the foregoing embodiments and examples:

1. An in vitro-transcribed (IVT) mRNA sequence initiator comprising a compound of Formula (I) or a salt or solvate thereof:

Formula (I)

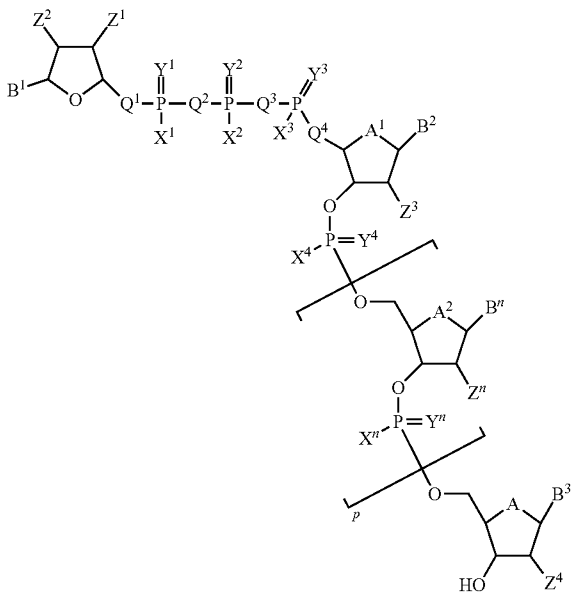

wherein $B^1$ is

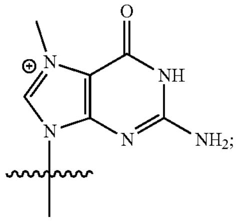 [SMILES: *n1c[n+](C)c2c(=O)[nH]c(N)nc21]

each $B^2$, $B^3$, and $B''$ is independently a natural, a modified, or an unnatural nucleobase;

each $Z^1$ and $Z^2$ is independently hydrogen, fluorine, —OH, —SH, —$CH_3$, —$CH_2CH_3$, —$OCH_3$, —$OCH_2CH_3$, —$SCH_3$, —$NH_2$, $NHCH_3$, or NHC(=O)$CH_3$;

each $Z^3$, $Z^4$, and $Z''$ is independently hydrogen, fluorine, —OH, —SH, —$CH_3$, —$CH_2CH_3$, —$OCH_3$, —$NH_2$, —$NHCH_3$, —NH(C(=O)$CH_3$), —$OCH_2CH_3$, —$OCH_2OCH_3$, —$OCH_2CH_2CH_3$, —OCH$(CH_3)_2$, —$SCH_3$, or —$OCH_2CH_2OCH_3$;

each $Q^1$ and $Q^4$ is independently —$CH_2$—, —CH=CH—, —$CH_2O$—, —$CH_2S$—, —$CH_2CH_2$—, —$CH_2CF_2$—, —$CH_2NH_2$—, —$CH_2$NH($CH_3$)—, or —$CH_2$N(C(=O)$CH_3$)—;

each $Q^2$ and $Q^3$ is independently —O—, —S—, —$CH_2$—, —$CF_2$—, —NH—, —N($CH_3$)—, or —N(C(=O)$CH_3$)—;

each $X^1$, $X^2$, $X^3$, $X^4$, and $X''$ is independently —OH, —SH, —O—, —S, —$NH_2$, —$NHCH_3$, —NH(C(=O)$CH_3$), —$CH_3$, —$CH_2CH_3$, —$CH_2CH_2CH_3$, —CH$(CH_3)_2$, —$OCH_3$, or —$OCH_2CH_3$;

each $Y^1$, $Y^2$, $Y^3$, $Y^4$, and $Y''$ is independently =O, =S, =NH, or =$NCH_3$;

each A, $A^1$, and $A^2$ is independently —O—, —S—, —$CH_2$—, —NH—, —N($CH_3$)— or —N(C(=O)$CH_3$)—; and p=0, 1, 2, 3, 4, 5 or 6, provided that the compound of Formula (I) satisfies one or more of the following proviso (i) to (iii): (i) at least one of $X^1$, $X^2$, $X^3$, $X^4$, and $X''$ is —SH or —S; (ii) at least one of $Y^1$, $Y^2$, $Y^3$, $Y^4$, and $Y''$ is =S; and (iii) at least one of A, $A^1$, and $A^2$ is —S—.

2. The IVT mRNA sequence initiator of clause 1, wherein at least one of $X^1$, $X^2$, $X^3$, $X^4$, and $X''$ is —SH or —$S^-$; at least one of $Y^1$, $Y^2$, $Y^3$, $Y^4$, and $Y''$ is =S; or at least one of A, $A^1$, and $A^2$ is —S—.

3. An in vitro-transcribed (IVT) mRNA sequence initiator comprising a compound of Formula (II) or a salt or solvate thereof:

Formula (II)

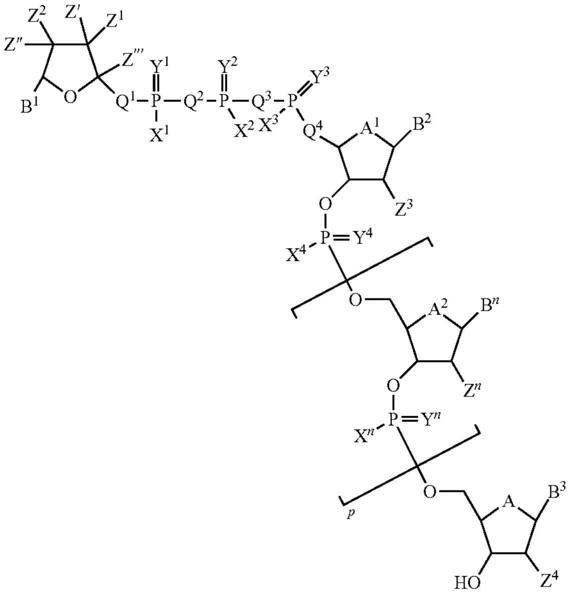

wherein $B^1$ is

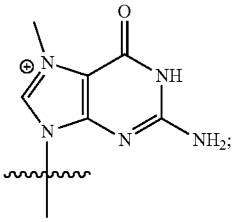 [SMILES: *n1c[n+](C)c2c(=O)[nH]c(N)nc21]

each $B^2$, $B^3$, and $B''$ is independently a natural, a modified, or an unnatural nucleobase;

each $Z^1$ and $Z^1$ is independently is hydrogen, fluorine, —OH, —SH, —$CH_3$, —$CH_2CH_3$, —$OCH_3$, —NH($CH_3$), —$NH_2$, —NH(C(=O)$CH_3$), or —$SCH_3$;

each $Z^2$ and Z" is independently fluorine, —OH, —SH, —$CH_3$, —$CH_2CH_3$, —$OCH_3$, —$SCH_3$, —$OCH_2CH_3$, —$NH_2$, $NHCH_3$, or NHC(=O)$CH_3$;

Z'" is hydrogen, fluorine, —$CH_3$, —$CH_2CH_3$, —$OCH_3$, or —$OCH_2CH_3$;

each $Z^3$, $Z^4$, and $Z''$ is independently hydrogen, fluorine, —OH, —$CH_3$, —$CH_2CH_3$, —$OCH_3$, —$NH_2$, —$NHCH_3$, —NH(C(=O)$CH_3$), —$OCH_2CH_3$, —$OCH_2OCH_3$, —$OCH_2CH_2CH_3$, —$OCH(CH_3)_2$, —$SCH_3$, or —$OCH_2CH_2OCH_3$;

each $Q^1$ and $Q^4$ is independently —CH=CH—, —$CH_2$—, —$CH_2O$—, —$CH_2S$—, —$CH_2CH_2$—, —$CH_2CF_2$—, —$CH_2NH_2$—, —$CH_2NH(CH_3)$—, or —$CH_2N$(C(=O)$CH_3$)—;

each $Q^2$ and $Q^3$ is independently —O—, —S—, —$CH_2$—, —$CF_2$—, —NH—, —N($CH_3$)—, or —N(C(=O)$CH_3$)—;

each $X^1$, $X^2$, $X^3$, $X^4$, and $X''$ is independently —OH, —SH, —O—, —S—, —$NH_2$, —$NHCH_3$, —NH(C(=O)$CH_3$), —$CH_3$, —$CH_2CH_3$, —$CH_2CH_2CH_3$, —$CH(CH_3)_2$, —$OCH_3$ or —$OCH_2CH_3$;

each $Y^1$, $Y^2$, $Y^3$, $Y^4$, and $Y''$ is independently =O, =S, =NH, or =$NCH_3$;

each A, $A^1$, and $A^2$ is independently —O—, —S—, —$CH_2$—, —NH—, —N($CH_3$)— or —N(C(=O)$CH_3$)—; and p=0, 1, 2, 3, 4, 5 or 6.

4. An in vitro-transcribed (IVT) mRNA sequence initiator comprising a compound of Formula (II) or a salt or solvate thereof:

Formula (II)

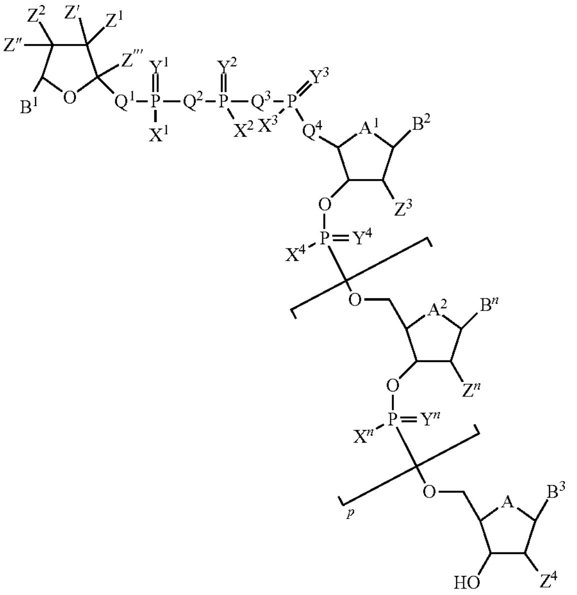

wherein $B^1$ is

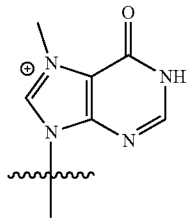

or;

each $B^2$, $B^3$, and $B''$ is independently a natural, a modified, or an unnatural nucleobase;

each Z' and Z" is independently is hydrogen, fluorine, —OH, —SH, —$CH_3$, —$CH_2CH_3$, —$OCH_3$, —NH($CH_3$), —$NH_2$, —NH(C(=O)$CH_3$), or —$SCH_3$;

$Z'''$ is hydrogen, fluorine, $—CH_3$, $—CH_2CH_3$, $—OCH_3$, or $—OCH_2CH_3$;

each $Z^1$ and $Z^2$ is independently hydrogen, fluorine, $—OH$, $—SH$, $—CH_3$, $—CH_2CH_3$, $—OCH_3$, $—SCH_3$, $—OCH_2CH_3$, $—NH_2$, $NHCH_3$, or $NHC(═O)CH_3$;

each $Z^3$, $Z^4$, and $Z''$ is independently hydrogen, fluorine, $—OH$, $—CH_3$, $—CH_2CH_3$, $—OCH_3$, $—NH_2$, $—NHCH_3$, $—NH(C(═O)CH_3)$, $—OCH_2CH_3$, $—OCH_2OCH_3$, $—OCH_2CH_2CH_3$, $—OCH(CH_3)_2$, $—SCH_3$, or $—OCH_2CH_2OCH_3$;

each $Q^1$ and $Q^4$ is independently $—CH═CH—$, $—CH_2—$, $—CH_2O—$, $—CH_2S—$, $—CH_2CH_2—$, $—CH_2CF_2—$, —

$CH_2NH_2—$, $—CH_2NH(CH_3)—$, or $—CH_2N(C(═O)CH_3)—$;

each $Q^2$ and $Q^3$ is independently $—O—$, $—S—$, $—CH_2—$, $—CF_2—$, $—NH—$, $—N(CH_3)—$, or $—N(C(═O)CH_3)—$;

each $X^1$, $X^2$, $X^3$, $X^4$, and $X''$ is independently $—OH$, $—SH$, $—O—$, $—S$, $—NH_2$, $—NHCH_3$, $—NH(C(═O)CH_3)$, $—CH_3$, $—CH_2CH_3$, $—CH_2CH_2CH_3$, $—CH(CH_3)_2$, $—OCH_3$ or $—OCH_2CH_3$;

each $Y^1$, $Y^2$, $Y^3$, $Y^4$, and $Y''$ is independently $═O$, $═S$, $═NH$, or $═NCH_3$;

each A, $A^1$, and $A^2$ is independently $—O—$, $—S—$, $—CH_2—$, $—NH—$, $—N(CH_3)—$ or $—N(C(═O)CH_3)—$; and p=0, 1, 2, 3, 4, 5 or 6.

5. The IVT mRNA sequence initiator of clause 1, wherein the initiator has a structure of Formula (I-a):

Formula (I-a)

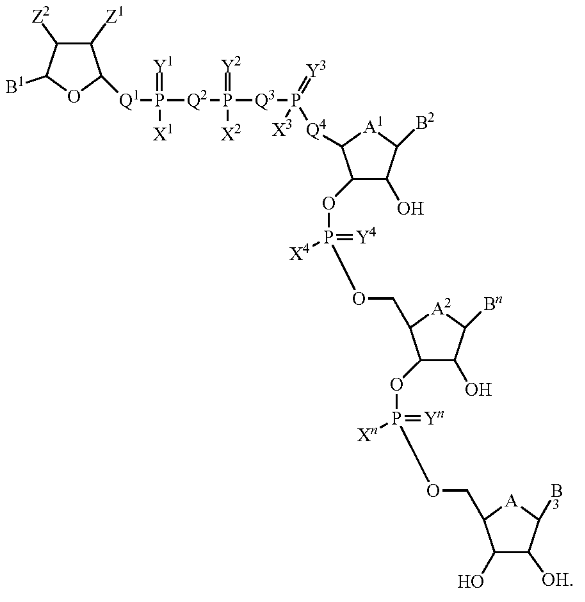

6. The IVT mRNA sequence initiator of clause 1, wherein the initiator has a structure of Formula (I-b):

Formula (I-b)

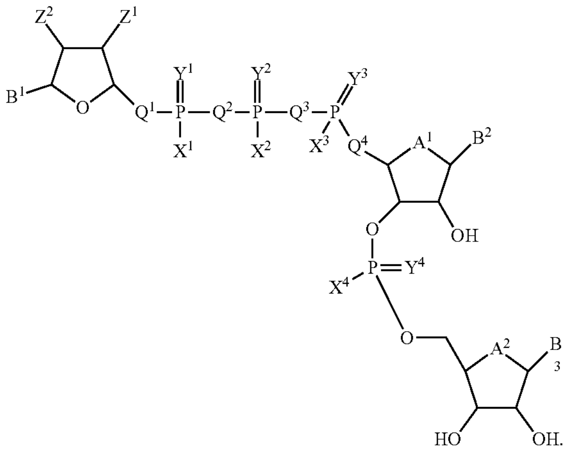

7. The IVT mRNA sequence initiator of clause 1, wherein the initiator has a structure of Formula (I-c):

Formula (I-c)

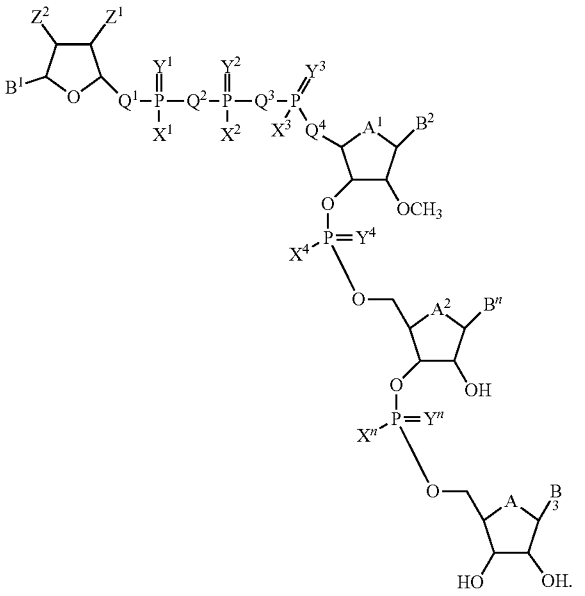

8. The IVT mRNA sequence initiator of clause 1, wherein the initiator has a structure of Formula (I-d):
Formula (I-d)
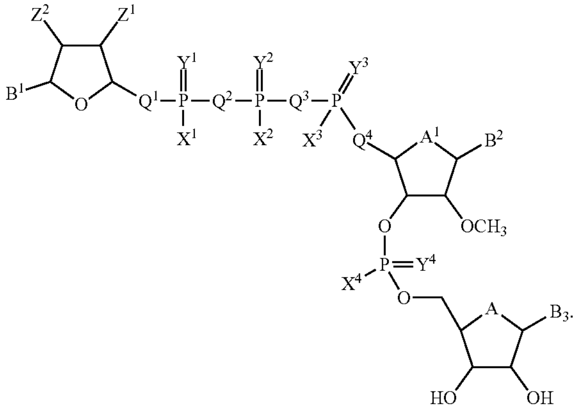
9. The IVT mRNA sequence initiator of clause 1, wherein the initiator has a structure of Formula (I-e):
Formula (I-e)
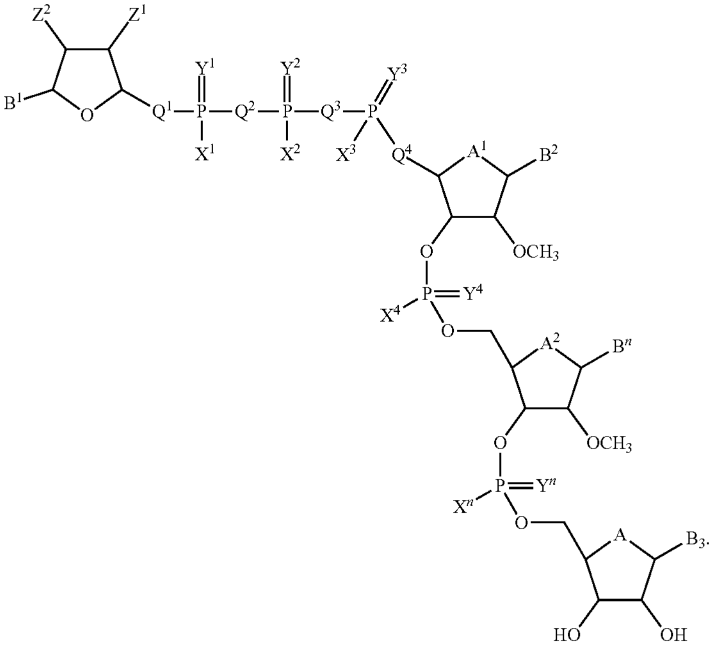

10. The IVT mRNA sequence initiator of clause 1, wherein the initiator has a structure of Formula (I-f):
Formula (I-f)
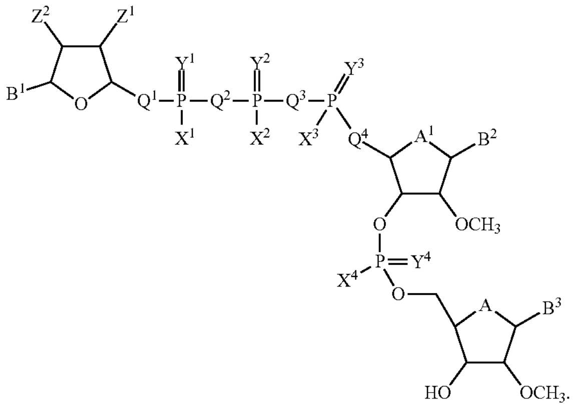
11. The IVT mRNA sequence initiator of clause 1, wherein the initiator has a structure of Formula (I-g):
Formula (I-g)
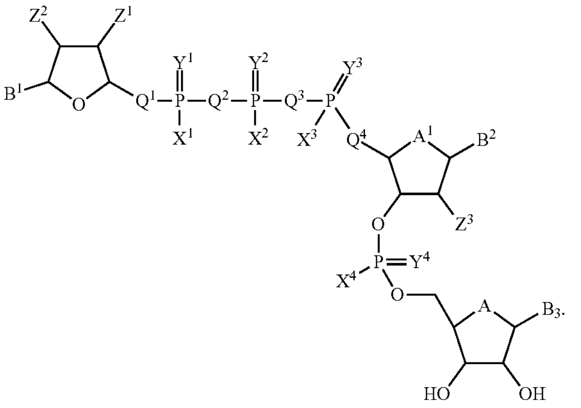
12. The IVT mRNA sequence initiator of claim 1, wherein the initiator has a structure of Formula (I-h):
Formula (I-h)
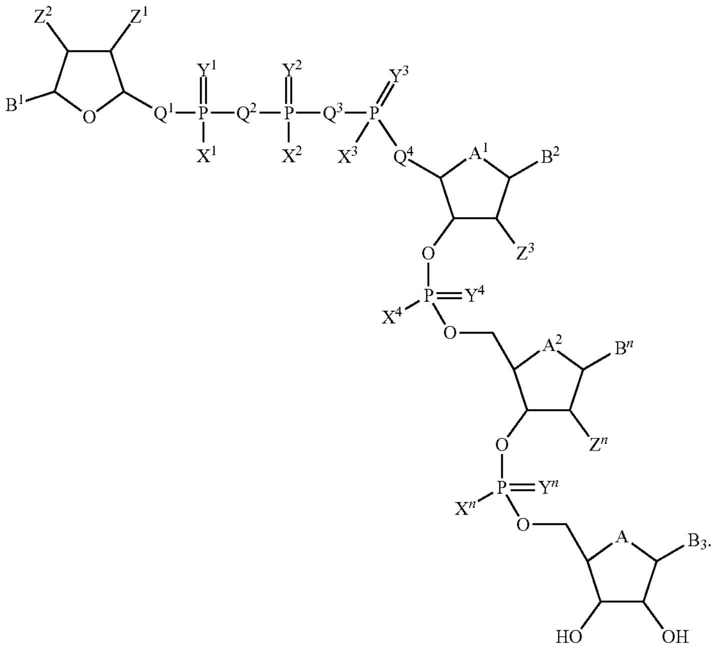

13. The IVT mRNA sequence initiator of clause 17 or 18, wherein the initiator has a structure of Formula (II-a):
Formula (II-a)
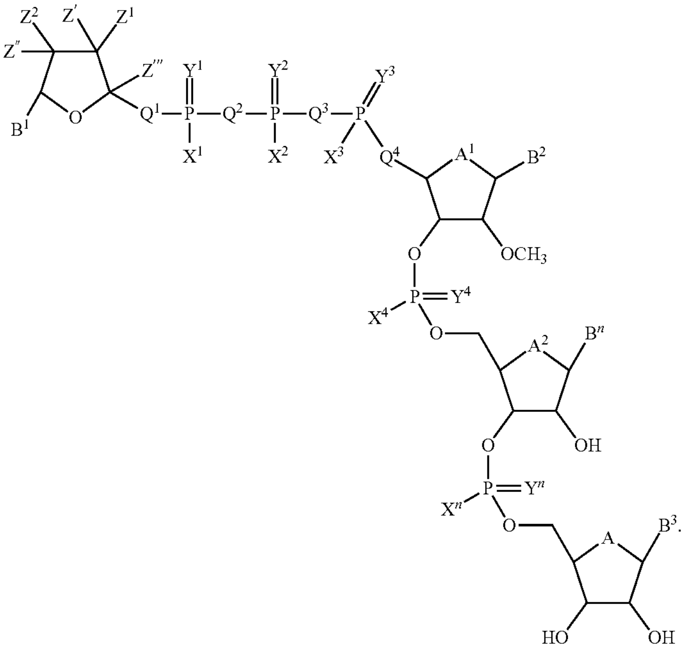
14. The IVT mRNA sequence initiator of clause 17 or 18, wherein the initiator has a structure of Formula (II-b):
Formula (II-b)
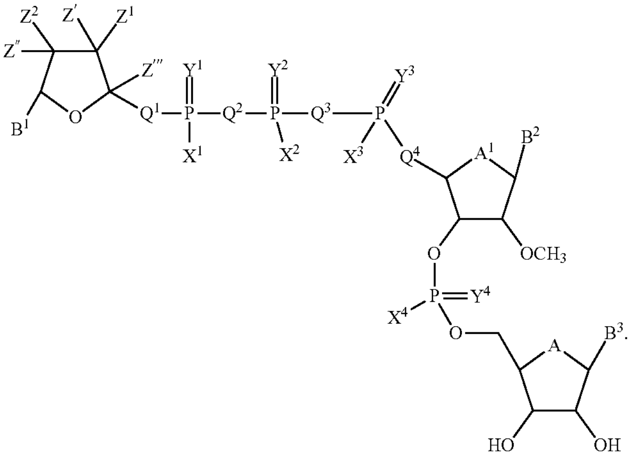

15. The IVT mRNA sequence initiator of clause 17 or 18, wherein the initiator has a structure of Formula (II-c):
Formula (II-c)
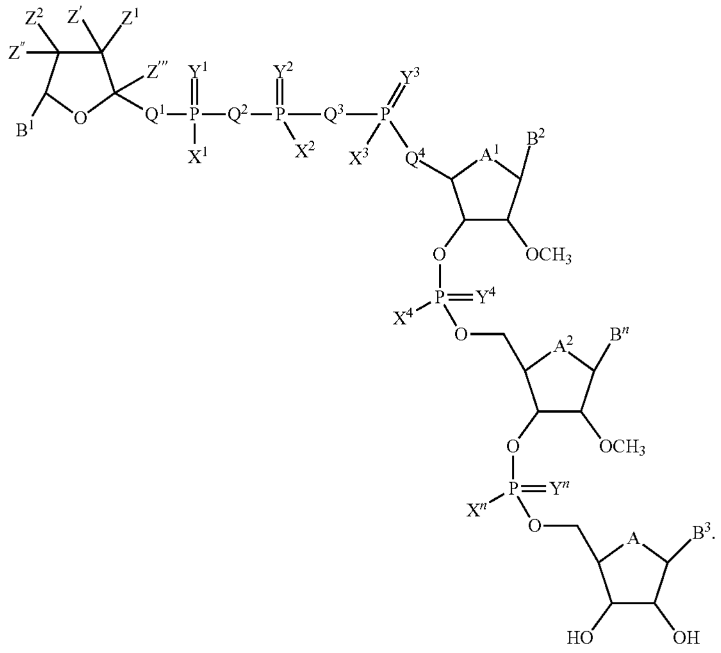
16. The IVT mRNA sequence initiator of clause 17 or 18, wherein the initiator has a structure of Formula (II-d):
Formula (II-d)
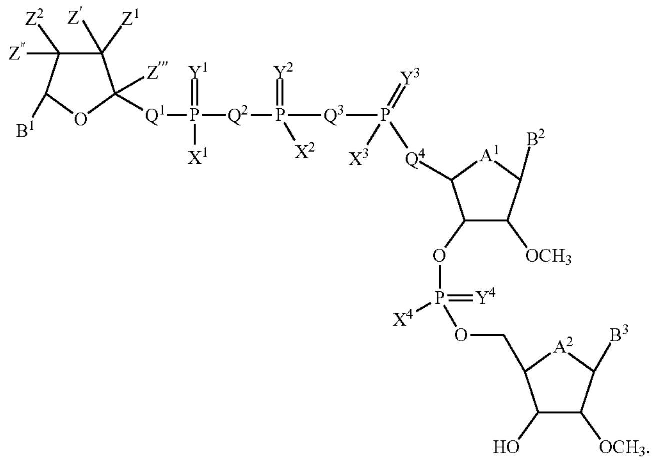

17. The IVT mRNA sequence initiator of clause 17 or 18, wherein the initiator has a structure of Formula (II-e):
Formula (II-e)
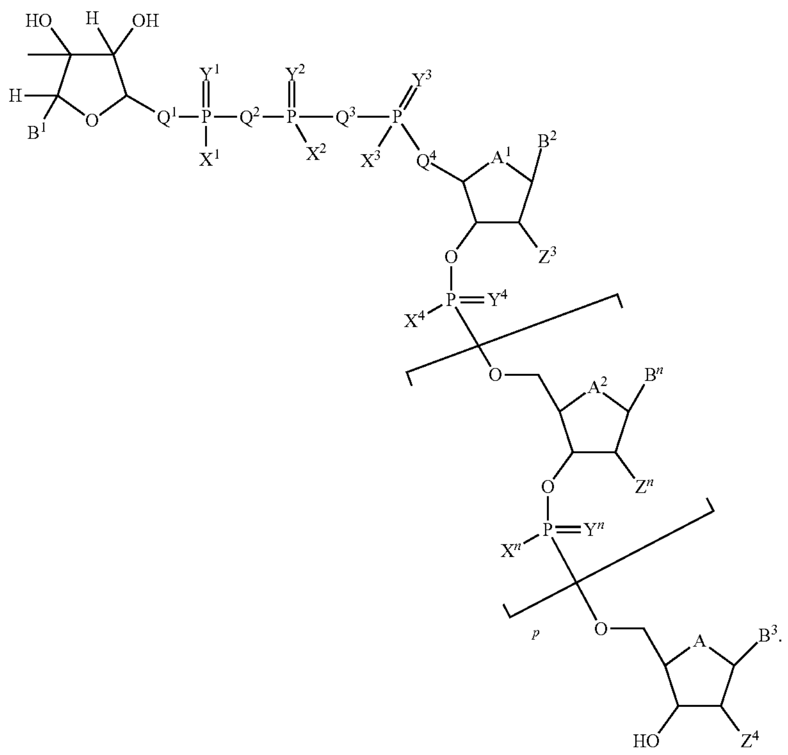
18. The IVT mRNA sequence initiator of clause 17 or 18, wherein the initiator has a structure of Formula (II-f):
Formula (II-f)
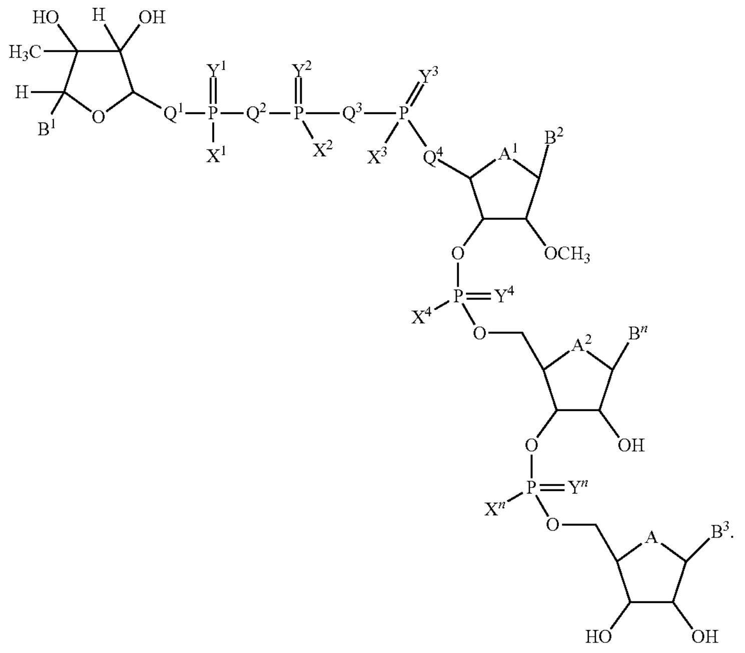

19. The IVT mRNA sequence initiator of clause 17 or 18, wherein the initiator has a structure of Formula (II-g):
Formula (II-g)
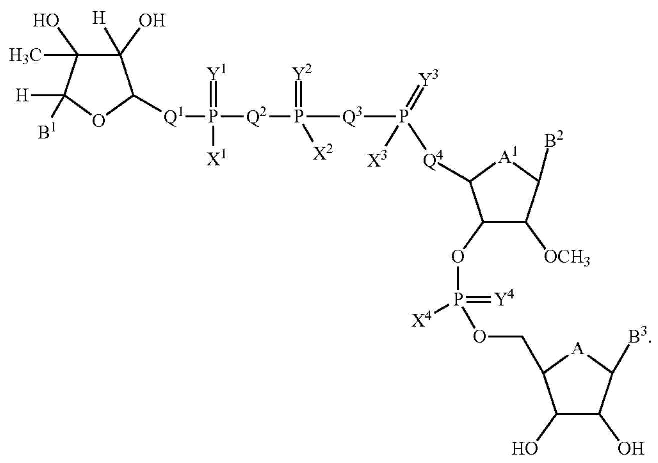
20. The IVT mRNA sequence initiator of clause 17 or 18, wherein the initiator has a structure of Formula (II-h):
Formula (II-h)
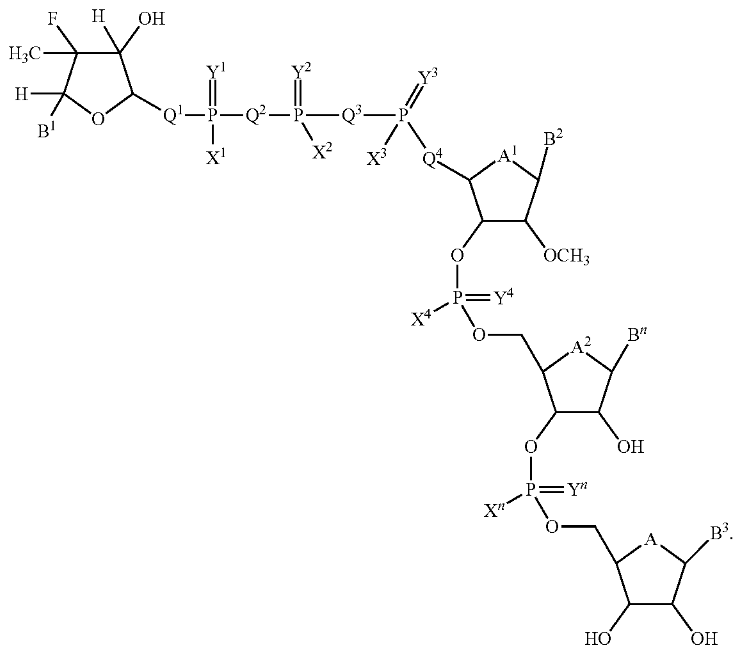

21. The IVT mRNA sequence initiator of clause 17 or 18, wherein the initiator has a structure of Formula (II-i)
Formula (II-i)
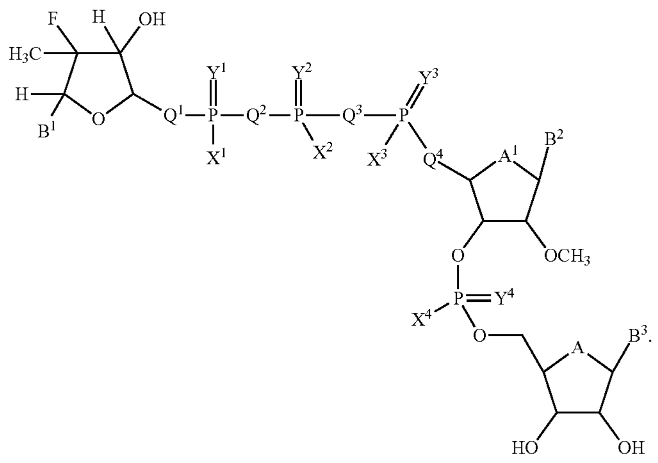
22. The IVT mRNA sequence initiator of clause 17 or 18, wherein the initiator has a structure of Formula (II-j):
Formula (II-j)
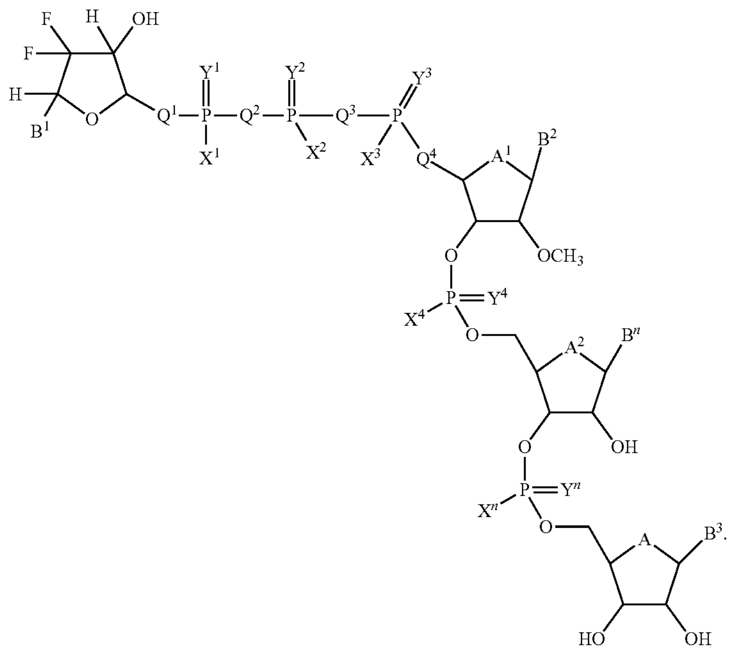

23. The IVT mRNA sequence initiator of clause 17 or 18, wherein the initiator has a structure of Formula (II-k):

Formula (II-k)

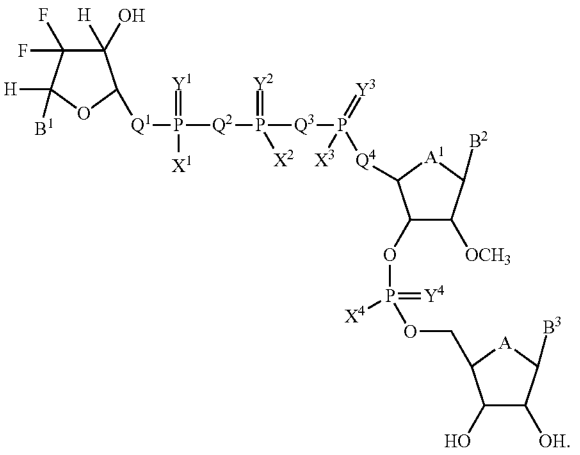

24. The IVT mRNA sequence initiator of clause 17 or 18, wherein the initiator has a structure of Formula (II-l):

Formula (II-l)

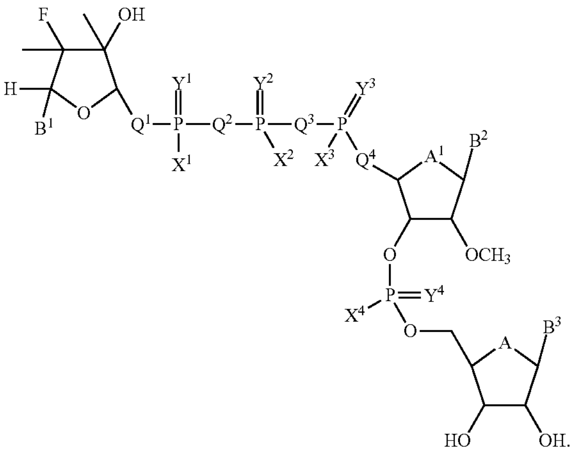

25. The IVT mRNA sequence initiator of clause 17 or 18, wherein the initiator has a structure of Formula (II-m):

Formula (II-m)

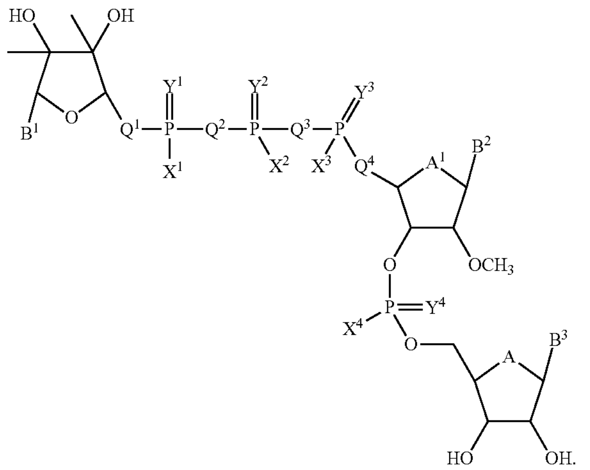

26. The IVT mRNA sequence initiator of clause 18, wherein the initiator has a structure of Formula (II-n):

Formula (II-n)

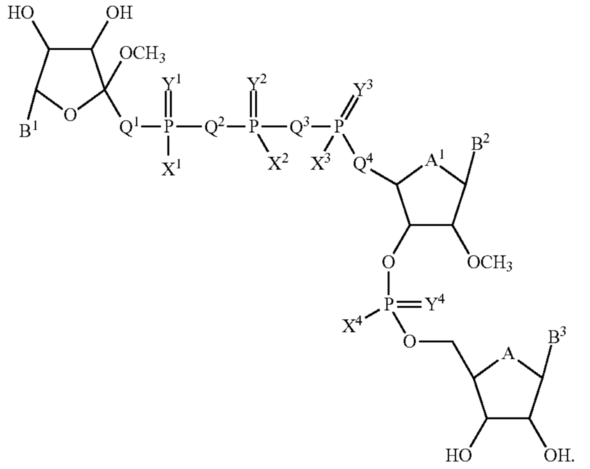

27. The IVT mRNA sequence initiator of clause 18, wherein the initiator has a structure of Formula (II-o):

Formula (II-o)

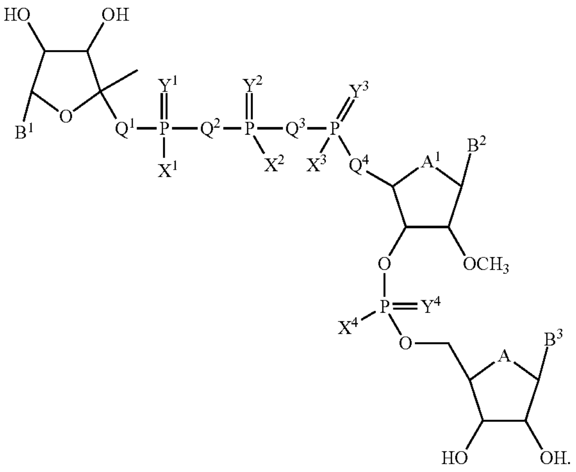

28. The IVT mRNA sequence initiator of clause 18, wherein the initiator has a structure of Formula (II-p):

Formula (II-p)

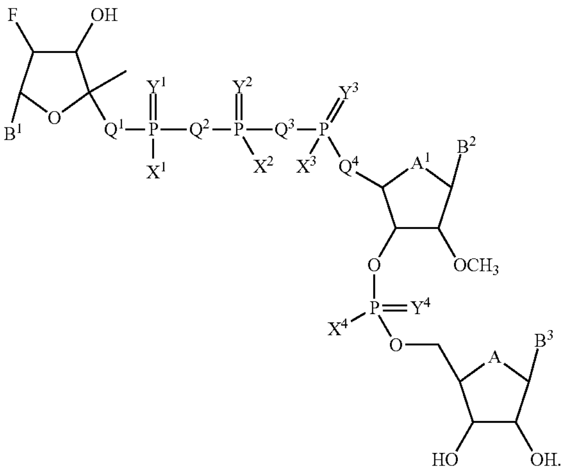

29. The IVT mRNA sequence initiator of clause 18, wherein the initiator has a structure of Formula (II-q):

Formula (II-q)

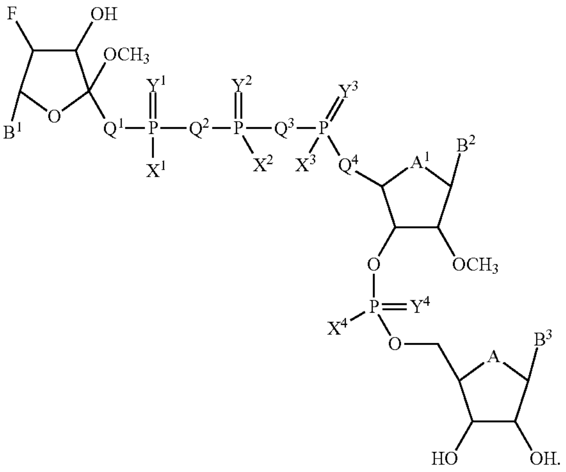

30. The IVT mRNA sequence initiator of clause 18, wherein the initiator has a structure of Formula (II-r):

Formula (II-r)

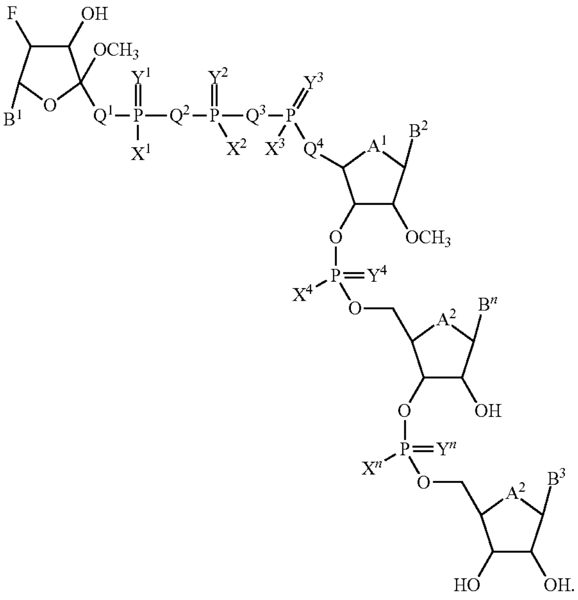

31. The IVT mRNA sequence initiator of clause 18, wherein the initiator has a structure of Formula (II-s):

Formula (II-s)

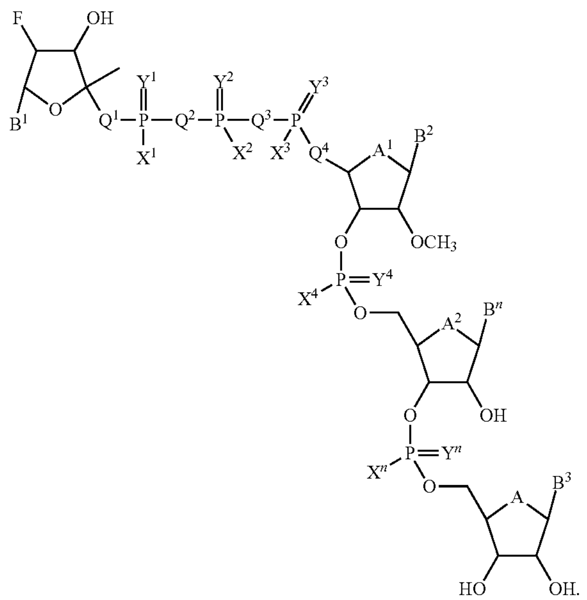

32. The IVT mRNA sequence initiator of clause 18, wherein the initiator has a structure of Formula (II-t):

Formula (II-t)

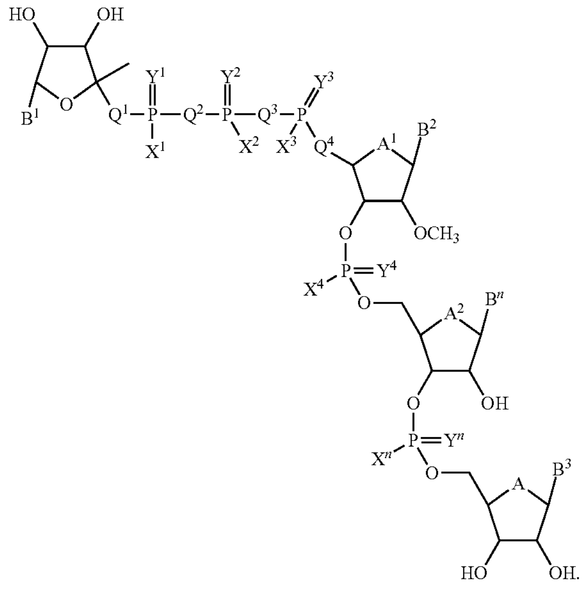

33. The IVT mRNA sequence initiator of clause 18, wherein the initiator has a structure of Formula (II-u):

Formula (II-u)

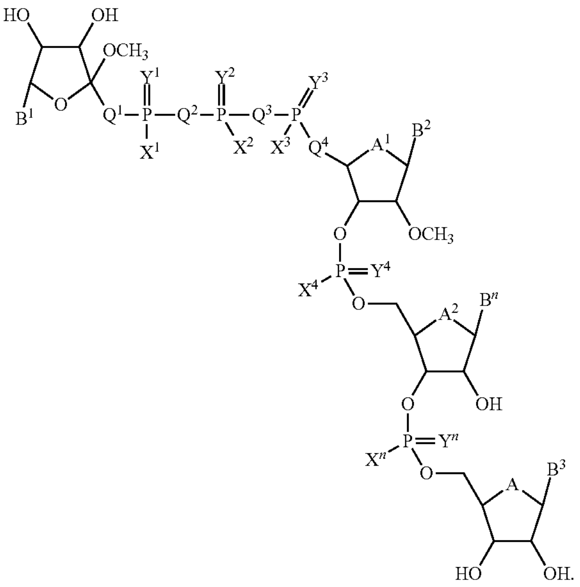

34. The IVT mRNA sequence initiator of any one of clauses 1-18, wherein $Z^3$ is hydrogen, fluorine, —OH, —$OCH_3$, - or —$OCH_2CH_3$.

35. The IVT mRNA sequence initiator of clause 48, wherein $Z^3$ is —$OCH_3$.

36. The IVT mRNA sequence initiator of clause 48, wherein each $Z^4$ and $Z''$ is independently —OH or —$OCH_3$.

37. The IVT mRNA sequence initiator of any one of clauses 1-18, wherein each $Z^3$, $Z^4$, and $Z''$ is independently —OH or —$OCH_3$.

38. The IVT mRNA sequence initiator of any one of clauses 18 or 25-51, wherein $B^1$ is

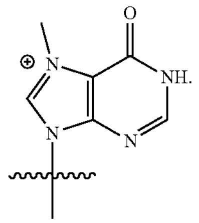 [SMILES: *n1c[n+](C)c2c(=O)[nH]cnc21]

39. The IVT mRNA sequence initiator of any one of clauses 18 or 25-51, wherein $B^1$ is

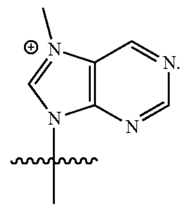 [SMILES: *n1c[n+](C)c2cncnc21]

40. The IVT mRNA sequence initiator of any one of clauses 18 or 25-51, wherein $B^1$ is

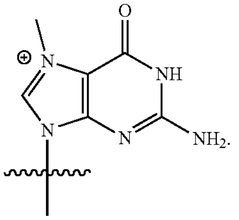 [SMILES: *n1c[n+](C)c2c(=O)[nH]c(N)nc21]

41. The IVT mRNA sequence initiator of any one of clauses 1-30, wherein $Z^1$ is fluorine, —OH, or —$OCH_3$.
42. The IVT mRNA sequence initiator of clause 55, wherein $Z^1$ is fluorine.
43. The IVT mRNA sequence initiator of clause 55, wherein $Z^1$ is —OH.
44. The IVT mRNA sequence initiator of clause 55, wherein $Z^1$ is —$OCH_3$.
45. The IVT mRNA sequence initiator of any one of clauses 1-30, wherein $Z^2$ is fluorine, —OH, or —$OCH_3$.
46. The IVT mRNA sequence initiator of clause 59, wherein $Z^2$ is fluorine.
47. The IVT mRNA sequence initiator of clause 59, wherein $Z^2$ is —OH.
48. The IVT mRNA sequence initiator of clause 59, wherein $Z^2$ is —$OCH_3$.
49. The IVT mRNA sequence initiator of any one of clauses 1-62, wherein $Q^1$ and $Q^4$ is —$CH_2O$—.
50. The IVT mRNA sequence initiator of any one of clauses 1-63, wherein each $Q^2$ and $Q^3$ is —O—.
51. The IVT mRNA sequence initiator of any one of clauses 1-64, wherein each $Y^1$ and $Y^3$ is ═O.
52. The IVT mRNA sequence initiator of any one of clauses 1-64, wherein each $Y^2$, $Y^4$, and $Y''$ is independently —O or ═S.
53. The IVT mRNA sequence initiator of any one of clauses 1-64, wherein one or more of $Y^1$, $Y^2$, $Y^3$, $Y^4$, and $Y''$ is ═S.
54. The IVT mRNA sequence initiator of clause 67, wherein $Y^2$ is ═S.
55. The IVT mRNA sequence initiator of clause 67, wherein $Y^4$ is ═S.
56. The IVT mRNA sequence initiator of any one of clauses 1-64, wherein each $Y^1$, $Y^2$, $Y^3$, $Y^4$, and $Y''$ is ═O.
57. The IVT mRNA sequence initiator of any one of clauses 1-70, wherein each $X^1$, $X^4$, and $X''$ is —$O^-$.
58. The IVT mRNA sequence initiator of any one of clauses 1-70, wherein each $X^2$ and $X^3$ is independently —O' or —S.
59. The IVT mRNA sequence initiator of clause 72, wherein $X^3$ is —O.
60. The IVT mRNA sequence initiator of any one of clauses 1-70, wherein one or more of $X^1$, $X^2$, $X^3$, $X^4$, and $X''$ is —S.
61. The IVT mRNA sequence initiator of clause 74, wherein $X^2$ is —S—.
62. The IVT mRNA sequence initiator of clause 74, wherein $X^4$ is —S—.
63. The IVT mRNA sequence initiator of any one of clauses 1-70, wherein each $X^1$, $X^2$, $X^3$, $X^4$, and $X''$ is —O.
64. The IVT mRNA sequence initiator of any one of clauses 1-77, wherein each A, $A^1$, and $A^2$ is —O—.
65. The IVT mRNA sequence initiator of any one of clauses 1-77, wherein one or more of A, $A^1$, and $A^2$ is —S—.
66. The IVT mRNA sequence initiator of any one of clauses 1-77 or 79, wherein A is —S- and $A^1$ and $A^2$ is —O—.
67. The IVT mRNA sequence initiator of any one of clauses 1-77 or 79, wherein $A^2$ is —S- and A and $A^1$ is —O—.
68. The IVT mRNA sequence initiator of any one of clauses 1-77, wherein A, $A^1$, and $A^2$ is —O—.
69. The IVT mRNA sequence initiator of any one of clauses 1, 17, or 48-81, wherein p is 0.
70. The IVT mRNA sequence initiator of any one of clauses 1, 17, or 48-81, wherein p is 1.
71. The IVT mRNA sequence initiator of any one of clauses 1, 17, or 48-81, wherein p is 2.
72. The IVT mRNA sequence initiator of any one of clauses 1-85, wherein each $B^2$, $B^3$, and $B''$ is independently adenine, cytosine, guanine, uracil, thymine, hypoxanthine, or purine.
73. The IVT mRNA sequence initiator of clause 86, wherein $B^2$ is adenine and $B^3$ is guanine.
74. The IVT mRNA sequence initiator of clause 86, wherein $B^2$ is guanine and $B^3$ is adenine.
75. The IVT mRNA sequence initiator of any one of clauses 1 to 88, wherein protein expression is increased.
76. The IVT mRNA sequence initiator of clauses 18-47, wherein $Q^1$ and $Q^4$ are —$CH_2O$—; $Q^2$ and $Q^3$ are —O—; each $X''$ is independently —OH, —SH, $O^-$, or S; each $Y''$ is independently ═O or —S; and $B^1$ is

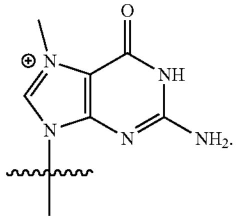 [SMILES: *n1c[n+](C)c2c(=O)[nH]c(N)nc21]

77. The IVT mRNA sequence initiator of clauses 18-47, wherein $Q^1$ and $Q^4$ are —$CH_2O$—; $Q^2$ and $Q^3$ are —O—; each $X''$ is independently —OH, —SH, $O^-$, or S; each $Y''$ is independently ═O or ═S; and $B^1$ is

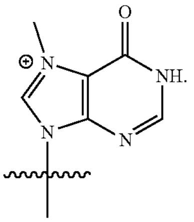 [SMILES: *n1c[n+](C)c2c(=O)[nH]cnc21]

78. The IVT mRNA sequence initiator of clauses 18-47, wherein $Q^1$ and $Q^4$ are —$CH_2O$—; $Q^2$ and $Q^3$ are —O—; each X" is independently —OH, —SH, $O^-$, or S; each Y" is independently —O or =S; and $B^1$ is

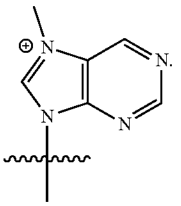 [SMILES: *n1c[n+](C)c2cncnc21]

79. The IVT mRNA sequence initiator of clauses 86-92, wherein $B^2$ is adenine.
80. The IVT mRNA sequence initiator of clauses 86-92, wherein $B^3$ is guanine.
81. A complex comprising an IVT mRNA sequence initiator and a DNA template, wherein the IVT mRNA sequence initiator comprises a compound of any one of clauses 1-94, wherein the DNA template comprises a promoter region comprising a transcriptional start site having a first nucleotide at nucleotide position +1, a second nucleotide at nucleotide position +2, and a third nucleotide at nucleotide position +3; and wherein the IVT mRNA sequence initiator is hybridized to the DNA template at least at nucleotide positions +1, +2, and +3.
82. A complex comprising an IVT mRNA sequence initiator and a DNA template, wherein the IVT mRNA sequence initiator comprises a compound of any one of clauses 1-94, wherein
    the DNA template comprises a promoter region comprising a transcriptional start site having a first nucleotide at nucleotide position +1 and a second nucleotide at nucleotide position +2; and
    wherein the IVT mRNA sequence initiator is hybridized to the DNA template at least at nucleotide positions +1 and +2.
83. An RNA molecule comprising the IVT mRNA sequence initiator according to any one of clauses 1-94.
84. The RNA of clause 97, wherein the RNA comprises a guide RNA or a nuclease mRNA.
85. The RNA of clause 97, wherein the RNA comprises an mRNA.
86. A method of expressing an mRNA comprising (a) contacting the mRNA of clause 99 with a cell or a cell lysate thereof and (b) expressing the mRNA
87. The method of clause 100, further comprising measuring the expression level of the mRNA.
88. The method of clause 100, wherein the expression level of the mRNA is at least 6-fold, 8-fold, or 20-fold greater compared to a corresponding mRNA without the IVT mRNA sequence initiator.
89. The method of clause 100, wherein the cell is a HeLa cell.
90. A method of reducing cellular immune stimulation of capped mRNA comprising (a) contacting a capped mRNA according to any one of clauses 1 to 94 with a cell reporter line and (b) measuring RIG-I activation in said cell reporter line.
91. The method of clause 104, wherein said cell reporter line is HEK-Lucia RIG-I model.
92. The method of any one of clauses 104 or 105, wherein cellular immune stimulation is reduced compared to an uncapped mRNA by at least 20%.
93. The method of clause 106, wherein cellular immune stimulation is reduced compared to an uncapped mRNA by at least 50%.
94. The method of clause 107, wherein cellular immune stimulation is reduced compared to an uncapped mRNA by at least 70%.
95. The method of clause 108, wherein cellular immune stimulation is reduced compared to an uncapped mRNA by at least 100%.
96. The method of clause 109, wherein cellular immune stimulation is reduced compared to an uncapped mRNA by at least 150%.
97. A cell containing an RNA molecule comprising the IVT mRNA sequence initiator according to any one of clauses 1-94.
98. A cell containing a polypeptide translated from an RNA molecule comprising the IVT mRNA sequence initiator according to any one of clauses 1-94.
99. A pharmaceutical composition comprising an RNA molecule comprising the IVT mRNA sequence initiator according to any one of clauses 1-94 and one or more of pharmaceutically acceptable excipients.
100. The pharmaceutical composition of clause 126, comprising lipid nanoparticles.
101. The pharmaceutical composition of clause 126, wherein the RNA is encapsulated in a-lipid nanoparticle.
102. A method for synthesizing an RNA molecule comprising:
    a. introducing the IVT mRNA sequence initiator according to any one of clauses 1-94 into a mixture comprising an RNA polymerase, and
    b. incubating the mixture for a time sufficient to allow for transcription of the RNA molecule.
103. The method of clause 81 wherein the mixture further comprises a DNA template and nucleoside triophosphates.
104. A method of gene editing comprising introducing into a cell an RNA molecule of clause 97 or 98, or pharmaceutical composition of any one of clauses 126-129, wherein the RNA molecule comprises guide RNA or a nuclease mRNA, wherein the RNA molecule is translated in the cell.
105. A method for reducing the risk of coronary disease in a subject in need thereof, comprising administering to the subject an effective amount of a pharmaceutical composition of any one of clauses 126-129.

SEQUENCE LISTING

```
Sequence total quantity: 5
SEQ ID NO: 1           moltype = RNA  length = 4929
FEATURE                Location/Qualifiers
misc_feature           1..4929
                       note = Description of Artificial Sequence:
                        Syntheticpolynucleotide
```

-continued

```
modified_base          7
                       mod_base = OTHER
                       note = N1-methylpseudouridine
modified_base          25
                       mod_base = OTHER
                       note = N1-methylpseudouridine
modified_base          35
                       mod_base = OTHER
                       note = N1-methylpseudouridine
modified_base          37
                       mod_base = OTHER
                       note = N1-methylpseudouridine
modified_base          49
                       mod_base = OTHER
                       note = N1-methylpseudouridine
modified_base          58
                       mod_base = OTHER
                       note = N1-methylpseudouridine
modified_base          63..64
                       mod_base = OTHER
                       note = N1-methylpseudouridine
modified_base          75
                       mod_base = OTHER
                       note = N1-methylpseudouridine
modified_base          78
                       mod_base = OTHER
                       note = N1-methylpseudouridine
modified_base          82
                       mod_base = OTHER
                       note = N1-methylpseudouridine
modified_base          94
                       mod_base = OTHER
                       note = N1-methylpseudouridine
modified_base          100
                       mod_base = OTHER
                       note = N1-methylpseudouridine
modified_base          130
                       mod_base = OTHER
                       note = N1-methylpseudouridine
modified_base          136
                       mod_base = OTHER
                       note = N1-methylpseudouridine
modified_base          145
                       mod_base = OTHER
                       note = N1-methylpseudouridine
modified_base          148
                       mod_base = OTHER
                       note = N1-methylpseudouridine
modified_base          151
                       mod_base = OTHER
                       note = N1-methylpseudouridine
modified_base          154
                       mod_base = OTHER
                       note = N1-methylpseudouridine
modified_base          166
                       mod_base = OTHER
                       note = N1-methylpseudouridine
modified_base          169
                       mod_base = OTHER
                       note = N1-methylpseudouridine
modified_base          180
                       mod_base = OTHER
                       note = N1-methylpseudouridine
modified_base          193
                       mod_base = OTHER
                       note = N1-methylpseudouridine
modified_base          199
                       mod_base = OTHER
                       note = N1-methylpseudouridine
modified_base          226
                       mod_base = OTHER
                       note = N1-methylpseudouridine
modified_base          229
                       mod_base = OTHER
                       note = N1-methylpseudouridine
modified_base          235
                       mod_base = OTHER
                       note = N1-methylpseudouridine
modified_base          250
```

-continued

```
                       mod_base = OTHER
                       note = N1-methylpseudouridine
modified_base          253
                       mod_base = OTHER
                       note = N1-methylpseudouridine
modified_base          256
                       mod_base = OTHER
                       note = N1-methylpseudouridine
modified_base          264
                       mod_base = OTHER
                       note = N1-methylpseudouridine
modified_base          271
                       mod_base = OTHER
                       note = N1-methylpseudouridine
modified_base          274
                       mod_base = OTHER
                       note = N1-methylpseudouridine
modified_base          286
                       mod_base = OTHER
                       note = N1-methylpseudouridine
modified_base          288
                       mod_base = OTHER
                       note = N1-methylpseudouridine
modified_base          292
                       mod_base = OTHER
                       note = N1-methylpseudouridine
modified_base          297..298
                       mod_base = OTHER
                       note = N1-methylpseudouridine
modified_base          306
                       mod_base = OTHER
                       note = N1-methylpseudouridine
modified_base          310
                       mod_base = OTHER
                       note = N1-methylpseudouridine
modified_base          313
                       mod_base = OTHER
                       note = N1-methylpseudouridine
modified_base          315
                       mod_base = OTHER
                       note = N1-methylpseudouridine
modified_base          328
                       mod_base = OTHER
                       note = N1-methylpseudouridine
modified_base          331
                       mod_base = OTHER
                       note = N1-methylpseudouridine
modified_base          343
                       mod_base = OTHER
                       note = N1-methylpseudouridine
modified_base          352
                       mod_base = OTHER
                       note = N1-methylpseudouridine
modified_base          355
                       mod_base = OTHER
                       note = N1-methylpseudouridine
modified_base          357..358
                       mod_base = OTHER
                       note = N1-methylpseudouridine
modified_base          364
                       mod_base = OTHER
                       note = N1-methylpseudouridine
modified_base          397
                       mod_base = OTHER
                       note = N1-methylpseudouridine
modified_base          400
                       mod_base = OTHER
                       note = N1-methylpseudouridine
modified_base          406
                       mod_base = OTHER
                       note = N1-methylpseudouridine
modified_base          409
                       mod_base = OTHER
                       note = N1-methylpseudouridine
modified_base          424
                       mod_base = OTHER
                       note = N1-methylpseudouridine
modified_base          436
                       mod_base = OTHER
```

-continued

| | |
|---|---|
| | note = N1-methylpseudouridine |
| modified_base | 442 |
| | mod_base = OTHER |
| | note = N1-methylpseudouridine |
| modified_base | 454 |
| | mod_base = OTHER |
| | note = N1-methylpseudouridine |
| modified_base | 457 |
| | mod_base = OTHER |
| | note = N1-methylpseudouridine |
| modified_base | 468 |
| | mod_base = OTHER |
| | note = N1-methylpseudouridine |
| modified_base | 478 |
| | mod_base = OTHER |
| | note = N1-methylpseudouridine |
| modified_base | 481 |
| | mod_base = OTHER |
| | note = N1-methylpseudouridine |
| modified_base | 483 |
| | mod_base = OTHER |
| | note = N1-methylpseudouridine |
| modified_base | 489..490 |
| | mod_base = OTHER |
| | note = N1-methylpseudouridine |
| modified_base | 492..493 |
| | mod_base = OTHER |
| | note = N1-methylpseudouridine |
| modified_base | 499 |
| | mod_base = OTHER |
| | note = N1-methylpseudouridine |
| modified_base | 511 |
| | mod_base = OTHER |
| | note = N1-methylpseudouridine |
| modified_base | 513..514 |
| | mod_base = OTHER |
| | note = N1-methylpseudouridine |
| modified_base | 654 |
| | mod_base = OTHER |
| | note = N1-methylpseudouridine |
| modified_base | 661 |
| | mod_base = OTHER |
| | note = N1-methylpseudouridine |
| modified_base | 667 |
| | mod_base = OTHER |
| | note = N1-methylpseudouridine |
| modified_base | 673 |
| | mod_base = OTHER |
| | note = N1-methylpseudouridine |
| modified_base | 688 |
| | mod_base = OTHER |
| | note = N1-methylpseudouridine |
| modified_base | 693 |
| | mod_base = OTHER |
| | note = N1-methylpseudouridine |
| modified_base | 700 |
| | mod_base = OTHER |
| | note = N1-methylpseudouridine |
| modified_base | 703 |
| | mod_base = OTHER |
| | note = N1-methylpseudouridine |
| modified_base | 714 |
| | mod_base = OTHER |
| | note = N1-methylpseudouridine |
| modified_base | 721 |
| | mod_base = OTHER |
| | note = N1-methylpseudouridine |
| modified_base | 735..736 |
| | mod_base = OTHER |
| | note = N1-methylpseudouridine |
| modified_base | 742 |
| | mod_base = OTHER |
| | note = N1-methylpseudouridine |
| modified_base | 745 |
| | mod_base = OTHER |
| | note = N1-methylpseudouridine |
| modified_base | 769 |
| | mod_base = OTHER |
| | note = N1-methylpseudouridine |

-continued

```
modified_base          781
                       mod_base = OTHER
                       note = N1-methylpseudouridine
modified_base          784
                       mod_base = OTHER
                       note = N1-methylpseudouridine
modified_base          793
                       mod_base = OTHER
                       note = N1-methylpseudouridine
modified_base          796
                       mod_base = OTHER
                       note = N1-methylpseudouridine
modified_base          798..799
                       mod_base = OTHER
                       note = N1-methylpseudouridine
modified_base          832
                       mod_base = OTHER
                       note = N1-methylpseudouridine
modified_base          855
                       mod_base = OTHER
                       note = N1-methylpseudouridine
modified_base          877
                       mod_base = OTHER
                       note = N1-methylpseudouridine
modified_base          879
                       mod_base = OTHER
                       note = N1-methylpseudouridine
modified_base          882
                       mod_base = OTHER
                       note = N1-methylpseudouridine
modified_base          886
                       mod_base = OTHER
                       note = N1-methylpseudouridine
modified_base          895
                       mod_base = OTHER
                       note = N1-methylpseudouridine
modified_base          897..898
                       mod_base = OTHER
                       note = N1-methylpseudouridine
modified_base          910
                       mod_base = OTHER
                       note = N1-methylpseudouridine
modified_base          919
                       mod_base = OTHER
                       note = N1-methylpseudouridine
modified_base          930..931
                       mod_base = OTHER
                       note = N1-methylpseudouridine
modified_base          933..934
                       mod_base = OTHER
                       note = N1-methylpseudouridine
modified_base          943
                       mod_base = OTHER
                       note = N1-methylpseudouridine
modified_base          954..955
                       mod_base = OTHER
                       note = N1-methylpseudouridine
modified_base          958
                       mod_base = OTHER
                       note = N1-methylpseudouridine
modified_base          961
                       mod_base = OTHER
                       note = N1-methylpseudouridine
modified_base          994
                       mod_base = OTHER
                       note = N1-methylpseudouridine
modified_base          996..997
                       mod_base = OTHER
                       note = N1-methylpseudouridine
modified_base          1006
                       mod_base = OTHER
                       note = N1-methylpseudouridine
modified_base          1009
                       mod_base = OTHER
                       note = N1-methylpseudouridine
modified_base          1018
                       mod_base = OTHER
                       note = N1-methylpseudouridine
modified_base          1023
```

-continued

```
                        mod_base = OTHER
                        note = N1-methylpseudouridine
modified_base           1035
                        mod_base = OTHER
                        note = N1-methylpseudouridine
modified_base           1045
                        mod_base = OTHER
                        note = N1-methylpseudouridine
modified_base           1047
                        mod_base = OTHER
                        note = N1-methylpseudouridine
modified_base           1054
                        mod_base = OTHER
                        note = N1-methylpseudouridine
modified_base           1066
                        mod_base = OTHER
                        note = N1-methylpseudouridine
modified_base           1069
                        mod_base = OTHER
                        note = N1-methylpseudouridine
modified_base           1093
                        mod_base = OTHER
                        note = N1-methylpseudouridine
modified_base           1099
                        mod_base = OTHER
                        note = N1-methylpseudouridine
modified_base           1102
                        mod_base = OTHER
                        note = N1-methylpseudouridine
modified_base           1104
                        mod_base = OTHER
                        note = N1-methylpseudouridine
modified_base           1108
                        mod_base = OTHER
                        note = N1-methylpseudouridine
modified_base           1114
                        mod_base = OTHER
                        note = N1-methylpseudouridine
modified_base           1123
                        mod_base = OTHER
                        note = N1-methylpseudouridine
modified_base           1126
                        mod_base = OTHER
                        note = N1-methylpseudouridine
modified_base           1131..1132
                        mod_base = OTHER
                        note = N1-methylpseudouridine
modified_base           1143..1144
                        mod_base = OTHER
                        note = N1-methylpseudouridine
modified_base           1147
                        mod_base = OTHER
                        note = N1-methylpseudouridine
modified_base           1150
                        mod_base = OTHER
                        note = N1-methylpseudouridine
modified_base           1162
                        mod_base = OTHER
                        note = N1-methylpseudouridine
modified_base           1183
                        mod_base = OTHER
                        note = N1-methylpseudouridine
modified_base           1192
                        mod_base = OTHER
                        note = N1-methylpseudouridine
modified_base           1194..1195
                        mod_base = OTHER
                        note = N1-methylpseudouridine
modified_base           1198
                        mod_base = OTHER
                        note = N1-methylpseudouridine
modified_base           1204
                        mod_base = OTHER
                        note = N1-methylpseudouridine
modified_base           1207
                        mod_base = OTHER
                        note = N1-methylpseudouridine
modified_base           1215
                        mod_base = OTHER
```

-continued

```
                         note = N1-methylpseudouridine
modified_base            1225
                         mod_base = OTHER
                         note = N1-methylpseudouridine
modified_base            1227..1228
                         mod_base = OTHER
                         note = N1-methylpseudouridine
modified_base            1243
                         mod_base = OTHER
                         note = N1-methylpseudouridine
modified_base            1258
                         mod_base = OTHER
                         note = N1-methylpseudouridine
modified_base            1273
                         mod_base = OTHER
                         note = N1-methylpseudouridine
modified_base            1276
                         mod_base = OTHER
                         note = N1-methylpseudouridine
modified_base            1288
                         mod_base = OTHER
                         note = N1-methylpseudouridine
modified_base            1306
                         mod_base = OTHER
                         note = N1-methylpseudouridine
modified_base            1315
                         mod_base = OTHER
                         note = N1-methylpseudouridine
modified_base            1318
                         mod_base = OTHER
                         note = N1-methylpseudouridine
modified_base            1327
                         mod_base = OTHER
                         note = N1-methylpseudouridine
modified_base            1351
                         mod_base = OTHER
                         note = N1-methylpseudouridine
modified_base            1353..1354
                         mod_base = OTHER
                         note = N1-methylpseudouridine
modified_base            1363
                         mod_base = OTHER
                         note = N1-methylpseudouridine
modified_base            1366
                         mod_base = OTHER
                         note = N1-methylpseudouridine
modified_base            1372
                         mod_base = OTHER
                         note = N1-methylpseudouridine
modified_base            1378
                         mod_base = OTHER
                         note = N1-methylpseudouridine
modified_base            1384
                         mod_base = OTHER
                         note = N1-methylpseudouridine
modified_base            1395..1396
                         mod_base = OTHER
                         note = N1-methylpseudouridine
modified_base            1407..1408
                         mod_base = OTHER
                         note = N1-methylpseudouridine
modified_base            1414
                         mod_base = OTHER
                         note = N1-methylpseudouridine
modified_base            1432
                         mod_base = OTHER
                         note = N1-methylpseudouridine
modified_base            1438
                         mod_base = OTHER
                         note = N1-methylpseudouridine
modified_base            1452
                         mod_base = OTHER
                         note = N1-methylpseudouridine
modified_base            1465
                         mod_base = OTHER
                         note = N1-methylpseudouridine
modified_base            1474
                         mod_base = OTHER
                         note = N1-methylpseudouridine
```

-continued

| | |
|---|---|
| modified_base | 1477<br>mod_base = OTHER<br>note = N1-methylpseudouridine |
| modified_base | 1486<br>mod_base = OTHER<br>note = N1-methylpseudouridine |
| modified_base | 1497<br>mod_base = OTHER<br>note = N1-methylpseudouridine |
| modified_base | 1507<br>mod_base = OTHER<br>note = N1-methylpseudouridine |
| modified_base | 1509..1510<br>mod_base = OTHER<br>note = N1-methylpseudouridine |
| modified_base | 1513<br>mod_base = OTHER<br>note = N1-methylpseudouridine |
| modified_base | 1528<br>mod_base = OTHER<br>note = N1-methylpseudouridine |
| modified_base | 1540<br>mod_base = OTHER<br>note = N1-methylpseudouridine |
| modified_base | 1543<br>mod_base = OTHER<br>note = N1-methylpseudouridine |
| modified_base | 1546<br>mod_base = OTHER<br>note = N1-methylpseudouridine |
| modified_base | 1555<br>mod_base = OTHER<br>note = N1-methylpseudouridine |
| modified_base | 1558<br>mod_base = OTHER<br>note = N1-methylpseudouridine |
| modified_base | 1564<br>mod_base = OTHER<br>note = N1-methylpseudouridine |
| modified_base | 1576<br>mod_base = OTHER<br>note = N1-methylpseudouridine |
| modified_base | 1591<br>mod_base = OTHER<br>note = N1-methylpseudouridine |
| modified_base | 1603<br>mod_base = OTHER<br>note = N1-methylpseudouridine |
| modified_base | 1606<br>mod_base = OTHER<br>note = N1-methylpseudouridine |
| modified_base | 1614<br>mod_base = OTHER<br>note = N1-methylpseudouridine |
| modified_base | 1636<br>mod_base = OTHER<br>note = N1-methylpseudouridine |
| modified_base | 1642<br>mod_base = OTHER<br>note = N1-methylpseudouridine |
| modified_base | 1645<br>mod_base = OTHER<br>note = N1-methylpseudouridine |
| modified_base | 1654<br>mod_base = OTHER<br>note = N1-methylpseudouridine |
| modified_base | 1657<br>mod_base = OTHER<br>note = N1-methylpseudouridine |
| modified_base | 1669<br>mod_base = OTHER<br>note = N1-methylpseudouridine |
| modified_base | 1680<br>mod_base = OTHER<br>note = N1-methylpseudouridine |
| modified_base | 1690<br>mod_base = OTHER<br>note = N1-methylpseudouridine |
| modified_base | 1692..1693 |

-continued

```
                      mod_base = OTHER
                      note = N1-methylpseudouridine
modified_base         1695..1696
                      mod_base = OTHER
                      note = N1-methylpseudouridine
modified_base         1716
                      mod_base = OTHER
                      note = N1-methylpseudouridine
modified_base         1725
                      mod_base = OTHER
                      note = N1-methylpseudouridine
modified_base         1729
                      mod_base = OTHER
                      note = N1-methylpseudouridine
modified_base         1755..1756
                      mod_base = OTHER
                      note = N1-methylpseudouridine
modified_base         1758
                      mod_base = OTHER
                      note = N1-methylpseudouridine
modified_base         1764..1765
                      mod_base = OTHER
                      note = N1-methylpseudouridine
modified_base         1768
                      mod_base = OTHER
                      note = N1-methylpseudouridine
modified_base         1777
                      mod_base = OTHER
                      note = N1-methylpseudouridine
modified_base         1780
                      mod_base = OTHER
                      note = N1-methylpseudouridine
modified_base         1789
                      mod_base = OTHER
                      note = N1-methylpseudouridine
modified_base         1807
                      mod_base = OTHER
                      note = N1-methylpseudouridine
modified_base         1810
                      mod_base = OTHER
                      note = N1-methylpseudouridine
modified_base         1813
                      mod_base = OTHER
                      note = N1-methylpseudouridine
modified_base         1819
                      mod_base = OTHER
                      note = N1-methylpseudouridine
modified_base         1834
                      mod_base = OTHER
                      note = N1-methylpseudouridine
modified_base         1837
                      mod_base = OTHER
                      note = N1-methylpseudouridine
modified_base         1854..1855
                      mod_base = OTHER
                      note = N1-methylpseudouridine
modified_base         1870
                      mod_base = OTHER
                      note = N1-methylpseudouridine
modified_base         1882
                      mod_base = OTHER
                      note = N1-methylpseudouridine
modified_base         1888
                      mod_base = OTHER
                      note = N1-methylpseudouridine
modified_base         1897
                      mod_base = OTHER
                      note = N1-methylpseudouridine
modified_base         1906
                      mod_base = OTHER
                      note = N1-methylpseudouridine
modified_base         1909
                      mod_base = OTHER
                      note = N1-methylpseudouridine
modified_base         1926..1927
                      mod_base = OTHER
                      note = N1-methylpseudouridine
modified_base         1929
                      mod_base = OTHER
```

| | |
|---|---|
| | note = N1-methylpseudouridine |
| modified_base | 1935..1936 |
| | mod_base = OTHER |
| | note = N1-methylpseudouridine |
| modified_base | 1939 |
| | mod_base = OTHER |
| | note = N1-methylpseudouridine |
| modified_base | 1960 |
| | mod_base = OTHER |
| | note = N1-methylpseudouridine |
| modified_base | 1969 |
| | mod_base = OTHER |
| | note = N1-methylpseudouridine |
| modified_base | 1972 |
| | mod_base = OTHER |
| | note = N1-methylpseudouridine |
| modified_base | 1977..1978 |
| | mod_base = OTHER |
| | note = N1-methylpseudouridine |
| modified_base | 1984 |
| | mod_base = OTHER |
| | note = N1-methylpseudouridine |
| modified_base | 1989 |
| | mod_base = OTHER |
| | note = N1-methylpseudouridine |
| modified_base | 1992 |
| | mod_base = OTHER |
| | note = N1-methylpseudouridine |
| modified_base | 1996 |
| | mod_base = OTHER |
| | note = N1-methylpseudouridine |
| modified_base | 2005 |
| | mod_base = OTHER |
| | note = N1-methylpseudouridine |
| modified_base | 2025..2026 |
| | mod_base = OTHER |
| | note = N1-methylpseudouridine |
| modified_base | 2031 |
| | mod_base = OTHER |
| | note = N1-methylpseudouridine |
| modified_base | 2035 |
| | mod_base = OTHER |
| | note = N1-methylpseudouridine |
| modified_base | 2059 |
| | mod_base = OTHER |
| | note = N1-methylpseudouridine |
| modified_base | 2067 |
| | mod_base = OTHER |
| | note = N1-methylpseudouridine |
| modified_base | 2073..2074 |
| | mod_base = OTHER |
| | note = N1-methylpseudouridine |
| modified_base | 2083 |
| | mod_base = OTHER |
| | note = N1-methylpseudouridine |
| modified_base | 2086 |
| | mod_base = OTHER |
| | note = N1-methylpseudouridine |
| modified_base | 2112..2113 |
| | mod_base = OTHER |
| | note = N1-methylpseudouridine |
| modified_base | 2116 |
| | mod_base = OTHER |
| | note = N1-methylpseudouridine |
| modified_base | 2125 |
| | mod_base = OTHER |
| | note = N1-methylpseudouridine |
| modified_base | 2133..2134 |
| | mod_base = OTHER |
| | note = N1-methylpseudouridine |
| modified_base | 2146 |
| | mod_base = OTHER |
| | note = N1-methylpseudouridine |
| modified_base | 2161 |
| | mod_base = OTHER |
| | note = N1-methylpseudouridine |
| modified_base | 2164 |
| | mod_base = OTHER |
| | note = N1-methylpseudouridine |

```
modified_base          2179
                       mod_base = OTHER
                       note = N1-methylpseudouridine
modified_base          2182
                       mod_base = OTHER
                       note = N1-methylpseudouridine
modified_base          2184
                       mod_base = OTHER
                       note = N1-methylpseudouridine
modified_base          2190
                       mod_base = OTHER
                       note = N1-methylpseudouridine
modified_base          2193..2194
                       mod_base = OTHER
                       note = N1-methylpseudouridine
modified_base          2200
                       mod_base = OTHER
                       note = N1-methylpseudouridine
modified_base          2202
                       mod_base = OTHER
                       note = N1-methylpseudouridine
modified_base          2212
                       mod_base = OTHER
                       note = N1-methylpseudouridine
modified_base          2221
                       mod_base = OTHER
                       note = N1-methylpseudouridine
modified_base          2226
                       mod_base = OTHER
                       note = N1-methylpseudouridine
modified_base          2230
                       mod_base = OTHER
                       note = N1-methylpseudouridine
modified_base          2242
                       mod_base = OTHER
                       note = N1-methylpseudouridine
modified_base          2256..2257
                       mod_base = OTHER
                       note = N1-methylpseudouridine
modified_base          2260
                       mod_base = OTHER
                       note = N1-methylpseudouridine
modified_base          2284
                       mod_base = OTHER
                       note = N1-methylpseudouridine
modified_base          2287
                       mod_base = OTHER
                       note = N1-methylpseudouridine
modified_base          2293
                       mod_base = OTHER
                       note = N1-methylpseudouridine
modified_base          2296
                       mod_base = OTHER
                       note = N1-methylpseudouridine
modified_base          2298..2299
                       mod_base = OTHER
                       note = N1-methylpseudouridine
modified_base          2317
                       mod_base = OTHER
                       note = N1-methylpseudouridine
modified_base          2323
                       mod_base = OTHER
                       note = N1-methylpseudouridine
modified_base          2332
                       mod_base = OTHER
                       note = N1-methylpseudouridine
modified_base          2343
                       mod_base = OTHER
                       note = N1-methylpseudouridine
modified_base          2346..2347
                       mod_base = OTHER
                       note = N1-methylpseudouridine
modified_base          2356
                       mod_base = OTHER
                       note = N1-methylpseudouridine
modified_base          2361
                       mod_base = OTHER
                       note = N1-methylpseudouridine
modified_base          2364..2365
```

-continued

```
                              mod_base = OTHER
                              note = N1-methylpseudouridine
modified_base                 2374
                              mod_base = OTHER
                              note = N1-methylpseudouridine
modified_base                 2380
                              mod_base = OTHER
                              note = N1-methylpseudouridine
modified_base                 2389
                              mod_base = OTHER
                              note = N1-methylpseudouridine
modified_base                 2400..2401
                              mod_base = OTHER
                              note = N1-methylpseudouridine
modified_base                 2413
                              mod_base = OTHER
                              note = N1-methylpseudouridine
modified_base                 2421
                              mod_base = OTHER
                              note = N1-methylpseudouridine
modified_base                 2431
                              mod_base = OTHER
                              note = N1-methylpseudouridine
modified_base                 2434
                              mod_base = OTHER
                              note = N1-methylpseudouridine
modified_base                 2440
                              mod_base = OTHER
                              note = N1-methylpseudouridine
modified_base                 2443
                              mod_base = OTHER
                              note = N1-methylpseudouridine
modified_base                 2457..2458
                              mod_base = OTHER
                              note = N1-methylpseudouridine
modified_base                 2461
                              mod_base = OTHER
                              note = N1-methylpseudouridine
modified_base                 2485
                              mod_base = OTHER
                              note = N1-methylpseudouridine
modified_base                 2488
                              mod_base = OTHER
                              note = N1-methylpseudouridine
modified_base                 2497
                              mod_base = OTHER
                              note = N1-methylpseudouridine
modified_base                 2500
                              mod_base = OTHER
                              note = N1-methylpseudouridine
modified_base                 2503
                              mod_base = OTHER
                              note = N1-methylpseudouridine
modified_base                 2509
                              mod_base = OTHER
                              note = N1-methylpseudouridine
modified_base                 2515
                              mod_base = OTHER
                              note = N1-methylpseudouridine
modified_base                 2517..2518
                              mod_base = OTHER
                              note = N1-methylpseudouridine
modified_base                 2533
                              mod_base = OTHER
                              note = N1-methylpseudouridine
modified_base                 2536
                              mod_base = OTHER
                              note = N1-methylpseudouridine
modified_base                 2548
                              mod_base = OTHER
                              note = N1-methylpseudouridine
modified_base                 2556
                              mod_base = OTHER
                              note = N1-methylpseudouridine
modified_base                 2566
                              mod_base = OTHER
                              note = N1-methylpseudouridine
modified_base                 2568..2569
                              mod_base = OTHER
```

-continued

```
                        note = N1-methylpseudouridine
modified_base           2581
                        mod_base = OTHER
                        note = N1-methylpseudouridine
modified_base           2584
                        mod_base = OTHER
                        note = N1-methylpseudouridine
modified_base           2593
                        mod_base = OTHER
                        note = N1-methylpseudouridine
modified_base           2607
                        mod_base = OTHER
                        note = N1-methylpseudouridine
modified_base           2616
                        mod_base = OTHER
                        note = N1-methylpseudouridine
modified_base           2626
                        mod_base = OTHER
                        note = N1-methylpseudouridine
modified_base           2638
                        mod_base = OTHER
                        note = N1-methylpseudouridine
modified_base           2641
                        mod_base = OTHER
                        note = N1-methylpseudouridine
modified_base           2650
                        mod_base = OTHER
                        note = N1-methylpseudouridine
modified_base           2677
                        mod_base = OTHER
                        note = N1-methylpseudouridine
modified_base           2680
                        mod_base = OTHER
                        note = N1-methylpseudouridine
modified_base           2685..2686
                        mod_base = OTHER
                        note = N1-methylpseudouridine
modified_base           2689
                        mod_base = OTHER
                        note = N1-methylpseudouridine
modified_base           2703..2704
                        mod_base = OTHER
                        note = N1-methylpseudouridine
modified_base           2718..2719
                        mod_base = OTHER
                        note = N1-methylpseudouridine
modified_base           2722
                        mod_base = OTHER
                        note = N1-methylpseudouridine
modified_base           2728
                        mod_base = OTHER
                        note = N1-methylpseudouridine
modified_base           2731
                        mod_base = OTHER
                        note = N1-methylpseudouridine
modified_base           2746
                        mod_base = OTHER
                        note = N1-methylpseudouridine
modified_base           2751..2752
                        mod_base = OTHER
                        note = N1-methylpseudouridine
modified_base           2764
                        mod_base = OTHER
                        note = N1-methylpseudouridine
modified_base           2779
                        mod_base = OTHER
                        note = N1-methylpseudouridine
modified_base           2800
                        mod_base = OTHER
                        note = N1-methylpseudouridine
modified_base           2812
                        mod_base = OTHER
                        note = N1-methylpseudouridine
modified_base           2821
                        mod_base = OTHER
                        note = N1-methylpseudouridine
modified_base           2839
                        mod_base = OTHER
                        note = N1-methylpseudouridine
```

```
modified_base          2851
                       mod_base = OTHER
                       note = N1-methylpseudouridine
modified_base          2854
                       mod_base = OTHER
                       note = N1-methylpseudouridine
modified_base          2863
                       mod_base = OTHER
                       note = N1-methylpseudouridine
modified_base          2869
                       mod_base = OTHER
                       note = N1-methylpseudouridine
modified_base          2872
                       mod_base = OTHER
                       note = N1-methylpseudouridine
modified_base          2881
                       mod_base = OTHER
                       note = N1-methylpseudouridine
modified_base          2884
                       mod_base = OTHER
                       note = N1-methylpseudouridine
modified_base          2890
                       mod_base = OTHER
                       note = N1-methylpseudouridine
modified_base          2893
                       mod_base = OTHER
                       note = N1-methylpseudouridine
modified_base          2917
                       mod_base = OTHER
                       note = N1-methylpseudouridine
modified_base          2920
                       mod_base = OTHER
                       note = N1-methylpseudouridine
modified_base          2923
                       mod_base = OTHER
                       note = N1-methylpseudouridine
modified_base          2929
                       mod_base = OTHER
                       note = N1-methylpseudouridine
modified_base          2983
                       mod_base = OTHER
                       note = N1-methylpseudouridine
modified_base          2992
                       mod_base = OTHER
                       note = N1-methylpseudouridine
modified_base          3004
                       mod_base = OTHER
                       note = N1-methylpseudouridine
modified_base          3013
                       mod_base = OTHER
                       note = N1-methylpseudouridine
modified_base          3025
                       mod_base = OTHER
                       note = N1-methylpseudouridine
modified_base          3028
                       mod_base = OTHER
                       note = N1-methylpseudouridine
modified_base          3043
                       mod_base = OTHER
                       note = N1-methylpseudouridine
modified_base          3058
                       mod_base = OTHER
                       note = N1-methylpseudouridine
modified_base          3073
                       mod_base = OTHER
                       note = N1-methylpseudouridine
modified_base          3075
                       mod_base = OTHER
                       note = N1-methylpseudouridine
modified_base          3079
                       mod_base = OTHER
                       note = N1-methylpseudouridine
modified_base          3081
                       mod_base = OTHER
                       note = N1-methylpseudouridine
modified_base          3084
                       mod_base = OTHER
                       note = N1-methylpseudouridine
modified_base          3088
```

-continued

```
                        mod_base = OTHER
                        note = N1-methylpseudouridine
modified_base           3106
                        mod_base = OTHER
                        note = N1-methylpseudouridine
modified_base           3108
                        mod_base = OTHER
                        note = N1-methylpseudouridine
modified_base           3112
                        mod_base = OTHER
                        note = N1-methylpseudouridine
modified_base           3124
                        mod_base = OTHER
                        note = N1-methylpseudouridine
modified_base           3130
                        mod_base = OTHER
                        note = N1-methylpseudouridine
modified_base           3139
                        mod_base = OTHER
                        note = N1-methylpseudouridine
modified_base           3147
                        mod_base = OTHER
                        note = N1-methylpseudouridine
modified_base           3154
                        mod_base = OTHER
                        note = N1-methylpseudouridine
modified_base           3163
                        mod_base = OTHER
                        note = N1-methylpseudouridine
modified_base           3166
                        mod_base = OTHER
                        note = N1-methylpseudouridine
modified_base           3177..3178
                        mod_base = OTHER
                        note = N1-methylpseudouridine
modified_base           3181
                        mod_base = OTHER
                        note = N1-methylpseudouridine
modified_base           3196
                        mod_base = OTHER
                        note = N1-methylpseudouridine
modified_base           3208
                        mod_base = OTHER
                        note = N1-methylpseudouridine
modified_base           3211
                        mod_base = OTHER
                        note = N1-methylpseudouridine
modified_base           3250
                        mod_base = OTHER
                        note = N1-methylpseudouridine
modified_base           3265
                        mod_base = OTHER
                        note = N1-methylpseudouridine
modified_base           3268
                        mod_base = OTHER
                        note = N1-methylpseudouridine
modified_base           3277
                        mod_base = OTHER
                        note = N1-methylpseudouridine
modified_base           3285
                        mod_base = OTHER
                        note = N1-methylpseudouridine
modified_base           3288
                        mod_base = OTHER
                        note = N1-methylpseudouridine
modified_base           3298
                        mod_base = OTHER
                        note = N1-methylpseudouridine
modified_base           3301
                        mod_base = OTHER
                        note = N1-methylpseudouridine
modified_base           3313
                        mod_base = OTHER
                        note = N1-methylpseudouridine
modified_base           3316
                        mod_base = OTHER
                        note = N1-methylpseudouridine
modified_base           3330..3331
                        mod_base = OTHER
```

-continued

| | |
|---|---|
| | note = N1-methylpseudouridine |
| modified_base | 3340 |
| | mod_base = OTHER |
| | note = N1-methylpseudouridine |
| modified_base | 3364 |
| | mod_base = OTHER |
| | note = N1-methylpseudouridine |
| modified_base | 3373 |
| | mod_base = OTHER |
| | note = N1-methylpseudouridine |
| modified_base | 3387..3388 |
| | mod_base = OTHER |
| | note = N1-methylpseudouridine |
| modified_base | 3391 |
| | mod_base = OTHER |
| | note = N1-methylpseudouridine |
| modified_base | 3403 |
| | mod_base = OTHER |
| | note = N1-methylpseudouridine |
| modified_base | 3406 |
| | mod_base = OTHER |
| | note = N1-methylpseudouridine |
| modified_base | 3421 |
| | mod_base = OTHER |
| | note = N1-methylpseudouridine |
| modified_base | 3433 |
| | mod_base = OTHER |
| | note = N1-methylpseudouridine |
| modified_base | 3442 |
| | mod_base = OTHER |
| | note = N1-methylpseudouridine |
| modified_base | 3445 |
| | mod_base = OTHER |
| | note = N1-methylpseudouridine |
| modified_base | 3457 |
| | mod_base = OTHER |
| | note = N1-methylpseudouridine |
| modified_base | 3468 |
| | mod_base = OTHER |
| | note = N1-methylpseudouridine |
| modified_base | 3487 |
| | mod_base = OTHER |
| | note = N1-methylpseudouridine |
| modified_base | 3490 |
| | mod_base = OTHER |
| | note = N1-methylpseudouridine |
| modified_base | 3499 |
| | mod_base = OTHER |
| | note = N1-methylpseudouridine |
| modified_base | 3505 |
| | mod_base = OTHER |
| | note = N1-methylpseudouridine |
| modified_base | 3508 |
| | mod_base = OTHER |
| | note = N1-methylpseudouridine |
| modified_base | 3514 |
| | mod_base = OTHER |
| | note = N1-methylpseudouridine |
| modified_base | 3526 |
| | mod_base = OTHER |
| | note = N1-methylpseudouridine |
| modified_base | 3529 |
| | mod_base = OTHER |
| | note = N1-methylpseudouridine |
| modified_base | 3537..3538 |
| | mod_base = OTHER |
| | note = N1-methylpseudouridine |
| modified_base | 3549..3550 |
| | mod_base = OTHER |
| | note = N1-methylpseudouridine |
| modified_base | 3555..3556 |
| | mod_base = OTHER |
| | note = N1-methylpseudouridine |
| modified_base | 3558 |
| | mod_base = OTHER |
| | note = N1-methylpseudouridine |
| modified_base | 3565 |
| | mod_base = OTHER |
| | note = N1-methylpseudouridine |

```
modified_base          3574
                       mod_base = OTHER
                       note = N1-methylpseudouridine
modified_base          3582
                       mod_base = OTHER
                       note = N1-methylpseudouridine
modified_base          3603
                       mod_base = OTHER
                       note = N1-methylpseudouridine
modified_base          3607
                       mod_base = OTHER
                       note = N1-methylpseudouridine
modified_base          3616
                       mod_base = OTHER
                       note = N1-methylpseudouridine
modified_base          3619
                       mod_base = OTHER
                       note = N1-methylpseudouridine
modified_base          3631
                       mod_base = OTHER
                       note = N1-methylpseudouridine
modified_base          3634
                       mod_base = OTHER
                       note = N1-methylpseudouridine
modified_base          3642
                       mod_base = OTHER
                       note = N1-methylpseudouridine
modified_base          3652
                       mod_base = OTHER
                       note = N1-methylpseudouridine
modified_base          3663..3664
                       mod_base = OTHER
                       note = N1-methylpseudouridine
modified_base          3667
                       mod_base = OTHER
                       note = N1-methylpseudouridine
modified_base          3669
                       mod_base = OTHER
                       note = N1-methylpseudouridine
modified_base          3678
                       mod_base = OTHER
                       note = N1-methylpseudouridine
modified_base          3685
                       mod_base = OTHER
                       note = N1-methylpseudouridine
modified_base          3687
                       mod_base = OTHER
                       note = N1-methylpseudouridine
modified_base          3694
                       mod_base = OTHER
                       note = N1-methylpseudouridine
modified_base          3703
                       mod_base = OTHER
                       note = N1-methylpseudouridine
modified_base          3706
                       mod_base = OTHER
                       note = N1-methylpseudouridine
modified_base          3727
                       mod_base = OTHER
                       note = N1-methylpseudouridine
modified_base          3747
                       mod_base = OTHER
                       note = N1-methylpseudouridine
modified_base          3750..3751
                       mod_base = OTHER
                       note = N1-methylpseudouridine
modified_base          3753..3754
                       mod_base = OTHER
                       note = N1-methylpseudouridine
modified_base          3756
                       mod_base = OTHER
                       note = N1-methylpseudouridine
modified_base          3766
                       mod_base = OTHER
                       note = N1-methylpseudouridine
modified_base          3769
                       mod_base = OTHER
                       note = N1-methylpseudouridine
modified_base          3774..3775
```

-continued

```
                              mod_base = OTHER
                              note = N1-methylpseudouridine
modified_base                 3777..3778
                              mod_base = OTHER
                              note = N1-methylpseudouridine
modified_base                 3790
                              mod_base = OTHER
                              note = N1-methylpseudouridine
modified_base                 3796
                              mod_base = OTHER
                              note = N1-methylpseudouridine
modified_base                 3811
                              mod_base = OTHER
                              note = N1-methylpseudouridine
modified_base                 3826
                              mod_base = OTHER
                              note = N1-methylpseudouridine
modified_base                 3829
                              mod_base = OTHER
                              note = N1-methylpseudouridine
modified_base                 3856
                              mod_base = OTHER
                              note = N1-methylpseudouridine
modified_base                 3859
                              mod_base = OTHER
                              note = N1-methylpseudouridine
modified_base                 3861
                              mod_base = OTHER
                              note = N1-methylpseudouridine
modified_base                 3879..3880
                              mod_base = OTHER
                              note = N1-methylpseudouridine
modified_base                 3889
                              mod_base = OTHER
                              note = N1-methylpseudouridine
modified_base                 3898
                              mod_base = OTHER
                              note = N1-methylpseudouridine
modified_base                 3901
                              mod_base = OTHER
                              note = N1-methylpseudouridine
modified_base                 3907
                              mod_base = OTHER
                              note = N1-methylpseudouridine
modified_base                 3916
                              mod_base = OTHER
                              note = N1-methylpseudouridine
modified_base                 3922
                              mod_base = OTHER
                              note = N1-methylpseudouridine
modified_base                 3925
                              mod_base = OTHER
                              note = N1-methylpseudouridine
modified_base                 3940
                              mod_base = OTHER
                              note = N1-methylpseudouridine
modified_base                 3954..3955
                              mod_base = OTHER
                              note = N1-methylpseudouridine
modified_base                 3970
                              mod_base = OTHER
                              note = N1-methylpseudouridine
modified_base                 3973
                              mod_base = OTHER
                              note = N1-methylpseudouridine
modified_base                 3997
                              mod_base = OTHER
                              note = N1-methylpseudouridine
modified_base                 4000
                              mod_base = OTHER
                              note = N1-methylpseudouridine
modified_base                 4017
                              mod_base = OTHER
                              note = N1-methylpseudouridine
modified_base                 4032
                              mod_base = OTHER
                              note = N1-methylpseudouridine
modified_base                 4041..4042
                              mod_base = OTHER
```

-continued

| | |
|---|---|
| | note = N1-methylpseudouridine |
| modified_base | 4057 |
| | mod_base = OTHER |
| | note = N1-methylpseudouridine |
| modified_base | 4062 |
| | mod_base = OTHER |
| | note = N1-methylpseudouridine |
| modified_base | 4069 |
| | mod_base = OTHER |
| | note = N1-methylpseudouridine |
| modified_base | 4072 |
| | mod_base = OTHER |
| | note = N1-methylpseudouridine |
| modified_base | 4075 |
| | mod_base = OTHER |
| | note = N1-methylpseudouridine |
| modified_base | 4078 |
| | mod_base = OTHER |
| | note = N1-methylpseudouridine |
| modified_base | 4087 |
| | mod_base = OTHER |
| | note = N1-methylpseudouridine |
| modified_base | 4111 |
| | mod_base = OTHER |
| | note = N1-methylpseudouridine |
| modified_base | 4120 |
| | mod_base = OTHER |
| | note = N1-methylpseudouridine |
| modified_base | 4129 |
| | mod_base = OTHER |
| | note = N1-methylpseudouridine |
| modified_base | 4132 |
| | mod_base = OTHER |
| | note = N1-methylpseudouridine |
| modified_base | 4138 |
| | mod_base = OTHER |
| | note = N1-methylpseudouridine |
| modified_base | 4144 |
| | mod_base = OTHER |
| | note = N1-methylpseudouridine |
| modified_base | 4147 |
| | mod_base = OTHER |
| | note = N1-methylpseudouridine |
| modified_base | 4161..4162 |
| | mod_base = OTHER |
| | note = N1-methylpseudouridine |
| modified_base | 4177 |
| | mod_base = OTHER |
| | note = N1-methylpseudouridine |
| modified_base | 4182..4183 |
| | mod_base = OTHER |
| | note = N1-methylpseudouridine |
| modified_base | 4186 |
| | mod_base = OTHER |
| | note = N1-methylpseudouridine |
| modified_base | 4200 |
| | mod_base = OTHER |
| | note = N1-methylpseudouridine |
| modified_base | 4210 |
| | mod_base = OTHER |
| | note = N1-methylpseudouridine |
| modified_base | 4222 |
| | mod_base = OTHER |
| | note = N1-methylpseudouridine |
| modified_base | 4225 |
| | mod_base = OTHER |
| | note = N1-methylpseudouridine |
| modified_base | 4228 |
| | mod_base = OTHER |
| | note = N1-methylpseudouridine |
| modified_base | 4234 |
| | mod_base = OTHER |
| | note = N1-methylpseudouridine |
| modified_base | 4242 |
| | mod_base = OTHER |
| | note = N1-methylpseudouridine |
| modified_base | 4249 |
| | mod_base = OTHER |
| | note = N1-methylpseudouridine |

-continued

```
modified_base          4251..4252
                       mod_base = OTHER
                       note = N1-methylpseudouridine
modified_base          4258
                       mod_base = OTHER
                       note = N1-methylpseudouridine
modified_base          4279
                       mod_base = OTHER
                       note = N1-methylpseudouridine
modified_base          4282
                       mod_base = OTHER
                       note = N1-methylpseudouridine
modified_base          4300
                       mod_base = OTHER
                       note = N1-methylpseudouridine
modified_base          4318
                       mod_base = OTHER
                       note = N1-methylpseudouridine
modified_base          4324
                       mod_base = OTHER
                       note = N1-methylpseudouridine
modified_base          4335
                       mod_base = OTHER
                       note = N1-methylpseudouridine
modified_base          4339
                       mod_base = OTHER
                       note = N1-methylpseudouridine
modified_base          4344..4345
                       mod_base = OTHER
                       note = N1-methylpseudouridine
modified_base          4348
                       mod_base = OTHER
                       note = N1-methylpseudouridine
modified_base          4350
                       mod_base = OTHER
                       note = N1-methylpseudouridine
modified_base          4354
                       mod_base = OTHER
                       note = N1-methylpseudouridine
modified_base          4365
                       mod_base = OTHER
                       note = N1-methylpseudouridine
modified_base          4375
                       mod_base = OTHER
                       note = N1-methylpseudouridine
modified_base          4411
                       mod_base = OTHER
                       note = N1-methylpseudouridine
modified_base          4413..4414
                       mod_base = OTHER
                       note = N1-methylpseudouridine
modified_base          4417
                       mod_base = OTHER
                       note = N1-methylpseudouridine
modified_base          4434
                       mod_base = OTHER
                       note = N1-methylpseudouridine
modified_base          4438
                       mod_base = OTHER
                       note = N1-methylpseudouridine
modified_base          4447
                       mod_base = OTHER
                       note = N1-methylpseudouridine
modified_base          4450
                       mod_base = OTHER
                       note = N1-methylpseudouridine
modified_base          4459
                       mod_base = OTHER
                       note = N1-methylpseudouridine
modified_base          4467..4468
                       mod_base = OTHER
                       note = N1-methylpseudouridine
modified_base          4480
                       mod_base = OTHER
                       note = N1-methylpseudouridine
modified_base          4483
                       mod_base = OTHER
                       note = N1-methylpseudouridine
modified_base          4486
```

-continued

```
                        mod_base = OTHER
                        note = N1-methylpseudouridine
modified_base           4501
                        mod_base = OTHER
                        note = N1-methylpseudouridine
modified_base           4510
                        mod_base = OTHER
                        note = N1-methylpseudouridine
modified_base           4513
                        mod_base = OTHER
                        note = N1-methylpseudouridine
modified_base           4521
                        mod_base = OTHER
                        note = N1-methylpseudouridine
modified_base           4546
                        mod_base = OTHER
                        note = N1-methylpseudouridine
modified_base           4567
                        mod_base = OTHER
                        note = N1-methylpseudouridine
modified_base           4570
                        mod_base = OTHER
                        note = N1-methylpseudouridine
modified_base           4576
                        mod_base = OTHER
                        note = N1-methylpseudouridine
modified_base           4578..4579
                        mod_base = OTHER
                        note = N1-methylpseudouridine
modified_base           4585
                        mod_base = OTHER
                        note = N1-methylpseudouridine
modified_base           4594
                        mod_base = OTHER
                        note = N1-methylpseudouridine
modified_base           4611..4612
                        mod_base = OTHER
                        note = N1-methylpseudouridine
modified_base           4617
                        mod_base = OTHER
                        note = N1-methylpseudouridine
modified_base           4620..4621
                        mod_base = OTHER
                        note = N1-methylpseudouridine
modified_base           4633
                        mod_base = OTHER
                        note = N1-methylpseudouridine
modified_base           4647
                        mod_base = OTHER
                        note = N1-methylpseudouridine
modified_base           4666
                        mod_base = OTHER
                        note = N1-methylpseudouridine
modified_base           4669
                        mod_base = OTHER
                        note = N1-methylpseudouridine
modified_base           4681
                        mod_base = OTHER
                        note = N1-methylpseudouridine
modified_base           4684
                        mod_base = OTHER
                        note = N1-methylpseudouridine
modified_base           4696
                        mod_base = OTHER
                        note = N1-methylpseudouridine
modified_base           4705
                        mod_base = OTHER
                        note = N1-methylpseudouridine
modified_base           4707
                        mod_base = OTHER
                        note = N1-methylpseudouridine
modified_base           4720
                        mod_base = OTHER
                        note = N1-methylpseudouridine
modified_base           4726
                        mod_base = OTHER
                        note = N1-methylpseudouridine
modified_base           4735
                        mod_base = OTHER
```

-continued

| | |
|---|---|
| | note = N1-methylpseudouridine |
| modified_base | 4782..4783 |
| | mod_base = OTHER |
| | note = N1-methylpseudouridine |
| modified_base | 4810 |
| | mod_base = OTHER |
| | note = N1-methylpseudouridine |
| modified_base | 4812 |
| | mod_base = OTHER |
| | note = N1-methylpseudouridine |
| modified_base | 4823..4824 |
| | mod_base = OTHER |
| | note = N1-methylpseudouridine |
| modified_base | 4827..4828 |
| | mod_base = OTHER |
| | note = N1-methylpseudouridine |
| modified_base | 4833 |
| | mod_base = OTHER |
| | note = N1-methylpseudouridine |
| modified_base | 4837..4838 |
| | mod_base = OTHER |
| | note = N1-methylpseudouridine |
| modified_base | 4840 |
| | mod_base = OTHER |
| | note = N1-methylpseudouridine |
| modified_base | 4848..4849 |
| | mod_base = OTHER |
| | note = N1-methylpseudouridine |
| modified_base | 4853..4854 |
| | mod_base = OTHER |
| | note = N1-methylpseudouridine |
| modified_base | 4856 |
| | mod_base = OTHER |
| | note = N1-methylpseudouridine |
| modified_base | 4862 |
| | mod_base = OTHER |
| | note = N1-methylpseudouridine |
| modified_base | 4867..4868 |
| | mod_base = OTHER |
| | note = N1-methylpseudouridine |
| modified_base | 4870..4871 |
| | mod_base = OTHER |
| | note = N1-methylpseudouridine |
| modified_base | 4873 |
| | mod_base = OTHER |
| | note = N1-methylpseudouridine |
| modified_base | 4875 |
| | mod_base = OTHER |
| | note = N1-methylpseudouridine |
| modified_base | 4879..4880 |
| | mod_base = OTHER |
| | note = N1-methylpseudouridine |
| modified_base | 4886 |
| | mod_base = OTHER |
| | note = N1-methylpseudouridine |
| modified_base | 4888 |
| | mod_base = OTHER |
| | note = N1-methylpseudouridine |
| modified_base | 4892 |
| | mod_base = OTHER |
| | note = N1-methylpseudouridine |
| modified_base | 4894..4895 |
| | mod_base = OTHER |
| | note = N1-methylpseudouridine |
| modified_base | 4898 |
| | mod_base = OTHER |
| | note = N1-methylpseudouridine |
| modified_base | 4900..4902 |
| | mod_base = OTHER |
| | note = N1-methylpseudouridine |
| modified_base | 4906 |
| | mod_base = OTHER |
| | note = N1-methylpseudouridine |
| modified_base | 4913 |
| | mod_base = OTHER |
| | note = N1-methylpseudouridine |
| modified_base | 4917 |
| | mod_base = OTHER |
| | note = N1-methylpseudouridine |

```
modified_base          4924
                       mod_base = OTHER
                       note = N1-methylpseudouridine
modified_base          4926
                       mod_base = OTHER
                       note = N1-methylpseudouridine
source                 1..4929
                       mol_type = other RNA
                       organism = synthetic construct
SEQUENCE: 1
aggaaataag agagaaaaga agagtaagaa gaaatataag agccaccatg agcgaggtgg  60
agttcagcca cgagtactgg atgcggcacg ccctgaccct ggccaagcgg gcccgggacg  120
agcgggaggt gcccgtgggc gccgtgctgg tgctgaacaa ccgggtgatc ggcgagggct  180
ggaaccgggc catcggcctg cacgacccca ccgcccacgc cgagatcatg gccctgcggc  240
agggcggcct ggtgatgcag aactaccggc tgatcgacgc caccctgtac gtgaccttcg  300
agccctgcgt gatgtgcgcc ggcgccatga tccacagccg gatcggccgg gtggtgttcg  360
gcgtgcggaa cgccaagacc ggcgccgccg gcagcctgat ggacgtgctg caccaccccg  420
gcatgaacca ccgggtggag atcaccgagg gcatcctggc cgacgagtgc gccgccctgc  480
tgtgccggtt cttccggatg ccccggcggg tgttcaacgc ccagaagaag gcccagagca  540
gcaccgacag cggcggcagc agcggcggca gcagcggcag cgagacaccc ggcaccagcg  600
agagcgccac ccccgagagc agcggcggca gcagcggcgg cagcgacaag aagtacagca  660
tcggcctggc catcggcacc aacagcgtgg gctgggccgt gatcaccgac gagtacaagg  720
tgcccagcaa gaagttcaag gtgctgggca acaccgaccg gcacagcatc aagaagaacc  780
tgatcggcgc cctgctgttc gacagcggcg agacagccga ggccacccgg ctgaagcgga  840
ccgcccggcg gcggtacacc cggcggaaga accggatctg ctacctgcag gagatcttca  900
gcaacgagat ggccaaggtg gacgacagct tcttccaccg gctggaggag agcttcctgg  960
tggaggagga caagaagcac gagcggcacc ccatcttcgg caacatcgtg gacgaggtgg  1020
cctaccacga gaagtacccc accatctacc acctgcggaa gaagctggtg gacagcaccg  1080
acaaggccga cctgcggctg atctacctgg ccctggccca catgatcaag ttccggggcc  1140
acttcctgat cgagggcgac ctgaaccccg acaacagcga cgtggacaag ctgttcatcc  1200
agctggtgca gacctacaac cagctgttcg aggagaaccc catcaacgcc agcggcgtgg  1260
acgccaaggc catcctgagc gcccggctga gcaagagccg gcggctggag aacctgatcg  1320
cccagctgcc cggcgagaag aagaacggcc tgttcggcaa cctgatcgcc ctgagcctgg  1380
gcctgacccc caacttcaag agcaacttcg acctggccga ggacgccaag ctgcagctga  1440
gcaaggacac ctacgacgac gacctggaca acctgctggc ccagatcggc gaccagtacg  1500
ccgacctgtt cctggccgcc aagaacctga gcgacgccat cctgctgagc gacatcctgc  1560
gggtgaacac cgagatcacc aaggcccccc tgagcgccag catgatcaag cggtacgacg  1620
agcaccacca ggacctgacc ctgctgaagg ccctggtgcg gcagcagctg cccgagaagt  1680
acaaggagat cttcttcgac cagagcaaga acggctacgc cggctacatc gacggcggcg  1740
ccagccagga ggagttctac aagttcatca agcccatcct ggagaagatg gacggcaccg  1800
aggagctgct ggtgaagctg aaccgggagg acctgctgcg gaagcagcgg accttcgaca  1860
acggcagcat cccccaccag atccacctgg gcgagctgca cgccatcctg cggcggcagg  1920
aggacttcta ccccttcctg aaggacaacc gggagaagat cgagaagatc ctgaccttcc  1980
ggatccccta ctacgtgggc cccctggccc ggggcaacag ccggttcgcc tggatgaccc  2040
gcaagagcga ggagacaatc acccccctgga acttcgagga ggtggtggac aagggcgcca  2100
gcgcccagag cttcatcgag cggatgacca acttcgacaa gaacctgccc aacgagaagg  2160
tgctgcccaa gcacagcctg ctgtacgagt acttcaccgt gtacaacgag ctgaccaagg  2220
tgaagtacgt gaccgagggc atgcggaagc ccgccttcct gagcggcgag cagaagaagg  2280
ccatcgtgga cctgctgttc aagaccaacc ggaaggtgac cgtgaagcag ctgaaggagg  2340
actacttcaa gaagatcgag tgcttcgaca gcgtggagat cagcggcgtg gaggaccggt  2400
tcaacgccag cctgggcacc taccacgacc tgctgaagat catcaaggac aaggacttcc  2460
tggacaacga ggagaacgag gacatcctgg aggacatcgt gctgaccctg accctgttcg  2520
aggaccggga gatgatcgag gagcggctga agacctacgc ccacctgttc gacgacaagg  2580
tgatgaagca gctgaagcgg cggcggtaca ccggctgggg ccggctgagc cggaagctga  2640
tcaacggcat ccgggacaag cagagcggca agaccatcct ggacttcctc aagagcgacg  2700
gcttcgccaa ccggaacttc atgcagctga tccacgacga cagcctgacc ttcaaggagg  2760
acatccagaa ggcccaggtg agcggccagg gcgacagcct gcacgagcac atcgccaacc  2820
tggccggcag ccccgccatc aagaagggca tcctgcagac cgtgaaggtg gtggacgagc  2880
tggtgaaggt gatgggccgg cacaagcccg agaacatcgt gatcgagatg gcccgggaga  2940
accagaccac ccagaagggc cagaagaaca gccgggagcg gatgaagcgg atcgaggagg  3000
gcatcaagga gctgggcagc cagatcctga aggagcaccc cgtggagaac acccagctgc  3060
agaacgagaa gctgtacctg tactacctgc agaacggccg ggacatgtac gtggaccagg  3120
agctggacat caaccggctg agcgactacg acgtggacca catcgtgccc cagagcttcc  3180
tgaaggacga cagcatcgac aacaaggtgc tgacccggag cgacaagaac cggggcaaga  3240
gcgacaacgt gcccagcgag gaggtggtga agaagatgaa gaactactgg cggcagctgc  3300
tgaacgccaa gctgatcacc cagcggaagt tcgacaacct gaccaaggcc gagcggggcg  3360
gcctgagcga gctggacaag gccggcttca tcaagcggca gctggtggag acacggcaga  3420
tcaccaagca cgtggcccag atcctggaca gccggatgaa caccaagtac gacgagaacg  3480
acaagctgat ccgggaggtg aaggtgatca ccctcaagag caagctggtg agcgacttcc  3540
ggaaggactt ccagttctac aaggtgcggg agatcaacaa ctaccaccac gcccacgacg  3600
cctacctgaa cgccgtggtg ggcaccgccc tgatcaagaa gtaccccaag ctggagagcg  3660
agttcgtgta cggcgactac aaggtgtacg acgtgcggaa gatgatcgcc aagagcgagc  3720
aggagatcgg caaggccacc gccaagtact tcttctacag caacatcatg aacttcttca  3780
agaccgagat caccctggcc aacggcgaga tccggaagcg gcccctgatc gagacaaacg  3840
gcgagacagg cgagatcgtg tgggacaagg gccgggactt cgccaccgtg cggaaggtgc  3900
tgagcatgcc ccaggtgaac atcgtgaaga agaccgaggt gcagaccggc ggcttcagca  3960
aggagagcat cctgcccaag cggaacagcg acaagctgat cgcccggaag aaggactggg  4020
accccaagaa gtacggcggc ttcgacagcc ccaccgtggc ctacagcgtg ctggtggtgg  4080
ccaaggtgga gaagggcaag agcaagaagc tcaagagcgt gaaggagctg ctgggcatca  4140
```

-continued

```
ccatcatgga gcggagcagc ttcgagaaga accccatcga cttcctggag gccaagggct  4200
acaaggaggt gaagaaggac ctgatcatca agctgcccaa gtacagcctg ttcgagctgg  4260
agaacggccg gaagcggatg ctggccagcg ccggcgagct gcagaagggc aacgagctgg  4320
ccctgcccag caagtacgtg aacttcctgt acctggccag ccactacgag aagctgaagg  4380
gcagccccga ggacaacgag cagaagcagc tgttcgtgga gcagcacaag cactacctgg  4440
acgagatcat cgagcagatc agcgagttca gcaagcgggt gatcctggcc gacgccaacc  4500
tggacaaggt gctgagcgcc tacaacaagc accgggacaa gcccatccgg gagcaggccg  4560
agaacatcat ccacctgttc accctgacca acctgggcgc ccccgccgcc ttcaagtact  4620
tcgacaccac catcgaccgg aagcggtaca ccagcaccaa ggaggtgctg gacgccaccc  4680
tgatccacca gagcatcacc ggcctgtacg agacacggat cgacctgagc cagctgggcg  4740
gcgacgaggg cgccgacaag cggaccgccg acggcagcga gttcgagagc cccaagaaga  4800
agcggaaggt gtgagcggcc gcttaattaa gctgccttct gcggggcttg ccttctggcc  4860
atgcccttct tctctccctt gcacctgtac ctcttggtct ttgaataaag cctgagtagg  4920
aagtctaga                                                         4929

SEQ ID NO: 2           moltype = DNA  length = 23
FEATURE                Location/Qualifiers
misc_feature           1..23
                       note = Description of Artificial Sequence:
                        Syntheticoligonucleotide
source                 1..23
                       mol_type = other DNA
                       organism = synthetic construct
SEQUENCE: 2
attatgctga gtgatatccc tct                                         23

SEQ ID NO: 3           moltype = DNA  length = 23
FEATURE                Location/Qualifiers
misc_feature           1..23
                       note = Description of Artificial Sequence:
                        Syntheticoligonucleotide
source                 1..23
                       mol_type = other DNA
                       organism = synthetic construct
SEQUENCE: 3
taatacgact cactataggg aga                                         23

SEQ ID NO: 4           moltype = AA  length = 6
FEATURE                Location/Qualifiers
REGION                 1..6
                       note = Description of Artificial Sequence: Synthetic6xHis
                        tag
source                 1..6
                       mol_type = protein
                       organism = synthetic construct
SEQUENCE: 4
HHHHHH                                                            6

SEQ ID NO: 5           moltype = AA  length = 4
FEATURE                Location/Qualifiers
REGION                 1..4
                       note = Description of Artificial Sequence: Syntheticpeptide
source                 1..4
                       mol_type = protein
                       organism = synthetic construct
SEQUENCE: 5
ALAL                                                              4
```

We claim:

1. An in vitro-transcribed (IVY) mRNA sequence initiator comprising a compound of formula (II) or a salt or solvate thereof:

Formula (II)

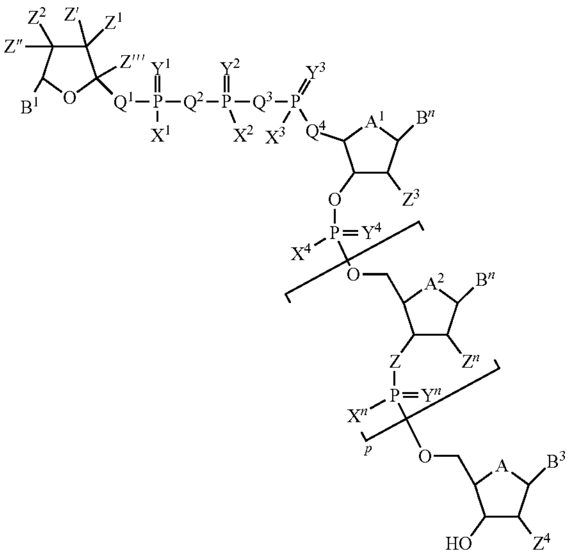

Wherein $B^1$ is

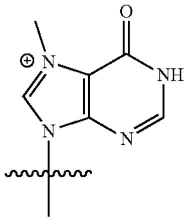

or

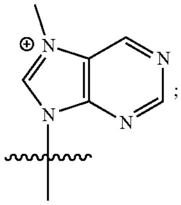

;

each $B^2$, $B^3$, and $B''$ is independently a natural, a modified, or an unnatural nucleobase;

each Z' and Z" is independently is hydrogen, fluorine, —OH, —SH, —$CH_3$, —$CH_2CH_3$, —$OCH_3$, —$NH(CH_3)$, —$NH_3$, —$NH(C(=O)CH_3)$, or —$SCH_3$;

Z''' is hydrogen, fluorine, —$CH_3$, —$CH_2CH_3$, —$OCH_3$, or —$OCH_2CH_3$;

each $Z^1$ and $Z^2$ is independently hydrogen, fluorine, —OH, —SH, —$CH_3$, —$CH_2CH_3$, —$OCH_3$, —$SCH_3$, —$OCH_2CH_3$, —$NH_2$, $NHCH_3$, or $NHC(=O)CH_3$;

each $Z^3$, $Z^4$, and $Z''$ is independently hydrogen, fluorine, —OH, —$CH_3$, —$CH_2CH_3$, —$OCH_3$, —$NH_2$, —$NHCH_3$, —$NH(C(=O)CH_3)$, —$OCH_2CH_3$, —$OCH_2OCH_3$, —$OCH_2CH_2CH_3$, —$OCH(CH_3)_2$, —$SCH_3$, or —$OCH_2CH_2OCH_3$;

each $Q^1$ and $Q^4$ is independently —CH=CH—, —$CH_2$—, —$CH_2O$—, —$CH_2S$—, —$CH_2CH_2$—, —$CH_2CF_2$—, —$CH_2NH_2$—, —$CH_2NH(CH_3)$—, or —$CH_2N(C(=O)CH_3)$;

each $Q^2$ and $Q^3$ is independently —O—, —S—, —$CH_2$—, —$CF_2$—, —NH—, —$N(CH_3)$—, or —$N(C(=O)CH_3)$—;

each $X^1$, $X^2$, $X^3$, $X^4$, and $X^5$ is independently —OH, —SH, —$O^-$, —$S^-$, —$NH_2$, —$NHCH_3$, —$NH(C(=O)CH_3)$, —$CH_3$, —$CH_2CH_3$, —$CH_2CH_2CH_3$, —$CH(CH_3)_2$—$OCH_3$ or —$OCH_2CH_3$;

each $Y^1$, $Y^2$, $Y^3$, $Y^4$, and $Y^5$ is independently =O, =S, =NH, or =$NCH_3$;

each A, $A^1$, and $A^2$ is independently —O—, —S—, —$CH_2$—, —NH—, —$N(CH_3)$— or —$N(C(=O)CH_3)$; and p=0, 1, 2, 3, 4, 5 or 6.

2. The in vitro-transcribed (IVT) mRNA sequence initiator of claim 1, comprising a structure of:

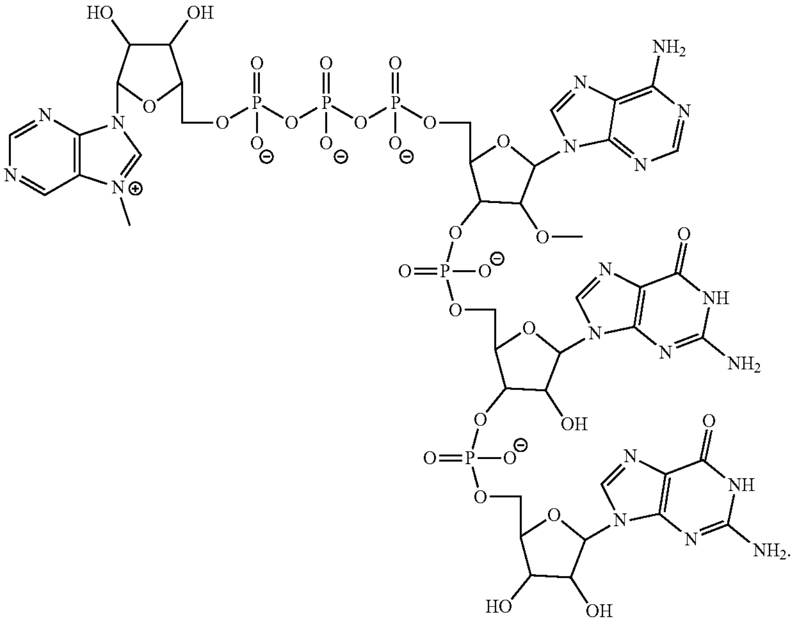 [SMILES: COC1C(OP(=O)([O-])OCC2OC(n3cnc4c(=O)[nH]c(N)nc43)C(O)C2OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4cncnc43)C(O)C2O)OC1n1cnc2c(N)ncnc21]

3. An mRNA sequence having a 5'-end region motif (I'):

Motif (I')

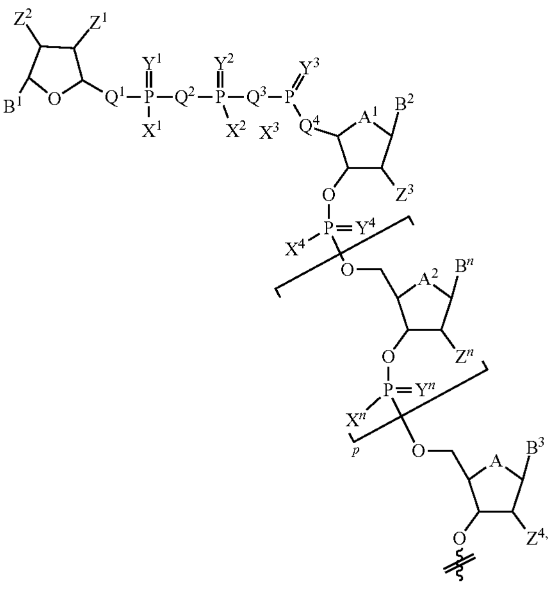

wherein $B^1$ is

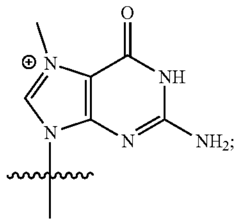 [SMILES: *n1c[n+](C)c2c(=O)[nH]c(N)nc21]

each $B^2$, $B^3$, and $B^n$ is independently a natural, a modified, or an unnatural nucleobase;

each of $Z^1$ and $Z^2$ is independently hydrogen, fluorine, —OH, —SH, —$CH_3$, —$CH_2CH_3$, —$OCH_3$, —$OCH_2CH_3$, —$SCH_3$, —$NH_2$, $NHCH_3$, or NHC(=O) $CH_3$;

$Z^3$ is —$OCH_3$, and each of $Z^4$ and $Z^n$ is independently hydrogen, fluorine, —OH, —SH, —$CH_3$, —$CH_2CH_3$, —$OCH_3$, —$NH_2$, —$NHCH_3$, —NH(C(=O)$CH_3$), —$OCH_2CH_3$, —$OCH_2OCH_3$, —$OCH_2CH_2CH_3$, —OCH$(CH_3)_2$, —$SCH_3$, or —$OCH_2CH_2OCH_3$;

each of $Q^1$ and $Q^4$ is independently —$CH_2$—, —CH=CH—, —$CH_2O$—, —$CH_2S$—, —$CH_2CH_2$—, —$CH_2CF_2$—, —$CH_2NH_2$—, —$CH_2NH(CH_3)$—, or —$CH_2N(C(=O)CH_3)$—;

each of $Q^2$ and $Q^3$ is independently —O—, —S—, —$CH_2$—, —$CF_2$—, —NH—, —N($CH_3$)—, or —N(C(=O)$CH_3$)—;

$X^4$ is —OH or —O', and each of $X^1$, $X^2$, $X^3$, [$X^4$,] and $X^n$ is independently —OH, —SH, —$O^-$, —$S^-$, —$NH_2$, —$NHCH_3$, —NH(C(=O)$CH_3$), —$CH_3$, —$CH_2CH_3$, —$CH_2CH_2CH_3$, —CH$(CH_3)_2$, —$OCH_3$, or —$OCH_2CH_3$;

$Y^4$ is =S, and each of $Y^1$, $Y^2$, $Y^3$, [$Y^4$,] and $Y^n$ is independently =O, =S, =NH, or =$NCH_3$;

each A, $A^1$, and $A^2$ is independently —O—, —S—, —$CH_2$—, —NH—, —N($CH_3$)— or —N(C(=O) $CH_3$)—; and p=0, 1, 2, 3, 4, 5 or 6.

4. The mRNA sequence having a 5'-end region motif (I') of claim 3, wherein the motif has a structure of Motif (I'-d):

Motif (I'-d)

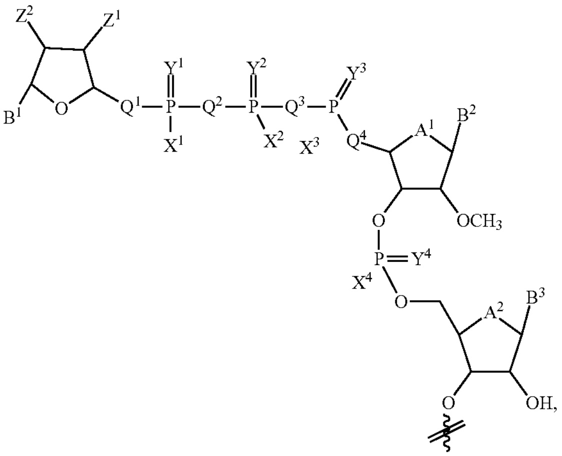

Wherein $B^2$ is adenine and $B^3$ is guanine;

each of $Q^1$ and 04 is —$CH_2O$—;

each of $Q^2$ and $Q^3$ is —O—;

each of $X^1$, $X^2$ and $X^3$ is —OH or —O;

each of $Y^1$, $Y^2$, and $Y^3$ is —O; and each of $A^1$ and A is —O—.

5. An in vitro-transcribed (IVT) mRNA sequence initiator comprising a structure of:
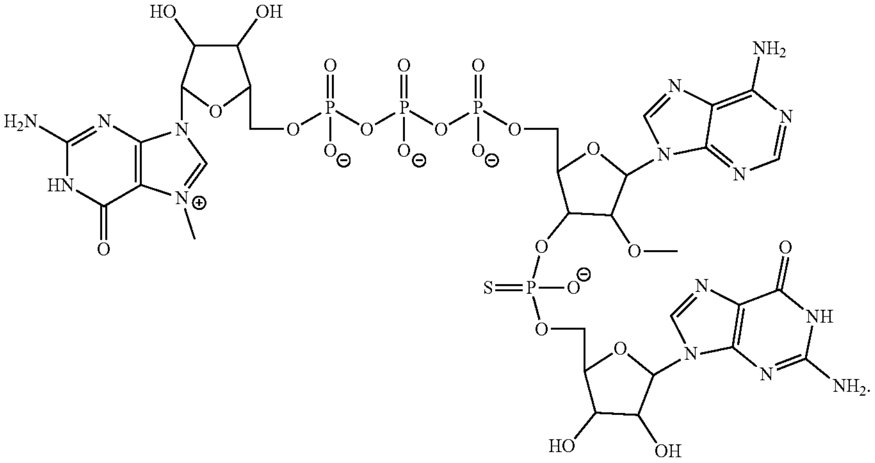 [SMILES: COC1C(OP([O-])(=S)OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(O)C2O)OC1n1cnc2c(N)ncnc21]
6. An in vitro-transcribed (IVT) mRNA sequence initiator comprising a structure of:
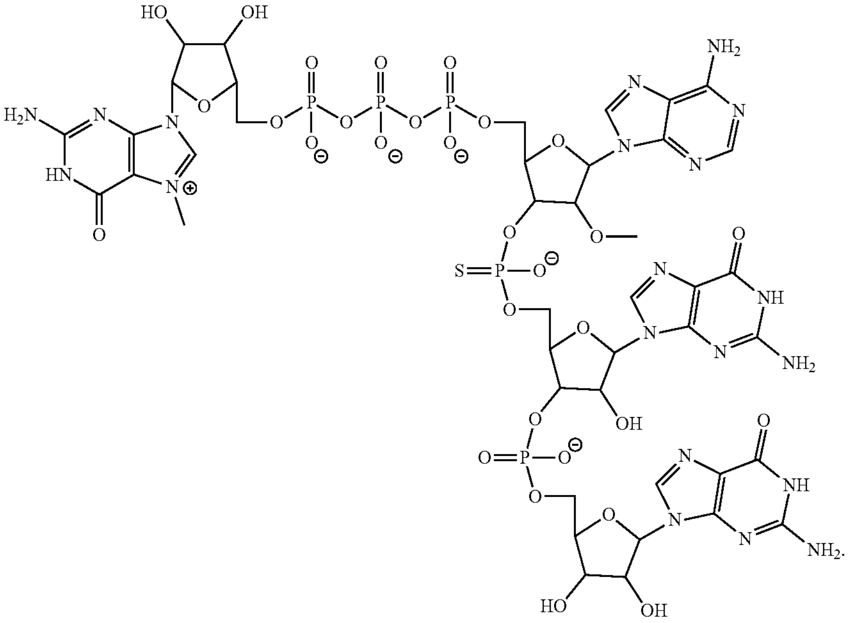 [SMILES: COC1C(OP([O-])(=S)OCC2OC(n3cnc4c(=O)[nH]c(N)nc43)C(O)C2OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(O)C2O)OC1n1cnc2c(N)ncnc21]
* * * * *